(12) United States Patent
Nagasawa et al.

(10) Patent No.: US 7,276,511 B2
(45) Date of Patent: Oct. 2, 2007

(54) BENZYLAMINE DERIVATIVE

(75) Inventors: Masaaki Nagasawa, Saitama (JP);
Nobuo Kawase, Saitama (JP);
Nobuyuki Tanaka, Saitama (JP);
Hideki Nakamura, Saitama (JP);
Naoki Tsuzuike, Saitama (JP);
Masakazu Murata, Saitama (JP)

(73) Assignee: Zeria Pharmaceutical Co., Ltd., Tokyo (JP)

( * ) Notice: Subject to any disclaimer, the term of this patent is extended or adjusted under 35 U.S.C. 154(b) by 5 days.

(21) Appl. No.: 10/566,252

(22) PCT Filed: Aug. 2, 2004

(86) PCT No.: PCT/JP2004/011065

§ 371 (c)(1),
(2), (4) Date: Jan. 30, 2006

(87) PCT Pub. No.: WO2005/012248

PCT Pub. Date: Feb. 10, 2005

(65) Prior Publication Data

US 2006/0194841 A1      Aug. 31, 2006

(30) Foreign Application Priority Data

Jul. 31, 2003   (JP) .............................. 2003-205114

(51) Int. Cl.
*A61K 31/438*   (2006.01)
*C07D 495/10*   (2006.01)

(52) U.S. Cl. .................. 514/278; 546/17; 546/18; 546/225; 546/229; 514/330; 514/331

(58) Field of Classification Search .............. 514/278, 514/330, 331; 546/17, 18, 225, 229
See application file for complete search history.

(56) References Cited

U.S. PATENT DOCUMENTS 5,789,422 A      8/1998   Reichard et al.
5,869,496 A  *  2/1999   Hale et al. ................. 514/278

FOREIGN PATENT DOCUMENTS

| JP | 8-505880 | 6/1996 |
| JP | 8-511522 | 12/1996 |
| JP | 11-043490 | 2/1999 |
| JP | 2001-507673 | 6/2001 |
| JP | 2002-520316 | 7/2002 |
| WO | 94/17045 | 8/1994 |
| WO | 94/26735 | 11/1994 |
| WO | 94/29309 | 12/1994 |

* cited by examiner

*Primary Examiner*—Charanjit S. Aulakh
(74) *Attorney, Agent, or Firm*—Oblon, Spivak, McClelland, Maier & Neustadt, P.C.

(57) ABSTRACT

The invention provides a compound which exhibits satisfactory peroral absorbability and excellent antagonistic activity against NK-1 receptor or NK-2 receptor. The compound is a benzylamine derivative represented by formula (1) or a salt thereof

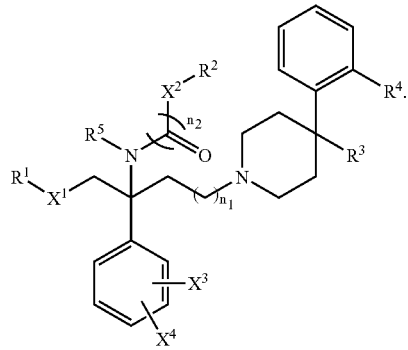

(1)

11 Claims, No Drawings

BENZYLAMINE DERIVATIVE

TECHNICAL FIELD

The present invention relates to a novel benzylamine derivative or a salt thereof which exhibits excellent antagonistic activity against substance P receptor (NK-1 receptor) or neurokinin A receptor (NK-2 receptor).

BACKGROUND ART

Tachykinins, which form a group of peptidergic neurotransmitters, play an important role in nociception functioning as a biowarning system, as well as the emotion cycle. Desctruction of such a biowarning system readily causes a variety of diseases and disorders inculuding irritable bowel syndrome (IBS), pain, anxiety, obstructive bronchial diseases, headache, and vomiting. In mammals, substance P, neurokinin A, and neurokinin B are known tachykinins, and these tachykinin species have high affinity with respect to NK-1 receptor, NK-2 receptor, and NK-3 receptor, respectively.

Tachykinin receptor antagonists have been used as drugs for treating various diseases caused by destruction of the biowarning system. For example, the following compounds (A), (B) and (C) are low-molecular weight non-peptidergic compounds known to exhibit antagonistic activity against both NK-1 receptor and NK-2 receptor (Patent Documents 1 to 3).

[F1]

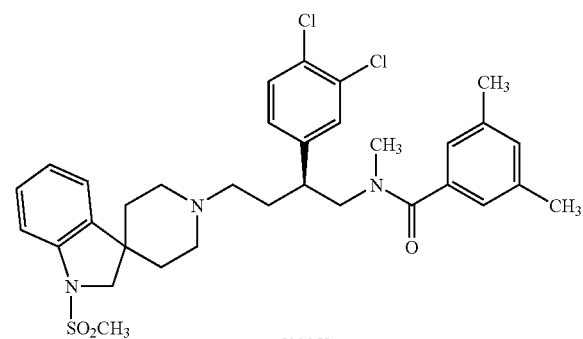

(A)

[0005]

[F2]

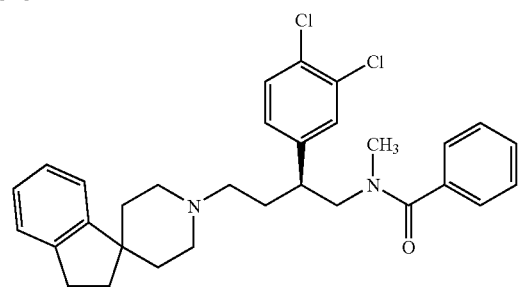

(B)

[0006]

[F3]

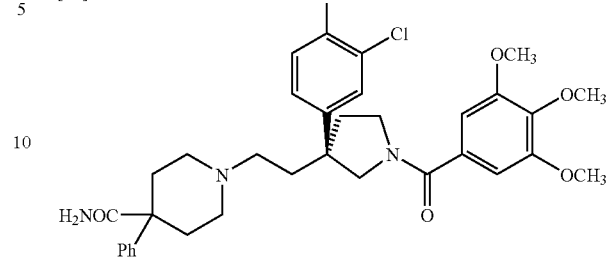

(C)

-continued

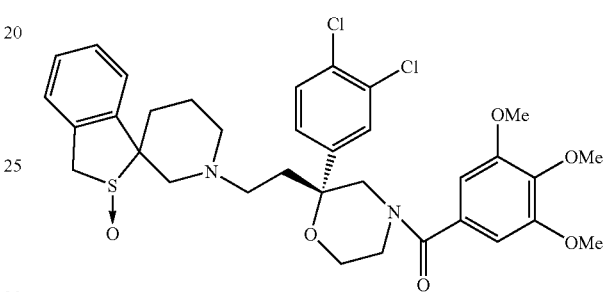

(D)

However, actually, compound (B) in vitro exhibits antagonistic activity only to NK-2 receptor. When any of compounds (A) to (C) are perorally administered, satisfactory antagonistic activity is not always attained (Patent Documents 2 and 4).

Meanwhile, the aforementioned optically active sulfoxide derivative (D) is known to exhibit excellent antagonistic activity against both NK-1 receptor and NK-2 receptor (see Patent Document 4). However, there are only a limited number of reports on low-molecular-weight compounds exhibiting antagonistic activity against NK-1 receptor or NK-2 receptor.

Patent Document 1: International Patent Publication WO94/29309 pamphlet)

Patent Document 2: International Patent Publication WO94/17045 pamphlet)

Patent Document 3: International Patent Publication WO94/26735 pamphlet)

Patent Document 4: Japanese Patent Application Laid-Open (kokai) No. 11-43490

DISCLOSURE OF THE INVENTION

Problems to be Solved by the Invention

Thus, an object of the present invention is to provide a compound which exhibits excellent peroral absorbability and excellent antagonistic activity against NK-1 receptor or NK-2 receptor and which is useful as a drug for preventing and/or treating diseases such as irritable bowel syndrome (IBS).

The present inventors have conducted extensive research over years on synthesis of derivatives having tachykinin antagonistic activity (particularly, substance P antagonistic activity and antagonistic activity against neurokinin A and neurokinin B) and pharmacological activity thereof, and have found that a novel benzylamine derivative and a salt thereof exhibit excellent peroral absorbability and remarkably excellent antagonistic activity against NK-1 receptor or NK-2 receptor. The present invention has been accomplished on the basis of this finding.

Accordingly, the present invention provides a benzylamine derivative represented by formula (1):

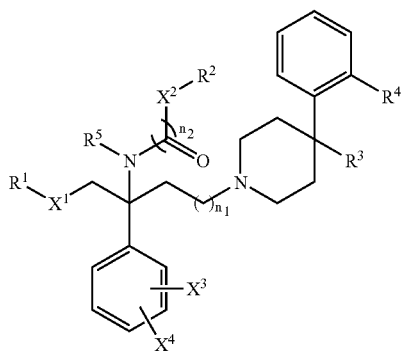

(1)

[wherein $X^1$ represents —N(CH$_3$)—, —NH—, or —O—;

$X^2$ represents a single bond, —NH—, an amido bond, an ester bond, —O—, —S—, or —CO—;

each of $X^3$ and $X^4$ represents a hydrogen atom or a halogen atom;

$R^1$ represents a hydrogen atom; a lower alkyl group; a phenyl group which may be substituted by 1 to 3 halogen atoms or cyano groups; a benzyl group which may be substituted by 1 to 3 lower alkyl groups, cyano groups, halogeno(lower alkyl) groups, or lower alkoxy groups; a benzoyl group which may be substituted by 1 to 3 lower alkyl groups, hydroxyl groups, halogeno(lower alkyl) groups, or lower alkoxy groups; a lower alkanoyl group which may be substituted by 1 to 5 halogen atoms, amino groups, or carbamoyl groups; a hydroxyl group; a carbamoyl group; a lower alkylsulfonyl group; a lower alkoxycarbonyl-lower alkyl group; a thienylcarbonyl group; a pyridylcarbonyl group; a lower alkylcarbonyl group; or a phenoxycarbonyl group;

$R^2$ represents a hydrogen atom, a lower alkyl group, a lower alkenyl group, a lower alkylsulfonyl group, a C3-C7 cycloalkyl group, a C6-C14 cycloalkyl-alkyl group, a C6-C14 aryl group, a C6-C14 aryloxy group, a C6-C14 aryloxy-lower alkyl group, C6-C14 arylthio-lower alkyl group, a C7-C16 aralkyl group, a lower alkoxycarbonyl-lower alkyl group, a lower alkoxy-lower alkyl group, an amino-lower alkyl group, a C7-C16 aralkyl group substituted by a C3-C7 cycloalkyl group, a halogeno(lower alkyl) carbonyl group, an indanyl group, a 1,2,3,4-tetrahydronaphthalenyl group, a xanthenyl group, a piperidinyl group, a pyrrolidinyl group, a morpholino group, a tetrahydroisoquinolyl group, an indolyl group, a chromenyl group, an isobenzofuranyl group, a tetrahydropyranyl group, a benzothienyl group, an adamantyl group, an adamantyl(lower alkyl) group, a fluorenyl group, a fluorenyl(lower alkyl) group, a pyridyl(lower alkyl) group, or an amino group which may be substuted by a phenyl group or a lower alkyl group (wherein a ring hydrogen of these group may be substituted by 1 to 5 atoms or groups selected from among a halogen atom, a lower alkyl group, a lower alkoxy group, a nitro group, an oxo group, a halogeno(lower alkyl) group, a C6-C14 aryl group, and a lower alkylamino group);

when $R^3$ represents a (lower alkanoyl)amino group, an amino(lower alkanoyl) group, an amino(lower alkanoyl) amino group, a di(lower alkyl)carbamoylamino group, or a C7-C16 aralkyloxy(lower alkyl) group, $R^4$ represents a hydrogen atom; or $R^3$ and $R^4$ may together form —SOCH$_2$—, —SO$_2$CH$_2$—, —NHCOCH$_2$—, —CH(OH)CH$_2$—, —OCH$_2$—, or —C(=NOH)CH$_2$—; $R^5$ represents a hydrogen atom or a lower alkyl group; $n_1$ is 1 or 2; and $n_2$ is 0 or 1] or a salt thereof.

The present invention also provides a drug containing, as an active ingredient, a benzylamine derivative represented by formula (1) or a salt thereof.

The present invention also provides a pharmaceutical composition containing a benzylamine derivative represented by formula (1) or a salt thereof, and a phramaceutically acceptable carrier therefor.

The present invention also provides use of a benzylamine derivative represented by formula (1) or a salt thereof for producing a drug.

The present invention also provides a method for treating irritable bowel syndrome, pain, anxiety, obstructive bronchial diseases, headache, or vomiting, characterized in that the method comprises administerring, in an effective amount, a benzylamine derivative represented by formula (1) or a salt thereof.

The benzylamine derivative of the present invention or a salt thereof exhibits remarkably excellent antagonistic activity against NK-1 receptor or NK-2 receptor. Thus, the drug of the present invention containing as an active ingredient the derivative or a salt thereof is a useful drug for preventing and/or treating various diseases and disorders such as disorders inculduing irritable bowel syndrome (IBS), pain, anxiety, and obstructive bronchial diseases.

BEST MODE FOR CARRYING OUT THE INVENTION

In the above formula (1), $X^1$ represents —N(CH$_3$)—, —NH—, or —O—, preferably —N(CH$_3$)— or —O—. $X^2$ represents a single bond, —NH—, an amido bond, an ester bond, —O—, —S—, or —CO—. As used herein, the amido bond is —NHCO— or —CONH—, and the ester bond is —OCO— or —COO—. $X^2$ is preferably a single bond, —NH—, an amido bond, an ester bond, —O—, or —CO—, more preferably a single bond or —NH—.

$X^3$ and $X^4$ each represent a halogen atom. Examples of the "halogen atom" include F, Cl, Br, and I. Preferably, both $X^3$ and $X^4$ are Cl, and the positions of the $X^3$ and $X^4$ are preferably the 3- and 4-positions.

Next, $R^1$ will be described.

The "lower alkyl group" is a C1-C6 linear, C1-C6 branched, or C3-C6 cyclic alkyl group, and specific examples include methyl, ethyl, n-propyl, isopropyl, n-butyl, isobutyl, sec-butyl, tert-butyl, n-pentyl, isopentyl, sec-pentyl, tert-pentyl, neopentyl, cyclopropyl, cyclopentyl, cyclohexyl. Among them, methyl, ethyl, propyl, and isopropyl are preferred, and methyl is more preferred.

The "phenyl group which may be substituted by 1 to 3 halogen atoms or cyano groups" is a non-substituted phenyl group, and a phenyl group which has been substituted by the above halogen atom or a cyano group. When the phenyl group has been substituted by a plurality of groups, the groups may be identical to or different from one another.

Specific examples of the phenyl group which has been substituted by a halogen atom include fluorophenyl, chlorophenyl, and bromophenyl, with chlorophenyl being preferred. Examples of the phenyl group which has been substituted by a cyano group include cyanophenyl.

The "benzyl group which may be substituted by a lower alkyl group, a cyano group, a halogeno(lower alkyl) group, or a lower alkoxy group" is a non-substituted benzyl group, or a substituted benzyl group derived from substitution of hydrogen on phenyl with a lower alkoxy group, a cyano group, a halogeno(lower alkyl) group, or a lower alkoxy group. The number of the substituents is preferably 2 or 3, more preferably 3.

As used herein, examples of the lower alkyl group include those described above. Examples of the "halogeno(lower alkyl) group" include trifluoromethyl, trichloromethyl, difluorochloromethyl, dichlorofluoromethyl, difluoromethyl, dichloromethyl, monofluoromethyl, monochloromethyl, 2,2,2-trifluoroethyl, and 3,3,3-trifluoropropyl. Examples of the "lower alkoxy group" include C1-C6 linear, C1-C6 branched, and C3-C6 cyclic alkoxy groups, such as methoxy, ethoxy, n-propoxy, isopropyloxy, n-butoxy, isobutyloxy, sec-butyloxy, tert-butyloxy, cyclopentyloxy, and cyclohexyloxy. Of these, methoxy, ethoxy, and n-propoxy are preferred, with methoxy being more preferred.

Specific examples of the benzyl group which has been substituted by a lower alkyl group include methylbenzyl, ethylbenzyl, and n-propylbenzyl.

Specific examples of the benzyl group which has been substituted by a cyano group include cyanobenzyl.

Specific examples of the benzyl group which has been substituted by a halogeno(lower alkyl) group include trifluoromethylbenzyl and bis(trifluoromethyl)benzyl.

Specific examples of the benzyl group which has been substituted by a lower alkoxy group include methoxybenzyl, dimethoxybenzyl, and 3,4,5-trimethoxybenzyl.

The "benzoyl group which may be substituted by 1 to 3 lower alkyl groups, hydroxyl groups, halogeno(lower alkyl) groups, or lower alkoxy groups" is a non-substituted benzoyl group, or a benzoyl group which has been substituted by the above lower alkyl group, a hydroxyl group, the above halogeno(lower alkyl) group, or the above lower alkoxy group. The number of the substituents is preferably 2 or 3. When the benzoyl group has been substituted by a plurality of groups, the groups may be identical to or different from one another.

Examples of the benzoyl group which has been substituted by a lower alkyl group or lower alkyl groups include methylbenzoyl, ethylbenzoyl, and n-propylbenzoyl. Examples of the benzoyl group which has been substituted by a lower alkoxy group or lower alkoxy groups include methoxybenzoyl, dimethoxybenzoyl and trimethoxybenzoyl. Examples of the benzoyl group which has been substituted by a halogeno(lower alkyl) group or halogeno(lower alkyl) groups include trifluoromethylbenzoyl and bis(trifluoromethyl)benzoyl. Examples of the benzoyl group which has been substituted by a hydroxyl group (or hydroxyl groups) or a lower alkoxy group (or lower alkoxy groups) include hydroxy(dimethoxy)benzoyl.

The "lower alkanoyl group which may be substituted by 1 to 5 of halogen atoms, amino groups, or carbamoyl groups" is a non-substituted lower alkanoyl group, or a lower alkanoyl group which has been substituted by 1 to 5 of the above halogen atoms, an amino group, and the carbamoyl groups described below. When the lower alkanoyl group has been substituted by a plurality of groups, the groups may be identical to or different from one another.

As used herein, the "lower alkanoyl group" is a C1-C8 alkanoyl group. Examples include formyl, acetyl, n-propionyl, n-butyryl, isobutyryl, and pivaloyl. Of these, acetyl, n-propionyl, isobutyryl, and pivaloyl are preferred, with isobutyryl being more preferred.

Examples of the alkanoyl group which has been substituted by the above halogen atom(s) include alkanoyl groups which have been substituted by 1 to 5 of F and Cl. Specific examples include fluoroacetyl, chloroacetyl, difluoroacetyl, dichloroacetyl, difluorochloroacetyl, trifluoroacetyl, trichloroacetyl, dichlorofluoroacetyl, 3,3,3-trifluoropropionyl, 3,3,3-trichloropropionyl, 4,4,4-trifluorobutyryl, and 4,4,4-trichlorobutyryl. Of these, trifluoroacetyl, difluoroacetyl, 2,2-difluoro-2-chloroacetyl, 3,3,3-trifluoropropionyl, and 4,4,4-trifluorobutyryl are preferred, with trifluoroacetyl and 3,3,3-trifluoropropionyl being more preferred.

Examples of the alkanoyl group which has been substituted by an amino group include aminoacetyl and 3-aminopropionyl. Examples of the alkanoyl group which has been substituted by a carbamoyl group include (chlorophenylcarbamoyl)formyl. The alkanoyl group may be substituted by a phenyl group which may have a substituent (e.g., the above alkoxy group, phenyl). Examples of the alkanoyl group include trimethoxyphenylacetyl and phenylacetyl.

The "carbamoyl group" is a non-substituted carbamoyl group, or a carbamoyl group which has been substituted by 1 to 2 groups such as the above lower alkyl groups, the above halogen atoms, a phenyl group, and a benzyl group. Examples of the substituted carbamoyl group include methylcarbamoyl, ethylcarbamoyl, n-propylcarbamoyl, isopropylcarbamoyl, n-butylcarbamoyl, sec-butylcarbamoyl, tert-butylcarbamoyl, n-pentylcarbamoyl, n-hexylcarbamoyl, cyclopropylcarbamoyl, cyclobutylcarbamoyl, cyclopentylcarbamoyl, cyclohexylcarbamoyl, cyclopropylmethylcarbamoyl, cyclopentylmethylcarbamoyl, dimethylcarbamoyl, methylethylcarbamoyl, diethylcarbamoyl, methylpropylcarbamoyl, methylisopropylcarbamoyl, methylcyclopropylcarbamoyl, methylcyclopropylmethylcarbamoyl, chlorobenzylaminocarbamoyl, fluorobenzylaminocarbamoyl, phenylmethylcarbamoyl, and diphenylmethylcarbamoyl.

The "lower alkylsulfonyl group" is a sulfonyl group which has been substituted by the above lower alkyl group. Specific examples include methylsulfonyl, ethylsulfonyl, n-propylsulfonyl, n-butylsulfonyl, and tert-butylsulfonyl, with methylsulfonyl being preferred.

The "(lower alkoxy)carbonyl(lower alkyl) group" is a group corresponding to the above lower alkyl group which has been substituted by a (lower alkoxy)carbonyl, which is formed of a lower alkoxy group as mentioned above and a carbonyl group. Specific examples include methoxycarbonylmethyl, ethoxycarbonylmethyl, 2-methoxycarbonylethyl, and 2-ethoxycarbonylethyl, with ethoxycarbonylmethyl being preferred.

The "(lower alkyl)carbonyl group" is a group which is formed of the above lower alkyl group and a carbonyl group. Examples include cyclopropylcarbonyl, cyclobutylcarbonyl, and cyclohexylcarbonyl.

Next, $R^2$ will be described. The ring-hydrogen(s) of the group represented by $R^2$ may be substituted by 1 to 5 groups selected from among halogen atoms, the above lower alkyl group, the above lower alkoxy group, a nitro group, an oxo group, the above halogeno(lower alkyl) group, the aryl group described later, and the (lower alkyl)amino group described later.

In the definition of $R^2$, the "lower alkyl group" is a C1-C8 linear or branched alkyl groups, and does not include the cyclic alkyl groups described later. Specific examples include methyl, ethyl, n-propyl, isopropyl, n-butyl, isobutyl, sec-butyl, tert-butyl, n-pentyl, isopentyl, sec-pentyl, tert-pentyl, neopentyl, n-hexyl, n-heptyl, and n-octyl.

The "lower alkenyl group" is a C2-C7 linear or branched alkenyl group. Examples include ethenyl (vinyl), 2-propenyl, 1-propenyl, 2-butenyl, 1,3-butadienyl, and isopropenyl.

The "lower alkylsulfonyl group" is similar to those listed above in relation to $R^1$.

Examples of the "C3-C7 cycloalkyl group" include cyclopropyl, cyclobutyl, cyclopentyl, cyclohexyl, and cycloheptyl. The cycloalkyl group may further be substituted by a phenyl group. Examples include phenylcyclopentyl. The branched alkyl group, which is formed of a cycloalkyl group and a linear alkyl group, will be described later in relation to the cycloalkyl-alkyl group.

The "C6-C14 cycloalkyl-alkyl group" is a group corresponding to the above lower alkyl group which has been substituted by a C3-C7 cycloalkyl group. As used herein, "the above lower alkyl group" is a lower alkyl group defined in relation to $R^1$. Specific examples include cyclopentylmethyl, cyclohexylmethyl, 2-cyclopentylethyl, 2-cyclohexylethyl, dicyclopentylmethyl, 2,2-dicyclopentylethyl, dicyclohexylmethyl, 2,2-dicyclohexylethyl.

Specific examples of the "C6-C14 aryl group" include phenyl and naphthyl, with phenyl being preferred.

Examples of the aryl group which has been substituted by a halogen atom or the like include chlorophenyl, fluorophenyl, bromophenyl, dichlorophenyl, difluorophenyl, dibromophenyl, methylphenyl, dimethylphenyl, methoxyphenyl, dimethoxyphenyl, trifluoromethylphenyl, bis(trifluoromethyl)phenyl, methylchlorophenyl, methoxychlorophenyl, methoxy(trifluoromethyl)phenyl, dichloromethylphenyl, chlorodimethylphenyl, dimethoxychlorophenyl, trifluorophenyl, trichlorophenyl, tribromophenyl, methoxyfluorochlorophenyl, methoxytrifluorophenyl, trifluoromethoxyphenyl, trimethoxyphenyl, phenylphenyl, dimethylaminophenyl, and nitrophenyl. Of these, trifluoromethylphenyl is preferred.

Examples of the "C6-C14 aryloxy group" include phenoxy.

Examples of the "C6-C14 aryloxy(lower alkyl) group" include phenoxymethyl.

Examples of the "C6-C14 arylthio(lower alkyl) group" include phenylthiomethyl.

The "C7-C16 aralkyl group" is a group formed of the above lower alkyl group and the above aryl group. Specific examples include benzyl, 1-phenylethyl, phenethyl, and naphthylmethyl.

The methylene group of the benzyl group may be substituted by a phenyl group which may have a substituent (examples of the substituent including the above lower alkyl group, halogen atoms, and the above lower alkoxy group). In addition, a group such as cyclopentane or cyclohexane may be spiro-bonded to the methylene group. The methylene group at the α- or β-position of the phenethyl group may be substituted by a phenyl group which may have a substituent (examples of the substituent including the above lower alkyl group, halogen atoms, and the above lower alkoxy group). Examples of the benzyl group which has been substituted by such a phenyl group include α-phenylbenzyl, α-methylbenzyl, α-methoxyphenylbenzyl, α-chlorophenylbenzyl, α-fluorophenylbenzyl, α-methoxyphenylbenzyl, α-methoxyphenyl-methoxybenzyl, α-methyl-α-phenylbenzyl, α-phenyl-chlorobenzyl, α-chlorophenyl-chlorobenzyl, α-cyclopropylbenzyl, α-cyclobutylbenzyl, α-cyclopentylbenzyl, α-cyclohexylbenzyl, and α-dimethylaminophenylbenzyl, with α-phenylbenzyl being preferred. Examples of the phenethyl group which has been substituted by a phenyl group include α,α-diphenylethyl, α,α-diphenylethyl, and β,β-diphenylethyl, with β,β-diphenylethyl being preferred.

Specific examples of the benzyl group derived from substitution of ring-hydrogen with a halogen atom or the like include chlorobenzyl, fluorobenzyl, bromobenzyl, dichlorobenzyl, difluorobenzyl, dibromobenzyl, methylbenzyl, dimethylbenzyl, trimethylbenzyl, methoxybenzyl, dimethoxybenzyl, trimethoxybenzyl, trifluoromethylbenzyl, and nitrobenzyl.

The "(lower alkoxy)carbonyl(lower alkyl) group" is similar to those listed above in relation to $R^1$. Ethoxycarbonylmethyl is preferred.

The "(lower alkoxy)(lower alkyl) group" is a group corresponding to the above lower alkyl group which has been substituted by the above lower alkoxy group. Examples include methoxymethyl, ethoxymethyl, n-propoxymethyl, ethoxymethyl, ethoxyethyl, and ethoxypropyl.

The "amino(lower alkyl) group" is, for example, a group corresponding to the above lower alkyl group which has been substituted by an amino group. The amino group may be substituted by the above aryl group or the above aralkyl group. Examples include phenylaminomethyl, phenylaminoethyl, benzylaminomethyl, and benzylaminoethyl.

The "C7-C16 aralkyl group which has been substituted by a C3-C7 cycloalkyl group" is a C7-C16 aralkyl group which has been substituted by the above C3-C7 cycloalkyl group. Examples include groups derived from a benzyl group whose methylene group has been substituted by a cyclopentyl group, a cyclohexyl group, a cycloheptyl group, or a similar group. Cyclopropylbenzyl, cyclobutylbenzyl, cyclopentylbenzyl, and cyclohexylbenzyl are preferred, among others.

The "halogeno(lower alkyl)carbonyl group" is a group formed of the above halogeno(lower alkyl) group and a carbonyl group. Examples include chloromethylcarbonyl, dichloromethylcarbonyl, fluoromethylcarbonyl, difluoromethylcarbonyl, chloroethylcarbonyl, 2,2-dichloroethylcarbonyl, fluoroethylcarbonyl, and 2,2-difluoroethylcarbonyl.

The "amino group which may be substituted by a phenyl group or a lower alkyl group" is a non-substituted amino group, or an amino group which has been substituted by a phenyl group or the above lower alkyl group (an amino group which has been substituted by the above lower alkyl group is referred to as "(lower alkyl)amino group"). The ring-hydrogen on phenyl may be substituted by any of the above substituents. Specific examples of the amino group which has been substituted by a phenyl group include phenylamino, N,N-diphenylamino, and tolylamino (p-methylphenylamino). Specific examples of the (lower alkyl) amino group include methylamino, dimethylamino, ethylamino, diethylamino, n-propylamino and N-cyclohexyl-N-methylamino. Specific examples of the amino group which has been substituted by the phenyl group and the (lower alkyl)amino group include N-phenyl-N-methylamino, N-cyclohexyl-N-phenylamino, N-tolyl-N-methylamino, and N-phenyl-N-ethylamino.

Other examples of the group represented by $R^2$ include fluorenyl, indanyl, 1,2,3,4-tetrahydronaphthalenyl, xanthenyl, piperidinyl, pyrrolidinyl, morpholino, tetrahydroisoquinolyl, indolyl, chromenyl, isobenzofuranyl, tetrahydropyranyl, benzothienyl, adamantyl, fluorenyl(lower alkyl), adamantyl(lower alkyl), and pyridyl(lower alkyl). The "fluorenyl(lower alkyl) group" is a group corresponding to the above lower alkyl group which has been substituted by a fluorenyl group, and examples include fluorenylmethyl. The "adamantyl(lower alkyl) group" is a group corresponding to the above lower alkyl group which has been substituted by an adamantyl group, and examples include adamantylmethyl. The "pyridyl(lower alkyl) group" is a group corresponding to the above lower alkyl group which has been substituted by a pyridyl group, and examples include pyridylmethyl. These groups may be substituted by any of the above substituents (1 to 5 atoms or groups selected from among halogen atoms, the above lower alkyl group, the above lower alkoxy group, nitro group, oxo group, the above halogeno(lower alkyl) group, the above aryl group, the above lower alkylamino group). Examples include methylindolyl and oxochromenyl.

Among these $R^2$, a C7-C16 aralkyl group, a lower alkyl group, a C6-C14 aryl group, a C3-C7 cycloalkyl group, and an amino group which may be substituted by a phenyl group or a lower alkyl group are preferred.

When $R^3$ represents a (lower alkanoyl)amino group, amino(lower alkanoyl) group, amino(lower alkanoyl)amino group, di(lower alkyl)carbamoylamino group, or aralkyloxy (lower alkyl) group, $R^4$ represents a hydrogen atom, or $R^3$ and $R^4$ together form —SOCH$_2$—, —SO$_2$CH$_2$—, —NH-COCH$_2$—, —C(=NOH)CH$_2$—, —CH(OH)CH$_2$—, or —OCH$_2$—. Preferably, $R^3$ and $R^4$ together form —SOCH$_2$—, —SO$_2$CH$_2$—, —NHCOCH$_2$—, —CH(OH)CH$_2$—, —OCH$_2$—, or —C(=NOH)CH$_2$—

As used herein, the "(lower alkanoyl)amino group" is an amino group which has been substituted by the above lower alkanoyl group. Specific examples include acetylamino, propionylamino, butyrylamino, and pivaloylamino. The "amino(lower alkanoyl) group" is a group corresponding to the above alkanoyl group which has been substituted by an amino group. Specific examples include aminoacetyl, aminopropionyl, and aminobutyryl. The "amino(lower alkanoyl)amino group" is a group corresponding to the above (lower alkanoyl)amino group which has been substituted by an amino group. Specific examples include aminoacetylamino, aminopropionylamino, aminobutyrylamino, and aminopivaloylamino. The "di(lower alkyl)carbamoylamino group" is an amino group which has been substituted by a carbamoyl group which has been substituted by two of the above lower alkyl groups. Examples include dimethylcarbamoylamino and diethylcarbamoylamino. The "aralkyloxy(lower alkyl) group" is a group corresponding to the above lower alkyl group which has been substituted by an aralkyloxy group having the above aralkyl group. Examples include benzyloxymethyl.

Examples of the lower alkyl group represented by $R^5$ include those listed above, with methyl being preferred.

$n_1$ denotes 1 or 2, with 1 being preferred. $n_2$ denotes 0 or 1, with 1 being preferred.

No particular limitation is imposed on the salt of the present invention and a salt thereof, so long as the salt is pharmaceutically acceptable. Examples of the salt include acid-addition salts such as hydrochlorides, sulfates, nitrates, hydrobromides, p-toluenesulfonates, methanesulfonates, fumarates, succinates, and lactates. Of these, hydrochlorides are preferred. The compound of the present invention and a salt thereof also encompass solvates thereof. The compound of the present invention includes optically active species attributable to an asymmetric carbon atom or other structural features. These optically active species and mixtures thereof also fall within the scope of the present invention.

The compound of the present invention or a salt thereof may be produced via an intermediate, for example, a 2-methylaminopentenol derivative (11). Specifically, compound (11) can be produced through the following scheme:

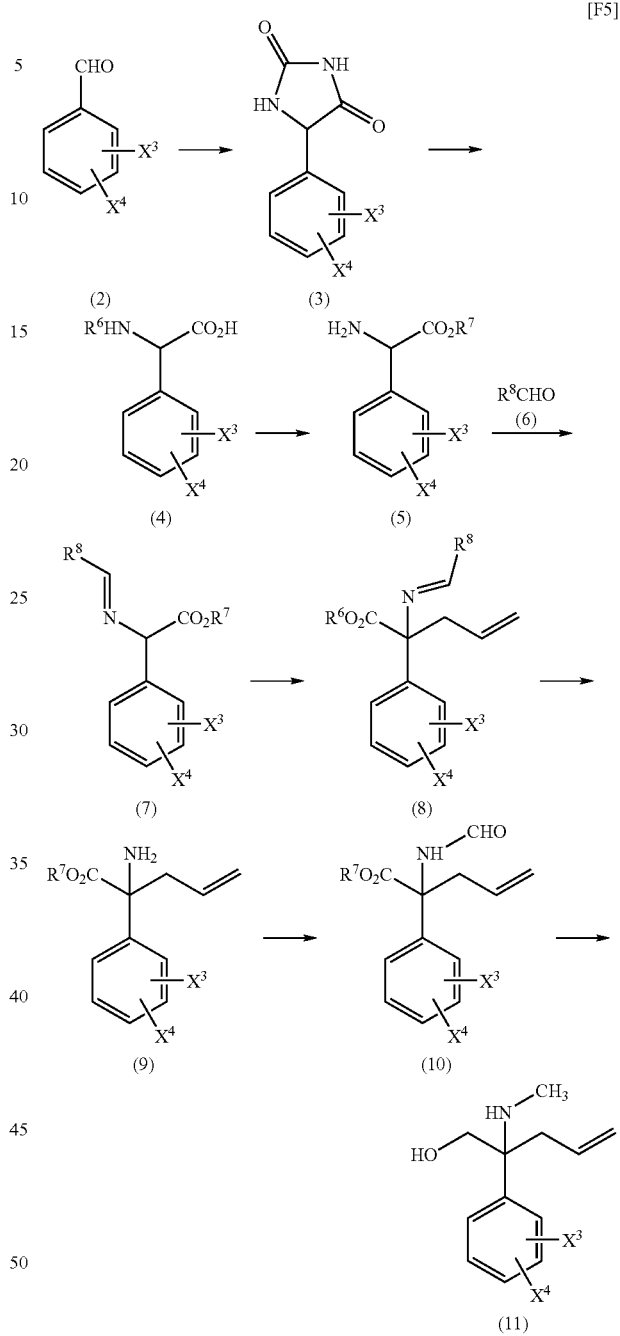

[wherein $X^3$ and $X^4$ have the same meanings as defined above; $R^6$ represents a protective group for an amino group; $R^7$ represents the aforementioned lower alkyl group; and $R^8$ represents a tert-butyl group or a phenyl group].

Specifically, commercial benzaldehyde (2) is dissolved in a solvent such as ethanol-water in the presence of ammonium carbonate, followed by reacting with potassium cyanate, to thereby form compound (3). The imidazolidine ring of the compound (3) is opened with a base, and amino groups are protected with an appropriate protective group, to thereby form compound (4). Examples of the base employed for opening the imidazolidine ring include sodium hydroxide, potassium hydroxide, and barium hydroxide. Among them, sodium hydroxide is preferred. Examples of the protective group include a benzyloxycarbonyl group (Z group), a trifluoroacetyl group, and a tert-butoxycarbonyl group (Boc group). Of these, a Boc group is preferred. Alternatively, benzaldehyde (2) can be produced through a known production method.

Subsequently, compound (4) is reacted with an acid source (i.e., reagent generating acid in the reaction system) in a solvent such as alcohol, whereby deprotection of amino groups and esterification can be performed. The thus-formed ester compound (5) is reacted with aldehyde (6) in the presence of a base in a solvent such as acetonitrile, to thereby form compound (7). Examples of the acid source employed in esterification include thionyl chloride, hydrochloric acid, sulfuric acid, nitric acid, hydrofluoric acid, hydrobromic acid, hydroiodic acid, p-toluenesulfonic acid, methanesulfonic acid, trifluoroacetic acid, trichloroacetic acid, acetic acid, and formic acid. Of these thionyl chloride is preferred. The aldehyde (6) is preferably benzaldehyde.

Compound (8) can be produced by dissolving compound (7) in an estric solvent such as ethyl acetate, in a halogen-containing solvent such as chloromethylene (preferably ethyl acetate) and treating the solution with allyl bromide in the presence of a base and a phase transfer catalyst. Examples of the base include potassium carbonate, sodium carbonate, sodium hydroxide, potassium hydroxide, potassium tert-butoxide. Examples of the phase transfer catalyst include n-tetrabutylammonium bromide, n-tetrabutylammonium chloride, and n-tetrabutylammonium sulfate.

The compound (8) is treated with acid to form compound (9), and subsequently, formic acid and acetic anhydride are reacted with compound (9), to thereby produce compound (10). The compound (10) is reduced, to thereby form an intermediate (11) for producing the compound of the present invention. Examples of the acid employed in treating of compound (8) include hydrochloric acid, sulfiruc acid, nitric acid, hydrofluoric acid, hydrobromic acid, and hydroiodic acid. Of these hydrochloric acid is preferred. Preferably, the compound (10) is reduced by use of a reducing agent such as aluminum lithium hydride, sodium borohydride, boroacetic acid (in situ preparation from sodium borohydride and acetic acid), diisobutylaluinum hydride, or sodium bis(2-methoxyethoxy)aluminum hydride (Red-Al).

Compound (11), which is a mixture of diastereomers, can be derived to an optically active species through routine optical resolution. For example, compound (11) is reacted with (+)-di-p-toluoyl-D-tartaric acid (hereinafter referred to as "(+)-DTTA"), to thereby form a diastereomer salt mixture containing a racemic mixture of compound (11) and an optical resolution agent. Subsequently, a diastereomer salt of interest is separated through precipitation or a similar technique, followed by optional recrystallization, and the thus-separated diastereomer salt is treated with alkali. The diesteromer salt not treated with alkali may also be used. Preferably, an optical active species of compound (11) is employed as an intermediate in production of the compound of the present invention.

The compound of the present invention or a salt thereof may be produced through the following scheme:

[F6]

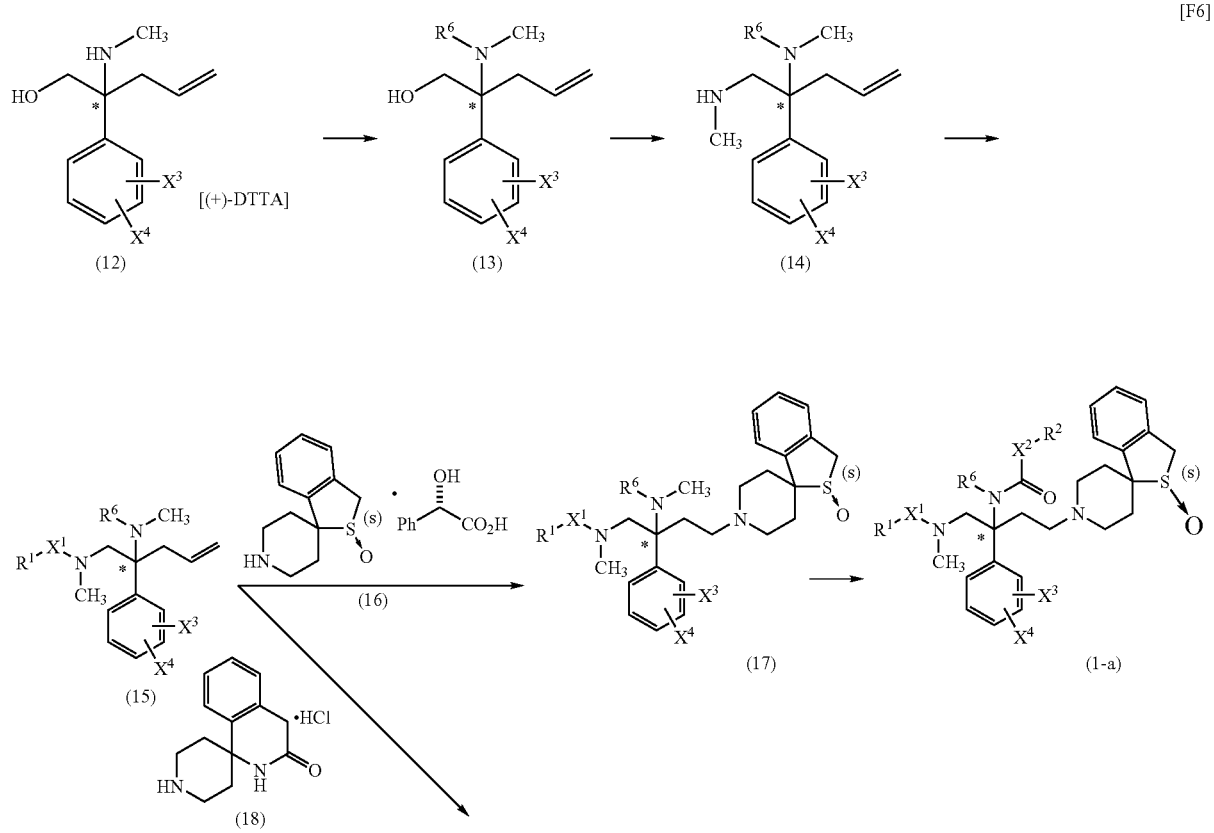

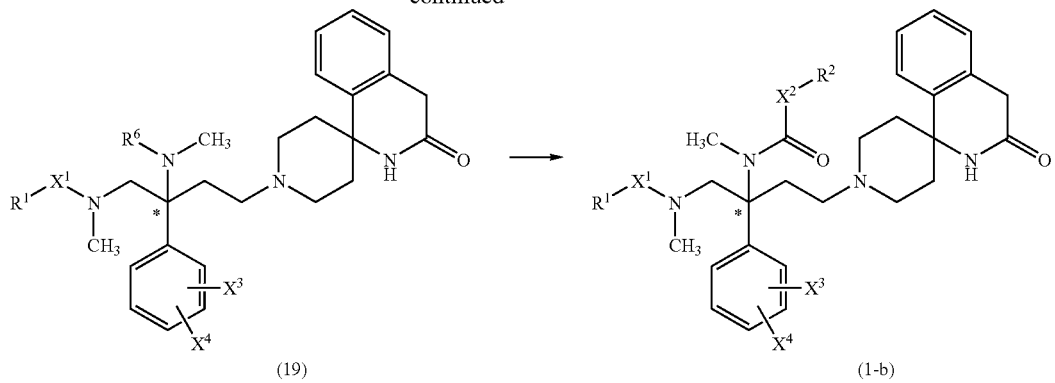

(19) → (1-b)

[wherein $R^1$, $R^2$, $R^6$, $X^1$, $X^3$ and $X^4$ have the same meanings as defined above].

The amino group of the optical active species (12) of compound (11), produced through the above method, is protected in a routine manner, to thereby form compound (13). The compound (13) is sequentially oxidized and methylaminated, to thereby produce compound (14). The oxidation may be performed by dissolving copound (13) in a solvent such as dimethyl sulfoxide, and treating the solution with sulfur trioxide-pyridine in the presence of a base such as triethylamine, or treating the solution with tetrapropylammonium perruthenate in the presence of N-methylmorpholine-N-oxide. Methylamination may be performed by dissolving aldehyde of compound (13) in a solvent such as methanol, adding methylamine to the solution, refluxing the mixture to thereby form an imine (Schiff base), and refluxing the imine with a reducing agent such as sodium borocyanohydride or sodium borohydride.

In order to produce compound (15) by introducing $R^1$ group in formula (1) into the amino group of compound (14), the compiund (14) is dissolved in a solvent such as acetonitrile, and acid chloride ($R^1$—Cl) is reacted with the solution in the presence of a base such as triethylamine. When acid chlorides, trifluoropropionyl chloride, pivaloyl chloride, and propionyl chloride, are used, compounds Nos. 1, 2, and 5, respectively, described later in the Examples can be produced. The acid chloride may be prepared from the corresponding carboxylic acid in a routine manner. In this case, reaction is preferably performed under cooling with ice. Alternatively, instead of acid chloride, anhydride of trifluoroacetic acid, chlorodifluoroacetic acid, etc. may also be employed for introducing $R^1$ group, whereby compounds Nos. 3 and 4 described later in the Examples can be produced.

Subsequently, the vinyl group of compound (15) is treated with osmium tetraoxide, to thereby form a diol species, which is oxidized by sodium periodate, to thereby form an aldehyde. The aldehyde is reacted with separately prepared spiro[benzo(c)thiophene-1(3H),4'-piperidine]-(2S)-oxide/(S)-(+)-mandelate (16), to thereby form the corresponding imine. This imine is reduced, to thereby produce compound (17). Examples of the reducing agent include sodium cyanoborohydride.

When the aldehyde obtained from compound (15) is reacted with spiro[isoquinoline-1(2H),4'-piperidine]-3(4H) monohydrochloride (18) instead of compound (16), followed by reacting a reducing agent, compound (19) can be produced.

Through reaction with the corresponding piperidine species, the invention compounds in which $R^3$ and $R^4$ together form —$SO_2CH_2$— or —$CH(OH)CH_2$— can be produced in a similar manner as described above.

Conversion of compound (17) to the compound of the present invention (1-a) may be carried out by deprotecting the amino group of compound (17) with trifluoroacetic acid or a similar reagent and reacting the deprotected species with an acid chloride ($R^2$—$X^2$—COCl) in a solvent such as acetonitrile in the presence of a base. For example, when 3,3-diphenylpropionyl chloride is used as an acid chloride, hydrochloride of compound No. 1 described later in the Examples can be produced. In this case, reaction is preferably performed under cooling with ice.

Conversion of compound (19) to the compound of the present invention (1-b) may be carried out by deprotecting compound (17) in a manner that employed in conversion to compound (1-a), and reacting the deprotected species with an isocyanate ($R^2$—NCO) in an inert solvent such as tetrahydrofuran. For example, when diphenylmethyl isosyanate is used as an isocyanate, hydrochlorides of compounds Nos. 3 and 4 described later in the Examples can be produced.

Compounds according to the present invention in which $X^2$ is —NHCO— or —OCO— can be produced in a similar manner as described above.

The compound of the present invention and a salt thereof exhibited excellent antagonistic activity against NK-1 receptor and/or NK-2 receptor as mentioned in the test Examples described later. Particularly, the following compounds and salts falling within the scope of the present invention exhibited remarkably excellent NK-2 receptor antagonistic activity, and antagonistic activity against NK-1 and NK-2 receptors.

(I) Compounds and Salts Exhibiting NK-2 Receptor Antagonistic Activity;

(1-1) Compounds and salts in which $X^2$ is a single bond.

(1-2) The above compounds and salts (1-1) in which $R^3$ and $R^4$ together form —$NHCOCH_3$— are more preferred.

(1-3) The above compounds and salts (1-2) in which $R^2$ represents a C6-C14 aryl group or a C7-C16 aralkyl group are particularly preferred. A ring hydrogen atom of these groups may be substituted by 1 to 5 atoms and groups selected from among a halogen atom, a lower alkyl group, a lower alkoxy group, a nitro group, an oxo group, a halogeno(lower alkyl) group, a C6-C14 aryl group, and a lower alkylamino group. Examples of the aryl group and aralkyl group include phenyl and trifluoromethylphenyl.

(II) Compounds and Salts Exhibiting NK-1 and NK-2 Receptors Antagonistic Activity;

(2-1) Compounds and salts in which $R^2$ represents a C6-C14 aryl group, or an amino group which may be substituted with a phenyl group. A ring hydrogen atom of these groups may be substituted by 1 to 5 atoms or groups selected from among a halogen atom, a lower alkyl group, a lower alkoxy group, a nitro group, an oxo group, a halogeno(lower alkyl) group, a C6-C14 aryl group, and a lower alkylamino group. Examples of the aryl group and amino group include α-phenylbenzyl, α-chlorophenylbenzyl, α-dimethylaminophenylbenzyl, α,α-diphenylethyl, β,β-diphenylethyl, and N,N-diphenylamino.

(2-2) The above compounds and salts (2-1) in which $X^1$ represents NH or a single bond are more preferred.

(2-3) The above compounds and salts (2-2) in which $R^3$ represents —$SOCH_2$— or —$NHCOCH_2$— are further more preferred.

(2-4) The above compounds and salts (2-3) in which $R^1$ represents a lower alkanoyl group which may be substituted by 1 to 5 halogen atoms are particularly preferred.

Accordingly, the compound of the present invention or a salt thereof is an effective ingredient as a drug, particularly as a drug for preventing and/or treating diseases related to tachykinin.

Examples of the diseases related to tachykinin include those related to the central nervous system, including anxiety, depression, psycopathy, and shizophrenia; nerve degeneration diseases including AIDS-associated dementia, senile dementia of Alzheimer type, Alzheimer's disease, Down's syndrome, demyelinating disease, amyotrophic lateral sclerosis, neuropathy, peripheral neuropathy, and neuralgia; respiratory diseases including chronic obstructive pulmonary disease, bronchitis, pneumonia, bronchoconstriction, asthma, cough; inflammatory diseases including Inflammatory Bowel Diesease (IBD), psoriasis, fibrositis, osteoarthritis, degenerative arthritis, and articular rheumatism; eczema; and allergic diseases including rhinitis; irritable diseases including those caused by vine plants; irritable bowel syndrome (IBS); ophthalmological diseases including conjunctivitis, vernal conjunctivitis, spring catarrh, destruction of the blood-aqueous humor barrier associated with various inflammatory ophthalmological diseases, elevation of inside pressure of the ocular chamber, miosis; skin diseases including contact dermatitis, atopic dermatitis, hives, and other skin diseases including eczema-like dermatitis; addictions including alcohol dependence; physically expressed pathological condition caused by stress; reflex sympathetic dystrophy including shoulder-hand syndrome; dysthymia; immunoenhancement- or immunosuppression-related diseases including undesired immunoreactions (such as rejection of grafts) and systemic lupus erythematosus; digestive diseases including diseases caused by abnormality of the nerve controlling the internal organs, colitis, ulcerative colitis, Crohn's disease; emesises induced by X-ray irradiation, chemotherapeutic agents, poisons, toxins, pregnancy, vestibular disorder, postoperative disease, gastrointestinal obstruction, reduction of gastrointestinal motility, visceral pain, migraine, increase in intracranial pressure, decrease in intracranial pressure, and an emesis as a side effect caused by administration of various drugs; bladder function disorders including cystitis and urinary incontinence; collagen disease, scleroderma, and eosinophilia caused by fascila hepatica; diseases caused by anomalous blood flow by vasodilatation or vasoconstriction, including angina, migraine, and Raynaud's disease; pains involving the pain-nociceptor, including migraine, headache, and toothache.

The compound of the present invention or a salt thereof may be administered perorally or parenterally. Examples of the peroral form include tablets, capsules, granules, powder, and syrup. Examples of the parenteral form include injections and suppositories.

Such drug preparations may be produced through any suitable known method by use of a variety of additives: excipients (e.g., sugar derivatives such as lactose, sucrose, glucose, mannite, and sorbit; starch derivatives such as corn starch, potato starch, α-starch, dextrin, and carboxymethylstarch; cellulose derivatives such as crystalline cellulose, low-substituted hydroxypropylcellulose, hydroxypropylmethylcellulose, carboxymethylcellulose, carboxymethylcellulose calcium, and internal-cross-linked carboxymethylcellulose sodium; organic excipients such as acacia, dextran, and pullulan; silicate derivatives such as light anhydrous silicic acid, synthetic aluminum silicate, and magnesium metasilicate aluminate; and inorganic excipients such as phosphates (e.g, calcium phosphate), carbonates (e.g., calcium carbonate), and sulfates (e.g., calcium sulfate)); lubricants (e.g., metal stearates such as stearic acid, calcium stearate, and magnesium stearate; talc; colloidal silica; waxes such as veegum and spermaceti; boric acid; adipic acid; sulfates such as sodium sulfate; glycol; fumaric acid; sodium benzoate; DL-leucine; fatty acid sodium salts; lauryl sulfates such as sodium lauryl sulfate and magnesium lauryl sulfate; silicates such as silicic acid anhydrate and silicic acid hydrate; and the aforementioned starch derivatives); binders (e.g., poly(vinylpyrrolidone), macrogol, and the same compounds as mentioned in relation to above excipients); disintegrants (e.g., the same compounds as mentioned in relation to the above excipients and chemically modified starch/cellulose species such as sodium croscarmellose, sodium carboxymethylstarch, and cross-linked poly(vinylpyrrolidone)), stabilizers (e.g., paraoxybenzoates such as methylparaben and propylparaben; alcohols such as chlorobutanol, benzyl alcohol, and phenylethyl alcohol; benzalkonium chloride; phenols such as phenol and cresol; thimerosal; dehydroacetic acid; and sorbic acid); sweetening and flavoring agents (e.g., generally employed sweeteners, sour agents, flavors), and diluents.

When the compound of the present invention or a salt thereof is employed as a drug, the dose to humans varies in accordance with the condition, age, sex, administration method, and other factors of patients. For example, in peroral administration, preferably 0.01 to 100 mg/kg-body weight, more preferably 0.1 to 50 mg/kg-body weight, is administered at a time, and in intravenous dimministration, preferably 0.01 to 100 mg/kg-body weight, more preferably 0.05 to 50 mg/kg-body weight, is administered at a time. The drug is preferably administered once to several times per day, depending on the condition.

EXAMPLES

The present invention will next be described in more detail by way of Examples, which should not be construed as limiting the invention thereto. In the following Examples, all the optically active species were derived through resolution by use of (+)-DTTA.

Example 1(a)

Synthesis of 5-(3,4-dichlorophenyl)-imidazolidine-2,4-dione

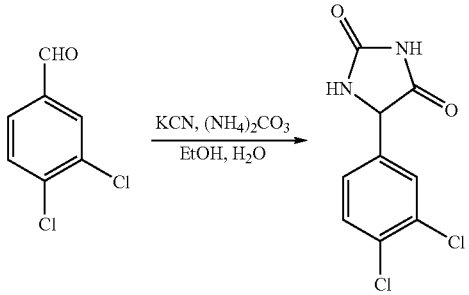

[F7]

3,4-Dichlorobenzaldehyde (500 g), potassium cyanide (279 g), and ammonium carbonate (824 g) were dissolved in a solvent mixture of ethanol (1.25 L) and water (1.25 L), followed by stirring at an internal temperature of 60 to 65° C. for 1 hour. The reaction mixture was left to cool to room temperature, and ethanol was evaporated under reduced pressure. Water was added to the residue, followed by filtration and drying, to thereby give the title compound (900 g). The title compound was used in the next step without further purification.

mp. 223.0-225.0° C.
MS (EI) m/z 244 (M+)
$^1$H-NMR (270 MHz, DMSO-$d_6$)δ ppm: 5.26 (1H, s), 7.35 (1H, dd, J=2.0, 8.5 Hz), 7.60 (1H, d, J=2.0 Hz), 7.69 (1H, d, J=8.0 Hz), 8.46 (1H, s), 10.90 (1H, br).

Example 1(b)

Synthesis of tert-butoxycarbonylamino-(3,4-dichlorophenyl)-acetic acid

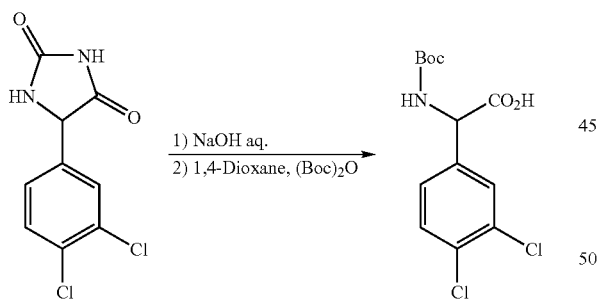

[F8]

5-(3,4-Dichlorophenyl)-imidazolidine-2,4-dione (900 g) was dissolved in 25% aqueous sodium hydroxide solution (3.66 L), followed by refluxing for 3 hours. The resultant mixture was cooled with ice to an internal temperature of 20° C. or lower. 1,4-Dioxane (1.83 L) and di-tert-butoxydicarbonate (936 g) were added to the mixture, and the mixture was stired at an internal temperature of 15 to 25° C. for one hour. Concentrated hydrochloric acid (2.4 L) and 1N aqueous potassium hydrogensulfate (1.7 L) were sequentially added to the mixture to adjust the pH to 4. The insoluble matter was passed through Celite, followed by washing with ethyl acetate. The filtrate was subjected to partitioning and then extraction with ethyl acetate. The organic layer was washed with saturated brine (1 L), dried over sodium sulfate anhydrate, and concentrated under reduced pressure, to thereby give the title compound (900 g). The title compound was used in the next step without further purification.

MS (EI) m/z 319 (M+)
$^1$H-NMR (270 MHz, DMSO-$d_6$, 60° C.)δ ppm: 1.37 (9H, s), 5.05 (1H, d, J=7.5 Hz), 7.19-7.51 (1H, br), 7.37 (1H, dd, J=2.0, 8.5 Hz), 7.56 (1H, d, J=8.5 Hz), 7.62 (1H, d, J=2.0 Hz).

Example 1(c)

Synthesis of ethyl amino-(3,4-dichlorophenyl)-acetate hydrochloride

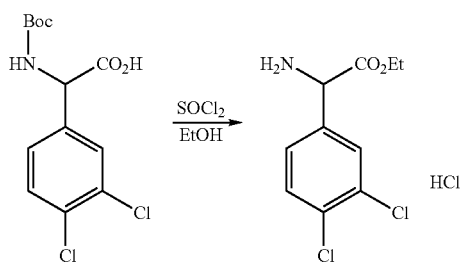

[F9]

tert-Butoxycarbonylamino-(3,4-dichlorophenyl)-acetic acid (900 g) was dissolved in ethanol (4.5 L). Thionyl chloride (417 mL) was added to the resultant solution, followed by refluxing for one hour. The reaction mixture was left to cool to room temperature. The solvent was evaporated under reduced pressure. Ethyl acetate was added to the residue, followed by filtration and drying, to thereby give the title compound (286 g, 35%, 3 steps).

mp. 171.0-174.0° C.
MS (EI) m/z 247 (M+)
$^1$H-NMR (270 MHz, DMSO-$d_6$)δ ppm: 1.15 (3H, t, J=7.0 Hz), 4.10-4.30 (2H, m), 5.37 (1H, s), 7.55 (1H, dd, J=2.0, 8.5 Hz), 7.75 (1H, d, J=8.5 Hz), 7.91 (1H, s), 9.35 (3H, br).

Example 1(d)

Synthesis of ethyl(benzylidene-amino)-(3,4-dichlorophenyl)acetate

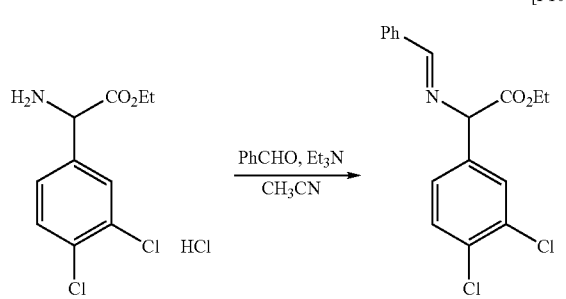

[F10]

Triethylamine (170 mL) and benzaldehyde (130 mL) were added to a suspension of ethyl amino-(3,4-dichlorophenyl)-acetate hydrochloride (350 g) in acetonitrile (1.5 L), followed by stirring at room temperature overnight. The insoluble matter was removed through Celite, followed by washing with ethyl acetate. The filtrate was subjected to partitioning with water and then extraction with ethyl acetate. The thus-obtained organic layer was washed with saturated brine, and then dried over sodium sulfate anhydrate. The solvent was removed under reduced pressure, to thereby give the title compound (425 g). The title compound was used in the next step without further purification.

MS (EI) m/z 335 (M$^+$)

$^1$H-NMR (270 MHz, CDCl$_3$)δ ppm: 1.24 (3H, t, J=7.0 Hz), 4.20 (2H, q, J=7.0 Hz), 5.10 (1H, s), 7.36-7.60 (5H, m), 7.66 (1H, s), 7.81-7.97 (2H, m), 8.36 (1H, s).

Example 1(e1)

Synthesis of ethyl 2-(benzylidene-amino)-2-(3,4-dichlorophenyl)-4-pentenoate

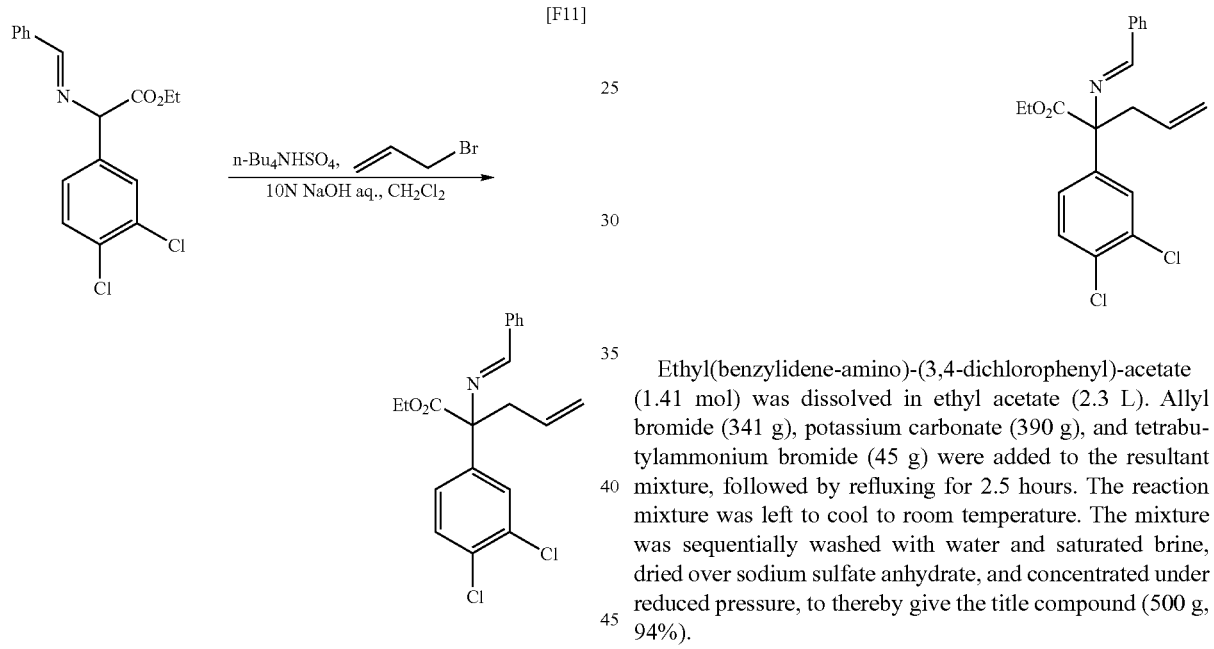

[F11]

Ethyl(benzylidene-amino)-(3,4-dichlorophenyl)acetate (425 g) was dissolved in methylene chloride (1.8 L). 10N Aqueous sodium hydroxide (1.2 L), allyl bromide (158 mL), and tetrabutylammonium sulfate (41 g) were added to the resultant solution, followed by stirring at room temperature for one hour. The reaction mixture was subjected to partitioning. Water (1 L) was added to the aqueous layer, and then the mixture was extracted with methylene chloride. The thus-obtained organic layer was washed with saturated brine, dried over sodium sulfate anhydrate, and concentrated under reduced pressure, to thereby give the title compound (518 g). The title compound was used in the next step without further purification.

MS (EI) m/z 375 (M$^+$)

$^1$H-NMR (270 MHz, CDCl$_3$)δ ppm: 1.20 (3H, t, J=7.0 Hz), 2.90 (1H, dd, J=7.0, 14 Hz), 3.05 (1H, dd, J=7.0, 14 Hz), 4.21 (2H, q, J=7.0 Hz), 4.92-5.10 (2H, m), 5.61-5.81 (1H, m), 7.30-7.60 (5H, m), 7.72 (1H, s), 7.80-7.93 (2H, m), 8.22 (1H, s).

Example 1(e2)

Synthesis of ethyl 2-(benzylidene-amino)-2-(3,4-dichlorophenyl)-4-pentenoate (Alternative Method)

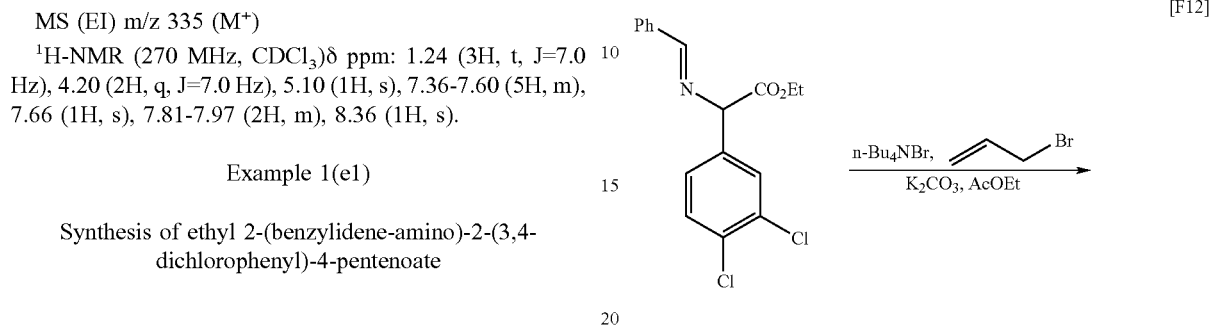

[F12]

Ethyl(benzylidene-amino)-(3,4-dichlorophenyl)-acetate (1.41 mol) was dissolved in ethyl acetate (2.3 L). Allyl bromide (341 g), potassium carbonate (390 g), and tetrabutylammonium bromide (45 g) were added to the resultant mixture, followed by refluxing for 2.5 hours. The reaction mixture was left to cool to room temperature. The mixture was sequentially washed with water and saturated brine, dried over sodium sulfate anhydrate, and concentrated under reduced pressure, to thereby give the title compound (500 g, 94%).

Example 1(f)

Synthesis of ethyl 2-amino-2-(3,4-dichlorophenyl)-4-pentenoate

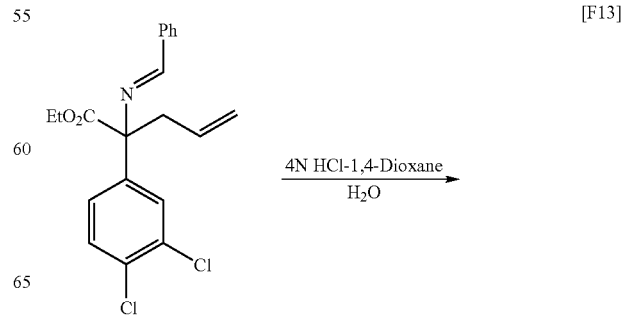

[F13]

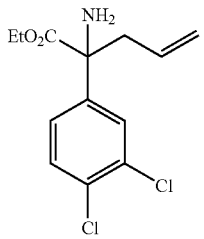

4N HCl-1,4-dioxane (308 mL) and water (65 mL) were added to ethyl 2-(benzylidene-amino)-2-(3,4-dichlorophenyl)-4-pentenoate (518 g), followed by stirring at room temperature for 3 hours. The reaction mixture was concentrated under reduced pressure. Water (1 L) and 1N aqueous hydrochloric acid (500 mL) were added to the residue, and the mixture was washed with diisopropyl ether (500 mL) three times. 25% Aqueous sodium hydroxide (250 mL) was added to the aqueous layer to adjust the pH to 9. The resultant mixture was extracted with ethyl acetate. The organic layer was washed with saturated brine and dried over sodium sulfate anhydrate. The solvent was removed under reduced pressure, to thereby give the title compound (231 g). The title compound was used in the next step without further purification.

MS (EI) m/z 287 (M+)

$^1$H-NMR (270 MHz, CDCl$_3$)δ ppm: 1.26 (3H, t, J=7.0 Hz), 1.75-2.05 (2H, br), 2.59 (1H, dd, J=8.0, 14.0 Hz), 2.94 (1H, dd, J=6.5, 14.0 Hz), 4.19 (2H, q, J=7.0 Hz), 5.16 (1H, s), 5.21 (1H, d, J=4.0 Hz), 5.58-5.80 (1H, m), 7.41 (2H, s), 7.72 (1H, s).

Example 1(g)

Synthesis of ethyl 2-(3,4-dichlorophenyl)-2-formylamino-4-pentenoate

[F14]
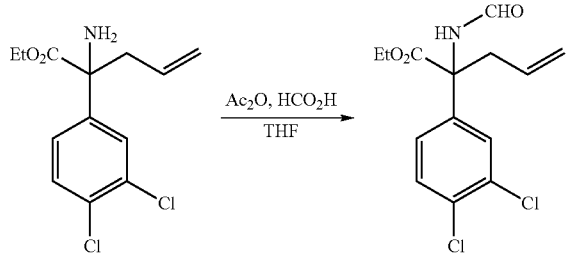

Under cooling on ice, formic acid (140 mL) was added to acetic anhydride (255 mL), followed by stirring at 50° C. for 30 minutes. The reaction mixture was cooled with ice. Subsequently, ethyl 2-amino-2-(3,4-dichlorophenyl)-4-pentenoate (298 g) in tetrahydrofuran (1.5 L) was added to the mixture, and the mixture was stirred at room temperature for 30 minutes. The reaction mixture was concentrated under reduced pressure. The residue was neutralized with saturated aqueous sodium bicarbonate. The resultant mixture was subjected to extraction with ethyl acetate. The organic layer was washed with saturated brine and dried over sodium sulfate anhydrate. The solvent was removed under reduced pressure, to thereby give the title compound (334 g). The title compound was used in the next step without further purification.

MS (EI) m/z 315 (M+)

$^1$H-NMR (270 MHz, CDCl$_3$)δ ppm: 1.20 (3H, t, J=7.0 Hz), 3.15 (1H, dd, J=7.5, 13.5 Hz), 3.60 (1H, dd, J=7.0, 13.5 Hz), 4.06-4.31 (2H, m), 5.13-5.32 (2H, m), 5.54-5.72 (1H, m), 7.09 (1H, s), 7.28 (1H, dd, J=2.5, 8.5 Hz), 7.42 (1H, d, J=8.5 Hz), 7.53 (1H, d, J=2.5 Hz), 8.20 (1H, s).

Example 1(h)

Synthesis of 2-(3,4-dichlorophenyl)-2-methylamino-4-pentenol hydrochloride

[F15]
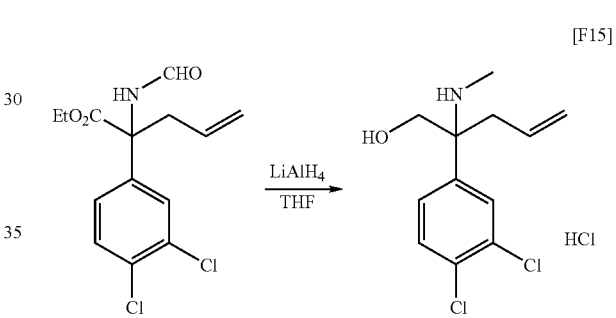

Under argon flow, lithium aluminum hydride (78 g) was suspended in dehydrated tetrahydrofuran (1 L). Ethyl 2-(3,4-dichlorophenyl)-2-formylamino-4-pentenoate (334 g) in dehydrated tetrahydrofuran (1 L) was added to the suspension at room temperature, followed by refluxing for 15 minutes. After the mixture was cooled with ice, water (78 mL), 15% aqueous sodium hydroxide (78 mL), and then water (234 mL) were added to the mixture, and the resultant mixture was stirred at room temperature for one hour. The insoluble matter was passed through Celite, followed by washing with ethyl acetate. The filtrate was dried over magnesium sulfate anhydrate and concentrated under reduced pressure until the volume of the solution was decreased to 1 L. 4N HCl-1,4-dioxane (260 mL) was added to the residue, and the mixture was concentrated under reduced pressure. Ethyl acetate was added to the residue, followed by filtration and drying, to thereby give the title compound (260 g, 69%, 5 steps).

mp. 225.5-232.5° C.

MS (EI) m/z 259 (M+)

$^1$H-NMR (270 MHz, DMSO-d$_6$)δ ppm: 2.38 (3H, s), 2.83 (2H, d, J=7.0 Hz), 3.94 (1H, d, J=12.0 Hz), 4.00 (1H, d, J=12.0 Hz), 5.00-5.20 (2H, m), 5.35-5.57 (1H, m), 5.98 (1H, br), 7.63 (1H, dd, J=1.5, 8.5 Hz), 7.71 (1H, d, J=8.5 Hz), 7.94(1H, d, J=1.5 Hz), 9.31 (1H, br), 9.62 (1H, br).

Example 1(i)

Optical Resolution of 2-(3,4-dichlorophenyl)-2-methylamino-4-pentenol (Synthesis of (+)-di-p-toluoyl-D-tartrate)

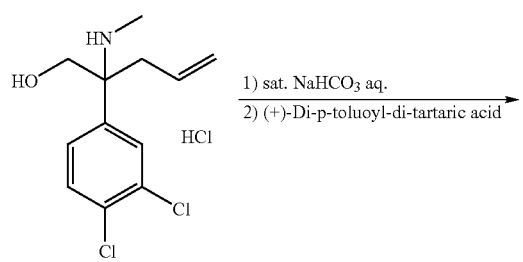

[F16]

Ethyl acetate (2 L) and saturated aqueous sodium bicarbonate (2 L) were added to 2-(3,4-dichlorophenyl)-2-methylamino-4-pentenol hydrochloride (260 g). The mixture was stirred until the solid was completely dissolved, and the solution was subjected to partitioning. Ethyl acetate layer was washed with saturated brine, dried over sodium sulfate anhydrate, and concentrated under reduced pressure until the volume of the mixture was reduced to 1 L. (+)-Di-p-toluoyl-D-tartaric acid (283 g) was added and dissolved in the residue under heat, followed by stirring at room temperature overnight. The crystals that precipitated was collected through filtration with suction and dried, to thereby give crude crystals (296 g). The crude crystals were recrystallized from ethyl acetate (1.5 L), to thereby give crystals (238 g). The crystals were recrystallized from ethyl acetate (6 L), to thereby give the title compound (194 g, 34%, 99.7% ee).

mp. 74.0-74.5° C.

MS (FAB) m/z 646 (M$^+$H)

$^1$H-NMR (270 MHz, DMSO-d$_6$)δ ppm: 2.26 (3H, s), 2.36 (6H, s), 2.66 (2H, d, J=7.0 Hz), 3.79 (1H, d, J=12.0 Hz), 3.84 (1H, d, J=12.0 Hz), 4.97-5.12 (2H, m), 5.35-5.57 (1H, m), 5.67 (2H, s), 7.31 (4H, d, J=8.0 Hz), 7.45 (1H, dd, J=2.0, 8.5 Hz), 7.63 (1H, d, J=8.5 Hz), 7.72 (1H, d, J=2.0 Hz), 7.84 (4H, d, J=8.0 Hz).

$[α]_D^{27}$=+87.7° (c=0.508, MeOH)

Example 1(j)

Optical Resolution of 2-(3,4-dichlorophenyl)-2-methylamino-4-pentenol (Synthesis of (−)-di-p-toluoyl-L-tartrate)

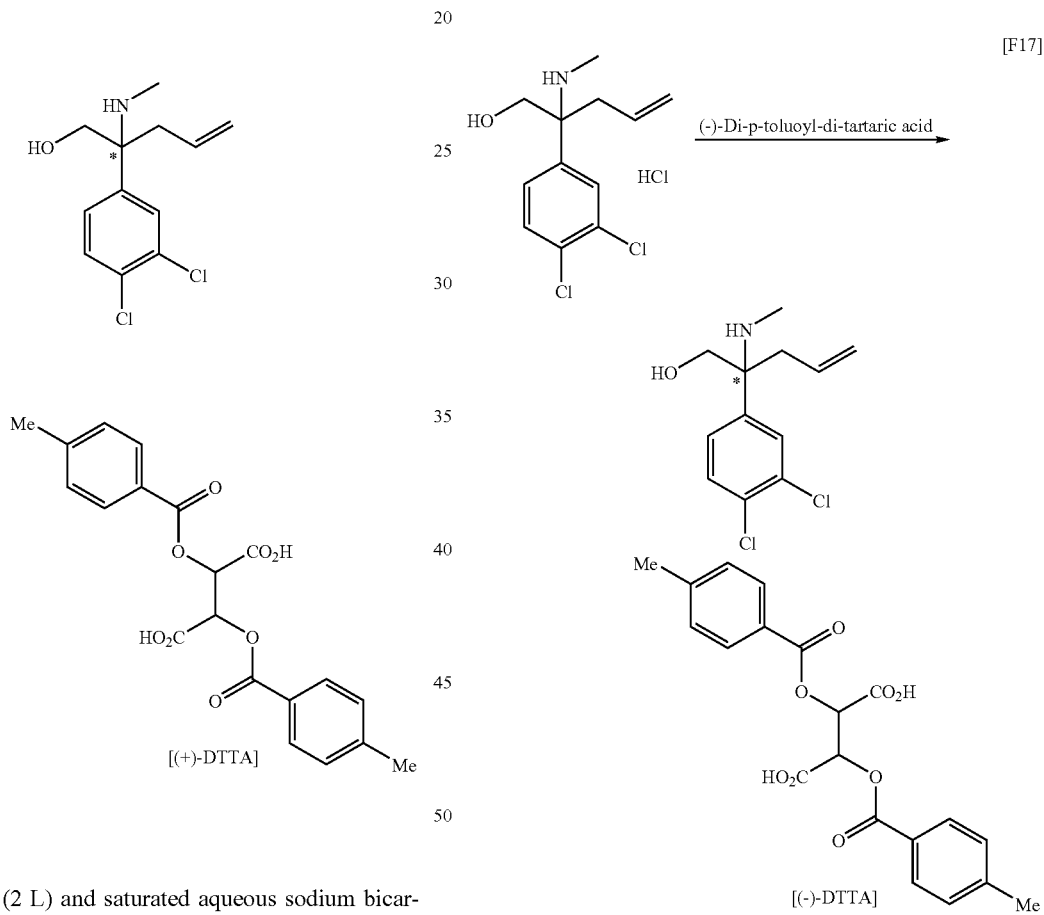

[F17]

2-(3,4-Dichlorophenyl)-2-methylamino-4-pentenol (10 g) was dissolved in ethyl acetate (25 mL), and (−)-di-p-toluoyl-L-tartaric acid (14.8 g) was added to and dissolved in the solution with heat, followed by stirring overnight at room temperature. The crystals that precipitated was collected through filtration with suction and dried, to thereby give crude crystals (11.7 g). The crude crystals were recrystallized from ethyl acetate (200 mL), to thereby give the title compound (8.3 g, 33%, 94.8% ee).

mp. 78.0-78.5° C.

$^1$H-NMR: coincide with (+)-form $[α]D^{27}$=−90.9° (c=0.507, MeOH)

Example 2

Synthesis of tert-butyl[1-(3,4-dichlorophenyl)-1-hydroxymethyl-3-butenyl]methylcarbamate

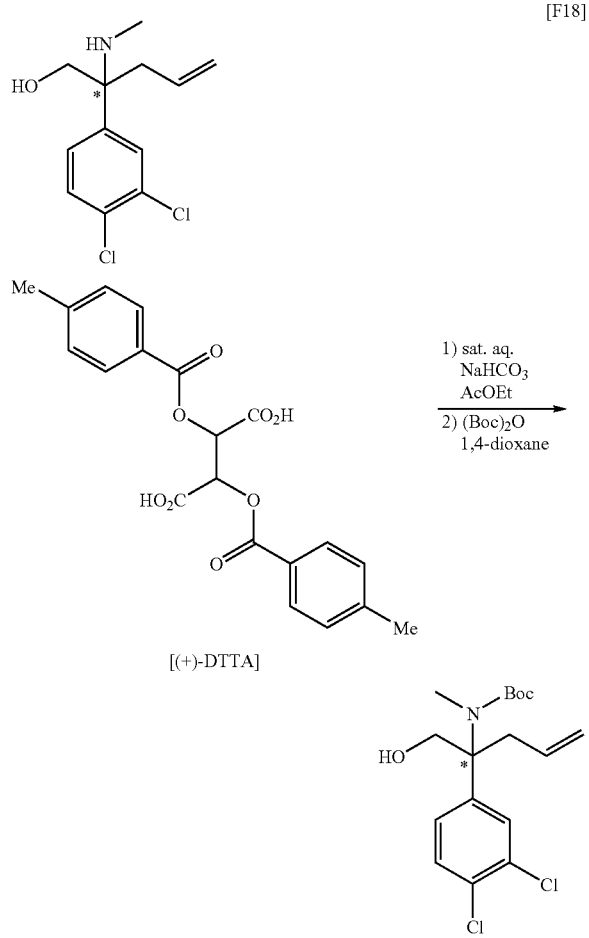

Ethyl acetate (500 mL) and saturated aqueous sodium bicarbonate (650 mL) were added to 2-(3,4-dichlorophenyl)-2-methylamino-4-pentenol (+)-di-p-toluoyl-D-tartrate (84.8 g). The insoluble matter was passed through Celite, followed by washing with ethyl acetate. The filtrate was partitioned. The ethyl acetate layer was washed with saturated brine, dried over sodium sulfate anhydrate, and concentrated under reduced pressure. The residue was dissolved in 1,4-dioxane (250 mL). Di-tert-butoxydicarbonate (30.5 g) was added to the resultant solution, followed by stirring at 100° C. overnight. The reaction mixture was concentrated under reduced pressure and the residue was purified through silica gel column chromatography (n-hexan:ethyl acetate=8:1 to 3:1), to thereby give the title compound (45.3 g, 99%).

MS (EI) m/z 359 (M+)

$^1$H-NMR (270 MHz, CDCl$_3$)δ ppm: 1.38 (9H, s), 2.75 (3H, s), 2.70-2.98 (2H, m), 3.68-3.82 (1H, m), 4.02-4.18 (1H, m), 5.10-5.25 (2H, m), 5.75-5.97 (1H, m), 7.12 (1H, dd, J=2.5, 8.5 Hz), 7.36 (1H, d, J=2.5 Hz), 7.41 (1H, d, J=8.5 Hz).

Example 3

Synthesis of tert-butyl[1-(3,4-dichlorophenyl)-1-formyl-3-butenyl]methylcarbamate

[F19]

tert-Butyl[1-(3,4-dichlorophenyl)-1-hydroxymethyl-3-butenyl]methylcarbamate (45 g) was dissolved in anhydrous dimethyl sulfoxide (320 mL), and triethylamine (87 mL) was added thereto. Under cooling with ice, sulfur trioxide-pyridine (31.7 g) was added, and the resultant mixture was stirred for 1 hour at room temperature. Ice-water (650 mL) was added to the reaction mixture, followed by extraction with ethyl acetate (500 mL). The organic layer was washed with saturated brine, dried over sodium sulfate anhydrate, and concentrated under reduced pressure. The residue was purified through silica gel column chromatography (n-hexane:ethyl acetate=10:1), to thereby give the title compound (35.5 g, 77%).

MS (EI) m/z 357 (M+)

$^1$H-NMR (270 MHz, CDCl$_3$)δ ppm: 1.47 (9H, s), 2.53-2.77 (4H; m), 3.32-3.50 (1H, m), 5.05-5.25 (2H, m), 5.83-6.07 (1H, m), 7.22 (1H, dd, J=2.5, 8.5 Hz), 7.46 (1H, d, J=2.5 Hz), 7.49 (1H, d, J=8.5 Hz), 9.36 (1H, s).

Example 4

Synthesis of tert-butyl[1-(3,4-dichlorophenyl)-1-methylaminomethyl-3-butenyl]methylcarbamate

[F20]

tert-Butyl[1-(3,4-dichlorophenyl)-1-formyl-3-butenyl]methylcarbamate (35 g) was dissolved in methanol (350 mL), and 40% methylamine-methanol solution (44 mL) was added thereto, followed by refluxing for 15 hours. The reaction mixture was cooled to room temperature, and sodium cyanoborohydride (12.5 g) was added thereto, followed by refluxing for 7 hours. The reaction mixture was concentrated under reduced pressure, and the residue was purified through silica gel column chromatography (sequentially through use of n-hexane:ethyl acetate=2:1 and chloroform:methanol=10:1 to 5:1), to thereby give the title compound (24.8 g, 70%).

MS (EI) m/z 372 (M+)

$^1$H-NMR (270 MHz, CDCl$_3$)δ ppm: 1.19 (9H, s), 2.33 (3H, s), 2.72-3.03 (4H, m), 3.10 (3H, s), 3.06-3.22 (1H, m), 5.08-5.20 (2H, m), 5.58-5.77 (1H, m), 7.08 (1H, dd, J=2.5, 8.5 Hz), 7.30-7.40 (2H, m).

Example 3-1

Synthesis of tert-butyl[1-(3,4-dichlorophenyl)-1-formyl-3-butenyl]methylcarbamate (Alternative Method)

[F21]

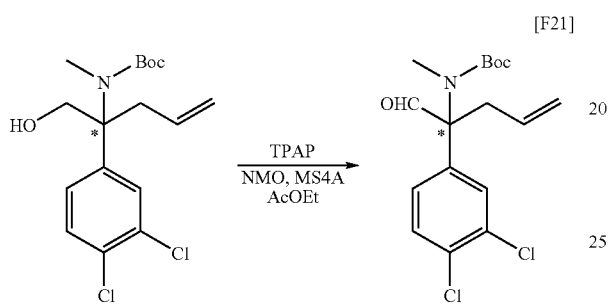

Ethyl acetate (100 mL) was added to tert-butyl[1-(3,4-dichlorophenyl)-1-formyl-3-butenyl]methylcarbamate (5.0 g), N-methylmorpholine-N-oxide (2.5 g), and molecular sieve 4A (powder), and the mixture was stirred for 20 minutes at room temperature. Tetrapropylammonium perruthenate (251 mg) was added to the mixture, and the resultant mixture was stirred for 1 hour at room temperature. The insoluble matter was removed by filtration through Celite, and the filtrate was sequentially washed with aqueous sodium sulfite, saturated brine, and saturated aqueous cupper sulfate, dried over sodium sulfate anhydrate, and concentrated under reduced pressure, to thereby give the title compound (4.63 g, 93%). The title compound was used in the next step without further purification.

Example 3-2

Synthesis of tert-butyl[1-(3,4-dichlorophenyl)-1-methyliminomethyl-3-butenyl]methylcarbamate

[F22]

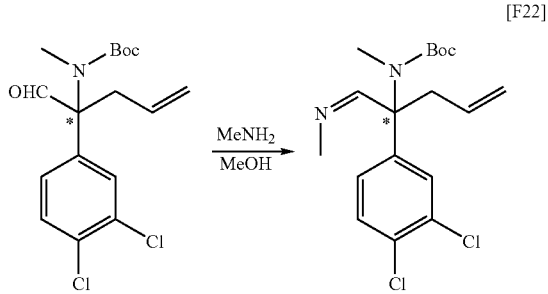

40% Methylamine-methanol solution (17.3 mL) was added to tert-butyl[1-(3,4-dichlorophenyl)-1-methyliminomethyl-3-butenyl]methylcarbamate (4.0 g), and the mixture was refluxed for 13 hours. The reaction mixture was concentrated under reduced pressure, and water was added to the residue, followed by extraction with toluene. The organic layer was sequentially washed with water and saturated brine, dried over sodium sulfate anhydrate, and concentrated under reduced pressure, to thereby give the title compound (3.70 g, 89%).

The title compound was used in the next step without further purification.

MS(EI)m/z 370(M+)

$^1$H-NMR(270 MHz, CDCl$_3$)δ ppm: 1.35(9H,s), 2.76(3H,s), 2.80-2.93(1H,m), 3.25(3H,d,J=2.0 Hz), 3.30-3.42(1H,m), 5.01-5.18(2H,m), 5.80-6.00(1H,m), 7.15(1H,dd,J=2.0, 8.5 Hz), 7.35-7.46(2H,m), 7.78(1H, s).

Example 3-3

Synthesis of tert-butyl[1-(3,4-dichlorophenyl)-1-methylaminomethyl-3-butenyl]methylcarbamate oxalate

[F23]

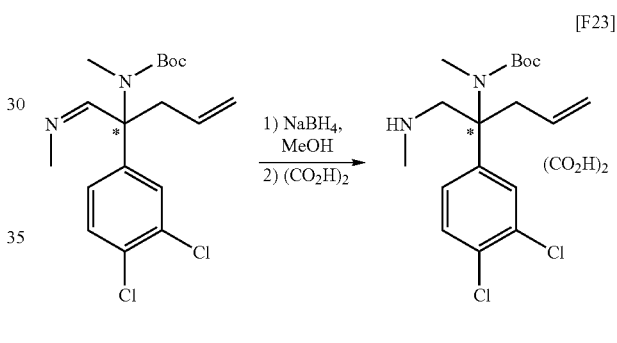

tert-Butyl[1-(3,4-dichlorophenyl)-1-methylaminomethyl-3-butenyl]methylcarbamate (1.7 g) was dissolved in methanol, and sodium boron hydride (174 mg) was added thereto, followed by stirring for 30 minutes at 50° C. Sodium boron hydride (173 mg) was added to the reaction mixture five times at intervals of 30 minutes, and the resultant mixture was stirred for 1.5 hours at 50° C. The reaction mixture was concentrated under reduced pressure, and water was added to the residue, followed by extraction with ethyl acetate, washing with saturated brine, and drying over sodium sulfate anhydrate. The drying agent was removed through filtration, and oxalic acid (425 mg) in ethyl acetate was added to the filtrate. The mixture was concentrated under reduced pressure, and isopropyl ether was added to the residue, followed by filtration with suction and drying, to thereby give the title compound (1.4 g, 66%).

$[\alpha]_D^{27}$=+2.7° (c=0.50,MeOH)

mp. 152.0-153.0° C.

MS(EI)m/z 372(M+)

$^1$H-NMR(270 MHz,DMSO-d$_6$)δppm: 1.12(9H,s), 2.60(3H,s), 2.81(1H,dd,J=6.5,13.5 Hz), 2.91-3.14(4H,m), 3.54-3.75(2H,m), 5.00-5.15(2H,m), 5.30-5.50(1H,m), 7.19 (1H,dd,J=2.0,8.5 Hz), 7.40(1H,d,J=2.0 Hz), 7.62(1H,d, J=8.5 Hz), 8.00-8.80(2H,br).

Example 5(a)

Synthesis of tert-butyl(1-(3,4-dichlorophenyl)-1-{[methyl-(3,3,3-trifluoro-propionyl)-amino]-methyl-3-butenyl}-methyl-carbamate

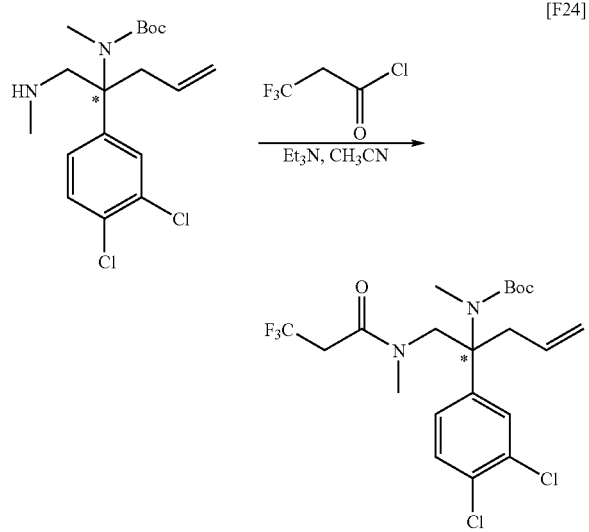

[F24]

tert-Butyl[1-(3,4-dichlorophenyl)-1-methylaminomethyl-3-butenyl]methylcarbamate (3.0 g) was dissolved in acetonitrile (30 mL), and triethylamine (1.7 mL) and 3,3,3,-trifluoropropionyl chloride (2.36 g) was added thereto under cooling with ice, followed by stirring for 1 hour under cooling with ice. The reaction mixture was concentrated under reduced pressure, and water was added to the residue, followed by extraction with ethyl acetate. The organic layer was washed with saturated brine, dried over sodium sulfate anhydrate, and concentrated under reduced pressure. The residue was purified through silica gel column chromatography (n-hexane:ethyl acetate=2:1), to thereby give the title compound (2.83 g, 73%).

MS (FAB) m/z 483 ((M+H)$^+$)

$^1$H-NMR (270 MHz, CDCl$_3$)δ ppm: 1.22 (9H, brs), 2.57 (1H, dd, J=6.5, 7.5 Hz), 2.74-2.90 (1H, m), 2.85 (3H, s), 3.07 (3H, s), 3.27-3.38 (2H, m), 4.0-4.20 (1H, m), 4.25-4.42 (1H, m), 4.85-5.04 (2H, m), 5.64-5.85 (1H, m), 7.00 (1H, dd, J=2.5, 8.5 Hz), 7.25 (1H, d, J=2.5 Hz), 7.37 (1H, d, J=8.5 Hz).

Example 5(a1)

Synthesis of tert-butyl(1-(3,4-dichlorophenyl)-1-{[methyl-(3,3,3-trifluoro-propionyl)-amino]-methyl}-3-butenyl)-methyl-carbamate (Alternative Method)

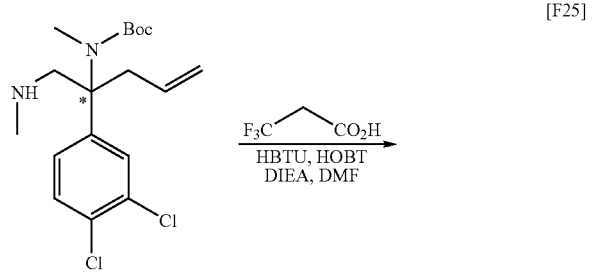

[F25]

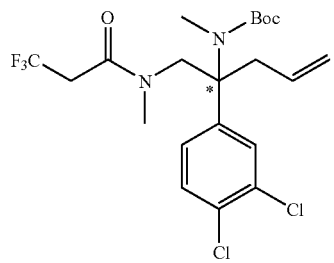

tert-Butyl[1-(3,4-dichlorophenyl)-1-methylaminomethyl-3-butenyl]methylcarbamate (5.0 g) was dissolved in N,N-dimethylformamide (50 mL), and, at room temperature, 3,3,3-trifluoropropionic acid (1.3 mL), [2-(1H)-benzotriazole-1-yl]-1,1,3,3-tetramethyluronium hexafluorophosphate (5.6 g), 1-hydroxybenzotriazole monohydrate (2.0 g), and N,N-diisopropylethylamine (3.5 mL) were added thereto, followed by stirring for 2 hours at room temperature. 3,3,3-Trifluoropropionic acid (0.6 mL), [2-(1H)-benzotriazole-1-yl]-1,1,3,3-tetramethyluronium hexafluorophosphate (2.5 g), 1-hydroxybenzotriazole monohydrate (1.0 g), and N,N-diisopropylethylamine (1.75 mL) were added to the reaction mixture, and the resultant mixture was stirred for 1 hour at room temperature. Water was added to the reaction mixture, and the mixture was extracted with ethyl acetate. The organic layer was sequentially washed with water and saturated brine, dried over sodium sulfate anhydrate, and concentrated under reduced pressure. The residue was purified through silica gel column chromatography (n-hexane:ethyl acetate=2:1), to thereby give the title compound (3.38 g, 52%).

MS (FAB) m/z 483 ((M+H)$^+$)

$^1$H-NMR (270 MHz, CDCl$_3$)δ ppm: 1.22 (9H, brs), 2.57 (1H, dd, J=6.5, 7.5 Hz), 2.74-2.90 (1H, m), 2.85 (3H, s), 3.07 (3H, s), 3.27-3.38 (2H, m), 4.05-4.20 (1H, m), 4.25-4.42 (1H, m), 4.85-5.04 (2H, m), 5.64-5.85 (1H, m), 7.00 (1H, dd, J=2.5, 8.5 Hz), 7.25 (1H, d, J=2.5 Hz), 7.37 (1H, d, J=8.5 Hz).

Example 5(b)

Synthesis of tert-butyl(1-(3,4-dichlorophenyl)-3,4-dihydroxy-1-{[methyl-(3,3,3-trifluoro-propionyl)-amino]-methyl}-butyl)-methyl-carbamate

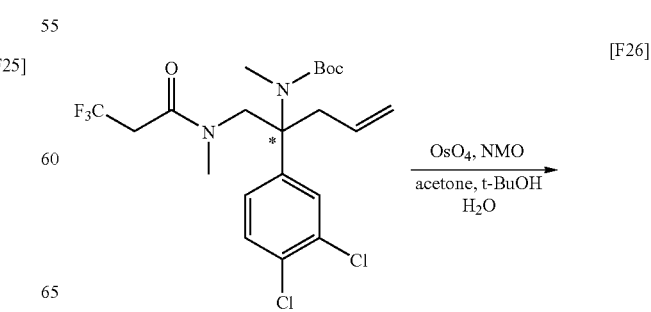

[F26]

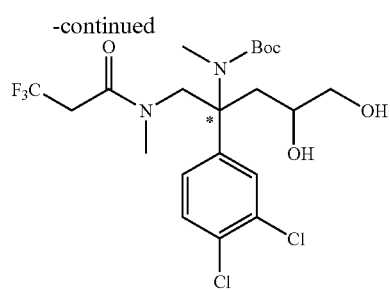

tert-Butyl(1-(3,4-dichlorophenyl)-1-{[methyl-(3,3,3-trifluoro-propionyl)-amino]-methyl}-3-butenyl)-methyl-carbamate (2.0 g) was dissolved in a solvent mixture of acetone (5 mL), 2-methyl-2-propanol (2.5 mL), and water (2.5 mL). Osmium tetraoxide (2.5% 2-methyl-2-propanol solution) (561 μL) and N-methylmorpholine N-oxide (971 mg) were added thereto, and the mixture was stirred overnight at room temperature. Aqueous sodium thiosulfate was added to the reaction mixture, and the mixture was stirred for 30 minutes at room temperature. The insoluble matter was removed by filtration through Celite, and the filtrate was concentrated under reduced pressure. Water was added to the residue, and the mixture was extracted with methylene chloride. The organic layer was washed with saturated brine, dried over sodium sulfate anhydrate, and concentrated under reduced pressure, to thereby give the title compound (1.95 g, 91%). The compound was used in the next step without further purification.

MS (FAB) m/z 518 ((M+H)$^+$)

$^1$H-NMR (270 MHz, CDCl$_3$)δ ppm: 1.20 (9H, brs), 1.93-2.53 (4H, m), 3.09 (3H, s), 3.00-3.62 (6H, m), 3.68-3.80 (2H, m), 4.68-5.38 (2H, m), 7.00-7.10 (1H, m), 7.20-7.32 (1H, m), 7.37-7.46 (1H, m).

Example 5(c)

Synthesis of tert-butyl(1-(3,4-dichlorophenyl)-1-{[methyl-(3,3,3-trifluoro-propionyl)-amino]-methyl}-3-oxo-propyl)-methyl-carbamate

[F27]

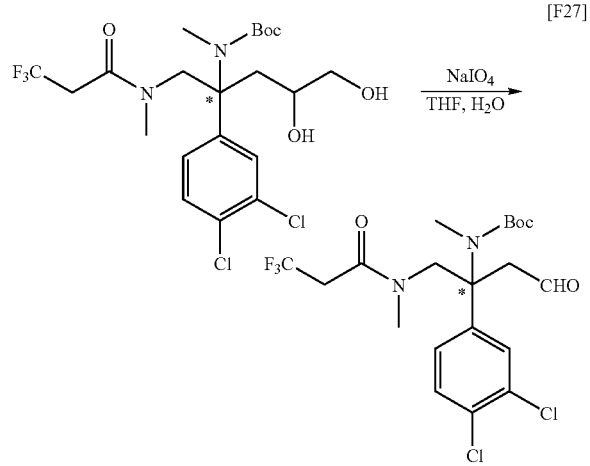

tert-Butyl(1-(3,4-dichlorophenyl)-3,4-dihydroxy-1-{[methyl-(3,3,3-trifluoro-propionyl)-amino]-methyl}-butyl)-methyl-carbamate (1.95 g) was dissolved in a mixture solvent of tetrahydrofuran (20 mL) and water (10 mL). Sodium periodate (1.61 g) was added thereto, and the mixture was stirred for 1 hours at room temperature. The reaction mixture was concentrated under reduced pressure, and water was added to the residue, followed by extraction with ethyl acetate. The organic layer was washed with saturated brine, dried over sodium sulfate anhydrate, and concentrated under reduced pressure, to thereby give the title compound (1.79 g, 98%). The compound was used in the next step without further purification.

MS (FAB) m/z 485 ((M+H)$^+$)

$^1$H-NMR (270 MHz, CDCl$_3$)δ ppm: 1.26 (9H, brs), 2.78 (3H, s), 2.94-3.14 (1H,m), 3.07 (3H, s), 3.18-3.37 (3H, m), 4.24 (1H, d, J=13.5 Hz), 4.52 (1H, d,J=13.5 Hz), 7.10 (1H, dd, J=2.0, 8.5 Hz), 7.33 (1H, d, J=2.0 Hz), 7.43 (1H, d,J=8.5 Hz), 9.67 (1H, t, J=2.0 Hz).

Example 5(d)

Synthesis of tert-butyl{1-(3,4-dichlorophenyl)-1-{[methyl-(3,3,3-trifluoro-propionyl)-amino]-methyl}-3-{spiro[benzo(c)thiophene-1(3H),4'-piperidine]-(2S)-oxide}-1'-yl-propyl}-methyl-carbamate

[F28]

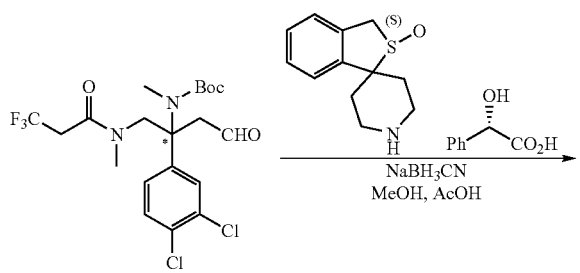

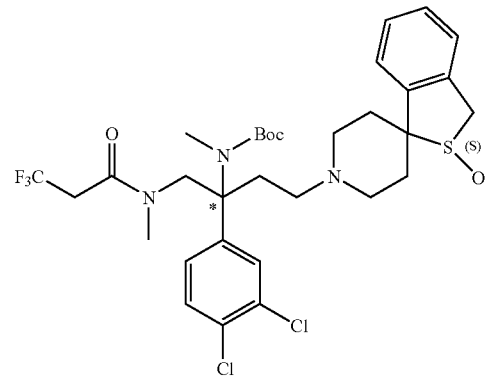

tert-Butyl(1-(3,4-dichlorophenyl)-1-{[methyl-(3,3,3-trifluoro-propionyl)-amino]-methyl}-3-oxo-propyl)-methyl-carbamate (1.0 g) was dissolved in methanol (20 mL). Spiro[benzo(c)thiophene-1(3H), 41-piperidine]-(2S)-oxide/(S)-(+)-mandelic acid salt (1.08 g) and sodium cyanoborohydride (191 mg) were added thereto. Acetic acid (0.3 mL) was added to the mixture to adjust the pH to 4, and the resultant mixture was stirred for 30 minutes at room temperature. The reaction mixture was concentrated under reduced pressure, and water was added to the residue, followed by extraction with chloroform. The organic layer was washed with saturated brine, dried over sodium sulfate anhydrate, and concentrated under reduced pressure. The residue was purified through silica gel column chromatography (sequentially through use of n-hexane:ethyl acetate=1:2 and chloroform:methanol=20:1 to 5:1), to thereby give the title compound (1.38 g, 97%).

MS (FAB) m/z 690 ((M+H)$^+$)

$^1$H-NMR (270 MHz, CDCl$_3$)δ ppm: 1.23 (9H, s), 1.51 (1H, d, J=13 Hz), 1.82-2.08 (2H, m), 2.15-2.68 (7H, m), 2.72-3.05 (2H, m), 2.89 (3H, s), 3.10 (3H, s), 3.20-3.42 (2H, m), 3.92-4.65 (2H, m), 3.97 (1H, d, J=17 Hz), 4.30 (1H, d, J=17 Hz), 7.05 (1H, dd, J=2.0, 8.5 Hz), 7.22-7.48 (6H, m).

Example 5(e)

Synthesis of N-{2-(3,4-dichlorophenyl)-2-methylamino-4-{spiro[benzo(c)thiophene-1(3H),4'-piperidine]-(2S)-oxide}-1'-yl-butyl}-3,3,3-trifluoro-N-methyl-propionamide

[F29]

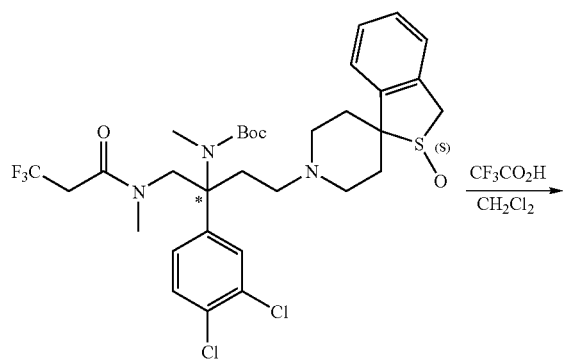

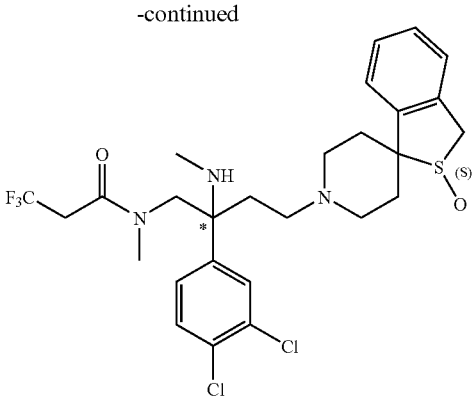

tert-Butyl{1-(3,4-dichlorophenyl)-1-{[methyl-(3,3,3-trifluoro-propionyl)-amino]-methyl}-3-{spiro[benzo(c)thiophene-1(3H),4'-piperidine]-(2S)-oxide}-1'-yl-propyl}-methyl-carbamate (1.38 g) was dissolved in methylene chloride (20 mL), and trifluoroacetic acid (10 mL) was added thereto, followed by stirring for 30 minutes at room temperature. The reaction mixture was neutralized with saturated aqueous sodium bicarbonate, and the mixture was extracted with methylene chloride. The organic layer was washed with saturated brine, dried over sodium sulfate anhydrate, and concentrated under reduced pressure, to thereby give the title compound (1.09 g, 92%). The compound was used in the next step without further purification.

MS (FAB) m/z 590 ((M+H)$^+$)

$^1$H-NMR (270 MHz, CDCl$_3$)δ ppm: 1.95-2.68 (10H, m), 2.26 (3H, s), 2.54 (3H, s), 2.92-3.28 (4H, m), 3.42 (1H, d, J=13 Hz), 3.93-4.12 (2H, m), 4.34 (1H,d, J=17 Hz), 7.25-7.42 (5H, m), 7.44 (1H, d, J=8.5 Hz), 7.63 (1H, d, J=2.0 Hz).

Example 5(f)

Synthesis of N-{2-(3,4-dichlorophenyl)-2-[(3,3-diphenylpropionyl)-methylamino]-4-{spiro[benzo(c)thiophene-1(3H),4'-piperidine]-(2S)-oxide}-1'-yl-butyl}-3,3,3-trifluoro-N-methyl-propionamide

[F30]

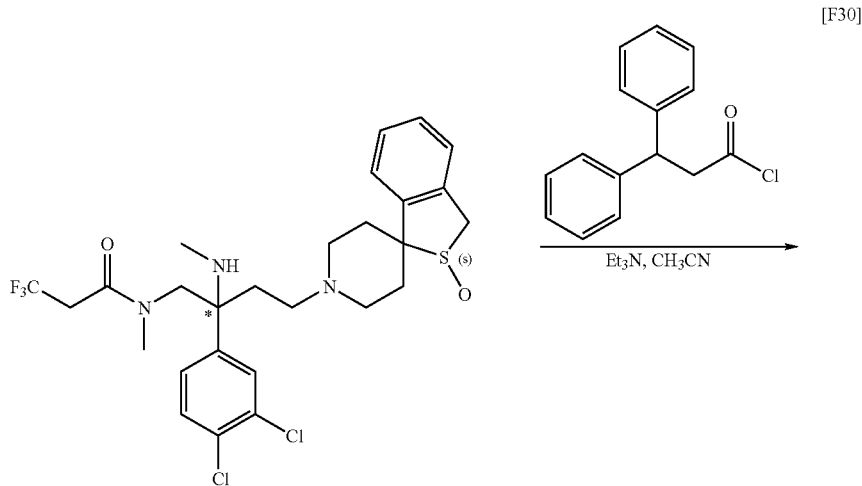

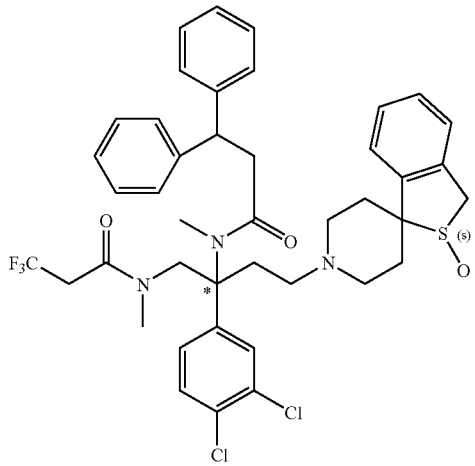

N-{2-(3,4-Dichlorophenyl)-2-methylamino-4-{spiro[benzo(c)thiophene-1(3H),4'-piperidine]-(2S)-oxide}-1'-yl-butyl}-3,3,3-trifluoro-N-methyl-propionamide (300 mg) was dissolved in acetonitrile (5 mL). Under cooling with ice, triethylamine (212 μL) and 3,3-diphenylpropionyl chloride (373 mg) were added thereto. Under cooling with ice, the mixture was stirred for 1 hour. The reaction mixture was concentrated under reduced pressure, and water was added to the residue, followed by extraction with ethyl acetate. The organic layer was washed with saturated brine, dried over sodium sulfate anhydrate, and concentrated under reduced pressure. The residue was purified through silica gel column chromatography (sequentially through use of ethyl acetate and ethyl acetate:methanol=20:1 to 5:1), to thereby give the title compound (350 mg, 86%).

$^1$H-NMR (270 MHz, CDCl$_3$)δ ppm: 1.44-1.58 (1H,m), 1.77-1.92 (1H,m), 1.97-2.47(7H,m), 2.56(3H,s), 2.65-2.85 (2H,m), 2.97-3.27(8H,m), 3.97(1H,d,J=16.5 Hz), 4.05-4.18 (1H,m), 4.29(1H,d,J=16.5 Hz), 4.22-4.42(1H,m), 4.61(1H, t,J=7.5 Hz), 6.72(1H,d,J=8.0 Hz), 7.10-7.37(16H,m).

Example 5(g)

Synthesis of N-{2-(3,4-dichlorophenyl)-2-[(3,3-diphenylpropionyl)-methylamino]-4-{spiro[benzo(c)thiophene-1(3H),4'-piperidine]-(2S)-oxide}-1'-yl-butyl}-3,3,3-trifluoro-N-methyl-propionamide hydrochloride (Compound No. 1)

[F31]

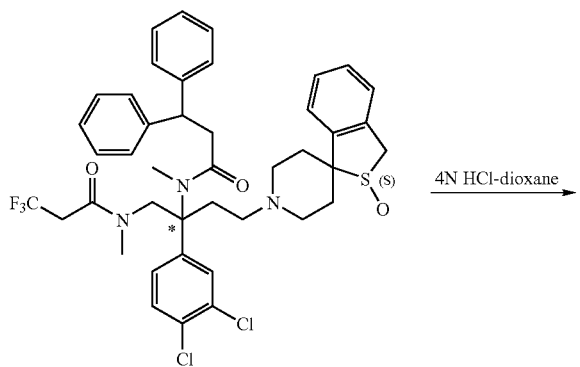

4N HCl-dioxane →

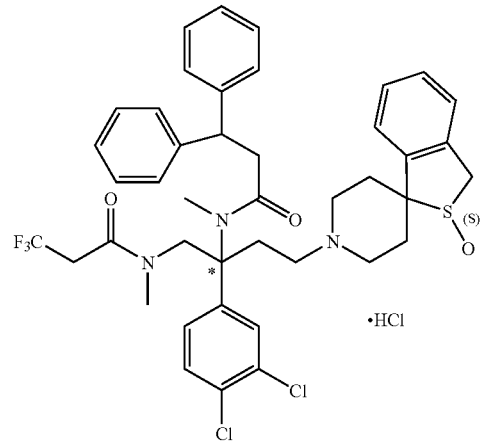

•HCl

N-{2-(3,4-Dichlorophenyl)-2-[(3,3-diphenylpropionyl)-methylamino]-4-{spiro[benzo(c)thiophene-1(3H),4'-piperidine]-(2S)-oxide}-1'-yl-butyl}-3,3,3-trifluoro-N-methyl-propionamide (350 mg) was dissolved in methylene chloride (2 mL). 4N HCl-1,4-dioxane (1 mL) was added thereto, and the mixutre was concentrated under reduced pressure. Ether was added to the residue, followed by filtration and drying, to thereby give the title compound (307 mg, 84%).

$[α]_D^{27}$=−14.1° (c=0.21,MeOH)

MS (FAB) m/z 798 ((M+H)$^+$)

$^1$H-NMR (270 MHz, DMSO-d$_6$)δ ppm: 1.88-2.02 (1H, m), 2.15-2.60 (6H, m), 2.68-2.86 (1H, m), 2.90-3.10 (3H, m), 3.20 (3H, s), 3.15-3.50 (6H, m), 3.52-3.95 (3H, m), 4.08 (1H, d, J=17 Hz), 4.23 (1H, d, J=12 Hz), 4.36 (2H, t,J=7.5 Hz), 4.69 (1H, d, J=17 Hz), 7.03-7.48 (17H, m), 10.45 (1H, br).

Example 6(a)

Synthesis of tert-butyl{1-(3,4-dichlorophenyl)-1-[(isobutyryl-methylamino)-methyl]-3-butenyl}-methyl-carbamate

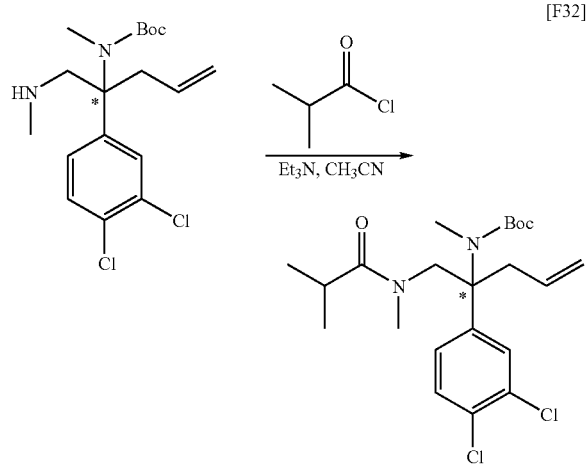

[F32]

tert-Butyl[1-(3,4-dichlorophenyl)-1-methylaminomethyl-3-butenyl]methylcarbamate (2.0 g) produced in Example 4 was dissolved in acetonitrile (40 mL). Under cooling with ice, triethylamine (1.49 mL) and isobutyryl chloride (1.12 mL) was added thereto. Under cooling with ice, the mixture was stirred for 1 hour. The reaction mixture was concentrated under reduced pressure, and water was added to the residue, followed by extraction with ethyl acetate. The organic layer was washed with saturated brine, dried over sodium sulfate anhydrate, and concentrated under reduced pressure. The residue was purified through silica gel column chromatography (n-hexane:ethyl acetate=3:1), to thereby give the title compound (1.53 g, 64%).

MS (FAB) m/z 443 ((M+H)$^+$)

$^1$H-NMR (270 MHz, CDCl$_3$)δ ppm: 1.14 (6H, d, J=7.0 Hz), 1.23 (9H, s), 2.55 (1H,dd, J=7.0, 13.5 Hz), 2.78 (3H, s), 2.78-2.85 (2H, m), 3.09 (3H, s), 4.08-4.16(2H, m), 4.86-4.99 (2H, m), 5.85-5.87 (1H, m), 7.02 (1H, dd, J=2.5, 8.5 Hz), 7.25 (1H, d, J=2.5 Hz), 7.36 (1H, d, J=8.5 Hz).

Example 6(b)

Synthesis of tert-butyl{1-(3,4-dichlorophenyl)-3,4-dihydroxy-1-[(isobutyryl-methylamino)-methyl]-butyl}-methyl-carbamate

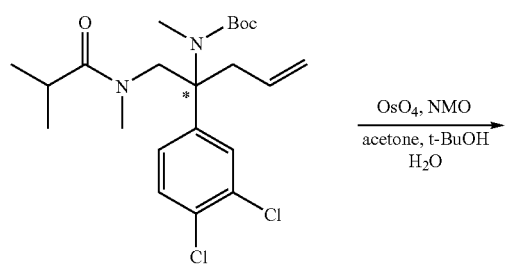

[F33]

-continued

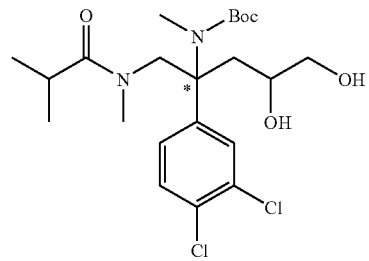

tert-Butyl{1-(3,4-dichlorophenyl)-1-[(isobutyryl-methylamino)-methyl]-3-butenyl}-methyl-carbamate (1.12 g) was dissolved in a mixture solvent of acetone (3 mL), 2-methyl-2-propanol (1.5 mL), and water (1.5 mL). Osmium tetraoxide (2.5% 2-methyl-2-propanol solution) (302 μL) and N-methylmorpholine N-oxide (592 mg) were added thereto, and the mixture was stirred for 2.5 days at room temperature. Aqueous sodium thiosulfate was added to the reaction mixture, and the resultant mixture was stirred for 10 minutes at room temperature. The insoluble matter was removed by filtration through Celite, and the filtrate was concentrated under reduced pressure. Water was added to the residue, and the mixture was extracted with methylene chloride. The organic layer was washed with saturated brine, dried over sodium sulfate anhydrate, and concentrated under reduced pressure, to thereby give the title compound (1.13 g, 94%). The compound was used in the next step without further purification.

MS (FAB) m/z 477 ((M+H)$^+$)

$^1$H-NMR (270 MHz, CDCl$_3$)δ ppm: 1.04-1.20 (15H, m), 1.90-2.23 (2H, m), 2.41 (1H, t, J=4.5 Hz), 2.65-3.65 (9H, m), 3.72 (2H, t, J=5.0 Hz), 5.02-5.28 (1H, m), 5.52-5.78 (1H, m), 7.00-7.15 (1H, m), 7.18-7.35 (1H, m), 7.40 (1H, d, J=8.5 Hz).

Example 6(c)

Synthesis of tert-butyl{1-(3,4-dichlorophenyl)-1-[(isobutyryl-methylamino)-methyl]-3-oxo-propyl}-methyl-carbamate

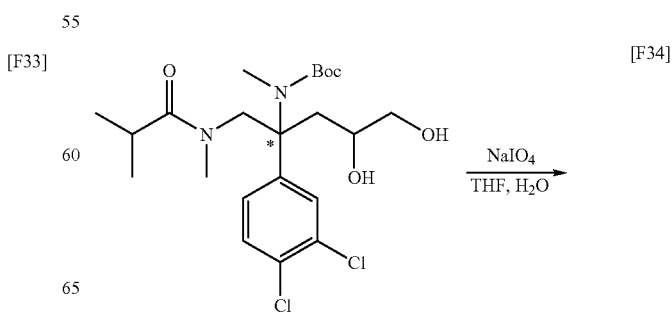

[F34]

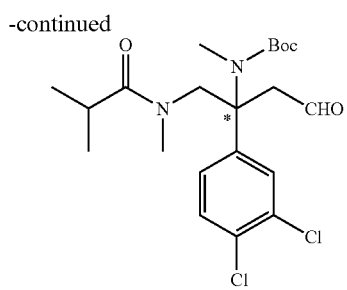

tert-Butyl{1-(3,4-dichlorophenyl)-3,4-dihydroxy-1-[(isobutyryl-methylamino)-methyl]-butyl}-methyl-carbamate (1.41 g) was dissolved in a mixture solvent of tetrahydrofuran (8 mL) and water (8 mL). Sodium periodate (1.3 g) was added thereto, and the mixture was stirred for 1 hour at room temperature. The reaction mixture was concentrated under reduced pressure, and water was added to the residue, followed by extraction with ethyl acetate. The organic layer was washed with saturated brine, dried over sodium sulfate anhydrate, and concentrated under reduced pressure, to thereby give the title compound (1.33 g, quantative amount). The compound was used in the next step without further purification.

MS (FAB) m/z 445 ((M+H)$^+$)

$^1$H-NMR (270 MHz, CDCl$_3$)δ ppm: 1.13 (6H, dd, J=3.0, 7.0 Hz), 1.23-1.29 (9H, m), 2.73 (3H, s), 2.76-2.84 (1H, m), 2.90 (1H, d, J=16 Hz), 3.11 (3H, s), 3.16(1H, d, J=16 Hz), 4.10-4.18 (1H, m), 4.45 (1H, d, J=13 Hz), 7.10 (1H, dd, J=2.5, 8.5 Hz), 7.33 (1H, d, J=2.5 Hz), 7.41 (1H, dd, J=2.5, 8.5 Hz), 9.71 (1H, t,J=2.0 Hz).

Example 6(d)

Synthesis of tert-butyl{1-(3,4-dichlorophenyl)-1-[(isobutyryl-methylamino)-methyl]-3-{spiro[benzo(c)thiophene-1(3H),4'-piperidine]-(2S)-oxide}-1'-yl-propyl}-methyl-carbamate

[F35]

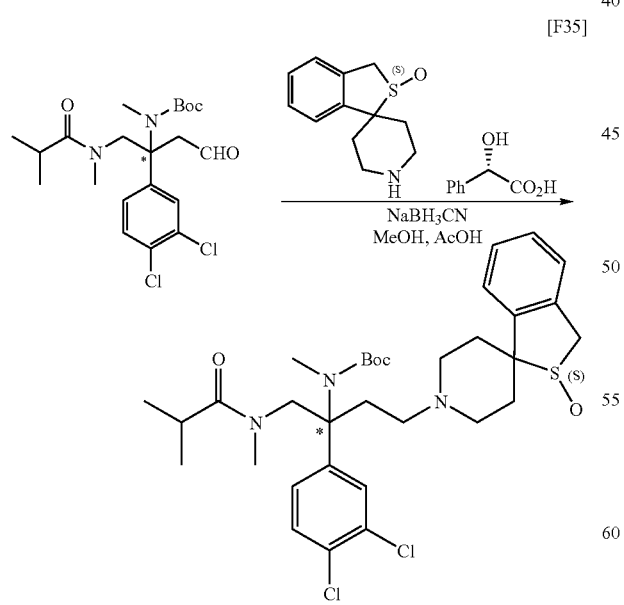

tert-Butyl{1-(3,4-dichlorophenyl)-1-[(isobutyryl-methylamino)-methyl]-3-oxo-propyl}-methyl-carbamate (1.33 g) was dissolved in methanol (15 mL). Spiro[benzo(c)thiophene-1(3H),4'-piperidine]-(2S)-oxide/(S)-(+)-mandelate (1.45 g) and sodium cyanoborohydride (257 mg) were added thereto. Acetic acid was added to the mixture to adjust the pH to 4, and the resultant mixture was stirred for 1 hour at room temperature. The reaction mixture was concentrated under reduced pressure, and water was added to the residue, followed by extraction with ethyl acetate. The organic layer was washed with saturated brine, dried over sodium sulfate anhydrate, and concentrated under reduced pressure. The residue was purified through silica gel column chromatography (sequentially through use of ethyl acetate and chloroform:methanol=20:1), to thereby give the title compound (1.85 g, 95%).

MS (FAB) m/z 650 ((M+H)$^+$)

$^1$H-NMR (270 MHz, CDCl$_3$)δ ppm: 1.16 (6H, dd, J=4.0, 6.5 Hz), 1.20-1.29 (9H, m), 1.50 (1H, d, J=15 Hz), 1.79-2.01 (2H, m), 2.17-2.52 (7H, m), 2.58-2.79 (2H, m), 2.82-2.87 (5H, m), 3.13 (3H, s), 3.97 (1H, d, J=17 Hz), 4.07-4.19 (1H,m), 4.29 (1H, d, J=17 Hz), 7.06 (1H, dd, J=2.0, 8.5 Hz), 7.19-7.33 (5H, m), 7.39 (1H, d, J=8.5 Hz).

Example 6(e)

Synthesis of N-[2-(3,4-dichlorophenyl)-2-methylamino-4-{spiro[benzo(c)thiophene-1(3H),4'-piperidine]-(2S)-oxide}-1'-yl-butyl]-N-methyl-isobutyrylamide

[F36]

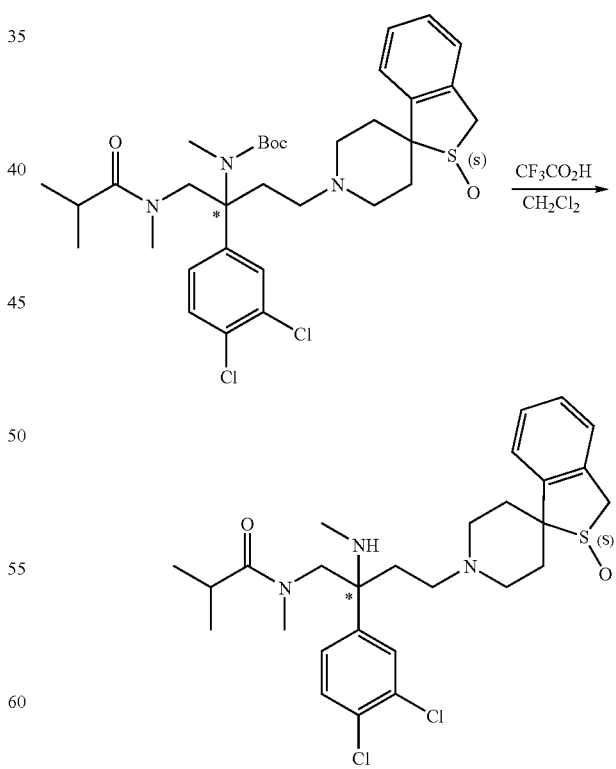

tert-Butyl{1-(3,4-dichlorophenyl)-1-[(isobutyryl-methylamino)-methyl]-3-{spiro[benzo(c)thiophene-1(3H),4'-piperidine]-(2S)-oxide}-1'-yl-propyl}-methyl-carbamate (1.85- g) was dissolved in methylene chloride (10 mL). Trifluoroacetic acid (5 mL) was added thereto, and the mixture was stirred for 2 hours at room temperature. The reaction mixture was neutralized with saturated aqueous sodium bicarbonate, and the mixture was extracted with methylene chloride. The organic layer was washed with saturated brine, dried over sodium sulfate anhydrate, and concentrated under reduced pressure, to thereby give the title compound (1.35 g, 86%). The compound was used in the next step without further purification.

MS (FAB) m/z 550 ((M+H)$^+$)

$^1$H-NMR (270 MHz, CDCl$_3$)δ ppm: 1.02 (3H, d, J=6.5 Hz), 1.09 (3H, d, J=7.0 Hz), 1.57-1.66 (4H, m), 2.05-2.17 (2H, m), 2.25(3H, s), 2.31-2.45 (4H, m), 2.53 (3H, s), 2.64-2.79 (2H, m), 2.97-3.09 (2H, m), 3.34-3.39 (1H, m), 3.83-4.00 (1H, m), 4.02 (1H, d, J=17 Hz), 4.35 (1H, d, J=17 Hz), 7.25-7.40 (5H, m), 7.43(1H, d, J=8.5 Hz), 7.58-7.65 (1H, m).

Example 6(f)

Synthesis of N-{2-(3,4-dichlorophenyl)-2-[(3,3-diphenylpropionyl)-methylamino]-4-{spiro[benzo(c)thiophene-1(3H),4'-piperidine]-(2S)-oxide}-1'-yl-butyl}-N-methyl-isobutylamide

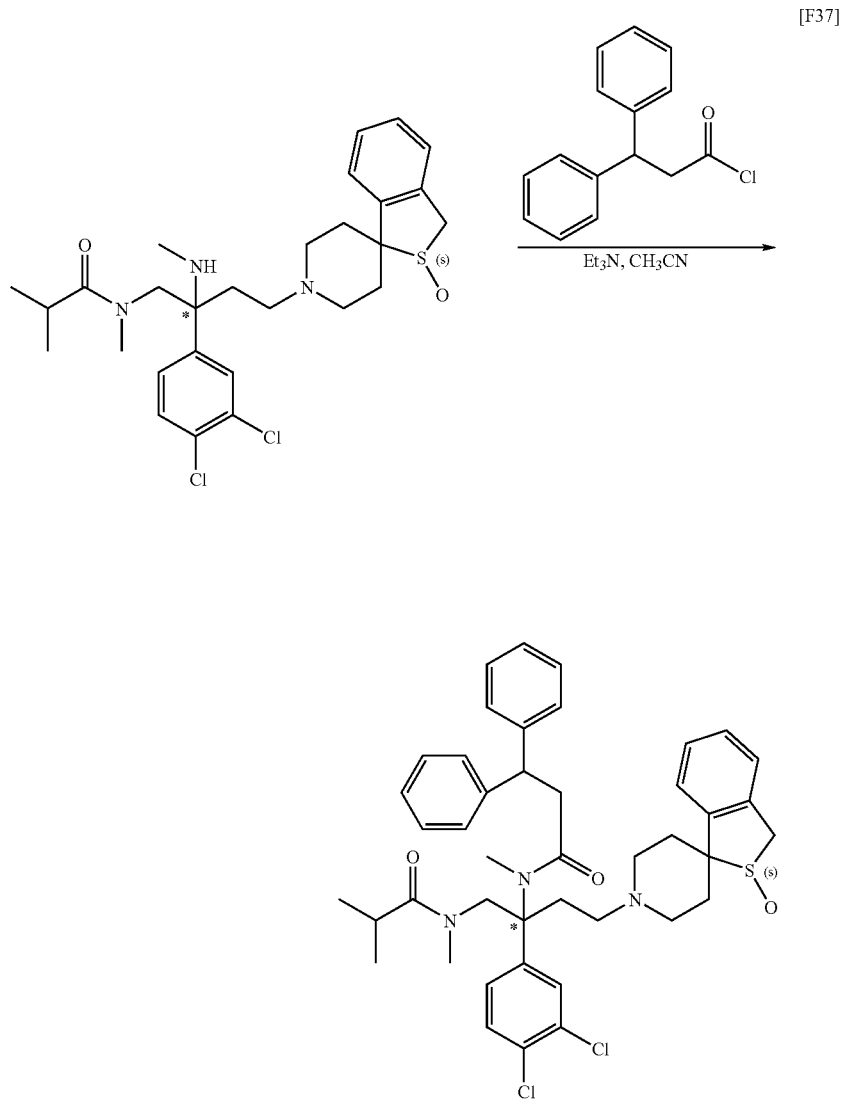

N-[2-(3,4-dichlorophenyl)-2-methylamino-4-{spiro[benzo(c)thiophene-1(3H),4'-piperidine]-(2S)-oxide}-1'-yl-butyl]-N-methyl-isobutylamide (1.0 g) was dissolved in acetonitrile (20 mL). Under cooling with ice, triethylamine (761 μL) and 3,3-diphenylpropionyl chloride (1.34 g) were added thereto, and the mixture was stirred for 1 hour at room temperature. The reaction mixture was concentrated under reduced pressure, and water was added to the residue, followed by extraction with ethyl acetate. The organic layer was washed with saturated brine, dried over sodium sulfate anhydrate, and concentrated under reduced pressure. The residue was purified through silica gel column chromatography (sequentially through use of ethyl acetate, ethyl acetate:methanol=20:1, and chloroform:methanol=20:1).

MS (FAB) m/z 758 ((M+H)$^+$)

$^1$H-NMR (270 MHz, CDCl$_3$)δ ppm: 1.07(3H,s), 1.09(3H, s), 1.42-1.55(1H,m), 1.76-1.90(1H,m), 1.94-2.06(1H,m), 2.10-2.47(7H,m), 2.54(3H,s), 2.63-2.88(3H,m), 3.00-3.18 (5H,m), 3.90-4.10(2H,m) 4.23-4.36(2H,m), 4.62(1H,t,J=7.5 Hz), 6.72(1H,d,J=8.5 Hz), 7.12-7.35(16H,m).

Example 6(g)

Synthesis of N-{2-(3,4-dichlorophenyl)-2-[(3,3-diphenylpropionyl)-methylamino]-4-{spiro[benzo(c)thiophene-1(3H),4'-piperidine]-(2S)-oxide}-1'-yl-butyl}-N-methyl-isobutylamide hydrochloride (Compound No. 2)

[F38]

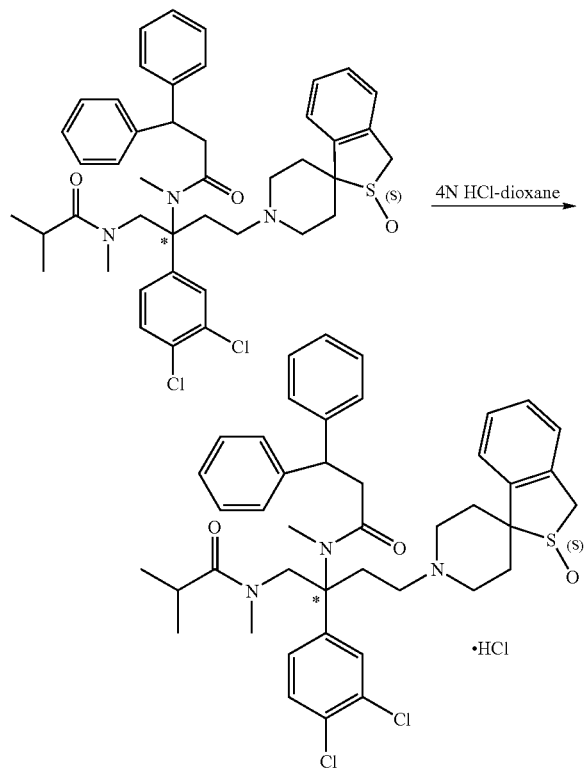

N-{2-(3,4-Dichlorophenyl)-2-[(3,3-diphenylpropionyl)-methylamino]-4-{spiro[benzo(c)thiophene-1(3H),4'-piperidine]-(2S)-oxide}-1'-yl-butyl}-N-methyl-isobutylamide was dissolved in methylene chloride. 4N HCl-1,4-dioxane was added thereto, and the mixture was concentrated under reduced pressure. Ether was added to the residue, followed by filtration and drying, to thereby give the title compound (1.15 g, 80%).

MS (FAB) m/z 758 ((M+H)$^+$)

$^1$H-NMR (270 MHz, DMSO-d$_6$)δ ppm: 0.98 (6H, dd, J=3.0, 6.5 Hz), 2.00 (1H, d, J=14.5 Hz), 2.09-2.29 (3H, m), 2.33-2.47 (2H, m), 2.64-2.79 (3H, m), 3.00-3.03 (3H, m), 3.20 (3H, s), 3.23-3.50 (6H, m), 3.60-3.90 (1H, m), 4.09 (1H, d, J=17 Hz), 4.22 (1H, d, J=10 Hz), 4.36 (1H, t, J=7.0 Hz), 4.70 (1H, d, J=17 Hz), 7.06-7.17 (3H, m), 7.22-7.33 (10H, m), 7.33-7.45 (4H, m), 10.33 (1H, br).

Example 7(a)

Synthesis of tert-butyl(1-(3,4-dichlorophenyl)-1-{[methyl-(2,2,2-trifluoroacetyl)-amino]-methyl}-3-butenyl)-methyl-carbamate

[F39]

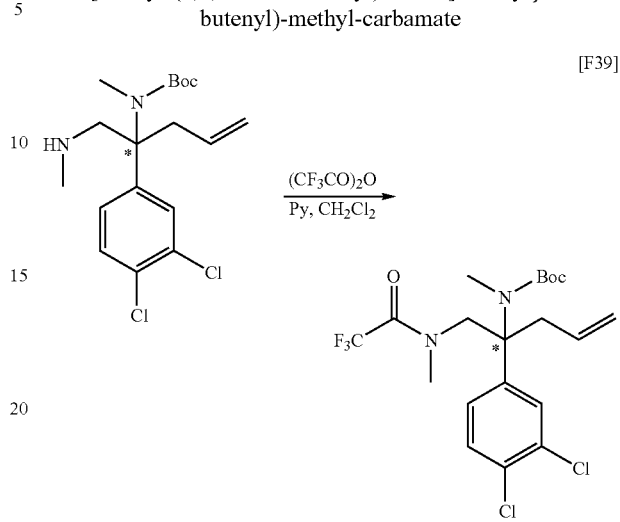

tert-Butyl[1-(3,4-dichlorophenyl)-1-methylaminomethyl-3-butenyl]methylcarbamate (240 mg) produced in Example 4 was dissolved in methylene chloride (5 mL). Under cooling with ice, pyridine (107 μL) and trifluoroacetic acid anhydride (186 μL) were added thereto. Under cooling with ice, the mixture was stirred for 40 minutes. Water was added to the reaction mixture, and the mixture was extracted with methylene chloride. The organic layer was washed with saturated brine, dried over sodium sulfate anhydrate, and concentrated under reduced pressure. The residue was purified through silica gel column chromatography (n-hexane:ethyl acetate=5:1), to thereby give the title compound (250 mg, 77%).

MS (FAB) m/z 469 ((M+H)$^+$)

$^1$H-NMR (270 MHz, CDCl$_3$)δ ppm: 1.26 (9H, s), 2.58 (1H, dd, J=7.0, 13.5 Hz), 2.77 (1H, dd, J=7.0, 13.5 Hz), 3.02 (3H, s), 3.07 (3H, s), 4.07-4.28 (1H, m), 4.43 (1H, d, J=13.5 Hz), 4.86-5.06 (2H, m), 5.55-5.75 (1H, m), 6.99 (1H, dd, J=2.5, 8.5 Hz), 7.24 (1H, d, J=2.5 Hz), 7.39 (1H, d, J=8.5 Hz).

Example 7(b)

Synthesis of tert-butyl{1-(3,4-dichlorophenyl)-3,4-dihydroxy-1-{[methyl-(2,2,2-trifluoroacetyl)-amino]-methyl}-butyl}-methyl-carbamate

[F40]

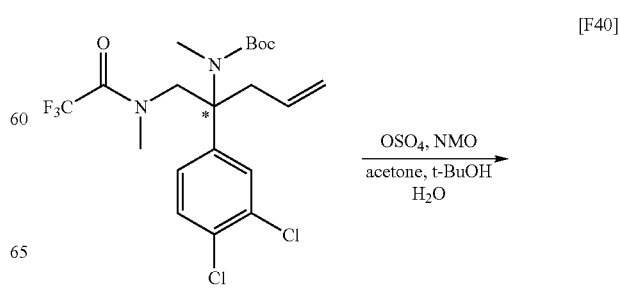

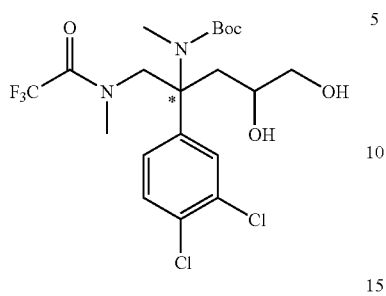

tert-Butyl(1-(3,4-dichlorophenyl)-1-{[methyl-(2,2,2-trifluoroacetyl)-amino]-methyl}-3-butenyl)-methyl-carbamate (659 mg) was dissolved in a mixture solvent of acetone (4 mL), 2-methyl-2-propanol (2 mL), and water (2 mL). Osmium tetraoxide (2.5% 2-methyl-2-propanol solution) (338 μL) and N-methylmorpholine N-oxide (329 mg) were added thereto, and the mixture was stirred overnight at room temperature. Aqueous sodium thiosulfate was added to the reaction mixture, and the resultant mixture was stirred for 30 minutes at room temperature. The insoluble matter was removed by filtration through Celite, and the filtrate was concentrated under reduced pressure. Water was added to the residue, and the mixture was extracted with methylene chloride. The organic layer was washed with saturated brine, dried over sodium sulfate anhydrate, and concentrated under reduced pressure, to thereby give the title compound (701 mg, quantative amount). The compound was used in the next step without further purification.

MS (FAB) m/z 503 ((M+H)$^+$)

$^1$H-NMR (270 MHz, CDCl$_3$)δ ppm: 1.24 (9H, brs), 1.76-1.88 (1H, m), 1.94-2.20 (2H, m), 2.26-2.50 (1H, m), 3.00-3.30 (6H, m), 3.38-3.63 (2H, m), 3.70-3.82 (1H, m), 3.90-4.20 (1H, m), 4.95-5.25 (1H, m), 7.00-7.15 (1H, m), 7.22-7.32 (1H, m), 7.40-7.50 (1H, m).

Example 7(c)

Synthesis of tert-butyl(1-(3,4-dichlorophenyl)-1-{methyl-(2,2,2-trifluoroacetyl)-amino}-methyl)-3-oxo-propyl)-methyl-carbamate

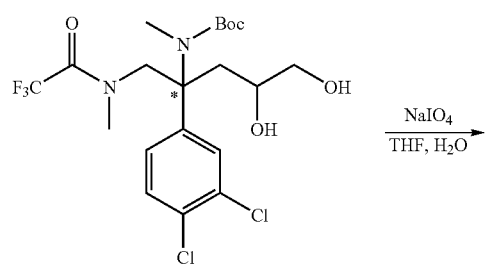

[F41]

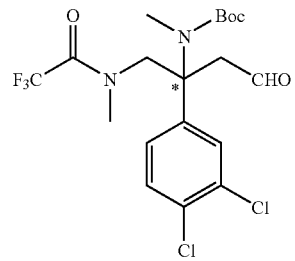

tert-Butyl(1-(3,4-dichlorophenyl)-3,4-dihydroxy-1-{[methyl-(2,2,2-trifluoroacetyl)-amino]-methyl}-butyl)-methyl-carbamate (701 mg) was dissolved in a mixture solvent of tetrahydrofuran (4 mL) and water (4 mL). Sodium periodate (596 mg) was added thereto, and the mixture was stirred for 1 hour at room temperature. The reaction mixture was concentrated under reduced pressure, and water was added to the residue, followed by extraction with ethyl acetate. The organic layer was washed with saturated brine, dried over sodium sulfate anhydrate, and concentrated under reduced pressure, to thereby give the title compound (633 mg, 97%). The compound was used in the next step without further purification.

MS (FAB) m/z 471 ((M+H)$^+$)

$^1$H-NMR (270 MHz, CDCl$_3$)δ ppm: 1.29 (9H, s), 2.95 (3H, s), 2.90-3.10 (1H, m), 3.04 (3H, s), 3.23 (1H, d, J=16 Hz), 4.37 (1H, d, J=13.5 Hz), 4.53 (1H, d, J=13.5 Hz), 7.11 (1H, dd, J=2.5, 8.5 Hz), 7.34 (1H, d, J=2.5 Hz), 7.44 (1H, d, J=8.5 Hz), 9.62 (1H, t, J=2.0 Hz).

Example 7(d)

Synthesis of tert-butyl{1-(3,4-dichlorophenyl)-1-{[methyl-(2,2,2-trifluoroacetyl)-amino]-methyl}-3-{spiro[isoquinoline-1(2H),4'-piperidine]-3(4H)-one}-1'-yl-propyl}-methyl-carbamate

[F42]

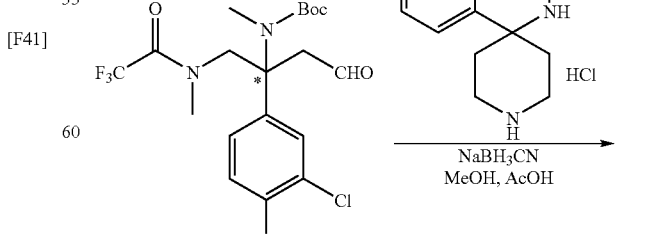

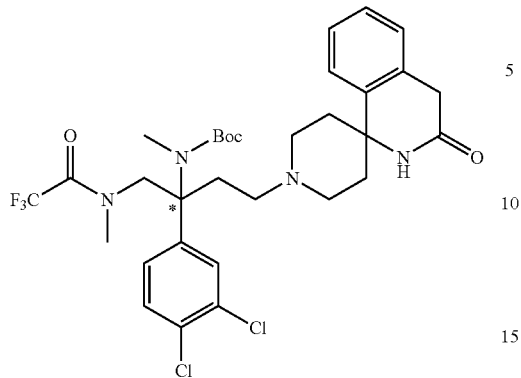

tert-Butyl(1-(3,4-dichlorophenyl)-1-{[methyl-(2,2,2-trifluoroacetyl)-amino]-methyl}-3-oxo-propyl)-methyl-carbamate (300 mg) was dissolved in methanol (5 mL). Spiro[isoquinoline-1(2H),4'-piperidine]-3(4H)-one hydrochloride (225 mg) and sodium cyanoborohydride (59 mg) were added thereto. Acetic acid (0.2 mL) was added to the mixture to adjust the pH to 4, and the mixutre was stirred for 30 minutes at room temperature. The reaction mixture was concentrated under reduced pressure, and water was added to the residue, followed by extraction with chloroform. The organic layer was washed with saturated brine, dried over sodium sulfate anhydrate, and concentrated under reduced pressure. The residue was purified through silica gel column chromatography (sequentially through use of n-hexane:ethyl acetate=1:2 and chloroform:methanol=20:1), to thereby give the title compound (323 mg, 76%).

MS (FAB) m/z 671 ((M+H)$^+$)

$^1$H-NMR (270 MHz, CDCl$_3$)δ ppm: 1.25 (9H, brs), 1.63-1.80 (2H, m), 1.90-2.30 (7H, m), 2.45-2.60 (1H, m), 2.71 (1H, d, J=10 Hz), 2.81 (1H, d, J=10 Hz), 3.0 5(3H, s), 3.12 (3H, s), 3.61 (2H, s), 4.05-4.28 (1H, m), 4.45-4.68 (1H, m), 6.29 (1H, s), 7.04 (1H, dd, J=2.5, 8.5 Hz), 7.10-7.38 (5H, m), 7.43 (1H, d, J=8.5 Hz).

Example 7(e)

Synthesis of N-{2-(3,4-dichlorophenyl)-2-methylamino-4-{spiro[isoquinoline-1(2H),4'-piperidine]-3(4H)-one}-1'-yl-butyl}-2,2,2-trifluoro-N-methyl-acetamide

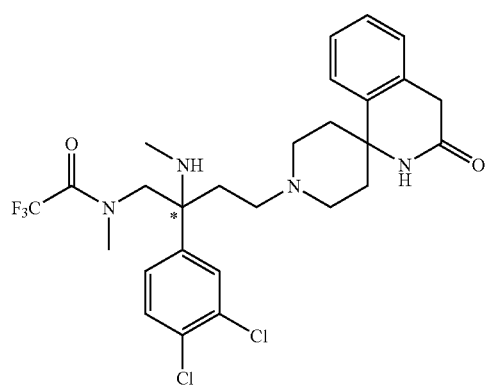

tert-Butyl{1-(3,4-dichlorophenyl)-1-{[methyl-(2,2,2-trifluoroacetyl)-amino]-methyl}-3-{spiro[isoquinoline-1(2H),4'-piperidine]-3(4H)-one}-1'-yl-propyl}-methyl-carbamate (323 mg) was dissolved in methylene chloride (4 mL). Trifluoroacetic acid (2 mL) was added thereto, and the mixture was stirred for 30 minutes at room temperature. The reaction mixture was neutralized with saturated aqueous sodium bicarbonate, and the mixture was extracted with methylene chloride. The organic layer was washed with saturated brine, dried over sodium sulfate anhydrate, and concentrated under reduced pressure, to thereby give the title compound (264 mg, 96%). The compound was used in the next step without further purification.

MS (FAB) m/z 571 ((M+H)$^+$)

$^1$H-NMR (270 MHz, CDCl$_3$)δ ppm: 1.73-1.88 (2H, m), 1.95-2.60 (9H, m), 2.28 (3H, s), 2.72 (3H, s), 2.88-3.03 (2H, m), 3.48 (1H, d, J=14 Hz), 3.64 (2H, s), 3.93 (1H, d, J=14 Hz), 6.36 (1H, s), 7.17 (1H, dd, J=2.5, 8.5 Hz), 7.23-7.42 (4H, m), 7.45 (1H, d, J=8.5 Hz), 7.63 (1H, d, J=2.5 Hz).

Synthesis of Example 7(f)

N-{2-(3-benzhydryl-1-methylureido)-2-(3,4-dihydrodichlorophenyl)-4-{spiro[isoquinoline-1(2H),4'-piperidine]-3(4H)-one}-1'-yl-butyl}-2,2,2-trifluoro-N-methyl-acetamide

[F43]

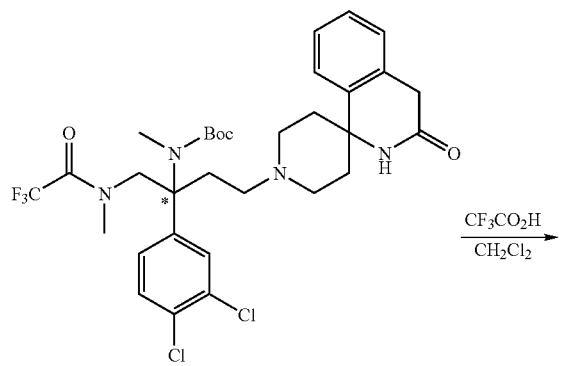

[F44]

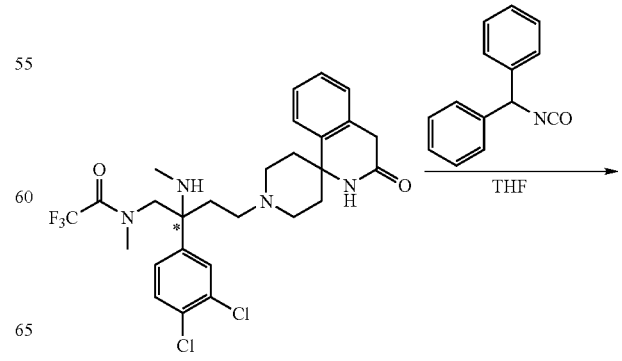

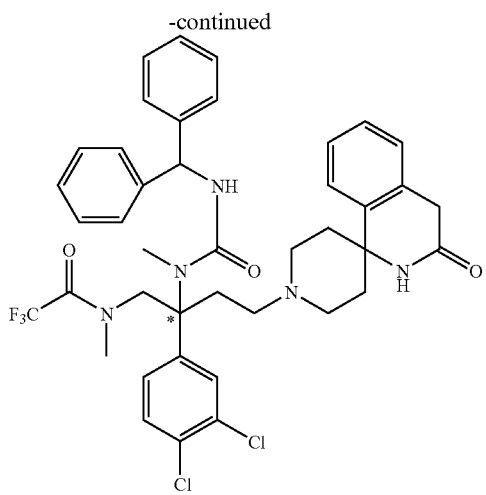

N-{2-(3,4-Dichlorophenyl)-2-methylamino-4-{spiro[isoquinoline-1(2H),4'-piperidine]-3(4H)-one}-1'-yl-butyl}-2,2,2-trifluoro-N-methyl-acetamide (264 mg) was dissolved in tetrahydrofuran (5 mL). Diphenylmethyl isocyanate (175 μL) was added thereto, and the mixture was stirred for 1 hour at room temperature. The reaction mixture was concentrated under reduced pressure, and the residue was purified through silica gel column chromatography (sequentially through use of n-hexane:ethyl acetate=1:2 and chloroform:methanol=20:1).

MS (FAB) m/z 780 ((M+H)$^+$)

$^1$H-NMR (270 MHz, CDCl$_3$)δ ppm: 1.55-1.80(2H,m), 1.93-2.27(7H,m), 2.41-2.57(1H,m), 2.68-2.85(2H,m), 2.89 (3H,s), 3.12(3H,s), 3.61(2H,s), 4.34(1H,d,J=13.5H z), 4.49 (1H,d,J=13.5 Hz), 5.07(1H,d,J=7.0 Hz), 5.99(1H,d,J=7.0 Hz), 6.24(1H,s), 7.03(1H,dd,J=2.0,8.5 Hz), 7.10-7.43(16H, m).

Example 7(g)

Synthesis of N-{2-(3-benzhydryl-1-methylureido)-2-(3,4-dihydrodichlorophenyl)-4-{spiro[isoquinoline-1(2H),4'-piperidine]-3(4H)-one}-1'-yl-butyl}-2,2,2-trifluoro-N-methyl-acetamide hydrochloride (Compound No. 3)

[F45]

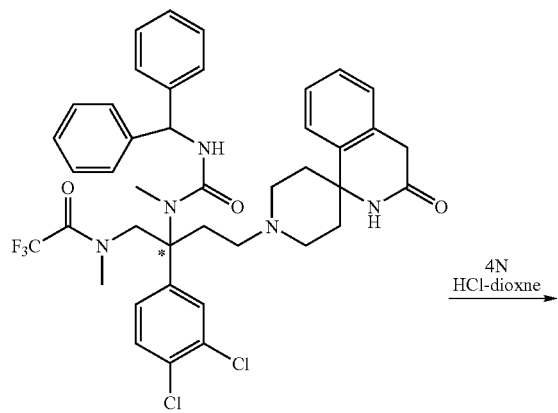

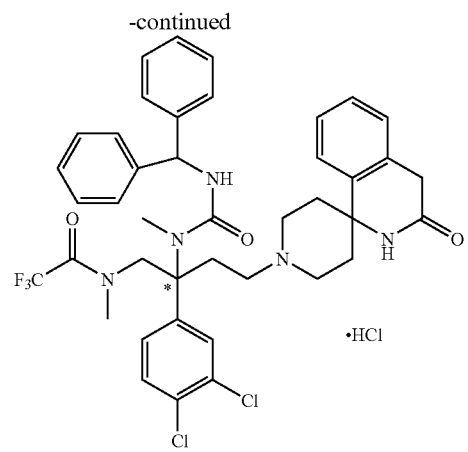

N-{2-(3-Benzhydryl-1-methylureido)-2-(3,4-dihydrodichlorophenyl)-4-{spiro[isoquinoline-1(2H),4'-piperidine]-3(4H)-one}-1'-yl-butyl}-2,2,2-trifluoro-N-methyl-acetamide was dissolved in methylene chloride. 4N HCl-1,4-dioxane was added thereto, and the mixture was concentrated under reduced pressure. Ether was added to the residue, followed by filtration and drying, to thereby give the title compound (319 mg, 85%).

MS (FAB) m/z 780 ((M+H)$^+$)

$^1$H-NMR (270 MHz, DMSO-d$_6$)δ ppm: 1.82-1.99 (2H, m), 2.75 (3H, s), 2.79-3.12 (2H, m), 3.07 (3H, s), 3.22-3.50 (8H, m), 3.53-3.65 (1H, m), 3.61 (2H, s), 4.18 (1H, d, J=13.5 Hz), 4.36 (1H, d, J=13.5 Hz), 5.85 (1H, d, J=7.5 Hz), 7.15-7.42 (15H, m), 7.52-7.62 (2H, m), 8.29 (1H, s), 10.77 (1H, br).

Example 8(a)

Synthesis of tert-butyl[1-{[(2-chloro-2,2-difluoroacetyl)-methylamino]-methyl}-1-(3,4-dichlorophenyl)-3-butenyl]methylcarbamate

[F46]

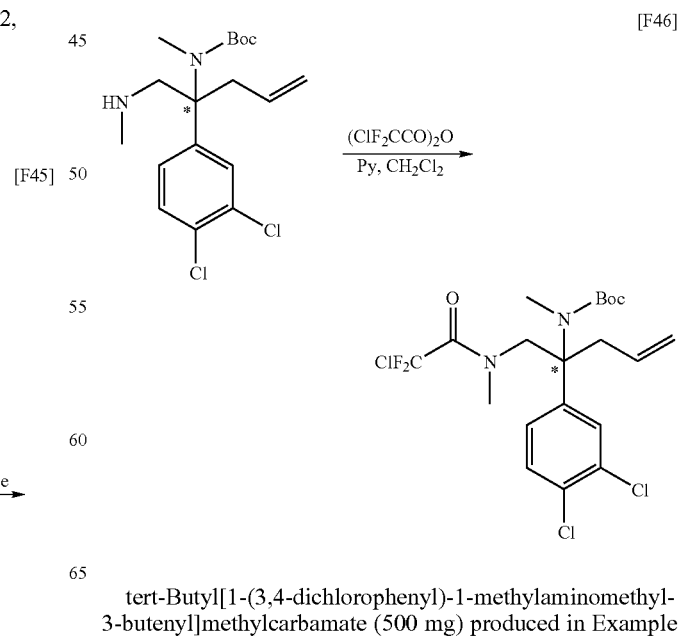

tert-Butyl[1-(3,4-dichlorophenyl)-1-methylaminomethyl-3-butenyl]methylcarbamate (500 mg) produced in Example 4 was dissolved in methylene chloride (10 mL). Under cooling with ice, pyridine (163 μL) and chlorodifluoroacetic acid anhydride (350 μL) were added thereto. Under cooling with ice, the mixture was stirred for 50 minutes. Saturated aqueous sodium bicarbonate was added to the reaction mixture, and the resultant mixture was extracted with methylene chloride. The organic layer was washed with saturated brine, dried over sodium sulfate anhydrate, and concentrated under reduced pressure. The residue was purified through silica gel column chromatography (n-hexane:ethyl acetate=4:1), to thereby give the title compound (300 mg, 46%).

MS (FAB) m/z 487 ((M+3H)$^+$), 485 ((M+H)$^+$)

$^1$H-NMR (270 MHz, CDCl$_3$)δ ppm: 1.26 (9H, s), 2.59 (1H, dd, J=7.0, 14 Hz), 2.78 (1H, dd, J=7.0, 14 Hz), 3.05 (3H, s), 3.09 (3H, s), 4.07-4.30 (1H, m), 4.40(1H, d, J=12.5 Hz), 4.89-5.01 (2H, m), 5.60-5.75 (1H, m), 7.00 (1H, dd, J=2.5, 8.5 Hz), 7.24 (1H, d, J=2.5 Hz), 7.38 (1H, d, J=8.5 Hz).

Example 8(b)

Synthesis of tert-butyl[1-{[(2-chloro-2,2-difluoro-acetyl)-methylamino]-methyl}-1-(3,4-dichlorophenyl)-3,4-dihydroxybutyl]methylcarbamate

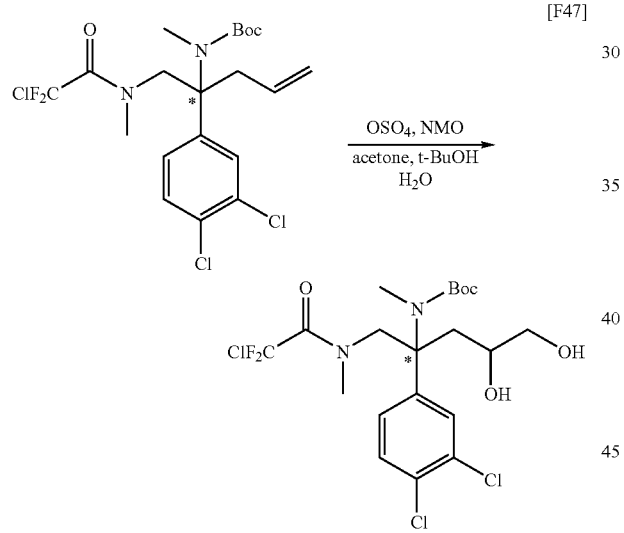

[F47]

tert-Butyl[1-{[(2-chloro-2,2-difluoroacetyl)-methylamino]-methyl}-1-(3,4-dichlorophenyl)-3-butenyl]methylcarbamate (300 mg) was dissolved in a mixture solvent of acetone (10 mL), 2-methyl-2-propanol (5 mL), and water (5 mL). Osmium tetraoxide (2.5% 2-methyl-2-propanol solution) (148 μL) and N-methylmorpholine N-oxide (218 mg) were added thereto, and the mixture was stirred overnight at room temperature. Aqueous sodium thiosulfate was added to the reaction mixture, and the resultant mixture was stirred for 30 minutes at room temperature. The insoluble matter was removed by filtration through Celite, and the filtrate was concentrated under reduced pressure. Water was added to the residue, and the mixture was extracted with methylene chloride. The organic layer was washed with saturated brine, dried over sodium sulfate anhydrate, and concentrated under reduced pressure, to thereby give the title compound (323 mg, quantative amount). The compound was used in the next step without further purification.

MS (FAB) m/z 521 ((M+3H)$^+$), 519 ((M+H)$^+$)

$^1$H-NMR (270 MHz, CDCl$_3$)δ ppm: 1.26 (9H, brs), 1.78-1.90(1H,m), 2.00-2.18 (2H, m), 2.41 (1H, t, J=4.5 Hz), 3.11 (3H, s), 3.20 (3H, s), 3.39-3.68 (1H, m), 3.72 (2H, t, J=4.5 Hz), 3.90-4.40 (1H, m), 4.90-5.44 (1H, m), 7.08 (1H, dd, J=2.0, 8.0 Hz), 7.29 (1H, d, J=2.0 Hz), 7.43 (1H, dd, J=4.5, 8.0 Hz).

Example 8(c)

Synthesis of tert-butyl[1-{[(2-chloro-2,2-difluoro-acetyl)-methylamino]-methyl}-1-(3,4-dichlorophenyl)-3-oxo-propyl]methylcarbamate

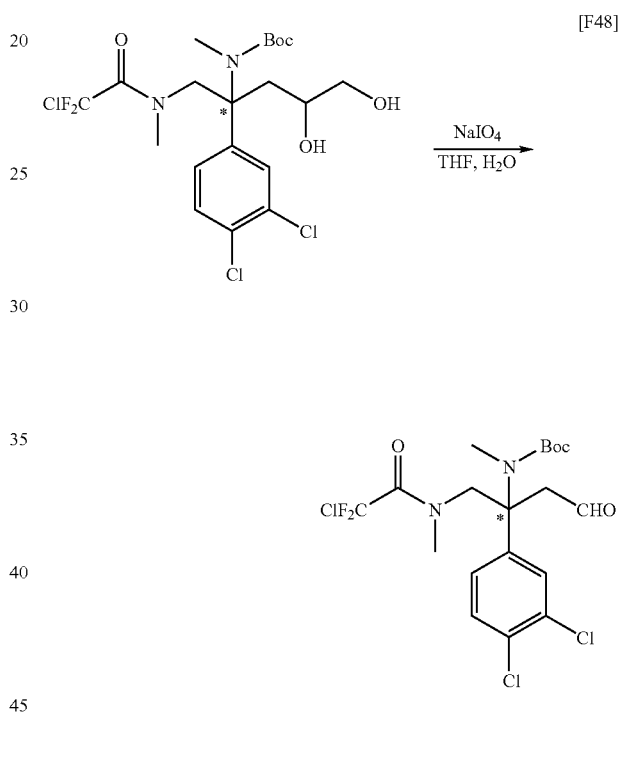

[F48]

tert-Butyl[1-{[(2-chloro-2,2-difluoroacetyl)-methylamino]-methyl}-1-(3,4-dichlorophenyl)-3,4-dihydroxybutyl]methylcarbamate (323 mg) was dissolved in a mixture solvent of tetrahydrofuran (3 mL) and water (3 mL). Sodium periodate (266 mg) was added thereto, and the mixture was stirred for 1.5 hours at room temperature. The reaction mixture was concentrated under reduced pressure, and water was added to the residue, followed by extraction with ethyl acetate. The organic layer was washed with saturated brine, dried over sodium sulfate anhydrate, and concentrated under reduced pressure, to thereby give the title compound (291 mg, 96%). The compound was used in the next step without further purification.

MS (FAB) m/z 489 ((M+3H)$^+$), 487 ((M+H)$^+$)

$^1$H-NMR (270 MHz, CDCl$_3$)δ ppm: 1.28 (9H, s), 2.97 (3H, s), 3.04 (1H, d, J=16.5 Hz), 3.07 (3H, s), 3.22 (1H, d, J=16.5 Hz), 4.36 (1H, d, J=13.5 Hz), 4.55 (1H,d, J=13.5 Hz), 7.12 (1H, dd, J=2.5, 8.5 Hz), 7.33 (1H, dd, J=2.5, 5.5 Hz), 7.43 (1H, dd, J=5.5, 8.5 Hz), 9.64 (1H, t, J=1.5 Hz).

Example 8(d)

Synthesis of tert-butyl{1-{[(2-chloro-2,2-difluoro-acetyl)-methylamino]-methyl}-1-(3,4-dichlorophenyl)-3-{spiro[benzo(c)thiophene-1(3H),4'-piperidine]-(2S)-oxide}-1'-yl-propyl}-methyl-carbamate

[F49]

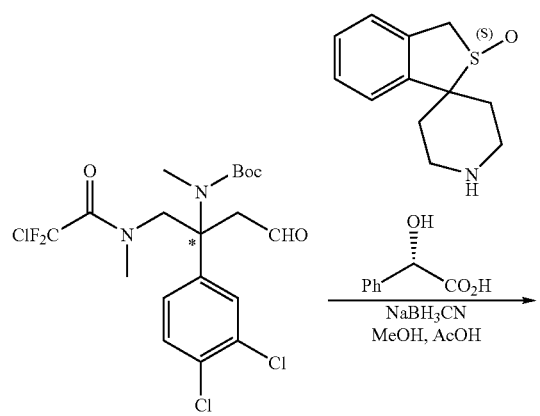

tert-Butyl[1-{[(2-chloro-2,2-difluoroacetyl)-methylamino]-methyl}-1-(3,4-dichlorophenyl)-3-oxo-propyl]methylcarbamate (956 mg) was dissolved in methanol (10 mL). Spiro[benzo(c)thiophene-1(3H),4'-piperidine]-(2S)-oxide/(S)-(+)-mandelate (878 mg) and sodium cyanoborohydride (156 mg) were added thereto. Acetic acid (0.3 mL) was added to the mixture to adjust the pH to 4, and the resultant mixture was stirred for 30 minutes at room temperature. The reaction mixture was concentrated under reduced pressure, and water was added to the residue, followed by extraction with ethyl acetate. The organic layer was washed with saturated brine, dried over sodium sulfate anhydrate, and concentrated under reduced pressure. The residue was purified through silica gel column chromatography (sequentially through use of n-hexane:ethyl acetate=1:2 and chloroform:methanol=20:1), to thereby give the title compound (1.31 g, 96%).

MS (FAB) m/z 694 ((M+3H)$^+$), 692 ((M+H)$^+$)

$^1$H-NMR (270 MHz, CDCl$_3$)δ ppm: 1.26 (9H, s), 1.51 (1H, d, J=15 Hz), 1.81-1.98 (1H, m), 2.01-2.44 (7H, m), 2.53-2.57 (1H, m), 2.74 (1H, d, J=12 Hz), 2.88(1H, d, J=12 Hz), 3.06 (3H, s), 3.11 (3H, s), 3.98 (1H, d, J=17 Hz), 4.10-4.27(1H, m), 4.30 (1H, d, J=17 Hz), 4.40-4.70 (1H, m), 7.05 (1H, dd, J=2.5, 8.5 Hz), 7.20-7.38 (5H, m), 7.42 (1H, d, J=8.5 Hz).

Example 8(e)

Synthesis of 2-chloro-N-{2-(3,4-dichlorophenyl)-2-methylamino-4-{spiro[benzo(c)thiophene-1(3H),4'-piperidine]-(2S)-oxide}-1'-yl-butyl}-2,2-difluoro-N-methyl-acetamide

[F50]

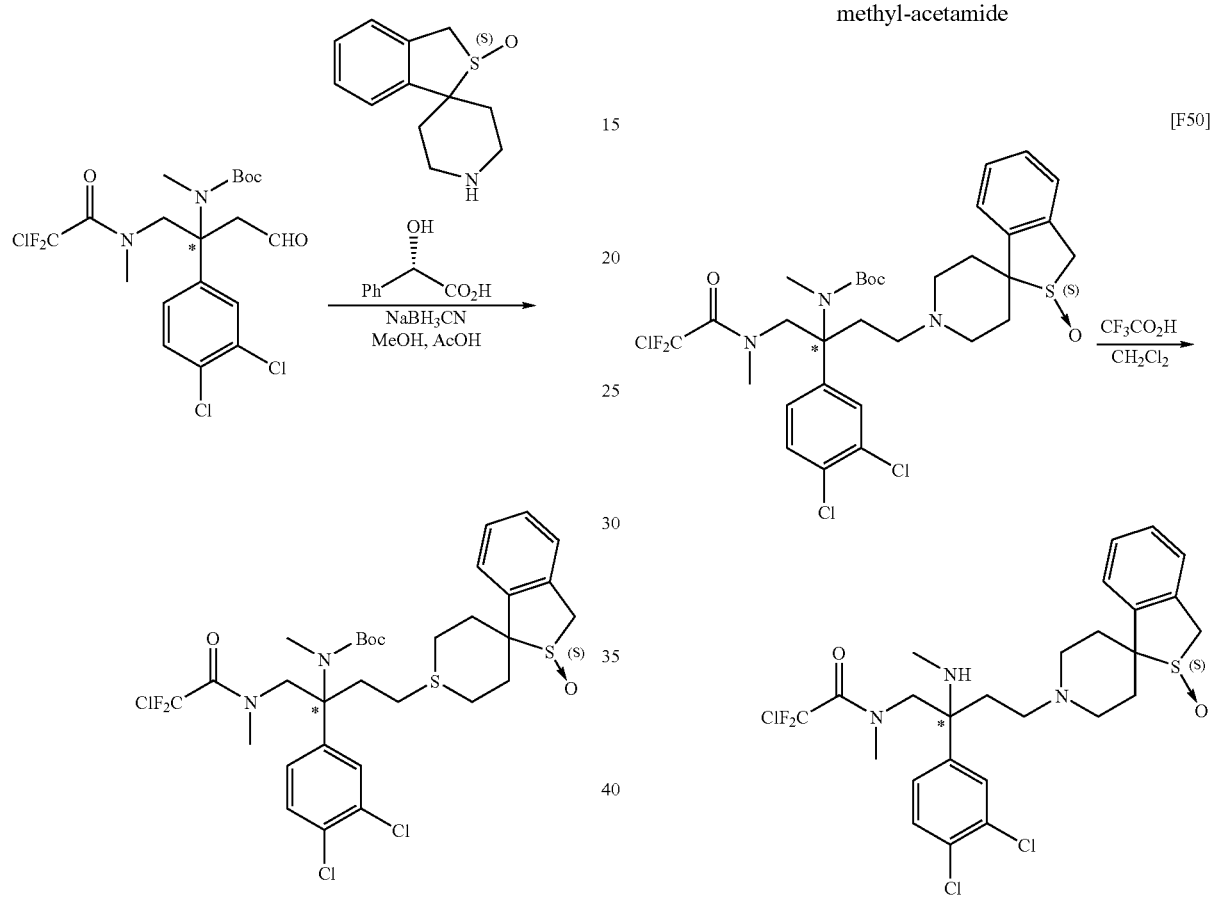

tert-Butyl{1-{[(2-chloro-2,2-difluoroacetyl)-methylamino]-methyl}-1-(3,4-dichlorophenyl)-3-{spiro[benzo(c)thiophene-1(3H),4'-piperidine]-(2S)-oxide}-1'-yl-propyl}-methyl-carbamate (1.31 g) was dissolved in methylene chloride (10 mL). Trifluoroacetic acid (5 mL) was added thereto, and the mixture was stirred for 45 minutes at room temperature. The reaction mixture was neutralized with saturated aqueous sodium bicarbonate, and the mixture was extracted with methylene chloride. The organic layer was washed with saturated brine, dried over sodium sulfate anhydrate, and concentrated under reduced pressure, to thereby give the title compound (970 mg, 87%). The compound was used in the next step without further purification.

MS (FAB) m/z 594 ((M+3H)$^+$), 592 ((M+H)$^+$)

$^1$H-NMR (270 MHz, CDCl$_3$)δ ppm: 1.57-1.65 (2H, m), 1.96-2.22 (3H, m), 2.28 (3H, s), 2.35-2.52 (6H, m), 2.75 (3H, t, J=2.0 Hz), 2.95 (1H, d, J=12 Hz), 3.06 (1H, d, J=10 Hz), 3.49 (1H, d, J=14 Hz), 3.91 (1H, d, J=14 Hz), 4.02 (1H, d, J=17 Hz), 4.34 (1H, d, J=17 Hz), 7.28-7.37 (5H, m), 7.45 (1H, d, J=8.5 Hz), 7.66(1H, d, J=2.5 Hz).

Example 8(f)

Synthesis of N-{2-(3-benzohydryl-1-methylureido)-2-(3,4-dichlorophenyl)-4-{spiro[benzo(c)thiophene-1(3H),4'-piperidine]-(2S)-oxide}-1'-yl-butyl}-2-chloro-2,2-difluoro-N-methyl-acetamide

Example 8(g)

Synthesis of N-{2-(3-benzohydryl-1-methylureido)-2-(3,4-dichlorophenyl)-4-{spiro[benzo(c)thiophene-1(3H),4'-piperidine]-(2S)-oxide}-1'-yl-butyl}-2-chloro-2,2-difluoro-N-methyl-acetamide hydrochloride (Compound No. 4)

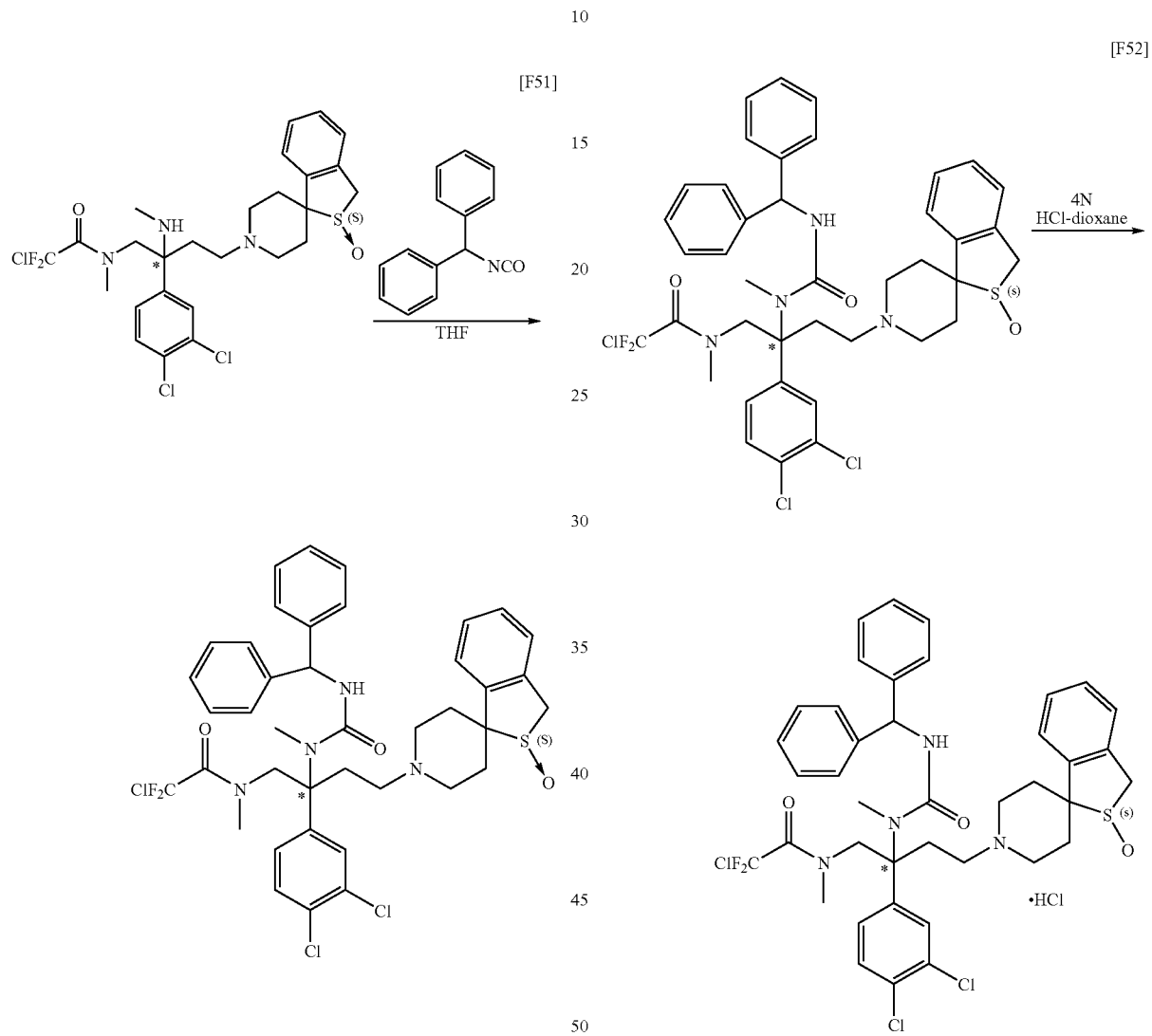

2-Chloro-N-{2-(3,4-dichlorophenyl)-2-methylamino-4-{spiro[benzo(c)thiophene-1(3H),4'-piperidine]-(2S)-oxide}-1'-yl-butyl}-2,2-difluoro-N-methyl-acetamide (85 mg) was dissolved in tetrahydrofuran (2 mL). Diphenylmethyl isocyanate (90 mg) was added thereto, and the mixture was stirred for 2 hours at room temperature. The reaction mixture was concentrated under reduced pressure, and the residue was purified through silica gel column chromatography (sequentially through use of n-hexane:ethyl acetate=1:2 and chloroform:methanol=20:1).

$^1$H-NMR (270 MHz, CDCl$_3$)δ ppm: 1.45-1.63(1H,m), 1.78-1.93(1H,m), 2.01-2.58(8H,m), 2.70-2.95(5H,m), 3.10 (3H,s), 3.98(1H,d,J=16.5 Hz), 4.30(1H,d,J=16.5 Hz), 4.42 (2H,br), 5.06(1H,d,J=7.0 Hz), 6.00(1H,d,J=7.0 Hz), 7.06 (1H,dd,J=2.5, 8.5 Hz), 7.10-7.33(16H,m).

N-{2-(3-benzohydryl-1-methylureido)-2-(3,4-dichlorophenyl)-4-{spiro[benzo(c)thiophene-1(3H),4'-piperidine]-(2S)-oxide}-1'-yl-butyl}-2-chloro-2,2-difluoro-N-methyl-acetamide was dissolved in methylene chloride. 4N HCl-1,4-dioxane was added thereto, and the mixture was concentrated under reduced pressure. Ether was added to the residue, followed by filtration and drying, to thereby give the title compound (104 mg, 88%).

MS (FAB) m/z: 803 ((M+3H)$^+$), 801 ((M+H)$^+$)

$^1$H-NMR (270 MHz, DMSO-d$_6$)δ ppm: 1.99 (1H, d, J=15 Hz), 2.26 (2H, d, J=13 Hz), 2.40-2.62 (1H, m), 2.70-2.88 (4H, m), 2.90-3.18 (7H, m), 3.20-3.43 (2H, m), 3.55 (2H, d, J=9.0 Hz), 4.08 (1H, d, J=17 Hz), 4.22-4.28 (2H, m), 4.68 (1H, d, J=17 Hz), 5.84 (1H, d, J=7.5 Hz), 7.22-7.40 (15H, m), 7.55 (2H, d, J=8.5 Hz), 10.78 (1H, br).

Example 9(a)

Synthesis of tert-butyl{1-(3,4-dichlorophenyl)-1-[(methylpropionylamino)-methyl]-3-butenyl-methyl-carbamate

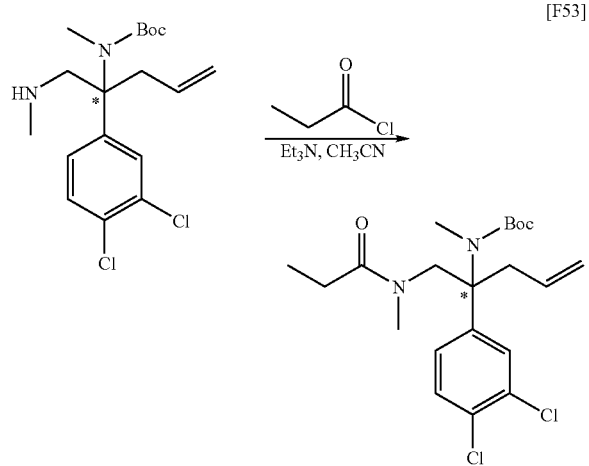

tert-Butyl[1-(3,4-dichlorophenyl)-1-methylaminomethyl-3-butenyl]methylcarbamate (2.0 g) produced in Example 4 was dissolved in acetonitrile (40 mL). Under cooling with ice, triethylamine (1.49 mL) and propionyl chloride (932 μL) were added thereto. Under cooling with ice, the mixture was stirred for 1 hour. The reaction mixture was concentrated under reduced pressure, and water was added to the residue, followed by extraction with ethyl acetate. The organic layer was washed with saturated brine, dried over sodium sulfate anhydrate, and concentrated under reduced pressure. The residue was purified through silica gel column chromatography (n-hexane:ethyl acetate=2:1), to thereby give the title compound (1.44 g, 63%).

MS (FAB) m/z 429 ((M+H)$^+$)

$^1$H-NMR (270 MHz, CDCl$_3$)δ ppm: 1.16 (3H, t, J=7.5 Hz), 1.19 (9H, brs), 2.35 (2H, q, J=7.5 Hz), 2.57 (1H, dd, J=7.5, 13.5 Hz), 2.75 (3H, s), 2.67-2.88 (1Hm), 3.08 (3H, s), 3.97-4.32 (2H, m), 4.82-5.03 (2H, m), 5.72-5.93 (1H, m), 7.01 (1H, dd, J=2.5, 8.5 Hz), 7.26 (1H, d, J=2.5 Hz), 7.36 (1H, d, J=8.5 Hz).

Example 9(b)

Synthesis of tert-butyl{1-(3,4-dichlorophenyl)-3,4-dihydroxy-1-[(methylpropionylamino)-methyl]-butyl}-methyl-carbamate

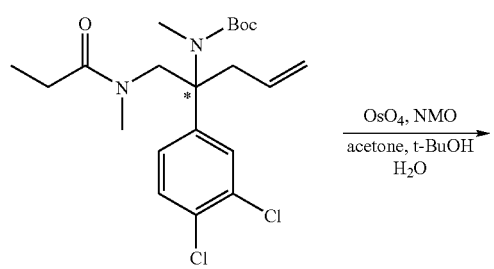

-continued

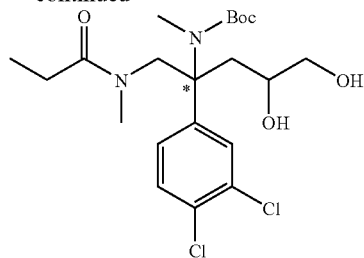

tert-Butyl(1-(3,4-dichlorophenyl)-1-[(methylpropionylamino)-methyl]-3-butenyl}-methyl-carbamate (1.0 g) was dissolved in a mixture solvent of acetone (3 mL), 2-methyl-2-propanol (1.5 mL), and water (1.5 mL). Osmium tetraoxide (2.5% 2-methyl-2-propanol solution) (278 μL) and N-methylmorpholine N-oxide (546 mg) were added thereto, and the mixture was stirred overnight at room temperature. Aqueous sodium thiosulfate was added to the reaction mixture, and the resultant mixture was stirred for 10 minutes at room temperature. The insoluble matter was removed by filtration through Celite, and the filtrate was concentrated under reduced pressure. Water was added to the residue, and the mixture was extracted with methylene chloride. The organic layer was washed with saturated brine, dried over sodium sulfate anhydrate, and concentrated under reduced pressure, to thereby give the title compound (1.09 g, quantative amount). The compound was used in the next step without further purification.

MS (FAB) m/z 463 ((M+H)$^+$)

$^1$H-NMR (270 MHz, CDCl$_3$)δ ppm: 0.93-1.45 (12H, m), 1.98-2.50 (7H, m), 2.80-3.80 (8H, m), 5.00-5.28 (1H, m), 5.50-5.75 (1H, m), 7.00-7.16 (1H, m), 7.20-7.32 (1H, m), 7.40 (1H, d, J=8.5 Hz).

Example 9(c)

Synthesis of tert-butyl{1-(3,4-dichlorophenyl)-1-[(methylpropionylamino)-methyl]-3-oxo-propyl}-methyl-carbamate

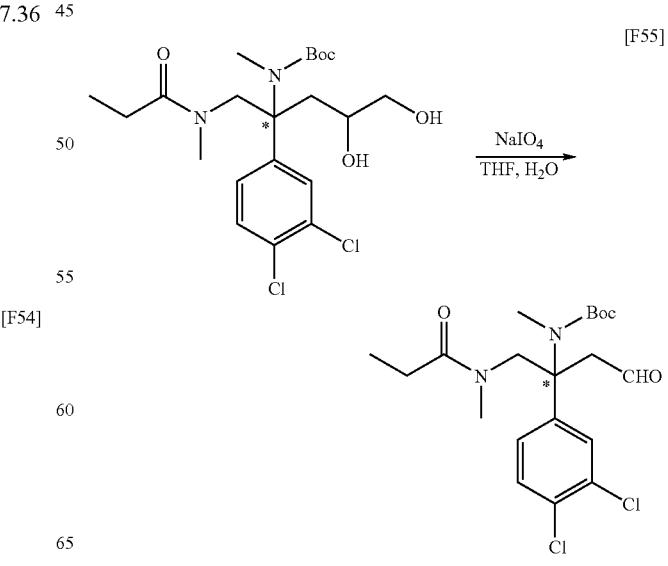

tert-Butyl{1-(3,4-dichlorophenyl)-3,4-dihydroxy-1-[(methylpropionylamino)-methyl]-butyl}-methyl-carbamate (1.09 g) was dissolved in a mixture solvent of tetrahydrofuran (8 mL) and water (8 mL). Sodium periodate (1.0 g) was added thereto, and the mixture was stirred for 1 hour at room temperature. The reaction mixture was concentrated under reduced pressure, and water was added to the residue, followed by extraction with ethyl acetate. The organic layer was washed with saturated brine, dried over sodium sulfate anhydrate, and concentrated under reduced pressure, to thereby give the title compound (1.05 g, quantative amount). The compound was used in the next step without further purification.

MS (FAB) m/z 431 ((M+H)$^+$)

$^1$H-NMR (270 MHz, CDCl$_3$)δ ppm: 1.15 (3H, t, J=7.5 Hz), 1.24 (9H, s), 2.35 (2H, q, J=7.5 Hz), 2.69 (3H, s), 2.95 (1H, d, J=14.5 Hz), 3.09 (3H, s), 3.20 (1H, d, J=14.5 Hz), 4.17 (1H, d, J=13.5 Hz), 4.44 (1H, d, J=13.5 Hz), 7.11 (1H, dd, J=2.5, 8.5 Hz), 7.33 (1H, d, J=2.5 Hz), 7.42 (1H, d, J=8.5 Hz), 9.71 (1H, t, J=2.0 Hz).

Example 9(d)

Synthesis of tert-butyl{1-(3,4-dichlorophenyl)-1-[(methylpropionylamino)-methyl]-3-{spiro[benzo(c)thiophene-1(3H),4'-piperidine]-(2S)-oxide}-1'-yl-propyl}-methyl-carbamate

[F56]

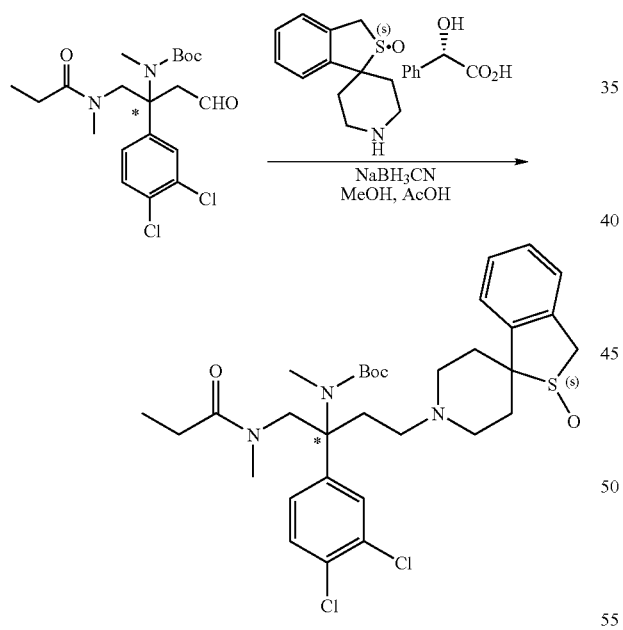

tert-Butyl{1-(3,4-dichlorophenyl)-1-[(methylpropionylamino)-methyl]-3-oxo-propyl}-methyl-carbamate (300 mg) was dissolved in methanol (5 mL). Spiro[benzo(c)thiophene-1(3H),4'-piperidine]-(2S)-oxide/(S)-(+)-mandelate (363 mg) and sodium cyanoborohydride (65 mg) was added thereto. Acetic acid was added to the mixture to adjust the pH to 4, and the mixture was stirred for 30 minutes at room temperature. The reaction mixture was concentrated under reduced pressure, and water was added to the residue, followed by extraction with chloroform. The organic layer was washed with saturated brine, dried over sodium sulfate anhydrate, and concentrated under reduced pressure. The residue was purified through silica gel column chromatography (sequentially through use of n-hexane:ethyl acetate=1:4 and chloroform:methanol=10:1), to thereby give the title compound (504 mg, 68%).

MS (FAB) m/z 636 ((M+H)$^+$)

$^1$H-NMR (270 MHz, CDCl$_3$)δ ppm: 1.18 (3H, t, J=7.5 Hz), 1.25 (9H, brs), 1.65-2.15 (6H, m), 2.20-3.25 (13H, m), 3.15 (3H, s), 4.00-4.25 (1H, m), 4.35-4.52 (1H, m), 7.12 (1H, d, J=8.5 Hz), 7.18-7.55 (6H, m).

Example 9(e)

Synthesis of N-[2-(3,4-dichlorophenyl)-2-methylamino-4-{spiro[benzo(c)thiophene-1(3H),4'-piperidine]-(2S)-oxide}-1'-yl-butyl]-N-methyl-propionamide

[F57]

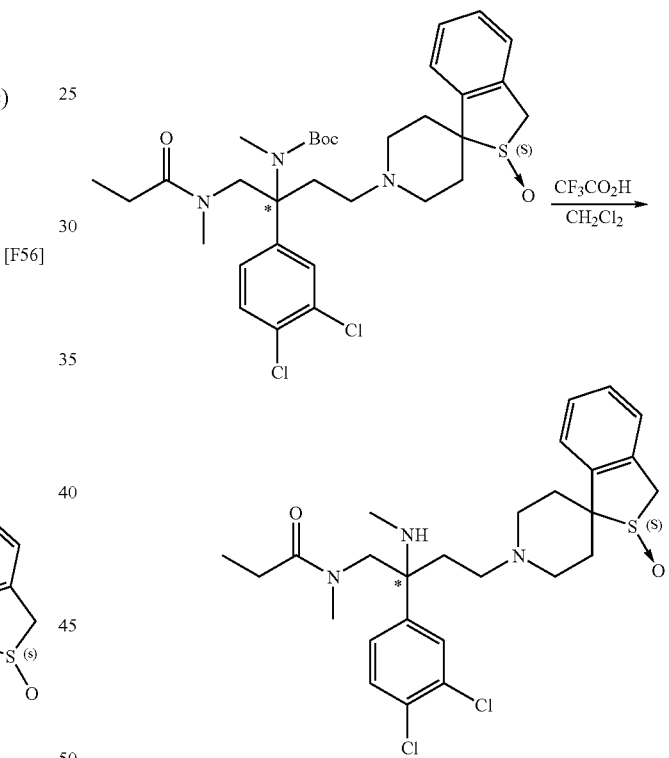

tert-Butyl{1-(3,4-dichlorophenyl)-1-[(isobutyrylmethylamino)-methyl]-3-{spiro[benzo(c)thiophene-1(3H),4'-piperidine]-(2S)-oxide}-1'-yl-propyl}-methyl-carbamate (504 mg) was dissolved in methylene chloride (10 mL). Trifluoroacetic acid (5 mL) was added thereto, and the mixture was stirred for 30 minutes at room temperature. The reaction mixture was neutralized with saturated aqueous sodium bicarbonate, and the mixture was extracted with methylene chloride. The organic layer was washed with saturated brine, dried over sodium sulfate anhydrate, and concentrated under reduced pressure, to thereby give the title compound (418 mg, 98%). The compound was used in the next step without further purification.

MS (FAB) m/z 536 ((M−H)$^+$)

$^1$H-NMR (270 MHz, CDCl$_3$)δ ppm: 0.78-0.93 (1H, m), 1.12 (3H, t, J=7.5 Hz), 1.06-1.18 (1H, m), 1.58-1.92 (3H, m), 2.10-2.66 (8H, m), 2.21 (3H, s), 2.29 (2H,q, J=7.5 Hz), 2.44 (3H, s), 3.96-4.14 (2H, m), 4.30-4.50 (2H, m), 7.13-7.58(7H, m).

Example 9(f)

Synthesis of N-{2-(3,4-dichlorophenyl)-2-[(3,3-diphenylpropionyl)-methylamino]-4-{spiro[benzo(c)thiophene-1(3H),4'-piperidine]-(2S)-oxide}-1'-yl-butyl}-N-methyl-propionamide

[F58]

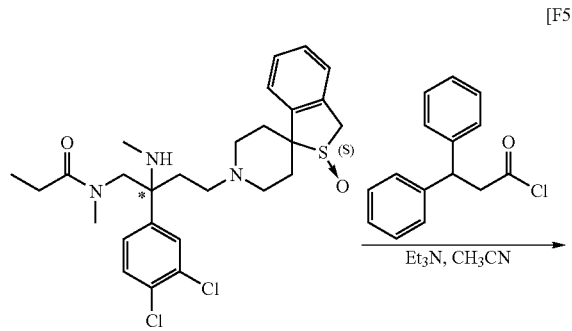

N-[2-(3,4-Dichlorophenyl)-2-methylamino-4-{spiro[benzo(c)thiophene-1(3H),4'-piperidine]-(2S)-oxide}-1'-yl-butyl]-N-methyl-propionamide (418 mg) was dissolved in acetonitrile (10 mL). Under cooling with ice, triethylamine (217 μL) and 3,3-diphenylpropionyl chloride (381 mg) were added thereto. Under cooling with ice, the mixture was stirred for 1 hour. The reaction mixture was concentrated under reduced pressure, and water was added to the residue, followed by extraction with ethyl acetate. The organic layer was washed with saturated brine, dried over sodium sulfate anhydrate, and concentrated under reduced pressure. The residue was purified through silica gel column chromatography (sequentially through use of n-hexane:ethyl acetate=1:4, ethyl acetate:methanol=10:1, and chloroform:methanol=10:1).

$^1$H-NMR (270 MHz, CDCl$_3$)δ ppm: 1.10(3H,t,J=7.5 Hz), 1.43-1.57(1H,m), 1.77-1.92(1H,m), 1.96-2.08(1H,m), 2.10-2.50(9H,m), 2.47(3H,s), 2.66-2.90(2H,m), 3.00-3.20(5H, m), 3.90-4.08(2H,m), 4.22-4.38(2H,m), 4.62(1H,t,J=7.5 Hz), 6.74(1H,d,J=8.5 Hz), 7.10-7.35(16H,m).

Example 9(g)

Synthesis of N-{2-(3,4-dichlorophenyl)-2-[(3,3-diphenylpropionyl)-methylamino]-4-{spiro[benzo(c)thiophene-1(3H),4'-piperidine]-(2S)-oxide}-1'-yl-butyl}-N-methyl-propionamide hydrochloride (Compound No. 5)

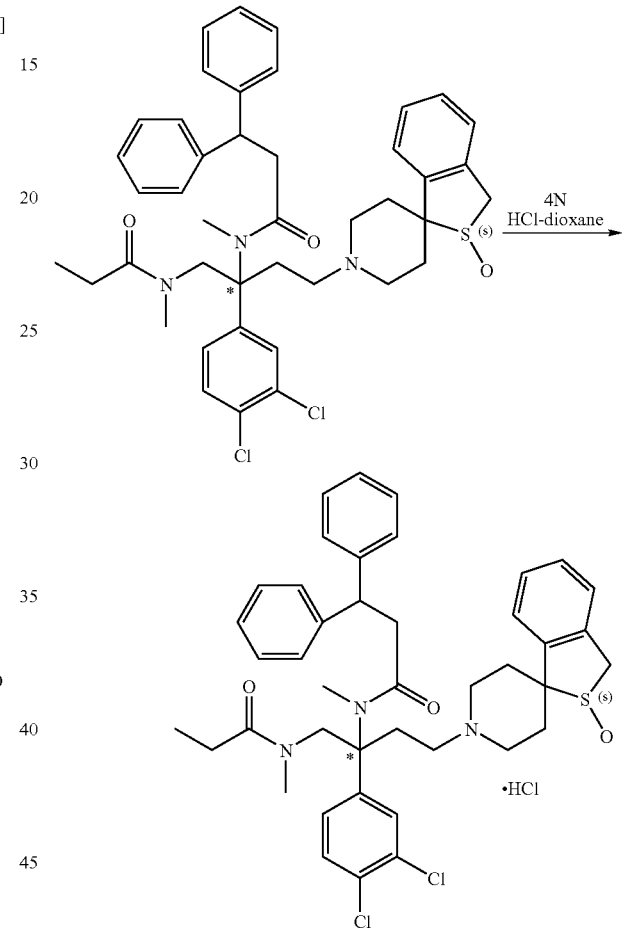

N-{2-(3,4-Dichlorophenyl)-2-[(3,3-diphenylpropionyl)-methylamino]-4-{spiro[benzo(c)thiophene-1(3H),4'-piperidine]-(2S)-oxide}-1'-yl-butyl}-N-methyl-propionamide was dissolved in methylene chloride. 4N HCl-1,4-dioxane was added thereto, and the mixture was concentrated under reduced pressure. Ether was added to the residue, followed by filtration and drying, to thereby give the title compound (388 mg, 64%).

MS (FAB) m/z 744 ((M+H)$^+$)

$^1$H-NMR (270 MHz, DMSO-d$_6$)δ ppm: 0.97 (3H, t, J=7.5 Hz), 1.96 (1H, d, J=14.5 Hz), 2.15-2.60 (13H, m), 2.88-3.52 (11H, m), 3.20 (3H, s), 3.41 (3H, s), 3.70-3.90 (1H, m), 4.08 (1H, d, J=17 Hz), 4.18 (1H, d, J=12.5 Hz), 4.36 (1H, t, J=7.0 Hz), 4.68 (1H, d, J=17 Hz), 7.00-7.50 (17H, m), 10.89 (1H, br).

Example 10

N-{2-[3-(2-Chloro-benzyl)-1-methyl-ureido]-2-(3,4-difluoro-phenyl)-4-{spiro[benzo(c)thiophene-1(3H),4'-piperidine]-(2S)-oxido}-1'-yl-butyl}-3,4,5-trimethoxy-N-methyl-benzamide hydrochloride (Compound No. 6)

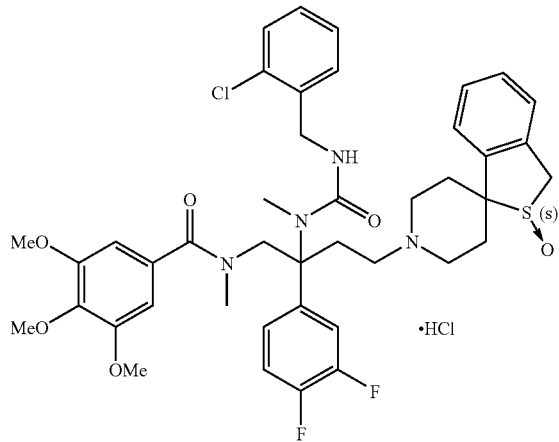

Racemic Compound

MS(FAB)m/z 809 ((M+H)$^+$)

$^1$H-NMR(270 MHz, DMSO-d$_6$)δppm: 1.92-2.10(1H,m), 2.18-2.32(2H,m), 2.40-2.88(4H,m), 3.06(3H,s), 3.00-3.30(5H,m), 3.43-3.82(12H,m), 3.90-4.13(2H,m), 4.20-4.30(2H,m), 4.43-4.57(1H,m), 4.67(1H,d,J=17 Hz), 6.63(2H,s), 7.10-7.60(12H,m), 10.6(1H,br).

Example 11

N-{2-[3-(2-Chloro-benzyl)-1-methyl-ureido]-2-phenyl-4-{spiro[benzo(c)thiophene-1(3H),4'-piperidine]-(2S)-oxido}-1'-yl-butyl}-3,4,5-trimethoxy-N-methyl-benzamide hydrochloride (Compound No. 7)

[F60]

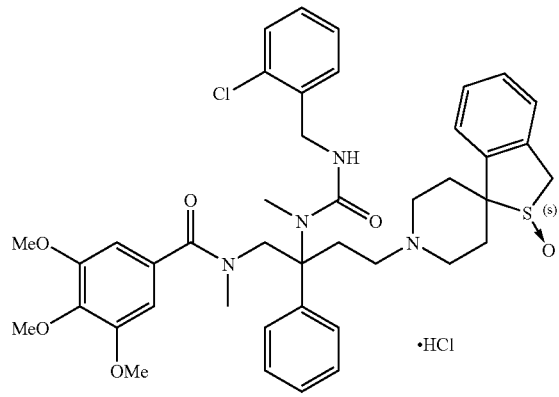

Racemic Compound

MS(FAB)m/z 773 ((M+H)$^+$)

$^1$H-NMR(270 MHz, DMSO-d$_6$)δppm: 1.92-2.08(1H,m), 2.20-2.40(4H,m), 2.58-2.90(3H,m), 2.94(3H,s), 3.00-3.30(5H,m), 3.47-3.97(12H,m), 4.07(1H,d,J=17 Hz), 4.22-4.34(2H,m), 4.60-4.78(2H,m), 6.59(2H,s), 7.03-7.14(1H,m), 7.20-7.52(13H,m), 10.6(1H,br).

Example 13

N-(2-Chloro-phenyl)-N'-{1-(3,4-dichloro-phenyl)-1-{[methyl-(3,3,3-trifluoro-propionyl)-amino]-methyl}-3-{spiro[benzo(c)thiophene-1(3H),4'-piperidine]-(2S)-oxido}-1'-yl-propyl}-N'-methyl-oxalamide hydrochloride (Compound No. 9)

[F62]

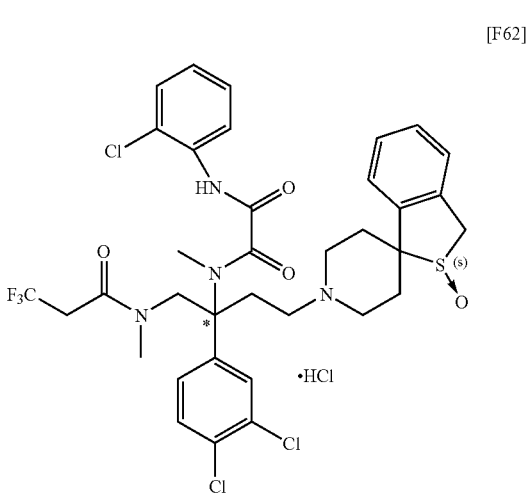

MS(FAB)m/z 772 ((M+H)$^+$)

$^1$H-NMR(270 MHz, DMSO-d$_6$)δppm: 1.92-2.10(1H,m), 2.20-2.40(2H,m), 2.52-2.94(5H,m), 3.00-3.42(7H,m), 3.50-3.80(5H,m), 3.92-4.10(1H,m), 4.09(1H,d,J=17 Hz), 4.54(1H,d,J=13.5 Hz), 4.70(1H,d,J=17 Hz), 7.25-7.40(7H,m), 7.53-7.70(4H,m), 10.34(1H,s), 10.72(1H,br).

Example 14

N-{1-(3,4-Dichloro-phenyl)-1-{[methyl-(3,3,3-trifluoro-propionyl)-amino]-methyl}-3-{spiro[benzo(c)thiophene-1(3H),4'-piperidine]-(2S)-oxido}-1'-yl-propyl}-N,N'-dimethyl-N'-phenyl-oxalamide hydlochloride (Compound No. 10)

[F63]

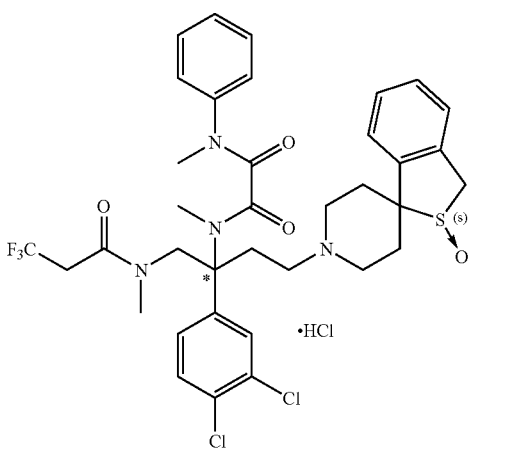

MS(FAB)m/z 751 ((M+H)⁺)
¹H-NMR(270 MHz, DMSO-$d_6$)δppm: 1.92-2.12(1H,m), 2.20-2.65(5H,m), 2.73-3.83(18H,m), 3.90-4.28(2H,m), 4.69 (1H,d,J=17 Hz), 6.64(1H,br), 7.26-7.60(11H,m), 10.68(1H, br).

Example 15

N-[2-(3-Benzhydryl-1-methyl-ureido)-2-(3,4-dichloro-phenyl)-4-{spiro[benzo(c)thiophene-1(3H), 4'-piperidine]-2,2-dioxido}-1'-yl-butyl]-2,2-difluoro-N-methyl-acetamide hydrochloride (Compound No. 11)

[F64]

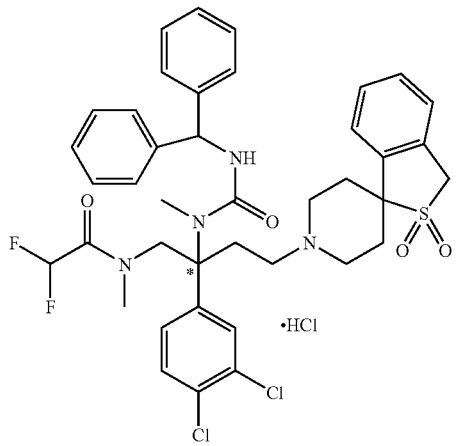

MS(FAB)m/z 783 ((M+H)⁺)
¹H-NMR(270 MHz, DMSO-$d_6$)δppm: 2.35-2.80(9H,m), 2.90-3.80(10H,m), 4.05-4.20(1H,m), 4.26(1H,d,J=13.5 Hz), 4.76(2H,s), 5.83(1H,d,J=7.5 Hz), 6.66(1H,t,J=52.5 Hz), 7.20-7.65(17H,m), 10.99(1H,br).

Example 16

N-[4-(4-Acetylamino-4-phenyl-piperidine-1'-yl)-2-(3-benzhydryl-1-methyl-ureido)-2-(3,4-dichlorophenyl)-butyl]-2,2-difluoro-N-methyl-acetamide hydrochloride (Compound No. 12)

[F65]

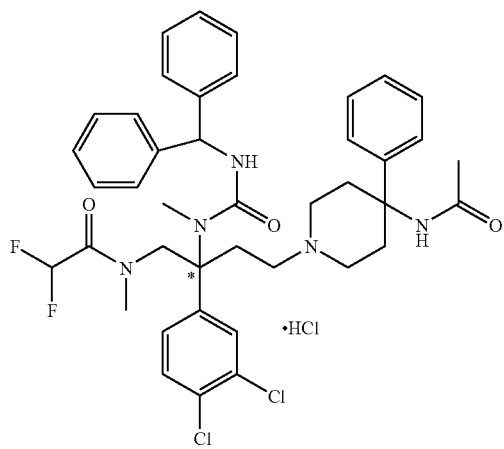

MS(FAB)m/z 764 ((M+H)⁺)
¹H-NMR(270 MHz, DMSO-$d_6$)δppm: 1.93(3H,s), 2.13-2.75(8H,m), 2.85-3.80(11H,m), 4.05-4.20(1H,m), 4.27(1H, d,J=13.5 Hz), 5.83(1H,d,J=7.5 Hz), 6.68(1H,t,J=52.5 Hz), 7.18-7.45(16H,m), 7.50-7.62(2H,m), 8.19(1H,s), 10.11(1H, br).

Example 17

N-{1-(3,4-Dichloro-phenyl)-1-{[methyl-(3,3,3-trifluoro-propionyl)-amino]-methyl}-3-{spiro[benzo(c)thiophene-1(3H),4'-piperidine]-(2S)-oxido}-1'-yl-propyl}-N-methyl-benzamide hydrochloride (Compound No. 13)

[F66]

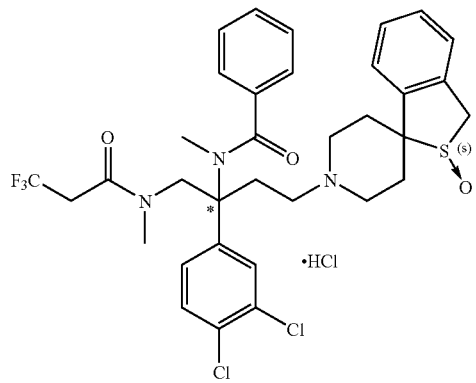

MS(FAB)m/z 694 ((M+H)⁺)
¹H-NMR(270 MHz, DMSO-$d_6$)δppm: 2.02(1H,d,J=16 Hz), 2.20-2.40(2H,m), 2.52-2.90(6H,m), 3.00-3.80(11H,m), 4.02-4.18(2H,m), 4.50(1H,d,J=13.5 Hz), 4.70(1H,d,J=17.5 Hz), 7.26-7.65(11H,m), 7.75(1H,s), 10.57(1H,br).

Example 18

N-[2-(3,4-Dichloro-phenyl)-2-(methyl-phenylacetyl-amino)-4-{spiro[benzo(c)thiophene-1(3H),4'-piperidine]-(2S)-oxido}-1'-yl-butyl]-3,3,3-trifluoro-N-methyl-propionamide hydrochloride (Compound No. 14)

[F67]

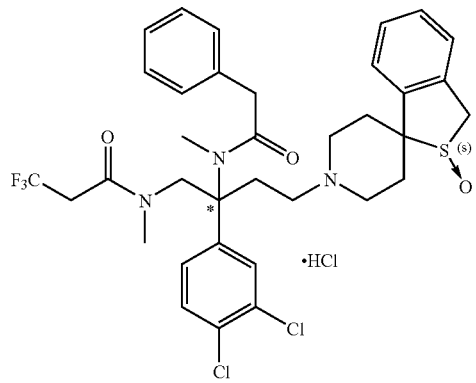

MS(FAB)m/z 708 ((M+H)⁺)
¹H-NMR(270 MHz, DMSO-$d_6$)δppm: 1.99(1H,d,J=15 Hz), 2.20-2.90(8H,m), 2.94-3.20(7H,m), 3.46-3.80(7H,m), 3.85-4.00(1H,m), 4.08(1H,d,J=17 Hz), 4.33(1H,d,J=14 Hz), 4.70(1H,d,J=17 Hz), 7.10-7.58(12H,m), 10.6(1H,br).

Example 19

1-[4-(3,4-Dichloro-phenyl)-4-(1-methyl-3-phenyl-ureido)-5-(3,4,5-trimethoxy-benzyloxy)-pentyl]-4-phenyl-piperidine-4-carboxylic acid amide (Compound No. 15)

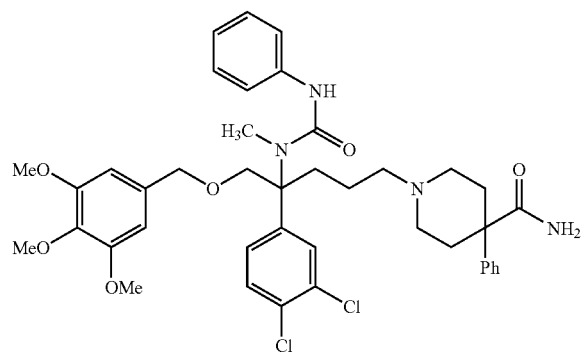

Racemic Compound

MS(FAB)m/z 763 ((M+H)$^+$)

$^1$H-NMR(270 MHz, CDCl$_3$)δppm: 1.20-1.38(2H,m), 1.95-2.10(4H,m), 2.16-2.40(6H,m), 2.42-2.58(2H,m), 3.05 (3H,s), 3.77(6H,s), 3.83(3H,s), 4.00(1H,d,J=10 Hz), 4.09 (1H,d,J=10 Hz), 4.48(2H,s), 5.18(2H,br), 6.44(2H,s), 6.86-7.00(3H,m), 7.18-7.40(10H,m), 7.45(1H,d,J=2.0 Hz).

Example 20

(3-(4-Carbamoyl-4-phenyl-piperidine-1-yl)-1-(3,4-dichloro-phenyl)-1-{[methyl-(3,4,5-trimethoxy-benzoyl)-amino]-methyl}-propyl)-methyl-carbamic acid phenyl ester hydrochloride (Compound No. 16)

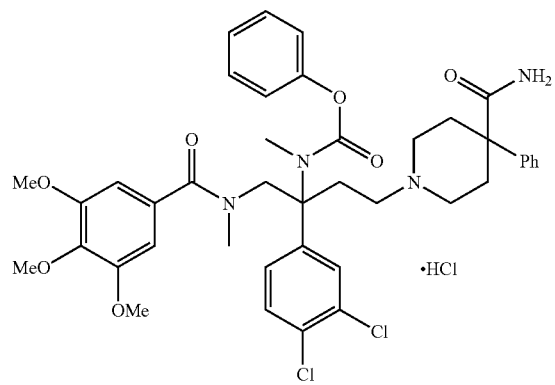

Racemic Compound

MS(FAB)m/z 777 ((M+H)$^+$)

$^1$H-NMR(270 MHz, DMSO-d$_6$)δppm: 2.00-2.20(2H,m), 2.52-3.40(16H,m), 3.50-3.82(2H,m), 3.68(3H,s), 3.80(6H, s), 3.90-4.10(1H,m), 4.57-4.72(1H,m), 6.66(2H,s), 6.93-7.60(11H,m), 7.67(1H,d,J=8.0 Hz), 7.78(1H,brs), 10.70(1H, br).

Example 21

[4-(4-Carbamoyl-4-phenyl-piperidine-1-yl)-1-(3,4-dichloro-phenyl)-1-(3,4,5-trimethoxy-benzyloxymethyl)-butyl]-methyl-carbamic acid phenyl ester hydrochloride (Compound No. 17)

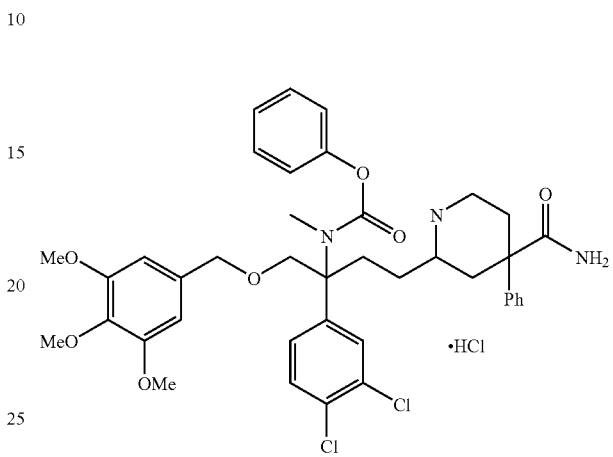

Racemic Compound

MS(FAB)m/z 764 ((M+H)$^+$)

$^1$H-NMR(270 MHz, CDCl$_3$)δppm: 2.24-2.80(8H,m), 2.86-3.15(4H,m), 3.31(3H,s), 3.38-3.52(2H,m), 3.82(9H,s), 3.90-4.10(2H,m), 4.44(2H,s), 5.22-5.38(2H,m), 6.45(2H,s), 6.80-7.08(2H,m), 7.10-7.48(11H,m), 12.18(1H,br).

Example 22

1-{4-(3,4-Dichloro-phenyl)-4-dimethylamino-5-[methyl-(3,4,5-trimethoxy-benzyl)-amino]-pentyl}-4-phenyl-piperidine-4-carboxylic acid amide (Compound No. 18)

Racemic Compound

MS(FAB)m/z 671 ((M+H)$^+$)

$^1$H-NMR(270 MHz, CDCl$_3$)δppm: 1.30-1.48(2H,m), 1.95-2.45(19H,m), 2.50-2.65(2H,m), 2.79(1H,d,J=14 Hz), 2.98(1H,d,J=14 Hz), 3.33(1H,d,J=13 Hz), 3.53(1H,d,J=13 Hz), 3.82(3H,s), 3.83(6H,s), 5.19(2H,br), 6.48(2H,s), 7.20-7.45(7H,m), 7.64(1H,s).

Example 23

1-[4-(3,4-Dichloro-phenyl)-4-dimethylamino-5-(3,4,5-trimethoxy-benzoylamino)-pentyl]-4-phenyl-piperidine-4-carboxylic acid amide (Compound No. 19)

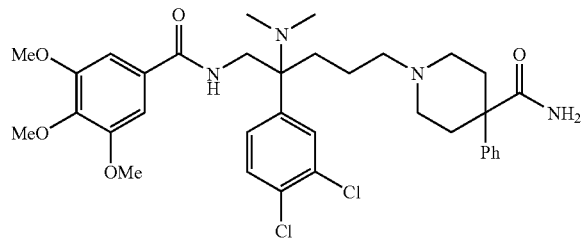

Racemic Compound

MS(FAB)m/z 671 ((M+H)$^+$)

$^1$H-NMR(270 MHz, CDCl$_3$)δppm: 1.33-1.56(2H,m), 1.72-1.88(1H,m), 1.94-2.10(3H,m), 2.20-2.40(12H,m), 2.44-2.58(2H,m), 3.67-3.78(1H,m), 3.82-4.00(10H,m), 5.15 (2H,br), 6.50-6.58(1H,m), 6.92(2H,s), 7.20-7.38(6H,m), 7.44(1H,d,J=8.5 Hz), 7.52(1H,d,J=2.0 Hz).

Example 24

1-[3-Amino-3-(3,4-dichloro-phenyl)-4-(3,4,5-trimethoxy-benzyloxy)-butyl]-4-phenyl-piperidine-4-carboxylic acid amide (Compound No. 20)

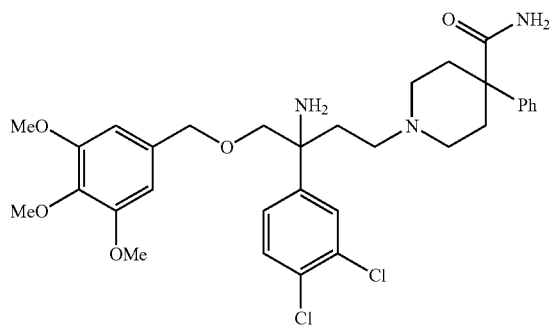

Racemic Compound

MS(FAB)m/z 616 ((M+H)$^+$)

$^1$H-NMR(270 MHz, CDCl$_3$)δ ppm: 1.78-2.70(14H,m), 3.52(2H,dd,J=9.0, 25.5 Hz), 3.80(6H,s), 3.83(3H,s), 4.41 (2H,dd,J=12, 26.5 Hz), 5.25(2H,br), 6.41(2H,s), 7.2.5-7.39 (7H,m), 7.59(1H,d,J=2.0 Hz).

Example 25

N-[1-(3,4-Dichloro-phenyl)-3-{spiro[((2S)-hydroxy)indan-1,4'-piperidine]}-1'-yl-1-(3,4,5-trimethoxy-benzyloxymethyl)-propyl]-N-methyl-oxamic acid ethyl ester hydrochloride (Compound No. 21)

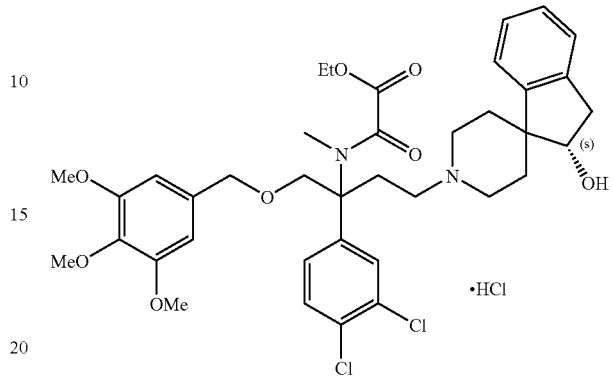

Racemic Compound

MS(FAB)m/z 729 ((M+H)$^+$)

$^1$H-NMR(270 MHz, DMSO-d$_6$)δ ppm: 1.09(3H,t,J=7.0 Hz) 1.56-1.67(1H,m), 1.88-2.34(4H,m), 2.60-3.00(5H,m), 3.08-3.78(14H,m), 3.92-4.10(2H,m), 4.31(2H,q,J=7.0 Hz), 4.27-4.50(3H,m), 5.05(1H,br), 6.50(2H,s), 6.54(2H,br), 7.05-7.50(5H,m), 7.63(1H,s), 7.65(1H,d,J=8.5 Hz), 10.16 (1H,br).

Example 26(a)

Synthesis of tert-butyl[2-(S)-(3,4-dichlorophenyl)-1-hydroxy(4-pentene)-2-yl]-methylcarbamate

[F75]

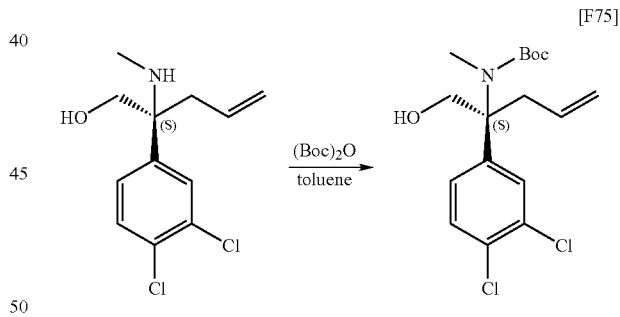

2-(S)-(3,4-Dichlorophenyl)-2-methylamino-4-pentenol (271.5 g) was dissolved in absolute toluene (1.0 L). At room temperature, a solution of di-tert-butylcarbonate (341.6 g) in absolute toluene (0.36 L) was added thereto, and the mixture was refluxed for 3 hours. Under cooling with ice, 28% aqueous ammonia (76 mL) was added to the reaction mixture, and the resultant mixture was stirred for 30 minutes. n-Hexane (0.8 L) was added to the reaction mixture. The organic layer was sequentially washed with water, 1.5% hydrochloric acid, water, saturated aqueous sodium bicarbonate, water, and saturated brine, and then dried over sodium sulfate anhydrate. The solvent was concentrated under reduced pressure, to thereby give the title compound (383 g). The compound was used in the next step without further purification.

MS (EI) m/z 359 (M$^+$)

¹H-NMR (270 MHz, CDCl₃) δ ppm: 1.38 (9H, s), 2.75 (3H, s), 2.70-2.98 (2H, m), 3.68-3.82 (1H, m), 4.02-4.18 (1H, m), 5.10-5.25 (2H, m), 5.75-5.97 (1H, m), 7.12 (1H, dd, J=2.5, 8.5 Hz), 7.36 (1H, d, J=2.5 Hz), 7.41 (1H, d, J=8.5 Hz).

Example 26(b)

Synthesis of tert-butyl[1-(S)-(3,4-dichlorophenyl)-1-formyl(3-butenyl)]methylcarbamate

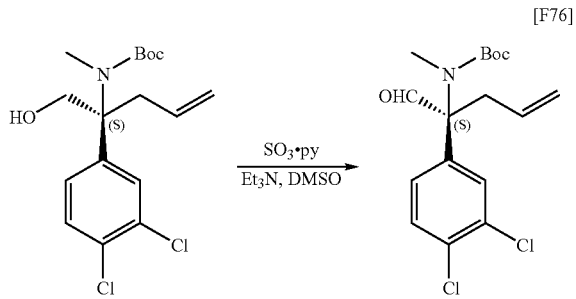

tert-Butyl[2-(S)-(3,4-dichlorophenyl)-1-hydroxy(4-pentene)-2-yl]-methylcarbamate (383 g) was dissolved in anhydrous dimethyl sulfoxide (1.92 L). At room temperature, triethylamine (636 g) was added thereto. Under cooling with ice, pyridine sulfur trioxide complex (499 g) was added to the mixture, and the resultant mixture was stirred for 3 hours at room temperature. The reaction mixture was poured into ice-water and then extracted with ethyl acetate. The organic layer was sequentially washed with saturated aqueous sodium bicarbonate, water, and saturated brine, and then dried over sodium sulfate anhydrate. The solvent was concentrated under reduced pressure, to thereby give the title compound (417.8 g). The compound was used in the next step without further purification.

MS (EI) m/z 357 (M⁺)

¹H-NMR (270 MHz, CDCl₃) δ ppm: 1.47 (9H, s), 2.53-2.77 (4H, m), 3.32-3.50 (1H, m), 5.05-5.25 (2H, m), 5.83-6.07 (1H, m), 7.22 (1H, dd, J=2.5, 8.5 Hz), 7.46 (1H, d, J=2.5 Hz), 7.49 (1H, d, J=8.5 Hz), 9.36 (1H, s).

Example 26(c)

Synthesis of tert-butyl[2-(S)-(3,4-dichlorophenyl)-1-methylimino(4-penten-2-yl)]methylcarbamate

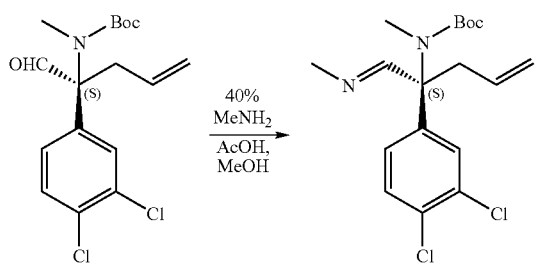

At room temperature, 40% methylamine-methanol solution (1,230 mL) was added to acetic acid (529 g), and the mixture was stirred for 20 minutes. A solution of tert-butyl [1-(S)-(3,4-dichlorophenyl)-1-formyl(3-butenyl)]methylcarbamate (330.1 g) in methanol (600 mL) was added to the reaction mixture, and the resultant mixture was refluxed for 1 hour. 40% Methylamine-methanol solution (137 mL) was further added to the mixture, and the resultant mixture was refluxed for another 15 minutes. The reaction mixture was poured into saturated aqueous sodium bicarbonate, extracted with ethyl acetate, sequentially washed with water and saturated brine, and dried over sodium sulfate anhydrate. The solvent was concentrated under reduced pressure, to thereby give the title compound (324.5 g). The compound was used in the next step without further purification.

MS (EI) m/z 370 (M⁺)

¹H-NMR (270 MHz, CDCl₃) δ ppm: 1.35 (9H, s), 2.76 (3H, s), 2.80-2.93 (1H, m), 3.25 (3H, d, J=2.0 Hz), 3.30-3.42 (1H, m), 5.01-5.18 (2H, m), 5.80-6.00 (1H, m), 7.15 (1H, dd, J=2.0, 8.5 Hz), 7.35-7.46 (2H, m), 7.78 (1H, s).

Example 26(d)

Synthesis of tert-butyl[2-(S)-(3,4-dichlorophenyl)-1-methylamino(4-penten-2-yl)]methylcarbamate

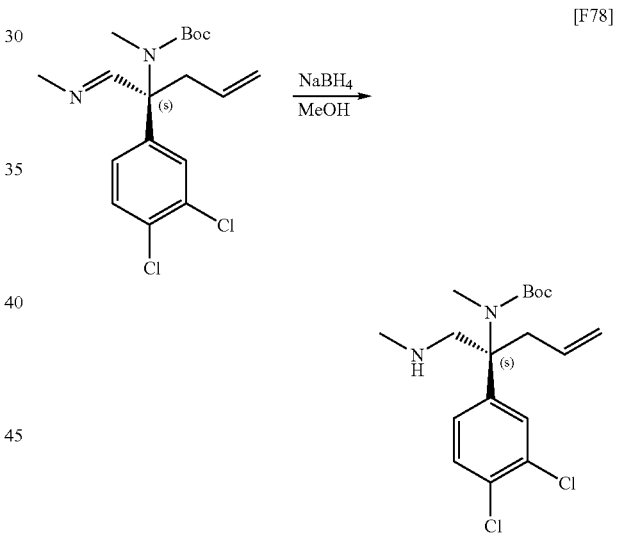

tert-Butyl[2-(S)-(3,4-dichlorophenyl)-1-methylimino(4-penten-2-yl)]methylcarbamate (314.5 g) was dissolved in methanol (2 L). Under cooling with ice, sodium boron hydride (38.5 g) was added thereto, and the mixture was stirred for 3 hours. Acetone (177 g) was added to the reaction mixture and then stirred for 30 minutes. The reaction mixture was poured into water, and the resultant mixture was extracted with ethyl acetate. The organic layer was sequentially washed with water and saturated brine and dried over sodium sulfate anhydrate. The solvent was concentrated under reduced pressure, and the residue was dissolved in methanol (2 L). Under cooling with ice, sodium boron hydride (16.0 g) was added thereto, and the mixture was stirred for 30 minutes. Acetone (49.2 g) was added to the reaction mixture, and the resultant mixture was stirred for 30 minutes. The reaction mixture was poured into water, and the mixture was extracted with ethyl acetate. The organic layer was sequentially washed with water and saturated brine and dried over sodium sulfate anhydrate. The solvent was concentrated under reduced pressure, to thereby give the title compound (318.8 g). The compound was used in the next step without further purification.

MS (EI) m/z 372 (M+)

$^1$H-NMR (270 MHz, CDCl$_3$)δ ppm: 1.19 (9H, s), 2.33 (3H, s), 2.72-3.03 (4H, m), 3.10 (3H, s), 3.06-3.22 (1H, m), 5.08-5.20 (2H, m), 5.58-5.77 (1H, m), 7.08 (1H, dd, J=2.5, 8.5 Hz), 7.30-7.40 (2H, m).

Example 26(e)

Synthesis of tert-butyl[1-(3,3,3-trifluoro-N-methyl-propanamido)-2-(S)-(3,4-dichlorophenyl)(4-penten-2-yl)]methylcarbamate

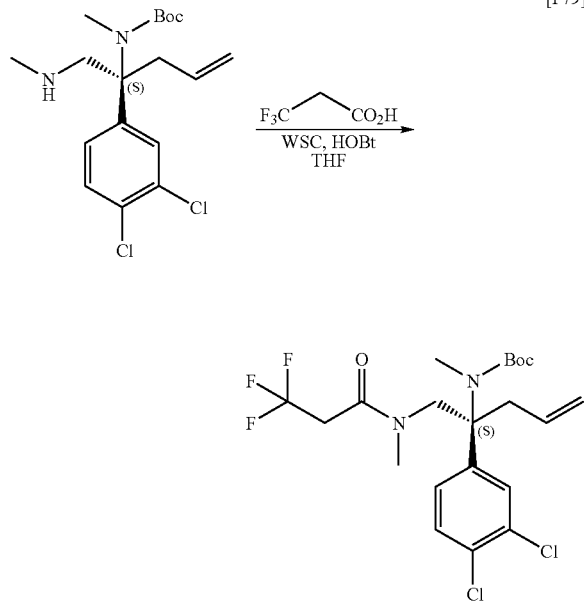

1-Hydroxybenzotriazole monohydrate (11.5 g) was dissolved in anhydrous tetrahydrofuran (0.8 L). At room temperature, 3,3,3-trifluoropropionic acid (120.3 g) was added thereto. Under cooling with ice, 1-[3-(dimethylaminopropyl)-3-ethylcarbodiimide hydrochloride (180.0 g) was added to the mixture, and the resultant mixture was stirred for 10 minutes at the same temperature. A solution of tert-butyl[2-(S)-(3,4-dichlorophenyl)-1-methylamino(4-penten-2-yl)]methylcarbamate (318.8 g) in anhydrous tetrahydrofuran (0.9 L) was added thereto, and the mixture was stirred for 2 hours at room temperature. The reaction mixture was poured into water, extracted with ethyl acetate, sequentially washed with water, aqueous citric acid, saturated aqueous sodium bicarbonate, and saturated brine, and dried over sodium sulfate anhydrate. The solvent was concentrated under reduced pressure, and the residue was purified through silica gel column chromatography (n-hexane:ethyl acetate=6:1 to 5:1 to 2:1 to 1:1), to thereby give the title compound (275.7 g, 69.7%, 5 steps).

MS (FAB) m/z 483 ((M+H)+)

$^1$H-NMR (270 MHz, CDCl$_3$)δ ppm: 1.22 (9H, brs), 2.57 (1H, dd, J=6.5, 7.5 Hz), 2.74-2.90 (1H, m), 2.85 (3H, s), 3.07 (3H, s), 3.27-3.38 (2H, m), 4.05-4.20 (1H, m), 4.25-4.42 (1H, m), 4.85-5.04 (2H, m), 5.64-5.85 (1H, m), 7.00 (1H, dd, J=2.5, 8.5 Hz), 7.25 (1H, d, J=2.5 Hz), 7.37 (1H, d, J=8.5 Hz).

Example 26(f)

Synthesis of tert-butyl{[2-(S)-(3,4-dichlorophenyl)-1-(3,3,3-trifluoro-N-methylpropanamido)-4,5-dihydroxy]pentan-2-yl}methylcarbamate

[F80]

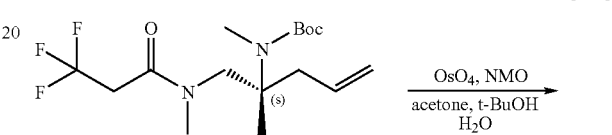
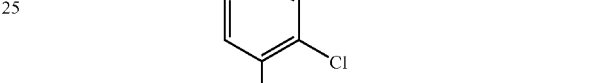
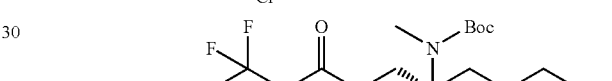

tert-Butyl[1-(3,3,3-trifluoro-N-methylpropanamido)-2-(S)-(3,4-dichlorophenyl)(4-penten-2-yl)]methylcarbamate (275.7 g) was dissolved in acetone (690 mL), and t-butyl alcohol (345 mL) and water (345 mL) were added thereto. At room temperature, N-methylmorpholine-N-oxide (103.3 g) and osmium tetraoxide (2.5% t-butyl alcohol solution) (58.0 mL) were added to the mixture, and the resultant mixture was stirred for 14 hours at the same temperature. Under cooling with ice, an aqueous solution (2 L) of sodium thiosulfate pentahydrate (276 g) was added to the reaction mixture, and then stirred for 15 minutes at the same temperature. Water was added to the reaction mixture, and the resultant mixture was extracted with ethyl acetate. The organic layer was sequentially washed with aqueous citric acid, water, saturated aqueous sodium bicarbonate, and saturated brine, and dried over sodium sulfate anhydrate. The solvent was concentrated under reduced pressure, to thereby give the title compound (297.8 g). The compound was used in the next step without further purification.

MS (FAB) m/z 518 ((M+H)+)

$^1$H-NMR (270 MHz, CDCl$_3$)δ ppm: 1.20 (9H, brs), 1.93-2.53 (4H, m), 3.09 (3H, s), 3.00-3.62 (6H, m), 3.68-3.80 (2H, m), 4.68-5.38 (2H, m), 7.00-7.10 (1H, m), 7.20-7.32 (1H, m), 7.37-7.46 (1H, m).

Example 26(g)

Synthesis of tert-butyl{[2-(S)-(3,4-dichlorophenyl)-1-(3,3,3-trifluoro-N-methylpropanamido)-4-oxo]butan-2-yl}methylcarbamate

[F81]

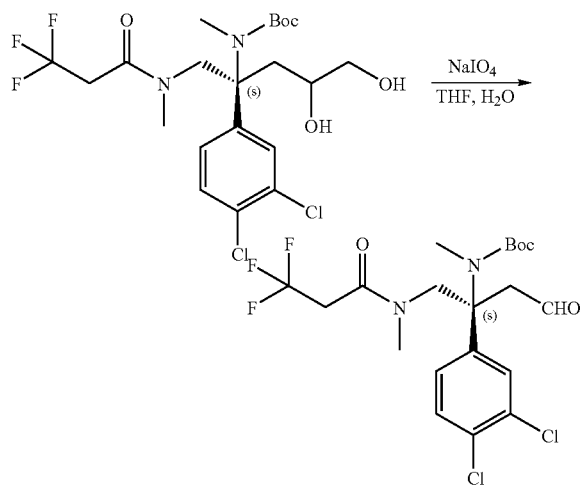

tert-Butyl{[2-(S)-(3,4-dichlorophenyl)-1-(3,3,3-trifluoro-N-methylpropanamido)-4,5-dihydroxy]pentan-2-yl}methylcarbamate (297.8 g) was dissolved in tetrahydrofuran (2.4 L). A solution of sodium periodate (246.0 g) in water (1.2 L) was added thereto, and the mixture was stirred for 30 minutes at room temperature. The reaction mixture was poured into water, extracted with ethyl acetate, sequentially washed with water and saturated brine, and dried over sodium sulfate anhydrate. The solvent was concentrated under reduced pressure, to thereby give the title compound (277.7 g). The compound was used in the next step without further purification.

MS (FAB) m/z 485 ((M+H)$^+$)

$^1$H-NMR (270 MHz, CDCl$_3$)δ ppm: 1.26 (9H, brs), 2.78 (3H, s), 2.94-3.14 (1H, m), 3.07 (3H, s), 3.18-3.37 (3H, m), 4.24 (1H, d, J=13.5 Hz), 4.52 (1H, d, J=13.5 Hz), 7.10 (1H, dd, J=2.0, 8.5 Hz), 7.33 (1H, d, J=2.0 Hz), 7.43 (1H, d, J=8.5 Hz), 9.67 (1H, t, J=2.0 Hz).

Example 26(h)

Synthesis of tert-butyl{[1-(3,3,3-trifluoro-N-methylpropanamido)-2-(S)-(3,4-dichlorophenyl)-4-[3-oxo-3,4-dihydro-2H-spiro(isoquinoline-1,4'-piperidin)-1'-yl]butan-2-yl]methylcarbamate

[F82]

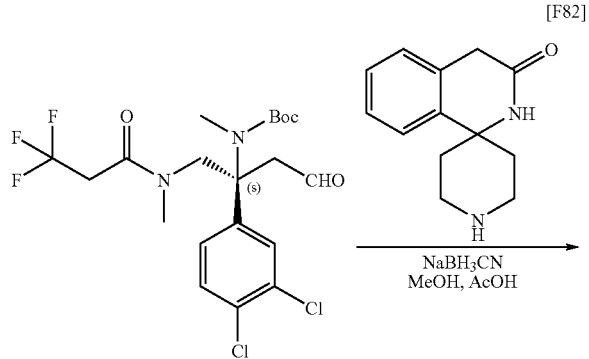

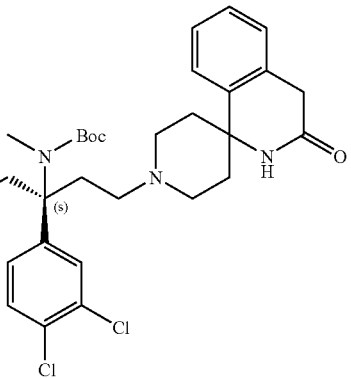

tert-Butyl{[2-(S)-(3,4-dichlorophenyl)-1-(3,3,3-trifluoro-N-methylpropanamido)-4-oxo]butan-2-yl}methylcarbamate (3.0 g) was dissolved in methanol (15 mL). Under cooling with ice, sodium cyanoborohydride (450 mg) and 3-oxo-3,4-dihydro-2H-spiro(isoquinoline-1,4'-piperidine) (1.47 g) were added thereto, and thereafter acetic acid (0.6 mL) was added thereto, followed by stirring for 30 minutes at room temperature. The reaction mixture was poured into saturated aqueous sodium bicarbonate, extracted with ethyl acetate, sequentially washed with water and saturated brine, and dried over sodium sulfate anhydrate. The solvent was concentrated under reduced pressure, to thereby give the title compound (4.23 g, 99.8%). The compound was used in the next step without further purification.

MS (FAB) m/z 685 ((M+H)$^+$)

$^1$H-NMR (400 MHz, CDCl$_3$)δ ppm: 1.24 (9H, s), 1.65-1.78 (2H, m), 1.87-2.30 (7H, m), 2.50-3.02 (6H, m), 3.12 (3H, s), 3.16-3.40 (2H, m), 3.61 (2H, s), 4.00-4.22 (1H, m), 4.45-4.67 (1H, m), 6.30 (1H, br), 7.02-7.07 (1H, m), 7.12-7.16 (1H, m), 7.22-7.44 (5H, m).

Example 26(i)

Synthesis of N-{2-(S)-(3,4-dichlorophenyl)-2-methylamino-4-[3-oxo-3,4-dihydro-2H-spiro(isoquinoline-1,4'-piperidin)-1'-yl]butyl}-3,3,3-trifluoro-N-methylpropanamido

[F83]

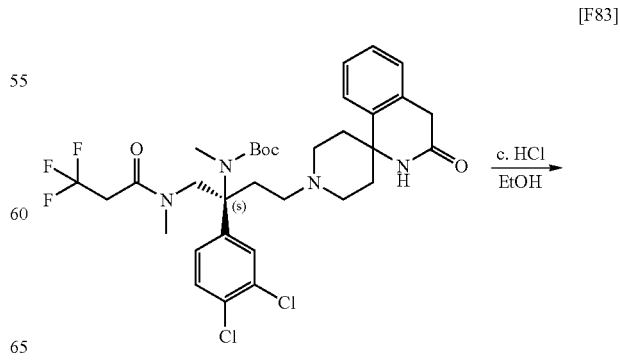

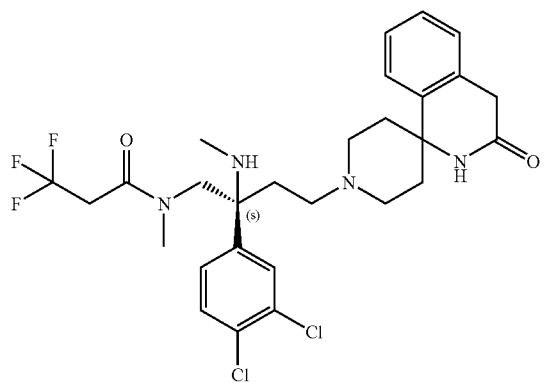
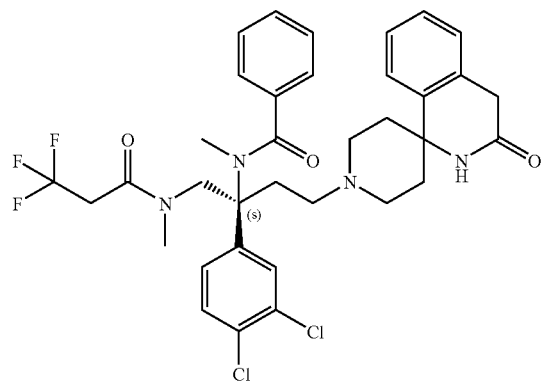

tert-Butyl{[1-(3,3,3-trifluoro-N-methylpropanamido)-2-(S)-(3,4-dichlorophenyl)-4-[3-oxo-3,4-dihydro-2H-spiro(isoquinoline-1,4'-piperidin)-1'-yl]butan-2-yl]methylcarbamate (4.22 g) was dissolved in ethanol (20 mL). Under cooling with ice, concentrated hydrochloric acid (20 mL) was added dropwise thereto, and the mixture was stirred for 1.5 hours at room temperature. The reaction mixture was poured into saturated aqueous sodium bicarbonate, and the mixture was extracted with ethyl acetate. The organic layer was sequentially washed with water and saturated brine, and then dried over sodium sulfate anhydrate. The solvent was concentrated under reduced pressure, to thereby give the title compound (3.55 g, 98.4%).

MS (FAB) m/z 585 ((M+H)$^+$)

$^1$H-NMR (400 MHz, CDCl$_3$)δ ppm: 1.80 (2H, d, J=12.5 Hz), 1.93-2.40 (11H, m), 2.47-2.60 (4H, m), 2.90-3.00 (2H, m), 3.18-3.20 (2H, m), 3.44 (1H, d, J=14 Hz), 3.64 (2H, s), 3.95 (1H, d, J=14 Hz), 6.37 (1H, br), 7.14-7.18 (1H, m), 7.24-7.40 (4H, m), 7.44 (1H, d, J=8.5 Hz), 7.62 (1H, d, J=2.0 Hz).

Example 26(j)

Synthesis of N-{1-(3,3,3-trifluoro-N-methylpropanamido)-2-(S)-(3,4-dichlorophenyl)-4-[3-oxo-3,4-dihydro-2H-spiro(isoquinoline-1,4'-piperidin)-1'-yl]butan-2-yl}-N-methylbenzamide N-{2-(S)-(3,4-Dichlorophenyl)-2-methylamino-4-[3-oxo-3,4-dihydro-2H-spiro(isoquinoline-1,4'-piperidin)-1'-yl]butyl}-3,3,3-trifluoro-N-methylpropanamide (440 mg) was dissolved in acetonitrile (5 mL). Under cooling with ice, triethylamine (314 µL) and benzoyl chloride (174 µL) were added thereto, and the mixture was stirred for 1 hour at the same temperature. Water was added to the reaction mixture, and the resultant mixture was extracted with ethyl acetate, sequentially washed with 0.5N aqueous hydrochloric acid, water, saturated aqueous sodium bicarbonate, and saturated brine, and dried over sodium sulfate anhydrate. The solvent was concentrated under reduced pressure, and the residue was purified through silica gel column chromatography (n-hexane ethyl acetate=1:1→ethyl acetate→ethyl acetate:methanol=10:1), to thereby give the title compound (442 mg, 85.5%) as white powder.

MS (FAB) m/z 689 ((M+H)$^+$)

$^1$H-NMR (400 MHz, CDCl$_3$)δ ppm: 1.69-1.80 (2H, m), 2.06-2.34 (6H, m), 2.42-2.54 (1H, m), 2.60-2.71 (1H, m), 2.77 (1H, d, J=11 Hz), 2.87 (1H, d, J=11 Hz), 3.02 (3H, s), 3.14 (3H, s), 3.18-3.39 (2H, m), 3.62 (2H, s), 4.45-4.60 (2H, m), 6.31 (1H, br), 7.12-7.16 (1H, m), 7.20-7.35 (4H, m), 7.37-7.48 (7H, m).

Example 26(k)

Synthesis of N-{1-(3,3,3-trifluoro-N-methylpropanamido)-2-(S)-(3,4-dichlorophenyl)-4-[3-oxo-3,4-dihydro-2H-spiro(isoquinoline-1,4'-piperidin)-1'-yl]butan-2-yl}-N-methylbenzamide hydrochloride (Compound No. 22)

[F84]
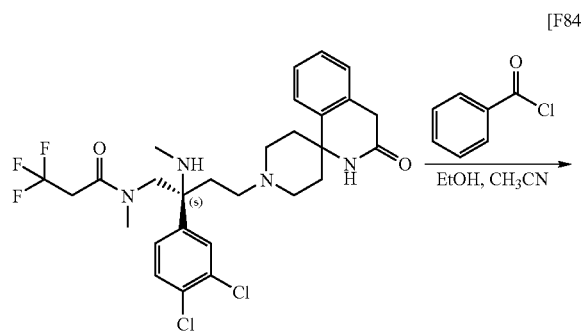

[F85]
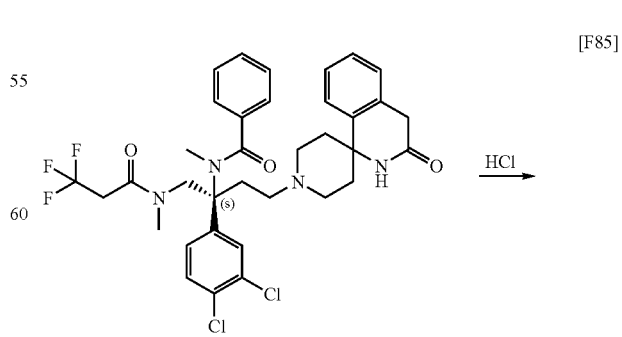

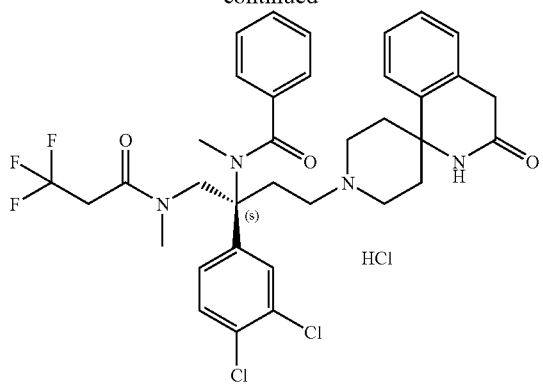

N-{1-(3,3,3-Trifluoro-N-methylpropanamido)-2-(S)-(3,4-dichlorophenyl)-4-[3-oxo-3,4-dihydro-2H-spiro(isoquinoline-1,4'-piperidin)-1'-yl]butan-2-yl}-N-methylbenzamide (442 mg) was dissolved in chloroform, and 4N HCl-1,4-dioxane (160 μL) was added thereto. The solvent was concentrated under reduced pressure. Ether was added to the residue, followed by filtration and drying, to thereby give the title compound (391 mg, 84.0%) as white powder.

MS (FAB) m/z 689 ((M+H)$^+$) (free form)

$^1$H-NMR (400 MHz, DMSO-d$_6$)δ ppm: 1.93 (2H, d, J=13 Hz), 2.48-2.62 (3H, m), 2.70-2.80 (4H, m), 2.88-3.14 (4H, m), 3.18-3.28 (1H, m), 3.33-3.53 (3H, m), 3.62 (2H, s), 3.72 (2H, q, J=11 Hz), 4.05-4.20 (1H, m), 4.53 (1H, d, J=14 Hz), 7.18-7.68 (11H, m), 7.77 (1H, d, J=2.0 Hz), 8.36 (1H, s), 10.56 (1H, br).

Example 27(a)

Synthesis of tert-butyl[1-(2,2,2-trifluoro-N-methylacetamide)-2-(S)-(3,4-dichlorophenyl)(4-penten-2-yl)]methylcarbamate

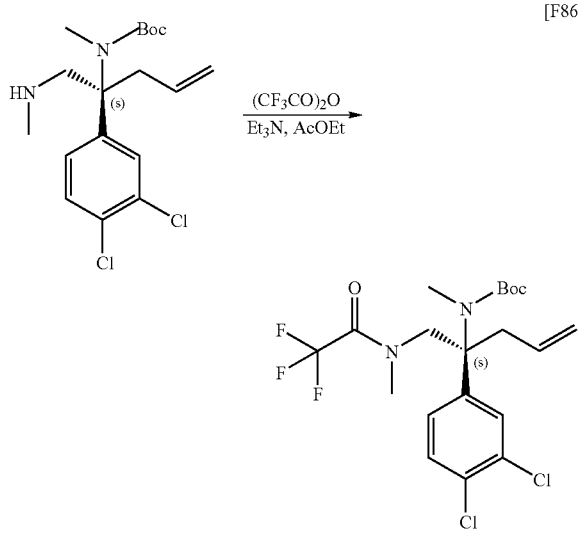

tert-Butyl[2-(S)-(3,4-dichlorophenyl)-1-methylamino(4-penten-2-yl)]methylcarbamate (3.55 g) synthesized in Example 26(d) was dissolved in ethyl acetate (20 mL). Under cooling with ice, triethylamine (2.65 mL) and trifluoroacetic acid anhydride (1.88 mL) were added thereto. At room temperature, the mixture was stirred for 45 minutes. The reaction mixture was neutralized with saturated aqueous sodium bicarbonate, extracted with ethyl acetate, sequentially washed with aqueous citric acid, saturated aqueous sodium bicarbonate, and saturated brine, and dried over sodium sulfate anhydrate. The solvent was concentrated under reduced pressure, and the residue was purified through silica gel column chromatography (n-hexane:ethyl acetate=10:1 to 2:1), to thereby give the title compound (4.22 g, 94.7%).

MS (FAB) m/z 469 ((M+H)$^+$)

$^1$H-NMR (270 MHz, CDCl$_3$)δ ppm: 1.26 (9H, s), 2.58 (1H, dd, J=7.0, 13.5 Hz), 2.77 (1H, dd, J=7.0, 13.5 Hz), 3.02 (3H, s), 3.07 (3H, s), 4.07-4.28 (1H, m), 4.43 (1H, d, J=13.5 Hz), 4.86-5.06 (2H, m), 5.55-5.75 (1H, m), 6.99 (1H, dd, J=2.5, 8.5 Hz), 7.24 (1H, d, J=2.5 Hz), 7.39 (1H, d, J=8.5 Hz).

Example 27(b)

Synthesis of tert-butyl{[2-(S)-(3,4-dichlorophenyl)-1-(2,2,2-trifluoro-N-methylacetamide)-4,5-dihydroxy]pentan-2-yl}methylcarbamate

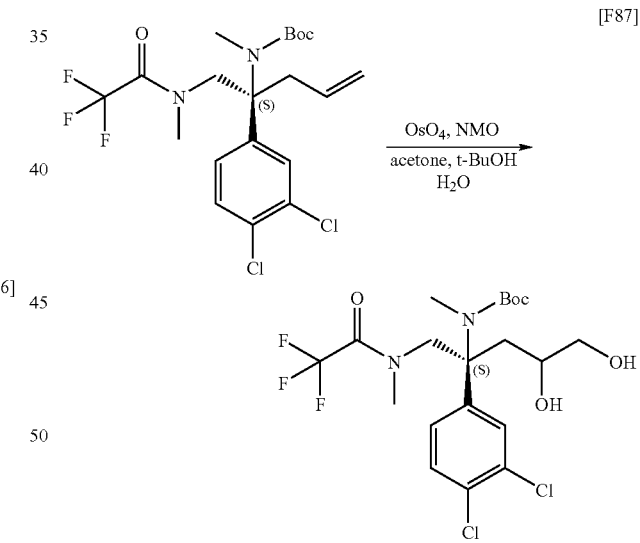

Similar to Example 26(f), the title compound was obtained (4.56 g, 98.9%) by use of tert-butyl[1-(2,2,2-trifluoro-N-methylacetamide)-2-(S)-(3,4-dichlorophenyl)(4-penten-2-yl)]methylcarbamate (4.3 g).

MS (FAB) m/z 503 ((M+H)$^+$)

$^1$H-NMR (270 MHz, CDCl$_3$)δ ppm: 1.24 (9H, brs), 1.76-1.88 (1H, m), 1.94-2.20 (2H, m), 2.26-2.50 (1H, m), 3.00-3.30 (6H, m), 3.38-3.63 (2H, m), 3.70-3.82 (1H, m), 3.90-4.20 (1H, m), 4.95-5.25 (1H, m), 7.00-7.15 (1H, m), 7.22-7.32 (1H, m), 7.40-7.50 (1H, m).

Example 27(c)

Synthesis of tert-butyl{[2-(S)-(3,4-dichlorophenyl)-1-(2,2,2-trifluoro-N-methylacetamide)-4-oxo]butan-2-yl)methylcarbamate

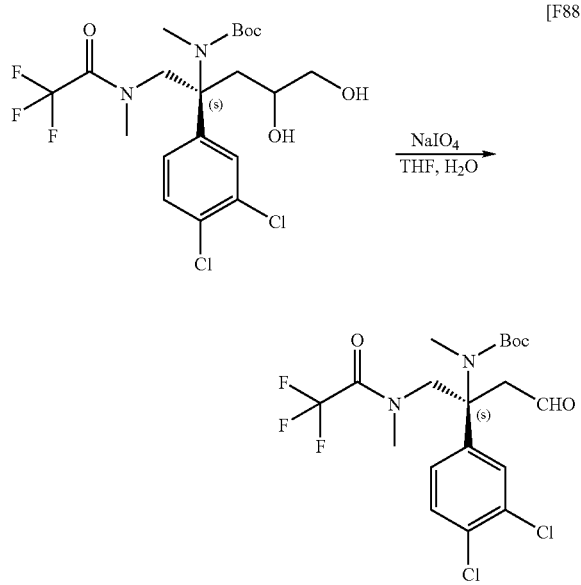

[F88]

Similar to Example 26(g), the title compound was obtained (4.17 g, 99.0%) by use of tert-butyl{[2-(S)-(3,4-dichlorophenyl)-1-(2,2,2-trifluoro-N-methylacetamide)-4,5-dihydroxy]pentan-2-yl}methylcarbamate (4.5 g).

MS (FAB) m/z 471 ((M+H)⁺)

¹H-NMR (270 MHz, CDCl₃)δ ppm: 1.29 (9H, s), 2.95 (3H, s), 2.90-3.10 (1H, m), 3.04 (3H, s), 3.23 (1H, d, J=16 Hz), 4.37 (1H, d, J=13.5 Hz), 4.53 (1H, d, J=13.5 Hz), 7.11 (1H, dd, J=2.5, 8.5 Hz), 7.34 (1H, d, J=2.5 Hz), 7.44 (1H, d, J=8.5 Hz), 9.62 (1H, t, J=2.0 Hz).

Example 27(d)

Synthesis of tert-butyl{[1-(2,2,2-trifluoro-N-methylacetamide)-2-(S)-(3,4-dichlorophenyl)-4-[3-oxo-3,4-dihydro-2H-spiro(isoquinoline-1,4'-piperidin)-1'-yl]butan-2-yl]methylcarbamate

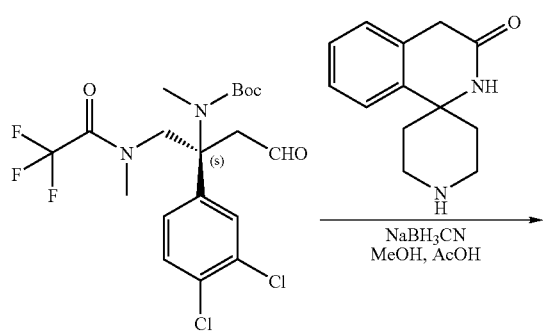

[F89]

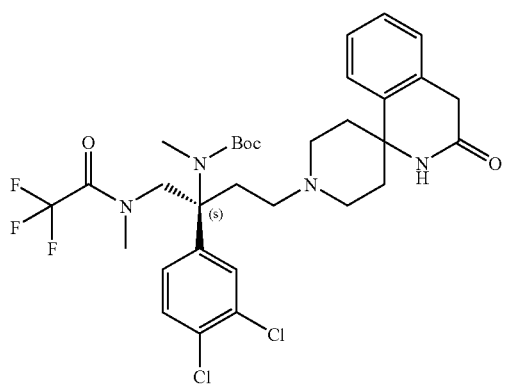

Similar to Example 26(h), the title compound was obtained (2.65 g, 94.9%) by use of tert-butyl{[2-(S)-(3,4-dichlorophenyl)-1-(2,2,2-trifluoro-N-methylacetamide)-4-oxo]butan-2-yl}methylcarbamate (1.96 g).

MS (FAB) m/z 671 ((M+H)⁺)

¹H-NMR (270 MHz, CDCl₃)δ ppm: 1.25 (9H, brs), 1.63-1.80 (2H, m), 1.90-2.30 (7H, m), 2.45-2.60 (1H, m), 2.71 (1H, d, J=10 Hz), 2.81 (1H, d, J=10 Hz), 3.05 (3H, s), 3.12 (3H, s), 3.61 (2H, s), 4.05-4.28 (1H, m), 4.45-4.68 (1H, m), 6.29 (1H, s), 7.04 (1H, dd, J=2.5, 8.5 Hz), 7.10-7.38 (5H, m), 7.43 (1H, d, J=8.5 Hz).

Example 27(e)

Synthesis of N-{2-(S)-(3,4-dichlorophenyl)-2-methylamino-4-[3-oxo-3,4-dihydro-2H-spiro(isoquinoline-1,4'-piperidin)-1'-yl]butyl}-2,2,2-trifluoro-N-methylacetamide

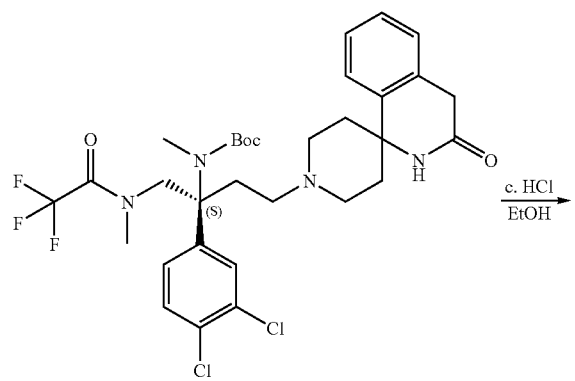

[F90]

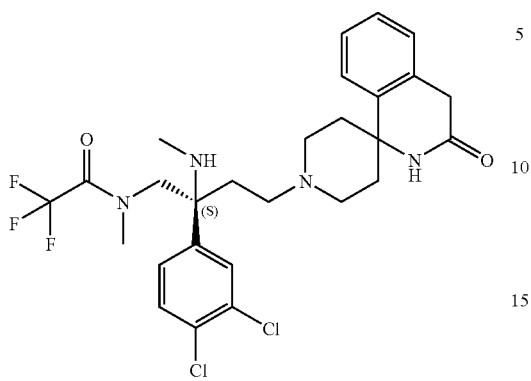

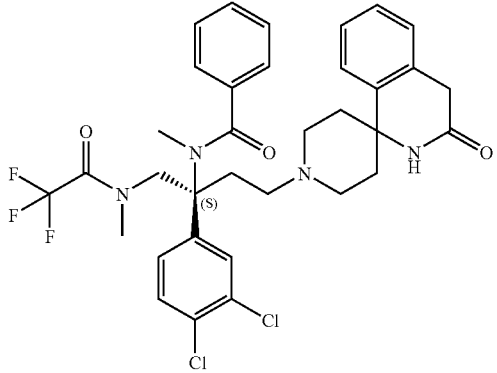

Similar to Example 26(i), the title compound was obtained (2.30 g, quant.) by use of tert-butyl{[1-(2,2,2-trifluoro-N-methylacetamide)-2-(S)-(3,4-dichlorophenyl)-4-[3-oxo-3,4-dihydro-2H-spiro(isoquinoline-1,4'-piperidin)-1'-yl]butan-2-yl]methylcarbamate (2.65 g).

MS (FAB) m/z 571 ((M+H)$^+$)

$^1$H-NMR (270 MHz, CDCl$_3$)δ ppm: 1.73-1.88 (2H, m), 1.95-2.60 (9H, m), 2.28 (3H, s), 2.72 (3H, s), 2.88-3.03 (2H, m), 3.48 (1H, d, J=14 Hz), 3.64 (2H, s), 3.93 (1H, d, J=14 Hz), 6.36 (1H, s), 7.17 (1H, dd, J=2.5, 8.5 Hz), 7.23-7.42 (4H, m), 7.45 (1H, d, J=8.5 Hz), 7.63 (1H, d, J=2.5 Hz).

Similar to Example 26(j), the title compound was obtained as white powder (1.48 g, 64.2%) by use of N-{2-(S)-(3,4-dichlorophenyl)-2-methylamino-4-[3-oxo-3,4-dihydro-2H-spiro(isoquinoline-1,4'-piperidin)-1'-yl]butyl}-2,2,2-trifluoro-N-methylacetamide (1.95 g).

MS (FAB) m/z 675 ((M+H)$^+$)

$^1$H-NMR (400 MHz, CDCl$_3$)δ ppm: 1.70-1.80 (2H, m), 2.06-2.32 (6H, m), 2.36-2.46 (1H, m), 2.62-2.72 (1H, m), 2.79 (1H, d, J=12 Hz), 2.87 (1H, d, J=12 Hz), 3.14 (3H, s), 3.16 (3H, s), 3.63 (2H, s), 4.56-4.67 (2H, m), 6.30 (1H, br), 7.13-7.17 (1H, m), 7.19-7.35 (4H, m), 7.38-7.47 (7H, m).

Example 27(f)

Synthesis of N-{1-(2,2,2-trifluoro-N-methylacetamide)-2-(S)-(3,4-dichlorophenyl)-4-[3-oxo-3,4-dihydro-2H-spiro(isoquinoline-1,4'-piperidin)-1'-yl]butan-2-yl}-N-methylbenzamide Example 27(g)

Synthesis of N-{1-(2,2,2-trifluoro-N-methylacetamide)-2-(S)-(3,4-dichlorophenyl)-4-[3-oxo-3,4-dihydro-2H-spiro(isoquinoline-1,4'-piperidin)-1'-yl]butan-2-yl}-N-methylbenzamide hydrochloride (Compound No. 23)

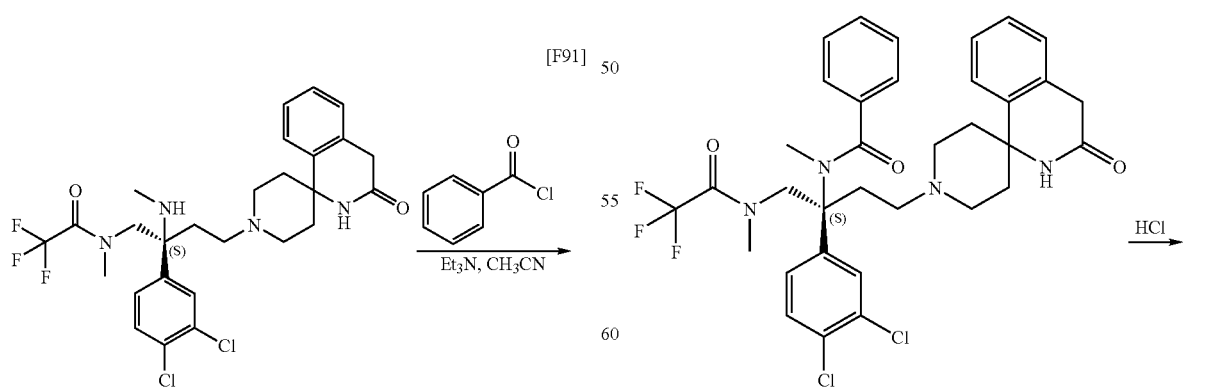

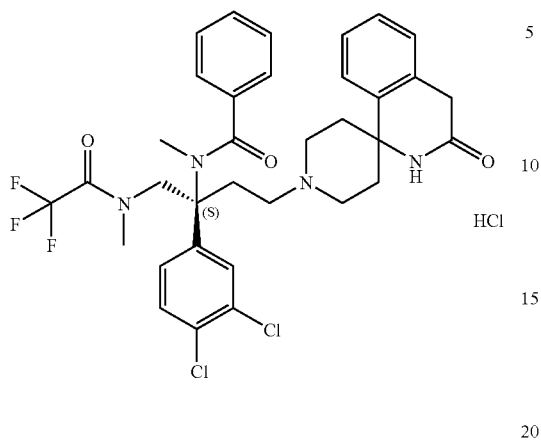

Similar to Example 26(k), the title compound was obtained as white powder (350 mg, 94.9%) by use of N-{1-(2,2,2-trifluoro-N-methylacetamide)-2-(S)-(3,4-dichlorophenyl)-4-[3-oxo-3,4-dihydro-2H-spiro(isoquinoline-1,4'-piperidin)-1'-yl]butan-2-yl}-N-methylbenzamide (350 mg).

MS(FAB)m/z 675 ((M+H)$^+$) (free form)

$^1$H-NMR (270 MHz, DMSO-d$_6$)δ ppm: 1.90-2.08 (2H, m), 2.42-2.87 (4H, m), 2.97 (3H, s), 3.04 (3H, s), 3.12-3.70 (8H, m), 4.25 (1H, d, J=14.5 Hz), 4.69 (1H, d, J=14.5 Hz), 7.15-7.77 (11H, m), 7.81 (1H, d, J=2.0 Hz), 8.26 (1H, s), 10.7 (1H, br).

Example 28(a)

Synthesis of N-{1-(2,2,2-trifluoro-N-methylacetamide)-2-(S)-(3,4-dichlorophenyl)-4-[3-oxo-3,4-dihydro-2H-spiro(isoquinoline-1,4'-piperidin)-1'-yl]butan-2-yl}-N-methyl-4-trifluoromethyl-benzamide Similar to Example 26(j), the title compound was obtained as pale yellow powder (172 mg, 66.1%) by use of N-{2-(S)-(3,4-dichlorophenyl)-2-methylamino-4-[3-oxo-3,4-dihydro-2H-spiro(isoquinoline-1,4'-piperidin)-1'-yl]butyl}-2,2,2-trifluoro-N-methylacetamide (200 mg) synthesized in Example 27(e) and 4-trifluoromethylbenzoyl chloride (156 μL).

MS (FAB) m/z 743 ((M+H)$^+$)

$^1$H-NMR (400 MHz, CDCl$_3$)δ ppm: 1.71-1.81 (2H, m), 2.06-2.32 (6H, m), 2.40-2.50 (1H, m), 2.58-2.68 (1H, m), 2.80 (1H, d, J=12 Hz), 2.87 (1H, d, J=12 Hz), 3.11 (3H, s), 3.13 (3H, s), 3.63 (2H, s), 4.49 (1H, d, J=13.5 Hz), 4.68 (1H, d, J=13.5 Hz), 6.29 (1H, br), 7.13-7.35 (5H, m), 7.44-7.48 (2H, m), 7.51 (2H, d, J=8.0 Hz), 7.71 (2H, d, J=8.0 Hz).

Example 28(b)

Synthesis of N-{1-(2,2,2-trifluoro-N-methylacetamide)-2-(S)-(3,4-dichlorophenyl)-4-[3-oxo-3,4-dihydro-2H-spiro(isoquinoline-1,4'-piperidin)-1'-yl]butan-2-yl}-N-methyl-4-trifluoromethyl-benzamide hydrochloride (Compound No. 24)

[F93]

[F94]

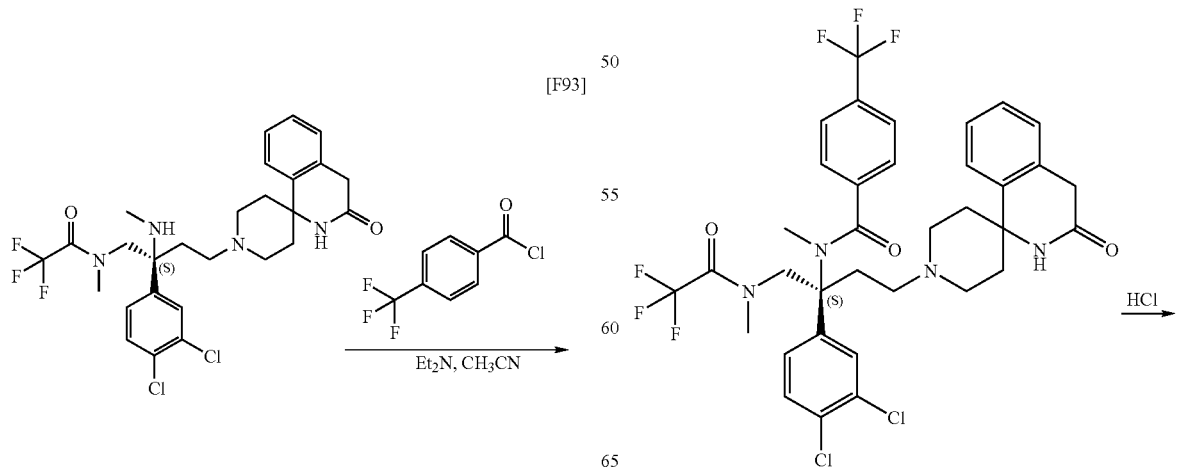

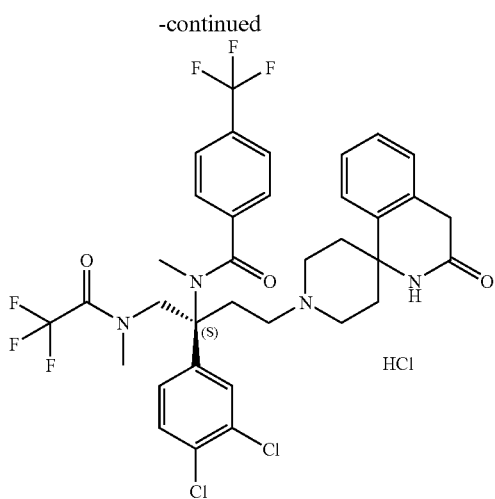

Similar to Example 26(k), the title compound was obtained as white powder (137 mg, 76.0%) by use of N-{1-(2,2,2-trifluoro-N-methylacetamide)-2-(S)-(3,4-dichlorophenyl)-4-[3-oxo-3,4-dihydro-2H-spiro(isoquinoline-1,4'-piperidin)-1'-yl]butan-2-yl}-N-methyl-4-trifluoromethyl-benzamide (172 mg).

MS (FAB) m/z 743 ((M+H)$^+$) (free form)

$^1$H-NMR (400 MHz, DMSO-d$_6$)δ ppm: 1.92-2.02 (2H, m), 2.47-2.63 (1H, m), 2.65-2.83 (2H, m), 2.90-3.08 (8H, m), 3.12-3.52 (3H, m), 3.55-3.65 (3H, m), 4.21 (1H, d, J=13.5 Hz), 4.76 (1H, d, J=13.5 Hz), 7.20-7.24 (1H, m), 7.27-7.40 (4H, m), 7.58-7.75 (4H, m), 7.82-7.90 (3H, m), 8.25 (1H, s), 10.76 (1H, br).

Example 29(a)

Synthesis of N-[2-(S)-(3,4-dichlorophenyl)-2-(methylamino)-4-pentenyl]-3,3,3-trifluoro-N-methylpropanamido

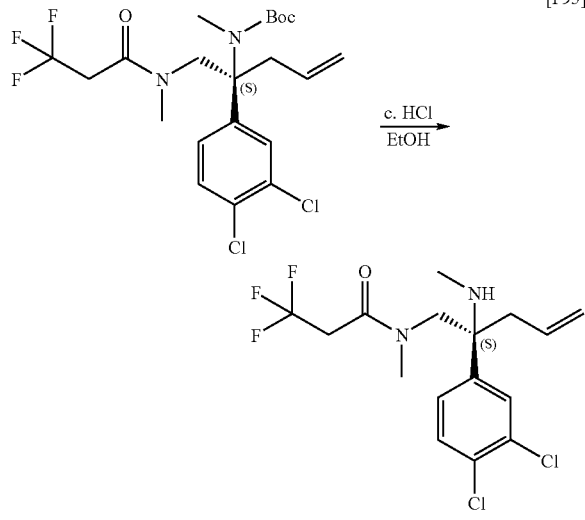

tert-Butyl[1-(3,3,3-trifluoro-N-methylpropanamido)-2-(S)-(3,4-dichlorophenyl)(4-penten-2-yl)]methylcarbamate (2.42 g) synthesized in Example 26(e) was dissolved in ethanol (15.4 mL). Under cooling with ice, concentrated hydrochloric acid (15.4 mL) was added thereto, and the mixture was stirred for 1.5 hours at room temperature. The reaction mixture was neutralized with saturated aqueous sodium bicarbonate, extracted with ethyl acetate, sequentially washed with water and saturated brine, and dried over sodium sulfate anhydrate. The solvent was concentrated under reduced pressure, to thereby give the title compound (2.10 g). The compound was used in the next step without further purification.

MS (FAB) m/z 383 ((M+H)$^+$)

$^1$H-NMR (400 MHz, CDCl$_3$)δ ppm: 1.52-1.72 (1H, br), 2.20 (3H, s), 2.56 (3H, s), 2.65 (2H, d, J=7.0 Hz), 3.11 (2H, dq, J=2.0, 10 Hz), 3.49 (1H, d, J=14 Hz), 3.76 (1H, d, J=14 Hz), 5.17-5.32 (2H, m), 5.78-5.90 (1H, m), 7.33 (1H, dd, J=2.0, 8.5 Hz), 7.42 (1H, d, J=8.5 Hz), 7.63 (1H, d, J=2.0 Hz).

Example 29(b)

Synthesis of N$^1$-[1-(3,3,3-trifluoro-N-methylpropanamido)-2-(S)-(3,4-dichlorophenyl)(4-penten-2-yl)]-N$^2$-ethyl-N$^1$-methyl-N$^2$-phenyloxalamide

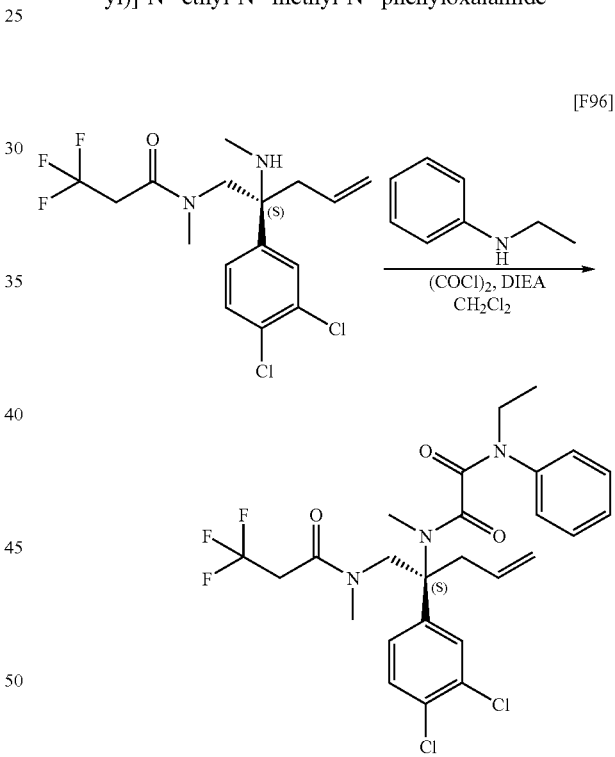

N-[2-(S)-(3,4-Dichlorophenyl)-2-(methylamino)-4-pentenyl]-3,3,3-trifluoro-N-methylpropanamide (200 mg) was dissolved in anhydrous methylene chloride (1 mL). Under cooling with ice, N,N-diisopropylethylamine (109 μL) and oxalyl chloride (109 μL) were added thereto, and the mixture was stirred for 30 minuites. A solution of N-ethylaniline (127 mg) in anhydrous methylene chloride (1 mL) was added to the reaction mixture, and the resultant mixture was stirred for 1 hour at room temperature. Water was added to the reaction mixture, extracted with methylene chloride, washed with saturated brine, and dried over sodium sulfate anhydrate. The solvent was concentrated under reduced pressure, and the residue was purified through silica gel column chromatography (n-hexane:ethyl acetate=3:1 to 1:1), to thereby give the title compound (221 mg, 75.8%).

MS (FAB) m/z 558 ((M+H)$^+$)

$^1$H-NMR (400 MHz, CDCl$_3$)δ ppm: 1.17 (3H, t, J=7.0 Hz), 2.42-2.50 (1H, m), 2.73-2.92 (4H, m), 2.99 (3H, s), 3.13-3.35 (2H, m), 3.72-3.86 (2H, m), 4.07-4.28 (2H, m), 4.75-4.92 (2H, m), 5.28-5.41 (1H, m), 6.10 (1H, br), 6.92 (1H, d, J=2.0 Hz), 7.02 (1H, d, J=8.5 Hz), 7.23-7.30 (2H, m), 7.45-7.52 (3H, m).

Example 29(c)

Synthesis of N$^1$-{1-(3,3,3-trifluoro-N-methylpropanamido)-2-(S)-(3,4-dichlorophenyl)-4-[spiro (benzo(c)thiophene-(2S)-oxido-1(3H),4'-piperidin)-1'-yl]butan-2-yl}-N$^1$-methyl-N$^2$-ethyl-N$^2$-phenyloxalamide

[F97]

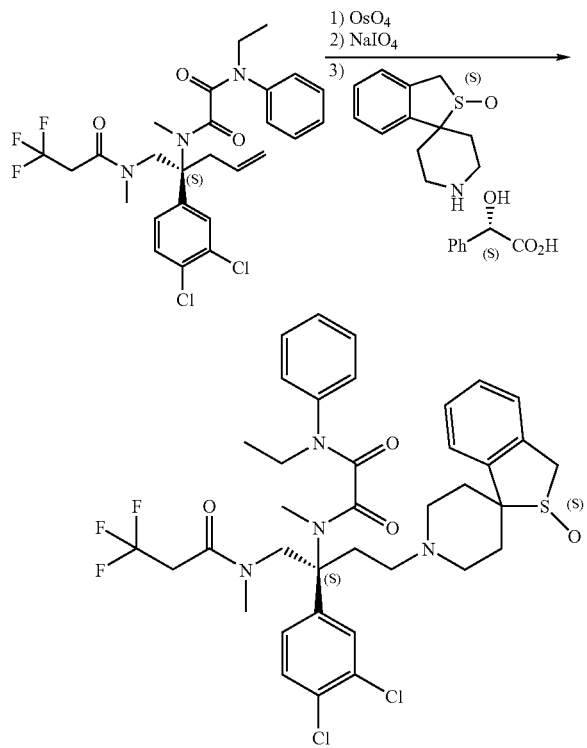

Similar to Example 26(f), N$^1$-{2-(S)-(3,4-dichlorophenyl)-1-(3,3,3-trifluoro-N-methylpropanamido)-4,5-dihydroxy}pentan-2-yl}-N$^2$-ethyl-N$^1$-methyl-N$^2$-phenyloxalamide was obtained (889 mg) by use of N$^1$-[1-(3,3,3-trifluoro-N-methylpropanamido)-2-(S)-(3,4-dichlorophenyl)(4-penten-2-yl)]-N$^2$-ethyl-N$^1$-methyl-N$^2$-phenyloxalamide (850 mg). Subsequently, similar to Example 26(g), N$^1$-{2-(S)-(3,4-dichlorophenyl)-1-(3,3,3-trifluoro-N-methylpropanamido)-4-oxo}butan-2-yl}-N$^2$-ethyl-N$^1$-methyl-N$^2$-phenyloxalamide was obtained (857 mg) by use of N$^1$-{2-(S)-(3,4-dichlorophenyl)-1-(3,3,3-trifluoro-N-methylpropanamido)-4,5-dihydroxy}pentan-2-yl}-N$^2$-ethyl-N$^1$-methyl-N$^2$-phenyloxalamide (889 mg). Thereafter, similar to Example 26(h), the title compound was obtained as white powder (736 mg, 63.2%, 3 steps) by use of N$^1$-{2-(S)-(3,4-dichlorophenyl)-1-(3,3,3-trifluoro-N-methylpropanamido)-4-oxo}butan-2-yl}-N$^2$-ethyl-N$^1$-methyl-N$^2$-phenyloxalamide (857 mg) and spiro(benzo(c)thiophene-(2S)-oxido-1(3H),4'-piperidine)/(S)-(+)-mandelate (616 mg).

MS (FAB) m/z 765 ((M+H)$^+$)

$^1$H-NMR (400 MHz, CDCl$_3$)δ ppm: 1.17 (3H, t, J=7.0 Hz), 1.49 (1H, d, J=13.5 Hz), 1.77-2.02 (3H, m), 2.12-2.22 (2H, m), 2.29-2.46 (4H, m), 2.63-2.73 (2H, m), 2.84 (3H, s), 3.04 (3H, s), 3.13-3.38 (2H, m), 3.70-3.90 (2H, m), 3.97 (1H, d, J=17 Hz), 4.10-4.18 (1H, m), 4.25-4.40 (2H, m), 6.20 (1H, br), 6.98-7.08 (2H, m), 7.24-7.35 (6H, m), 7.43-7.54 (3H, m).

Example 29(d)

Synthesis of N$^1$-{1-(3,3,3-trifluoro-N-methylpropanamido)-2-(S)-(3,4-dichlorophenyl)-4-[spiro (benzo(c)thiophene-(2S)-oxido-1(3H),4'-piperidin)-1'-yl]butan-2-yl}-N$^1$-methyl-N$^2$-ethyl-N$^2$-phenyloxalamide hydrochloride (Compound No. 25)

[F98]

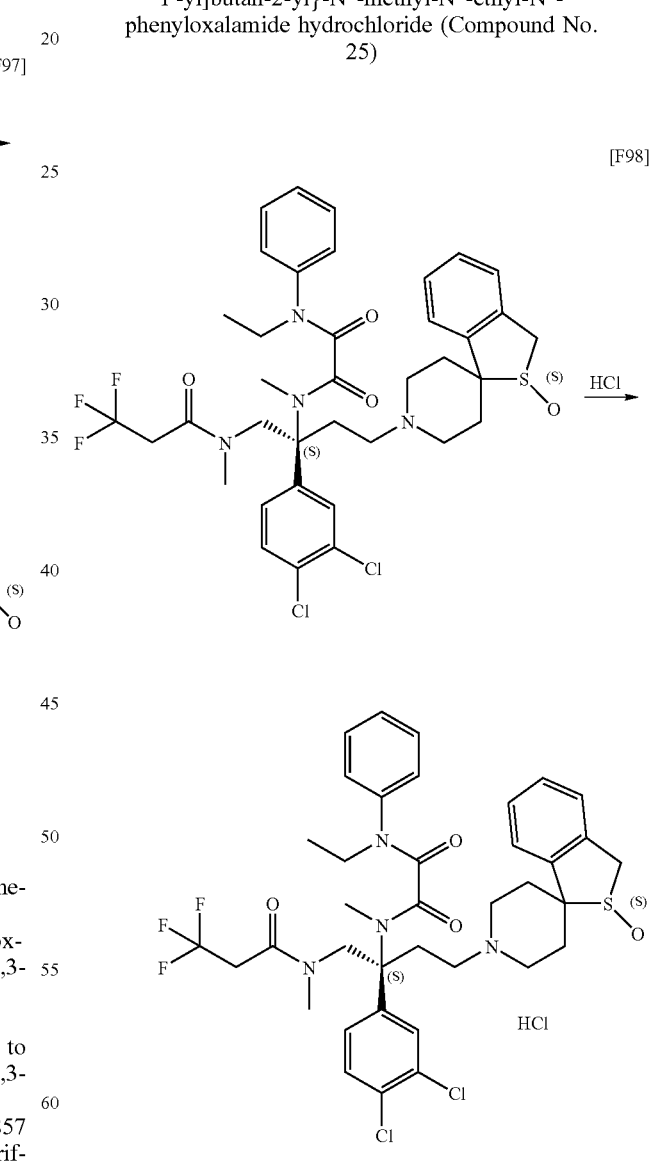

Similar to Example 26(k), the title compound was obtained as white powder (611 mg, 83.1%) by use of $N^1$-{1-(3,3,3-trifluoro-N-methylpropanamido)-2-(S)-(3,4-dichlorophenyl)-4-[spiro(benzo(c)thiophene-(2S)-oxido-1(3H),4'-piperidin)-1'-yl]butan-2-yl}-$N^1$-methyl-$N^2$-ethyl-$N^2$-phenyloxalamide (736 mg).

$[α]_D^{28}$=−27.7° (c 0.501, MeOH)

$^1$H-NMR (400 MHz, DMSO-$d_6$)δ ppm: 1.04 (3H, t, J=7.0 Hz), 1.92-2.07 (1H, m), 2.20-2.40 (5H, m), 2.70-3.12 (5H, m), 3.14 (3H, s), 3.25-3.45 (4H, m), 3.60-3.80 (4H, m), 3.86-4.00 (1H, m), 4.04-4.18 (2H, m), 4.68 (1H, d, J=17 Hz), 6.63 (1H, br), 7.22-7.58 (11H, m), 10.70 (1H, br).

Example 30(a)

Synthesis of tert-butyl{[1-(2,2,2-trifluoro-N-methylacetamide)-2-(S)-(3,4-dichlorophenyl)-4-[spiro(benzo(c)thiophene-(2S)-oxido-1(3H),4'-piperidin)-1'-yl]butan-2-yl]methylcarbamate

[F99]

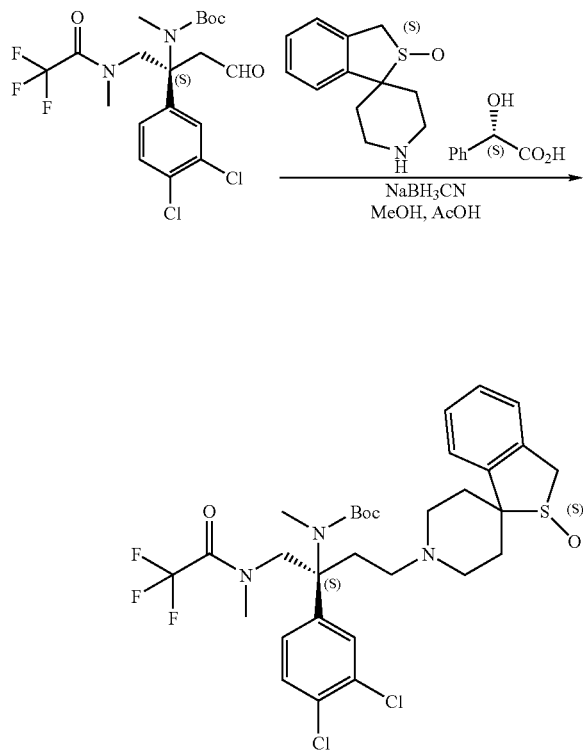

Similar to Example 26(h), the title compound was obtained (1.34 g, 93.4%) by use of tert-butyl{[2-(S)-(3,4-dichlorophenyl)-1-(2,2,2-trifluoro-N-methylacetamide)-4-oxo]butan-2-yl}methylcarbamate (1.0 g) synthesized in Example 27(c) and spiro(benzo(c)thiophene-(2S)-oxido-1(3H),4'-piperidine)/(S)-(+)-mandelate (871 mg).

MS (FAB) m/z 676 ((M+H)$^+$)

$^1$H-NMR (400 MHz, CDCl$_3$)δ ppm: 1.25 (9H, brs), 1.82-1.93 (1H, m), 1.96-2.08 (2H, m), 2.14-2.44 (6H, m), 2.48-2.60 (1H, m), 2.70-2.80 (1H, m), 2.83-2.92 (1H, m), 3.02 (3H, s), 3.10(3H, s), 3.98 (1H, d, J=16.5 Hz), 4.07-4.33 (1H, m), 4.30 (1H, d, J=16.5 Hz), 4.43-4.60 (1H, m), 7.03-7.07 (1H, m), 7.25-7.35 (5H, m), 7.42 (1H, d, J=8.5 Hz).

Example 30(b)

Synthesis of N-{1-(2,2,2-trifluoro-N-methylacetamide)-2-(S)-(3,4-dichlorophenyl)-4-[spiro(benzo(c)thiophene-(2S)-oxido-1(3H),4'-piperidin)-1'-yl]butan-2-yl}-N-methylbenzamide

[F100]

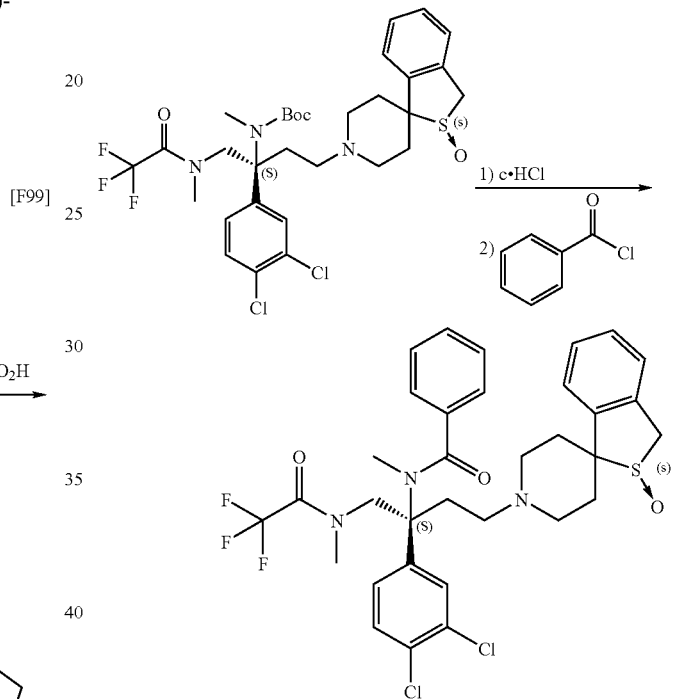

Similar to Example 26(i), N-{2-(S)-(3,4-dichlorophenyl)-2-methylamino-4-[3-oxo-3,4-dihydro-2H-spiro(isoquinoline-1,4'-piperidin)-1'-yl]butyl}-2,2,2-trifluoro-N-methylacetamide was obtained (1.22 g, 92.2%) by use of tert-butyl{[1-(2,2,2-trifluoro-N-methylacetamide)-2-(S)-(3,4-dichlorophenyl)-4-[spiro(benzo(c)thiophene-(2S)-oxido-1(3H),4'-piperidin)-1'-yl]butan-2-yl]methylcarbamate (1.30 g). Subsequently, similar to Example 36(j), the title compound was obtained as white powder (77 mg, 65.4%) by use of N-{2-(S)-(3,4-dichlorophenyl)-2-methylamino-4-[3-oxo-3,4-dihydro-2H-spiro(isoquinoline-1,4'-piperidin)-1'-yl]butyl}-2,2,2-trifluoro-N-methylacetamide (100 mg).

MS (FAB) m/z 680 ((M+H)$^+$)

$^1$H-NMR (400 MHz, CDCl$_3$)δ ppm: 1.50-1.60 (1H, m), 1.83-1.96 (1H, m), 2.05-2.50 (7H, m), 2.63-2.75 (1H, m), 2.81 (1H, d, J=12 Hz), 2.94 (1H, d, J=12 Hz), 3.12 (3H, s), 3.13 (3H, s), 3.99 (1H, d, J=16.5 Hz), 4.31 (1H, d, J=16.5 Hz), 4.55 (1H, d, J=13.5 Hz), 4.67 (1H, d, J=13.5 Hz), 7.22 (1H, dd, J=2.5, 8.0 Hz), 7.27-7.36 (4H, m), 7.38-7.47 (7H, m).

Example 30(c)

Synthesis of N-{1-(2,2,2-trifluoro-N-methylacetamide)-2-(S)-(3,4-dichlorophenyl)-4-[spiro(benzo(c)thiophene-(2S)-oxido-1(3H),4'-piperidin)-1'-yl]butan-2-yl}-N-methylbenzamide hydrochloride
(Compound No. 26)

[F101]

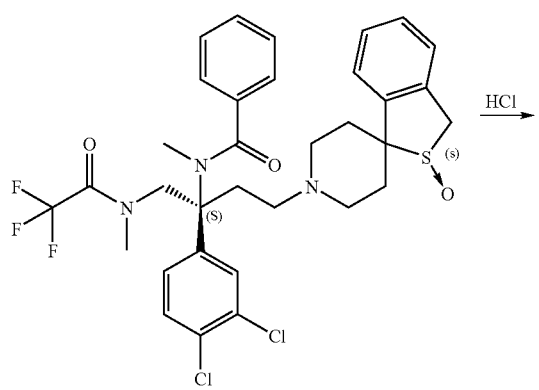

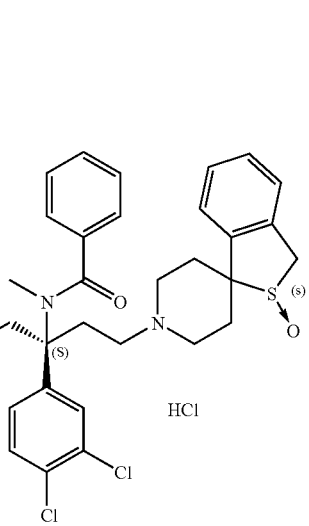

Similar to Example 26(k), the title compound was obtained as pale yellow powder (63 mg, 77.7%) by use of N-{1-(2,2,2-trifluoro-N-methylacetamide)-2-(S)-(3,4-dichlorophenyl)-4-[spiro(benzo(c)thiophene-(2S)-oxido-1(3H),4'-piperidin)-1'-yl]butan-2-yl}-N-methylbenzamide (77 mg).

$[\alpha]_D^{28}$=+9.2° (c 0.509, MeOH)

$^1$H-NMR (400 MHz, DMSO-$d_6$)δ ppm: 2.07 (1H, d, J=16 Hz), 2.18-2.35 (2H,m), 2.60-2.82 (3H, m), 2.94 (3H, s), 3.05 (3H, s), 3.06-3.30 (4H, m), 3.60-3.78 (2H, m), 4.09 (1H, d, J=17 Hz), 4.18-4.28 (1H, m), 4.63 (1H, d, J=17 Hz), 4.70 (1H, d, J=17 Hz), 7.31 (1H, d, J=7.0 Hz), 7.35-7.58 (9H, m), 7.64 (1H, d, J=8.5 Hz), 7.79 (1H, s), 10.46 (1H, br).

Referential Example 1

Synthesis of (methylphenylamino)-oxo-acetyl chloride

[F102]

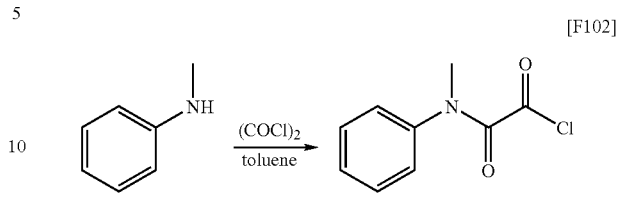

N-methylaniline (1.0 g) was dissolved in toluene (10 mL). Under cooling with ice, oxalyl chloride (4.07 mL) was added thereto, and the temperature of the mixture was lowered to room temperature, followed by stirring for 1 hour. The reaction mixture was concentrated under reduced pressure, to thereby give the title compound (1.06 g, 86.8%) as a brown oil. The compound was used without further purification.

Referential Example 2

Synthesis of oxo-phenylamino-acetyl chloride

[F103]

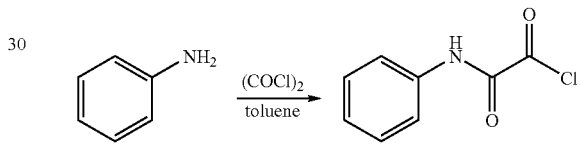

Similar to Referential Example 1, aniline hydrochloride (3.0 g) was dissolved in benzen (10 mL), and oxalyl chloride (10 mL) was added thereto under cooling with ice. The temperature of the mixture was then returned to room temperature, and the mixture was stirred overnight. The reaction mixture was concentrated under reduced pressure, to thereby give the title compound (3.26 g, 76.6%) as a brown oil.

Referential Example 3

Synthesis of (ethylphenylamino)-oxo-acetyl chloride

[F104]

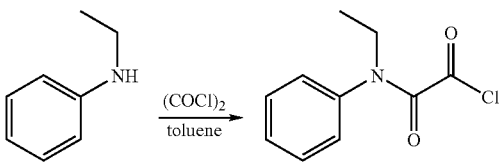

Similar to Referential Example 1, N-ethylaniline (1.0 g) was dissolved in toluene (10 mL), and oxalyl chloride (4.0 mL) was added thereto under cooling with ice. The temperature of the mixture was then returned to room temperature, and the mixture was stirred for 1 hour. The reaction mixture was concentrated under reduced pressure, to thereby give the title compound (2.05 g) as a brown oil. The compound was used without further purification.

Example 31(a)

Synthesis of N¹-{1-(3,3,3-trifluoro-N-methylpropanamido)-2-(S)-(3,4-dichlorophenyl)-4-[3-oxo-3,4-dihydro-2H-spiro(isoquinoline-1,4'-piperidin)-1'-yl]butan-2-yl}-N¹,N²-dimethyl-N²-phenyloxalamide

Example 31(b)

Synthesis of N¹-{1-(3,3,3-trifluoro-N-methylpropanamido)-2-(S)-(3,4-dichlorophenyl)-4-[3-oxo-3,4-dihydro-2H-spiro(isoquinoline-1,4'-piperidin)-1'-yl]butan-2-yl}-N¹,N²-dimethyl-N²-phenyloxalamide hydrochloride (Compound No. 27)

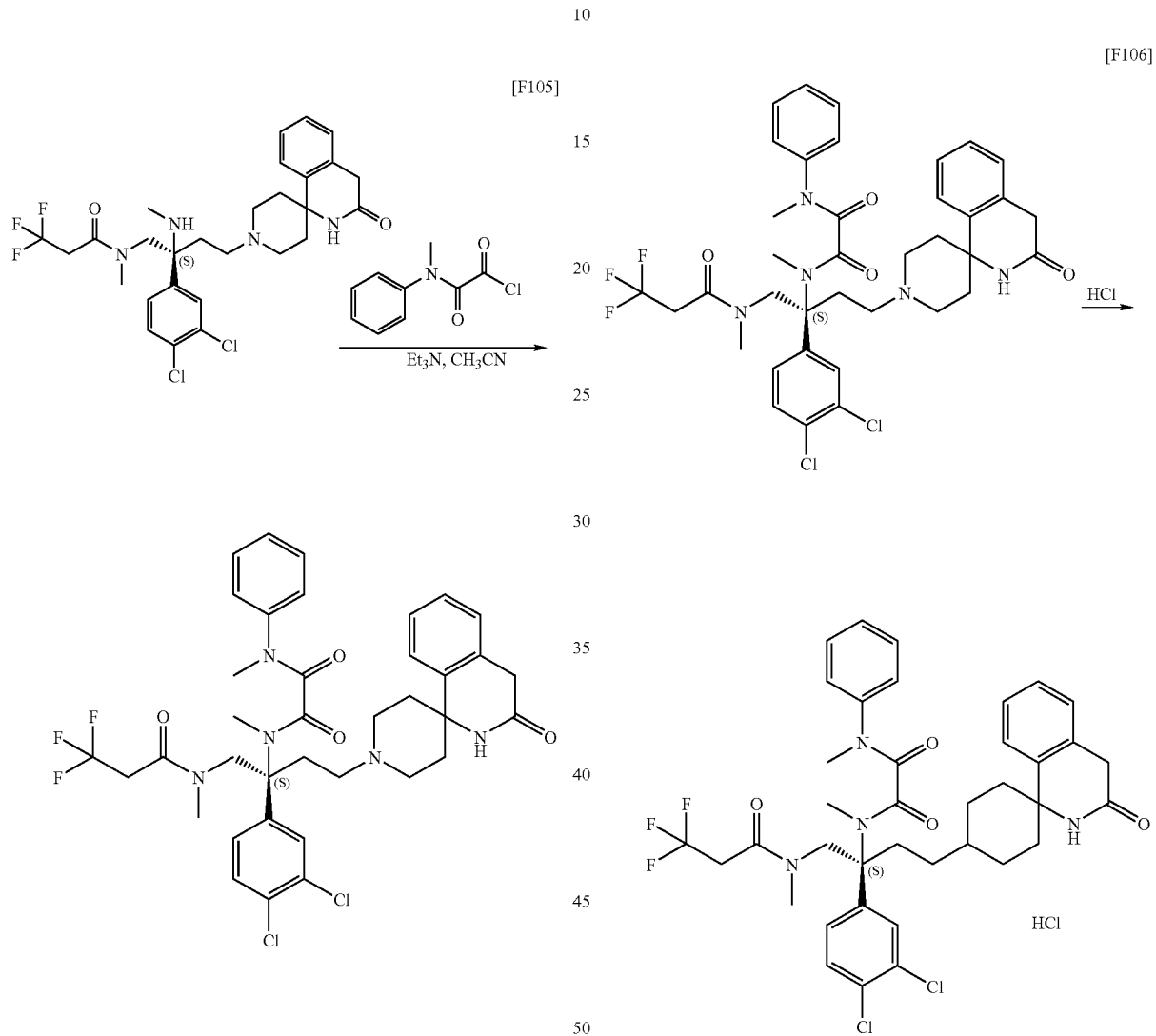

Similar to Example 26(j), the title compound was obtained (105 mg, 82.2%) by use of N-{2-(S)-(3,4-dichlorophenyl)-2-methylamino-4-[3-oxo-3,4-dihydro-2H-spiro(isoquinoline-1,4'-piperidin)-1'-yl]butyl}-3,3,3-trifluoro-N-methylpropanamide (100 mg) and (methylphenylamino)-oxo-acetyl chloride (68 mg) synthesized in Referential Example 1.

MS (FAB) m/z 746 ((M+H)⁺)

¹H-NMR (400 MHz, CDCl₃) δ ppm: 1.64-1.74 (2H, m), 1.80-1.96 (2H, m), 2.00-2.24 (5H, m), 2.35-2.47 (1H, m), 2.60-2.73 (2H, m), 2.83 (3H, s), 3.03 (3H, s), 3.12-3.39 (5H, m), 3.61 (2H, s), 4.09-4.20 (1H, m), 4.27-4.40 (1H, m), 6.18-6.32 (2H, m), 6.97-7.01 (1H, m), 7.07 (1H, d, J=8.5 Hz), 7.12-7.16 (1H, m), 7.22-7.34 (5H, m), 7.42-7.53 (3H, m).

Similar to Example 26(k), the title compound was obtained as pale yellow powder (81 mg, 73.4%) by use of N¹-{1-(3,3,3-trifluoro-N-methylpropanamido)-2-(S)-(3,4-dichlorophenyl)-4-[3-oxo-3,4-dihydro-2H-spiro(isoquinoline-1,4'-piperidin)-11'-yl]butan-2-yl}-N¹,N²-dimethyl-N²-phenyloxalamide (105 mg).

[α]_D²⁸ = −55.4° (c 0.505, MeOH)

¹H-NMR (400 MHz, DMSO-d₆) δ ppm: 1.84-1.97 (2H, m), 2.28-2.75 (5H, m), 2.82-2.96 (1H, m), 3.11 (3H, s), 3.15-3.48 (10H, m), 3.61 (2H, s), 3.65-3.77 (2H, m), 3.83-3.98 (1H, m), 4.12-4.25 (1H, m), 6.65 (1H, s), 7.18-7.80 (11H, m), 8.35 (1H, s), 10.44 (1H, br).

Example 32(a)

Synthesis of tert-butyl{[1-(3,3,3-trifluoro-N-methyl-propanamido)-2-(S)-(3,4-dichlorophenyl)-4-[spiro(benzo(c)thiophene-2,2-dioxido-1(3H),4'-piperidin)-1'-yl]butan-2-yl]methylcarbamate

[F107]

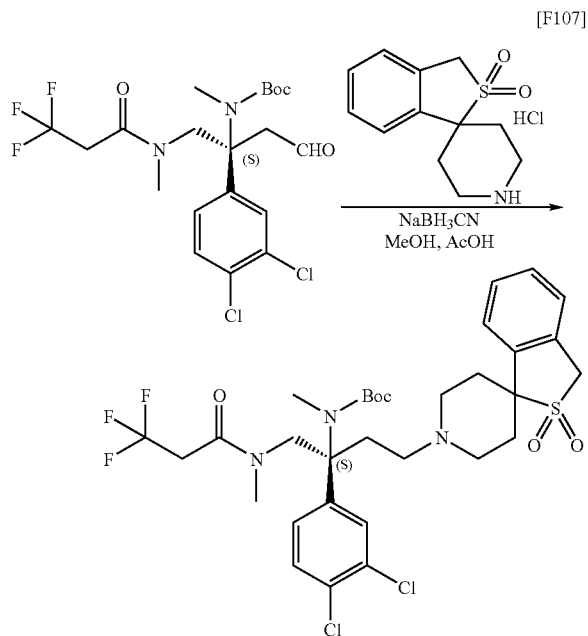

Similar to Example 26(h), the title compound was obtained (398 mg, 69.9%) by use of tert-butyl{[2-(S)-(3,4-dichlorophenyl)-1-(3,3,3-trifluoro-N-methylpropanamido)-4-oxo]butan-2-yl}methylcarbamate (390 mg) and spiro(benzo(c)thiophene-2,2-dioxido-1(3H),4'-piperidine) (242 mg).

MS (FAB) m/z 706 ((M+H)$^+$)

$^1$H-NMR (400 MHz, CDCl$_3$)δ ppm: 1.24 (9H, s), 1.93-2.38 (7H, m), 2.47-2.77 (5H, m), 2.92 (3H, s), 3.11 (3H, s), 3.18-3.40 (2H, m), 3.90-4.17 (1H, m), 4.29 (2H, s), 4.40-4.66 (1H, m), 7.04 (1H, dd, J=2.0, 8.5 Hz), 7.21-7.43 (6H, m).

Example 32(b)

Synthesis of N-{1-(3,3,3-trifluoro-N-methylpropanamido)-2-(S)-(3,4-dichlorophenyl)-4-[spiro(benzo(c)thiophene-2,2-dioxido-1(3H),4'-piperidin)-1'-yl]butan-2-yl)-N-methyl-phenylacetamide

[F108]

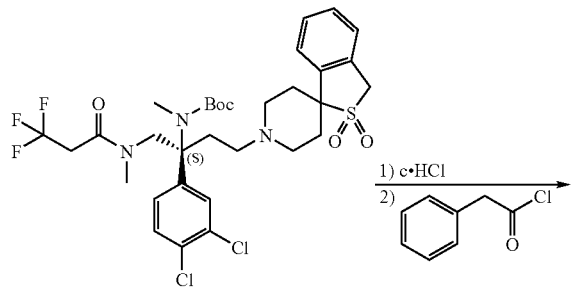

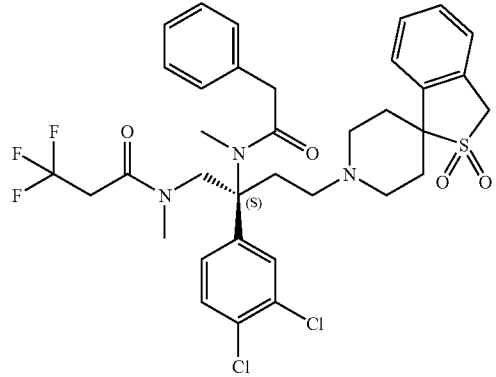

Similar to Example 26(i), N-{2-(S)-(3,4-dichlorophenyl)-2-methylamino-4-[spiro(benzo(c)thiophene-2,2-dioxido-1(3H),4'-piperidin)-1'-yl]}butyl}-3,3,3-trifluoro-N-methyl-propanamide was obtained (326 mg, 95.3%) by use of tert-butyl{[1-(3,3,3-trifluoro-N-methylpropanamido)-2-(S)-(3,4-dichlorophenyl)-4-[spiro(benzo(c)thiophene-2,2-dioxido-1(3H),4'-piperidin)-1'-yl]butan-2-yl]methylcarbamate (398 mg). Subsequently, similar to Example 26(j), the title compound was obtained as white powder (546 mg, quant.) by use of N-{2-(S)-(3,4-dichlorophenyl)-2-methylamino-4-[spiro(benzo(c)thiophene-2,2-dioxido-1(3H),4'-piperidin)-1'-yl]}butyl}-3,3,3-trifluoro-N-methylpropanamide (450 mg) and phenylacetyl chloride (196 μL).

MS (FAB) m/z 724 ((M+H)$^+$)

$^1$H-NMR (400 MHz, CDCl$_3$)δ ppm: 1.93-2.20 (4H, m), 2.26-2.40 (3H, m), 2.43-2.74 (5H, m), 2.76 (3H, s), 3.09 (3H, s), 3.11-3.28 (2H, m), 3.69 (2H, s), 4.22-4.34 (3H, m), 4.40 (1H, d, J=14 Hz), 6.94-6.98 (1H, m), 7.17-7.39 (11H, m).

Example 32(c)

Synthesis of N-(1-(3,3,3-trifluoro-N-methylpropanamido)-2-(S)-(3,4-dichlorophenyl)-4-[spiro(benzo(c)thiophene-2,2-dioxido-1(3H),4'-piperidin)-1'-yl]butan-2-yl}-N-methyl-phenylacetamide hydrochloride (Compound No. 28)

[F109]

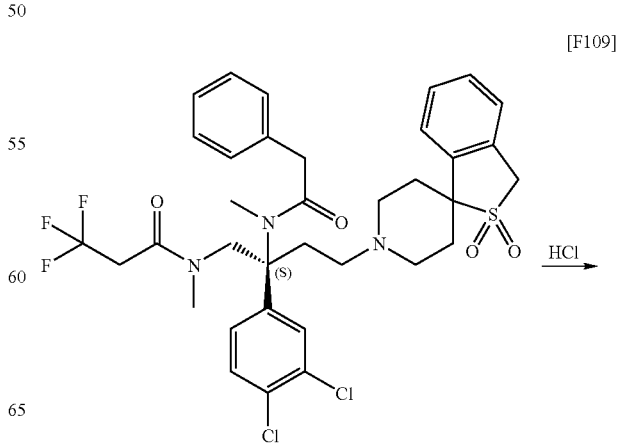

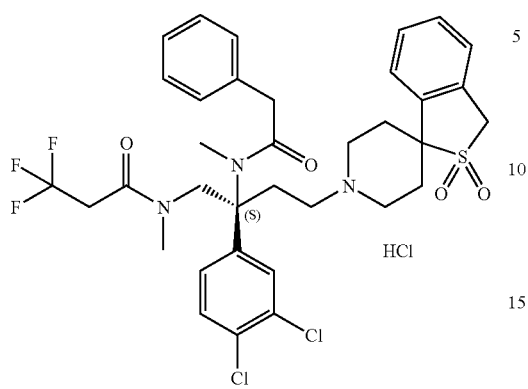

Similar to Example 26(k), the title compound was obtained as white powder (476 mg, 84.6%) by use of N-{1-(3,3,3-trifluoro-N-methylpropanamido)-2-(S)-(3,4-dichlorophenyl)-4-[spiro(benzo(c)thiophene-2,2-dioxido-1(3H),4'-piperidin)-1'-yl]butan-2-yl}-N-methyl-phenylacetamide (546 mg).

$[\alpha]_D^{28}$=−30.4° (c 0.509, MeOH)

$^1$H-NMR (400 MHz, DMSO-d$_6$)δ ppm: 2.30-2.55 (4H, m), 2.60-2.78 (3H, m), 3.05-3.28 (6H, m), 3.34 (3H, s), 3.47-3.80 (6H, m), 3.83-3.98 (1H, m), 4.30-4.40 (1H, m), 4.75 (2H, s), 7.10-7.60 (12H, m), 10.95 (1H, br).

Example 33(a)

Synthesis of N$^1$-{1-(2,2,2-trifluoro-N-methylacetamide)-2-(S)-(3,4-dichlorophenyl)-4-[3-oxo-3,4-dihydro-2H-spiro(isoquinoline-1,4'-piperidin)-1'-yl]butan-2-yl}-N$^1$-methyl-N$^2$-phenyloxalamide

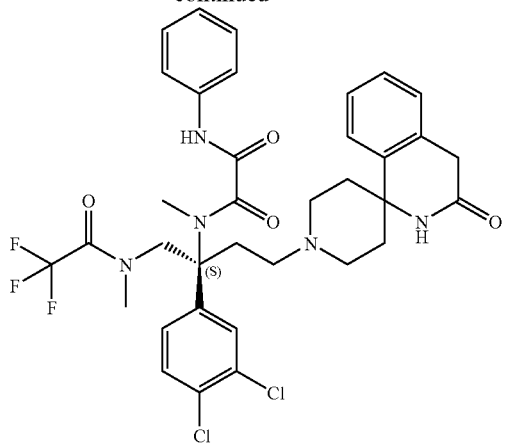

Similar to Example 26(j), the title compound was obtained (433 mg, 50.6%) by use of N-{2-(S)-(3,4-dichlorophenyl)-2-methylamino-4-[3-oxo-3,4-dihydro-2H-spiro(isoquinoline-1,4'-piperidin)-1'-yl]butyl}-2,2,2-trifluoro-N-methylacetamide (680 mg) synthesized in Example 27(e) and oxo-phenylamino-acetyl chloride (653 mg) synthesized in Referential Example 2.

MS (FAB) m/z 718 ((M+H)$^+$)

$^1$H-NMR (400 MHz, CDCl$_3$)δ ppm: 1.67-1.78 (2H, m), 2.00-2.30 (6H, m), 2.34-2.46 (1H, m), 2.52-2.62 (1H, m), 2.73-2.87 (2H, m), 3.01 (3H, s), 3.48 (3H, s), 3.61 (2H, s), 4.08-4.24 (1H, m), 4.75 (1H, d, J=14 Hz), 6.36 (1H, br), 7.11-7.40 (9H, m), 7.45 (1H, d, J=8.5 Hz), 7.56 (2H, d, J=8.0 Hz), 8.84 (1H, br).

Example 33(b)

Synthesis of N$^1$-{1-(2,2,2-trifluoro-N-methylacetamide)-2-(S)-(3,4-dichlorophenyl)-4-[3-oxo-3,4-dihydro-2H-spiro(isoquinoline-1,4'-piperidin)-1'-yl]butan-2-yl}-N$^1$-methyl-N$^2$-phenyloxalamide hydrochloride (Compound No. 29)

[F111]

[F110]

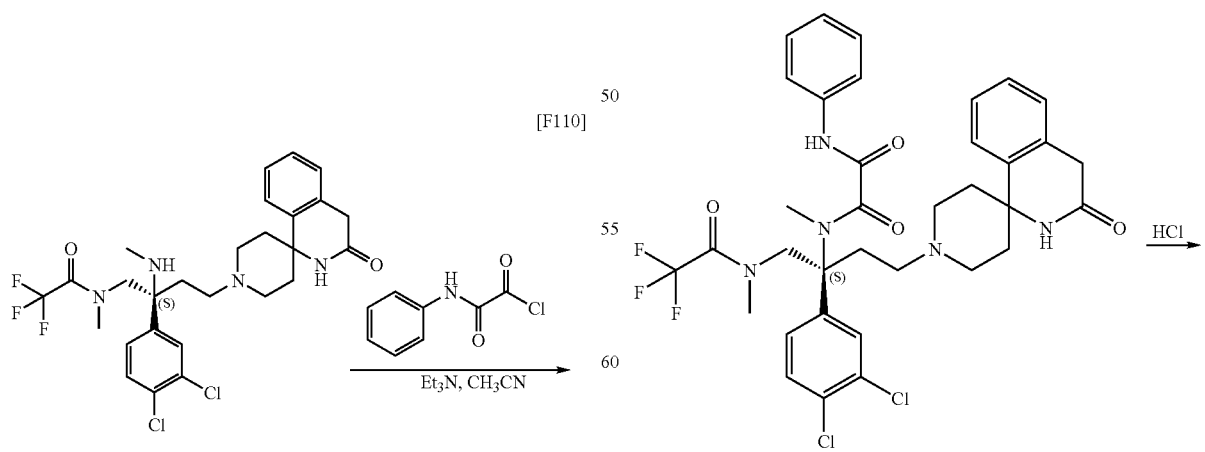

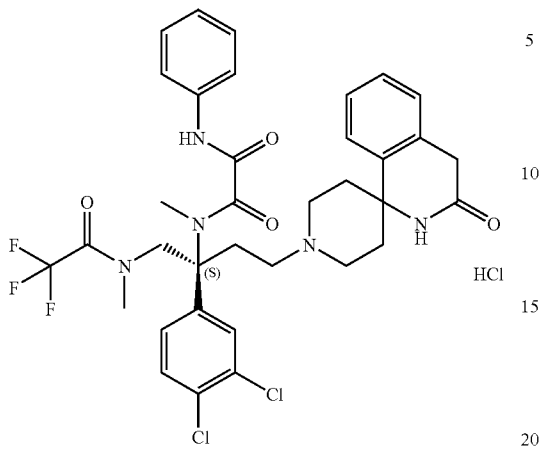

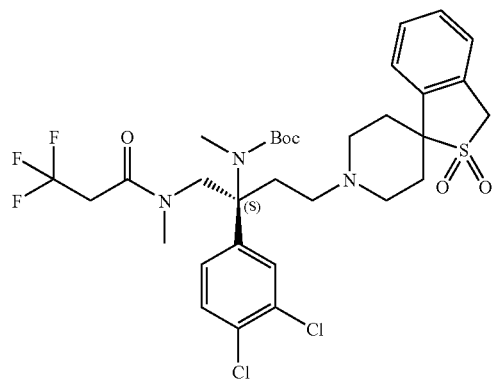

Similar to Example 26(k), the title compound was obtained as yellow powder (350 mg, 94.9%) by use of $N^1$-{1-(2,2,2-trifluoro-N-methylacetamide)-2-(S)-(3,4-dichlorophenyl)-4-[3-oxo-3,4-dihydro-2H-spiro(isoquinoline-1,4'-piperidin)-1'-yl]butan-2-yl}-$N^1$-methyl-$N^2$-phenyloxalamide (350 mg).

$[\alpha]_D^{28} = -32.9°$ (c 0.515, MeOH)

$^1$H-NMR (400 MHz, DMSO-$d_6$)δ ppm: 1.93-2.06 (2H, m), 2.37-2.78 (9H, m), 3.16 (3H, s), 3.18-3.27 (1H, m), 3.46-3.72 (5H, m), 4.15 (1H, d, J=15 Hz), 4.58 (1H, d, J=15 Hz), 7.10-7.55 (9H, m), 7.68-7.71 (2H, m), 7.77 (1H, s), 8.37 (1H, s), 10.35 (1H, br), 10.86 (1H, s).

Similar to Example 26(h), the title compound was obtained (1.45 g, quant.) by use of tert-butyl{[2-(S)-(3,4-dichlorophenyl)-1-(3,3,3-trifluoro-N-methylpropanamido)-4-oxo]butan-2-yl}methylcarbamate (1.0 g) and spiro(benzo(c)thiophene-(2S)-oxido-1(3H),4'-piperidine)/(S)-(+)-mandelate (846 mg).

MS (FAB) m/z 690 ((M+H)$^+$)

$^1$H-NMR (270 MHz, CDCl$_3$)δ ppm: 1.23 (9H, s), 1.51 (1H, d, J=13 Hz), 1.82-2.08 (2H, m), 2.15-2.68 (7H, m), 2.72-3.05 (2H, m), 2.89 (3H, s), 3.10 (3H, s), 3.20-3.42 (2H, m), 3.92-4.65 (2H, m), 3.97 (1H, d, J=17 Hz), 4.30 (1H, d, J=17 Hz), 7.05 (1H, dd, J=2.0, 8.5 Hz), 7.22-7.48 (6H, m).

Example 34(a)

Synthesis of tert-butyl{[1-(3,3,3-trifluoro-N-methylpropanamido)-2-(S)-(3,4-dichlorophenyl)-4-[spiro(benzo(c)thiophene-(2S)-oxido-1(3H),4'-piperidin)-1'-yl]butan-2-yl]methylcarbamate Example 34(b)

Synthesis of N-{2-(S)-(3,4-dichlorophenyl)-2-methylamino-4-[spiro(benzo(c)thiophene-(2S)-oxido-1(3H),4'-piperidin)-1'-yl]butyl}-3,3,3-trifluoro-N-methylpropanamido

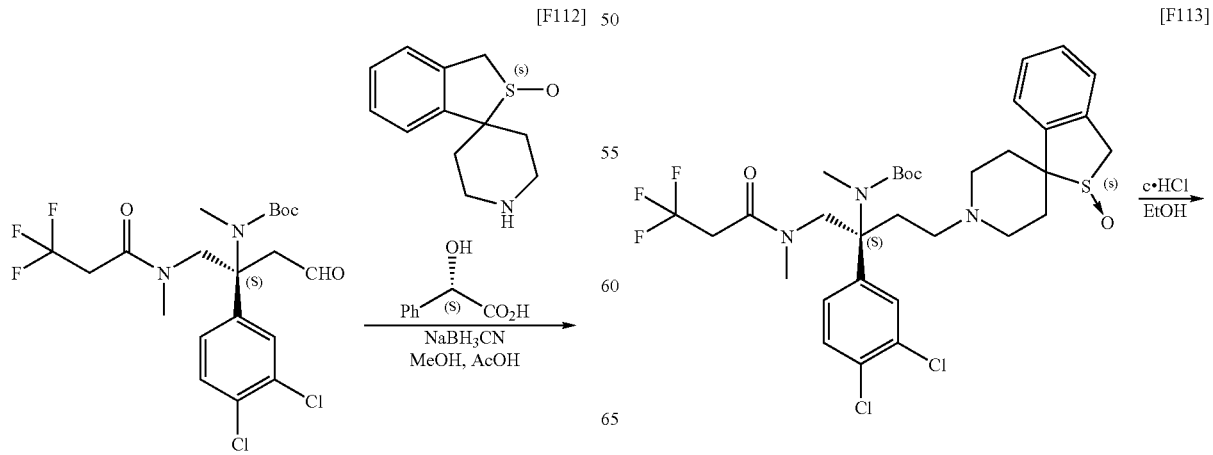

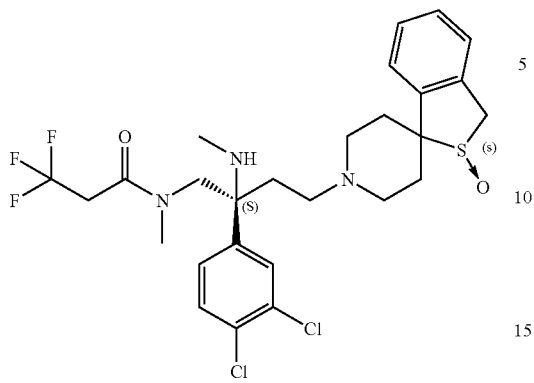

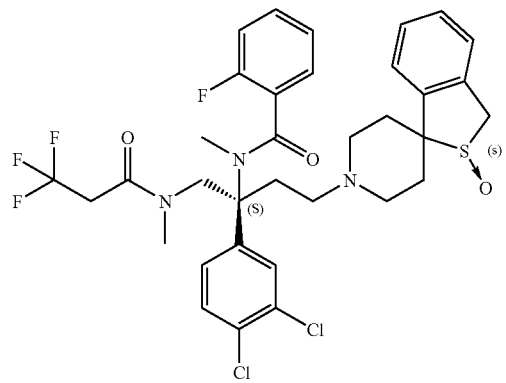

Similar to Example 26(i), the title compound was obtained (1.02 g, 92.2%) by use of tert-butyl{[1-(3,3,3-trifluoro-N-methylpropanamido)-2-(S)-(3,4-dichlorophenyl)-4-[spiro(benzo(c)thiophene-(2S)-oxido-1(3H),4'-piperidin)-1-yl]butan-2-yl]methylcarbamate (1.33 g).

MS (FAB) m/z 590 ((M+H)$^+$)

$^1$H-NMR (270 MHz, CDCl$_3$)δ ppm: 1.95-2.68 (10H, m), 2.26 (3H, s), 2.54 (3H, s), 2.92-3.28 (4H, m), 3.42 (1H, d, J=13 Hz), 3.93-4.12 (2H, m), 4.34 (1H, d, J=17 Hz), 7.25-7.42 (5H, m), 7.44 (1H, d, J=8.5 Hz), 7.63 (1H, d, J=2.0 Hz).

Similar to Example 26(j), the title compound was obtained (682 mg, quant.) by use of N-{2-(S)-(3,4-dichlorophenyl)-2-methylamino-4-[spiro(benzo(c)thiophene-(2S)-oxido-1(3H),4'-piperidin)-1'-yl]butyl}-3,3,3-trifluoro-N-methylpropanamide (550 mg) and 2-fluorobenzoyl chloride (278 μL).

MS (FAB) m/z 712 ((M+H)$^+$)

$^1$H-NMR (400 MHz, CDCl$_3$)δ ppm: 1.54-1.65 (1H, m), 2.02-2.16 (1H, m), 2.23-2.68 (9H, m), 2.75-2.86 (1H, m), 2.93 (3H, s), 3.05 (3H, s), 3.20-3.40 (2H, m), 4.01 (1H, d, J=17 Hz), 4.25-4.45 (2H, m), 4.63-4.73 (1H, m), 7.05-7.50 (11H, m).

Example 34(c)

Synthesis of N-{1-(3,3,3-trifluoro-N-methylpropanamido)-2-(S)-(3,4-dichlorophenyl)-4-[spiro(benzo(c)thiophene-(2S)-oxido-1-(3H),4'-piperidin)-1'-yl]butan-2-yl}-N-methyl-2-fluorobenzamide Example 34(d)

Synthesis of N-{1-(3,3,3-trifluoro-N-methylpropanamido)-2-(S)-(3,4-dichlorophenyl)-4-[spiro(benzo(c)thiophene-(2S)-oxido-1(3H),4'-piperidin)-1'-yl]butan-2-yl}-N-methyl-2-fluorobenzamide hydrochloride (Compound No. 30)

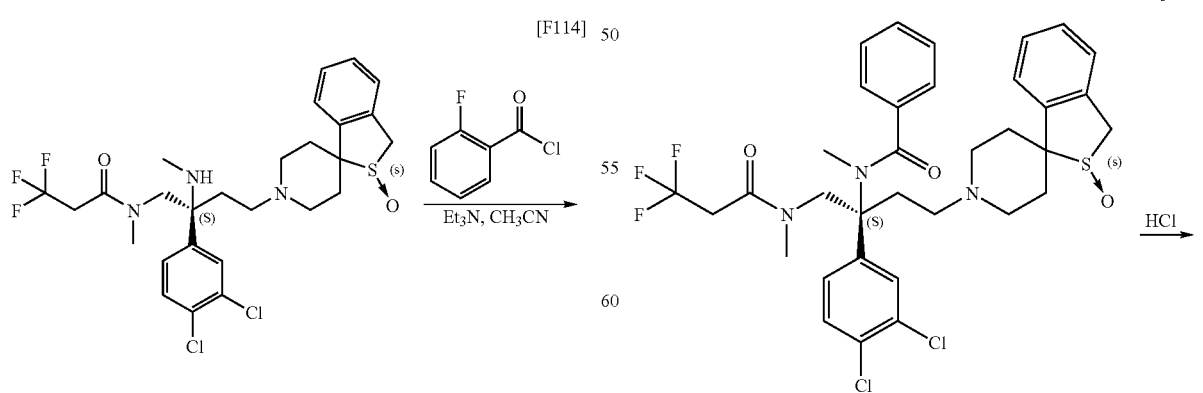

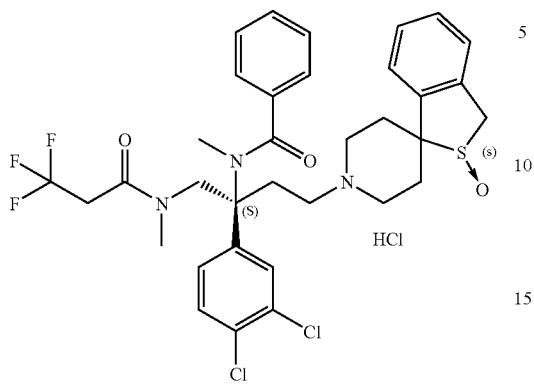

Similar to Example 26(k), the title compound was obtained as white powder (594 mg, 85.2%) by use of N-{1-(3,3,3-trifluoro-N-methylpropanamido)-2-(S)-(3,4-dichlorophenyl)-4-[spiro(benzo(c)thiophene-(2S)-oxido-1(3H),4'-piperidin)-1'-yl]butan-2-yl}-N-methyl-2-fluorobenzamide (682 mg).

$^1$H-NMR (400 MHz, DMSO-$d_6$)δ ppm: 2.00 (1H, d, J=15 Hz), 2.22-2.40 (2H, m), 2.52-2.95 (6H, m), 3.03-3.43 (8H, m), 3.54-3.64 (1H, m), 3.67-3.78 (2H, m), 4.03-4.20 (2H, m), 4.44-4.56 (1H, m), 4.70 (1H, d, J=17 Hz), 7.28-7.54 (9H, m), 7.63 (1H, d, J=8.5 Hz), 7.69 (1H, s), 10.85 (1H, br)

Example 35(a)

Synthesis of N-{1-(3,3,3-trifluoro-N-methylpropanamido)-2-(S)-(3,4-dichlorophenyl)-4-[spiro(benzo(c)thiophene-(2S)-oxido-1(3H),4'-piperidin)-1'-yl]butan-2-yl}-N-methyl-4-trifluoromethylbenzamide

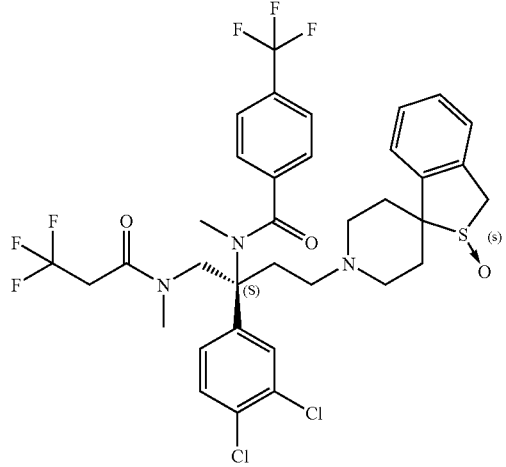

Similar to Example 26(j), the title compound was obtained (466 mg, 65.6%) by use of N-{2-(S)-(3,4-dichlorophenyl)-2-methylamino-4-[spiro(benzo(c)thiophene-(2S)-oxido-1(3H),4'-piperidin)-1'-yl]butyl}-3,3,3-trifluoro-N-methylpropanamide (550 mg) synthesized in Example 34(b) and 4-trifluoromethylbenzoyl chloride (483 μL).

MS (FAB) m/z 762 ((M+H)$^+$)

$^1$H-NMR (400 MHz, CDCl$_3$)δ ppm: 1.58-1.68 (1H, m), 2.08-2.21 (1H, m), 2.33-2.73 (7H, m), 2.80-3.10 (9H, m), 3.20-3.37 (2H, m), 4.03 (1H, d, J=17 Hz), 4.20-4.47 (2H, m), 4.75 (1H, d, J=14 Hz), 7.20-7.35 (5H, m), 7.42-7.54 (4H, m), 7.65-7.72 (2H, m).

Example 35(b)

Synthesis of N-{1-(3,3,3-trifluoro-N-methylpropanamido)-2-(S)-(3,4-dichlorophenyl)-4-[spiro(benzo(c)thiophene-(2S)-oxido-1(3H),4'-piperidin)-1'-yl]butan-2-yl}-N-methyl-4-trifluoromethylbenzamide hydrochloride (Compound No. 31)

[F116]

[F117]

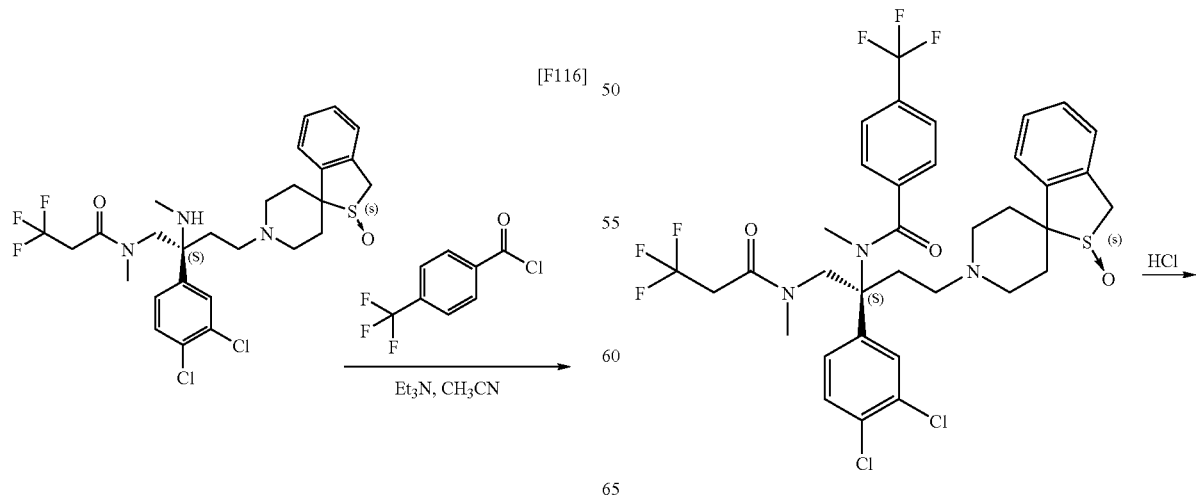

-continued

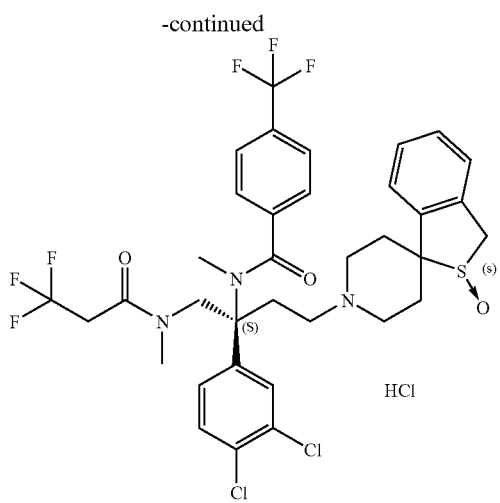

Similar to Example 26(k), the title compound was obtained as pale yellow powder (376 mg, 77.0%) by use of N-{1-(3,3,3-trifluoro-N-methylpropanamido)-2-(S)-(3,4-dichlorophenyl)-4-[spiro(benzo(c)thiophene-(2S)-oxido-1(3H),4'-piperidin)-1'-yl]butan-2-yl}-N-methyl-4-trifluoromethylbenzamide (466 mg).

$[\alpha]_D^{28}$=+6.1° (c 0.502, MeOH)

¹H-NMR (400 MHz, DMSO-d₆)δ ppm: 2.01 (1H, d, J=14.5 Hz), 2.20-2.40 (2H, m), 2.54-2.90 (5H, m), 3.00-3.20 (2H, m), 3.07 (3H, s), 3.23-3.42 (2H, m), 3.57-3.75 (5H, m), 4.03-4.13 (2H, m), 4.57 (1H, d, J=13 Hz), 4.70 (1H, d, J=17 Hz), 7.27-7.47 (3H, m), 7.55 (1H, d, J=8.5 Hz), 7.61 (1H, d, J=8.5 Hz), 7.70 (2H, d, J=8.0 Hz), 7.77 (1H, s), 7.84-7.90 (2H, m), 8.14 (1H, d, J=8.0 Hz), 10.82 (1H, br).

Example 36(a)

Synthesis of tert-butyl[1-(N-methylisobutylamide)-2-(S)-(3,4-dichlorophenyl)(4-penten-2-yl)]methylcarbamate

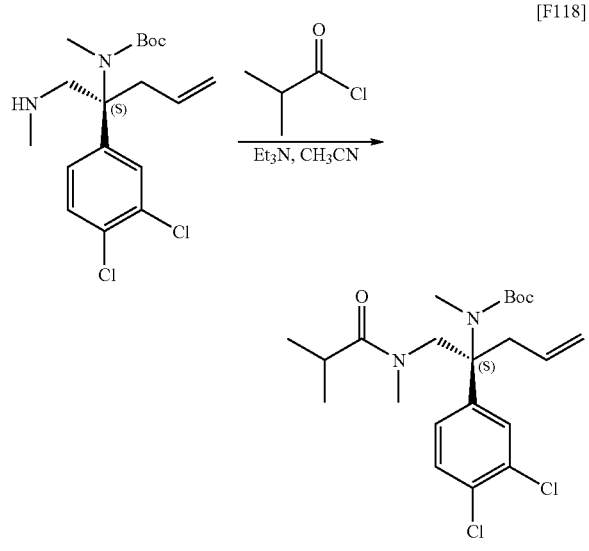

tert-Butyl[2-(S)-(3,4-dichlorophenyl)-1-methylamino(4-penten-2-yl)]methylcarbamate (2.0 g) synthesized in Example 26(d) was dissolved in acetonitrile (40 mL). Under cooling with ice, triethylamine (1.49 mL) and isobutyryl chloride (1.12 mL) were added thereto. Under cooling with ice, the mixture was stirred for 1 hour. The reaction mixture was concentrated under reduced pressure, and water was added to the residue, followed by extraction with ethyl acetate. The organic layer was washed with saturated brine, dried over sodium sulfate anhydrate, and concentrated under reduced pressure. The residue was purified through silica gel column chromatography (n-hexane:ethyl acetate=3:1), to thereby give the title compound (1.53 g, 64.0%).

MS (FAB) m/z 443 ((M+H)⁺)

¹H-NMR (270 MHz, CDCl₃)δ ppm: 1.14 (6H, d, J=7.0 Hz), 1.23 (9H, s), 2.55 (1H, dd, J=7.0, 13.5 Hz), 2.78 (3H, s), 2.78-2.85 (2H, m), 3.09 (3H, s), 4.08-4.16 (2H, m), 4.86-4.99 (2H, m), 5.85-5.87 (1H, m), 7.02 (1H, dd, J=2.5, 8.5 Hz), 7.25 (1H, d, J=2.5 Hz), 7.36 (1H, d, J=8.5 Hz).

Example 36(b)

Synthesis of tert-butyl{[2-(S)-(3,4-dichlorophenyl)-1-(N-methylisobutylamide)-4,5-dihydroxy]pentan-2-yl}methylcarbamate

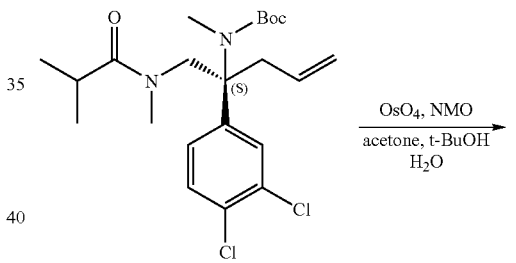

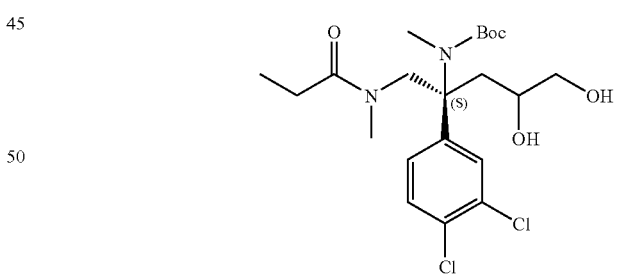

Similar to Example 26(f), the title compound was obtained (1.13 g, 94%) by use of tert-butyl[1-(N-methylisobutylamide)-2-(S)-(3,4-dichlorophenyl)(4-penten-2-yl)]methylcarbamate (1.12 g).

MS (FAB) m/z 477 ((M+H)⁺)

¹H-NMR (270 MHz, CDCl₃)δ ppm: 1.04-1.20 (15H, m), 1.90-2.23 (2H, m), 2.41 (1H, t, J=4.5 Hz), 2.65-3.65 (8H, m), 3.72 (2H, t, J=5.0 Hz), 5.02-5.28 (1H, m), 5.52-5.78 (1H, m), 7.00-7.15 (1H, m), 7.18-7.35 (1H, m), 7.40 (1H, d, J=8.5 Hz).

Example 36(c)

Synthesis of tert-butyl{[2-(S)-(3,4-dichlorophenyl)-1-(N-methylisobutylamide)-4-oxo]butan-2-yl}methylcarbamate

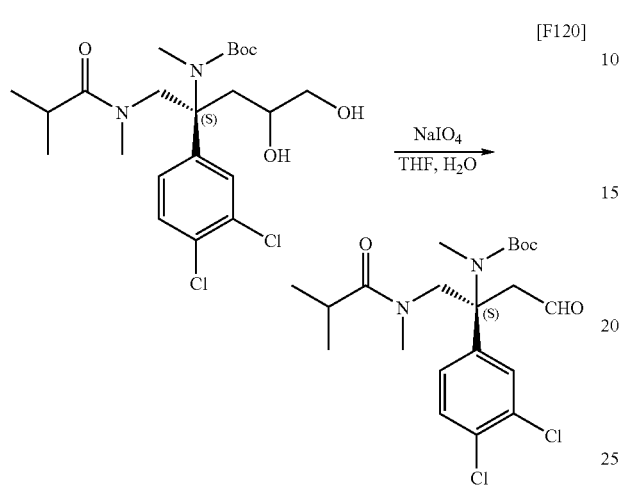

[F120]

Similar to Example 26(g), the title compound was obtained (4.17 g, 99.0%) by use of tert-butyl{[2-(S)-(3,4-dichlorophenyl)-1-(N-methylisobutylamide)-4,5-dihydroxy]pentan-2-yl}methylcarbamate (4.5 g).

MS (FAB) m/z 445 ((M+H)⁺)

¹H-NMR (270 MHz, CDCl₃)δ ppm: 1.13 (6H, dd, J=3.0, 7.0 Hz), 1.23-1.29 (9H, m), 2.73 (3H, s), 2.76-2.84 (1H, m), 2.90 (1H, d, J=16 Hz), 3.11 (3H, s), 3.16 (1H, d, J=16 Hz), 4.10-4.18 (1H, m), 4.45 (1H, d, J=13 Hz), 7.10 (1H, dd, J=2.5, 8.5 Hz), 7.33 (1H, d, J=2.5 Hz), 7.41 (1H, dd, J=2.5, 8.5 Hz), 9.71 (1H, t, J=2.0 Hz).

Example 36(d)

Synthesis of tert-butyl{[1-(N-methylisobutylamide)-2-(S)-(3,4-dichlorophenyl)-4-[spiro(benzo(c)thiophene-(2S)-oxido-1(3H),4'-piperidin)-1'-yl]butan-2-yl]methylcarbamate

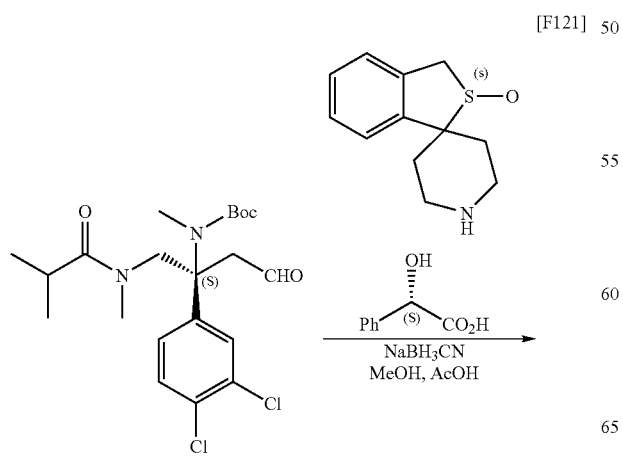

[F121]

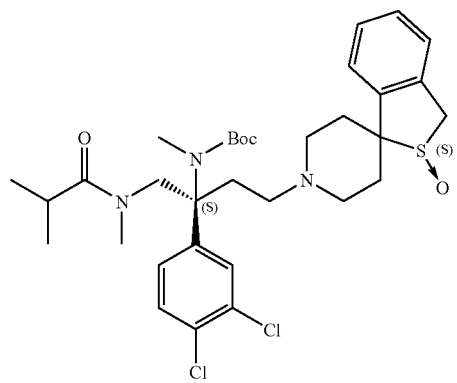

Similar to Example 26(h), the title compound was obtained (1.85 g, 95%) by use of tert-butyl{[2-(S)-(3,4-dichlorophenyl)-1-(N-methylisobutylamide)-4-oxo]butan-2-yl}methylcarbamate (1.33 g) and spiro(benzo(c)thiophene-(2S)-oxido-1(3H),4'-piperidine)/(S)-(+)-mandelate (1.45 g).

MS (FAB) m/z 650 ((M+H)⁺)

¹H-NMR (270 MHz, CDCl₃)δ ppm: 1.16 (6H, dd, J=4.0, 6.5 Hz), 1.20-1.29 (9H, m), 1.50 (1H, d, J=15 Hz), 1.79-2.01 (2H, m), 2.17-2.52 (7H, m), 2.58-2.79 (2H, m), 2.82-2.87 (5H, m), 3.13 (3H, s), 3.97 (1H, d, J=17 Hz), 4.07-4.19 (1H, m), 4.29 (1H, d, J=17 Hz), 7.06 (1H, dd, J=2.0, 8.5 Hz), 7.19-7.33 (5H, m), 7.39 (1H, d, J=8.5 Hz).

Example 36(e)

Synthesis of N-{2-(S)-(3,4-dichlorophenyl)-2-methylamino-4-[spiro(benzo(c)thiophene-(2S)-oxido-1(3H), 4'-piperidin-1'-yl]butyl}-N-methylisobutylamide

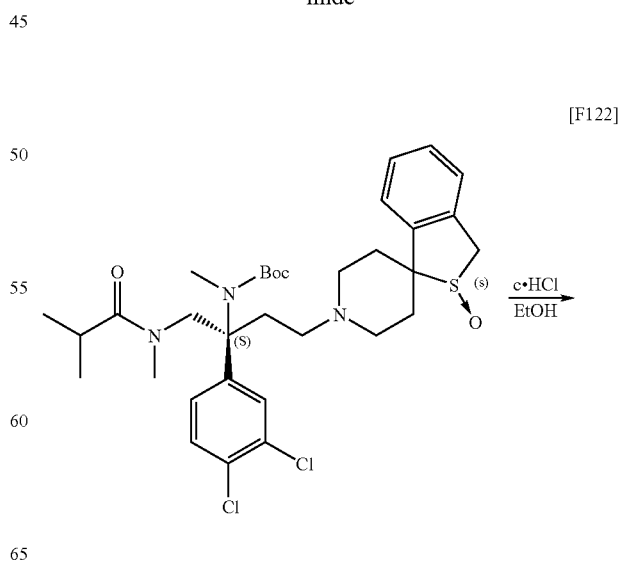

[F122]

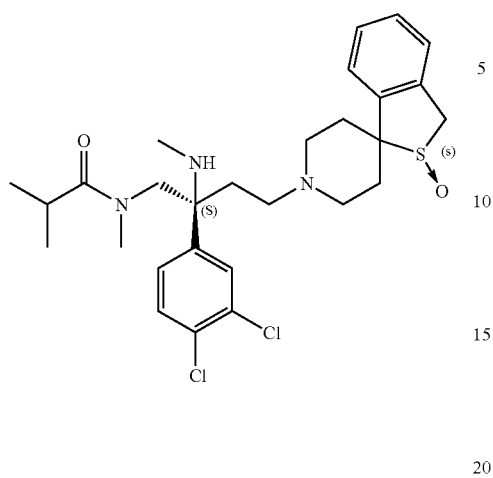

Similar to Example 26(i), the title compound was obtained (1.35 g, 86%) by use of tert-butyl{[1-(N-methyl-isobutylamide)-2-(S)-(3,4-dichlorophenyl)-4-[spiro(benzo(c)thiophene-(2S)-oxido-1(3H),4'-piperidin)-1'-yl]butan-2-yl]methylcarbamate (1.85 g).

MS (FAB) m/z 550 ((M+H)$^+$)

$^1$H-NMR (270 MHz, CDCl$_3$)δ ppm: 1.02 (3H, d, J=6.5 Hz), 1.09 (3H, d, J=7.0 Hz), 1.57-1.66 (4H, m), 2.05-2.17 (2H, m), 2.25 (3H, s), 2.31-2.45 (4H, m), 2.53 (3H, s), 2.64-2.79 (2H, m), 2.97-3.09 (2H, m), 3.34-3.39 (1H, m), 3.83-4.00 (1H, m), 4.02 (1H, d, J=17 Hz), 4.35 (1H, d, J=17 Hz), 7.25-7.40 (5H, m), 7.43 (1H, d, J=8.5 Hz), 7.58-7.65 (1H, m).

Example 36(f)

Synthesis of N-{1-(N-methylisobutylamide)-2-(S)-(3,4-dichlorophenyl)-4-[spiro(benzo(c)thiophene-(2S)-oxido-1(3H),4'-piperidin)-1'-yl]butan-2-yl}-N-methylbenzamide

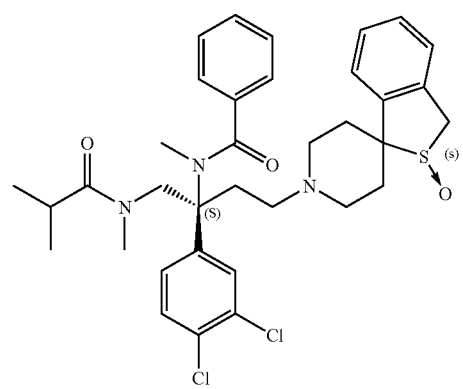

Similar to Example 26(j), the title compound was obtained as white powder (100 mg, 83.9%) by use of N-{2-(S)-(3,4-dichlorophenyl)-2-methylamino-4-[spiro(benzo(c)thiophene-(2S)-oxido-1(3H),4'-piperidin)-1'-yl]butyl}-N-methylisobutylamide (100 mg).

MS (FAB) m/z 654 ((M+H)$^+$)

$^1$H-NMR (400 MHz, CDCl$_3$)δ ppm: 1.10-1.17 (6H, m), 1.49-1.60 (1H, m), 1.82-1.93 (1H, m), 2.08-2.53 (8H, m), 2.68-2.90 (3H, m), 2.96 (3H, s), 3.15 (3H, s), 3.98 (1H, d, J=17 Hz), 4.31 (1H, d, J=17 Hz), 4.38-4.53 (2H, m), 7.21-7.36 (5H, m), 7.39-7.48 (7H, m).

Example 36(g)

Synthesis of N-{1-(N-methylisobutylamide)-2-(S)-(3,4-dichlorophenyl)-4-[spiro(benzo(c)thiophene-(2S)-oxido-1(3H),4'-piperidin)-1'-yl]butan-2-yl}-N-methylbenzamide hydrochloride (Compound No. 32)

[F123]

[F124]

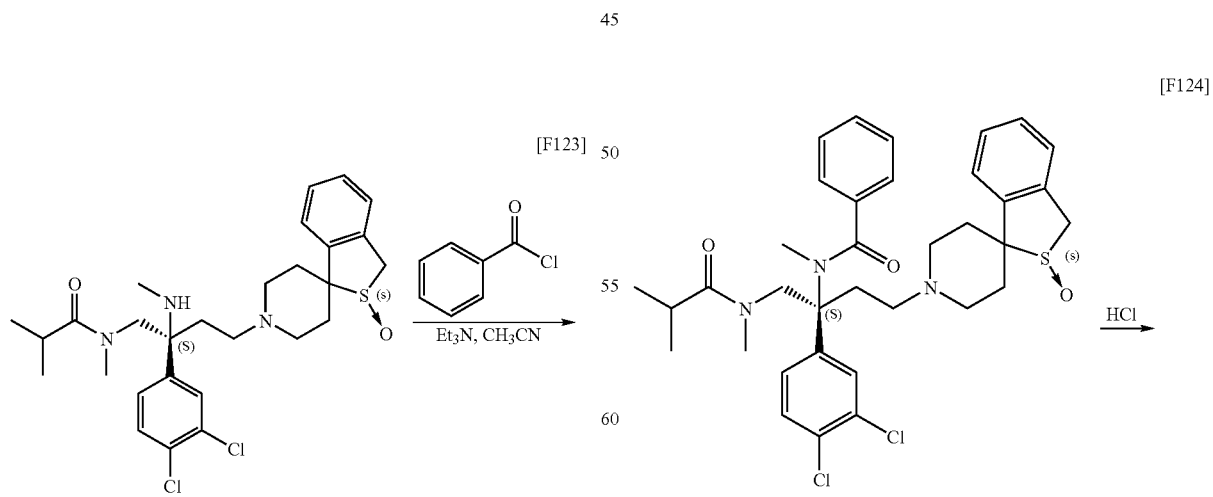

-continued

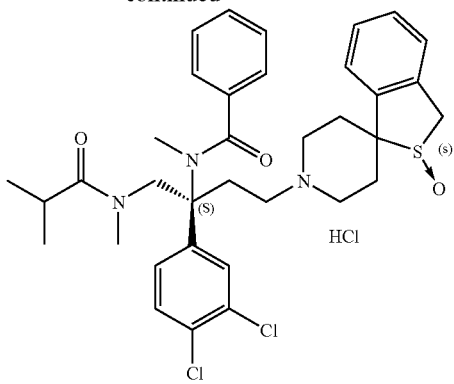

Similar to Example 26(k), the title compound was obtained as white powder (84 mg, 79.4%) by use of N-{1-(N-methylisobutylamide)-2-(S)-(3,4-dichlorophenyl)-4-[spiro(benzo(c)thiophene-(2S)-oxido-1(3H),4'-piperidin)-1'-yl]butan-2-yl}-N-methylbenzamide (100 mg).

$[α]_D^{28}$=−4.2° (c 0.511, MeOH)

$^1$H-NMR (400 MHz, DMSO-$d_6$)δ ppm: 1.00-1.04 (6H, m), 2.03 (1H, d, J=15.5 Hz), 2.22-2.45 (2H, m), 2.52-2.60 (1H, m), 2.65-2.95 (5H, m), 3.05-3.25 (2H, m), 3.10 (3H, s), 3.57 (3H, s), 3.57-3.75 (2H, m), 3.98-4.13 (2H, m), 4.40-4.50 (1H, m), 4.70 (1H, d, J=17 Hz), 7.28-7.65 (11H, m), 7.74 (1H, s), 10.96 (1H, br).

Example 37(a)

Synthesis of $N^1$-{1-(N-methylisobutylamide)-2-(S)-(3,4-dichlorophenyl)-4-[spiro(benzo(c)thiophene-(2S)-oxido-1(3H),4'-piperidin)-1'-yl]butan-2-yl}-$N^1$, $N^2$-dimethyl-$N^2$-phenyloxalamide

[125]

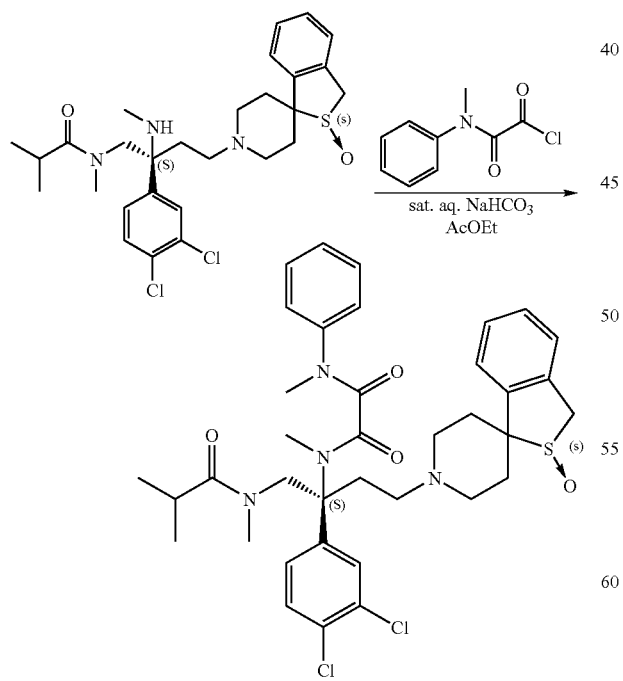

N-{2-(S)-(3,4-Dichlorophenyl)-2-methylamino-4-[spiro(benzo(c)thiophene-(2S)-oxido-1(3H),4'-piperidin)-1'-yl]butyl}-N-methylisobutylamide (100 mg) synthesized in Example 36(e) was dissolved in ethyl acetate (1 mL). At room temperature, saturated aqueous sodium bicarbonate (1 mL) and (methylphenylamino)-oxo-acetyl chloride (107 mg) synthesized in Referential Example 1 were added thereto, and the mixture was stirred for 1 hour at the same temperature. The reaction mixture was subjected to partitioning, extracted with ethyl acetate, washed with saturated brine, and dried over sodium sulfate anhydrate. The solvent was concentrated under reduced pressure, and the residue was purified through silica gel column chromatography (n-hexane:ethyl acetate=1:1→ethyl acetate→ethyl acetate:methanol=20:1), to thereby give the title compound (115 mg, 88.8%) as white powder.

MS (FAB) m/z 711 ((M+H)$^+$)

$^1$H-NMR (400 MHz, CDCl$_3$)δ ppm: 1.09 (3H, d, J=6.5 Hz), 1.10 (3H, d, J=6.5 Hz), 1.45-1.52 (1H, m), 1.75-1.92 (2H, m), 2.02-2.48 (8H, m), 2.62-2.84 (5H, m), 3.02 (3H, s), 3.33 (3H, s), 4.29 (1H, d, J=17 Hz), 4.05-4.26 (2H, m), 4.29 (1H, d, J=17 Hz), 6.30 (1H, br), 7.03 (1H, d, J=2.0 Hz), 7.08 (1H, d, J=8.5 Hz), 7.25-7.35 (6H, m), 7.44-7.50 (3H, m).

Example 37(b)

Synthesis of $N^1$-{1-(N-methylisobutylamide)-2-(S)-(3,4-dichlorophenyl)-4-[spiro(benzo(c)thiophene-(2S)-oxido-1(3H), 41-piperidin)-1'-yl]butan-2-yl}-$N^1$,$N^2$-dimethyl-$N^2$-phenyloxalamide hydrochloride (Compound No. 33)

[F126]

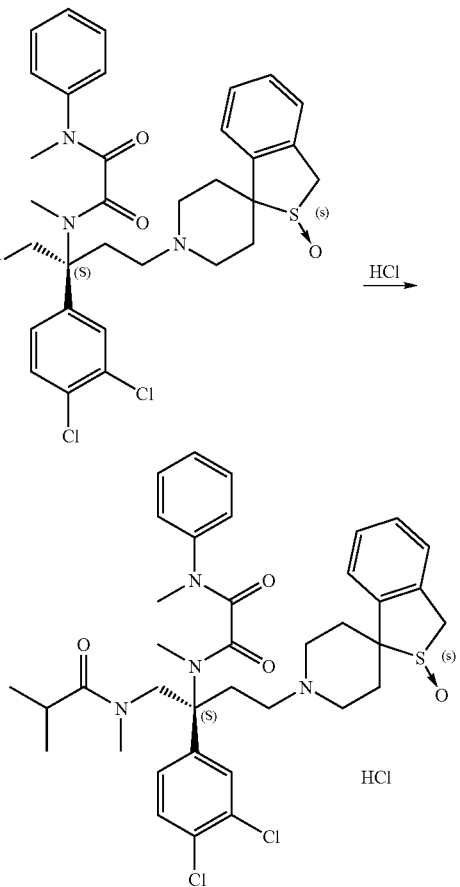

Similar to Example 26(k), the title compound was obtained as white powder (102 mg, 84.2%) by use of N¹-{1-(N-methylisobutylamide)-2-(S)-(3,4-dichlorophenyl)-4-[spiro(benzo(c)thiophene-(2S)-oxido-1(3H),4'-piperidin)-1'-yl]butan-2-yl}-N¹,N²-dimethyl-N²-phenyloxalamide (115 mg).

$[\alpha]_D^{29}$=−42.0° (c 0.437, MeOH)

¹H-NMR (400 MHz, DMSO-d₆)δ ppm: 0.95-1.00 (6H, m), 2.01 (1H, d, J=18.5 Hz), 2.22-2.36 (3H, m), 2.40-2.50 (2H, m), 2.60-2.90 (3H, m), 2.92-3.05 (2H, m), 3.09 (3H, s), 3.24 (3H, s), 3.30-3.50 (4H, m), 3.70-3.90 (1H, m), 4.09 (1H, d, J=17 Hz), 4.10-4.25 (1H, m), 4.69 (1H, d, J=17 Hz), 6.65 (1H, br), 7.30-7.47 (9H, m), 7.50-7.60 (3H, m), 10.79 (1H, br).

Example 38(a)

Synthesis of tert-butyl[1-(N-methyl-propionamide)-2-(S)-(3,4-dichlorophenyl)(4-penten-2-yl)]methylcarbamate

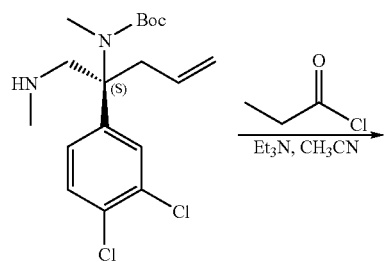

[F127]

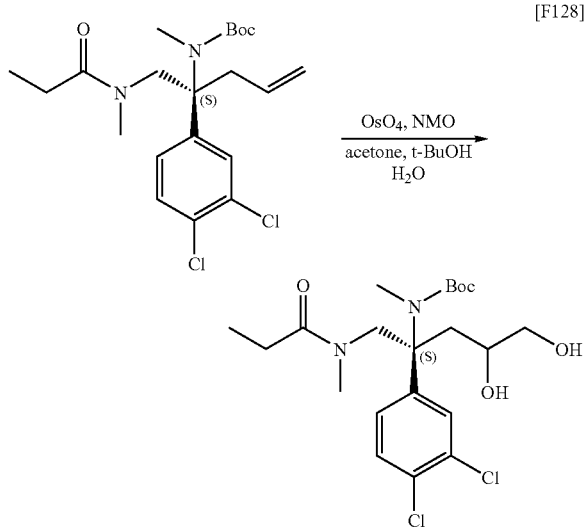

Similar to Example 36(a), the title compound was obtained (1.12 g, 65.2%) by use of tert-butyl[2-(S)-(3,4-dichlorophenyl)-1-methylamino(4-penten-2-yl)]methylcarbamate (1.49 g) synthesized in Example 26(d) and propionyl chloride (417 μL).

MS (FAB) m/z 429 ((M+H)⁺)

¹H-NMR (270 MHz, CDCl₃)δ ppm: 1.16 (3H, t, J=7.5 Hz), 1.19 (9H, brs), 2.35 (2H, q, J=7.5 Hz), 2.57 (1H, dd, J=7.5, 13.5 Hz), 2.75 (3H, s), 2.67-2.88 (1H, m), 3.08 (3H, s), 3.97-4.32 (2H, m), 4.82-5.03 (2H, m), 5.72-5.93 (1H, m), 7.01 (1H, dd, J=2.5, 8.5 Hz), 7.26 (1H, d, J=2.5 Hz), 7.36 (1H, d, J=8.5 Hz).

Example 38(b)

Synthesis of tert-butyl{[2-(S)-(3,4-dichlorophenyl)-1-(N-methyl-propionamide)-4,5-dihydroxy]pentan-2-yl}methylcarbamate

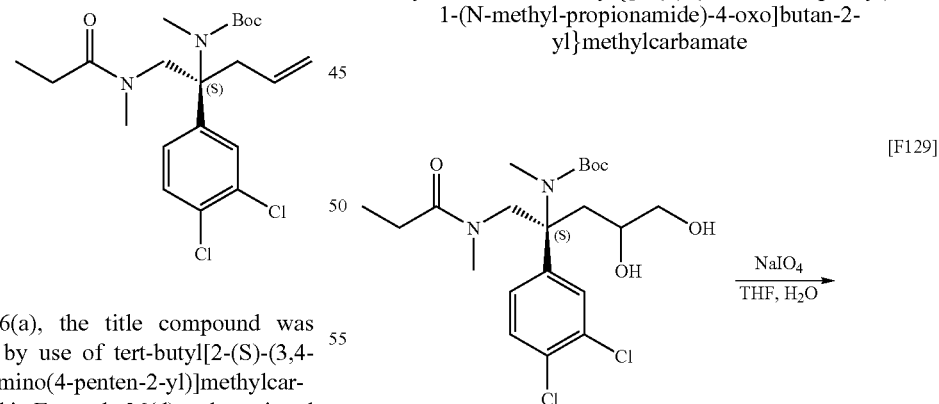

[F128]

Similar to Example 26(f), the title compound was obtained (1.09 g, quant) by use of tert-butyl[1-(N-methyl-propionamide)-2-(S)-(3,4-dichlorophenyl)(4-penten-2-yl)]methylcarbamate (1.0 g).

MS (FAB) m/z 463 ((M+H)⁺)

¹H-NMR (270 MHz, CDCl₃)δ ppm: 0.93-1.45 (12H, m), 1.98-2.50 (7H, m), 2.80-3.80 (8H, m), 5.00-5.28 (1H, m), 5.50-5.75 (1H, m), 7.00-7.16 (1H, m), 7.20-7.32 (1H, m), 7.40 (1H, d, J=8.5 Hz).

Example 38(c)

Synthesis of tert-butyl{[2-(S)-(3,4-dichlorophenyl)-1-(N-methyl-propionamide)-4-oxo]butan-2-yl}methylcarbamate

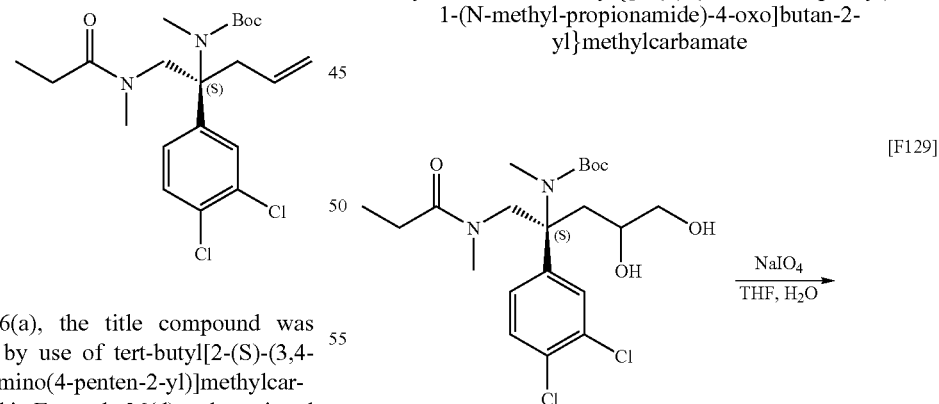

[F129]

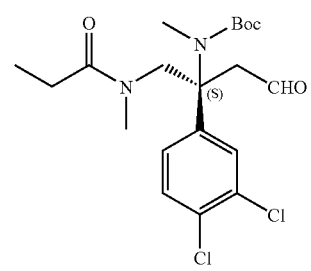

Similar to Example 26(g), the title compound was obtained (1.05 g, 99.0%) by use of tert-butyl{[2-(S)-(3,4-dichlorophenyl)-1-(N-methyl-propionamide)-4,5-dihydroxy]pentan-2-yl}methylcarbamate (1.09 g).

MS (FAB) m/z 431 ((M+H)$^+$)

$^1$H-NMR (270 MHz, CDCl$_3$)δ ppm: 1.15 (3H, t, J=7.5 Hz), 1.24 (9H, s), 2.35 (2H, q, J=7.5 Hz), 2.69 (3H, s), 2.95 (1H, d, J=14.5 Hz), 3.09 (3H, s), 3.20 (1H, d, J=14.5 Hz), 4.17 (1H, d, J=13.5 Hz), 4.44 (1H, d, J=13.5 Hz), 7.11 (1H, dd, J=2.5, 8.5 Hz), 7.33 (1H, d, J=2.5 Hz), 7.42 (1H, d, J=8.5 Hz), 9.71 (1H, t, J=2.0 Hz).

Example 38(d)

Synthesis of tert-butyl{[1-(N-methyl-propionamide)-2-(S)-(3,4-dichlorophenyl)-4-[spiro(benzo(c)thiophene-(2S)-oxido-1(3H),4'-piperidin)-1'-yl]butan-2-yl]methylcarbamate

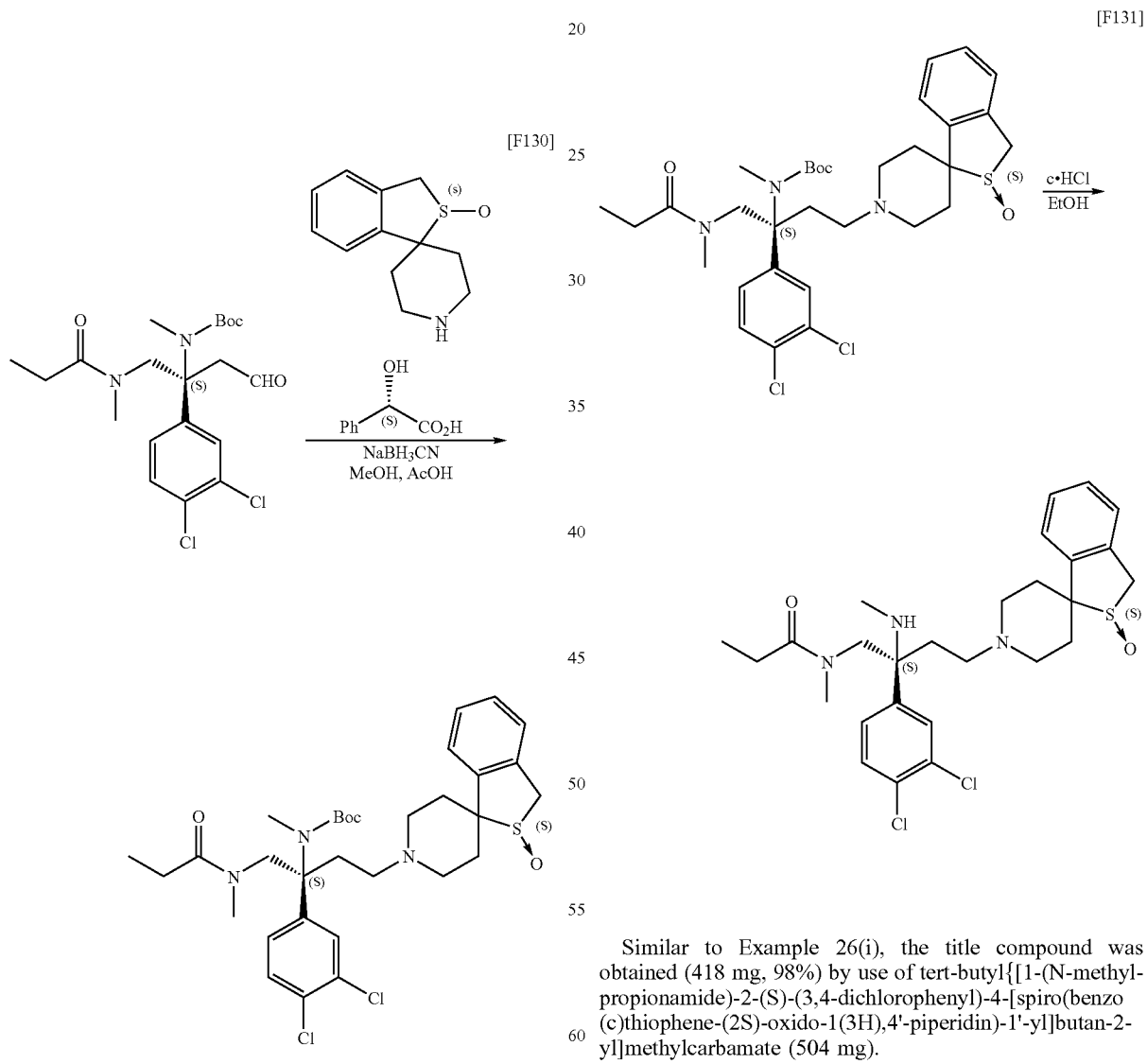

Similar to Example 26(h), the title compound was obtained (504 mg, 68%) by use of tert-butyl{[2-(S)-(3,4-dichlorophenyl)-1-(N-methyl-propionamide)-4-oxo]butan-2-yl}methylcarbamate (300 mg) and spiro(benzo(c)thiophene-(2S)-oxido-1(3H),4'-piperidine)/(S)-(+)-mandelate (363 mg).

MS (FAB) m/z 636 ((M+H)$^+$)

$^1$H-NMR (270 MHz, CDCl$_3$)δ ppm: 1.18 (3H, t, J=7.5 Hz), 1.25 (9H, brs), 1.65-2.15 (6H, m), 2.20-3.25 (13H, m), 3.15 (3H, s), 4.00-4.25 (1H, m), 4.35-4.52 (1H, m), 7.12 (1H, d, J=8.5 Hz), 7.18-7.55 (6H, m).

Example 38(e)

Synthesis of N-{2-(S)-(3,4-dichlorophenyl)-2-methylamino-4-[spiro(benzo(c)thiophene-(2S)-oxido-1(3H),4'-piperidin)-1'-yl]butyl}-N-methyl-propionamide Similar to Example 26(i), the title compound was obtained (418 mg, 98%) by use of tert-butyl{[1-(N-methyl-propionamide)-2-(S)-(3,4-dichlorophenyl)-4-[spiro(benzo(c)thiophene-(2S)-oxido-1(3H),4'-piperidin)-1'-yl]butan-2-yl]methylcarbamate (504 mg).

MS (FAB) m/z 536 ((M+H)$^+$)

$^1$H-NMR (270 MHz, CDCl$_3$)δ ppm: 0.78-0.93 (1H, m), 1.12 (3H, t, J=7.5 Hz), 1.06-1.18 (1H, m), 1.58-1.92 (3H, m), 2.10-2.66 (8H, m), 2.21 (3H, s), 2.29 (2H, q, J=7.5 Hz), 2.44 (3H, s), 3.96-4.14 (2H, m), 4.30-4.50 (2H, m), 7.13-7.58 (7H, m).

Example 38(f)

Synthesis of N-{1-(N-methyl-propionamide)-2-(S)-(3,4-dichlorophenyl)-4-[spiro(benzo(c)thiophene-(2S)-oxido-1(3H),4'-piperidin)-1'-yl]butan-2-yl}-N-methylbenzamide

Example 38(g)

Synthesis of N-{1-(N-methyl-propionamide)-2-(S)-(3,4-dichlorophenyl)-4-[spiro(benzo(c)thiophene-(2S)-oxido-1(3H),4'-piperidin)-1'-yl]butan-2-yl}-N-methylbenzamide hydrochloride (Compound No. 34)

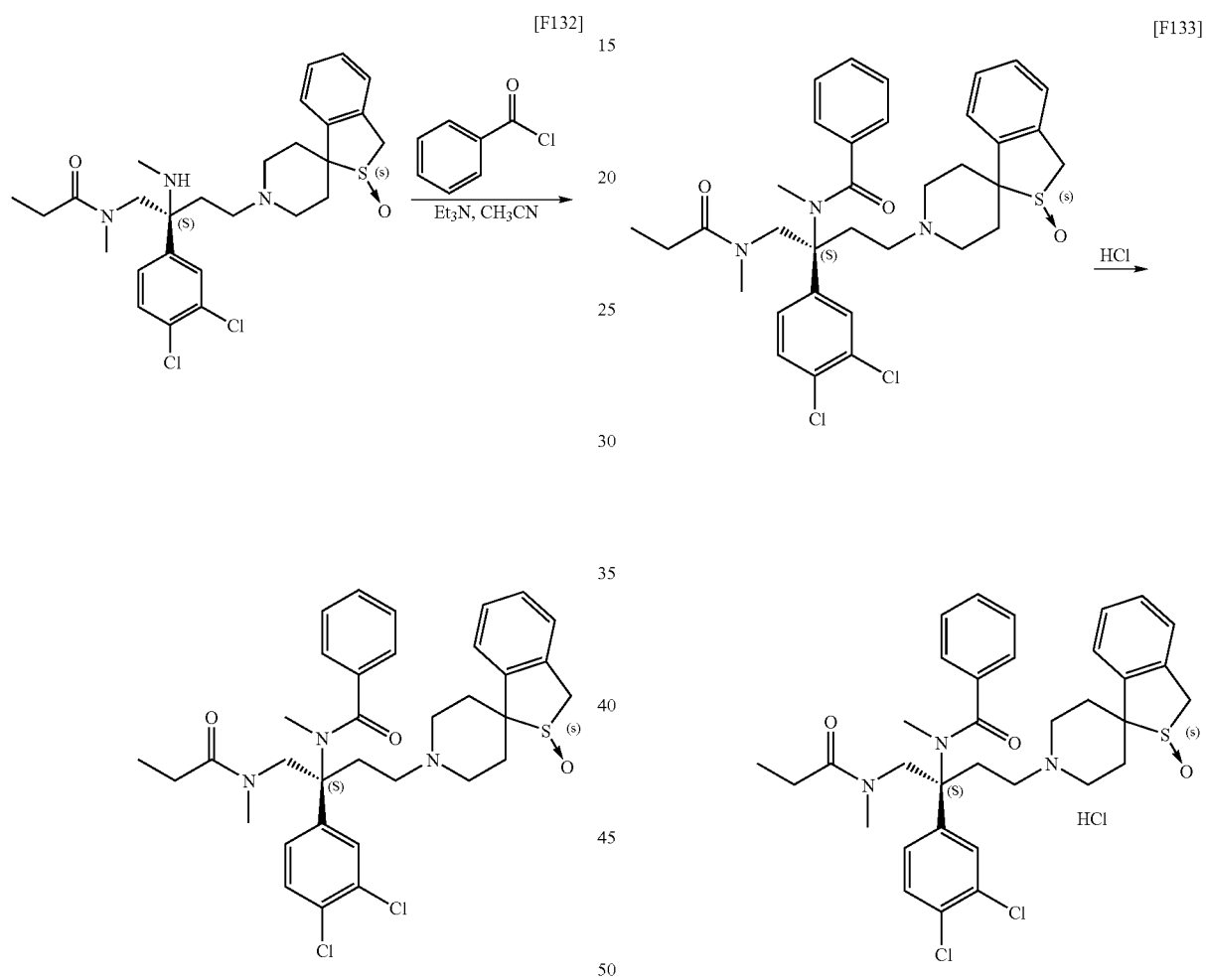

Similar to Example 26(j), the title compound was obtained as white powder (543 mg, 82.3%) by use of N-{2-(S)-(3,4-dichlorophenyl)-2-methylamino-4-[spiro(benzo(c)thiophene-(2S)-oxido-1(3H),4'-piperidin)-1'-yl]butyl}-N-methyl-propionamide (550 mg).

MS (FAB) m/z 640 ((M+H)$^+$)

$^1$H-NMR (400 MHz, CDCl$_3$)δ ppm: 1.15 (3H, t, J=7.0 Hz), 1.50-1.60 (1H, m), 1.85-1.97 (1H, m), 2.12-2.58 (9H, m), 2.70-3.03 (6H, m), 3.13 (3H, s), 3.98 (1H, d, J=17 Hz), 4.31 (1H, d, J=17 Hz), 4.33-4.54 (2H, m), 7.20-7.35 (5H, m), 7.39-7.48 (7H, m).

Similar to Example 26(k), the title compound was obtained as white powder (473 mg, 82.4%) by use of N-{1-(N-methyl-propionamide)-2-(S)-(3,4-dichlorophenyl)-4-[spiro(benzo(c)thiophene-(2S)-oxido-1(3H), 4]-piperidin)-1'-yl]butan-2-yl}-N-methylbenzamide (543 mg).

[α]D$^{28}$=+24.1° (c 0.508, MeOH)

$^1$H-NMR (400 MHz, DMSO-d$_6$)δ ppm: 1.02 (3H, t, J=7.5 Hz), 2.04 (1H, d, J=15.5 Hz), 2.23-2.40 (4H, m), 2.50-2.62 (1H, m), 2.71 (3H, s), 2.78-2.92 (1H, m), 3.03-3.25 (6H, m), 3.27-3.42 (1H, m), 3.60-3.70 (2H, m), 4.03-4.15 (2H, m), 4.38-4.47 (1H, m), 4.69 (1H, d, J=17 Hz), 7.27-7.65 (12H, m), 7.74 (1H, s), 10.67 (1H, br).

Example 39(a)

Synthesis of $N^1$-{1-(N-methyl-propionamide)-2-(S)-(3,4-dichlorophenyl)-4-[spiro(benzo(c)thiophene-(2S)-oxido-1(3H),4'-piperidin)-1'-yl]butan-2-yl}-$N^1$,$N^2$-dimethyl-$N^2$-phenyloxalamide

Example 39(b)

Synthesis of $N^1$-{1-(N-methyl-propionamide)-2-(S)-(3,4-dichlorophenyl)-4-[spiro(benzo(c)thiophene-(2S)-oxido-1(3H),4'-piperidin)-1'-yl]butan-2-yl}-$N^1$,$N^2$-dimethyl-$N^2$-phenyloxalamide hydrochloride (Compound No. 35)

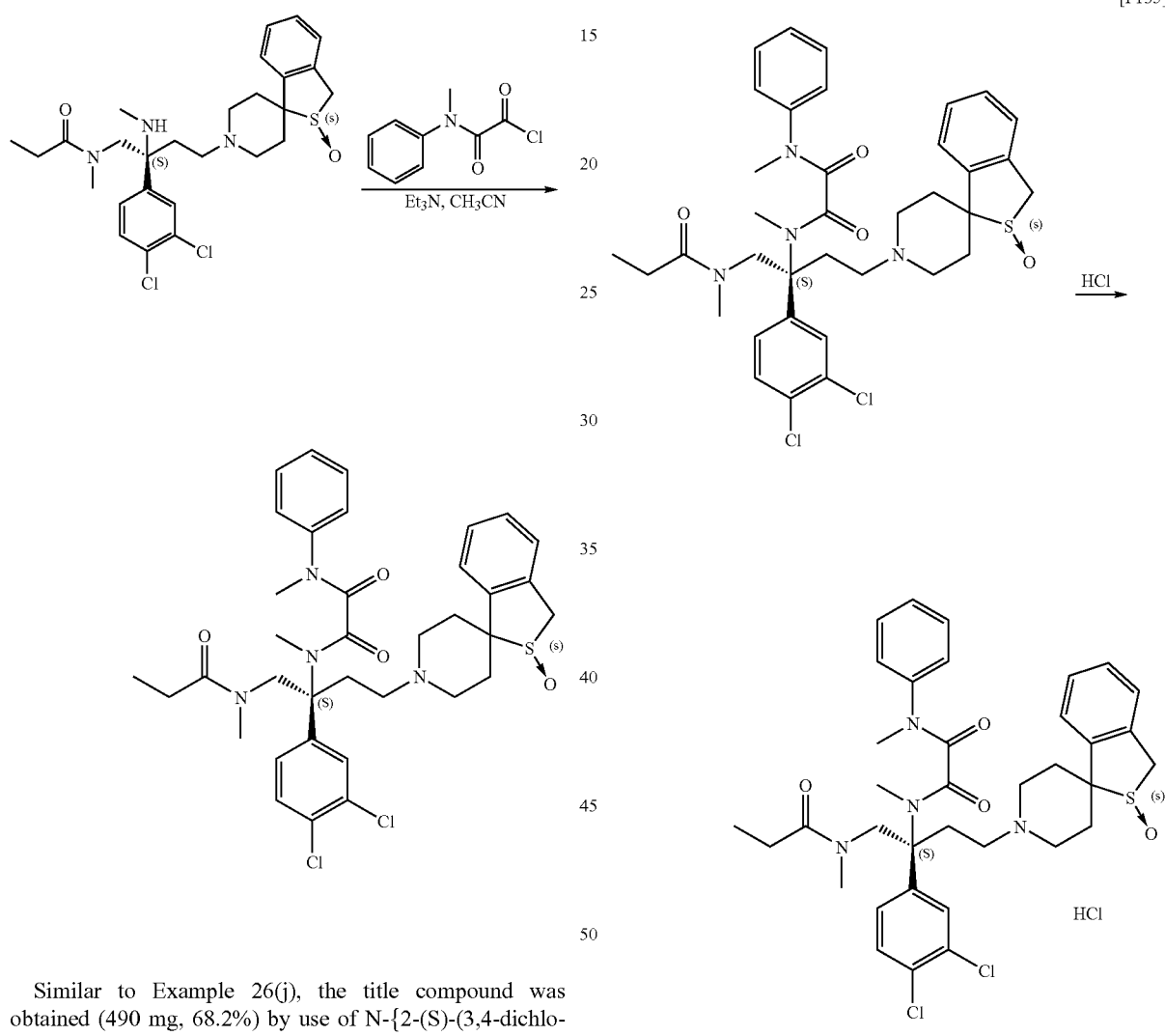

Similar to Example 26(j), the title compound was obtained (490 mg, 68.2%) by use of N-{2-(S)-(3,4-dichlorophenyl)-2-methylamino-4-[spiro(benzo(c)thiophene-(2S)-oxido-1(3H),4'-piperidin)-1'-yl]butyl}-N-methyl-propionamide (550 mg) synthesized in Example 38(e) and (methylphenylamino)-oxo-acetyl chloride (407 mg) synthesized in Referential Example 1.

MS (FAB) m/z 697 ((M+H)$^+$)

$^1$H-NMR (400 MHz, CDCl$_3$)δ ppm 1.14 (3H, t, J=7.0 Hz), 1.45-1.53 (1H, m), 1.78-1.95 (2H, m), 2.03-2.48 (10H, m), 2.65-2.80 (4H, m), 3.01 (3H, s), 3.33 (3H, s), 3.98 (1H, d, J=17 Hz), 4.10-4.20 (2H, m), 4.29 (1H, d, J=17 Hz), 6.33 (1H, br), 7.03 (1H, d, J=2.0 Hz), 7.09 (1H, d, J=8.5 Hz), 7.22-7.35 (6H, m), 7.44-7.51 (3H, m).

Similar to Example 26(k), the title compound was obtained as white powder (404 mg, 78.4%) by use of $N^1$-{1-(N-methyl-propionamide)-2-(S)-(3,4-dichlorophenyl)-4-[spiro(benzo(c)thiophene-(2S)-oxido-1(3H),4'-piperidin)-1'-yl]butan-2-yl}-$N^1$,$N^2$-dimethyl-$N^2$-phenyloxalamide (490 mg).

$[α]_D^{28}$=−37.6° (c 0.501, MeOH)

$^1$H-NMR (400 MHz, DMSO-d$_6$)δ ppm: 1.09 (3H, t, J=7.0 Hz), 1.97-2.07 (1H, m), 2.18-2.45 (7H, m), 2.60-2.85 (2H, m), 2.90-3.07 (3H, m), 3.11 (3H, s), 3.23 (3H, s), 3.27-3.53 (4H, m), 3.72-3.88 (1H, m), 4.05-4.20 (2H, m), 4.69 (1H, d, J=17 Hz), 6.64 (1H, br), 7.25-7.55 (11H, m), 10.42 (1H, br).

Example 40(a)

Synthesis of tert-butyl[1-(N-methyl-acetamide)-2-(S)-(3,4-dichlorophenyl)(4-penten-2-yl)]methylcarbamate

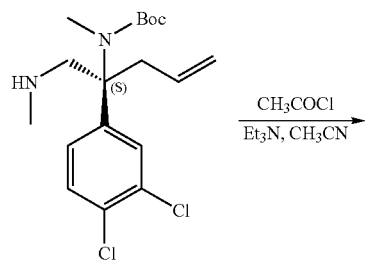

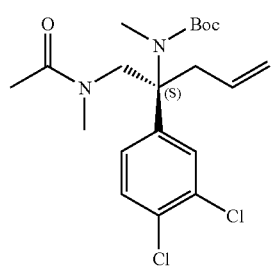

Similar to Example 36(a), the title compound was obtained (936 mg) by use of tert-butyl[2-(S)-(3,4-dichlorophenyl)-1-methylamino(4-penten-2-yl)]methylcarbamate (679 mg) synthesized in Example 26(d) and acetyl chloride (500 μL).

MS (FAB) m/z 415 ((M+H)$^+$)

$^1$H-NMR (270 MHz, CDCl$_3$)δ ppm: 1.20 (9H, brs), 2.12 (3H, s), 2.50-2.90 (5H, m), 3.09 (3H, s), 3.96-4.32 (2H, m), 4.82-5.02 (2H, m), 5.65-5.88 (1H, m), 7.01 (1H, dd, J=2.5, 8.5 Hz), 7.26 (1H, d, J=2.5 Hz), 7.36 (1H, d, J=8.5 Hz).

Example 40(b)

Synthesis of tert-butyl{[2-(S)-(3,4-dichlorophenyl)-1-(N-methyl-acetamide)-4-oxo]butan-2-yl}methylcarbamate

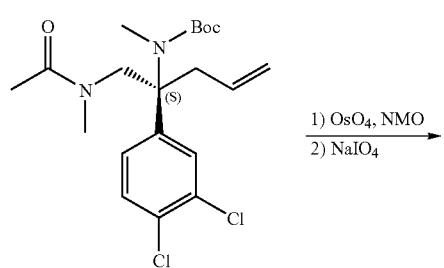

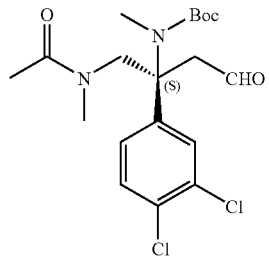

Similar to Example 26(f), tert-butyl{[2-(S)-(3,4-dichlorophenyl)-1-(N-methyl-acetamide)-4,5-dihydroxy]pentan-2-yl}methylcarbamate was obtained (995 mg) by use of tert-butyl[1-(N-methyl-acetamide)-2-(S)-(3,4-dichlorophenyl)(4-penten-2-yl)]methylcarbamate (936 mg). Subsequently, similar to Example 26(g), the title compound was obtained (792 mg) by use of tert-butyl{[2-(S)-(3,4-dichlorophenyl)-1-(N-methyl-acetamide)-4,5-dihydroxy]pentan-2-yl}methylcarbamate (995 mg).

MS (FAB) m/z 417 ((M+H)$^+$)

$^1$H-NMR (400 MHz, CDCl$_3$)δ ppm: 1.26 (9H, s), 2.11 (3H, s), 2.72 (3H, s), 2.96 (1H, d, J=16 Hz), 3.09 (3H, s), 3.20 (1H, d, J=16 Hz), 4.08-4.25 (1H, m), 4.45-4.50 (1H, m), 7.08-7.15 (1H, m), 7.25-7.47 (2H, m), 9.68 (1H, br).

Example 40(c)

Synthesis of tert-butyl{[1-(N-methyl-acetamide)-2-(S)-(3,4-dichlorophenyl)-4-[3-oxo-3,4-dihydro-2H-spiro(isoquinoline-1,4'-piperidin)-1'-yl]butan-2-yl]methylcarbamate

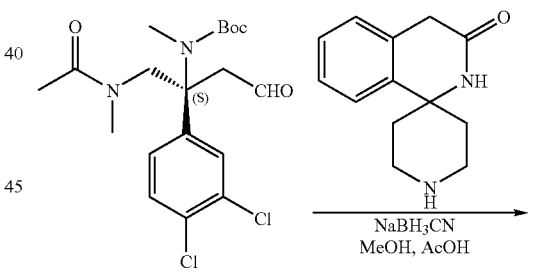

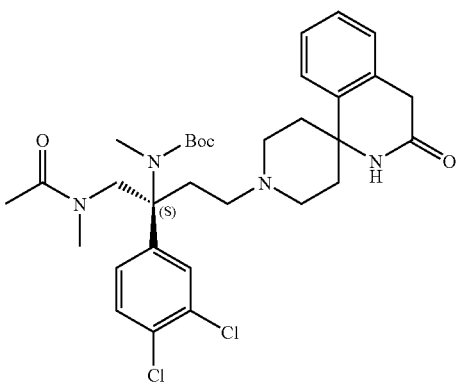

125

Similar to Example 26(h), the title compound was obtained (519 mg, 46.2%, 4 steps) by use of tert-butyl{[2-(S)-(3,4-dichlorophenyl)-1-(N-methyl-acetamide)-4-oxo]butan-2-yl}methylcarbamate (792 mg).

MS (FAB) m/z 617 ((M+H)$^+$)

$^1$H-NMR (400 MHz, CDCl$_3$)δ ppm: 1.20 (9H, brs), 1.66-1.80 (2H, m), 1.90-2.35 (11H, m), 2.50-2.98 (5H, m), 3.13 (3H, s), 3.61 (2H, s), 4.07-4.20 (2H, m), 6.28 (1H, br), 7.03-7.20 (2H, m), 7.23-7.48 (5H, m).

Example 40(d)

Synthesis of N-{2-(S)-(3,4-dichlorophenyl)-2-methylamino-4-[3-oxo-3,4-dihydro-2H-spiro(isoquinoline-1,4'-piperidin)-1'-yl]butyl}-N-methyl-acetamide

126

$^1$H-NMR (400 MHz, CDCl$_3$)δ ppm: 1.76-1.86 (2H, m), 1.93-2.42 (13H, m), 2.46 (3H, s), 2.53-2.65 (1H, m), 2.92-3.02 (2H, m), 3.33 (1H, d, J=14 Hz), 3.42-3.60 (1H, m), 3.64 (2H, s), 3.94 (1H, d, J=14 Hz), 6.33 (1H, br), 7.14-7.19 (1H, m), 7.24-7.47 (5H, m), 7.60-7.64 (1H, m).

Example 40(e)

Synthesis of N-{1-(N-methyl-acetamide)-2-(S)-(3,4-dichlorophenyl)-4-[3-oxo-3,4-dihydro-2H-spiro(isoquinoline-1,4'-piperidin)-1'-yl]butan-2-yl}-N-methylbenzamide

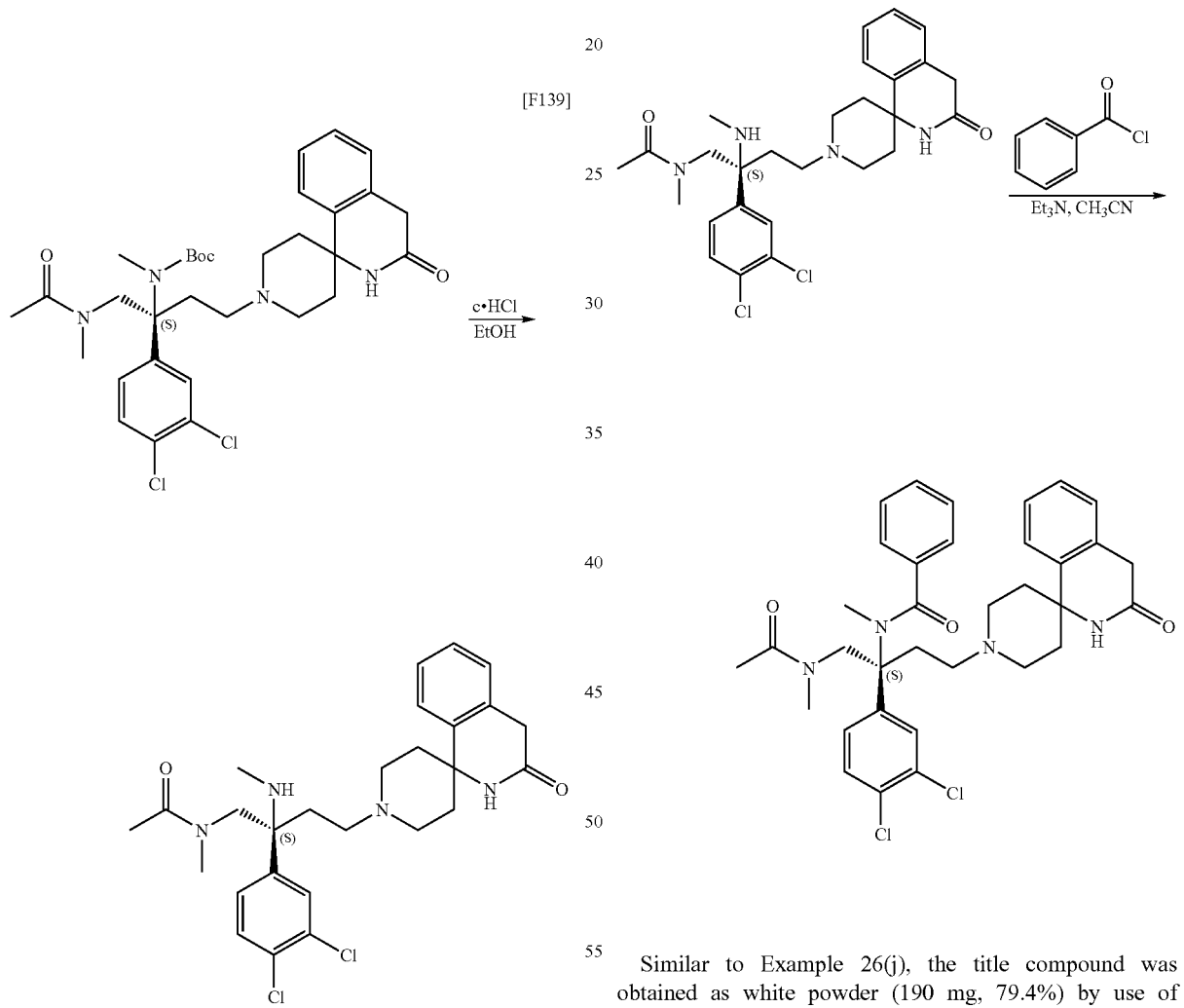

Similar to Example 26(i), the title compound was obtained (397 mg, 91.3%) by use of tert-butyl{[1-(N-methyl-acetamide)-2-(S)-(3,4-dichlorophenyl)-4-[3-oxo-3,4-dihydro-2H-spiro(isoquinoline-1,4'-piperidin)-1'-yl]butan-2-yl]methylcarbamate (519 mg).

MS (FAB) m/z 517 ((M+H)$^+$)

Similar to Example 26(j), the title compound was obtained as white powder (190 mg, 79.4%) by use of N-{2-(S)-(3,4-dichlorophenyl)-2-methylamino-4-[3-oxo-3,4-dihydro-2H-spiro(isoquinoline-1,4'-piperidin)-1'-yl]butyl}-N-methyl-acetamide (199 mg).

MS (FAB) m/z 621 ((M+H)$^+$)

$^1$H-NMR (400 MHz, CDCl$_3$)δ ppm: 1.92-2.22 (7H, m), 2.32-2.47 (3H, m), 2.50-2.60 (3H, m), 2.67-2.74 (1H, m), 2.80-2.88 (1H, m), 2.94 (3H, s), 3.13 (3H, s), 3.81 (2H, s), 4.36-4.50 (2H, m), 7.18 (1H, dd, J=2.0, 8.5 Hz), 7.23-7.63 (12H, m).

Example 40(f)

Synthesis of N-{1-(N-methyl-acetamide)-2-(S)-(3,4-dichlorophenyl)-4-[3-oxo-3,4-dihydro-2H-spiro(isoquinoline-1,4'-piperidin)-1'-yl]butan-2-yl}-N-methylbenzamide hydrochloride (Compound No. 36)

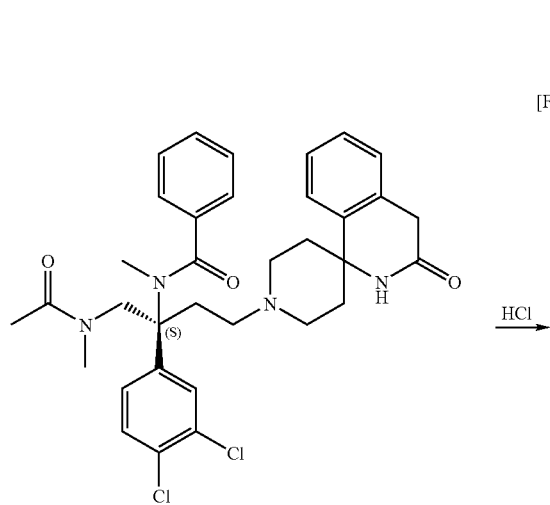

[F141]

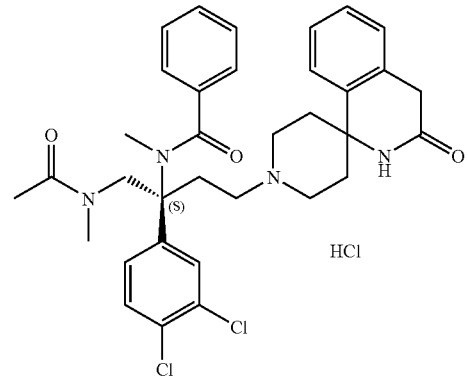

Similar to Example 26(k), the title compound was obtained as white powder (350 mg, 94.9%) by use of N-{1-(N-methyl-acetamide)-2-(S)-(3,4-dichlorophenyl)-4-[3-oxo-3,4-dihydro-2H-spiro(isoquinoline-1,4'-piperidin)-1'-yl]butan-2-yl}-N-methylbenzamide (350 mg).

$[\alpha]_D^{28}$=+6.1° (c 0.313, MeOH)

$^1$H-NMR (400 MHz, DMSO-d$_6$)δ ppm: 1.96 (2H, d, J=14.5 Hz), 2.07 (3H, s), 2.42-2.58 (1H, m), 2.65-2.78 (4H, m), 2.85-3.03 (2H, m), 3.11 (3H, s), 3.21-3.48 (6H, m), 3.62 (2H, s), 4.02-4.17 (1H, m), 4.42 (1H, d, J=14 Hz), 7.20-7.24 (1H, m), 7.27-7.39 (3H, m), 7.47 (5H, s), 7.54 (1H, dd, J=2.0, 8.5 Hz), 7.63 (1H, d, J=8.5 Hz), 7.77 (1H, d, J=2.0 Hz), 8.30 (1H, s), 10.24 (1H, br).

Example 41(a)

Synthesis of tert-butyl{[2-(S)-(3,4-dichlorophenyl)-1-(N-methyl-trimethylacetamide)-4-oxo]butan-2-yl}methylcarbamate

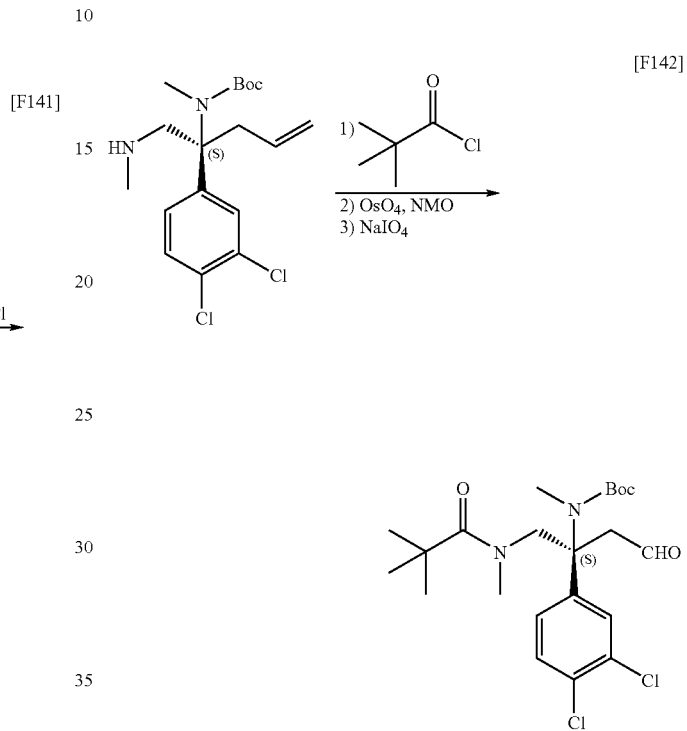

[F142]

Similar to Example 36(a), tert-butyl[1-(N-methyl-trimethylacetamide)-2-(S)-(3,4-dichlorophenyl)(4-penten-2-yl)]methylcarbamate was obtained (1.60 g) by use of tert-butyl [2-(S)-(3,4-dichlorophenyl)-1-methylamino(4-penten-2-yl)]methylcarbamate (1.23 g) synthesized in Example 26(d) and pivaloyl chloride (0.49 mL). Subsequently, similar to Example 26(f), tert-butyl{[2-(S)-(3,4-dichlorophenyl)-1-(N-methyl-trimethylacetamide)-4,5-dihydroxy]pentan-2-yl}methylcarbamate (1.62 g) was obtained by use of tert-butyl[1-(N-methyl-trimethylacetamide)-2-(S)-(3,4-dichlorophenyl)(4-penten-2-yl)]methylcarbamate (1.60 g). Thereafter, similar to Example 26(g), tert-butyl{[1-(S)-(3,4-dichlorophenyl)-1-(N-methyl-trimethylacetamide)-3,4-dihydroxy]butyl}methylcarbamate (1.62 g) was obtained by use of tert-butyl{[2-(S)-(3,4-dichlorophenyl)-1-(N-methyl-trimethylacetamide)-4,5-dihydroxy]pentan-2-yl}methylcarbamate (1.60 g). Thereafter, similar to Example 26(g), the title compound was obtained (1.40 g, 92.6%, 3 steps) by use of tert-butyl{[1-(S)-(3,4-dichlorophenyl)-1-(N-methyl-trimethylacetamide)-3,4-dihydroxy]butyl}methylcarbamate (1.60 g).

MS (FAB) m/z 459 ((M+H)$^+$)

$^1$H-NMR (400 MHz, CDCl$_3$)δ ppm: 1.23 (9H, brs), 1.28 (9H, s), 2.82 (3H, s), 2.80-2.92 (1H, m), 3.07-3.18 (4H, m), 4.15-4.28 (1H, m), 4.36-4.48 (1H, m), 7.10 (1H, dd, J=2.5, 8.5 Hz), 7.33 (1H, d, J=2.5 Hz), 7.41 (1H, d, J=8.5 Hz), 9.69 (1H, t, J=2.0 Hz).

Example 41(b)

Synthesis of tert-butyl{[1-(N-methyl-trimethylaceta-mide)-2-(S)-(3,4-dichlorophenyl)-4-[spiro(benzo(c)thiophene-(2S)-oxido-1(3H),4'-piperidin)-1'-yl]bu-tan-2-yl]methylcarbamate

Example 41(c)

Synthesis of N-{2-(S)-(3,4-dichlorophenyl)-2-me-thylamino-4-[spiro(benzo(c)thiophene-(2S)-oxido-1(3H),4'-piperidin)-1'-yl]butyl}-N-methyl-trimethy-lacetamide

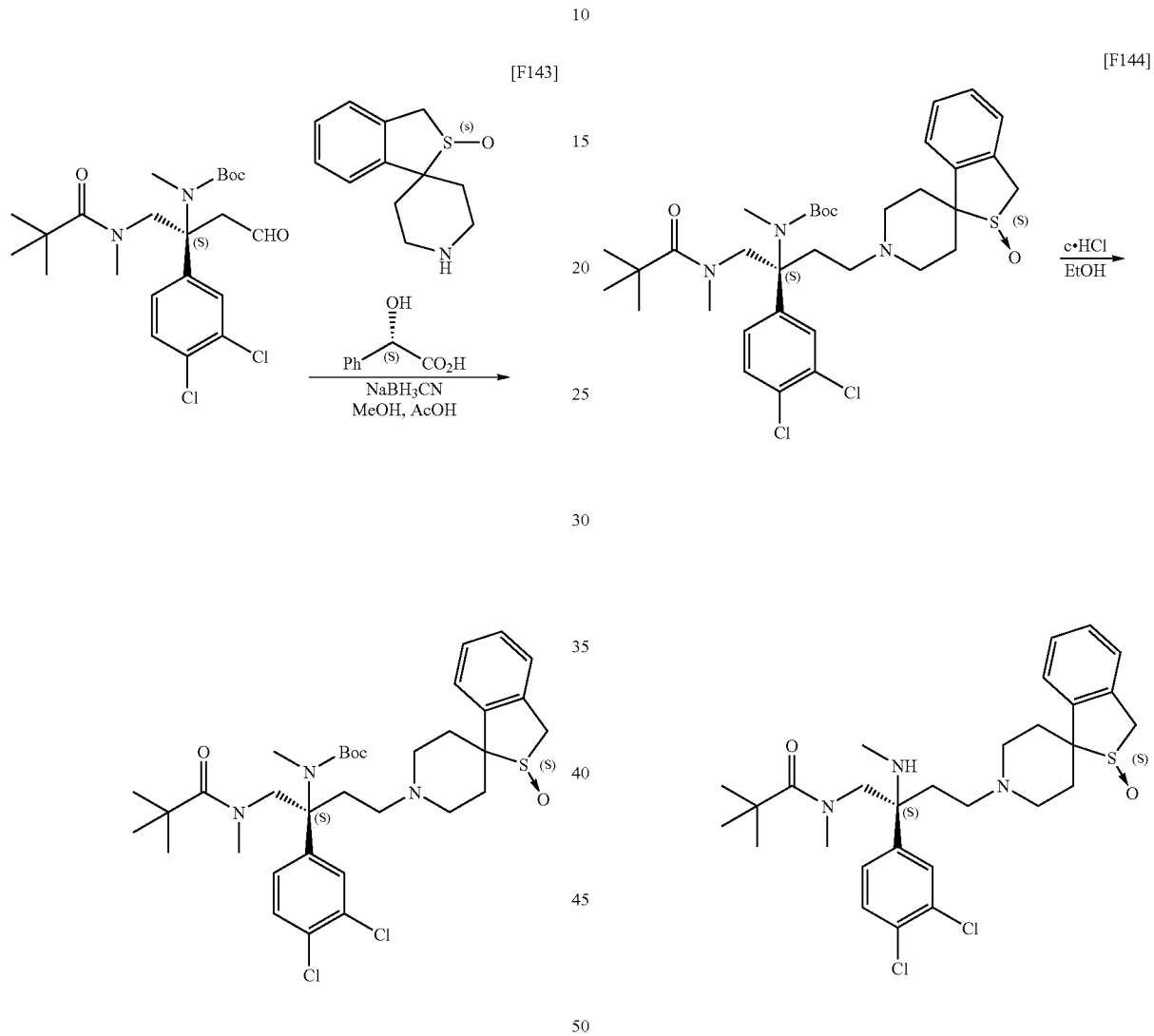

Similar to Example 26(h), the title compound was obtained (748 mg) by use of tert-butyl{[2-(S)-(3,4-dichlorophenyl)-1-(N-methyl-trimethylacetamide)-4-oxo]butan-2-yl}methylcarbamate (500 mg) and spiro(benzo(c)thiophene-(2S)-oxido-1(3H),4'-piperidine)/(S)-(+)-mandelate (448 mg).

MS (FAB) m/z 664 ((M+H)$^+$)

$^1$H-NMR (400 MHz, CDCl$_3$)δ ppm: 1.20 (9H, brs), 1.30 (9H, s), 1.45-1.55 (1H, m), 1.80-1.98 (2H, m), 2.13-2.28 (3H, m), 2.32-2.47 (3H, m), 2.50-2.62 (1H, m), 2.68-2.78 (1H, m), 2.82-3.00 (4H, m), 3.13 (3H, s), 3.97 (1H, d, J=17 Hz), 3.90-4.20 (1H, m), 4.29 (1H, d, J=17 Hz), 4.47-4.70 (1H, m), 7.05-7.09 (1H, m), 7.25-7.33 (5H, m), 7.38 (1H, d, J=8.5 Hz).

Similar to Example 26(i), the title compound was obtained (532 mg, 86.4%, 2 steps) by use of tert-butyl{[1-(N-methyl-trimethylacetamide)-2-(S)-(3,4-dichlorophenyl)-4-[spiro(benzo(c)thiophene-(2S)-oxido-1(3H),4'-piperidin)-1'-yl]butan-2-yl]methylcarbamate (730 mg).

MS (FAB) m/z 564 ((M+H)$^+$)

$^1$H-NMR (400 MHz, CDCl$_3$)δ ppm: 1.20 (9H, s), 1.52-1.75 (2H, m), 1.95-2.20 (3H, m), 2.23 (3H, s), 2.32-2.58 (6H, m), 2.61 (3H, s), 2.90-3.15 (2H, m), 3.23-3.33 (1H, m), 3.92-4.07 (2H, m), 4.34 (1H, d, J=17 Hz), 7.29-7.38 (5H, m), 7.42 (1H, d, J=8.5 Hz), 7.62 (1H, br).

Example 41(d)

Synthesis of N¹-{1-(N-methyl-trimethylacetamide)-2-(S)-(3,4-dichlorophenyl)-4-[spiro(benzo(c)thiophene-(2S)-oxido-1(3H),4'-piperidin)-1'-yl]butan-2-yl}-N¹-methyl-N²-ethyl-N²-phenyloxalamide

Example 41(e)

Synthesis of N¹-{[1-(N-methyl-trimethylacetamide)-2-(S)-(3,4-dichlorophenyl)-4-[spiro(benzo(c)thiophene-(2S)-oxido-1(3H),4'-piperidin)-1'-yl]butan-2-yl}-N¹-methyl-N²-ethyl-N²-phenyloxalamide hydrochloride (Compound No. 37)

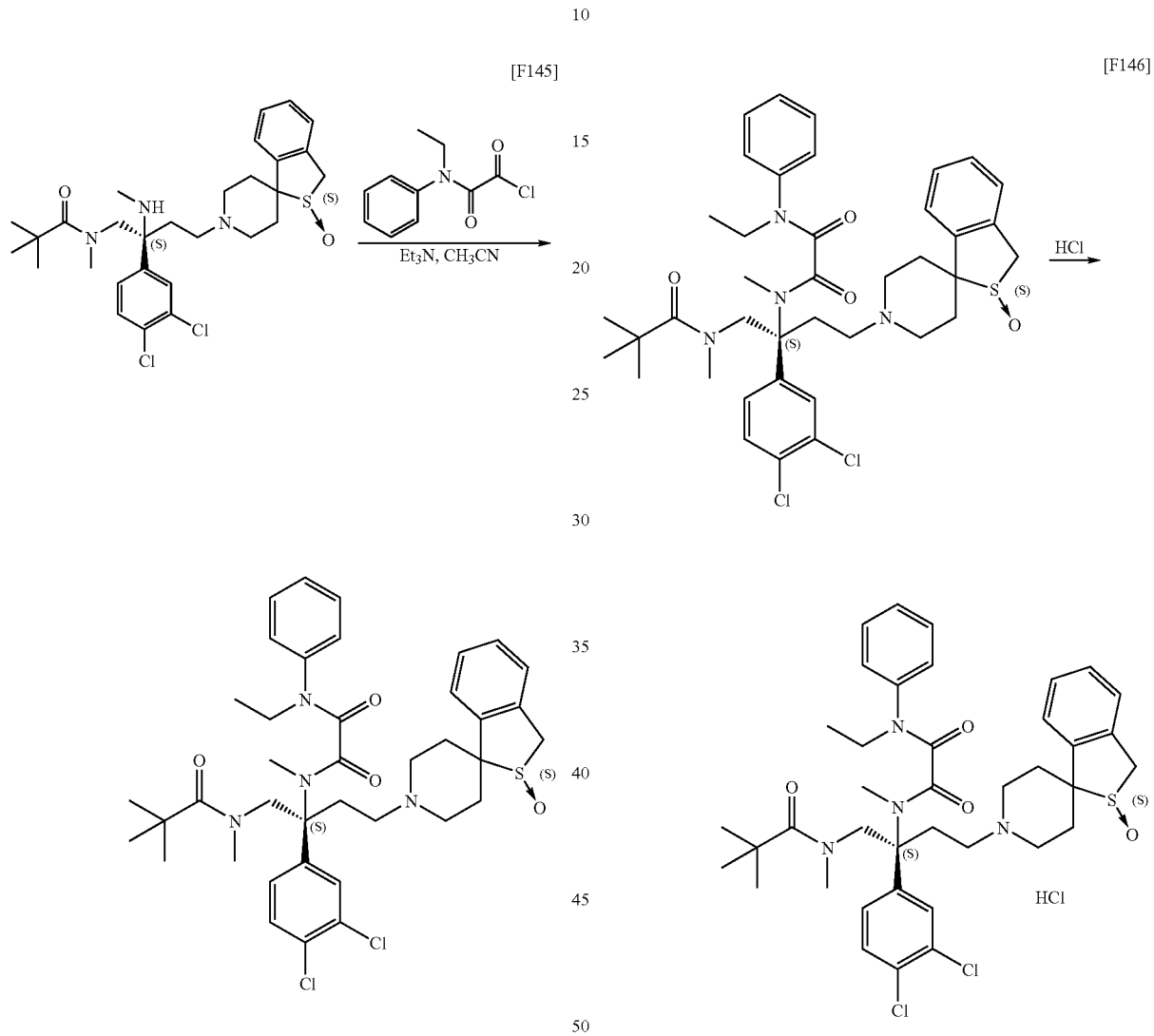

[F145]

[F146]

Similar to Example 26(j), the title compound was obtained (111 mg, 82.4%) by use of N-{2-(S)-(3,4-dichlorophenyl)-2-methylamino-4-[spiro(benzo(c)thiophene-(2S)-oxido-1(3H),4'-piperidin)-1'-yl]butyl}-N-methyl-trimethylacetamide (60 mg).

MS (FAB) m/z 739 ((M+H)⁺)

¹H-NMR (400 MHz, CDCl₃)δ 5 ppm 1.25 (9H, s), 1.25 (3H, t, J=7.0 Hz), 1.44-1.52 (1H, m), 1.78-1.92 (2H, m), 1.98-2.10 (1H, m), 2.13-2.27 (2H, m), 2.30-2.43 (4H, m), 2.64-2.78 (2H, m), 2.86 (3H, s), 3.05 (3H, s), 3.72-3.88 (2H, m), 3.97 (1H, d, J=17 Hz), 4.05-4.35 (3H, m), 6.25 (1H, br), 7.02-7.07 (2H, m), 7.25-7.35 (6H, m), 7.45-7.52 (3H, m).

Similar to Example 26(k), the title compound was obtained as white powder (88 mg, 75.6%) by use of N¹-{1-(N-methyl-trimethylacetamide)-2-(S)-(3,4-dichlorophenyl)-4-[spiro(benzo(c)thiophene-(2S)-oxido-1(3H),4'-piperidin)-1'-yl]butan-2-yl}-N¹-methyl-N²-ethyl-N²-phenyloxalamide (111 mg).

$[\alpha]_D^{28}$=−38.4° (c 0.513, MeOH)

¹H-NMR (400 MHz, DMSO-d₆)δ ppm: 1.05 (3H, t, J=7.0 Hz), 1.16 (9H, s), 1.98-2.57 (6H, m), 2.73-2.87 (2H, m), 2.92-3.18 (5H, m), 3.25-3.62 (6H, m), 3.68-3.78 (2H, m), 4.10 (1H, d, J=17 Hz), 4.15-4.32 (1H, m), 4.70 (1H, d, J=17 Hz), 7.22-7.60 (12H, m), 10.47 (1H, br).

Example 42(a)

Synthesis of tert-butyl{[1-(N-methyl-trimethylacetamide)-2-(S)-(3,4-dichlorophenyl)-4-[3-oxo-3,4-dihydro-2H-spiro(isoquinoline-1,4'-piperidin)-1'-yl]butan-2-yl]methylcarbamate

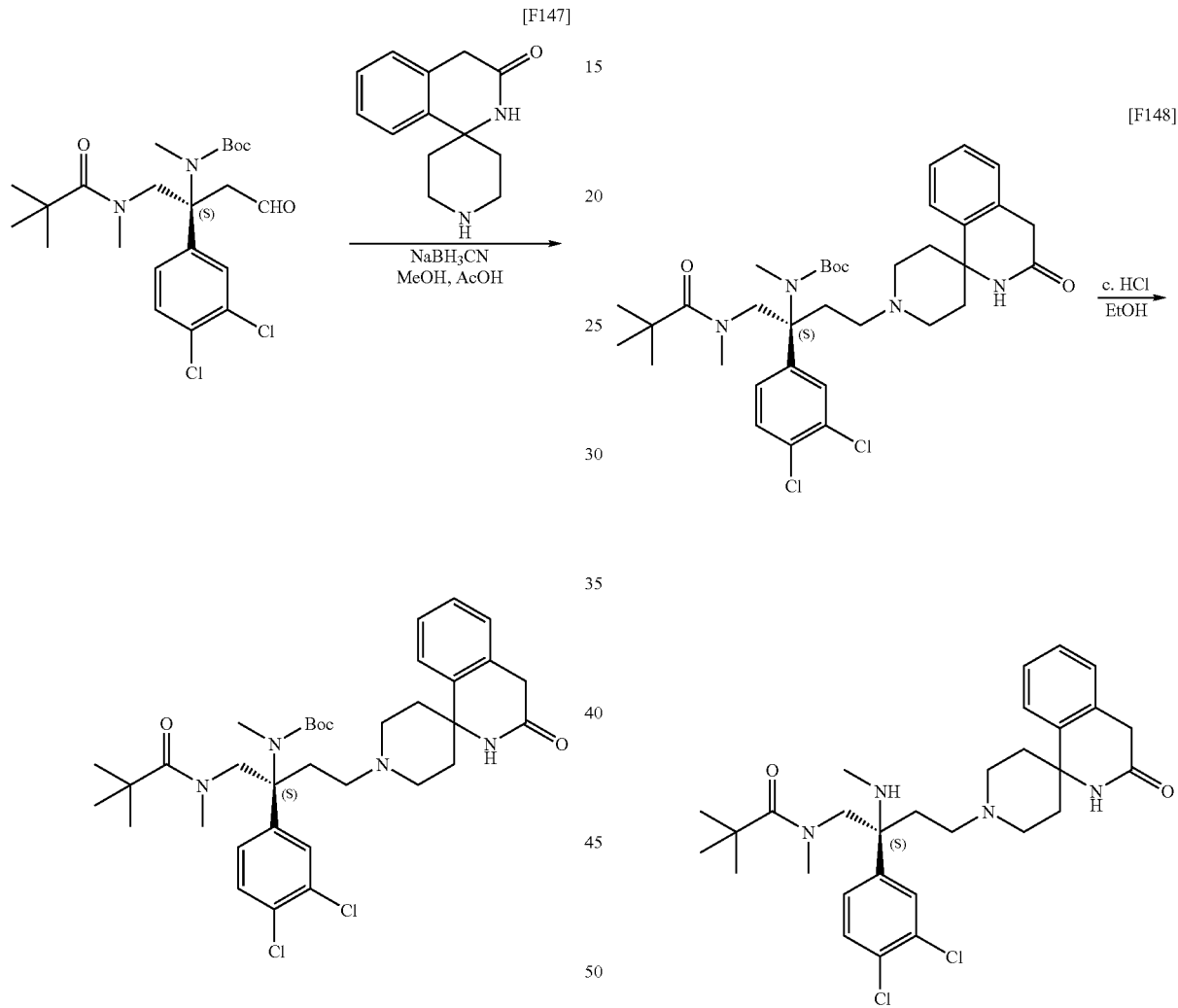

Similar to Example 26(h), the title compound was obtained (723 mg) by use of tert-butyl{[1-(S)-(3,4-dichlorophenyl)-1-(N-methyl-trimethylacetamide)-3-oxo]propyl}methylcarbamate (500 mg) synthesized in Example 41(a).

MS (FAB) m/z 659 ((M+H)⁺)

¹H-NMR (400 MHz, CDCl₃)δ ppm: 1.18 (9H, brs), 1.30 (9H, s), 1.63-1.77 (2H, m), 1.82-1.93 (1H, m), 2.02-2.30 (6H, m), 2.50-2.62 (1H, m), 2.68-2.78 (1H, m), 2.80-3.02 (4H, m), 3.14 (3H, s), 3.62 (2H, s), 3.85-4.12 (1H, m), 4.30-4.68 (1H, m), 6.31 (1H, br), 7.06 (1H, dd, J=2.0, 8.5 Hz), 7.12-7.15 (1H, m), 7.22-7.36 (4H, m), 7.39 (1H, d, J=8.5 Hz).

Example 42(b)

Synthesis of N-{2-(S)-(3,4-dichlorophenyl)-2-methylamino-4-[3-oxo-3,4-dihydro-2H-spiro(isoquinoline-1,4'-piperidin)-1'-yl]butyl}-N-methyl-trimethylacetamide Similar to Example 26(i), the title compound was obtained (528 mg, 89.0%, 2 steps) by use of tert-butyl{[1-(N-methyl-trimethylacetamide)-2-(S)-(3,4-dichlorophenyl)-4-[3-oxo-3,4-dihydro-2H-spiro(isoquinoline-1,4'-piperidin)-1'-yl]butan-2-yl]methylcarbamate (700 mg).

MS (FAB) m/z 559 ((M+H)⁺)

¹H-NMR (400 MHz, CDCl₃)δ ppm: 1.20 (9H, s), 1.60-1.88 (3H, m), 1.95-2.58 (11H, m), 2.61 (3H, s), 2.90-3.04 (2H, m), 3.32 (1H, d, J=14 Hz), 3.64 (2H, s), 3.93 (1H, d, J=14 Hz), 6.42 (1H, br), 7.16 (1H, d, J=7.0 Hz), 7.24-7.45 (5H, m), 7.62 (1H, s).

135
Example 42(c)

Synthesis of N¹-{1-(N-methyl-trimethylacetamide)-2-(S)-(3,4-dichlorophenyl)-4-[3-oxo-3,4-dihydro-2H-spiro(isoquinoline-1,4'-piperidin)-1'-yl]butan-2-yl}-N¹-methyl-N²-ethyl-N²-phenyloxalamide

136
Example 42(d)

Synthesis of N¹-{1-(N-methyl-trimethylacetamide)-2-(S)-(3,4-dichlorophenyl)-4-[3-oxo-3,4-dihydro-2H-spiro(isoquinoline-1,4'-piperidin)-1'-yl]butan-2-yl}-N¹-methyl-N²-ethyl-N²-phenyloxalamide hydrochloride (Compound No. 38)

[F149]

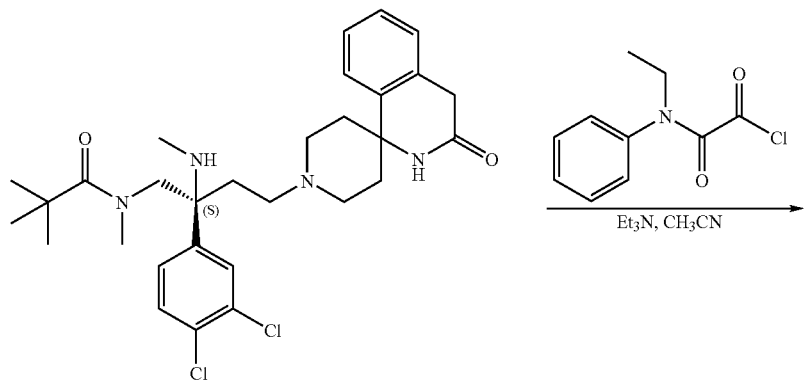

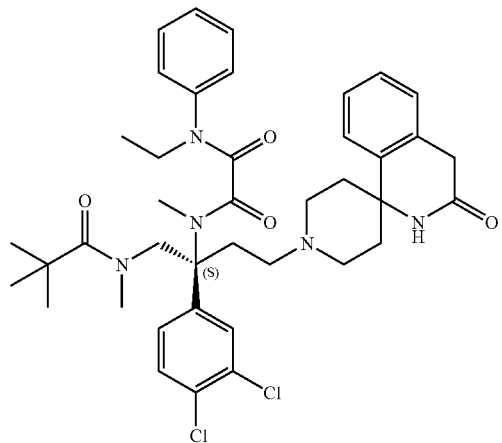

Similar to Example 26(j), the title compound was obtained (114 mg, 85.2%) by use of N-{2-(S)-(3,4-dichlorophenyl)-2-methylamino-4-[3-oxo-3,4-dihydro-2H-spiro(isoquinoline-1,4'-piperidin)-1'-yl]butyl}-N-methyl-trimethylacetamide and (ethylphenylamino)-oxo-acetyl chloride (53 mg) synthesized in Referential Example 3.

MS (FAB) m/z 734 ((M+H)⁺)

¹H-NMR (400 MHz, CDCl₃)δ ppm: 1.16 (3H, t, J=7.0 Hz), 1.26 (9H, s), 1.60-1.73 (2H, m), 1.77-1.89 (1H, m), 1.95-2.23 (6H, m), 2.32-2.45 (1H, m), 2.62-2.74 (2H, m), 2.83 (3H, s), 3.07 (3H, s), 3.62 (2H, s), 3.70-3.89 (2H, m), 4.05-4.29 (2H, m), 6.17-6.35 (2H, m), 7.00-7.07 (2H, m), 7.11-7.16 (1H, m), 7.21-7.30 (4H, m), 7.30-7.37 (1H, m), 7.42-7.54 (3H, m).

[F150]

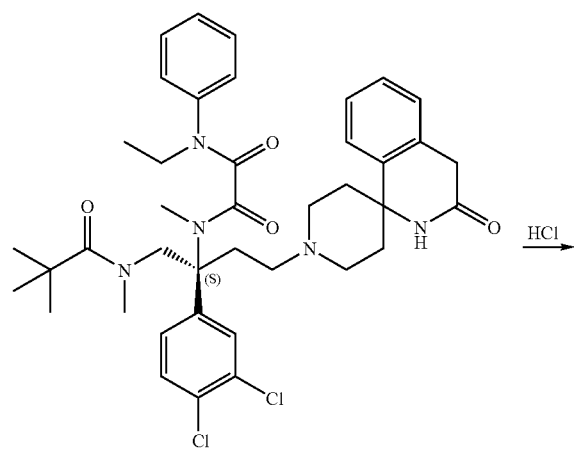

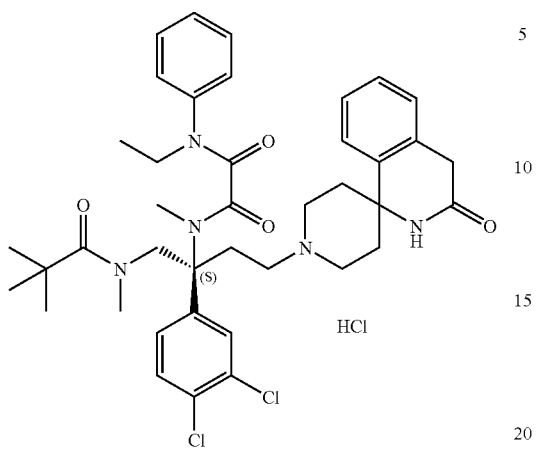

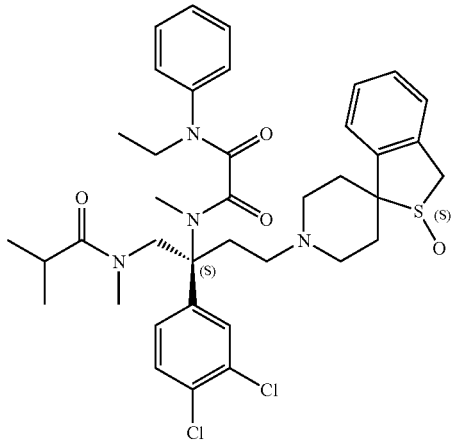

Similar to Example 26(k), the title compound was obtained as white powder (75 mg, 62.7%) by use of N¹-{1-(N-methyl-trimethylacetamide)-2-(S)-(3,4-dichlorophenyl)-4-[3-oxo-3,4-dihydro-2H-spiro(isoquinoline-1,4'-piperidin)-1'-yl]butan-2-yl}-N¹-methyl-N²-ethyl-N²-phenyloxalamide (114 mg).

[α]$_D^{28}$=−64.9° (c 0.505, MeOH)

¹H-NMR (400 MHz, DMSO-d$_6$)δ ppm: 1.05 (3H, t, J=7.0 Hz), 1.18 (9H, s), 1.90-2.00 (2H, m), 2.18-2.90 (8H, m), 3.10 (3H, s), 3.16-3.53 (6H, m), 3.60-3.78 (4H, m), 4.22-4.38 (1H, m), 6.52 (1H, br), 7.20-7.60 (11H, m), 8.37 (1H, s), 10.53 (1H, br).

Example 43(a)

Synthesis of N¹-{1-(N-methylisobutylamide)-2-(S)-(3,4-dichlorophenyl)-4-[spiro(benzo(c)thiophene-(2S)-oxido-1(3H),4'-piperidin)-1'-yl]butan-2-yl}-N¹-methyl-N²-ethyl-N²-phenyloxalamide Similar to Example 26(j), the title compound was obtained (92 mg, 69.6%) by use of N-{2-(S)-(3,4-dichlorophenyl)-2-methylamino-4-[spiro(benzo(c)thiophene-(2S)-oxido-1(3H),4'-piperidin)-1'-yl]butyl}-N-methylisobutylamide (100 mg) synthesized in Example 36(e) and (ethylphenylamino)-oxo-acetyl chloride (77 mg) synthesized in Referential Example 3.

MS (FAB) m/z 725 ((M+H)⁺)

¹H-NMR (400 MHz, CDCl$_3$)δ ppm: 1.09 (3H, d, J=6.5 Hz), 1.11 (3H, d, J=6.5 Hz), 1.17 (3H, t, J=7.0 Hz), 1.44-1.52 (1H, m), 1.77-1.92 (2H, m), 2.00-2.10 (1H, m), 2.13-2.23 (2H, m), 2.28-2.45 (4H, m), 2.63-2.86 (6H, m), 3.05 (3H, s), 3.70-3.90 (2H, m), 3.97 (1H, d, J=17 Hz), 4.03-4.33 (2H, m), 4.29 (1H, d, J=17 Hz), 6.25 (1H, br), 7.01-7.08 (2H, m), 7.25-7.35 (6H, m), 7.43-7.54 (3H, m).

Example 43(b)

Synthesis of N¹-{1-(N-methylisobutylamide)-2-(S)-(3,4-dichlorophenyl)-4-[spiro(benzo(c)thiophene-(2S)-oxido-1(3H),4'-piperidin)-1'-yl]butan-2-yl}-N¹-methyl-N²-ethyl-N²-phenyloxalamide hydrochloride (Compound No. 39)

[F152]

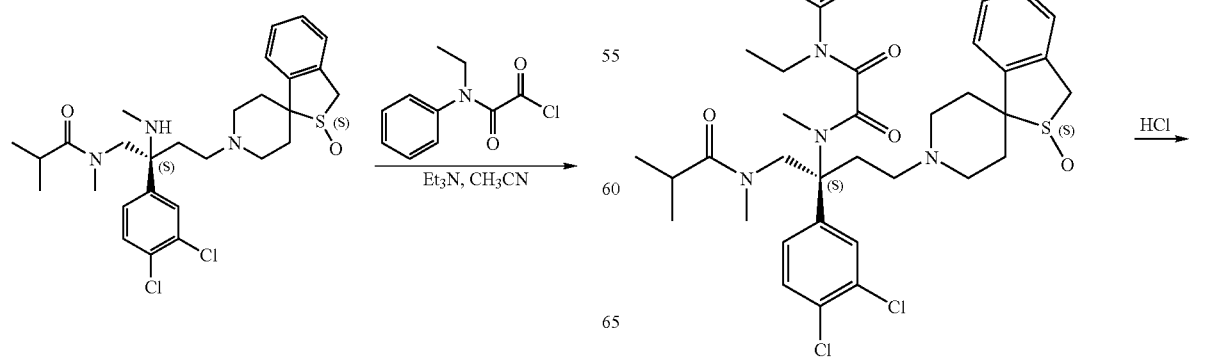

[F151]

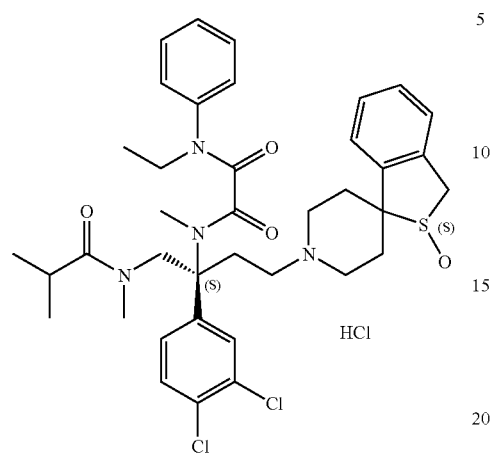

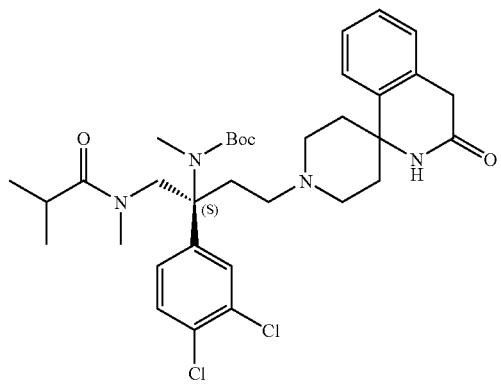

Similar to Example 26(k), the title compound was obtained as white powder (65 mg, 67.1%) by use of N¹-{1-(N-methylisobutylamide)-2-(S)-(3,4-dichlorophenyl)-4-[spiro(benzo(c)thiophene-(2S)-oxido-1(3H),4'-piperidin)-1'-yl]butan-2-yl}-N¹-methyl-N²-ethyl-N²-phenyloxalamide (92 mg).

$[\alpha]_D^{28}$=−44.3°(c 0.508, MeOH)

¹H-NMR (400 MHz, DMSO-$d_6$)δ ppm: 0.98 (6H, t, J=7.0 Hz), 1.05 (3H, t, J=7.0 Hz), 1.98-2.07 (1H, m), 2.22-2.58 (6H, m), 2.73-2.86 (3H, m), 2.95-3.10 (2H, m), 3.12 (3H, s), 3.30-3.53 (4H, m), 3.67-3.78 (3H, m), 4.05-4.20 (2H, m), 4.70 (1H, d, J=17 Hz), 7.25-7.58 (12H, m), 10.52 (1H, br).

Example 44(a)

Synthesis of tert-butyl{[1-(N-methylisobutylamide)-2-(S)-(3,4-dichlorophenyl)-4-[3-oxo-3,4-dihydro-2H-spiro(isoquinoline-1,4'-piperidin)-1'-yl]butan-2-yl]methylcarbamate Similar to Example 26(h), the title compound was obtained (1.30 g, 91.5%) by use of tert-butyl{[1-(S)-(3,4-dichlorophenyl)-1-(N-7-methylisobutylamide)-3-oxo]propyl}methylcarbamate (1.0 g) synthesized in Example 36(c).

MS (FAB) m/z 645 ((M+H)⁺)

¹H-NMR (270 MHz, CDCl₃)δ ppm: 1.10-1.40 (15H, m), 1.62-2.00 (2H, m), 2.07-2.40 (5H, m), 2.58-2.68 (1H, m), 2.69 (3H, s), 2.79-3.06 (3H, m), 3.13 (3H, s), 3.62 (3H, s), 3.62-3.72 (1H, m), 3.85-4.15 (1H, m), 4.30-4.70 (2H, m), 6.30-6.40 (2H, m), 7.05-7.58 (6H, m).

Example 44(b)

Synthesis of N-{2-(S)-(3,4-dichlorophenyl)-2-methylamino-4-[3-oxo-3,4-dihydro-2H-spiro(isoquinoline-1,4'-piperidin)-1'-yl]butyl}-N-methylisobutylamide

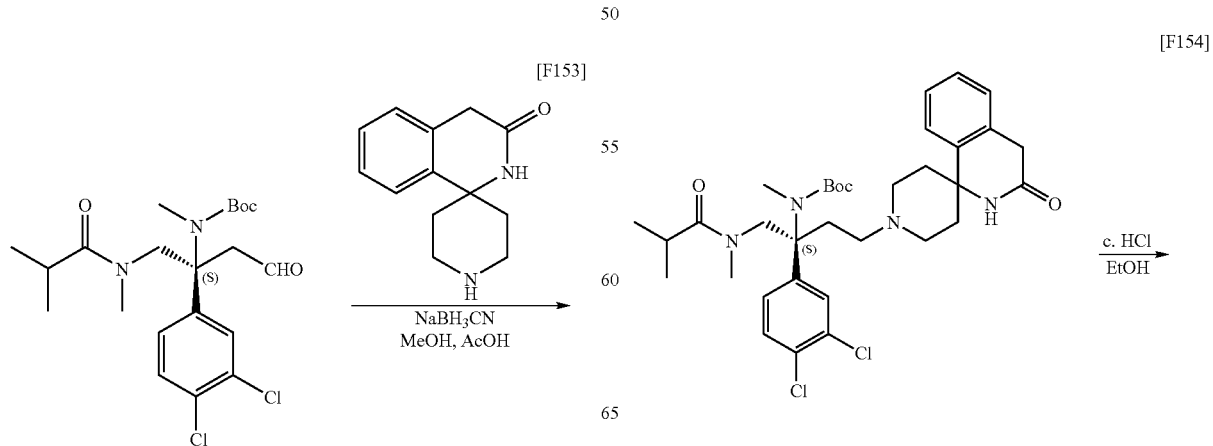

-continued

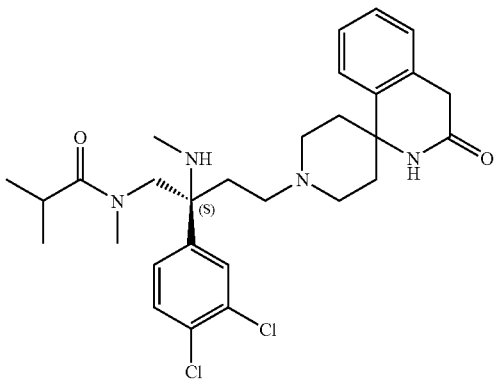

Similar to Example 26(i), the title compound was obtained (950 mg, 86.6%) by use of tert-butyl{[1-(N-methylisobutylamide)-2-(S)-(3,4-dichlorophenyl)-4-[3-oxo-3,4-dihydro-2H-spiro(isoquinoline-1,4'-piperidin)-1'-yl]butan-2-yl]methylcarbamate (1.30 g).

MS (FAB) m/z 545 ((M+H)$^+$)

$^1$H-NMR (400 MHz, CDCl$_3$)δ ppm: 1.02 (3H, d, J=6.5 Hz), 1.08 (3H, d, J=6.5 Hz), 1.75-1.87 (3H, m), 1.95-2.45 (7H, m), 2.53 (3H, s), 2.50-2.77 (2H, m), 2.87-3.07 (3H, m), 3.36 (1H, d, J=13 Hz), 3.61 (1H, d, J=10 Hz), 3.64 (3H, s), 3.92 (1H, d, J=13 Hz), 6.36 (1H, br), 7.13-7.18 (1H, m), 7.24-7.47 (5H, m), 7.61 (1H, d, J=2.0 Hz).

Example 44(c)

Synthesis of N$^1$-{1-(N-methylisobutylamide)-2-(S)-(3,4-dichlorophenyl)-4-[3-oxo-3,4-dihydro-2H-spiro(isoquinoline-1,4'-piperidin)-1'-yl]butan-2-yl}-N$^1$-methyl-N$^2$-ethyl-N$^2$-phenyloxalamide

[F155]

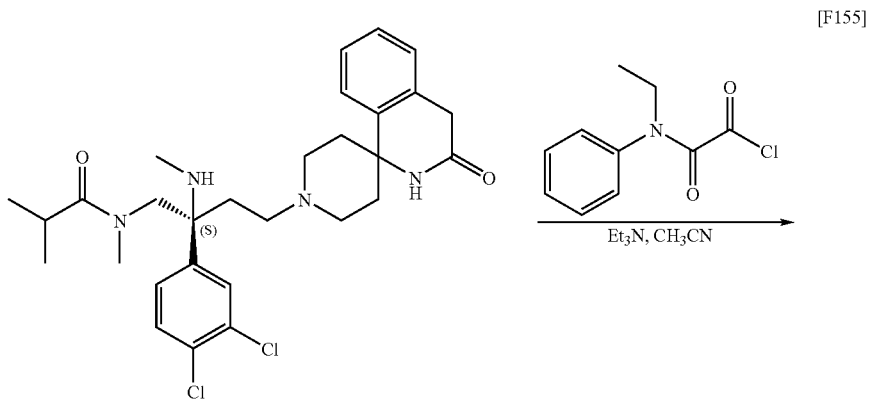

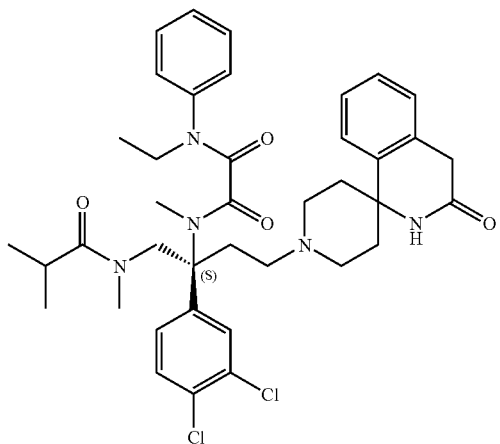

Similar to Example 26(j), the title compound was obtained as white powder (80 mg, 60.7%) by use of N-{2-(S)-(3,4-dichlorophenyl)-2-methylamino-4-[3-oxo-3,4-dihydro-2H-spiro(isoquinoline-1,4'-piperidin)-1'-yl]butyl}-N-methylisobutylamide (100 mg) and (ethylphenylamino)-oxo-acetyl chloride (77 mg) synthesized in Referential Example 3.

MS (FAB) m/z 720 ((M+H)$^+$)

$^1$H-NMR (400 MHz, CDCl$_3$)δ ppm: 1.09 (3H, d, J=7.0 Hz), 1.10 (3H, d, J=7.0 Hz), 1.15 (3H, t, J=7.0 Hz), 1.63-1.73 (1H, m), 1.77-1.87 (1H, m), 1.96-2.25 (7H, m), 2.37-2.48 (1H, m), 2.60-2.87 (6H, m), 3.07 (3H, s), 3.61 (2H, s), 3.70-3.90 (2H, m), 4.02-4.30 (2H, m), 6.19-6.32 (2H, m), 7.00-7.08 (2H, m), 7.11-7.16 (1H, m), 7.21-7.35 (5H, m), 7.43-7.54 (3H, m).

Example 44(d)

Synthesis of N$^1$-{1-(N-methylisobutylamide)-2-(S)-(3,4-dichlorophenyl)-4-[3-oxo-3,4-dihydro-2H-spiro(isoquinoline-1,4'-piperidin)-1'-yl]butan-2-yl}-N$^1$-methyl-N$^2$-ethyl-N$^2$-phenyloxalamide hydrochloride (Compound No. 40)

[F156]

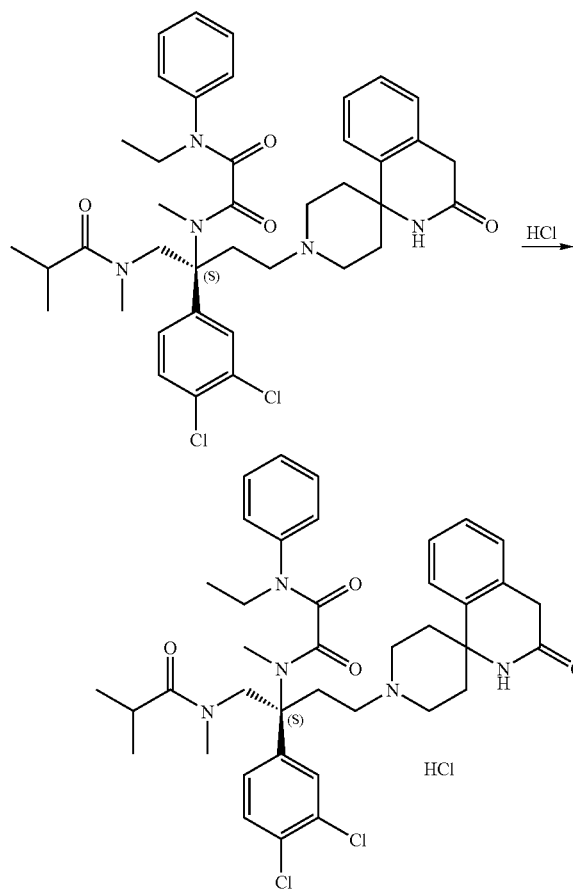

Similar to Example 26(k), the title compound was obtained as white powder (55 mg, 65.4%) by use of N$^1$-{1-(N-methylisobutylamide)-2-(S)-(3,4-dichlorophenyl)-4-[3-oxo-3,4-dihydro-2H-spiro(isoquinoline-1,4'-piperidin)-1'-yl]butan-2-yl}-N$^1$-methyl-N$^2$-ethyl-N$^2$-phenyloxalamide (80 mg).

[α]$_D$$^{28}$=−72.5° (c 0.434, MeOH)

$^1$H-NMR (400 MHz, DMSO-d$_6$)δ ppm: 0.99 (6H, t, J=7.0 Hz), 1.05 (3H, t, J=7.0 Hz), 1.99-2.00 (2H, m), 2.18-2.95 (9H, m), 3.10 (3H, s), 3.15-3.50 (5H, m), 3.62 (2H, s), 3.68-3.78 (3H, m), 4.15-4.27 (1H, m), 6.59 (1H, br), 7.20-7.60 (11H, m), 8.38 (1H, s), 10.68 (1H, br).

Example 45(a)

Synthesis of N$^1$-{1-(3,3,3-trifluoro-N-methylpropanamido)-2-(S)-(3,4-dichlorophenyl)-4-[3-oxo-3,4-dihydro-2H-spiro(isoquinoline-1,4'-piperidin)-1'-yl]butan-2-yl}-N$^1$-methyl-N$^2$-ethyl-N$^2$-phenyloxalamide

[F157]

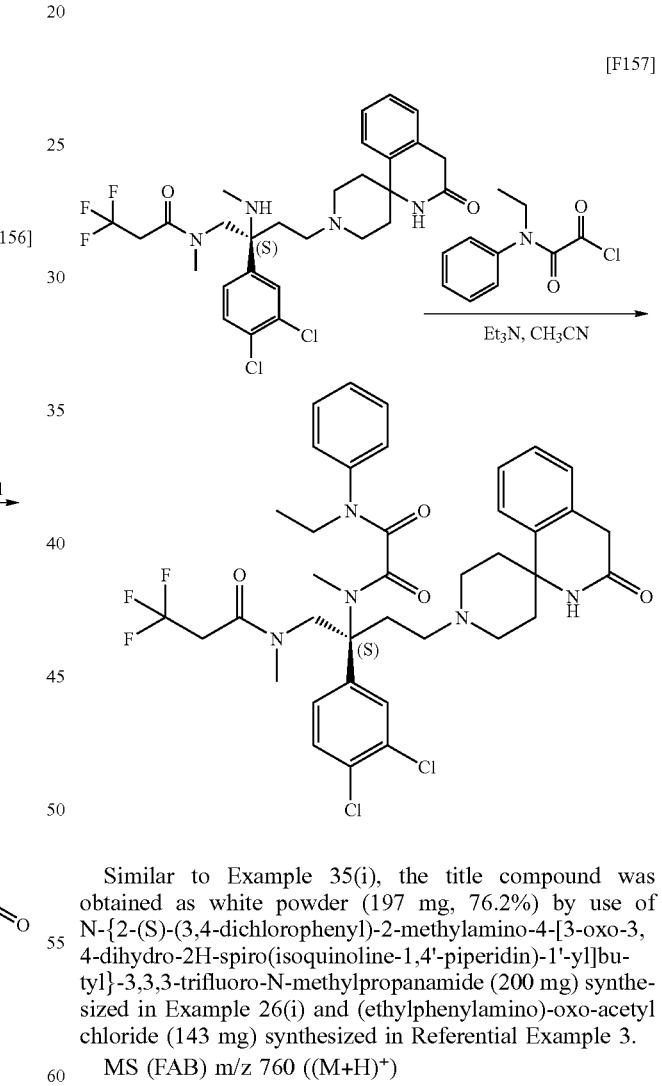

Similar to Example 35(i), the title compound was obtained as white powder (197 mg, 76.2%) by use of N-{2-(S)-(3,4-dichlorophenyl)-2-methylamino-4-[3-oxo-3,4-dihydro-2H-spiro(isoquinoline-1,4'-piperidin)-1'-yl]butyl}-3,3,3-trifluoro-N-methylpropanamide (200 mg) synthesized in Example 26(i) and (ethylphenylamino)-oxo-acetyl chloride (143 mg) synthesized in Referential Example 3.

MS (FAB) m/z 760 ((M+H)$^+$)

$^1$H-NMR (400 MHz, CDCl$_3$)δ ppm: 1.17 (3H, t, J=7.0 Hz), 1.62-1.72 (2H, m), 1.78-1.93 (2H, m), 1.98-2.22 (5H, m), 2.32-2.44 (1H, m), 2.60-2.73 (2H, m), 2.83 (3H, s), 3.06 (3H, s), 3.12-3.38 (2H, m), 3.61 (2H, s), 3.70-3.90 (2H, m), 4.07-4.18 (1H, m), 4.28-4.38 (1H, m), 6.14-6.29 (2H, m), 6.97-7.08 (2H, m), 7.12-7.16 (1H, m), 7.21-7.37 (5H, m), 7.43-7.54 (3H, m).

Example 45(b)

Synthesis of N¹-{1-(3,3,3-trifluoro-N-methylpropanamido)-2-(S)-(3,4-dichlorophenyl)-4-[3-oxo-3,4-dihydro-2H-spiro(isoquinoline-1,4'-piperidin)-1'-yl]butan-2-yl}-N¹-methyl-N²-ethyl-N²-phenyloxalamide hydrochloride (Compound No. 41)

Example 46(a)

Synthesis of N-{2-(S)-(N-methyl-2,2-diphenylacetamide)-2-(3,4-dichlorophenyl)-4-[spiro(benzo(c)thiophene-(2S)-oxido-1(3H),4'-piperidin)-1'-yl]butyl}-3,3,3-trifluoro-N-methylpropanamido

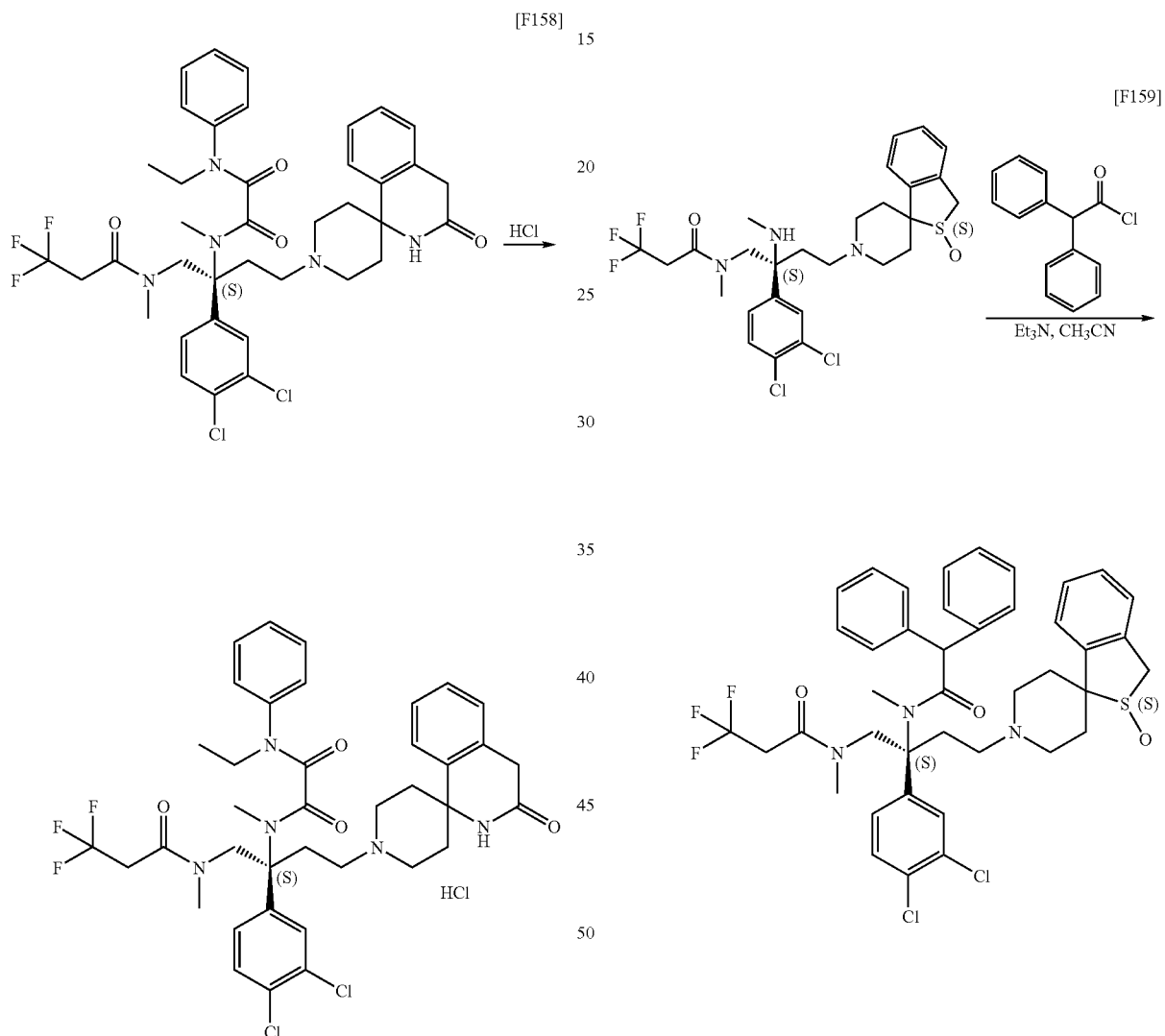

Similar to Example 26(k), the title compound was obtained as white powder (172 mg, 83.3%) by use of N¹-{1-(3,3,3-trifluoro-N-methylpropanamido)-2-(S)-(3,4-dichlorophenyl)-4-[3-oxo-3,4-dihydro-2H-spiro(isoquinoline-1,4'-piperidin)-1'-yl]butan-2-yl}-N¹-methyl-N²-ethyl-N²-phenyloxalamide (197 mg).

$[\alpha]_D^{28}$=−56.4° (c 0.509, MeOH)

¹H-NMR (400 MHz, DMSO-d₆)δ ppm: 1.19 (3H, t, J=7.0 Hz), 1.85-1.98 (2H, m), 2.25-2.60 (5H, m), 2.65-2.97 (2H, m), 3.13 (3H, s), 3.15-3.50 (5H, m), 3.61 (3H, s), 3.63-3.78 (4H, m), 3.80-3.97 (1H, m), 4.10-4.23 (1H, m), 6.61 (1H, br), 7.18-7.58 (11H, m), 8.38 (1H, br), 10.25 (1H, br).

Similar to Example 26(j), the title compound was obtained (500 mg, 47.5%) by use of N-{2-(S)-(3,4-dichlorophenyl)-2-methylamino-4-[spiro(benzo(c)thiophene-(2S)-oxido-1(3H),4'-piperidin)-1'-yl]butyl}-3,3,3-trifluoro-N-methylpropanamide (790 mg) synthesized in Example 34(b) and diphenylacetyl chloride (1.55 g).

MS (FAB) m/z 784 ((M+H)⁺)

¹H-NMR (400 MHz, CDCl₃)δ ppm: 1.43-1.58 (1H, m), 1.80-2.10 (2H, m), 2.16-2.60 (7H, m), 2.66-2.93 (5H, m), 3.02-3.30 (5H, m), 3.97 (1H, d, J=17 Hz), 4.10-4.40 (2H, m), 4.45-4.58 (1H, m), 5.21 (1H, br), 6.97 (1H, dd, J=2.0, 8.5 Hz), 7.10-7.40 (16H, m).

Example 46(b)

Synthesis of N-{2-(S)-(N-methyl-2,2-diphenylacetamide)-2-(3,4-dichlorophenyl)-4-[spiro(benzo(c)thiophene-(2S)-oxido-1(3H),4'-piperidin)-1'-yl]butyl}-3,3,3-trifluoro-N-methylpropanamido hydrochloride (Compound No. 42)

Example 47(a)

Synthesis of N-{2-(S)-(N-methyl-2,2-diphenylacetamide)-2-(3,4-dichlorophenyl)-4-[3-oxo-3,4-dihydro-2H-spiro(isoquinoline-1,4'-piperidin)-1'-yl]butyl}-3,3,3-trifluoro-N-methylpropanamido

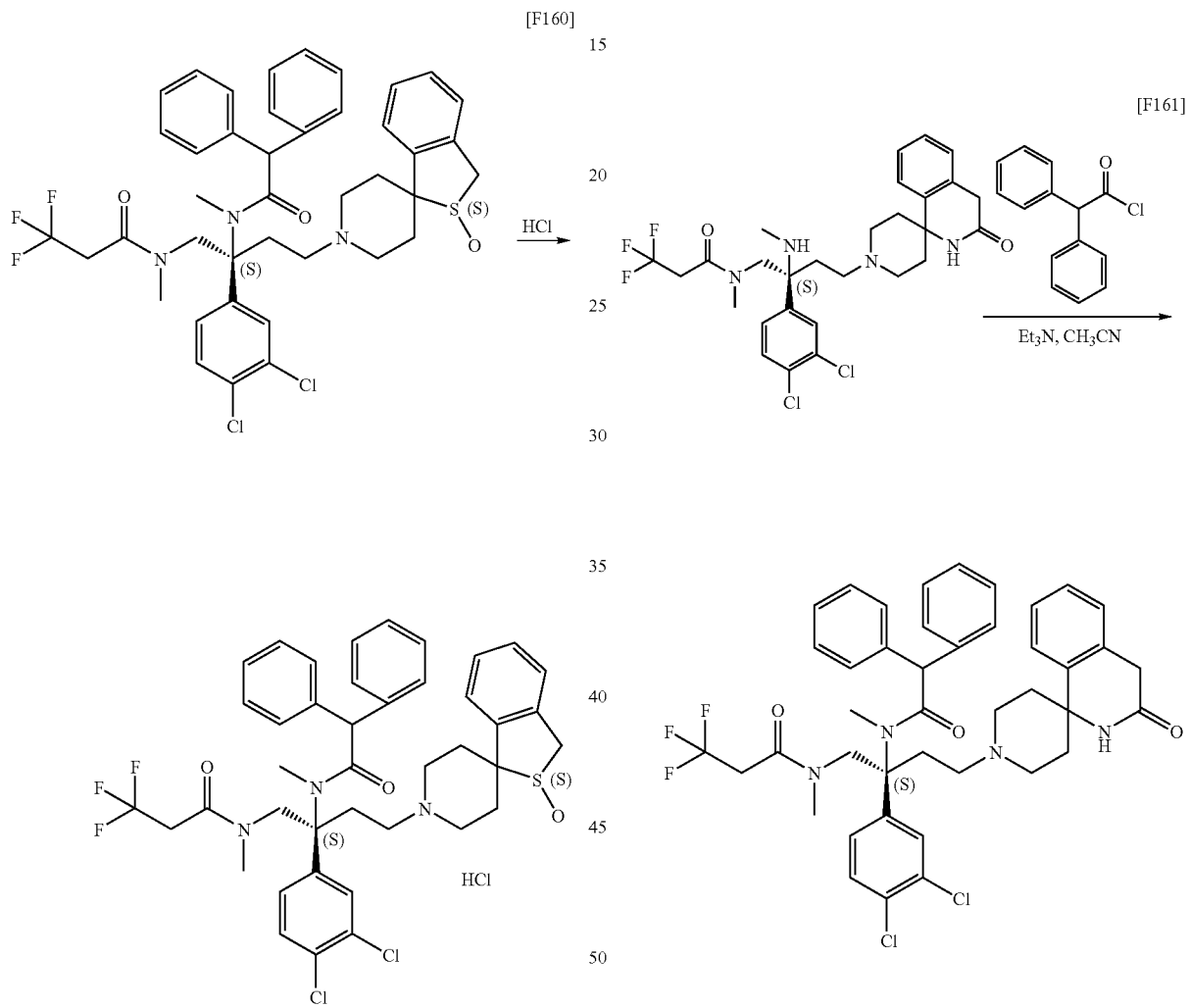

Similar to Example 26(k), the title compound was obtained as pale yellow powder (434 mg, 85.2%) by use of N-{2-(S)-(N-methyl-2,2-diphenylacetamide)-2-(3,4-dichlorophenyl)-4-[spiro(benzo(c)thiophene-(2S)-oxido-1(3H),4'-piperidin)-1'-yl]butyl}-3,3,3-trifluoro-N-methylpropanamide (500 mg).

$[\alpha]_D^{28} = -7.7°$ (c 0.506, MeOH)

$^1$H-NMR (400 MHz, DMSO-$d_6$) δ ppm: 1.92-2.02 (1H, m), 2.18-2.47 (4H, m), 2.57-2.86 (3H, m), 2.95-3.22 (8H, m), 3.48-3.73 (5H, m), 4.09 (1H, d, J=17 Hz), 4.21-4.35 (1H, m), 4.71 (1H, d, J=17 Hz), 5.57 (1H, s), 7.10-7.50 (17H, m), 10.60 (1H, br).

Similar to Example 26(j), the title compound was obtained (190 mg, 26.6%) by use of N-{2-(S)-(3,4-dichlorophenyl)-2-methylamino-4-[3-oxo-3,4-dihydro-2H-spiro(isoquinoline-1,4'-piperidin)-1'-yl]butyl}-3,3,3-trifluoro-N-methylpropanamide (536 mg) synthesized in Example 26(i) and diphenylacetyl chloride (1.06 g).

MS (FAB) m/z 779 ((M+H)$^+$)

$^1$H-NMR (400 MHz, CDCl$_3$) δ ppm: 1.60-1.76 (2H, m), 1.87-2.40 (7H, m), 2.44-2.58 (1H, m), 2.63-2.72 (5H, m), 3.03-3.32 (5H, m), 3.61 (2H, s), 4.20-4.35 (1H, m), 4.38-4.50 (1H, m), 5.22 (1H, s), 6.27 (1H, br), 6.97 (1H, dd, J=2.0, 8.5 Hz), 7.10-7.40 (16H, m).

Example 47(b)

Synthesis of N-{2-(S)-(N-methyl-2,2-diphenylacetamide)-2-(3,4-dichlorophenyl)-4-[3-oxo-3,4-dihydro-2H-spiro(isoquinoline-1,4'-piperidin)-1'-yl]butyl}-3,3,3-trifluoro-N-methylpropanamido hydrochloride (Compound No. 43)

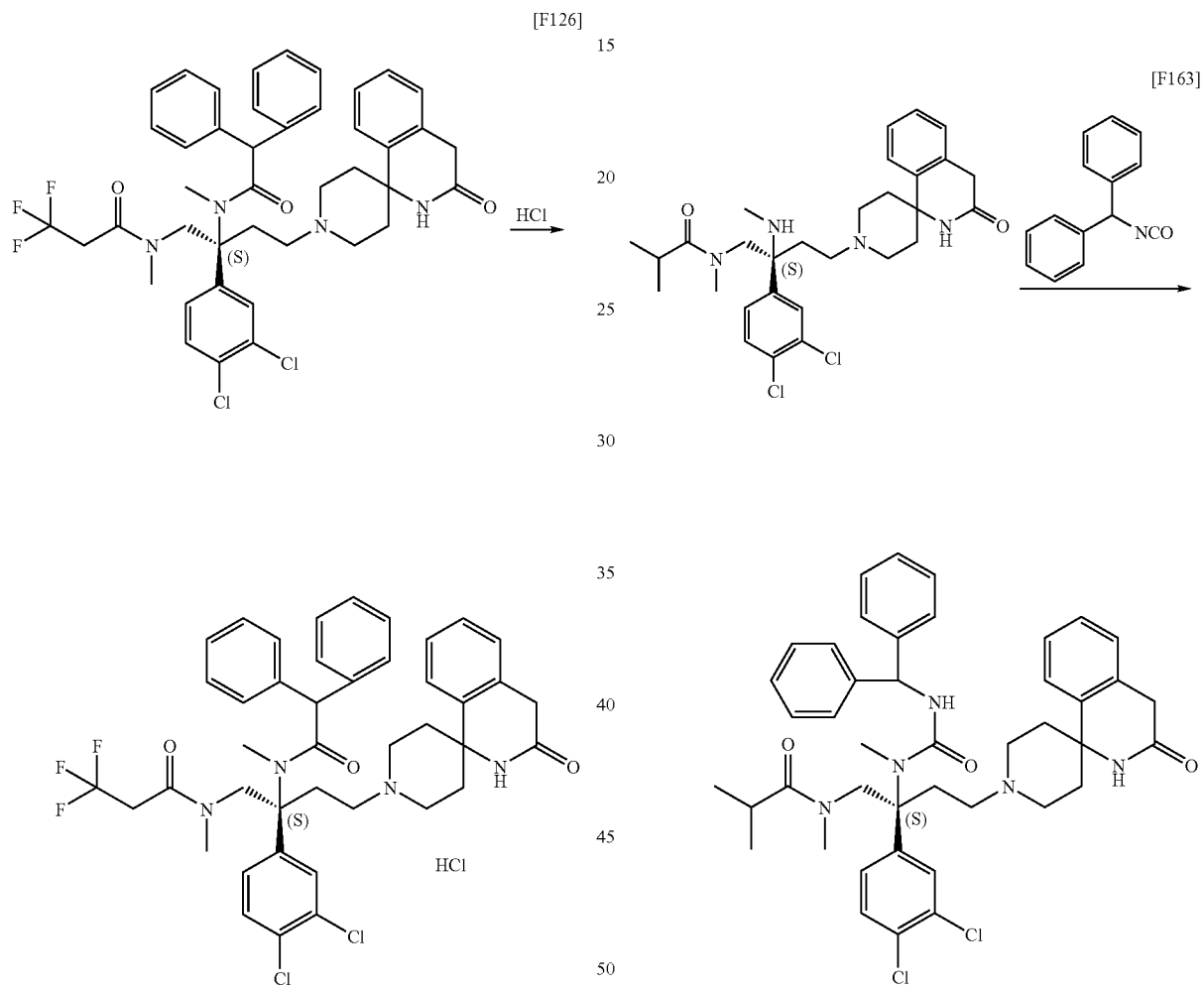

Similar to Example 26(k), the title compound was obtained as white powder (136 mg, 68.3%) by use of N-{2-(S)-(N-methyl-2,2-diphenylacetamide)-2-(3,4-dichlorophenyl)-4-[3-oxo-3,4-dihydro-2H-spiro(isoquinoline-1,4'-piperidin)-1'-yl]butyl}-3,3,3-trifluoro-N-methylpropanamide (190 mg).

$[\alpha]_D^{28} = -11.7°$ (c 0.512, MeOH)

¹H-NMR (400 MHz, DMSO-d₆)δ ppm: 1.89 (2H, d, J=14.5 Hz), 2.31-2.70 (5H, m), 2.98-3.10 (1H, m), 3.18 (3H, s), 3.20-3.53 (6H, m), 3.58-3.75 (5H, m), 3.88-4.06 (1H, m), 4.26-4.37 (1H, m), 5.58 (1H, s), 7.11-7.38 (15H, m), 7.46 (1H, d, J=2.0 Hz), 7.58 (1H, d, J=8.5 Hz), 8.36 (1H, s), 10.41 (1H, br).

Example 48(a)

Synthesis of 1-{1-(N-methyl-isobutylamide)-2-(S)-(3,4-dichlorophenyl)-4-[3-oxo-3,4-dihydro-2H-spiro(isoquinoline-1,4'-piperidin)-1'-yl]butan-2-yl}-3-benzhydryl-1-methylurea N-{2-(S)-(3,4-Dichlorophenyl)-2-methylamino-4-[3-oxo-3,4-dihydro-2H-spiro(isoquinoline-1,4'-piperidin)-1'-yl]butyl}-N-methylisobutylamide (157 mg) synthesized in Example 44(b) was dissolved in tetrahydrofuran (2 mL). Diphenylmethyl isocyanate (109 μL) was added thereto at room temperature, and the mixture was stirred for 30 minutes at the same temperature. The reaction mixture was concentrated under reduced pressure, and the residue was purified through silica gel column chromatography (n-hexane:ethyl acetate=1:4→chloroform:methanol=10:1), to thereby give the title compound (205 mg, 94.3%).

MS (FAB) m/z 754 ((M+H)⁺)

¹H-NMR (400 MHz, CDCl₃)δ ppm: 1.10 (3H, d, J=7.0 Hz), 1.11 (3H, d, J=7.0 Hz), 1.62-1.75 (2H, m), 1.93-2.30 (7H, m), 2.46-2.60 (1H, m), 2.65-2.90 (6H, m), 3.16 (3H, s), 3.62 (2H, s), 4.07-4.20 (1H, m), 4.24-4.40 (1H, m), 4.92 (1H, d, J=7.0 Hz), 5.99 (1H, d, J=7.0 Hz), 6.27 (1H, br), 7.02-7.16 (6H, m), 7.20-7.38 (11H, m).

Example 48(b)

Synthesis of 1-{1-(N-methyl-isobutylamide)-2-(S)-(3,4-dichlorophenyl)-4-[3-oxo-3,4-dihydro-2H-spiro(isoquinoline-1,4'-piperidin)-1'-yl]butan-2-yl}-3-benzhydryl-1-methylureahydrochloride (Compound No. 44)

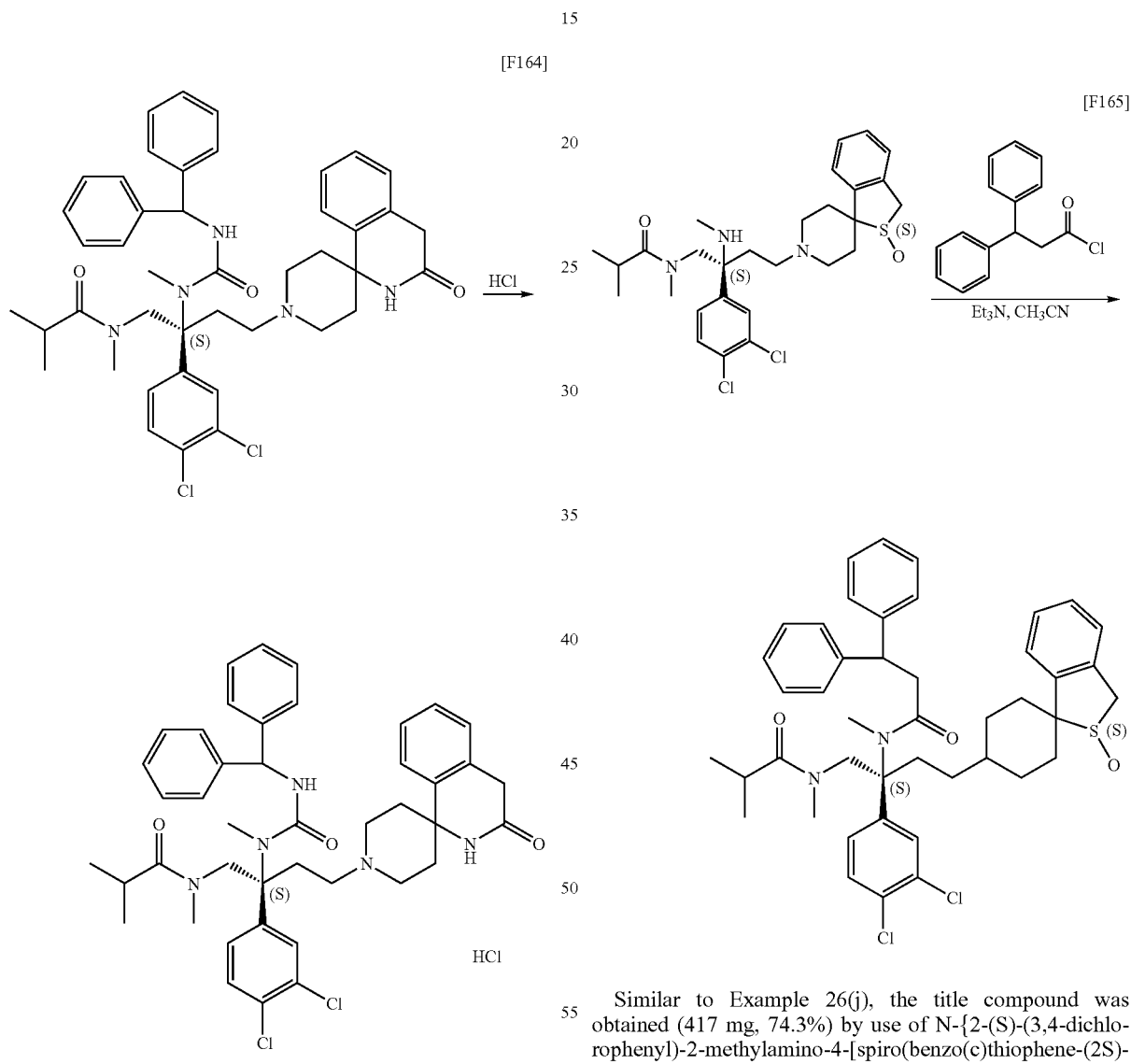

Similar to Example 26(k), the title compound was obtained as white powder (178 mg, 82.7%) by use of 1-{1-(N-methyl-isobutylamide)-2-(S)-(3,4-dichlorophenyl)-4-[3-oxo-3,4-dihydro-2H-spiro(isoquinoline-1,4'-piperidin)-1'-yl]butan-2-yl}-3-benzhydryl-1-methylurea (205 mg).

$[\alpha]_D^{28}$=−22.2° (c 0.503, MeOH)

$^1$H-NMR (400 MHz, DMSO-d$_6$)δ ppm: 1.01 (6H, d, J=7.0 Hz), 1.85-1.97 (2H, m), 2.20-2.60 (6H, m), 2.72-3.18 (7H, m), 3.25-3.50 (5H, m), 3.73 (2H, s), 3.80-4.00 (1H, m), 4.20-4.32 (1H, m), 5.82 (1H, d, J=8.0 Hz), 7.13-7.38 (15H, m), 7.48-7.60 (2H, m), 8.35 (1H, s), 10.20 (1H, br).

Example 49(a)

Synthesis of N-{2-(S)-(N-methyl-3,3-diphenylpropanamido)-2-(3,4-dichlorophenyl)-4-[spiro(benzo(c)thiophene-(2S)-oxido-1(3H),4'-piperidin)-1'-yl]butyl}-N-methyl-isobutylamide Similar to Example 26(j), the title compound was obtained (417 mg, 74.3%) by use of N-{2-(S)-(3,4-dichlorophenyl)-2-methylamino-4-[spiro(benzo(c)thiophene-(2S)-oxido-1(3H),4'-piperidin)-1'-yl]butyl}-N-methylisobutylamide (408 mg) synthesized in Example 46(e) and 3,3-diphenylpropionyl chloride (544 mg).

MS (FAB) m/z 758 ((M+H)$^+$)

$^1$H-NMR (270 MHz, CDCl$_3$)δ ppm: 1.07 (3H, s), 1.09 (3H, s), 1.42-1.55 (1H, m), 1.76-1.90 (1H, m), 1.94-2.06 (1H, m), 2.10-2.47 (7H, m), 2.54 (3H, s), 2.63-2.88 (3H, m), 3.00-3.18 (5H, m), 3.90-4.10 (2H, m), 4.23-4.36 (2H, m), 4.62 (1H, t, J=7.5 Hz), 6.72 (1H, d, J=8.5 Hz), 7.12-7.35 (16H, m).

Example 49(b)

Synthesis of N-{2-(S)-(N-methyl-3,3-diphenylpropanamido)-2-(3,4-dichlorophenyl)-4-[spiro(benzo(c)thiophene-(2S)-oxido-1(3H),4'-piperidin)-1'-yl]butyl}-N-methyl-isobutylamide hydrobromide
(Compound No. 45)

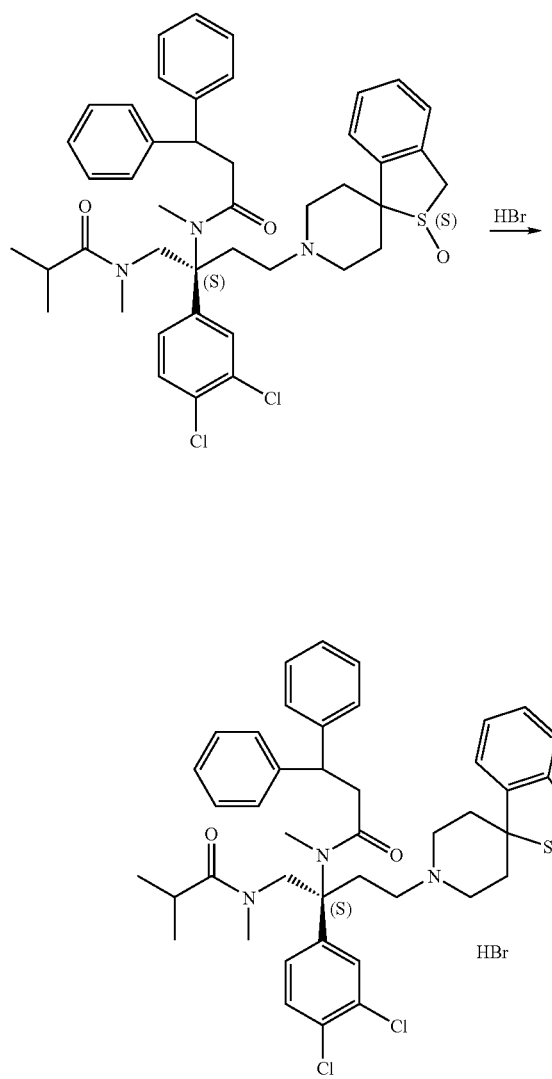

N-{2-(S)-(3,4-Dichlorophenyl)-2-methylamino-4-[spiro(benzo(c)thiophene-(2S)-oxido-1(3H),4'-piperidin)-1'-yl]butyl}-N-methylisobutylamide (11.0 g) was dissolved in ethanol (50 mL). An aqueous solution (50 mL) of 48% hydrobromic acid (2.45 g) was added thereto at 55° C. The temperature of the mixture was lowered to room temperature, and 50% aqueous ethanol (100 mL) was added to the mixture. The crystals were collected through filtration and dried, to thereby give the title compound (8.5 g, 83%) as pale yellow crystals.

Mp: 172.4-173.8° C. (dec.)

$[\alpha]_D^{27} = -23.3°$ (c 0.207, MeOH)

$^1$H-NMR (400 MHz, DMSO-$d_6$)δ ppm: 0.98 (3H, d, J=6.0 Hz), 0.99 (3H, d, J=6.0 Hz), 2.00-2.19 (2H, m), 2.22-2.34 (2H, m), 2.37-2.45 (2H, m), 2.60-2.81 (2H, m), 2.98-3.43 (11H, m), 3.47-3.57 (2H, m), 3.64-3.76 (1H, m), 4.10 (1H, d, J=17 Hz), 4.17-4.28 (1H, m), 4.36 (1H, t, J=7.5 Hz), 4.71 (1H, d, J=17 Hz), 7.06-7.18 (3H, m), 7.22-7.32 (9H, m), 7.36-7.43 (5H, m), 9.55 (1H, br).

Example 50(a)

Synthesis of 1-{1-(2,2,2-trifluoro-N-methylacetamide)-2-(S)-(3,4-dichlorophenyl)-4-[3-oxo-3,4-dihydro-2H-spiro(isoquinoline-1,4'-piperidin)-1'-yl]butan-2-yl}-3-benzhydryl-1-methylurea

[F167]

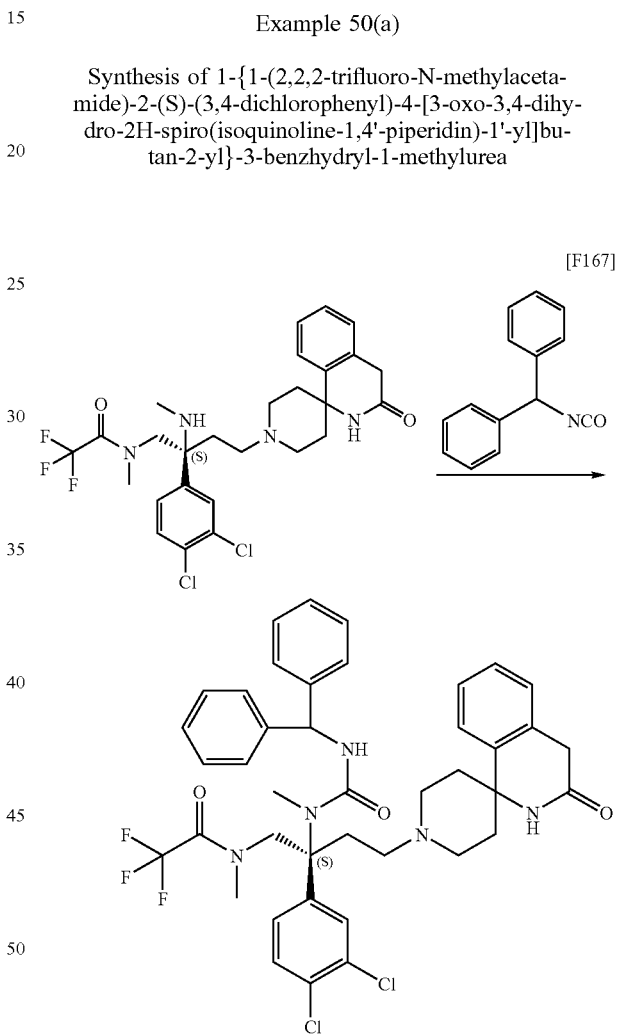

Similar to Example 48(a), the title compound was obtained (355 mg, 98.4%) by use of N-{2-(S)-(3,4-dichlorophenyl)-2-methylamino-4-[3-oxo-3,4-dihydro-2H-spiro(isoquinoline-1,4'-piperidin)-1'-yl]butyl}-2,2,2-trifluoro-N-methylacetamide (264 mg) synthesized in Example 27(e).

MS (FAB) m/z 780 ((M+H)$^+$)

$^1$H-NMR (270 MHz, CDCl$_3$)δ ppm: 1.55-1.80 (2H, m), 1.93-2.27 (7H, m), 2.41-2.57 (1H, m), 2.68-2.85 (2H, m), 2.89 (3H, s), 3.12 (3H, s), 3.61 (2H, s), 4.34 (1H, d, J=13.5 Hz), 4.49 (1H, d, J=13.5 Hz), 5.07 (1H, d, J=7.0 Hz), 5.99 (1H, d, J=7.0 Hz), 6.24 (1H, s), 7.03 (1H, dd, J=2.0, 8.5 Hz), 7.10-7.43 (16H, m).

Example 50(b)

Synthesis of 1-{1-(2,2,2-trifluoro-N-methylacetamide)-2-(S)-(3,4-dichlorophenyl)-4-[3-oxo-3,4-dihydro-2H-spiro(isoquinoline-1,4'-piperidin)-1'-yl]butan-2-yl}-3-benzhydryl-1-methylurea sulfate (Compound No. 46)

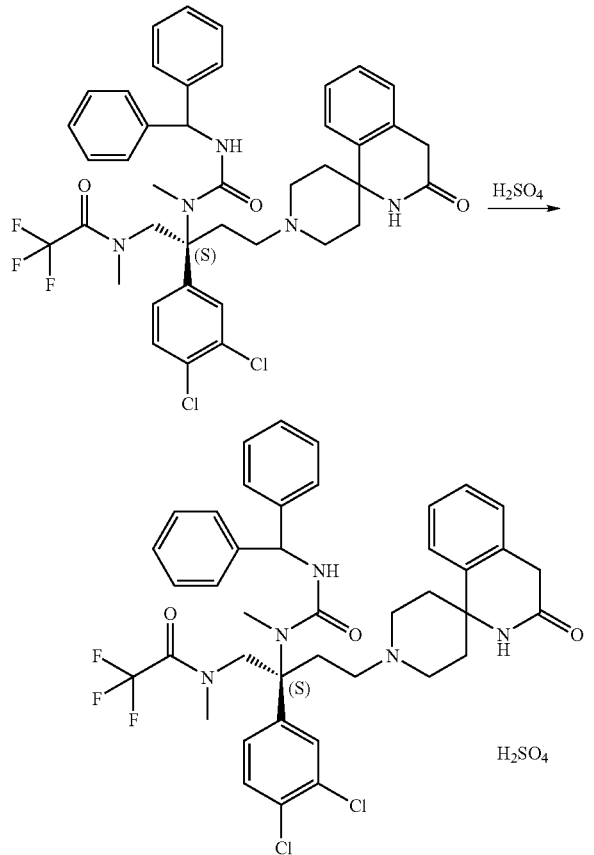

1-{1-(2,2,2-Trifluoro-N-methylacetamide)-2-(S)-(3,4-dichlorophenyl)-4-[3-oxo-3,4-dihydro-2H-spiro(isoquinoline-1,4'-piperidin)-1'-yl]butan-2-yl}-3-benzhydryl-1-methylurea (8.2 g) was dissolved in ethanol (30 mL). At an internal temperature of 30° C., a solution of concentrated sulfuric acid (1.07 g) in ethanol (10 mL) was added thereto. The temperature of the mixture was lowered to room temperature, and ethanol:isopropyl ether (5:2) mixture solution (30 mL) was added to the mixture. The crystals were collected through filtration and dried, to thereby give the title compound (8.12 g, 88.0%) as white crystals.

Mp: 185.9-186.0° C. (dec.)

$[\alpha]_D^{28}$=−5.9° (c 0.209, MeOH)

$^1$H-NMR (400 MHz, DMSO-$d_6$)δ ppm: 1.96 (2H, d, J=14 Hz), 2.24-2.38 (2H, m), 2.41-2.56 (2H, m), 2.73 (3H, s), 2.85-2.98 (1H, m), 3.03-3.16 (4H, m), 3.27-3.53 (4H, m), 3.63 (2H, s), 4.09-4.22 (1H, m), 4.38 (1H, d, J=13.5 Hz), 5.85 (1H, d, J=7.5 Hz), 7.20-7.37 (16H, m), 7.56 (1H, d, J=2.0 Hz), 7.59 (1H, d, J=8.5 Hz), 8.27 (1H, s), 9.18 (2H, br).

Example 51(a)

Synthesis of phenyl[1-(3,3,3-trifluoro-N-methylpropanamido)-2-(S)-(3,4-dichlorophenyl)-4-penten-2-yl]methylcarbamate

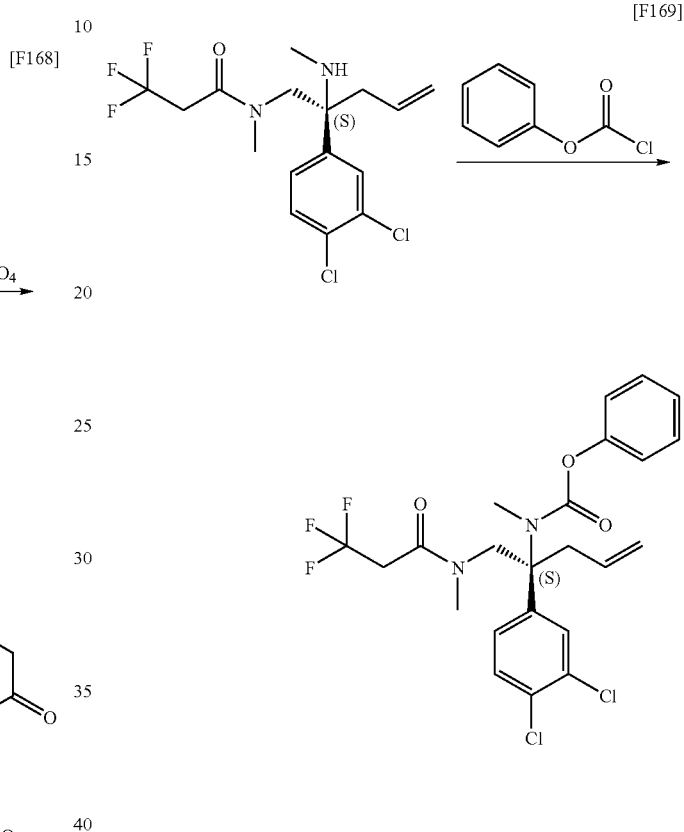

N-[2-(S)-(3,4-Dichlorophenyl)-2-methylamino-4-pentene-1'-yl]-3,3,3-trifluoro-N-methylpropanamide (400 mg) synthesized in Example 29(a) was dissolved in ethyl acetate (4 mL). At room temperature, saturated aqueous sodium bicarbonate (4 mL) and phenyl chloroformate (0.26 mL) were added thereto, and the mixture was stirred for 2 hours at the same temperature. Subsequently, phenyl chloroformate (0.26 mL) was added to the reaction mixture, and the resultant mixture was stirred for another 2 hours. The reaction mixture was extracted with ethyl acetate, sequentially washed with water and saturated brine, and dried over sodium sulfate anhydrate. The solvent was concentrated under reduced pressure, and the residue was purified through silica gel column chromatography (n-hexane:ethyl acetate=2:1), to thereby give the title compound (498 mg, 94.8%).

MS (FAB) m/z 503 ((M+H)$^+$)

$^1$H-NMR (400 MHz, CDCl$_3$)δ ppm: 2.73 (1H, dd, J=6.5, 13.5 Hz), 2.87 (3H, s), 2.92-3.06 (1H, m), 3.12-3.36 (2H, m), 3.18 (3H, s), 3.98-4.17 (1H, m), 4.44-4.62 (1H, m), 5.04 (1H, d, J=17.0 Hz), 5.08 (1H, d, J=10.5 Hz), 5.75-5.89 (1H, m), 6.90-7.07 (2H, m), 7.11 (1H, dd, J=2.5, 8.5 Hz), 7.13-7.19 (1H, m), 7.25-7.38 (3H, m), 7.41 (1H, d, J=8.5 Hz).

Example 51(b)

Synthesis of phenyl[1-(3,3,3-trifluoro-N-methylpropanamido)-2-(S)-(3,4-dichlorophenyl)-5-hydroxy-pentan-2-yl]methylcarbamate

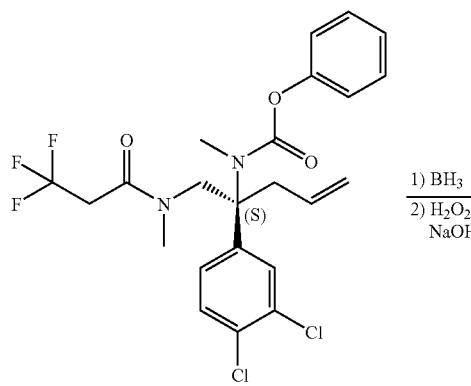

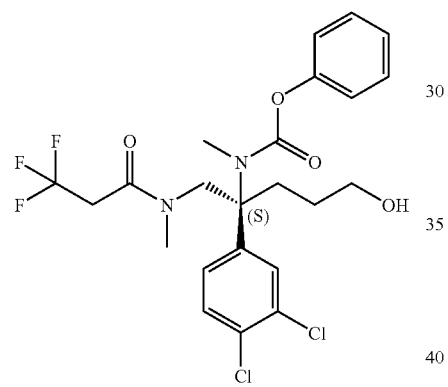

Under argon, phenyl[1-(3,3,3-trifluoro-N-methylpropanamido)-2-(S)-(3,4-dichlorophenyl)-4-penten-2-yl]methylcarbamate (410 mg) was dissolved in anhydrous tetrahydrofuran (4 mL). Under cooling with ice, a 1.06M solution (0.80 mL) of borane tetrahydrofuran complex in tetrahydrofuran was added thereto, and the mixture was stirred for 1 hour. Water (0.3 mL), 3N aqueous sodium hydroxide (0.9 mL), and 30% aqueous hydrogen peroxide (0.9 mL) were added to the reaction mixture, and the resultant mixture was stirred for 1 hour at room temperature. The reaction mixture was extracted with ethyl acetate, sequentially washed with water and saturated brine, and dried over sodium sulfate anhydrate. The solvent was concentrated under reduced pressure, and the residue was purified through silica gel column chromatography (n-hexane:ethyl acetate=1:2), to thereby give the title compound (311 mg, 70.0%).

MS (FAB) m/z 521 ((M+H)$^+$)

$^1$H-NMR (400 MHz, CDCl$_3$)δ ppm: 1.05-1.21 (1H, m), 1.64-1.78 (1H, m), 1.85-1.97 (2H, m), 2.17-2.30 (1H, m), 2.97 (3H, s), 3.20-3.41 (2H, m), 3.28 (3H, s), 3.48-3.59 (1H, m), 3.60-3.69 (1H, m), 4.23-4.57 (2H, m), 6.88-7.04 (2H, m), 7.10 (1H, dd, J=2.0, 8.5 Hz), 7.13-7.20 (1H, m), 7.25-7.38 (3H, m), 7.41 (1H, d, J=8.5 Hz).

Example 51(c)

Synthesis of phenyl[1-(3,3,3-trifluoro-N-methylpropanamido)-2-(S)-(3,4-dichlorophenyl)-5-oxo-pentan-2-yl]methylcarbamate

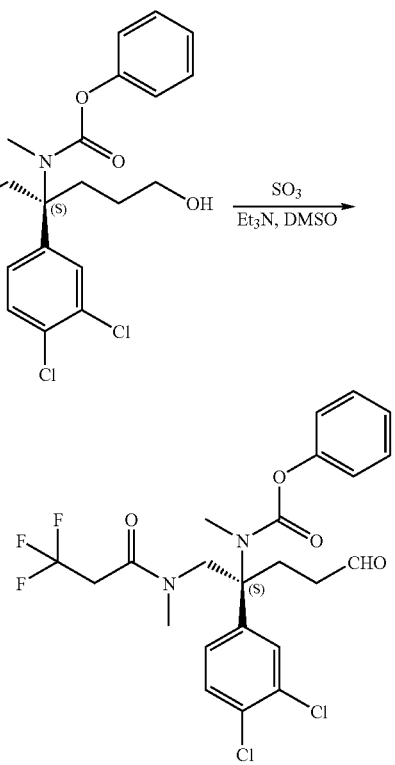

Under argon, phenyl[1-(3,3,3-trifluoro-N-methylpropanamido)-2-(S)-(3,4-dichlorophenyl)-5-hydroxy-pentan-2-yl]methylcarbamate (100 mg) was dissolved in anhydrous dimethyl sulfoxide (1.0 mL). At room temperature, triethylamine (0.16 mL) and pyridine sulfur trioxide complex (94 mg) were added thereto, and the mixture was stirred for 4 hours at room temperature. Water was added to the reaction mixture, and the mixture was extracted with ethyl acetate. The organic layer was sequentially washed with water and saturated brine and dried over sodium sulfate anhydrate. The solvent was concentrated under reduced pressure, to thereby give the title compound (115 mg).

MS (FAB) m/z 519 ((M+H)$^+$)

$^1$H-NMR (400 MHz, CDCl$_3$)δ ppm: 2.07-2.23 (2H, m), 2.28-2.40 (1H, m), 2.78-2.90 (1H, m), 2.96 (3H, s), 3.18-3.39 (2H, m), 3.29 (3H, 5), 4.20-4.53 (2H, m), 6.81-7.05 (2H, m), 7.11 (1H, dd, J=2.0, 8.5 Hz), 7.17 (1H, t, J=7.5 Hz), 7.24-7.37 (3H, m), 7.43 (1H, d, J=8.5 Hz), 9.65 (1H, s).

Example 51(d)

Synthesis of phenyl{1-(3,3,3-trifluoro-N-methylpropanamido)-2-(S)-(3,4-dichlorophenyl)-5-[spiro(benzo(c)thiophene-(2S)-oxido-1(3H),4'-piperidin)-1'-yl]pentan-2-yl}methylcarbamate

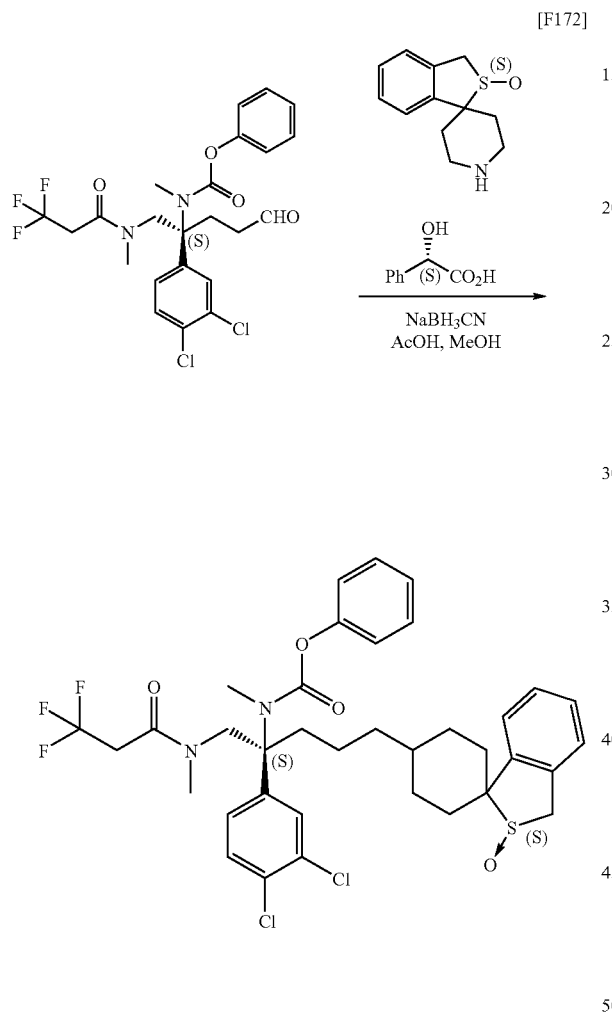

Phenyl{[1-(3,3,3-trifluoro-N-methylpropanamido)-2-(S)-(3,4-dichlorophenyl)-5-oxo-pentan-2-yl]methylcarbamate (115 mg) was dissolved in methanol (1 mL). Under cooling with ice, sodium cyanoborohydride (14 mg) and spiro(benzo(c)thiophene-(2S)-oxido-1(3H),4'-piperidine)/(S)-(+)-mandelate (79 mg) were added thereto, and then acetic acid (19 μL) was added thereto. The temperature of the mixture was then returned to room temperature, and the mixture was stirred for 30 minutes. The reaction mixture was poured into saturated aqueous sodium bicarbonate, and the mixture was extracted with ethyl acetate, washed with saturated brine, and dried over sodium sulfate anhydrate. The solvent was concentrated under reduced pressure, and the residue was purified through silica gel column chromatography (ethyl acetate→ethyl acetate:methanol=10:1), to thereby give the title compound (97 mg, 69.7%, two steps).

MS (FAB) m/z 724 ((M+H)$^+$)

$^1$H-NMR (400 MHz, CDCl$_3$)δ ppm: 0.97-1.17 (1H, m), 1.51-1.77 (2H, m), 1.82-2.09 (3H, m), 2.25-2.49 (6H, m), 2.80-2.98 (2H, m), 3.02 (3H, s), 3.17-3.47 (2H, m), 3.28 (3H, s), 3.99 (1H, d, J=16.5 Hz), 4.18-4.38 (2H, m), 4.43-4.55 (1H, m), 6.87-7.06 (1H, m), 7.08-7.19 (2H, m), 7.25-7.43 (9H, m).

Example 51(e)

Synthesis of phenyl{1-(3,3,3-trifluoro-N-methylpropanamido)-2-(S)-(3,4-dichlorophenyl)-5-[spiro(benzo(c)thiophene-(2S)-oxido-1(3H),4'-piperidin)-1'-yl]pentan-2-yl}methylcarbamate hydrochloride (Compound No. 591)

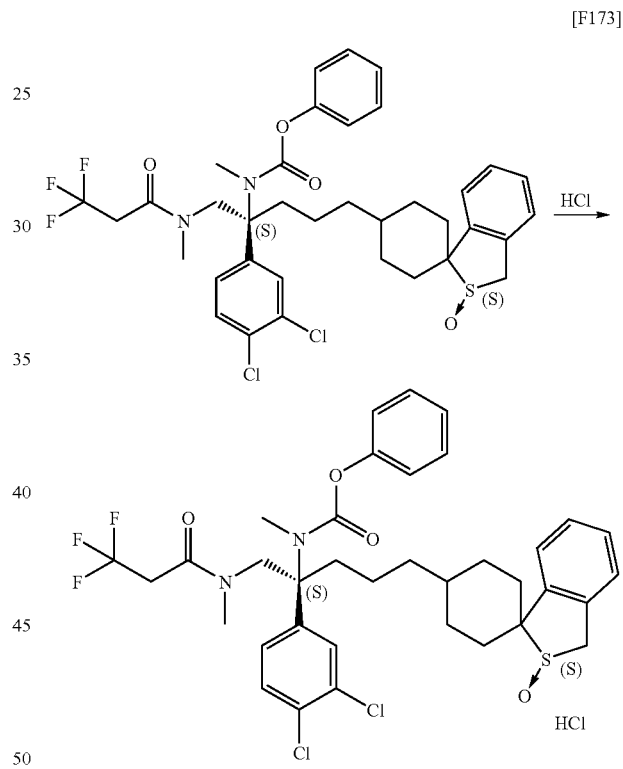

Phenyl{1-(3,3,3-trifluoro-N-methylpropanamido)-2-(S)-(3,4-dichlorophenyl)-5-[spiro(benzo(c)thiophene-(2S)-oxido-1(3H),4'-piperidin)-1'-yl]pentan-2-yl]methylcarbamate (97 mg) was dissolved in ethyl acetate. 4N HCl-1,4-dioxane (0.1 mL) was added thereto, and the solvent was concentrated under reduced pressure. Ether was added to the residue, followed by filtration and drying, to thereby give the title compound (70 mg, 68.6%) as white powder.

$^1$H-NMR (400 MHz, DMSO-d$_6$)δ ppm: 1.15-1.43 (1H, m), 1.75-1.93 (1H, m), 1.95-2.20 (3H, m), 2.25 (1H, d, J=14.0 Hz), 2.34-2.48 (1H, m), 2.73-3.19 (8H, m), 3.27 (3H, s), 3.47-3.57 (1H, m), 3.59-3.88 (3H, m), 4.08 (1H, d, J=17.0 Hz), 4.13-4.42 (2H, m), 4.68 (1H, d, J=17.0 Hz), 6.40-6.67 (1H, m), 6.93-7.10 (1H, m), 7.11-7.22 (1H, m), 7.25-7.46 (7H, m), 7.52-7.69 (2H, m), 10.70 (1H, br).

Example 52(a)

Synthesis of 4-chlorophenyl[1-(3,3,3-trifluoro-N-methylpropanamido)-2-(S)-(3,4-dichlorophenyl)-4-penten-2-yl]methylcarbamate

[F174]

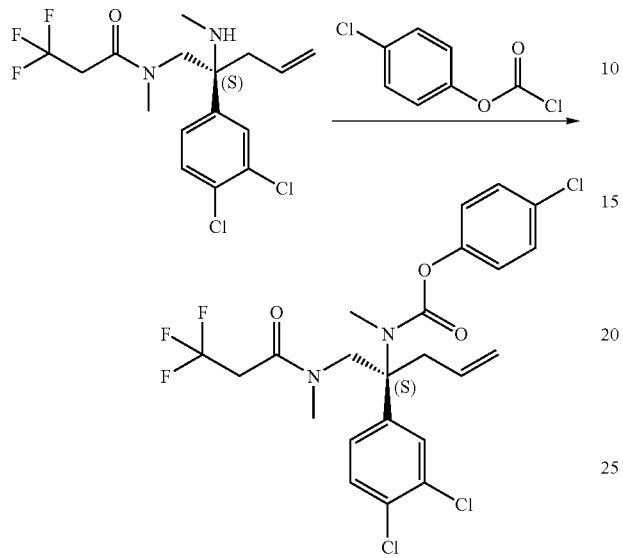

Similar to Example 51(a), the title compound was obtained (303 mg, >100%) by use of N-[2-(S)-(3,4-dichlorophenyl)-2-methylamino-4-pentene-1'-yl]-3,3,3-trifluoro-N-methylpropanamide (200 mg) synthesized in Example 4(a) and 4-chlorophenyl chloroformate (0.29 mL).

MS (FAB) m/z 537 ((M+H)$^+$)

$^1$H-NMR (400 MHz, CDCl$_3$)δ ppm: 2.74 (1H, dd, J=6.0, 13.5 Hz), 2.85 (3H, s), 2.92-3.33 (3H, m), 3.15 (3H, s), 3.84-4.06 (1H, m), 4.50-4.73 (1H, m), 4.98-5.12 (2H, m), 5.71-5.88 (1H, m), 6.87-7.06 (2H, m), 7.10 (1H, dd, J=2.5, 8.5 Hz), 7.21-7.32 (2H, m), 7.34 (1H, d, J=2.5 Hz), 7.42 (1H, d, J=8.5 Hz).

Example 52(b)

Synthesis of 4-chlorophenyl{1-(3,3,3-trifluoro-N-methylpropanamido)-2-(S)-(3,4-dichlorophenyl)-5-[spiro(benzo(c)thiophene-(2S)-oxido-1(3H), 41-piperidin)-1'-yl]pentan-2-yl}methylcarbamate

[F175]

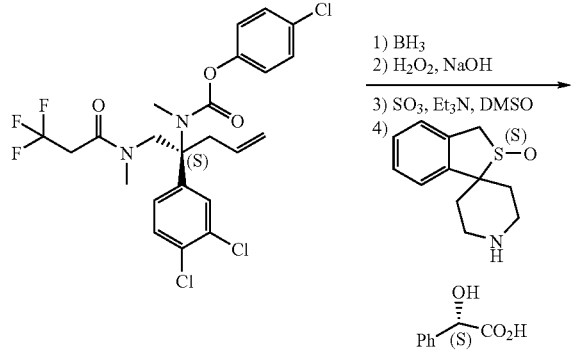

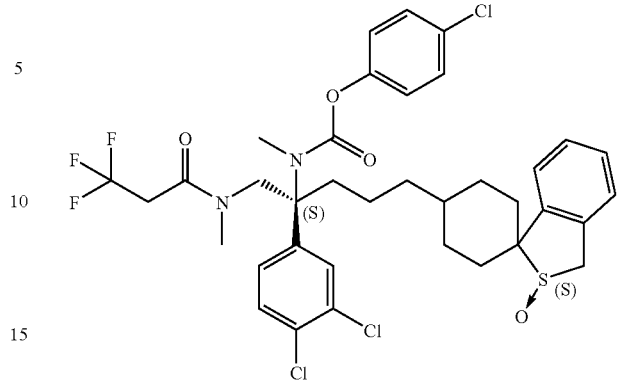

Similar to Example 51(b), 4-chlorophenyl[1-(3,3,3-trifluoro-N-methylpropanamido)-2-(S)-(3,4-dichlorophenyl)-5-hydroxy-pentan-2-yl]methylcarbamate (180 mg) was obtained by use of 4-chlorophenyl[1-(3,3,3-trifluoro-N-methylpropanamido)-2-(S)-(3,4-dichlorophenyl)-4-penten-2-yl]methylcarbamate (296 mg). Subsequently, similar to Example 51(c), 4-chlorophenyl[1-(3,3,3-trifluoro-N-methylpropanamido)-2-(S)-(3,4-dichlorophenyl)-5-oxo-pentan-2-yl]methylcarbamate (167 mg) was obtained by use of 4-chlorophenyl[1-(3,3,3-trifluoro-N-methylpropanamido)-2-(S)-(3,4-dichlorophenyl)-5-hydroxy-pentan-2-yl]methylcarbamate (174 mg). Thereafter, similar to Example 51(d), the title compound was obtained as white powder (136 mg, 36.3%, 4 steps) by use of 4-chlorophenyl[1-(3,3,3-trifluoro-N-methylpropanamido)-2-(S)-(3,4-dichlorophenyl)-5-oxo-pentan-2-yl]methylcarbamate (167 mg).

MS (FAB) m/z 760 ((M+H)$^+$)

$^1$H-NMR (400 MHz, CDCl$_3$)δ ppm: 1.00-1.17 (1H, m), 1.52-1.71 (2H, m), 1.82-2.08 (3H, m), 2.25-2.47 (6H, m), 2.82-3.09 (2H, m), 2.98 (3H, s), 3.17-3.43 (2H, m), 3.25 (3H, s), 3.99 (1H, d, J=16.5 Hz), 4.20-4.52 (3H, m), 6.83-7.02 (1H, br), 7.10 (1H, dd, J=2.0, 8.5 Hz), 7.20-7.36 (8H, m), 7.40 (1H, d, J=8.5 Hz).

Example 52(c)

Synthesis of 4-chlorophenyl(1-(3,3,3-trifluoro-N-methylpropanamido)-2-(S)-(3,4-dichlorophenyl)-5-[spiro(benzo(c)thiophene-(2S)-oxido-1(3H),4'-piperidin)-1'-yl]pentan-2-yl}methylcarbamate hydrochloride (Compound No. 633)

[F176]

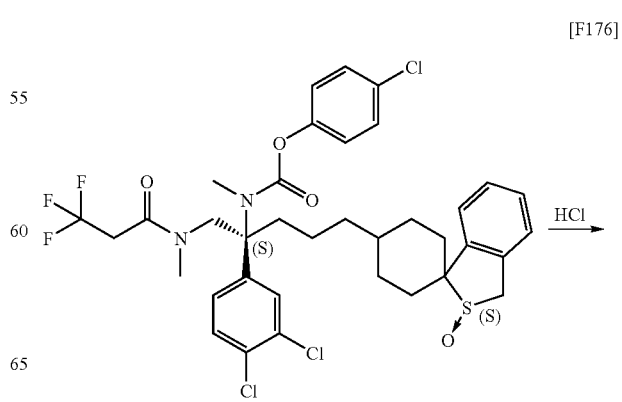

-continued

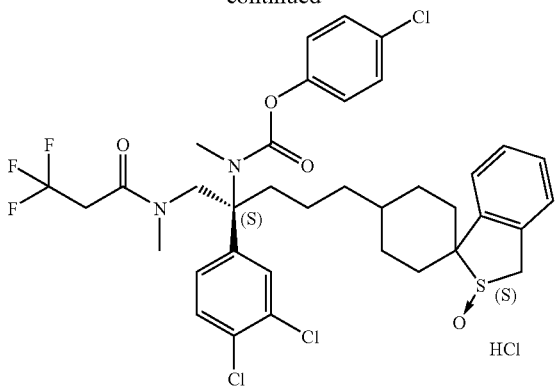

Similar to Example 51(e), the title compound was obtained as white powder (80 mg, 56.2%) by use of 4-chlorophenyl{1-(3,3,3-trifluoro-N-methylpropanamido)-2-(S)-(3,4-dichlorophenyl)-5-[spiro(benzo(c)thiophene-(2S)-oxido-1(3H),4'-piperidin)-1'-yl]pentan-2-yl}methylcarbamate (136 mg).

$^1$H-NMR (400 MHz, DMSO-$d_6$)δ ppm: 1.21-1.47 (1H, m), 1.76-1.91 (1H, m), 1.94-2.19 (3H, m), 2.25 (1H, d, J=14.0 Hz), 2.35-2.48 (1H, m), 2.77-3.18 (8H, m), 3.25 (3H, s), 3.47-3.55 (1H, m), 3.59-3.87 (3H, m), 4.04-4.53 (3H, m), 4.68 (1H, d, J=17.0 Hz), 6.51-6.73 (1H, m), 7.03-7.17 (1H, m), 7.29-7.46 (7H, m), 7.55-7.67 (2H, m), 10.73 (1H, br).

Example 53(a)

Synthesis of 3-fluorophenyl[1-(3,3,3-trifluoro-N-methylpropanamido)-2-(S)-(3,4-dichlorophenyl)-4-penten-2-yl]methylcarbamate

[F177]

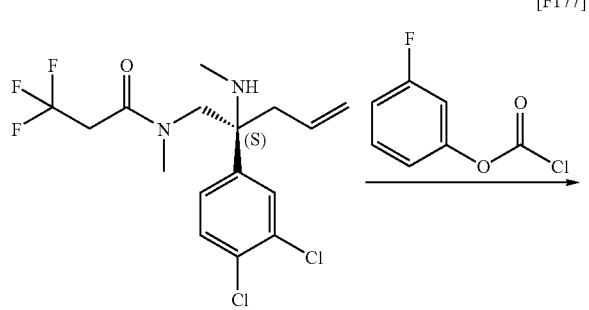

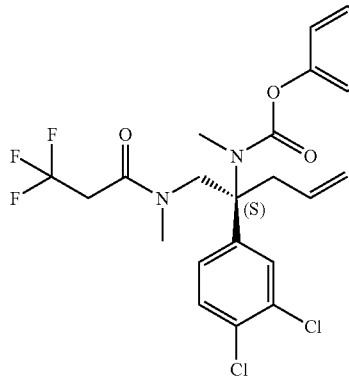

Similar to Example 51(a), the title compound was obtained (256 mg, 94.1%) by use of N-[2-(S)-(3,4-dichlorophenyl)-2-(methylamino)-4-pentene-1'-yl]-3,3,3-trifluoro-N-methylpropanamide (200 mg) synthesized in Example 4(a) and 3-fluorophenyl chloro formate (873 mg).

MS (FAB) m/z 521 ((M+H)$^+$)

$^1$H-NMR (400 MHz, CDCl$_3$)δ ppm: 2.75 (1H, dd, J=6.0, 13.5 Hz), 2.85 (3H, s), 2.92-3.05 (1H, m), 3.09-3.32 (2H, m), 3.16 (3H, s), 3.90-4.07 (1H, m), 4.52-4.72 (1H, m), 5.05 (1H, d, J=17.0 Hz), 5.09 (1H, d, J=10.0 Hz), 5.72-5.89 (1H, m), 6.68-6.95 (3H, m), 7.11 (1H, dd, J=2.5, 8.5 Hz), 7.22-7.31 (1H, m), 7.35 (1H, d, J=2.5 Hz), 7.42 (1H, d, J=8.5 Hz).

Example 53(b)

Synthesis of 3-fluorophenyl{1-(3,3,3-trifluoro-N-methylpropanamido)-2-(S)-(3,4-dichlorophenyl)-5-[spiro(benzo(c)thiophene-(2S)-oxido-1(3H),4'-piperidin)-1'-yl]pentan-2-yl}methylcarbamate

[F178]

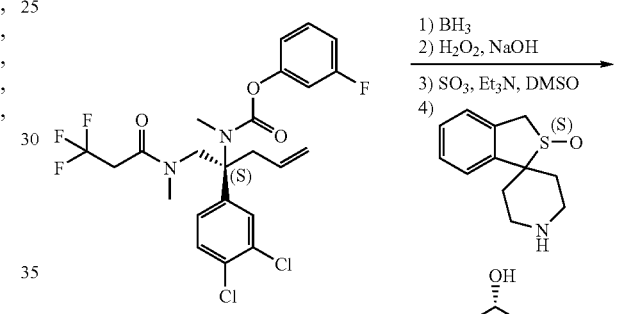

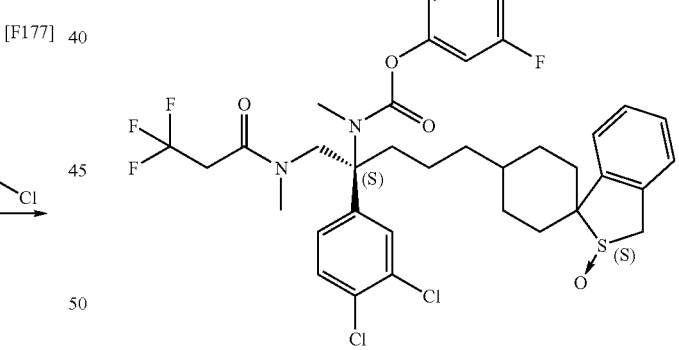

Similar to Example 51(b), 3-fluorophenyl[1-(3,3,3-trifluoro-N-methylpropanamido)-2-(S)-(3,4-dichlorophenyl)-5-hydroxy-pentan-2-yl]methylcarbamate was obtained (110 mg) by use of 3-fluorophenyl[1-(3,3,3-trifluoro-N-methylpropanamido)-2-(S)-(3,4-dichlorophenyl)(4-penten-2-yl)]methylcarbamate (236 mg) Subsequently, similar to Example 51(c), 3-fluorophenyl[1-(3,3,3-trifluoro-N-methylpropanamido)-2-(S)-(3,4-dichlorophenyl)-5-oxo-pentan-2-yl]methylcarbamate was obtained (117 mg) by use of 3-fluorophenyl[1-(3,3,3-trifluoro-N-methylpropanamido)-2-(S)-(3,4-dichlorophenyl)-5-hydroxy-pentan-2-yl] methylcarbamate (105 mg) Thereafter, similar to Example 51(d), the title compound was obtained as white powder (102 mg, 36.6%, 4 steps) by use of 3-fluorophenyl[1-(3,3, 3-trifluoro-N-methylpropanamido)-2-(S)-(3,4-dichlorophenyl)-5-oxo-pentan-2-yl]methylcarbamate (114 mg).

MS (FAB) m/z 742 ((M+H)$^+$)

$^1$H-NMR (400 MHz, CDCl$_3$)δ ppm: 0.97-1.18 (1H, m), 1.53-2.09 (5H, m), 2.25-2.48 (6H, m), 2.80-3.09 (2H, m), 2.99 (3H, s), 3.14-3.44 (2H, m), 3.26 (3H, s), 3.99 (1H, d, J=16.5 Hz), 4.20-4.57 (3H, m), 6.66-6.92 (2H, m), 7.10 (1H, dd, J=2.0, 8.5 Hz), 7.20-7.37 (7H, m), 7.41 (1H, d, J=8.5 Hz).

Example 53(c)

Synthesis of 3-fluorophenyl{1-(3,3,3-trifluoro-N-methylpropanamido)-2-(S)-(3,4-dichlorophenyl)-5-[spiro(benzo(c)thiophene-(2S)-oxido-1(3H),4'-piperidin)-1'-yl]pentan-2-yl}methylcarbamate hydrochloride (Compound No. 634)

oxido-1(3H),4'-piperidin)-1'-yl]pentan-2-yl}methylcarbamate (102 mg).

$^1$H-NMR (400 MHz, DMSO-d$_6$)δ ppm: 1.21-1.44 (1H, m), 1.76-1.91 (1H, m), 1.93-2.20 (3H, m), 2.25 (1H, d, J=14.0 Hz), 2.34-2.47 (1H, m), 2.78-3.18 (8H, m), 3.25 (3H, s), 3.47-3.89 (4H, m), 4.03-4.50 (3H, m), 4.68 (1H, d, J=17.0 Hz), 6.38-6.64 (1H, m), 6.86-7.11 (2H, m), 7.28-7.47 (6H, m), 7.53-7.69 (2H, m), 10.72 (1H, br).

Example 54(a)

Synthesis of 2-methoxyphenyl[1-(3,3,3-trifluoro-N-methylpropanamido)-2-(S)-(3,4-dichlorophenyl)-4-penten-2-yl]methylcarbamate

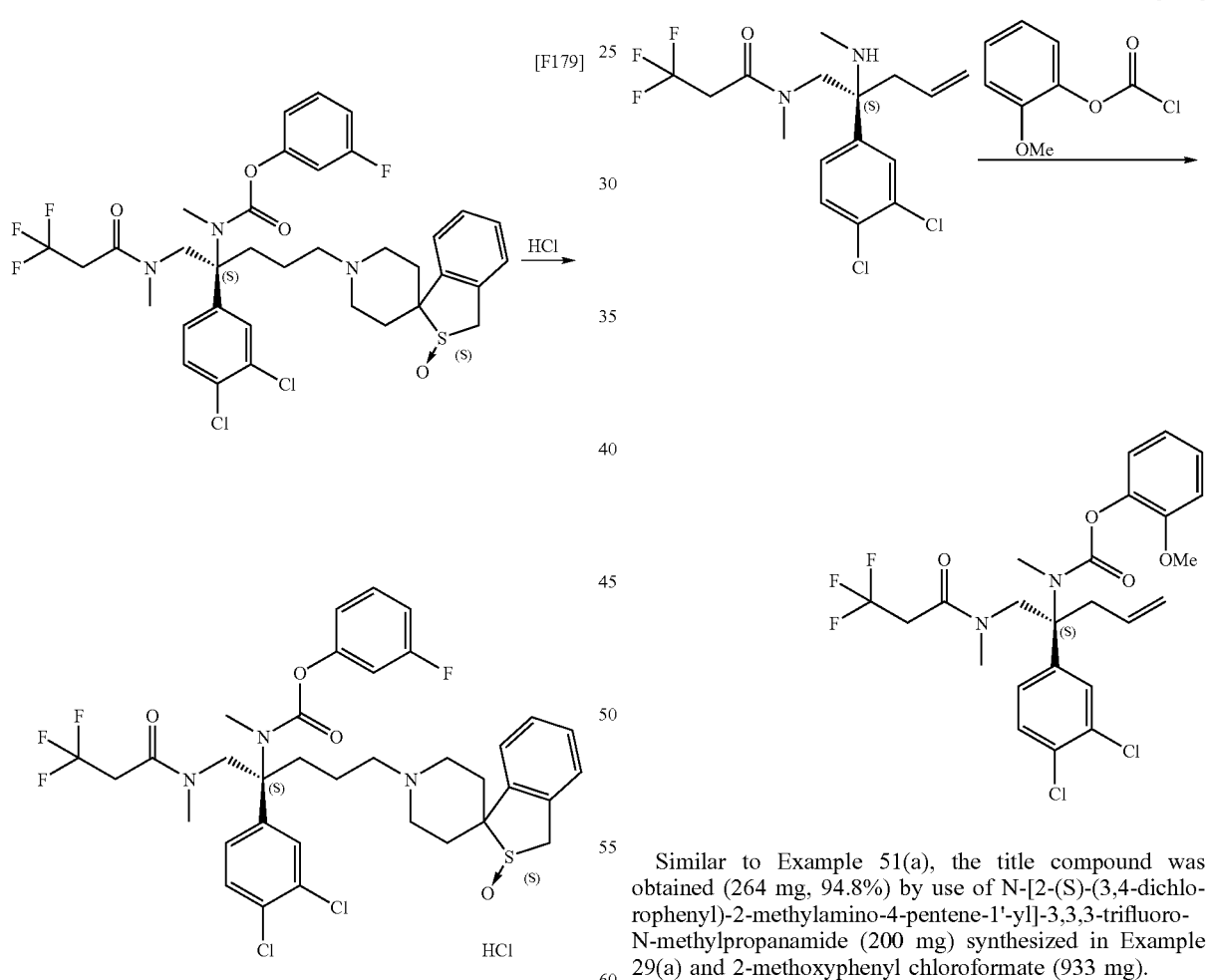

Similar to Example 51(a), the title compound was obtained (264 mg, 94.8%) by use of N-[2-(S)-(3,4-dichlorophenyl)-2-methylamino-4-pentene-1'-yl]-3,3,3-trifluoro-N-methylpropanamide (200 mg) synthesized in Example 29(a) and 2-methoxyphenyl chloroformate (933 mg).

MS (FAB) m/z 533 ((M+H)$^+$)

$^1$H-NMR (400 MHz, CDCl$_3$)δ ppm: 2.68 (1H, dd, J=7.0, 13.5 Hz), 2.90 (1H, dd, J=7.0, 13.5 Hz), 2.97 (3H, s), 3.18-3.39 (2H, m), 3.25 (3H, s), 3.78 (3H, s), 4.24-4.47 (2H, m), 4.98 (1H, d, J=17.0 Hz), 5.03 (1H, d, J=10.0 Hz), 5.72-5.86 (1H, m), 6.82-6.99 (3H, m), 7.07-7.17 (2H, m), 7.35 (1H, d, J=2.0 Hz), 7.38 (1H, d, J=8.5 Hz).

Similar to Example 51(e), the title compound was obtained as white powder (84 mg, 78.7%) by use of 3-fluorophenyl{1-(3,3,3-trifluoro-N-methylpropanamido)-2-(S)-(3,4-dichlorophenyl)-5-[spiro(benzo(c)thiophene-(2S)-

Example 54(b)

Synthesis of 2-methoxyphenyl{1-(3,3,3-trifluoro-N-methylpropanamido)-2-(S)-(3,4-dichlorophenyl)-5-[spiro(benzo(c)thiophene-(2S)-oxido-1(3H),4'-piperidin)-1'-yl]pentan-2-yl}methylcarbamate

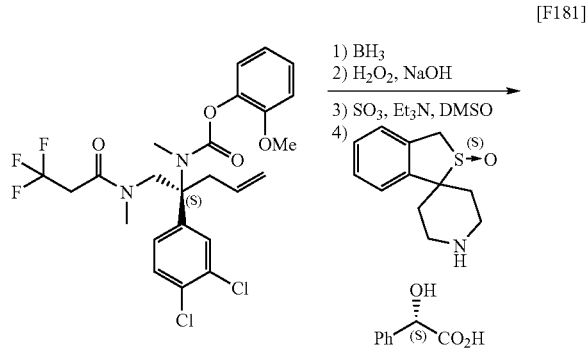

Similar to Example 51(b), 2-methoxyphenyl[1-(3,3,3-trifluoro-N-methylpropanamido)-2-(S)-(3,4-dichlorophenyl)-5-hydroxy-pentan-2-yl]methylcarbamate was obtained (178 mg) by use of 2-methoxyphenyl[1-(3,3,3-trifluoro-N-methylpropanamido)-2-(S)-(3,4-dichlorophenyl)-4-penten-2-yl]methylcarbamate (258 mg). Subsequently, similar to Example 51(c), 2-methoxyphenyl[1-(3,3,3-trifluoro-N-methylpropanamido)-2-(S)-(3,4-dichlorophenyl)-5-oxo-pentan-2-yl]methylcarbamate was obtained (193 mg) by use of 2-methoxyphenyl[1-(3,3,3-trifluoro-N-methylpropanamido)-2-(S)-(3,4-dichlorophenyl)-5-hydroxy-pentan-2-yl]methylcarbamate (170 mg). Thereafter, similar to Example 51(d), the title compound was obtained as white powder (179 mg, 51.6%, 4 steps) by use of 2-methoxyphenyl[1-(3,3,3-trifluoro-N-methylpropanamido)-2-(S)-(3,4-dichlorophenyl)-5-oxo-pentan-2-yl]methylcarbamate (193 mg).

MS (FAB) m/z 754 ((M+H)$^+$)

$^1$H-NMR (400 MHz, CDCl$_3$)δ ppm: 0.89-1.12 (1H, m), 1.58 (1H, dd, J=1.5, 15.0 Hz), 1.64-1.80 (1H, m), 1.82-2.02 (3H, m), 2.24-2.49 (6H, m), 2.82-2.98 (2H, m), 3.08 (3H, s), 3.31 (3H, s), 3.18-3.49 (2H, m), 3.76 (3H, s), 3.98 (1H, d, J=16.5 Hz), 4.07-4.22 (1H, m), 4.31 (1H, d, J=16.5 Hz), 4.53-4.78 (1H, m), 6.81-6.92 (2H, m), 7.07-7.16 (2H, m), 7.25-7.40 (7H, m).

Example 54(c)

Synthesis of 2-methoxyphenyl{1-(3,3,3-trifluoro-N-methylpropanamido)-2-(S)-(3,4-dichlorophenyl)-5-[spiro(benzo(c)thiophene-(2S)-oxido-1(3H),4'-piperidin)-1'-yl]pentan-2-yl}methylcarbamate hydrochloride (Compound No. 636)

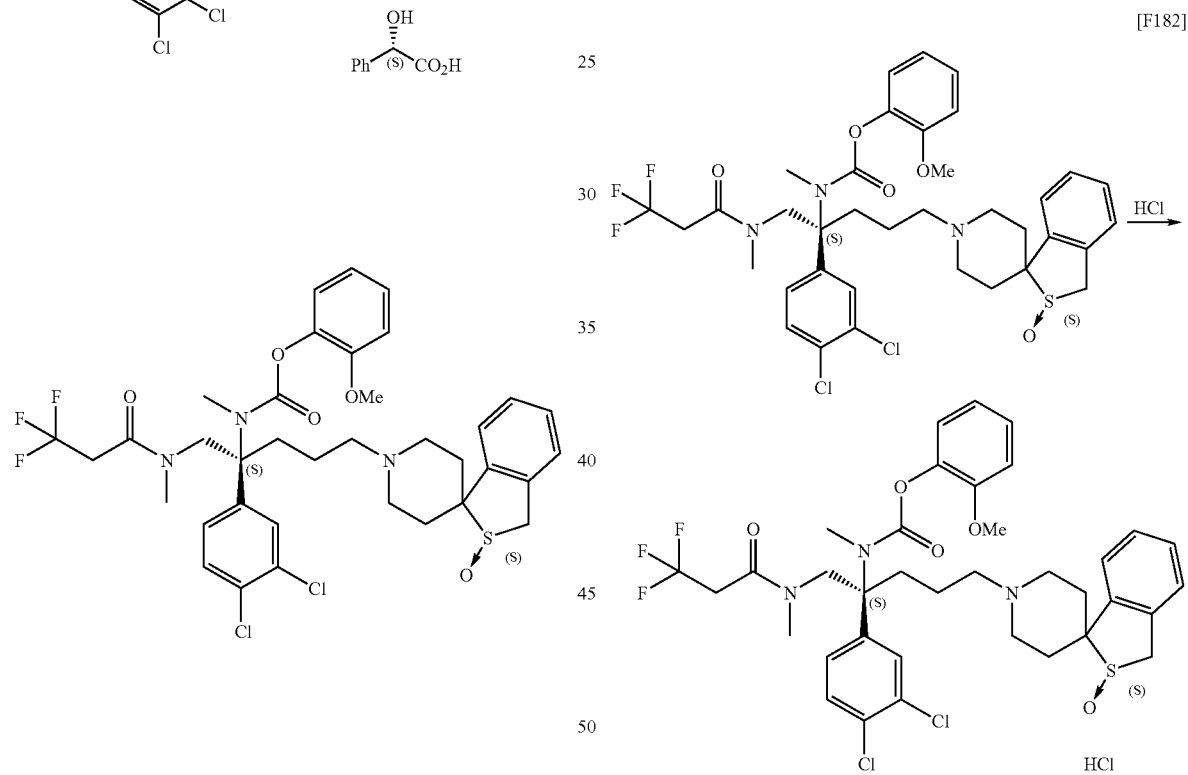

Similar to Example 51(e), the title compound was obtained as white powder (114 mg, 60.8%) by use of 2-methoxyphenyl{1-(3,3,3-trifluoro-N-methylpropanamido)-2-(S)-(3,4-dichlorophenyl)-5-[spiro(benzo(c)thiophene-(2S)-oxido-1(3H),4'-piperidin)-1'-yl]pentan-2-yl}methylcarbamate (179 mg).

$^1$H-NMR (400 MHz, DMSO-d$_6$)δ ppm: 1.13-1.44 (1H, m), 1.78-2.16 (4H, m), 2.24 (1H, d, J=14.0 Hz), 2.34-2.48 (1H, m), 2.80-3.18 (8H, m), 3.30 (3H, s), 3.45-3.55 (1H, m), 3.57 (3H, s), 3.60-3.92 (3H, m), 3.97-4.17 (2H, m), 4.31-4.49 (1H, m), 4.68 (1H, d, J=17.0 Hz), 6.79-7.09 (3H, m), 7.11-7.20 (1H, m), 7.29-7.46 (5H, m), 7.52-7.66 (2H, m), 10.55 (1H, br).

Example 55(a)

Synthesis of 3-methoxyphenyl[1-(3,3,3-trifluoro-N-methylpropanamido)-2-(S)-(3,4-dichlorophenyl)-4-penten-2-yl]methylcarbamate

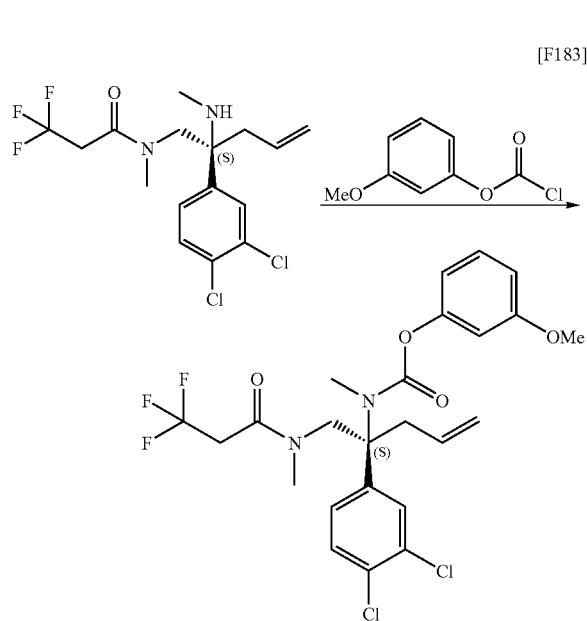

[F183]

Similar to Example 51(a), the title compound was obtained (263 mg, 94.5%) by use of N-[2-(S)-(3,4-dichlorophenyl)-2-methylamino-4-pentene-1'-yl]-3,3,3-trifluoro-N-methylpropanamide (200 mg) synthesized in Example 4(a) and 3-methoxyphenyl chloroformate (933 mg).

MS (FAB) m/z 533 ((M+H)$^+$)

$^1$H-NMR (400 MHz, CDCl$_3$)δ ppm: 2.66-2.79 (1H, m), 2.89 (3H, s), 2.92-3.05 (1H, m), 3.10-3.37 (2H, m), 3.18 (3H, s), 3.75 (3H, s), 3.96-4.19 (1H, m), 4.40-4.69 (1H, m), 5.04 (1H, d, J=17.0 Hz), 5.08 (1H, d, J=10.5 Hz), 5.72-5.88 (1H, m), 6.45-6.67 (2H, m), 6.71 (1H, d, J=7.5 Hz), 7.11 (1H, dd, J=2.0, 8.5 Hz), 7.15-7.25 (1H, m), 7.33-7.39 (1H, m), 7.41 (1H, d, J=8.5 Hz).

Example 55(b)

Synthesis of 3-methoxyphenyl{1-(3,3,3-trifluoro-N-methylpropanamido)-2-(S)-(3,4-dichlorophenyl)-5-[spiro(benzo(c)thiophene-(2S)-oxido-1(3H),4'-piperidin)-1'-yl]pentan-2-yl}methylcarbamate

[F184]

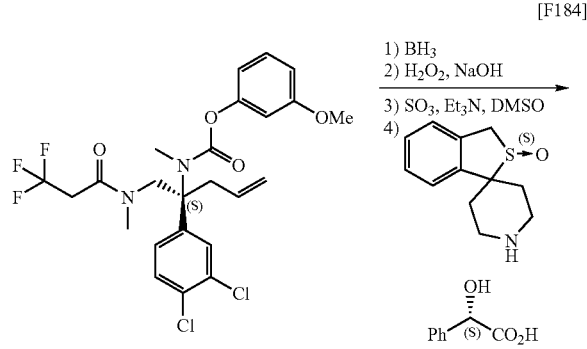

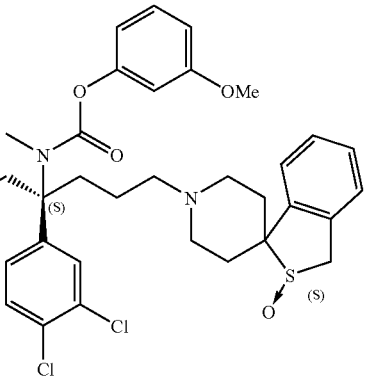

-continued

Similar to Example 51(b), 3-methoxyphenyl[1-(3,3,3-trifluoro-N-methylpropanamido)-2-(S)-(3,4-dichlorophenyl)-5-hydroxy-pentan-2-yl]methylcarbamate (167 mg) was obtained by use of 3-methoxyphenyl[1-(3,3,3-trifluoro-N-methylpropanamido)-2-(S)-(3,4-dichlorophenyl)(4-penten-2-yl)]methylcarbamate (256 mg) Subsequently, similar to Example 51(c), 3-methoxyphenyl[1-(3,3,3-trifluoro-N-methylpropanamido)-2-(S)-(3,4-dichlorophenyl)-5-oxo-pentan-2-yl]methylcarbamate (135 mg) was obtained by use of 3-methoxyphenyl[1-(3,3,3-trifluoro-N-methylpropanamido)-2-(S)-(3,4-dichlorophenyl)-5-hydroxy-pentan-2-yl]methylcarbamate (160 mg). Thereafter, similar to Example 51(d), the title compound was obtained as white powder (84 mg, 24.3%, 4 steps) by use of 3-methoxyphenyl[1-(3,3,3-trifluoro-N-methylpropanamido)-2-(S)-(3,4-dichlorophenyl)-5-oxo-pentan-2-yl]methylcarbamate (135 mg).

MS (FAB) m/z 754 ((M+H)$^+$)

$^1$H-NMR (400 MHz, CDCl$_3$)δ ppm: 0.94-1.14 (1H, m), 1.58 (1H, dd, J=2.0, 15.0 Hz), 1.63-1.76 (1H, m), 1.83-2.06 (3H, m), 2.23-2.47 (6H, m), 2.82-2.97 (2H, m), 3.02 (3H, s), 3.15-3.46 (2H, m), 3.27 (3H, s), 3.73 (3H, s), 3.99 (1H, d, J=16.5 Hz), 4.20-4.37 (2H, m), 4.40-4.63 (1H, m), 6.46-6.62 (1H, m), 6.67-6.74 (1H, m), 7.11 (1H, dd, J=2.0, 8.5 Hz), 7.14-7.23 (1H, m), 7.25-7.38 (6H, m), 7.41 (1H, d, J=8.5 Hz).

Example 55(c)

Synthesis of 3-methoxyphenyl{1-(3,3,3-trifluoro-N-methylpropanamido)-2-(S)-(3,4-dichlorophenyl)-5-[spiro(benzo(c)thiophene-(2S)-oxido-1(3H), 4l-piperidin)-1'-yl]pentan-2-yl}methylcarbamate hydrochloride (Compound No. 637)

[F185]

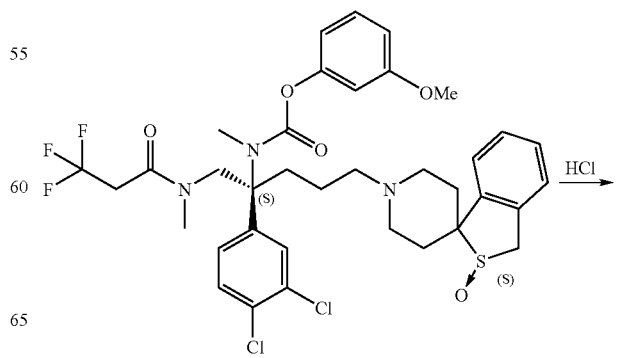

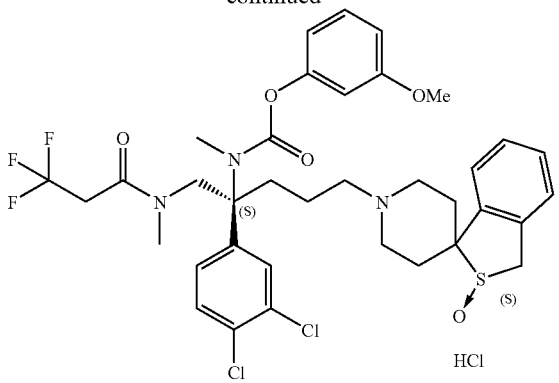

Similar to Example 51(e), the title compound was obtained as white powder (70 mg, 79.7%) by use of 3-methoxyphenyl{1-(3,3,3-trifluoro-N-methylpropanamido)-2-(S)-(3,4-dichlorophenyl)-5-[spiro(benzo(c)thiophene-(2S)-oxido-1(3H),4'-piperidin)-1'-yl]pentan-2-yl}methylcarbamate (84 mg).

$^1$H-NMR (400 MHz, DMSO-$d_6$)δ ppm: 1.17-1.43 (1H, m), 1.77-2.19 (4H, m), 2.25 (1H, d, J=14.0 Hz), 2.32-2.47 (1H, m), 2.78-3.18 (8H, m), 3.25 (3H, s), 3.46-3.88 (7H, m), 4.02-4.45 (3H, m), 4.68 (1H, d, J=17.0 Hz), 6.12-6.33 (1H, m), 6.51-6.82 (2H, m), 7.13-7.26 (1H, m), 7.38-7.46 (5H, m), 7.53-7.73 (2H, m), 10.61 (1H, br).

Example 56(a)

Synthesis of 2-fluorophenyl[1-(3,3,3-trifluoro-N-methylpropanamido)-2-(S)-(3,4-dichlorophenyl)-4-penten-2-yl]methylcarbamate

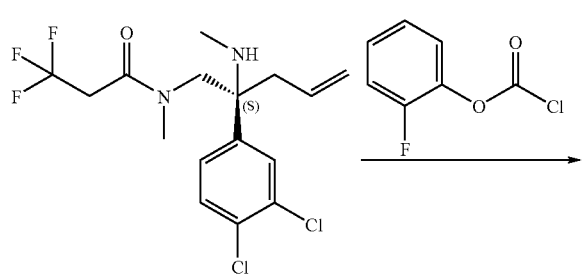

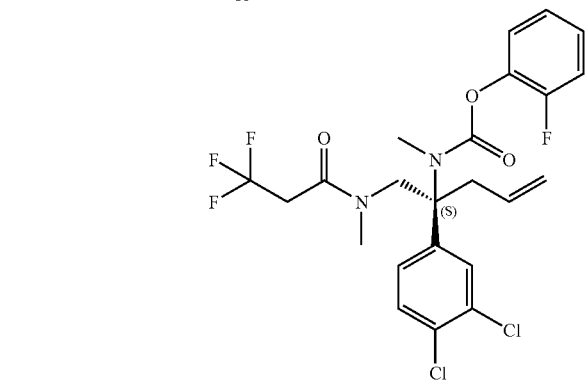

Similar to Example 51(a), the title compound was obtained (286 mg, >100%) by use of N-[2-(S)-(3,4-dichlorophenyl)-2-(methylamino)-4-pentene-1'-yl]-3,3,3-trifluoro-N-methylpropanamide (200 mg) synthesized in Example 4(a) and 2-fluorophenyl chloroformate (873 mg).

MS (FAB) m/z 521 ((M+H)$^+$)

$^1$H-NMR (400 MHz, CDCl$_3$)δ ppm: 2.72 (1H, dd, J=6.5, 13.5 Hz), 2.87-3.04 (1H, m), 2.93 (3H, s), 3.10-3.40 (2H, m), 3.22 (3H, s), 4.16-4.50 (2H, m), 5.00 (1H, dd, J=1.5, 17.0 Hz), 5.05 (1H, dd, J=1.5, 10.5 Hz), 5.69-5.84 (1H, m), 7.01-7.19 (5H, m), 7.33 (1H, d, J=2.0 Hz), 7.40 (1H, d, J=8.5 Hz).

Example 56(b)

Synthesis of 2-fluorophenyl{1-(3,3,3-trifluoro-N-methylpropanamido)-2-(S)-(3,4-dichlorophenyl)-5-[spiro(benzo(c)thiophene-(2S)-oxido-1(3H),4'-piperidin)-1'-yl]pentan-2-yl}methylcarbamate

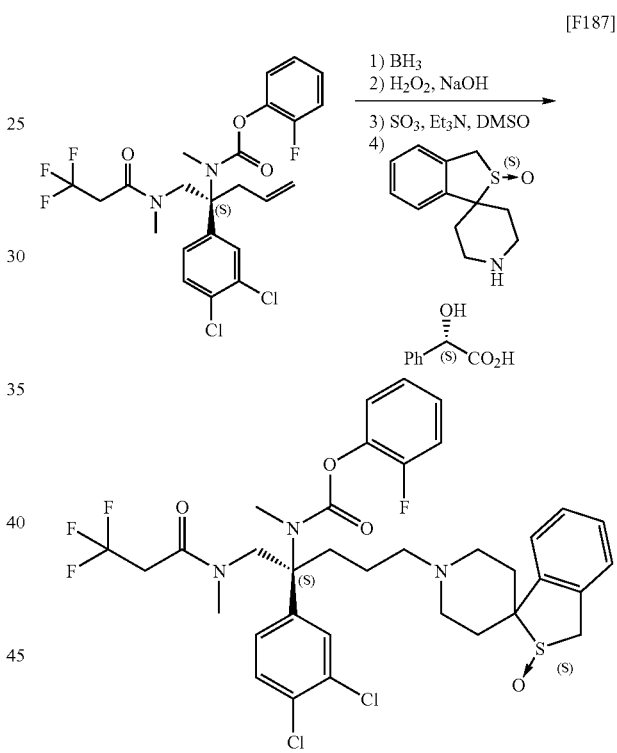

Similar to Example 51(b), 2-fluorophenyl[1-(3,3,3-trifluoro-N-methylpropanamido)-2-(S)-(3,4-dichlorophenyl)-5-hydroxy-pentan-2-yl]methylcarbamate was obtained (130 mg) by use of 2-fluorophenyl[1-(3,3,3-trifluoro-N-methylpropanamido)-2-(S)-(3,4-dichlorophenyl)-4-penten-2-yl]methylcarbamate (278 mg). Subsequently, similar to Example 51(c), 2-fluorophenyl[1-(3,3,3-trifluoro-N-methylpropanamido)-2-(S)-(3,4-dichlorophenyl)-5-oxo-pentan-2-yl]methylcarbamate (122 mg) was obtained by use of 2-fluorophenyl[1-(3,3,3-trifluoro-N-methylpropanamido)-2-(S)-(3,4-dichlorophenyl)-5-hydroxy-pentan-2-yl]methylcarbamate (123 mg). Thereafter, similar to Example 51 (d), the title compound was obtained as white powder (101 mg, 26.1%, 4 steps) by use of 2-fluorophenyl[1-(3,3,3-trifluoro-N-methylpropanamido)-2-(S)-(3,4-dichlorophenyl)-5-oxo-pentan-2-yl]methylcarbamate (122 mg).

MS (FAB) m/z 742 ((M+H)$^+$)

¹H-NMR (400 MHz, CDCl₃)δ ppm: 0.92-1.11 (1H, m), 1.52-1.77 (2H, m), 1.82-2.06 (3H, m), 2.24-2.49 (6H, m), 2.82-2.97 (2H, m), 3.05 (3H, s), 3.17-3.48 (2H, m), 3.31 (3H, s), 3.98 (1H, d, J=16.5 Hz), 4.08-4.25 (1H, m), 4.31 (1H, d, J=16.5 Hz), 4.52-4.70 (1H, m), 7.01-7.20 (4H, m), 7.25-7.36 (6H, m), 7.39 (1H, d, J=8.5 Hz).

¹H-NMR (400 MHz, DMSO-d₆)δ ppm: 1.16-1.40 (1H, m), 1.78-1.92 (1H, m), 1.96-2.19 (3H, m), 2.25 (1H, d, J=14.5 Hz), 2.33-2.47 (1H, m), 2.78-3.19 (8H, m), 3.32 (3H, s), 3.46-3.91 (4H, m), 4.02-4.40 (3H, m), 4.69 (1H, d, J=17.0 Hz), 7.07-7.45 (9H, m), 7.53-7.67 (2H, m), 10.58 (1H, br).

Example 56(c)

Synthesis of 2-fluorophenyl{1-(3,3,3-trifluoro-N-methylpropanamido)-2-(S)-(3,4-dichlorophenyl)-5-[spiro(benzo(c)thiophene-(2S)-oxido-1(3H),4'-piperidin)-1'-yl]pentan-2-yl}methylcarbamate hydrochloride (Compound No. 638)

Example 57(a)

Synthesis of 4-fluorophenyl[1-(3,3,3-trifluoro-N-methylpropanamido)-2-(S)-(3,4-dichlorophenyl)-4-penten-2-yl]methylcarbamate

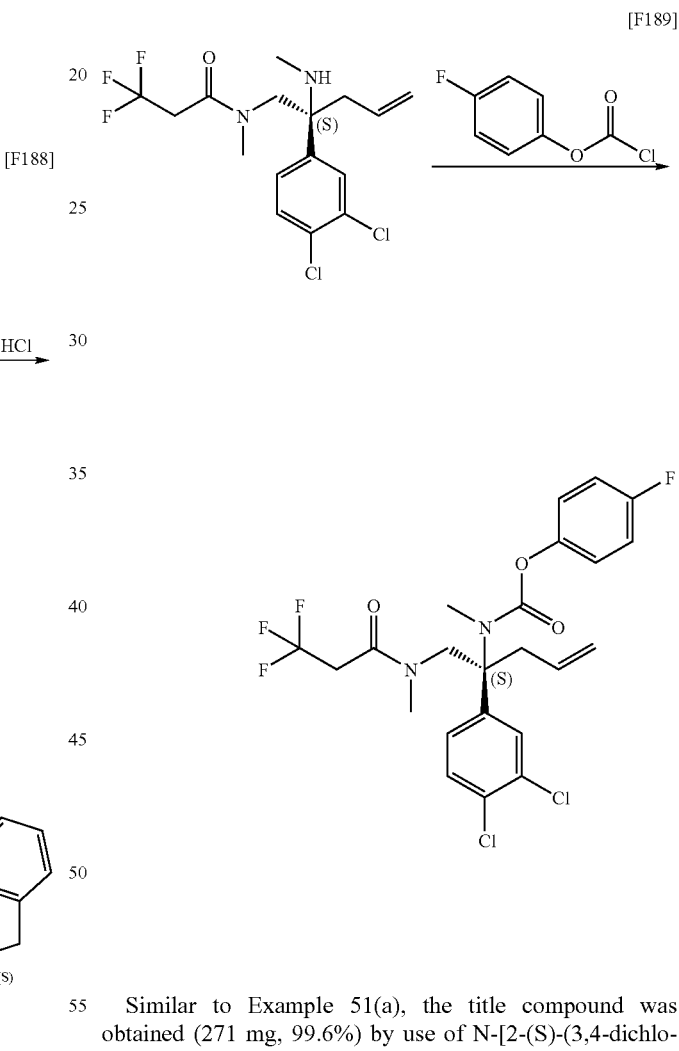

Similar to Example 51(e), the title compound was obtained as white powder (73 mg, 68.9%) by use of 2-fluorophenyl{1-(3,3,3-trifluoro-N-methylpropanamido)-2-(S)-(3,4-dichlorophenyl)-5-[spiro(benzo(c)thiophene-(2S)-oxido-1(3H),4'-piperidin)-1'-yl]pentan-2-yl}methylcarbamate (101 mg).

Similar to Example 51(a), the title compound was obtained (271 mg, 99.6%) by use of N-[2-(S)-(3,4-dichlorophenyl)-2-(methylamino)-4-pentene-1'-yl]-3,3,3-trifluoro-N-methylpropanamide (200 mg) synthesized in Example 29(a) and 4-fluorophenyl chloroformate (873 mg).

MS (FAB) m/z 521 ((M+H)⁺)

¹H-NMR (400 MHz, CDCl₃)δ ppm: 2.74 (1H, dd, J=6.5, 13.5 Hz), 2.85 (3H, s), 2.93-3.05 (1H, m), 3.09-3.33 (2H, m), 3.16 (3H, s), 3.88-4.08 (1H, m), 4.49-4.70 (1H, m), 5.04 (1H, d, J=17.0 Hz), 5.09 (1H, d, J=10.5 Hz), 5.72-5.87 (1H, m), 6.90-7.06 (4H, m), 7.11 (1H, dd, J=2.5, 8.5 Hz), 7.34 (1H, d, J=2.5 Hz), 7.42 (1H, d, J=8.5 Hz).

Example 57(b)

Synthesis of 4-fluorophenyl{1-(3,3,3-trifluoro-N-methylpropanamido)-2-(S)-(3,4-dichlorophenyl)-5-[spiro(benzo(c)thiophene-(2S)-oxido-1(3H),4'-piperidin)-1'-yl]pentan-2-yl}methylcarbamate

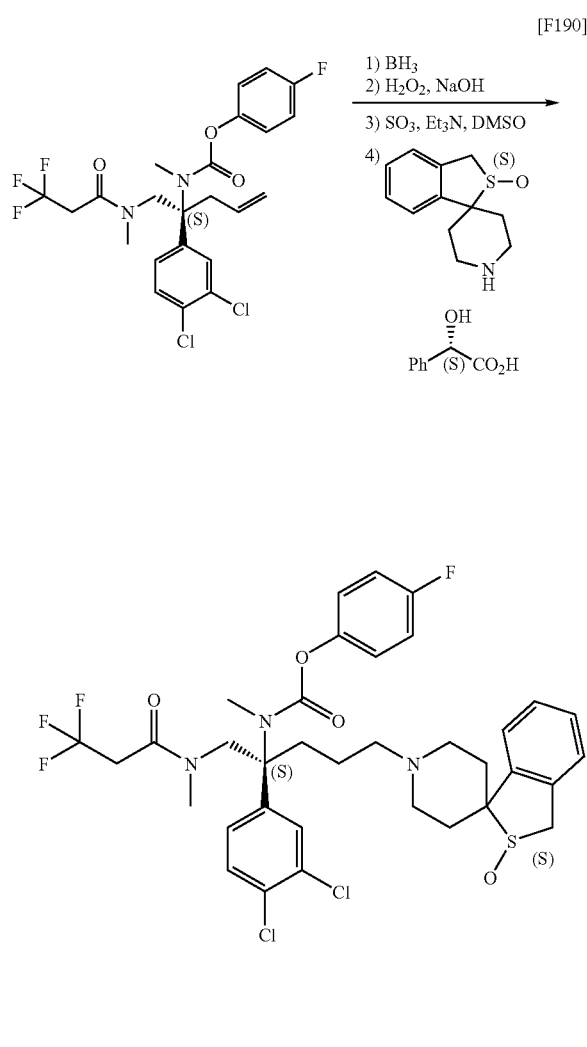

Similar to Example 51(b), 4-fluorophenyl[1-(3,3,3-trifluoro-N-methylpropanamido)-2-(S)-(3,4-dichlorophenyl)-5-hydroxy-pentan-2-yl]methylcarbamate was obtained (91 mg) by use of 4-fluorophenyl[1-(3,3,3-trifluoro-N-methyl-propanamido)-2-(S)-(3,4-dichlorophenyl)-4-penten-2-yl]methylcarbamate (238 mg) Subsequently, similar to Example 51(c), 4-fluorophenyl[1-(3,3,3-trifluoro-N-methyl-propanamido)-2-(S)-(3,4-dichlorophenyl)-5-oxo-pentan-2-yl]methylcarbamate was obtained (96 mg) by use of 4-fluorophenyl[1-(3,3,3-trifluoro-N-methylpropanamido)-2-(S)-(3,4-dichlorophenyl)-5-hydroxy-pentan-2-yl]methylcarbamate (85 mg). Thereafter, similar to Example 51 (d), the title compound was obtained as white powder (58 mg, 16.6%, 4 steps) by use of 4-fluorophenyl[1-(3,3,3-trifluoro-N-methylpropanamido)-2-(S)-(3,4-dichlorophenyl)-5-oxo-pentan-2-yl]methylcarbamate (96 mg).

MS (FAB) m/z 742 ((M+H)$^+$)

$^1$H-NMR (400 MHz, CDCl$_3$)δ ppm: 0.98-1.18 (1H, m), 1.52-1.76 (2H, m), 1.83-2.08 (3H, m), 2.26-2.48 (6H, m), 2.82-3.11 (2H, m), 2.99 (3H, s), 3.16-3.47 (2H, m), 3.26 (3H, s), 3.99 (1H, d, J=16.5 Hz), 4.23-4.56 (3H, m), 6.90-7.03 (3H, m), 7.10 (1H, dd, J=2.0, 8.5 Hz), 7.25-7.36 (6H, m), 7.40 (1H, d, J=8.5 Hz).

Example 57(c)

Synthesis of 4-fluorophenyl{1-(3,3,3-trifluoro-N-methylpropanamido)-2-(S)-(3,4-dichlorophenyl)-5-[spiro(benzo(c)thiophene-(2S)-oxido-1(3H),4'-piperidin)-1'-yl]pentan-2-yl}methylcarbamate hydrochloride (Compound No. 639)

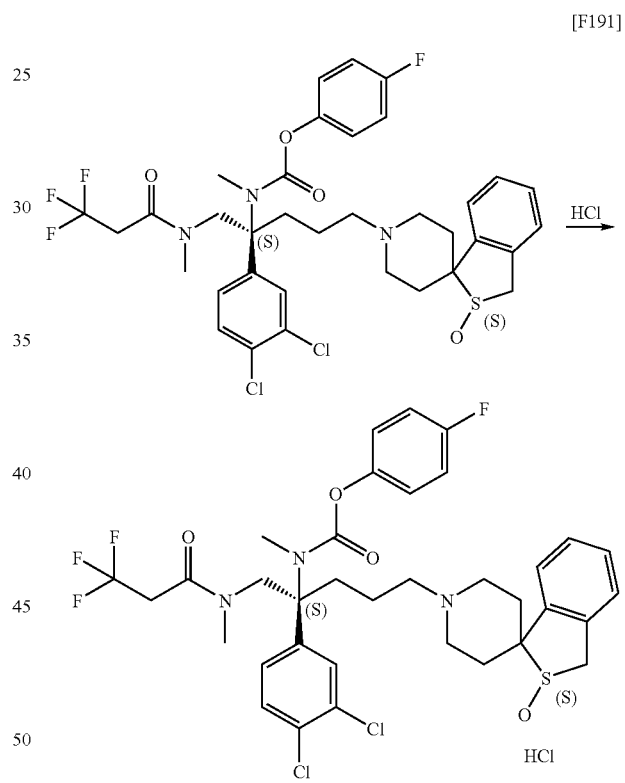

Similar to Example 51(c), the title compound was obtained as white powder (41 mg, 67.5%) by use of 4-fluorophenyl{1-(3,3,3-trifluoro-N-methylpropanamido)-2-(S)-(3,4-dichlorophenyl)-5-[spiro(benzo(c)thiophene-(2S)-oxido-1(3H),4'-piperidin)-1'-yl]pentan-2-yl}methylcarbamate (58 mg).

$^1$H-NMR (400 MHz, DMSO-d$_6$)δ ppm: 1.18-1.42 (1H, m), 1.76-1.90 (1H, m), 1.95-2.17 (3H, m), 2.25 (1H, d, J=14.0 Hz), 2.31-2.46 (1H, m), 2.79-3.18 (8H, m), 3.26 (3H, s), 3.48-3.88 (4H, m), 4.03-4.42 (3H, m), 4.68 (1H, d, J=17.0 Hz), 6.48-6.69 (1H, m), 7.01-7.22 (3H, m), 7.26 (1H, d, J=6.5 Hz), 7.29-7.45 (4H, m), 7.53-7.67 (2H, m), 10.59 (1H, br).

Example 58(a)

Synthesis of 4-methoxyphenyl[1-(3,3,3-trifluoro-N-methylpropanamido)-2-(S)-(3,4-dichlorophenyl)-4-penten-2-yl]methylcarbamate

[F192]

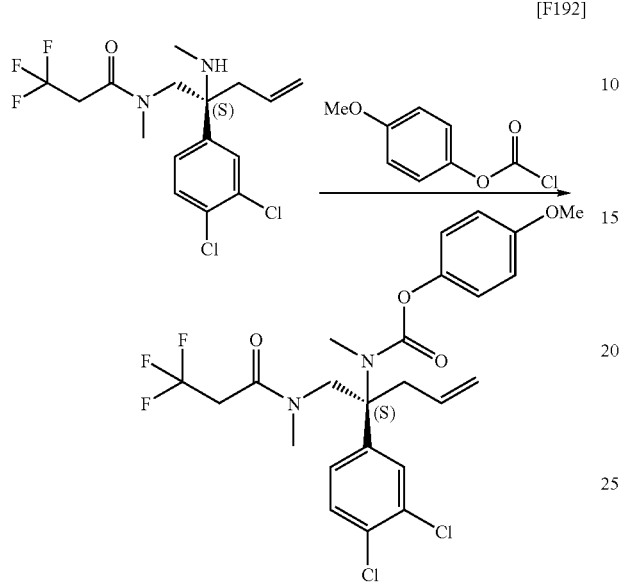

Similar to Example 51(a), the title compound was obtained (190 mg, 68.2%) by use of N-[2-(S)-(3,4-dichlorophenyl)-2-(methylamino)-4-pentene-1'-yl]-3,3,3-trifluoro-N-methylpropanamide (200 mg) synthesized in Example 4(a) and 4-methoxyphenyl chloroformate (0.31 mL).

MS (FAB) m/z 533 ((M+H)$^+$)

$^1$H-NMR (400 MHz, CDCl$_3$)δ ppm: 2.72 (1H, dd, J=6.5, 13.5 Hz), 2.86 (3H, s), 2.92-3.04 (1H, m), 3.08-3.36 (2H, m), 3.17 (3H, s), 3.75 (3H, s), 3.97-4.18 (1H, m), 4.40-4.64 (1H, m), 5.02 (1H, d, J=17.0 Hz), 5.07 (1H, d, J=10.5 Hz), 5.72-5.89 (1H, m), 6.69-6.99 (4H, m), 7.10 (1H, dd, J=2.0, 8.5 Hz), 7.34 (1H, d, J=2.0 Hz), 7.41 (1H, d, J=8.5 Hz).

Example 58(b)

Synthesis of 4-methoxyphenyl{1-(3,3,3-trifluoro-N-methylpropanamido)-2-(S)-(3,4-dichlorophenyl)-5-[spiro(benzo(c)thiophene-(2S)-oxido-1(3H),4'-piperidin)-1'-yl]pentan-2-yl}methylcarbamate

[F193]

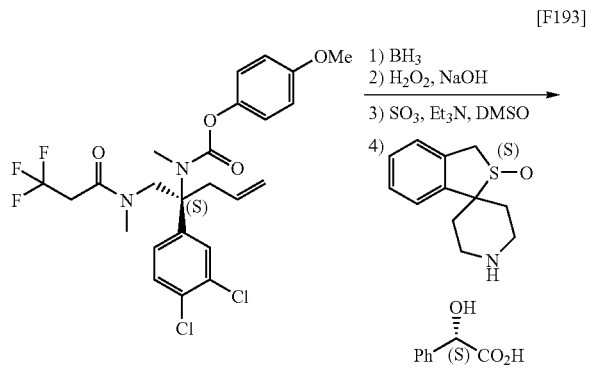

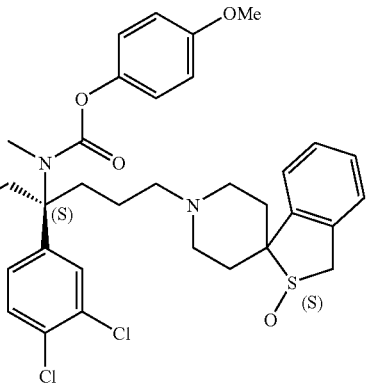

Similar to Example 51(b), 4-methoxyphenyl[1-(3,3,3-trifluoro-N-methylpropanamido)-2-(S)-(3,4-dichlorophenyl)-5-hydroxy-pentan-2-yl]methylcarbamate was obtained (109 mg) by use of 4-methoxyphenyl[1-(3,3,3-trifluoro-N-methylpropanamido)-2-(S)-(3,4-dichlorophenyl)-4-penten-2-yl]methylcarbamate (190 mg). Subsequently, similar to Example 51(c), 4-methoxyphenyl[1-(3,3,3-trifluoro-N-methylpropanamido)-2-(S)-(3,4-dichlorophenyl)-5-oxo-pentan-2-yl]methylcarbamate was obtained (150 mg) by use of 4-methoxyphenyl[1-(3,3,3-trifluoro-N-methylpropanamido)-2-(S)-(3,4-dichlorophenyl)-5-hydroxy-pentan-2-yl] methylcarbamate (106 mg). Thereafter, similar to Example 51(d), the title compound was obtained as white powder (105 mg, 39.8%, 4 steps) by use of 4-methoxyphenyl[1-(3,3,3-trifluoro-N-methylpropanamido)-2-(S)-(3,4-dichlorophenyl)-5-oxo-pentan-2-yl]methylcarbamate (150 mg).

MS (FAB) m/z 754 ((M+H)$^+$)

$^1$H-NMR (400 MHz, CDCl$_3$)δ ppm: 0.96-1.18 (1H, m), 1.53-1.79 (2H, m), 1.83-2.08 (3H, m), 2.24-2.48 (6H, m), 2.82-3.08 (2H, m), 3.01 (3H, s), 3.16-3.46 (2H, m), 3.26 (3H, s), 3.75 (3H, s), 3.99 (1H, d, J=16.5 Hz), 4.17-4.37 (2H, m), 4.41-4.51 (1H, m), 6.74-6.98 (3H, m), 7.10 (1H, dd, J=2.0, 8.5 Hz), 7.25-7.37 (6H, m), 7.40 (1H, d, J=8.5 Hz).

Example 58(c)

Synthesis of 4-methoxyphenyl{1-(3,3,3-trifluoro-N-methylpropanamido)-2-(s)-(3,4-dichlorophenyl)-5-[spiro(benzo(c)thiophene-(2S)-oxido-1(3H),4'-piperidin)-1'-yl]pentan-2-yl}methylcarbamate hydrochloride (Compound No. 640)

[F149]

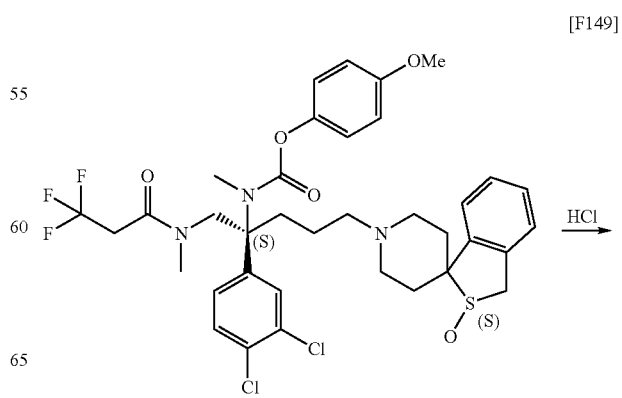

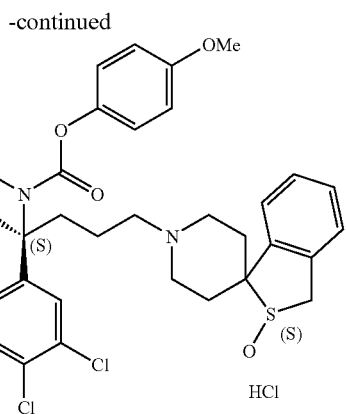

Similar to Example 51(e), the title compound was obtained as white powder (62 mg, 56.4%) by use of 4-methoxyphenyl{1-(3,3,3-trifluoro-N-methylpropanamido)-2-(S)-(3,4-dichlorophenyl)-5-[spiro(benzo(c)thiophene-(2S)-oxido-1(3H),4'-piperidin)-1'-yl]pentan-2-yl}methylcarbamate (105 mg).

$^1$H-NMR (400 MHz, DMSO-d$_6$)δ ppm: 1.15-1.47 (1H, m), 1.77-1.92 (1H, m), 1.94-2.20 (3H, m), 2.25 (1H, d, J=13.0 Hz), 2.39-2.48 (1H, m), 2.78-3.16 (8H, m), 3.26 (3H, s), 3.45-3.55 (1H, m), 3.61-3.89 (3H, m), 3.70 (3H, s), 4.04-4.38 (3H, m), 4.68 (1H, d, J=17.0 Hz), 6.32-6.60 (1H, m), 6.74-7.08 (3H, m), 7.28-7.46 (5H, m), 7.51-7.68 (2H, m), 10.88 (1H, br).

Example 59(a)

Synthesis of 4-tolyl[1-(3,3,3-trifluoro-N-methylpropanamido)-2-(S)-(3,4-dichlorophenyl)-4-penten-2-yl]methylcarbamate

[F195]

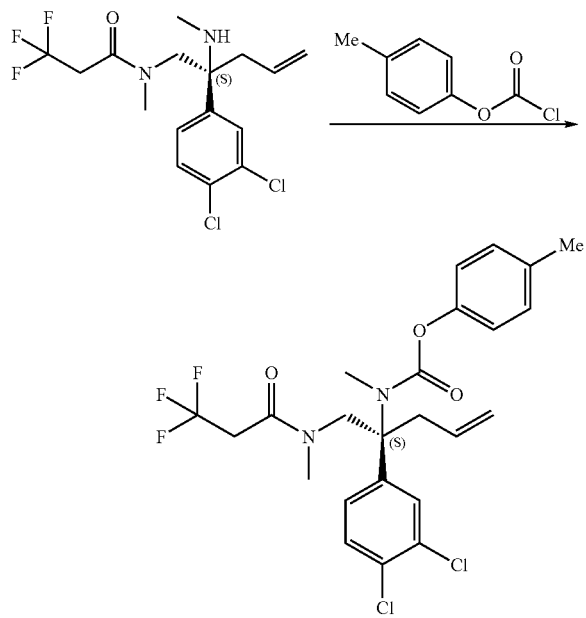

Similar to Example 51(a), the title compound was obtained (260 mg, 96.3%) by use of N-[2-(S)-(3,4-dichlorophenyl)-2-methylamino-4-pentene-1'-yl]-3,3,3-trifluoro-N-methylpropanamide (200 mg) synthesized in Example 4(a) and 4-tolyl chloroformate (174 mg).

MS (FAB) m/z 517 ((M+H)$^+$)

$^1$H-NMR (400 MHz, CDCl$_3$)δ ppm: 2.29 (3H, s), 2.72 (1H, dd, J=6.5, 13.5 Hz), 2.87 (3H, s), 2.91-3.04 (1H, m), 3.08-3.36 (2H, m), 3.17 (3H, s), 3.98-4.22 (1H, m), 4.38-4.62 (1H, m), 4.97-5.10 (2H, m), 5.73-5.88 (1H, m), 6.76-6.98 (2H, m), 7.04-7.16 (3H, m), 7.34 (1H, d, J=2.0 Hz), 7.40 (1H, d, J=8.5 Hz).

Example 59(b)

Synthesis of 4-tolyl{1-(3,3,3-trifluoro-N-methylpropanamido)-2-(S)-(3,4-dichlorophenyl)-5-[spiro(benzo(c)thiophene-(2S)-oxido-1(3H),4'-piperidin)-1'-yl]pentan-2-yl}methylcarbamate

[F196]

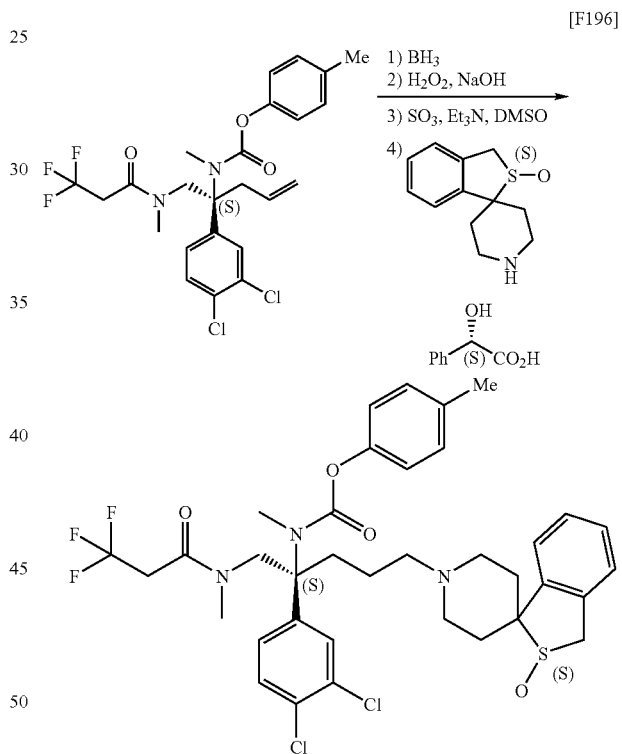

Similar to Example 51(b), 4-tolyl{[1-(3,3,3-trifluoro-N-methylpropanamido)-2-(S)-(3,4-dichlorophenyl)-5-hydroxy]pentan-2-yl}methylcarbamate was obtained (160 mg) by use of 4-tolyl[1-(3,3,3-trifluoro-N-methylpropanamido)-2-(S)-(3,4-dichlorophenyl)-4-penten-2-yl]methylcarbamate (250 mg). Subsequently, similar to Example 51(c), 4-tolyl [1-(3,3,3-trifluoro-N-methylpropanamido)-2-(S)-(3,4-dichlorophenyl)-5-hydroxy-pentan-2-yl]methylcarbamate was obtained (185 mg) by use of (4-tolyl[1-(3,3,3-trifluoro-N-methylpropanamido)-2-(S)-(3,4-dichlorophenyl)-5-hydroxy-pentan-2-yl]methylcarbamate (154 mg). Thereafter, similar to Example 51(d), the title compound was obtained as white powder (131 mg, 36.9%, 4 steps) by use of 4-tolyl[1-(3,3,3-trifluoro-N-methylpropanamido)-2-(S)-(3,4-dichlorophenyl)-5-oxo-pentan-2-yl]methylcarbamate (185 mg).

MS (FAB) m/z 738 ((M+H)$^+$)

$^1$H-NMR (400 MHz, CDCl$_3$) δ ppm: 0.95-1.13 (1H, m), 1.54-1.76 (2H, m), 1.82-2.06 (3H, m), 2.22-2.48 (6H, m), 2.28 (3H, s), 2.80-2.97 (2H, m), 3.01 (3H, s), 3.15-3.45 (2H, m), 3.27 (3H, s), 3.99 (1H, d, J=16.5 Hz), 4.16-4.37 (2H, m), 4.42-4.61 (1H, br), 6.73-6.93 (1H, m), 7.03-7.14 (3H, m), 7.25-7.36 (6H, m), 7.39 (1H, d, J=8.5 Hz).

Example 59(c)

Synthesis of 4-tolyl{1-(3,3,3-trifluoro-N-methylpropanamido)-2-(S)-(3,4-dichlorophenyl)-5-[spiro(benzo(c)thiophene-(2S)-oxido-1(3H),4'-piperidin)-1'-yl]pentan-2-yl}methylcarbamate hydrochloride (Compound No. 652)

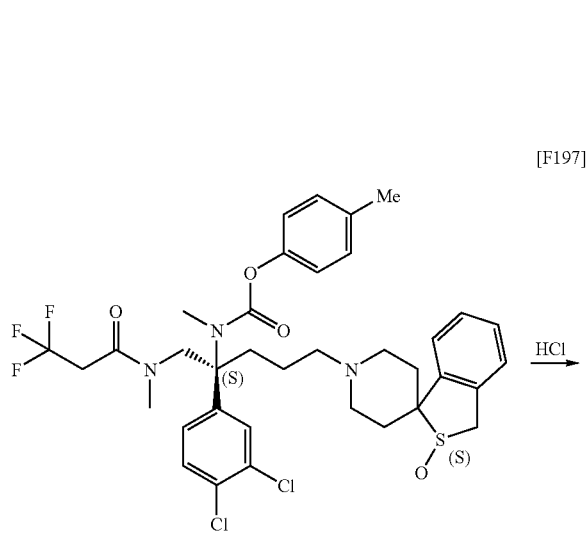

[F197]

Similar to Example 51(e), the title compound was obtained as white powder (77 mg, 56.1%) by use of 4-tolyl{1-(3,3,3-trifluoro-N-methylpropanamido)-2-(S)-(3,4-dichlorophenyl)-5-[spiro(benzo(c)thiophene-(2S)-oxido-1(3H),4'-piperidin)-1'-yl]pentan-2-yl}methylcarbamate (131 mg).

$^1$H-NMR (400 MHz, DMSO-d$_6$) δ ppm: 1.16-1.42 (1H, m), 1.76-2.30 (5H, m), 2.24 (3H, s), 2.35-2.48 (1H, m), 2.77-3.18 (8H, m), 3.26 (3H, s), 3.46-3.89 (4H, m), 4.08 (1H, d, J=17.0 Hz), 4.14-4.36 (2H, m), 4.68 (1H, d, J=17.0 Hz), 6.31-6.55 (1H, m), 6.83-6.99 (1H, m), 7.02-7.19 (2H, m), 7.30-7.45 (5H, m), 7.53-7.67 (2H, m), 10.69 (1H, br).

Example 60(a)

Synthesis of 2,3-dichlorophenyl[1-(3,3,3-trifluoro-N-methylpropanamido)-2-(S)-(3,4-dichlorophenyl)-4-penten-2-yl]methylcarbamate

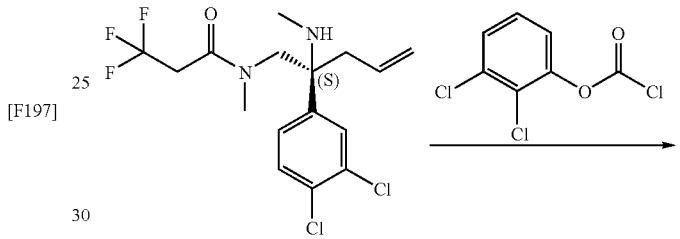

[F198]

Similar to Example 51(a), the title compound was obtained (300 mg, 100%) by use of N-[2-(S)-(3,4-dichlorophenyl)-2-methylamino-4-pentene-1'-yl]-3,3,3-trifluoro-N-methylpropanamide (200 mg) synthesized in Example 29(a) and 2,3-dichlorophenyl chloroformate (588 mg).

MS (FAB) m/z 571 ((M+H)$^+$)

$^1$H-NMR (400 MHz, CDCl$_3$) δ ppm: 2.73 (1H, dd, J=6.5, 14.0 Hz), 2.88 (3H, s), 2.90 (1H, dd, J=7.5, 14.0 Hz), 3.15-3.46 (2H, m), 3.23 (3H, s), 4.03-4.17 (1H, m), 4.50 (1H, d, J=13.5 Hz), 4.99-5.12 (2H, m), 5.74-5.89 (1H, m), 6.97-7.07 (1H, m), 7.11 (1H, dd, J=2.0, 8.5 Hz), 7.14-7.22 (1H, m), 7.31 (1H, d, J=8.0 Hz), 7.36 (1H, d, J=2.0 Hz), 7.41 (1H, d, J=8.5 Hz).

Example 60(b)

Synthesis of 2,3-dichlorophenyl{1-(3,3,3-trifluoro-N-methylpropanamido)-2-(S)-(3,4-dichlorophenyl)-5-[spiro(benzo(c)thiophene-(2S)-oxido-1(3H),4'-piperidin)-1'-yl]pentan-2-yl}methylcarbamate

[F199]

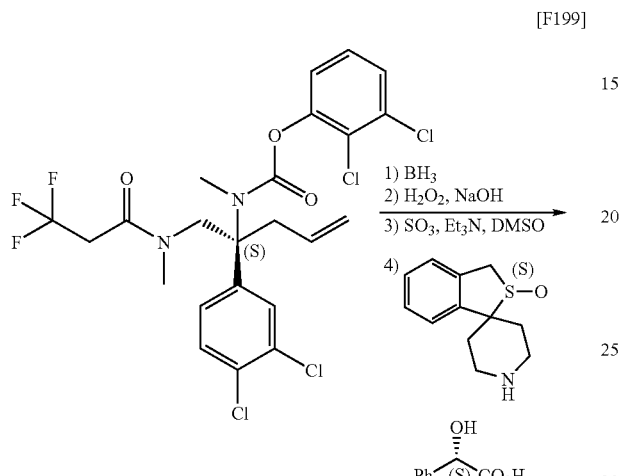

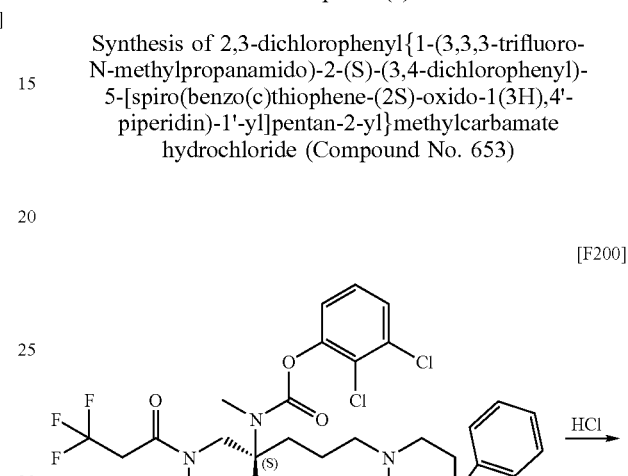

Similar to Example 51(b), 2,3-dichlorophenyl[1-(3,3,3-trifluoro-N-methylpropanamido)-2-(S)-(3,4-dichlorophenyl)-5-hydroxy-pentan-2-yl]methylcarbamate was obtained (130 mg) by use of 2,3-dichlorophenyl[1-(3,3,3-trifluoro-N-methylpropanamido)-2-(S)-(3,4-dichlorophenyl)-4-penten-2-yl]methylcarbamate (290 mg). Subsequently, similar to Example 51(c), 2,3-dichlorophenyl[1-(3,3,3-trifluoro-N-methylpropanamido)-2-(S)-(3,4-dichlorophenyl)-5-oxo-pentan-2-yl]methylcarbamate was obtained (126 mg) by use of 2,3-dichlorophenyl[1-(3,3,3-trifluoro-N-methylpropanamido)-2-(S)-(3,4-dichlorophenyl)-5-hydroxy-pentan-2-yl]methylcarbamate (123 mg). Thereafter, similar to Example 51(d), the title compound was obtained as white powder (124 mg, 32.6%, 4 steps) by use of 2,3-dichlorophenyl[1-(3,3,3-trifluoro-N-methylpropanamido)-2-(S)-(3,4-dichlorophenyl)-5-oxo-pentan-2-yl]methylcarbamate (126 mg).

MS (FAB) m/z 792 ((M+H)$^+$)

$^1$H-NMR (400 MHz, CDCl$_3$)δ ppm: 1.01-1.20 (1H, m), 1.53-1.75 (2H, m), 1.82-2.07 (3H, m), 2.25-2.48 (6H, m), 2.82-3.07 (2H, m), 3.00 (3H, s), 3.16-3.43 (2H, m), 3.32 (3H, s), 3.99 (1H, d, J=16.5 Hz), 4.18-4.58 (3H, m), 6.92-7.04 (1H, m), 7.08-7.21 (2H, m), 7.25-7.43 (7H, m).

Example 60(c)

Synthesis of 2,3-dichlorophenyl{1-(3,3,3-trifluoro-N-methylpropanamido)-2-(S)-(3,4-dichlorophenyl)-5-[spiro(benzo(c)thiophene-(2S)-oxido-1(3H),4'-piperidin)-1'-yl]pentan-2-yl}methylcarbamate hydrochloride (Compound No. 653)

[F200]

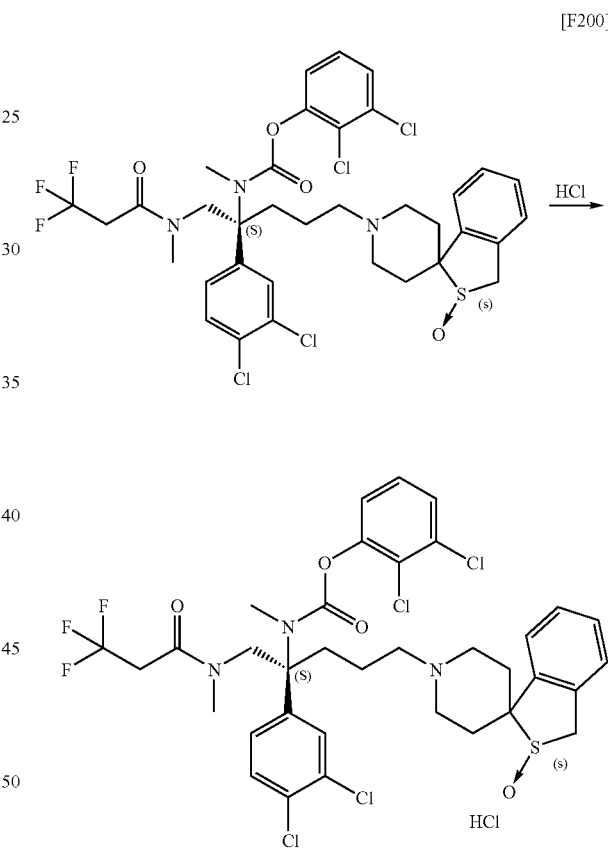

Similar to Example 51(e), the title compound was obtained as white powder (89 mg, 56.1%) by use of 2,3-dichlorophenyl{1-(3,3,3-trifluoro-N-methylpropanamido)-2-(S)-(3,4-dichlorophenyl)-5-[spiro(benzo(c)thiophene-(2S)-oxido-1(3H),4'-piperidin)-1'-yl]pentan-2-yl}methylcarbamate (124 mg).

$^1$H-NMR (400 MHz, DMSO-d$_6$)δ ppm: 1.25-1.48 (1H, m), 1.78-2.32 (5H, m), 2.40-2.49 (1H, m), 2.76-3.17 (8H, m), 3.24-3.55 (4H, m), 3.62-3.88 (3H, m), 4.04-4.40 (3H, m), 4.69 (1H, d, J=17.0 Hz), 7.24-7.45 (7H, m), 7.47-7.66 (3H, m), 10.84 (1H, br).

Example 61(a)

Synthesis of 3,4-dichlorophenyl[1-(3,3,3-trifluoro-N-methylpropanamido)-2-(S)-(3,4-dichlorophenyl)-4-penten-2-yl]methylcarbamate

Example 61(b)

Synthesis of 3,4-dichlorophenyl{1-(3,3,3-trifluoro-N-methylpropanamido)-2-(S)-(3,4-dichlorophenyl)-5-[spiro(benzo(c)thiophene-(2S)-oxido-1(3H),4'-piperidin)-1'-yl]pentan-2-yl}methylcarbamate

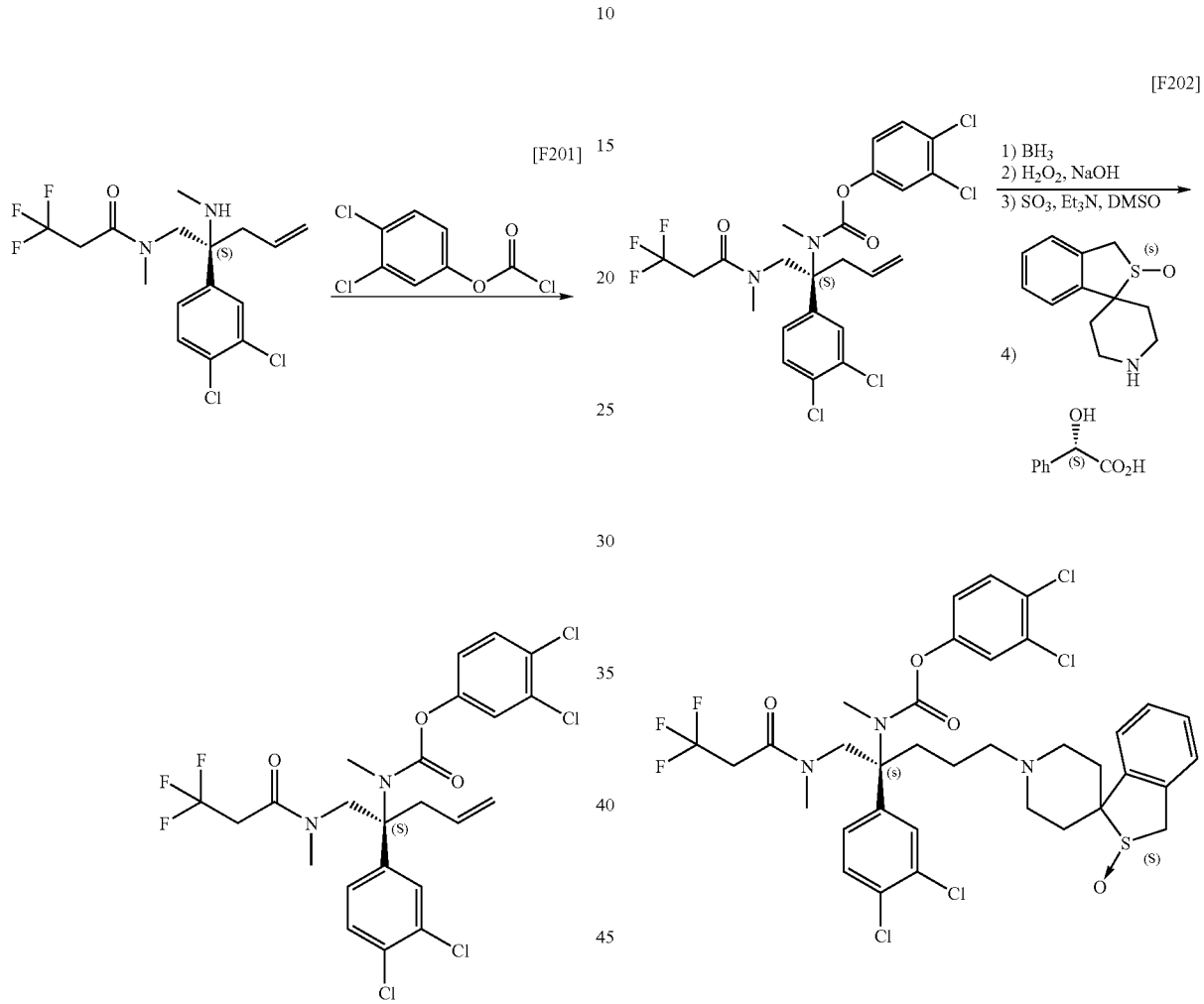

Similar to Example 51(a), the title compound was obtained (271 mg, 90.7%) by use of N-[2-(S)-(3,4-dichlorophenyl)-2-(methylamino)-4-pentene-1'-yl]-3,3,3-trifluoro-N-methylpropanamide (200 mg) synthesized in Example 29(a) and 3,4-dichlorophenyl chloroformate (588 mg).

MS (FAB) m/z 571 ((M+H)$^+$)

$^1$H-NMR (400 MHz, CDCl$_3$) δ ppm: 2.70-2.81 (1H, m), 2.84 (3H, s), 2.92-3.33 (3H, m), 3.12 (3H, s), 3.77-3.96 (1H, m), 4.60-4.79 (1H, m), 5.06 (1H, d, J=17.0 Hz), 5.10 (1H, d, J=10.5 Hz), 5.69-5.88 (1H, m), 6.85-7.00 (1H, m), 7.10 (1H, dd, J=2.5, 8.5 Hz), 7.14-7.25 (1H, m), 7.32-7.46 (3H, m).

Similar to Example 51(b), 3,4-dichlorophenyl[1-(3,3,3-trifluoro-N-methylpropanamido)-2-(S)-(3,4-dichlorophenyl)-5-hydroxy-pentan-2-yl]methylcarbamate was obtained (102 mg) by use of 3,4-dichlorophenyl[1-(3,3,3-trifluoro-N-methylpropanamido)-2-(S)-(3,4-dichlorophenyl)-4-penten-2-yl]methylcarbamate (260 mg). Subsequently, similar to Example 51(c), 3,4-dichlorophenyl[1-(3,3,3-trifluoro-N-methylpropanamido)-2-(S)-(3,4-dichlorophenyl)-5-oxo-pentan-2-yl]methylcarbamate was obtained (99 mg) by use of 3,4-dichlorophenyl[1-(3,3,3-trifluoro-N-methylpropanamido)-2-(S)-(3,4-dichlorophenyl)-5-hydroxy-pentan-2-yl]methylcarbamate (96 mg). Thereafter, similar to Example 51(d), the title compound was obtained as white powder (99 mg, 29.2%, 4 steps) by use of 3,4-dichlorophenyl[1-(3,3,3-trifluoro-N-methylpropanamido)-2-(S)-(3,4-dichlorophenyl)-5-oxo-pentan-2-yl]methylcarbamate (99 mg).

MS (FAB) m/z 792 ((M+H)$^+$)

¹H-NMR (400 MHz, CDCl₃)δ ppm: 1.02-1.19 (1H, m), 1.52-1.75 (2H, m), 1.83-2.10 (3H, m), 2.27-2.48 (6H, m), 2.79-3.07 (2H, m), 2.98 (3H, s), 3.14-3.42 (2H, m), 3.23 (3H, s), 3.99 (1H, d, J=16.5 Hz), 4.22-4.48 (3H, m), 6.82-6.96 (1H, m), 7.06-7.20 (2H, m), 7.24-7.45 (7H, m).

Example 61(c)

Synthesis of 3,4-dichlorophenyl{1-(3,3,3-trifluoro-N-methylpropanamido)-2-(S)-(3,4-dichlorophenyl)-5-[spiro(benzo(c)thiophene-(2S)-oxido-1(3H),4'-piperidin)-1'-yl]pentan-2-yl}methylcarbamate hydrochloride (Compound No. 654)

J=13.5 Hz), 2.39-2.50 (1H, m), 2.80-3.18 (8H, m), 3.24 (3H, s), 3.46-3.55 (1H, m), 3.60-3.88 (3H, m), 3.97-4.14 (2H, m), 4.40-4.57 (1H, m), 4.68 (1H, d, J=17.0 Hz), 7.07-7.21 (1H, m), 7.30-7.69 (9H, m), 10.97 (1H, br).

Example 62(a)

Synthesis of 3,4-difluorophenyl[1-(3,3,3-trifluoro-N-methylpropanamido)-2-(S)-(3,4-dichlorophenyl)-4-penten-2-yl]methylcarbamate

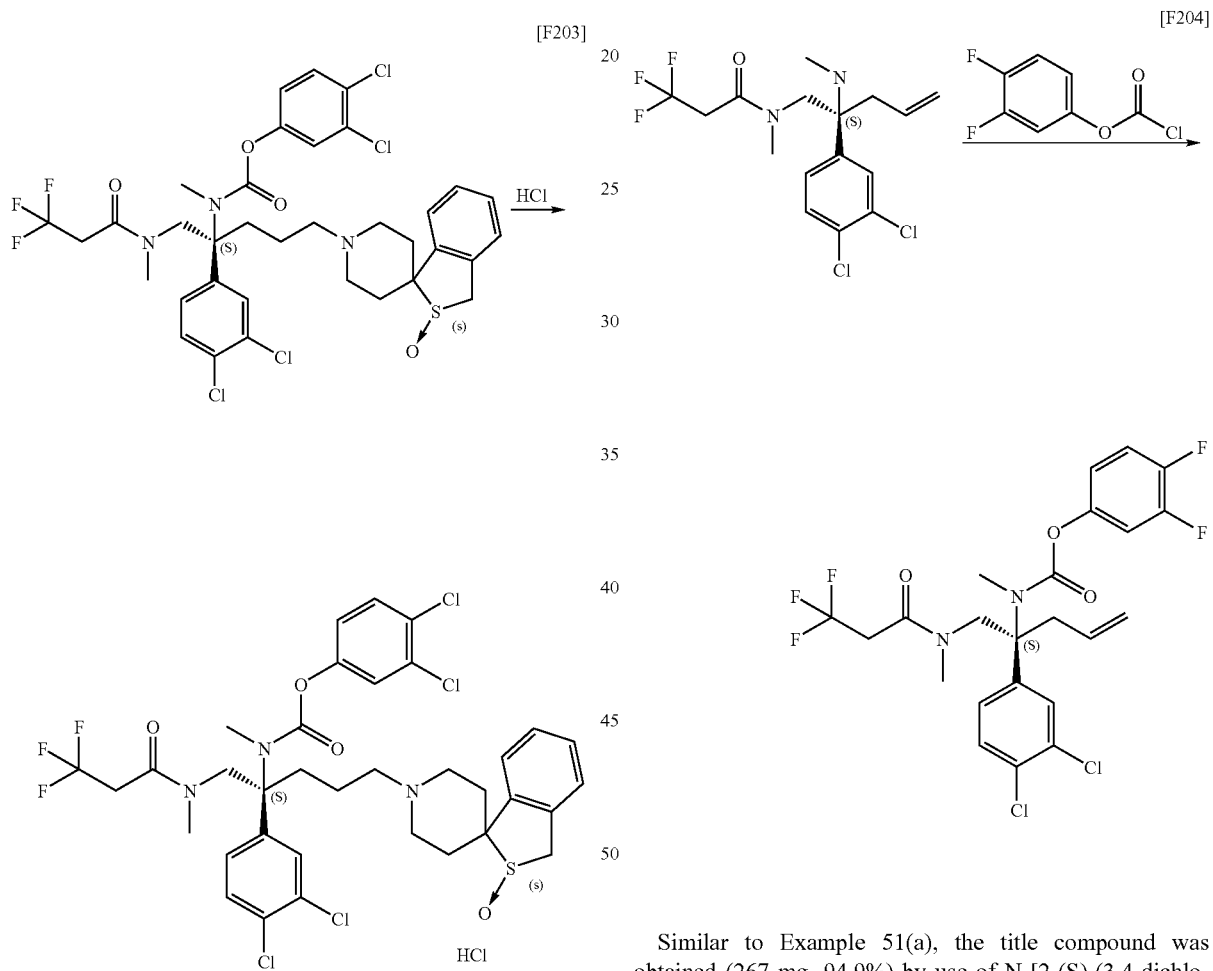

Similar to Example 51(c), the title compound was obtained as white powder (62 mg, 59.9%) by use of 3,4-dichlorophenyl{1-(3,3,3-trifluoro-N-methylpropanamido)-2-(S)-(3,4-dichlorophenyl)-5-[spiro(benzo(c)thiophene-(2S)-oxido-1(3H),4'-piperidin)-1'-yl]pentan-2-yl}methylcarbamate (99 mg).
¹H-NMR (400 MHz, DMSO-d₆)δ ppm: 1.27-1.47 (1H, m), 1.75-1.90 (1H, m), 1.95-2.20 (3H, m), 2.26 (1H, d, Similar to Example 51(a), the title compound was obtained (267 mg, 94.9%) by use of N-[2-(S)-(3,4-dichlorophenyl)-2-(methylamino)-4-pentene-1'-yl]-3,3,3-trifluoro-N-methylpropanamide (200 mg) synthesized in Example 4(a) and 3,4-difluorophenyl chloroformate (502 mg).

MS (FAB) m/z 539 ((M+H)⁺)

¹H-NMR (400 MHz, CDCl₃)δ ppm: 2.68-2.81 (1H, m), 2.85 (3H, s), 2.91-3.34 (3H, m), 3.13 (3H, s), 3.76-3.96 (1H, m), 4.60-4.80 (1H, m), 5.06 (1H, d, J=17.0 Hz), 5.10 (1H, d, J=10.5 Hz), 5.70-5.86 (1H, m), 6.70-6.99 (2H, m), 7.03-7.15 (2H, m), 7.34 (1H, d, J=2.0 Hz), 7.42 (1H, d, J=8.5 Hz).

Example 62(b)

Synthesis of 3,4-difluorophenyl{1-(3,3,3-trifluoro-N-methylpropanamido)-2-(S)-(3,4-dichlorophenyl)-5-[spiro(benzo(c)thiophene-(2S)-oxido-1(3H),4'-piperidin)-1'-yl]-pentan-2-yl}methylcarbamate

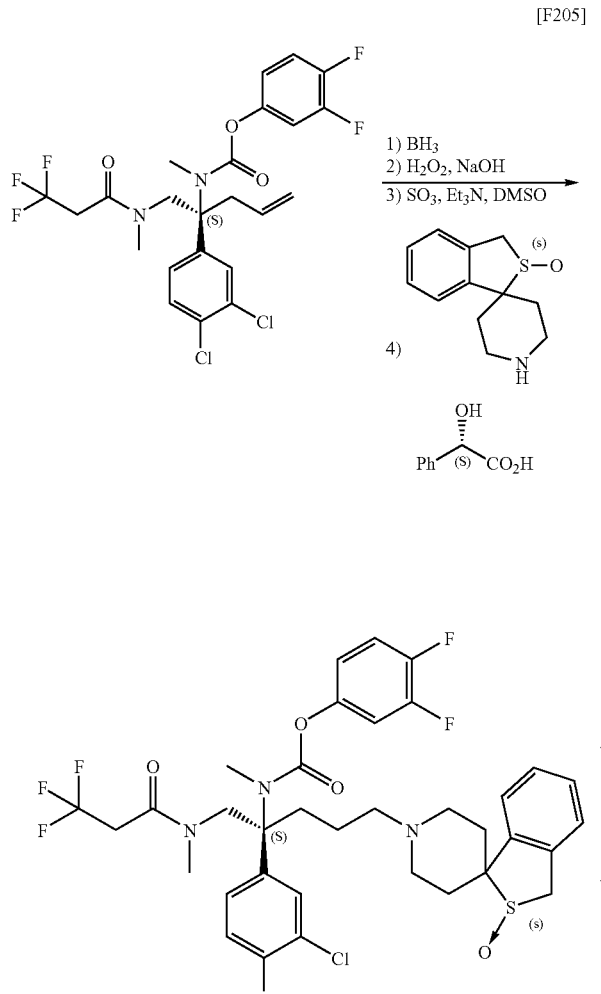

Similar to Example 51(b), 3,4-difluorophenyl[1-(3,3,3-trifluoro-N-methylpropanamido)-2-(S)-(3,4-dichlorophenyl)-5-hydroxy-pentan-2-yl]methylcarbamate was obtained (119 mg) by use of 3,4-difluorophenyl[1-(3,3,3-trifluoro-N-methylpropanamido)-2-(S)-(3,4-dichlorophenyl)-4-penten-2-yl]methylcarbamate (255 mg). Subsequently, similar to Example 51(c), 3,4-difluorophenyl[1-(3,3,3-trifluoro-N-methylpropanamido)-2-(S)-(3,4-dichlorophenyl)-5-oxo-pentan-2-yl]methylcarbamate was obtained (113 mg) by use of 3,4-difluorophenyl[1-(3,3,3-trifluoro-N-methylpropanamido)-2-(S)-(3,4-dichlorophenyl)-5-hydroxy-pentan-2-yl] methylcarbamate (110 mg). Thereafter, similar to Example 51(d), the title compound was obtained as white powder (128 mg, 38.5%, 4 steps) by use of 3,4-difluorophenyl[1-(3,3,3-trifluoro-N-methylpropanamido)-2-(S)-(3,4-dichlorophenyl)-5-oxo-pentan-2-yl]methylcarbamate (113 mg).

MS (FAB) m/z 760 ((M+H)$^+$)

$^1$H-NMR (400 MHz, CDCl$_3$)δ ppm 1.02-1.17 (1H, m), 1.52-1.69 (2H, m), 1.84-2.10 (3H, m), 2.27-2.47 (6H, m), 2.82-3.05 (2H, m), 2.98 (3H, s), 3.15-3.43 (2H, m), 3.24 (3H, s), 3.99 (1H, d, J=16.5 Hz), 4.23-4.46 (3H, m), 6.70-6.96 (2H, m), 7.03-7.14 (2H, m), 7.25-7.36 (5H, m), 7.41 (1H, d, J=8.5 Hz).

Example 62(c)

Synthesis of 3,4-difluorophenyl{1-(3,3,3-trifluoro-N-methylpropanamido)-2-(S)-(3,4-dichlorophenyl)-5-[spiro(benzo(c)thiophene-(2S)-oxido-1(3H),4'-piperidin)-1'-yl]pentan-2-yl}methylcarbamate hydrochloride (655)

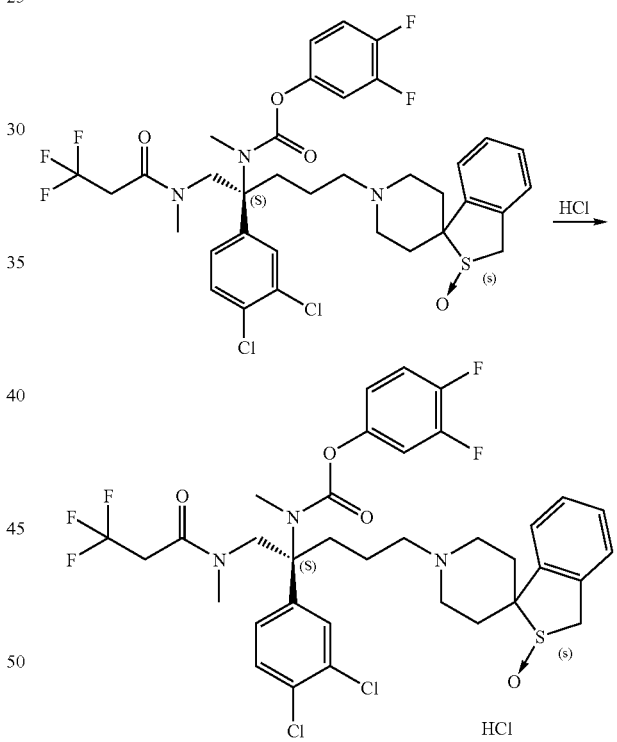

Similar to Example 51(e), the title compound was obtained as white powder (78 mg, 58.2%) by use of 3,4-difluorophenyl{1-(3,3,3-trifluoro-N-methylpropanamido)-2-(S)-(3,4-dichlorophenyl)-5-[spiro(benzo(c)thiophene-(2S)-oxido-1(3H),4'-piperidin)-1'-yl]pentan-2-yl}methylcarbamate (128 mg).

$^1$H-NMR (400 MHz, DMSO-d$_6$)δ ppm: 1.23-1.47 (1H, m), 1.77-1.90 (1H, m), 1.95-2.21 (3H, m), 2.26 (1H, d, J=13.5 Hz), 2.39-2.50 (1H, m), 2.81-3.17 (8H, m), 3.24 (3H, s), 3.45-3.86 (4H, m), 4.00-4.14 (2H, m), 4.36-4.55 (1H, m), 4.69 (1H, d, J=17.0 Hz), 6.90-7.02 (1H, m), 7.27-7.47 (7H, m), 7.52-7.69 (2H, m), 10.93 (1H, br).

Example 63(a)

Synthesis of N-[2-(S)-(3,4-dichlorophenyl)-2-(methylamino)-4-pentenyl]-2,2,2-trifluoro-N-methylacetamide

[F207]

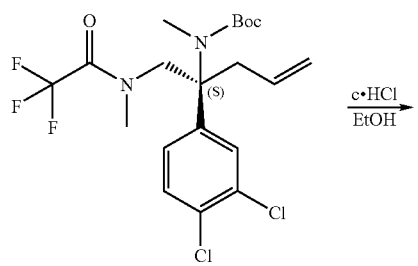

Similar to Example 29(a), the title compound was obtained (3.59 g, 90.9%) by use of tert-butyl[1-(2,2,2-trifluoro-N-methylacetamide)-2-(S)-(3,4-dichlorophenyl)-4-penten-2-yl]methylcarbamate (5.0 g) synthesized in Example 27(a).

MS (FAB) m/z 369 ((M+H)$^+$)

$^1$H-NMR (400 MHz, CDCl$_3$)δ ppm: 2.22 (3H, s), 2.62-2.74 (2H, m), 2.72 (3H, s), 3.51 (1H, d, J=14.0 Hz), 3.74 (1H, d, J=14.0 Hz), 5.19-5.28 (2H, m), 5.73-5.86 (1H, m), 7.34 (1H, dd, J=2.0, 8.5 Hz), 7.43 (1H, d, J=8.5 Hz), 7.63 (1H, d, J=2.0 Hz).

Example 63(b)

Synthesis of phenyl[1-(2,2,2-trifluoro-N-methylacetamide)-2-(S)-(3,4-dichlorophenyl)-4-penten-2-yl]methylcarbamate

[F208]

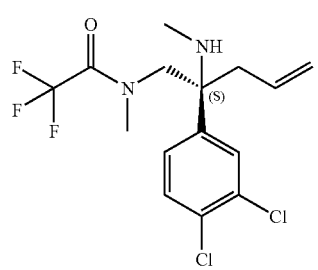

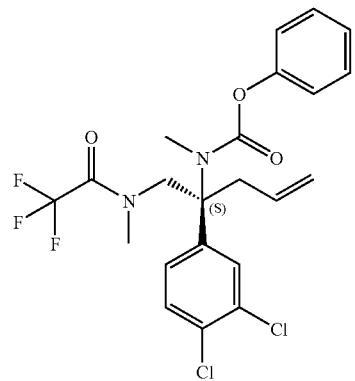

Similar to Example 51(a), the title compound was obtained (303 mg, >100%) by use of N-[2-(S)-(3,4-dichlorophenyl)-2-(methylamino)-4-pentene-1'-yl]-2,2,2-trifluoro-N-methylacetamide (200 mg) and phenyl chloroformate (0.29 mL).

MS (FAB) m/z 537 ((M+H)$^+$)

$^1$H-NMR (400 MHz, CDCl$_3$)δ ppm: 2.75 (1H, dd, J=6.5, 14.0 Hz), 2.94 (1H, dd, J=7.5, 14.0 Hz), 3.02 (3H, s), 3.20 (3H, s), 4.13-4.28 (1H, m), 4.46-4.67 (1H, m), 5.02-5.16 (2H, m), 5.67-5.80 (1H, m), 6.93-7.08 (2H, m), 7.10 (1H, dd, J=2.5, 8.5 Hz), 7.14-7.20 (1H, m), 7.27-7.37 (3H, m), 7.42 (1H, d, J=8.5 Hz).

Example 63(c)

Synthesis of phenyl{1-(2,2,2-trifluoro-N-methylacetamide)-2-(S)-(3,4-dichlorophenyl)-5-[spiro(benzo(c)thiophene-(2S)-oxido-1(3H),4'-piperidin)-1'-yl]pentan-2-yl}methylcarbamate

[F209]

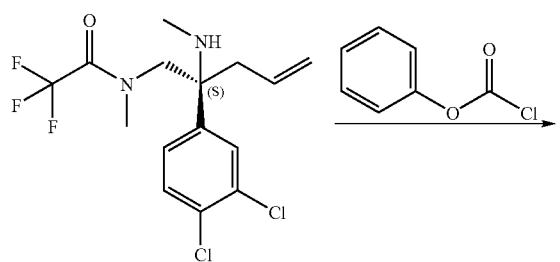

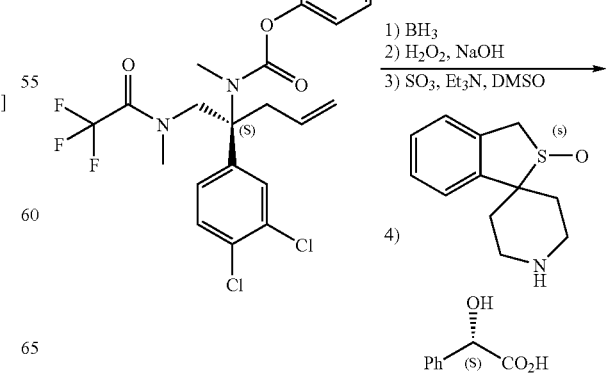

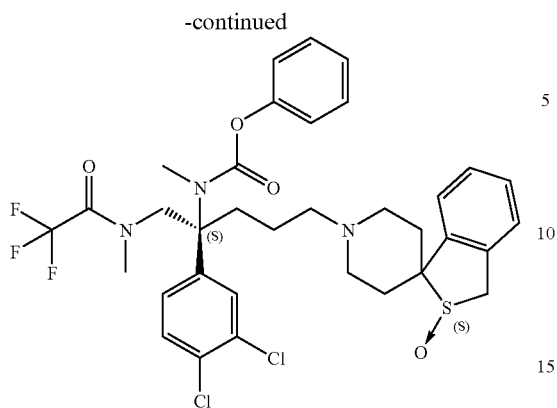

Similar to Example 51(b), phenyl[1-(2,2,2-trifluoro-N-methylacetamide)-2-(S)-(3,4-dichlorophenyl)-5-hydroxy-pentan-2-yl]methylcarbamate was obtained (180 mg) by use of phenyl [1-(2,2,2-trifluoro-N-methylacetamide)-2-(S)-(3,4-dichlorophenyl)-4-penten-2-yl]methylcarbamate (296 mg). Subsequently, similar to Example 51(c), phenyl[1-(2,2,2-trifluoro-N-methylacetamide)-2-(S)-(3,4-dichlorophenyl)-5-oxo-pentan-2-yl]methylcarbamate was obtained (167 mg) by use of phenyl[1-(2,2,2-trifluoro-N-methylacetamide)-2-(S)-(3,4-dichlorophenyl)-5-hydroxy-pentan-2-yl]methylcarbamate (174 mg). Thereafter, similar to Example 51(d), the title compound was obtained as white powder (136 mg, 36.3%, 4 steps) by use of phenyl[1-(2,2,2-trifluoro-N-methylacetamide)-2-(S)-(3,4-dichlorophenyl)-5-oxo-pentan-2-yl]methylcarbamate (167 mg).

MS (FAB) m/z 710 ((M+H)$^+$)

$^1$H-NMR (400 MHz, CDCl$_3$)δ ppm: 0.97-1.14 (1H, m), 1.53-1.76 (2H, m), 1.87-2.02 (3H, m), 2.25-2.48 (6H, m), 2.80-2.98 (2H, m), 3.14 (3H, s), 3.30 (3H, s), 4.00 (1H, d, J=16.5 Hz), 4.25-4.42 (2H, m), 4.47-4.61 (1H, m), 6.86-7.03 (1H, m), 7.10 (1H, dd, J=2.0, 8.5 Hz), 7.18 (1H, t, J=7.5 Hz), 7.25-7.37 (8H, m), 7.41 (1H, d, J=8.5 Hz).

Example 63(d)

Synthesis of phenyl{1-(2,2,2-trifluoro-N-methylacetamide)-2-(S)-(3,4-dichlorophenyl)-5-[spiro(benzo(c)thiophene-(2S)-oxido-1(3H),4'-piperidin)-1'-yl]pentan-2-yl}methylcarbamate hydrochloride
(Compound No. 642)

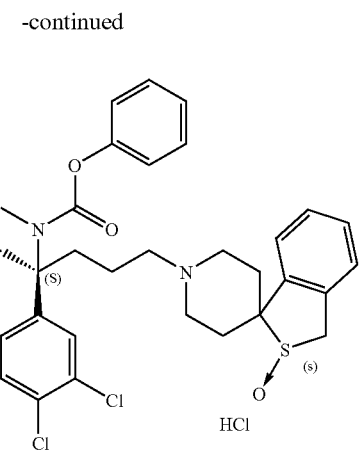

Similar to Example 51(e), the title compound was obtained as white powder (80 mg, 56.2%) by use of phenyl{1-(2,2,2-trifluoro-N-methylacetamide)-2-(S)-(3,4-dichlorophenyl)-5-[spiro(benzo(c)thiophene-(2S)-oxido-1(3H),4'-piperidin)-1'-yl]pentan-2-yl}methylcarbamate (136 mg).

$^1$H-NMR (400 MHz, DMSO-d$_6$)δ ppm: 1.22-1.48 (1H, m), 1.70-1.90 (1H, m), 1.95-2.22 (3H, m), 2.26 (1H, d, J=14.5 Hz), 2.34-2.47 (1H, m), 2.83-3.20 (8H, m), 3.24 (3H, s), 3.47-3.68 (2H, m), 4.08 (1H, d, J=17.0 Hz), 4.22-4.57 (2H, m), 4.68 (1H, d, J=17.0 Hz), 6.44-6.74 (1H, m), 6.95-7.23 (2H, m), 7.26-7.47 (7H, m), 7.56-7.72 (2H, m), 10.77 (1H, br).

Example 64(a)

Synthesis of phenyl[1-(2,2,2-trifluoro-N-methylacetamide)-2-(S)-(3,4-dichlorophenyl)-5-(4-carbamoyl-4-phenylpiperidine-1'-yl)pentan-2-yl]methylcarbamate

[F210]

[F211]

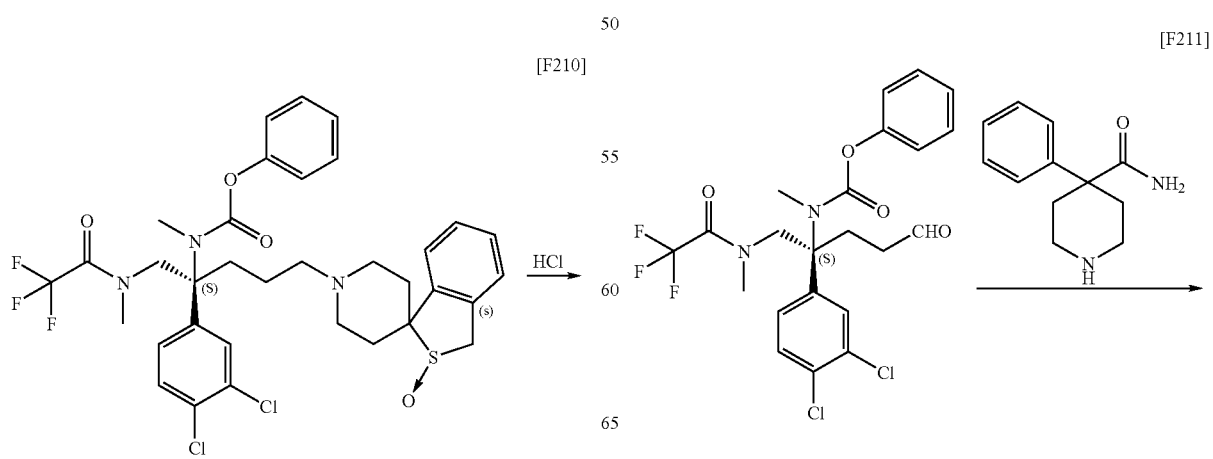

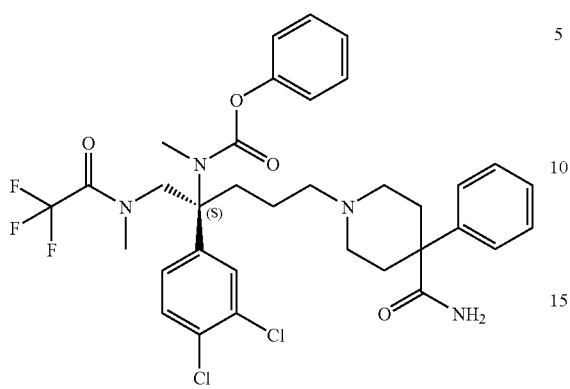

Subsequently, similar to Example 26(h), the title compound was obtained as white powder (70 mg, 67.8%) by use of phenyl[1-(2,2,2-trifluoro-N-methylacetamide)-2-(S)-(3,4-dichlorophenyl)-5-oxo-pentan-2-yl]methylcarbamate (120 mg) synthesized in Example 63(c) and 4-phenylpiperidine-4-carboxamide (62 mg).

MS (FAB) m/z 693 ((M+H)+)

¹H-NMR (400 MHz, CDCl₃)δ ppm: 0.95-1.10 (1H, m), 1.50-1.65 (1H, m), 1.85-2.10 (4H, m), 2.25-2.58 (8H, m), 3.12 (3H, s), 3.25 (3H, s), 4.22-4.58 (2H, m), 5.25 (2H, br), 6.91-7.43 (13H, m).

Example 64(b)

Synthesis of phenyl[1-(2,2,2-trifluoro-N-methylacetamide)-2-(S)-(3,4-dichlorophenyl)-5-(4-carbamoyl-4-phenylpiperidine-1'-yl)pentan-2-yl]methylcarbamate hydrochloride (Compound No. 578)

[F212]

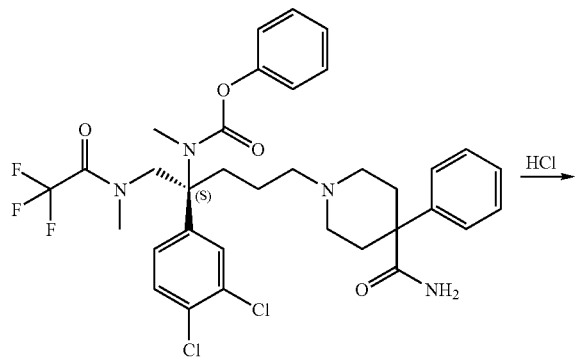

Similar to Example 26(k), the title compound was obtained as white powder (80 mg, 56.2%) by use of phenyl [1-(2,2,2-trifluoro-N-methylacetamide)-2-(S)-(3,4-dichlorophenyl)-5-(4-carbamoyl-4-phenylpiperidine-1'-yl)pentan-2-yl]methylcarbamate (136 mg).

¹H-NMR (400 MHz, DMSO-d₆)δ ppm: 1.25-1.37 (1H, m), 1.60-1.82 (1H, m), 1.95-2.13 (3H, m), 2.58-3.13 (9H, m), 3.21 (3H, s), 3.36 (3H, s), 3.45-3.58 (1H, m), 4.05-4.57 (3H, m), 6.90-7.50 (11H, m), 7.58-7.70 (2H, m), 9.95 (1H, br).

Example 65(a)

Synthesis of tert-butyl[1-(3,4,5-trimethoxy-N-methylbenzamide)-2-(S)-(3,4-dichlorophenyl)-4-penten-2-yl]methylcarbamate

[F213]

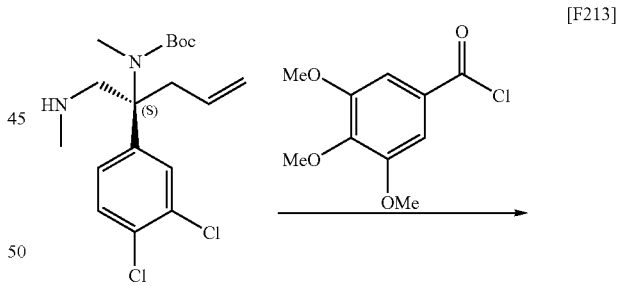

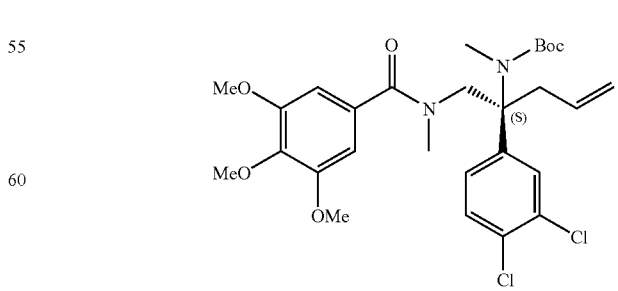

tert-Butyl[1-methylamino-2-(S)-(3,4-dichlorophenyl)-4-penten-2-yl]methylcarbamate (500 mg) synthesized in Example 26(d) was dissolved in ethyl acetate (5 mL). Under cooling with ice, sodium hydrogencarbonate (225 mg) and water (2.5 mL) were added thereto, and thereafter 3,4,5-trimethoxybenzoyl chloride (309 mg) was added to the mixture, followed by stirring for 30 minutes at the same temperature. Saturated aqueous sodium bicarbonate was added to the reaction mixture, and the resultant mixture was extracted with ethyl acetate, washed with saturated brine, and dried over sodium sulfate anhydrate. The solvent was concentrated under reduced pressure, and the residue was purified through silica gel column chromatography (n-hexane:ethyl acetate=7:1 to 4:1 to 2:1 to 1:1), to thereby give the title compound (715 mg, 93.8%).

MS (FAB) m/z 567 ((M+H)$^+$)

$^1$H-NMR (400 MHz, CDCl$_3$)δ ppm: 1.22 (9H, s), 2.65-2.80 (4H, m), 2.95-3.05 (1H, m), 3.17 (3H, s), 3.86 (3H, s), 3.88 (6H, s), 4.20-4.48 (2H, m), 4.97-5.10 (2H, m), 5.80-5.94 (1H, m), 6.60 (2H, s), 7.10-7.18 (1H, m), 7.34-7.44 (2H, m).

Example 65(b)

Synthesis of N-[2-(S)-(3,4-dichlorophenyl)-2-(methylamino)-4-pentene-1'-yl]-3,4,5-trimethoxy-N-methylbenzamide

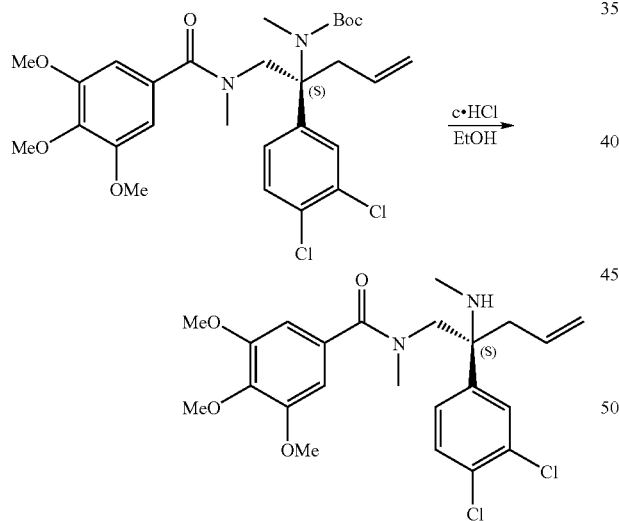

[F214]

Similar to Example 29(a), the title compound was obtained (171 mg, 89.5%) by use of tert-butyl[1-(3,4,5-trimethoxy-N-methylbenzamide)-2-(S)-(3,4-dichlorophenyl)-4-penten-2-yl]methylcarbamate (232 mg).

MS (FAB) m/z 467 ((M+H)$^+$)

$^1$H-NMR (400 MHz, CDCl$_3$)δ ppm: 1.71 (1H, br), 2.28 (3H, s), 2.60 (3H, s), 2.68-2.82 (2H, m), 3.68 (1H, d, J=14.5 Hz), 3.83 (3H, s), 3.84 (6H, s), 3.80-3.90 (1H, m), 5.18-5.28 (2H, m), 5.77-5.90 (1H, m), 6.37 (2H, s), 7.40-7.48 (2H, m), 7.75-7.82 (1H, m).

Example 65(c)

Synthesis of phenyl[1-(3,4,5-trimethoxy-N-methylbenzamide)-2-(S)-(3,4-dichlorophenyl)-4-penten-2-yl]methylcarbamate

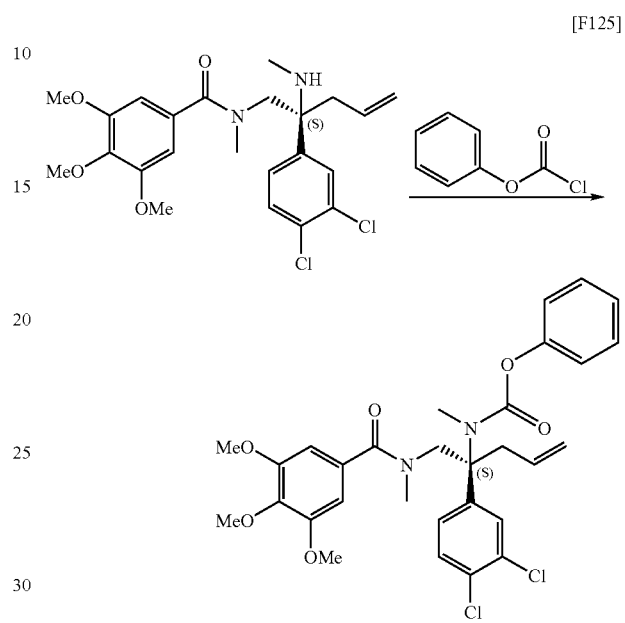

[F125]

Similar to Example 51(a), the title compound was obtained (170 mg, 78.2%) by use of N-[2-(S)-(3,4-dichlorophenyl)-2-methylamino-4-pentene-1'-yl]-3,4,5-trimethoxy-N-methylbenzamide (171 mg) and phenyl chloroformate (174 mg).

MS (FAB) m/z 587 ((M+H)$^+$)

$^1$H-NMR (400 MHz, CDCl$_3$)δ ppm: 2.80-2.98 (4H, m), 3.14 (3H, s), 3.28-3.40 (1H, m), 3.77 (6H, s), 3.86 (3H, s), 3.95-4.09 (1H, m), 4.68-4.82 (1H, m), 5.05-5.17 (2H, m), 5.70-5.88 (1H, m), 6.61 (2H, s), 6.87-7.03 (1H, m), 7.13-7.18 (1H, m), 7.22-7.33 (4H, m), 7.43-7.52 (2H, m).

Example 65(d)

Synthesis of phenyl{1-(3,4,5-trimethoxy-N-methylbenzamide)-2-(S)-(3,4-dichlorophenyl)-5-[spiro(benzo(c)thiophene-(2S)-oxido-1(3H),4'-piperidin)-1'-yl]pentan-2-yl}methylcarbamate

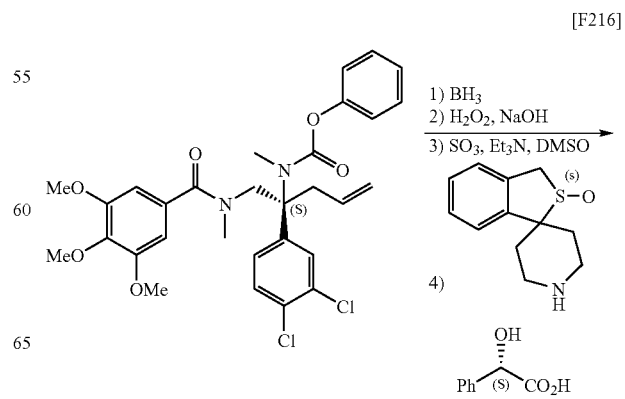

[F216]

-continued

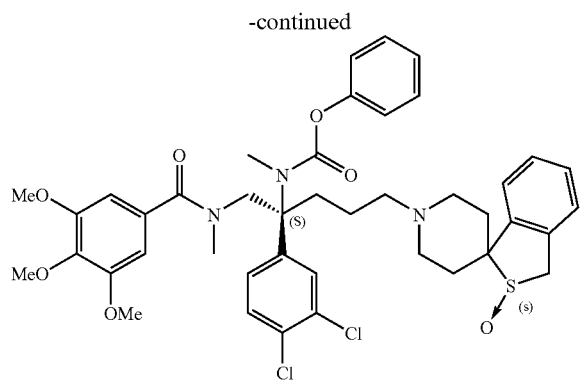

Similar to Example 51(b), phenyl[1-(3,4,5-trimethoxy-N-methylbenzamide)-2-(S)-(3,4-dichlorophenyl)-5-hydroxy-pentan-2-yl]methylcarbamate was obtained (77 mg) by use of phenyl[1-(3,4,5-trimethoxy-N-methylbenzamide)-2-(S)-(3,4-dichlorophenyl)-4-penten-2-yl]methylcarbamate (170 mg). Subsequently, similar to Example 51(c), phenyl[1-(3,4,5-trimethoxy-N-methylbenzamide)-2-(S)-(3,4-dichlorophenyl)-5-oxo-pentan-2-yl]methylcarbamate was obtained (87 mg) by use of phenyl[1-(3,4,5-trimethoxy-N-methylbenzamide)-2-(S)-(3,4-dichlorophenyl)-5-hydroxy-pentan-2-yl]methylcarbamate (77 mg). Thereafter, similar to Example 51(d), the title compound was obtained as white powder (70 mg, 29.8%, 4 steps) by use of phenyl[1-(3,4,5-trimethoxy-N-methylbenzamide)-2-(S)-(3,4-dichlorophenyl)-5-oxo-pentan-2-yl]methylcarbamate (87 mg).

MS (FAB) m/z 808 ((M+H)$^+$)

$^1$H-NMR (400 MHz, CDCl$_3$)δ ppm: 1.27-1.30 (1H, m), 1.51-1.60 (1H, m), 1.65-1.82 (1H, m), 1.87-2.12 (2H, m), 2.25-2.47 (7H, m), 2.80-3.00 (5H, m), 3.26 (3H, s), 3.81 (6H, s), 3.86 (3H, s), 3.98 (1H, d, J=16.5 Hz), 4.07-4.17 (1H, m), 4.30 (1H, d, J=16.5 Hz), 4.36-4.58 (1H, m), 6.64 (2H, s), 6.85-7.05 (2H, m), 7.13-7.19 (1H, m), 7.21-7.35 (7H, m), 7.43-7.48 (2H, m).

Example 65(e)

Synthesis of phenyl{1-(3,4,5-trimethoxy-N-methyl-benzamide)-2-(S)-(3,4-dichlorophenyl)-5-[spiro(benzo(c)thiophene-(2S)-oxido-1(3H),4'-piperidin)-1'-yl]pentan-2-yl}methylcarbamate hydrochloride (Compound No. 589)

[F217]

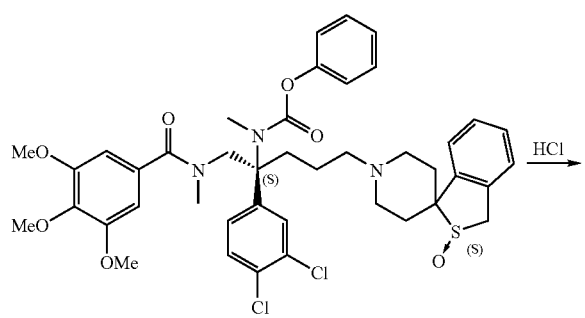

-continued

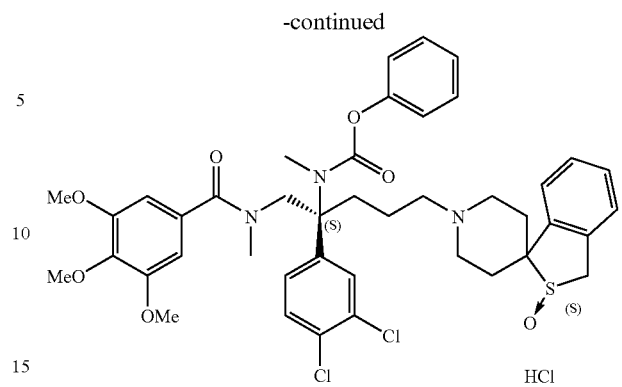

Similar to Example 26(k), the title compound was obtained as white powder (50 mg, 68.4%) by use of phenyl{1-(3,4,5-trimethoxy-N-methylbenzamide)-2-(S)-(3,4-dichlorophenyl)-5-[spiro(benzo(c)thiophene-(2S)-oxido-1(3H),4'-piperidin)-1'-yl-]pentan-2-yl}methylcarbamate (70 mg).

$^1$H-NMR (400 MHz, DMSO-d$_6$)δ ppm: 1.80-2.00 (2H, m), 2.13-2.27 (2H, m), 2.32-2.48 (2H, m), 2.58-2.97 (3H, m), 3.01-3.20 (4H, m), 3.28-3.42 (6H, m), 3.54-3.72 (4H, m), 3.81 (6H, s), 4.06 (1H, d, J=17.0 Hz), 4.12-4.60 (2H, m), 4.65 (1H, d, J=17.0 Hz), 6.73 (2H, s), 6.90-7.85 (12H, m), 10.58 (1H, br).

Example 66(a)

Synthesis of 1-(3,4,5-trimethoxybenzyloxy)-2-(S)-(3,4-dichlorophenyl)-2-(N-methylamino)-4-pentene

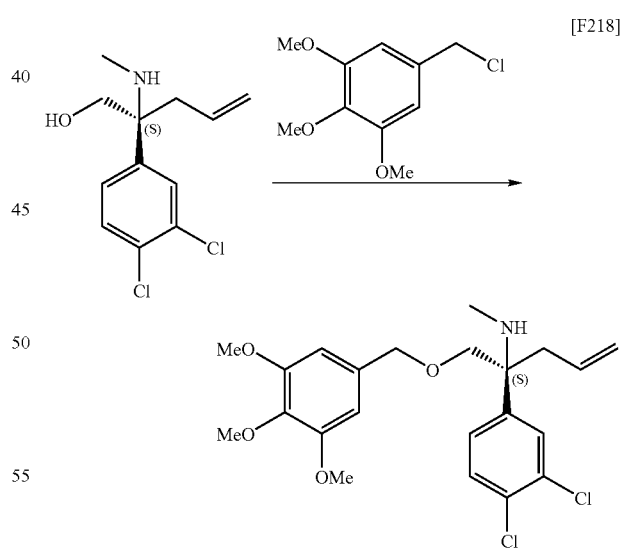

[F218]

Under argon, a solution of 2-(S)-(3,4-dichlorophenyl)-2-methylamino-4-penten-1-ol (8.5 g) in anhydrous N,N-dimethylformamide (50 mL) was added to a suspension of sodium hydride (1.5 g) in anhydrous N,N-dimethylformamide (50 mL) under cooling with ice, and the mixture was stirred for 1 hour at room temperature. A solution of 3,4,5-trimethoxybenzyl chloride (7.8 g) in anhydrous N,N-dimethylformamide (30 mL) was added to the reaction mixture under cooling with ice, and the resultant mixture was stirred overnight at room temperature. The reaction mixture was poured into ice-water, extracted with ether, sequentially washed with water and saturated brine, and dried over sodium sulfate anhydrate. The solvent was concentrated under reduced pressure, and the residue was purified through silica gel column chromatography (n-hexane:ethyl acetate=5:1 to 2:1→ethyl acetate), to thereby give the title compound (11.8 g, 81.8%).

MS (FAB) m/z 440 ((M+H)$^+$)

$^1$H-NMR (400 MHz, CDCl$_3$)δ ppm: 1.58 (1H, br), 2.17 (3H, s), 2.45-2.62 (2H, m), 3.59 (1H, d, J=17.0 Hz), 3.61 (1H, d, J=17.0. Hz), 3.83 (6H, s), 3.84 (3H, s), 4.43 (1H, d, J=18.0 Hz), 4.46 (1H, d, J=18.0 Hz), 5.01-5.09 (2H, m), 5.53-5.66 (1H, m), 6.47 (2H, s), 7.26 (1H, dd, J=2.0, 8.5 Hz), 7.39 (1H, d, J=8.5 Hz), 7.53 (1H, d, J=2.0 Hz).

Example 66(b)

Synthesis of tert-butyl[1-(3,4,5-trimethoxybenzyloxy)-2-(S)-(3,4-dichlorophenyl)-4-penten-2-yl]methylcarbamate

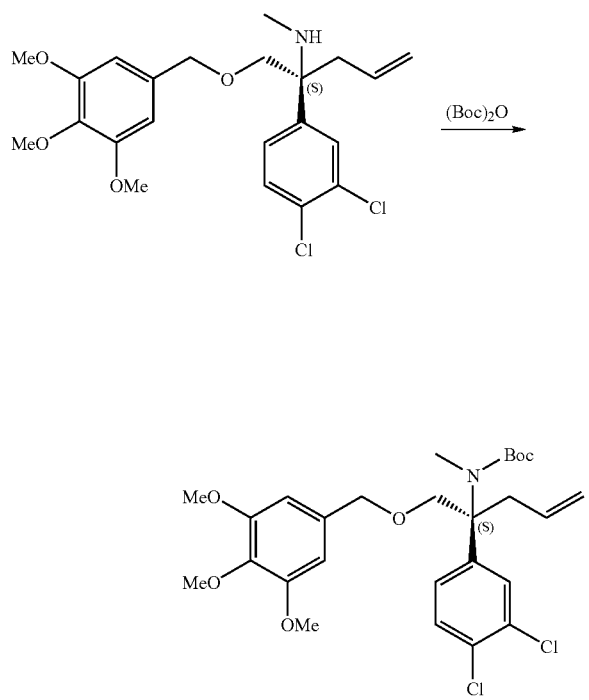

[F219]

Similar to Example 26(a), the title compound was obtained (9.98 g, 69.2%) by use of 1-(3,4,5-trimethoxybenzyloxy)-2-(S)-(3,4-dichlorophenyl)-2-(N-methylamino)-4-pentene (11.8 g).

MS (FAB) m/z 540 ((M+H)$^+$)

$^1$H-NMR (400 MHz, CDCl$_3$)δ ppm: 1.18 (9H, brs), 2.78 (1H, dd, J=7.0, 13.0 Hz), 3.10 (3H, s), 3.16 (1H, dd, J=7.0, 13.0 Hz), 3.72-3.87 (2H, m), 3.80 (6H, s), 3.83 (3H, s), 4.33 (1H, d, J=12.0 Hz), 4.38 (1H, d, J=12.0 Hz), 5.07-5.15 (2H, m), 5.63-5.76 (1H, m), 6.35 (2H, s), 7.09 (1H, dd, J=2.0, 8.5 Hz), 7.32-7.37 (2H, m).

Example 66(c)

Synthesis of tert-butyl{1-(3,4,5-trimethoxybenzyloxy)-2-(S)-(3,4-dichlorophenyl)-5-[spiro(benzo(c)thiophene-(2S)-oxido-1(3H),4'-piperidin)-1'-yl]pentan-2-yl}methylcarbamate

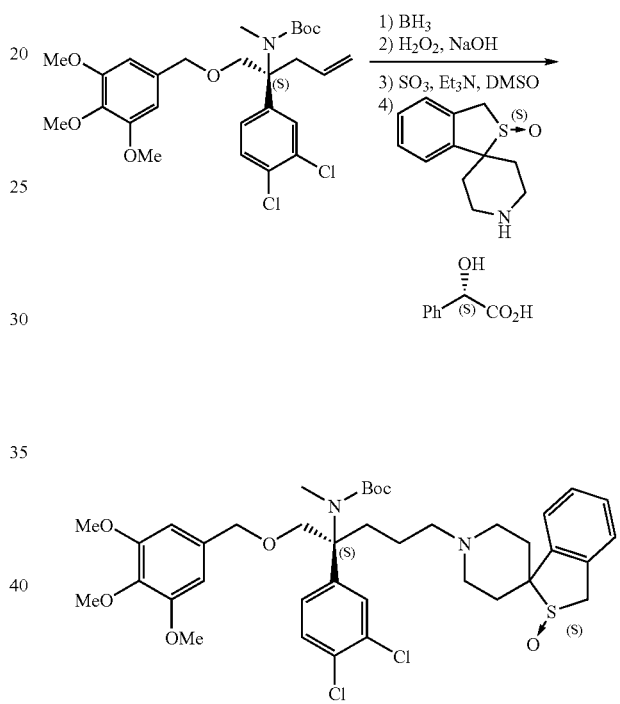

[F220]

Similar to Example 51(b), tert-butyl[1-(3,4,5-trimethoxybenzyloxy)-2-(S)-(3,4-dichlorophenyl)-5-hydroxy-pentan-2-yl]methylcarbamate was obtained (1.25 g, 56.0%) by use of tert-butyl[1-(3,4,5-trimethoxybenzyloxy)-2-(S)-(3,4-dichlorophenyl)-4-penten-2-yl]methylcarbamate (2.17 g). Subsequently, similar to Example 51(c), tert-butyl[1-(3,4,5-trimethoxybenzyloxy)-2-(S)-(3,4-dichlorophenyl)-5-oxo-pentan-2-yl]methylcarbamate was obtained (1.0 g, 78.1%) by use of tert-butyl[1-(3,4,5-trimethoxybenzyloxy)-2-(S)-(3,4-dichlorophenyl)-5-hydroxy-pentan-2-yl]methylcarbamate (1.25 g). Thereafter, similar to Example 51(d), the title compound was obtained (1.62 g, >100%) by use of tert-butyl[1-(3,4,5-trimethoxybenzyloxy)-2-(S)-(3,4-dichlorophenyl)-5-oxo-pentan-2-yl]methylcarbamate (1.0 g).

MS (FAB) m/z 761 ((M+H)$^+$)

$^1$H-NMR (400 MHz, CDCl$_3$)δ ppm: 1.90 (9H, brs), 1.60-1.72 (4H, m), 1.92-2.08 (2H, m), 2.30-2.50 (6H, m), 2.82-2.90 (1H, m), 2.95-3.02 (1H, m), 3.13 (3H, s), 3.81 (6H, s), 3.82 (3H, s), 3.83-3.90 (2H, m), 4.01 (1H, d, J=17.0 Hz), 4.33 (1H, d, J=17.0 Hz), 4.35-4.38 (2H, m), 6.37 (2H, s), 7.10 (1H, dd, J=2.0, 8.5 Hz), 7.25-7.37 (6H, m).

Example 66(d)

Synthesis of 1-(3,4,5-trimethoxybenzyloxy)-2-(S)-(3,4-dichlorophenyl)-2-(N-methylamino)-5-[spiro(benzo(c)thiophene-(2S)-oxido-1(3H),4'-piperidin)-1'-yl]pentane

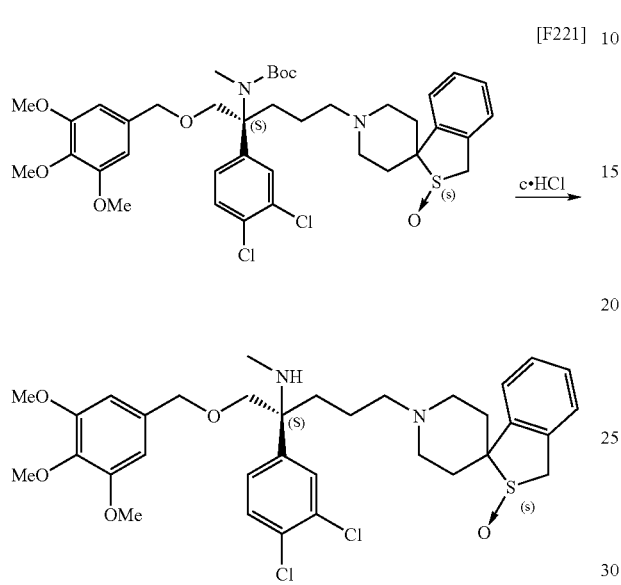

Similar to Example 26(i), the title compound was obtained (1.14 g, 95.7%) by use of tert-butyl{1-(3,4,5-trimethoxybenzyloxy)-2-(S)-(3,4-dichlorophenyl)-5-[spiro(benzo(c)thiophene-(2S)-oxido-1(3H),4'-piperidin)-1'-yl]pentan-2-yl}methylcarbamate (1.62 g).

MS (FAB) m/z 661 ((M+H)$^+$)

$^1$H-NMR (400 MHz, CDCl$_3$)δ ppm: 1.32-1.83 (6H, m), 1.90-2.02 (1H, m), 2.19 (3H, s), 2.27-2.46 (6H, m), 2.76-2.98 (2H, m), 3.59-3.69 (2H, m), 3.83 (6H, s), 3.84 (3H, s), 4.00 (1H, d, J=17.0 Hz), 4.32 (1H, d, J=17.0 Hz), 4.44 (1H, d, J=12.0 Hz), 4.48 (1H, d, J=12.0 Hz), 6.46 (2H, s), 7.24-7.36 (5H, m), 7.39 (1H, d, J=8.5 Hz), 7.54 (1H, d, J=2.0 Hz).

Example 66(e)

Synthesis of 1-{1-(3,4,5-trimethoxybenzyloxy)-2-(S)-(3,4-dichlorophenyl)-5-[spiro(benzo(c)thiophene-(2S)-oxido-1(3H),4'-piperidin)-1'-yl]pentan-2-yl}-3-cyclohexyl-1-methylurea

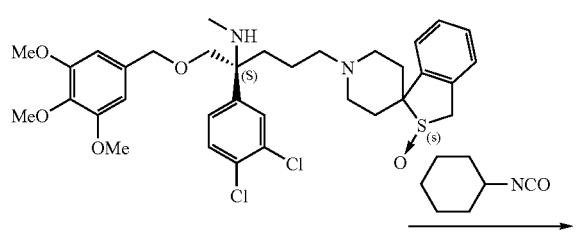

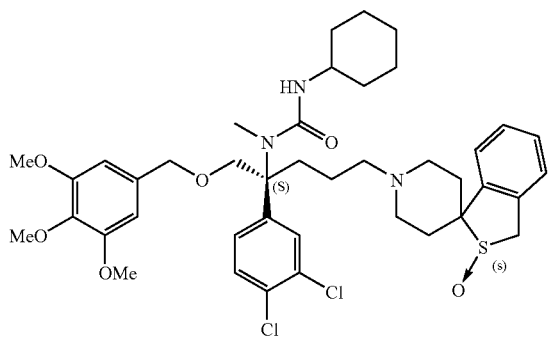

Similar to Example 48(a), the title compound was obtained (55 mg, 92.5%) by use of 1-(3,4,5-trimethoxybenzyloxy)-2-(S)-(3,4-dichlorophenyl)-2-(N-methylamino)-5-[spiro(benzo(c)thiophene-(2S)-oxido-1(3H),4'-piperidin)-1'-yl]pentane (50 mg) and cyclohexyl isocyanate (50 μL).

MS (FAB) m/z 786 ((M+H)$^+$)

$^1$H-NMR (400 MHz, CDCl$_3$)δ ppm: 0.78-0.94 (2H, m), 1.02-1.44 (4H, m), 1.47-1.78 (5H, m), 1.88-2.12 (3H, m), 2.15-2.24 (1H, m), 2.28-2.45 (6H, m), 2.78-2.86 (1H, m), 2.90-2.98 (4H, m), 3.42-3.52 (2H, m), 3.82 (6H, s), 3.82 (3H, s), 3.94-4.04 (3H, m), 4.30-4.44 (3H, m), 4.58 (1H, d, J=7.5 Hz), 6.39 (2H, s), 7.17 (1H, dd, J=2.0, 8.0 Hz), 7.27-7.35 (4H, m), 7.37 (1H, d, J=8.5 Hz), 7.42 (1H, d, J=2.0 Hz).

Example 66(f)

Synthesis of 1-{1-(3,4,5-trimethoxybenzyloxy)-2-(S)-(3,4-dichlorophenyl)-5-[spiro(benzo(c)thiophene-(2S)-oxido-1(3H),4'-piperidin)-1'-yl]pentan-2-yl}-3-cyclohexyl-1-methylurea hydrochloride (Compound No. 599)

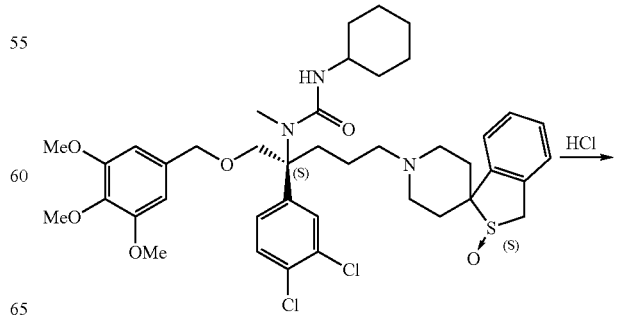

-continued

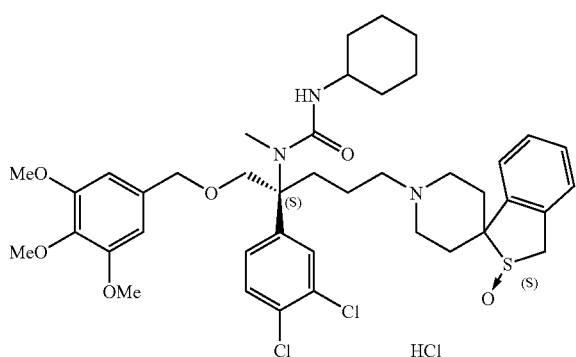

Similar to Example 26(k), the title compound was obtained as white powder (45 mg, 78.1%) by use of 1-{1-(3,4,5-trimethoxybenzyloxy)-2-(S)-(3,4-dichlorophenyl)-5-[spiro(benzo(c)thiophene-(2S)-oxido-1(3H),4'-piperidin)-1'-yl]pentan-2-yl}-3-cyclohexyl-1-methylurea (55 mg).

$^1$H-NMR (400 MHz, DMSO-d$_6$)δ ppm: 0.98-1.32 (7H, m), 1.47-1.80 (7H, m), 1.92-2.02 (1H, m), 2.08-2.42 (4H, m), 2.81-2.93 (1H, m), 2.97 (3H, s), 3.02-3.40 (5H, m), 3.60 (3H, s), 3.71 (6H, s), 3.84 (1H, d, J=10.0 Hz), 3.96 (1H, d, J=10.0 Hz), 4.09 (1H, d, J=17.0 Hz), 4.32-4.42 (2H, m), 4.66 (1H, d, J=17.0 Hz), 6.00-6.10 (1H, m), 6.45 (2H, s), 7.24 (1H, dd, J=2.0, 8.5 Hz), 7.30-7.50 (5H, m), 7.53 (1H, d, J=8.5 Hz), 10.78 (1H, br).

Example 67(a)

Synthesis of 1-{1-(3,4,5-trimethoxybenzyloxy)-2-(S)-(3,4-dichlorophenyl)-5-[spiro(benzo(c)thiophene-(2S)-oxido-1(3H), 41-piperidin)-1'-yl]pentan-2-yl}-3-(3-fluorophenyl)-1-methylurea

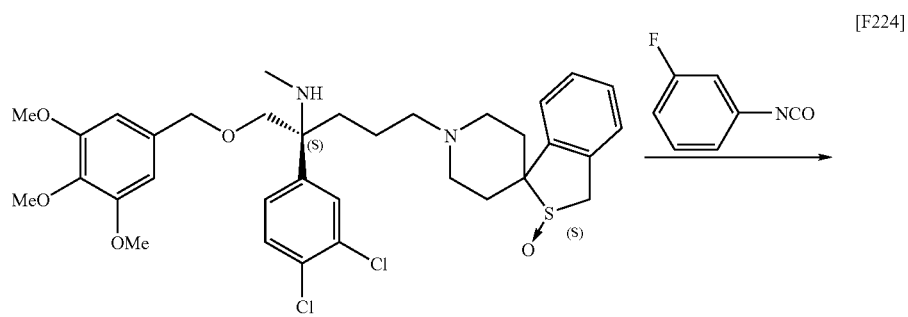

[F224]

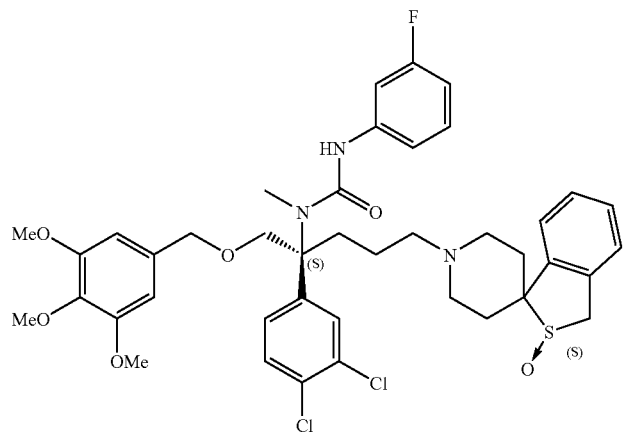

Similar to Example 48(a), the title compound was obtained (50 mg, 82.8%) by use of 1-(3,4,5-trimethoxybenzyloxy)-2-(S)-(3,4-dichlorophenyl)-2-(N-methylamino)-5-[spiro(benzo(c)thiophene-(2S)-oxido-1(3H),4'-piperidin)-1'-yl]pentane (50 mg) and 3-fluorophenyl isocyanate (50 μL).

MS (FAB) m/z 798 ((M+H)$^+$)

$^1$H-NMR (400 MHz, CDCl$_3$)δ ppm: 1.20-1.42 (2H, m), 1.52-1.62 (1H, m), 1.88-1.98 (1H, m), 2.03-2.12 (2H, m), 2.25-2.44 (6H, m), 2.71-2.79 (1H, m), 2.86-2.94 (1H, m), 3.08 (3H, s), 3.78 (6H, s), 3.83 (3H, s), 3.99 (1H, d, J=6.5 Hz), 4.00 (1H, d, J=17.0 Hz), 4.08-4.17 (1H, m), 4.32 (1H, d, J=17.0 Hz), 4.52 (2H, s), 6.47 (2H, s), 6.50 (1H, dd, J=1.5, 8.0 Hz), 6.59 (1H, dt, J=1.5, 8.0 Hz), 6.92 (1H, dt, J=1.5, 8.0 Hz), 6.99-7.06 (1H, m), 7.20 (1H, dd, J=2.0, 8.5 Hz), 7.24-7.36 (5H, m), 7.46 (1H, d, J=2.0 Hz), 7.49-7.51 (1H, m).

Example 67(b)

Synthesis of 1-{1-(3,4,5-trimethoxybenzyloxy)-2-(S)-(3,4-dichlorophenyl)-5-[spiro(benzo(c)thiophene-(2S)-oxido-1(3H),4'-piperidin)-1'-yl]pentan-2-yl}-3-(3-fluorophenyl)-1-methylurea hydrochloride (Compound No. 615)

[F225]

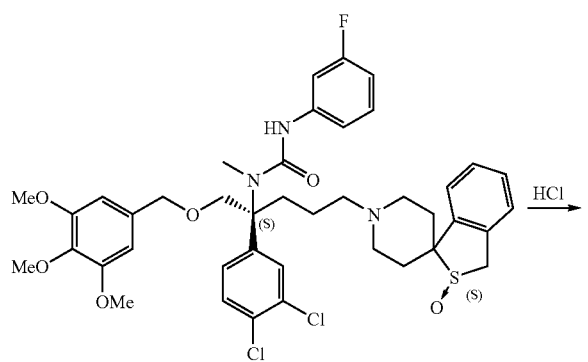

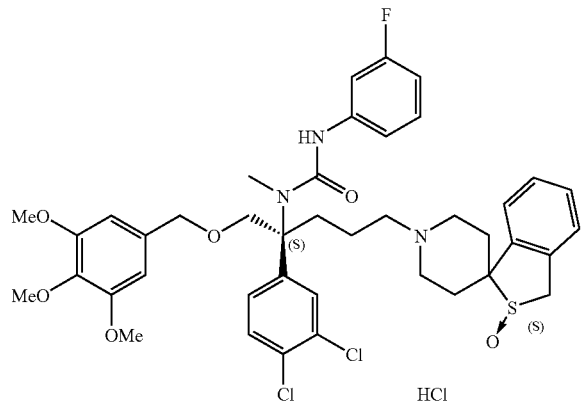

Similar to Example 26(k), the title compound was obtained as white powder (40 mg, 76.5%) by use of 1-{1-(3,4,5-trimethoxybenzyloxy)-2-(S)-(3,4-dichlorophenyl)-5-[spiro(benzo(c)thiophene-(2S)-oxido-1(3H),4'-piperidin)-1'-yl]pentan-2-yl}-3-(3-fluorophenyl)-1-methylurea (50 mg).

$^1$H-NMR (400 MHz, DMSO-d$_6$)δ ppm: 1.62-1.87 (2H, m), 1.93-2.02 (1H, m), 2.17-2.48 (4H, m), 2.77-2.89 (1H, m), 3.00-3.24 (7H, m), 3.50-3.67 (5H, m), 3.70 (6H, s), 3.92 (1H, d, J=10.0 Hz), 4.05 (1H, d, J=10.0 Hz), 4.09 (1H, d, J=17.0 Hz), 4.38 (1H, d, J=12.0 Hz), 4.42 (1H, d, J=12.0 Hz), 4.66 (1H, d, J=17.0 Hz), 6.46 (2H, s), 6.66-6.76 (1H, m), 7.11-7.45 (8H, m), 7.52-7.61 (2H, m), 8.73 (1H, s), 10.62 (1H, br).

Example 68(a)

Synthesis of 1-{1-(3,4,5-trimethoxybenzyloxy)-2-(S)-(3,4-dichlorophenyl)-5-[spiro(benzo(c)thiophene-(2S)-oxido-1(3H),4'-piperidin)-1'-yl]pentan-2-yl}-3-[3-(trifluoromethyl)phenyl]-1-methylurea

[F226]

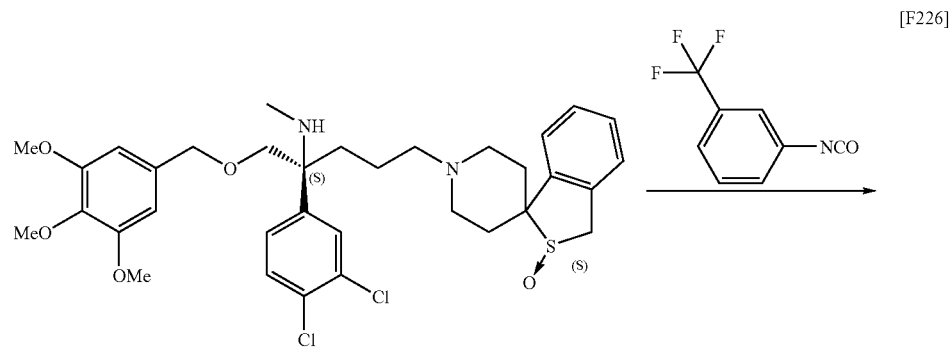

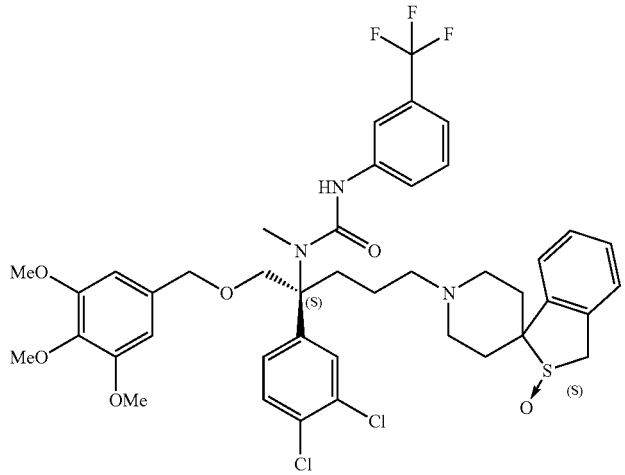

Similar to Example 48(a), the title compound was obtained (60 mg, 93.5%) by use of 1-(3,4,5-trimethoxybenzyloxy)-2-(S)-(3,4-dichlorophenyl)-2-(N-methylamino)-5-[spiro(benzo(c)thiophene-(2S)-oxido-1(3H),4'-piperidin)-1'-yl]pentane (50 mg) and 3-trifluoromethylphenyl isocyanate (50 μL).

MS (FAB) m/z 848 ((M+H)$^+$)

$^1$H-NMR (400 MHz, CDCl$_3$)δ ppm: 1.20-1.42 (2H, m), 1.52-1.60 (1H, m), 1.88-1.98 (1H, m), 2.03-2.10 (2H, m), 2.23-2.44 (7H, m), 2.70-2.78 (1H, m), 2.85-2.92 (1H, m), 3.09 (3H, s), 3.78 (6H, s), 3.83 (3H, s), 3.97-4.03 (2H, m), 4.08-4.17 (1H, m), 4.32 (1H, d, J=17.0 Hz), 4.54 (2H, s), 6.47 (2H, s), 6.98-7.02 (1H, m), 7.12-7.23 (3H, m), 7.24-7.36 (5H, m), 7.45 (1H, d, J=2.0 Hz), 7.61 (1H, br).

Example 68(b)

Synthesis of 1-{1-(3,4,5-trimethoxybenzyloxy)-2-(S)-(3,4-dichlorophenyl)-5-[spiro(benzo(c)thiophene-(2S)-oxido-1(3H),4'-piperidin)-1'-yl]pentan-2-yl}-3-[3-(trifluoromethyl)phenyl]-1-methylurea hydrochloride (Compound No. 616)

[F227]

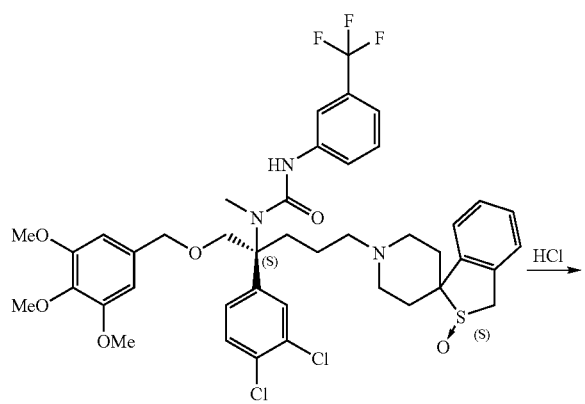

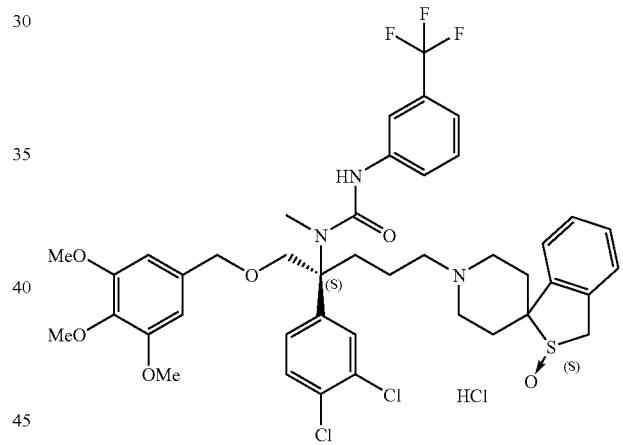

Similar to Example 26(k), the title compound was obtained as white powder (53 mg, 84.7%) by use of 1-{1-(3,4,5-trimethoxybenzyloxy)-2-(S)-(3,4-dichlorophenyl)-5-[spiro(benzo(c)thiophene-(2S)-oxido-1(3H),4'-piperidin)-1'-yl]pentan-2-yl}-3-[3-(trifluoromethyl)phenyl]-1-methylurea (60 mg).

$^1$H-NMR (400 MHz, DMSO-d$_6$)δ ppm: 1.63-1.87 (2H, m), 1.97 (1H, d, J=15.0 Hz), 2.18-2.47 (4H, m), 2.77-2.88 (1H, m), 3.03-3.25 (7H, m), 3.50-3.58 (6H, m), 3.70 (6H, s), 3.93 (1H, d, J=10.0 Hz), 4.06 (1H, d, J=10.0 Hz), 4.09 (1H, d, J=17.0 Hz), 4.38 (1H, d, J=12.0 Hz), 4.43 (1H, d, J=12.0 Hz), 4.66 (1H, d, J=17.0 Hz), 6.46 (2H, s), 7.24 (1H, d, J=7.5 Hz), 7.28-7.46 (5H, m), 7.52-7.58 (2H, m), 7.65 (1H, d, J=8.0 Hz), 7.82 (1H, s), 8.87 (1H, s), 10.60 (1H, br).

Example 69(a)

Synthesis of 1-{1-(3,4,5-trimethoxybenzyloxy)-2-(S)-(3,4-dichlorophenyl)-5-[spiro(benzo(c)thiophene(2S)-oxido-1(3H),4'-piperidine)-1'-yl]pentan-2-yl}-3-(2-fluorobenzyl)-1-methylurea

Example 69(b)

Synthesis of 1-{1-(3,4,5-trimethoxybenzyloxy)-2-(S)-(3,4-dichlorophenyl)-5-[spiro(benzo(c)thiophene(2S)-oxido-1(3H),4'-piperidine)-1'-yl]pentan-2-yl}-3-(2-fluorobenzyl)-1-methylurea hydrochloride (Compound No. 617)

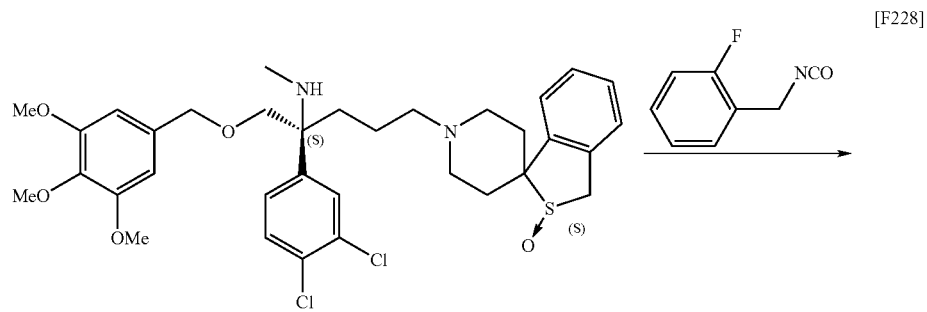

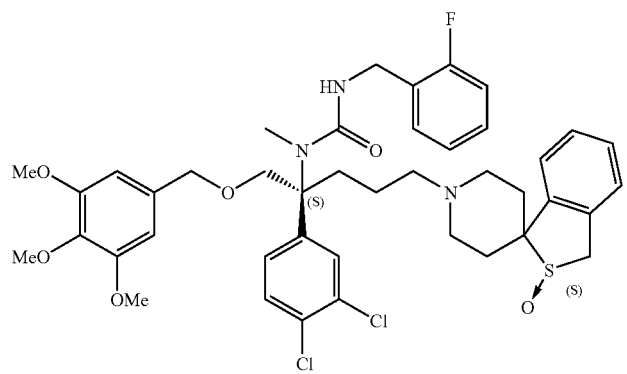

Similar to Example 48(a), the title compound was obtained (50 mg, 81.4%) by use of 1-(3,4,5-trimethoxybenzyloxy)-2-(S)-(3,4-dichlorophenyl)-2-(N-methylamino)-5-[spiro(benzo(c)thiophene-(2S)-oxido-1(3H),4'-piperidine)-1'-yl]pentane (50 mg) and 2-fluorobenzyl isocyanate (50 μL).

MS (FAB) m/z 812 ((M+H)$^+$)

$^1$H-NMR (400 MHz, CDCl$_3$)δ ppm: 1.30–1.40 (2H, m), 1.52–1.60 (1H, m), 1.88–2.10 (2H, m), 2.14–2.45 (7H, m), 2.74–2.82 (1H, m), 2.88–2.94 (1H, m), 3.01 (3H, s), 3.80 (6H, s), 3.82 (3H, s), 3.84–4.04 (3H, m), 4.21–4.39 (5H, m), 5.13 (1H, t, J=6.0 Hz), 6.37 (2H, s), 6.93–7.06 (2H, m), 7.09–7.24 (3H, m), 7.25–7.38 (6H, m).

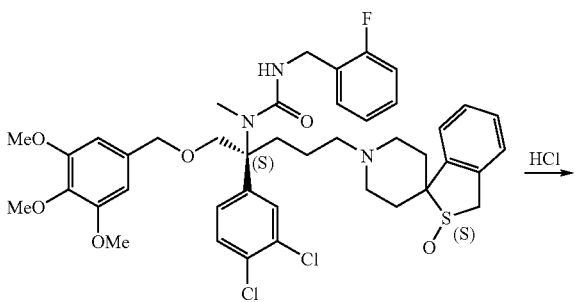

-continued

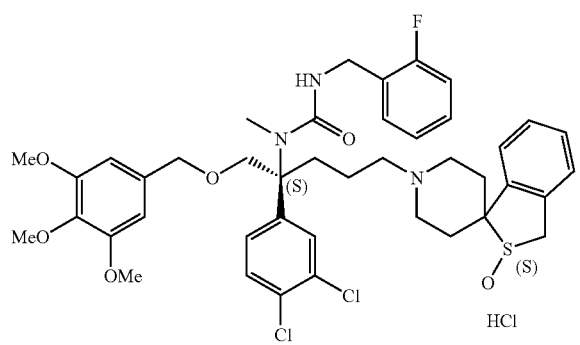

Similar to Example 26(k), the title compound was obtained as white powder (40 mg, 76.6%) by use of 1-{1-(3,4,5-trimethoxybenzyloxy)-2-(S)-(3,4-dichlorophenyl)-5-[spiro(benzo(c)thiophene(2S)-oxido-1(3H),4'-piperidin)-1'-yl]pentan-2-yl}-3-(2-fluorobenzyl)-1-methylurea (50 mg).

$^1$H-NMR (400 MHz, DMSO-d$_6$) δ ppm: 1.59 (1H, br), 1.78 (1H, br), 1.96 (1H, d, J=15.0 Hz), 2.10-2.28 (2H, m), 2.32-2.46 (2H, m), 2.82-2.92 (1H, m), 2.98-3.28 (7H, m), 3.44-3.53 (6H, m), 3.71 (6H, s), 3.85 (1H, d, J=10.0 Hz), 3.97 (1H, d, J=10.0 Hz), 4.10 (1H, d, J=17.0 Hz), 4.17-4.22 (2H, m), 4.35 (1H, d, J=12.0 Hz), 4.39 (1H, d, J=12.0 Hz), 4.67 (1H, d J=17.0 Hz), 6.45 (2H, s), 7.03-7.13 (3H, m), 7.20-7.55 (8H, m), 10.79 (1H, br).

Example 70(a)

Synthesis of 1-{1-(3,4,5-trimethoxybenzyloxy)-2-(S)-(3,4-dichlorophenyl)-5-[spiro(benzo(c)thiophene(2S)-oxido-1(3H),4'-piperidin)-1'-yl]pentan-2-yl}-3-(3-fluorobenzyl)-1-methylurea Similar to Example 48(a), the title compound was obtained (60 mg, 97.6%) by use of 1-(3,4,5-trimethoxybenzyloxy)-2-(S)-(3,4-dichlorophenyl)-2-(N-methylamino)-5-[spiro(benzo(c)thiophene-(2S)-oxido-1(3H),4'-piperidin)-1'-yl]pentane (50 mg) and 3-fluorobenzyl isocyanate (50 µL).

MS (FAB) m/z 812 ((M+H)$^+$)

$^1$H-NMR (400 MHz, CDCl$_3$) δ ppm: 1.34-1.43 (2H, m), 1.57 (1H, dd, J=2.0, 15.0 Hz), 1.78 (1H, br), 1.90-2.00 (1H, m), 2.02-2.12 (1H, m), 2.17-2.46 (7H, m), 2.77-2.84 (1H, m), 2.90-2.97 (1H, m), 3.03 (3H, s), 3.80 (6H, s), 3.82 (3H, s), 3.95-4.04 (3H, m), 4.23 (1H, dq, J=5.5, 15.0 Hz), 4.33 (1H, d, J=17.0 Hz), 4.37 (1H, d, J=12.0 Hz), 4.40 (1H, d, J=12.0 Hz), 5.12 (1H, t, J=5.5 Hz), 6.37 (2H, s), 6.76-6.93 (3H, m), 7.15 (1H, dd, J=2.0, 8.5 Hz), 7.18-7.37 (6H, m), 7.39 (1H, d, J=2.0 Hz).

Example 70(b)

Synthesis of 1-{1-(3,4,5-trimethoxybenzyloxy)-2-(S)-(3,4-dichlorophenyl)-5-[spiro(benzo(c)thiophene (2S)-oxido-1(3H),4'-piperidin)-1'-yl]pentan-2-yl}-3-(3-fluorobenzyl)-1-methylurea hydrochloride (Compound No. 618)

[F231]

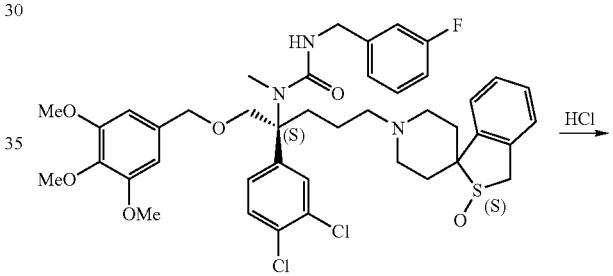

[F230]

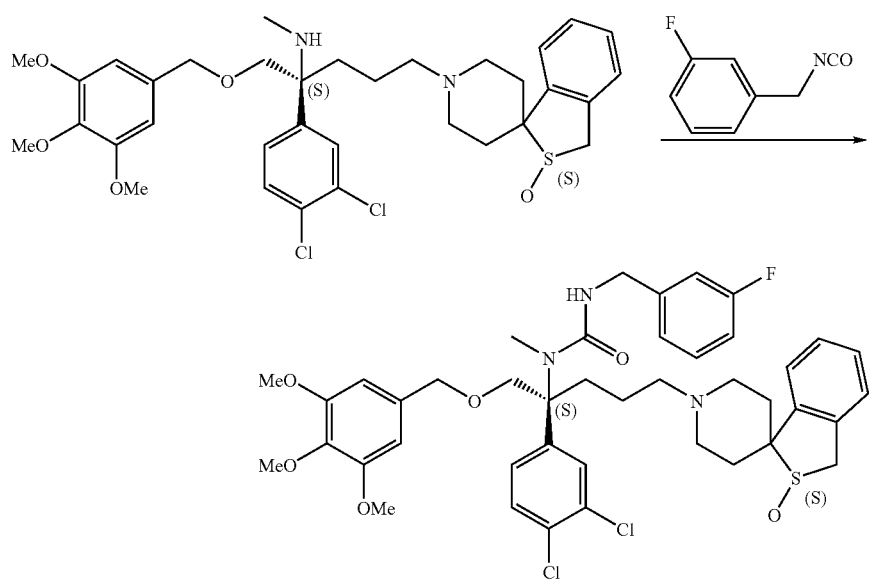

-continued

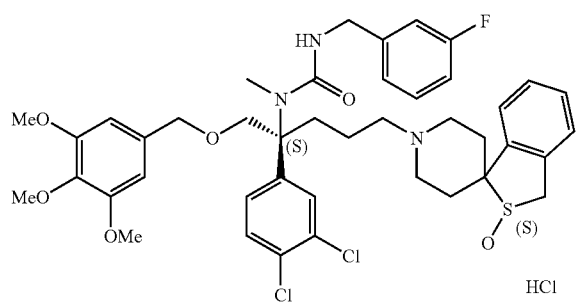

HCl

Similar to Example 26(k), the title compound was obtained as white powder (50 mg, 80.0%) by use of 1-{1-(3,4,5-trimethoxybenzyloxy)-2-(S)-(3,4-dichlorophenyl)-5-[spiro(benzo(c)thiophene(2S)-oxido-1(3H),4'-piperidin)-1'-yl]pentan-2-yl}-3-(3-fluorobenzyl)-1-methylurea (60 mg).

$^1$H-NMR (400 MHz, DMSO-$d_6$)δ ppm: 1.57 (1H, br), 1.77 (1H, br), 1.96 (1H, d, J=14.5 Hz), 2.10-2.46 (4H, m), 2.74-2.87 (1H, m), 2.98-3.20 (7H, m), 3.45-3.63 (6H, m), 3.71 (6H, s), 3.86 (1H, d, J=10.0 Hz), 3.97 (1H, d, J=10.0 Hz), 4.05-4.23 (3H, m), 4.35 (1H, d, J=12.0 Hz), 4.39 (1H, d, J=12.0 Hz), 4.67 (1H, d, J=17.0 Hz), 6.45 (2H, s), 6.93-7.05 (3H, m), 7.10-7.18 (1H, m), 7.23-7.48 (6H, m), 7.51 (1H, d, J=8.5 Hz), 10.51 (1H, br).

Example 71(a)

Synthesis of 1-{1-(3,4,5-trimethoxybenzyloxy)-2-(S)-(3,4-dichlorophenyl)-5-[spiro(benzo(c)thiophene(2S)-oxido-1(3H),4'-piperidin)-1'-yl]pentan-2-yl}-3-(4-fluorobenzyl)-1-methylurea Similar to Example 48(a), the title compound was obtained (55 mg, 89.5%) by use of 1-(3,4,5-trimethoxybenzyloxy)-2-(S)-(3,4-dichlorophenyl)-2-(N-methylamino)-5-[spiro(benzo(c)thiophene-(2S)-oxido-1(3H),4'-piperidin)-1'-yl]pentane (50 mg) and 4-fluorobenzyl isocyanate (50 μL).

MS (FAB) m/z 812 ((M+H)$^+$)

$^1$H-NMR (400 MHz, CDCl$_3$)δ ppm: 1.32-1.43 (2H, m), 1.53-1.60 (1H, m), 1.90-2.10 (2H, m), 2.17-2.45 (7H, m), 2.75-2.83 (1H, m), 2.90-2.97 (1H, m), 3.02 (3H, s), 3.80 (6H, s), 3.83 (3H, s), 3.93-4.04 (3H, m), 4.11-4.25 (2H, m), 4.33 (1H, d, J=17.0 Hz), 4.38 (2H, s), 5.03 (1H, t, J=5.5 Hz), 6.36 (2H, s), 6.90-6.96 (2H, m), 6.99-7.04 (2H, m), 7.14 (1H, dd, J=2.0, 8.5 Hz), 7.25-7.36 (5H, m), 7.38 (1H, d, J=2.0 Hz).

Example 71(b)

Synthesis of 1-{1-(3,4,5-trimethoxybenzyloxy)-2-(S)-(3,4-dichlorophenyl)-5-[spiro(benzo(c)thiophene(2S)-oxido-1(3H),4'-piperidin)-1'-yl]pentan-2-yl}-3-(4-fluorobenzyl)-1-methylurea hydrochloride
(Compound No. 621)

[F233]

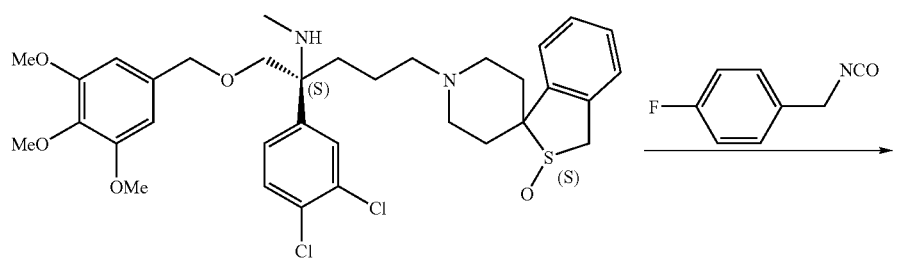

HCl

[F232]

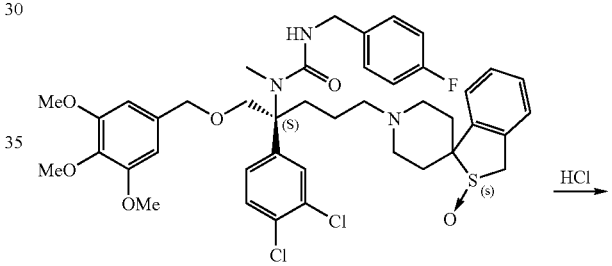

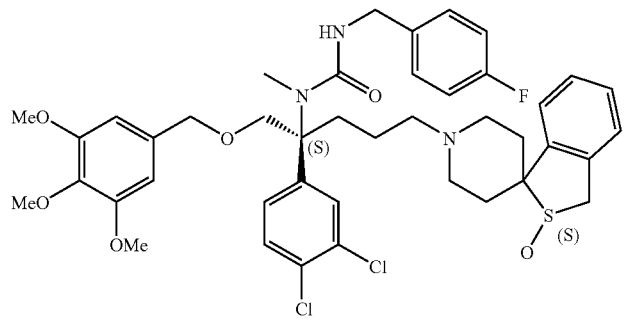

217

-continued

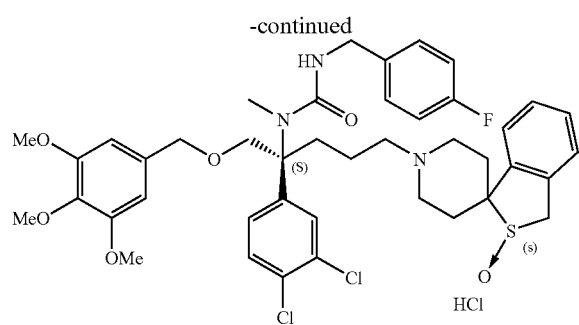

HCl

Similar to Example 26(k), the title compound was obtained as white powder (40 mg, 69.6%) by use of 1-{1-(3,4,5-trimethoxybenzyloxy)-2-(S)-(3,4-dichlorophenyl)-5-[spiro(benzo(c)thiophene(2S)-oxido-1(3H),4'-piperidin)-1'-yl]pentan-2-yl}-3-(4-fluorobenzyl)-1-methylurea (55 mg).

$^1$H-NMR (400 MHz, DMSO-d$_6$)δ ppm: 1.52-1.65 (1H, m), 1.73-1.86 (1H, m), 1.92-2.00 (1H, m), 2.12-2.28 (2H, m), 2.34-2.47 (2H, m), 2.83-2.97 (1H, m), 2.99-73.18 (6H, m), 3.45-3.64 (7H, m), 3.71 (6H, s), 3.85 (1H, d, J=10.0 Hz), 3.98 (1H, d, J=10.0 Hz), 4.06-4.16(3H, m), 4.34 (1H, d, J=12.0 Hz), 4.39 (1H, d, J=12.0 Hz), 4.66 (1H, d, J=17.0 Hz), 6.44 (2H, s), 7.04-7.13 (3H, m), 7.17-7.27 (3H, m), 7.31-7.45 (3H, m), 7.46 (1H, d, J=2.0 Hz), 7.53 (1H, d, J=8.5 Hz), 10.91 (1H, br).

Table 1 shows other compounds and salts of the present invention produced in accordance with any of the production processes described above.

TABLE 1

| Compound No. | R¹ | R² | R³ | R⁴ | Spiro | R⁵ | X¹ | X² | X³ | X⁴ | n1 | n2 | Salt | Quaternary carbon | Form |
|---|---|---|---|---|---|---|---|---|---|---|---|---|---|---|---|
| 47 | Propionyl | Diphenylmethyl | —SOCH₂— | | | CH₃ | NCH₃ | Single bond | 3-Cl | 4-Cl | 1 | 1 | HCl | S | Amorphous |
| 48 | Methyl | 3,4,5-Trimethoxyphenyl | CONH₂ | H | | CH₃ | O | Single bond | 3-Cl | 4-Cl | 1 | 1 | Free | racemic | Amorphous |
| 49 | isobutyryl | 2,2-Diphenylethyl | —NHCOCH₂— | | | CH₃ | NCH₃ | Single bond | 3-Cl | 4-Cl | 1 | 1 | HCl | S | Amorphous |
| 50 | iso-Butyryl | Diphenylmethyl | —SOCH₂— | | S | CH₃ | NCH₃ | Single bond | 3-Cl | 4-Cl | 1 | 1 | HCl | S | Amorphous |
| 51 | iso-Butyryl | 2,2-Diphenylethyl | —SO₂CH₂— | | | CH₃ | NCH₃ | Single bond | 3-Cl | 4-Cl | 1 | 1 | HCl | S | Amorphous |
| 52 | iso-Butyryl | Diphenylmethyl | —SOCH₂— | | | CH₃ | NCH₃ | Single bond | 3-Cl | 4-Cl | 1 | 1 | HCl | R | Amorphous |
| 53 | iso-Butyryl | 2,2-Diphenylethyl | —SOCH₂— | | | CH₃ | NCH₃ | Single bond | 3-Cl | 4-Cl | 1 | 1 | HCl | S | Amorphous |
| 54 | Difluoroacetyl | 2,2-Diphenylethyl | —SOCH₂— | | | CH₃ | NCH₃ | Single bond | 3-Cl | 4-Cl | 1 | 0 | Free | racemic | Amorphous |
| 55 | Benzyl | H | CONH₂ | H | | CH₃ | O | Single bond | 3-Cl | 4-Cl | 1 | 1 | HCl | S | Amorphous |
| 56 | Acetyl | Diphenylmethyl | —SOCH₂— | | S | CH₃ | NCH₃ | Single bond | 3-Cl | 4-Cl | 1 | 1 | Free | racemic | Amorphous |
| 57 | Acetyl | 2,2-Diphenylethyl | —SOCH₂— | | S | CH₃ | NCH₃ | Single bond | 3-Cl | 4-Cl | 1 | 1 | HCl | S | Amorphous |
| 58 | 4-Cyanophenyl | 3,4,5-Trimethoxyphenyl | CONH₂ | H | | CH₃ | O | Single bond | 3-Cl | 4-Cl | 1 | 1 | Free | racemic | Amorphous |
| 59 | 4-Cyanobenzyl | 3,4,5-Trimethoxyphenyl | CONH₂ | H | | CH₃ | O | Single bond | 3-Cl | 4-Cl | 1 | 1 | Free | racemic | Amorphous |
| 60 | 3,4,5-Trimethoxyphenylacetyl | 3,4,5-Trimethoxyphenyl | NHAc | H | | CH₃ | O | Single bond | 3-Cl | 4-Cl | 1 | 1 | Free | racemic | Amorphous |
| 61 | 3,4,5-Trimethoxybenzyl | 1-Methyl-1H-indol-3-yl | CONH₂ | H | | CH₃ | O | Single bond | 3-Cl | 4-Cl | 1 | 1 | Free | racemic | Amorphous |
| 62 | 3,4,5-Trimethoxybenzyl | 4-Oxo-4H-chromen-2-yl | CONH₂ | H | | CH₃ | O | Single bond | 3-Cl | 4-Cl | 1 | 1 | Free | racemic | Amorphous |
| 63 | 3,4,5-Trimethoxybenzyl | 2-Benzofuranyl | CONH₂ | H | | CH₃ | O | Single bond | 3-Cl | 4-Cl | 1 | 1 | Free | racemic | Amorphous |
| 64 | 3,4,5-Trimethoxybenzyl | 3-Benzothienyl | CONH₂ | H | | CH₃ | O | Single bond | 3-Cl | 4-Cl | 1 | 1 | Free | racemic | Amorphous |
| 65 | 3,4,5-Trimethoxybenzyl | Methyl | CONH₂ | H | | CH₃ | O | Single bond | 3-Cl | 4-Cl | 1 | 0 | Free | racemic | Amorphous |
| 66 | 3,4,5-Trimethoxybenzyl | H | CONH₂ | H | | CH₃ | O | Single bond | 3-Cl | 4-Cl | 1 | 1 | Free | racemic | Amorphous |
| 67 | 3,4,5-Trimethoxybenzyl | Methyl | NHAc | H | | CH₃ | O | Single bond | 3-Cl | 4-Cl | 1 | 0 | Free | racemic | Amorphous |
| 68 | 3,4,5-Trimethoxybenzyl | H | CONH₂ | H | | CH₃ | O | Single bond | 3-Cl | 4-Cl | 1 | 0 | Free | racemic | Amorphous |
| 69 | 3,4,5-Trimethoxybenzyl | Methyl | CONH₂ | H | | CH₃ | O | Single bond | 3-Cl | 4-Cl | 1 | 1 | Free | racemic | Amorphous |
| 70 | 3,4,5-Trimethoxybenzyl | n-Propyl | CONH₂ | H | | CH₃ | O | Single bond | 3-Cl | 4-Cl | 1 | 1 | Free | racemic | Amorphous |
| 71 | 3,4,5-Trimethoxybenzyl | 3,4,5-Trimethoxyphenyl | CONH₂ | H | | CH₃ | O | Single bond | 3-Cl | 4-Cl | 1 | 1 | Free | racemic | Amorphous |
| 72 | 3,4,5-Trimethoxybenzyl | Cyclopropyl | CONH₂ | H | | CH₃ | O | Single bond | 3-Cl | 4-Cl | 1 | 1 | Free | racemic | Amorphous |
| 73 | 3,4,5-Trimethoxybenzyl | Cyclobutyl | CONH₂ | H | | CH₃ | O | Single bond | 3-Cl | 4-Cl | 1 | 1 | Free | racemic | Amorphous |
| 74 | 3,4,5-Trimethoxybenzyl | Cyclopentyl | CONH₂ | H | | CH₃ | O | Single bond | 3-Cl | 4-Cl | 1 | 1 | Free | racemic | Amorphous |
| 75 | 3,4,5-Trimethoxybenzyl | Ethoxycarbonylmethyl | CONH₂ | H | | CH₃ | O | Single bond | 3-Cl | 4-Cl | 1 | 1 | HCl | racemic | Amorphous |
| 76 | 3,4,5-Trimethoxybenzyl | Ethyl | CONH₂ | H | | CH₃ | O | Single bond | 3-Cl | 4-Cl | 1 | 0 | HCl | racemic | Amorphous |
| 77 | 3,4,5-Trimethoxybenzyl | Ethoxymethyl | CONH₂ | H | | CH₃ | O | Single bond | 3-Cl | 4-Cl | 1 | 1 | Free | racemic | Amorphous |
| 78 | 3,4,5-Trimethoxybenzyl | Methansulphonyl | CONH₂ | H | | CH₃ | O | Single bond | 3-Cl | 4-Cl | 1 | 0 | Free | racemic | Amorphous |
| 79 | 3,4,5-Trimethoxybenzyl | Phenylthiomethyl | CONH₂ | H | | CH₃ | O | Single bond | 3-Cl | 4-Cl | 1 | 1 | HCl | racemic | Amorphous |
| 80 | 3,4,5-Trimethoxybenzoyl | 3,4,5-Trimethoxyphenyl | —SOCH₂— | | S | CH₃ | O | Single bond | 3-Cl | 4-Cl | 1 | 1 | HCl | S | Amorphous |
| 81 | 3,4,5-Trimethoxybenzoyl | 3,4,5-Trimethoxyphenyl | —SOCH₂— | | S | CH₃ | O | Single bond | 3-Cl | 4-Cl | 1 | 1 | HCl | R | Amorphous |
| 82 | 3,4,5-Trimethoxybenzoyl | 3,4,5-Trimethoxyphenyl | —SOCH₂— | | S | CH₂CH₃ | O | Single bond | 3-Cl | 4-Cl | 1 | 1 | HCl | racemic | Amorphous |
| 83 | 3,4,5-Trimethoxybenzoyl | Cyclohexyl | CONH₂ | H | | CH₃ | NCH₃ | Single bond | 3-Cl | 4-Cl | 1 | 1 | Free | racemic | Amorphous |
| 84 | 3,4,5-Trimethoxybenzoyl | H | CONH₂ | H | | CH₃ | NCH₃ | Single bond | 3-Cl | 4-Cl | 1 | 0 | Free | racemic | Amorphous |
| 85 | 3,4,5-Trimethoxybenzoyl | 2,2-Dimethylpropyl | CONH₂ | H | | CH₃ | NCH₃ | Single bond | 3-Cl | 4-Cl | 1 | 1 | Free | racemic | Amorphous |
| 86 | 3,4,5-Trimethoxybenzoyl | 3,4,5-Trimethoxyphenyl | CONH₂ | H | | CH₃ | NCH₃ | Single bond | 3-Cl | 4-Cl | 1 | 1 | Free | racemic | Amorphous |
| 87 | 3,4,5-Trimethoxybenzoyl | 3,4,5-Trimethoxyphenyl | CONH₂ | H | | CH₃ | NCH₃ | Single bond | 3-Cl | 4-Cl | 1 | 1 | Free | racemic | Amorphous |
| 88 | 3,4,5-Trimethoxybenzoyl | Phenyl | CONH₂ | H | | CH₃ | NCH₃ | Single bond | 3-Cl | 4-Cl | 1 | 1 | HCl | racemic | Amorphous |
| 89 | 3,4,5-Trimethoxybenzoyl | Cyclohexyl | CONH₂ | H | | CH₃ | NCH₃ | Single bond | 3-Cl | 4-Cl | 1 | 1 | Free | racemic | Amorphous |

TABLE 1-continued

| Compound No. | R¹ | R² | R³ | R⁴ | Spiro | R⁵ | X¹ | X² | X³ | X⁴ | n1 | n2 | Salt | Quaternary carbon | Form |
|---|---|---|---|---|---|---|---|---|---|---|---|---|---|---|---|
| 90 | 3,4,5-Trimethoxybenzoyl | Benzyl | CONH₂ | H | | CH₃ | NCH₃ | Single bond | 3-Cl | 4-Cl | 1 | 1 | HCl | racemic | Amorphous |
| 91 | 3,4,5-Trimethoxybenzoyl | H | CONH₂ | H | | CH₃ | O | Single bond | 3-Cl | 4-Cl | 1 | 0 | Free | racemic | Amorphous |
| 92 | 3,4,5-Trimethoxybenzoyl | Benzylaminomethyl | —SOCH₂— | | | CH₃ | NCH₃ | Single bond | 3-Cl | 4-Cl | 1 | 1 | 2HCl | racemic | Amorphous |
| 93 | 3,4,5-Trimethoxybenzoyl | 1-Pipelidyl | —SOCH₂— | | s | CH₃ | NCH₃ | Single bond | 3-Cl | 4-Cl | 1 | 1 | HCl | racemic | Amorphous |
| 94 | 3,4,5-Trimethoxybenzoyl | 1-Pyrrolidinyl | —SOCH₂— | | s | CH₃ | NCH₃ | Single bond | 3-Cl | 4-Cl | 1 | 1 | HCl | racemic | Amorphous |
| 95 | 3,4,5-Trimethoxybenzoyl | Phenylaminomethyl | —SOCH₂— | | s | CH₃ | NCH₃ | Single bond | 3-Cl | 4-Cl | 1 | 1 | HCl | racemic | Amorphous |
| 96 | 3,4,5-Trimethoxybenzoyl | H | —SOCH₂— | | s | CH₃ | NCH₃ | Single bond | 3-Cl | 4-Cl | 1 | 1 | HCl | S | Amorphous |
| 97 | 3,4,5-Trimethoxybenzoyl | H | —SOCH₂— | | s | CH₃ | NCH₃ | Single bond | 3-Cl | 4-Cl | 1 | 0 | 2HCl | R | Amorphous |
| 98 | 3,4,5-Trimethoxybenzoyl | 3,4,5-Trimethoxyphenyl | —SOCH₂— | | s | CH₃ | NCH₃ | Single bond | 3-Cl | 4-Cl | 1 | 0 | 2HCl | S | Amorphous |
| 99 | 3,4,5-Trimethoxybenzoyl | 3,4,5-Trimethoxyphenyl | —SOCH₂— | | s | CH₃ | NCH₃ | Single bond | 3-Cl | 4-Cl | 1 | 1 | HCl | R | Amorphous |
| 100 | 3,3,3-Trifluoropropionyl | 2,2-Diphenylethyl | —NHCOCH₂— | | | CH₃ | NCH₃ | Single bond | 3-Cl | 4-Cl | 1 | 1 | HCl | S | Amorphous |
| 101 | 3,3,3-Trifluoropropionyl | 2,2-Diphenylethyl | —SO₂CH₂— | | | CH₃ | NCH₃ | Single bond | 3-Cl | 4-Cl | 1 | 1 | HCl | S | Amorphous |
| 102 | 3,3,3-Trifluoropropionyl | Diphenylmethyl | —SO₂CH₂— | | | CH₃ | NCH₃ | Single bond | 3-Cl | 4-Cl | 1 | 1 | HCl | S | Amorphous |
| 103 | 3,3,3-Trifluoropropionyl | 2,2-Diphenylethyl | —SOCH₂— | | s | CH₃ | NCH₃ | Single bond | 3-Cl | 4-Cl | 1 | 1 | HCl | S | Amorphous |
| 104 | 2-Chlorobenzylaminocarbonyl | H | —SOCH₂— | | s | CH₃ | NCH₃ | Single bond | 3-Cl | 4-Cl | 1 | 0 | 2HCl | R | Amorphous |
| 105 | 2-Chloro-2-difluoroacetyl | 2,2-Diphenylethyl | —SOCH₂— | | s | CH₃ | NCH₃ | Single bond | 3-Cl | 4-Cl | 1 | 1 | HCl | S | Amorphous |
| 106 | Thiophene-2-carbonyl | Cyclopentyl | —SOCH₂— | | s | CH₃ | NCH₃ | Ester bond | 3-Cl | 4-Cl | 1 | 1 | HCl | racemic | Amorphous |
| 107 | Pyridin-2-carbonyl | Cyclopentyl | —SOCH₂— | | s | CH₃ | NCH₃ | Ester bond | 3-Cl | 4-Cl | 1 | 1 | HCl | racemic | Amorphous |
| 108 | Phenylacetyl | Cyclopentyl | —SOCH₂— | | s | CH₃ | NCH₃ | Ester bond | 3-Cl | 4-Cl | 1 | 1 | HCl | racemic | Amorphous |
| 109 | Phenoxycarbonyl | Cyclopentyl | —SOCH₂— | | s | CH₃ | O | Ester bond | 3-Cl | 4-Cl | 1 | 1 | HCl | racemic | Amorphous |
| 110 | Cyclohexylcarbonyl | Cyclopentyl | —SOCH₂— | | s | CH₃ | O | Ester bond | 3-Cl | 4-Cl | 1 | 1 | HCl | racemic | Amorphous |
| 111 | Benzyl | Ethyl | —NHCOCH₂— | H | | CH₃ | O | Ester bond | 3-Cl | 4-Cl | 1 | 1 | Free | racemic | Amorphous |
| 112 | Benzyl | Ethyl | —SOCH₂— | | s | CH₃ | NCH₃ | Ester bond | 3-Cl | 4-Cl | 1 | 1 | Free | racemic | Amorphous |
| 113 | Benzyl | iso-Propyl | —SOCH₂— | | s | CH₃ | O | Ester bond | 3-Cl | 4-Cl | 1 | 1 | HCl | racemic | Amorphous |
| 114 | Benzyl | iso-Propyl | —NHCOCH₂— | H | | CH₃ | O | Ester bond | 3-Cl | 4-Cl | 1 | 1 | HCl | racemic | Amorphous |
| 115 | Benzoyl | Cyclopentyl | —SOCH₂— | | s | CH₃ | O | Ester bond | 3-Cl | 4-Cl | 1 | 1 | HCl | racemic | Amorphous |
| 116 | 4-Methoxybenzoyl | Ethyl | —SOCH₂— | | s | CH₃ | NCH₃ | Ester bond | 3-Cl | 4-Cl | 1 | 1 | HCl | racemic | Amorphous |
| 117 | 3,5-Dimethoxybenzoyl | Ethyl | —SOCH₂— | | s | CH₃ | O | Ester bond | 3-Cl | 4-Cl | 1 | 1 | HCl | racemic | Amorphous |
| 118 | 3,5-Bis(trifluoromethyl)benzoyl | Ethyl | —SOCH₂— | | s | CH₃ | O | Ester bond | 3-Cl | 4-Cl | 1 | 1 | HCl | racemic | Amorphous |
| 119 | 3,4,5-Trimethoxybenzoyl | n-Propyl | —SOCH₂— | | s | CH₃ | O | Ester bond | 3-Cl | 4-Cl | 1 | 1 | HCl | racemic | Amorphous |
| 120 | 3,4,5-Trimethoxybenzoyl | Benzyl | CONH₂ | H | | CH₃ | O | Ester bond | 3-Cl | 4-Cl | 1 | 1 | Free | racemic | Amorphous |
| 121 | 3,4,5-Trimethoxybenzoyl | H | CONH₂ | H | | CH₃ | O | Ester bond | 3-Cl | 4-Cl | 1 | 1 | Free | racemic | Amorphous |
| 122 | 3,4,5-Trimethoxybenzoyl | Ethyl | CONH₂ | H | | CH₃ | O | Ester bond | 3-Cl | 4-Cl | 1 | 1 | HCl | racemic | Amorphous |
| 123 | 3,4,5-Trimethoxybenzoyl | Methyl | NHAc | H | | CH₃ | O | Ester bond | 3-Cl | 4-Cl | 1 | 1 | HCl | racemic | Amorphous |
| 124 | 3,4,5-Trimethoxybenzoyl | Ethyl | —NHCOCH₂— | H | | CH₃ | O | Ester bond | 3-Cl | 4-Cl | 1 | 1 | HCl | racemic | Amorphous |
| 125 | 3,4,5-Trimethoxybenzoyl | Ethyl | —SOCH₂— | | s | CH₃ | O | Ester bond | 3-Cl | 4-Cl | 1 | 1 | HCl | racemic | Amorphous |
| 126 | 3,4,5-Trimethoxybenzoyl | Ethyl | CONH₂ | H | | CH₃ | O | Ester bond | 3-Cl | 4-Cl | 1 | 1 | HCl | racemic | Amorphous |
| 127 | 3,4,5-Trimethoxybenzoyl | Benzyl | CONH₂ | H | | CH₃ | O | Ester bond | 3-Cl | 4-Cl | 1 | 1 | HCl | racemic | Amorphous |
| 128 | 3,4,5-Trimethoxybenzoyl | Cyclopropyl | CONH₂ | H | | CH₃ | O | Ester bond | 3-Cl | 4-Cl | 1 | 1 | HCl | racemic | Amorphous |
| 129 | 3,4,5-Trimethoxybenzoyl | Cyclohexyl | CONH₂ | H | | CH₃ | O | Ester bond | 3-Cl | 4-Cl | 1 | 1 | HCl | racemic | Amorphous |
| 130 | 3,4,5-Trimethoxybenzoyl | Phenyl | CONH₂ | H | | CH₃ | O | Ester bond | 3-Cl | 4-Cl | 1 | 1 | HCl | racemic | Amorphous |
| 131 | 3,4,5-Trimethoxybenzoyl | Ethyl | —C(=NOH)CH₂— | H | | CH₃ | O | Ester bond | 3-Cl | 4-Cl | 1 | 1 | Free | racemic | Amorphous |
| 132 | 3,4,5-Trimethoxybenzoyl | Ethyl | NHCONMe₂ | H | | CH₃ | O | Ester bond | 3-Cl | 4-Cl | 1 | 1 | HCl | racemic | Amorphous |
| 133 | 3,4,5-Trimethoxybenzoyl | Ethyl | —COCH₂— | | | CH₃ | O | Ester bond | 3-Cl | 4-Cl | 1 | 1 | HCl | racemic | Amorphous |
| 134 | 3,4,5-Trimethoxybenzoyl | Ethyl | CONH₂ | H | | H | O | Ester bond | 3-Cl | 4-Cl | 1 | 1 | Free | racemic | Amorphous |
| 135 | 3,4,5-Trimethoxybenzoyl | Cyclopentyl | CONH₂ | H | | CH₃ | O | Ester bond | 3-Cl | 4-Cl | 1 | 1 | HCl | racemic | Amorphous |
| 136 | 3,4,5-Trimethoxybenzoyl | iso-Butyl | CONH₂ | H | | CH₃ | O | Ester bond | 3-Cl | 4-Cl | 1 | 1 | Free | racemic | Amorphous |
| 137 | 3,4,5-Trimethoxybenzoyl | Ethyl | —NHCOCH₂— | H | | CH₃ | O | Ester bond | 3-Cl | 4-Cl | 1 | 1 | Free | racemic | Amorphous |

TABLE 1-continued

| Compound No. | R¹ | R² | R³ | R⁴ | Spiro | R⁵ | X¹ | X² | X³ | X⁴ | n1 | n2 | Salt | Quaternary carbon | Form |
|---|---|---|---|---|---|---|---|---|---|---|---|---|---|---|---|
| 138 | 3,4,5-Trimethoxybenzoyl | Ethyl | —SOCH₂— | | S | CH₃ | O | Ester bond | 3-Cl | 4-Cl | 1 | 1 | Free | racemic | Amorphous |
| 139 | 3,4,5-Trimethoxybenzoyl | iso-Propyl | —NHCOCH₂— | | | CH₃ | O | Ester bond | 3-Cl | 4-Cl | 1 | 1 | HCl | racemic | Amorphous |
| 140 | 3,4,5-Trimethoxybenzoyl | iso-Propyl | —SOCH₂— | | S | CH₃ | O | Ester bond | 3-Cl | 4-Cl | 1 | 1 | HCl | racemic | Amorphous |
| 141 | 3,4,5-Trimethoxybenzoyl | iso-Propyl | CONH₂ | H | | CH₂CH₂CH₃ | O | Ester bond | 3-Cl | 4-Cl | 1 | 1 | HCl | racemic | Amorphous |
| 142 | 3,4,5-Trimethoxybenzoyl | Ethyl | CONH₂ | H | | CH₃ | O | Ester bond | 3-Cl | 4-Cl | 1 | 1 | HCl | racemic | Amorphous |
| 143 | 3,4,5-Trimethoxybenzoyl | Cyclopentylmethyl | —NHCOCH₂— | | | CH₃ | O | Ester bond | 3-Cl | 4-Cl | 1 | 1 | HCl | racemic | Amorphous |
| 144 | 3,4,5-Trimethoxybenzoyl | Cyclohexyl | —SOCH₂— | | S | CH₃ | O | Ester bond | 3-Cl | 4-Cl | 1 | 1 | HCl | racemic | Amorphous |
| 145 | 3,4,5-Trimethoxybenzoyl | Cyclopentyl | —SOCH₂— | | S | CH₃ | O | Ester bond | 3-Cl | 4-Cl | 1 | 1 | HCl | racemic | Amorphous |
| 146 | 3,4,5-Trimethoxybenzoyl | Cyclopentyl | —SOCH₂— | | S | CH₃ | O | Ester bond | 3-Cl | 4-Cl | 1 | 1 | HCl | racemic | Amorphous |
| 147 | 3,4,5-Trimethoxybenzoyl | Cyclopentyl | —SOCH₂— | | S | CH₃ | O | Ester bond | 3-Cl | 4-Cl | 1 | 1 | HCl | S | Amorphous |
| 148 | 3,4,5-Trimethoxybenzoyl | Cyclopentyl | —SOCH₂— | | S | CH₃ | O | Ester bond | 3-Cl | 4-Cl | 1 | 1 | HCl | R | Amorphous |
| 149 | 3,4,5-Trimethoxybenzoyl | 2-Indanyl | —SOCH₂— | | S | CH₃ | NCH₃ | Ester bond | 3-Cl | 4-Cl | 1 | 1 | HCl | S | Amorphous |
| 150 | 3,4,5-Trimethoxybenzoyl | Ethyl | CONH₂ | H | | CH₃ | O | Ester bond | 3-Cl | 4-Cl | 1 | 1 | Free | racemic | Amorphous |
| 151 | 3,4,5-Trimethoxybenzoyl | Cyclopentyl | —SOCH₂— | | S | CH₃ | NCH₃ | Ester bond | 3-Cl | 4-Cl | 1 | 1 | HCl | racemic | Amorphous |
| 152 | 3,4,5-Trimethoxybenzoyl | Cyclohexyl | —SOCH₂— | | S | CH₃ | NCH₃ | Ester bond | 3-Cl | 4-Cl | 1 | 1 | HCl | S | Amorphous |
| 153 | 3,4,5-Trimethoxybenzoyl | Cyclopentyl | —SOCH₂— | | S | CH₃ | NCH₃ | Ester bond | 3-Cl | 4-Cl | 1 | 1 | HCl | R | Amorphous |
| 154 | 3,4,5-Trimethoxybenzoyl | iso-Propyl | —SOCH₂— | | S | CH₃ | NCH₃ | Ester bond | 3-Cl | 4-Cl | 1 | 1 | HCl | racemic | Amorphous |
| 155 | 3,4,5-Trimethoxybenzoyl | Cyclopentyl | —NHCOCH₂— | | | CH₃ | NH | Ester bond | 3-Cl | 4-Cl | 1 | 1 | HCl | racemic | Amorphous |
| 156 | 3,4,5-Trimethoxybenzoyl | Cyclohexyl | —SOCH₂— | | S | CH₃ | NCH₃ | Ester bond | 3-Cl | 4-Cl | 1 | 1 | HCl | racemic | Amorphous |
| 157 | 3,4,5-Trimethoxybenzoyl | iso-Propyl | —SOCH₂— | | S | CH₃ | NCH₃ | Ester bond | 3-Cl | 4-Cl | 1 | 1 | HCl | S | Amorphous |
| 158 | 3,4,5-Trimethoxybenzoyl | Cyclopentyl | —SOCH₂— | | S | CH₃ | O | Ester bond | 3-Cl | 4-Cl | 1 | 1 | HCl | S | Amorphous |
| 159 | 3,4,5-Trimethoxybenzoyl | 4-Tetrahydro-2H-pyranyl | —SOCH₂— | | S | CH₃ | NCH₃ | Ester bond | 3-Cl | 4-Cl | 1 | 1 | HCl | racemic | Amorphous |
| 160 | 3,4,5-Trimethoxybenzoyl | 2-Chlorophenyl | —SOCH₂— | | S | CH₃ | NCH₃ | Ester bond | 3-Cl | 4-Cl | 1 | 1 | HCl | S | Amorphous |
| 161 | 3,4,5-Trimethoxybenzoyl | Cyclopentyl | —SOCH₂— | | S | CH₃ | O | Ester bond | 3-Cl | 4-Cl | 1 | 1 | HCl | racemic | Amorphous |
| 162 | 2-Methoxybenzoyl | Diphenylmethyl | —SOCH₂— | | S | CH₃ | NH | Amide bond | 3-Cl | 4-Cl | 1 | 1 | HCl | S | Amorphous |
| 163 | Acetyl | Phenyl | CONH₂ | H | | CH₃ | O | Amide bond | 3-Cl | 4-Cl | 1 | 1 | HCl | racemic | Amorphous |
| 164 | 3,4,5-Trimethoxybenzoyl | Cyclohexyl | CONH₂ | H | | CH₃ | O | Amide bond | 3-Cl | 4-Cl | 1 | 1 | HCl | racemic | Amorphous |
| 165 | 3,4,5-Trimethoxybenzoyl | Phenyl | —SOCH₂— | | S | CH₃ | O | Amide bond | 3-Cl | 4-Cl | 1 | 1 | HCl | racemic | Amorphous |
| 166 | 3,4,5-Trimethoxybenzoyl | 2-Chlorophenyl | —SOCH₂— | | S | CH₃ | O | Amide bond | 3-Cl | 4-Cl | 1 | 1 | HCl | S | Amorphous |
| 167 | 3,4,5-Trimethoxybenzoyl | 3-Methoxy-5-trifluoromethylphenyl | —SOCH₂— | | S | CH₃ | O | Amide bond | 3-Cl | 4-Cl | 1 | 1 | HCl | S | Amorphous |
| 168 | 3,4,5-Trimethoxybenzoyl | Cyclohexyl | —SOCH₂— | | S | CH₃ | O | Amide bond | 3-Cl | 4-Cl | 1 | 1 | HCl | racemic | Amorphous |
| 169 | 3,4,5-Trimethoxybenzoyl | 3,5-Difluorophenyl | —SOCH₂— | | S | CH₃ | O | Amide bond | 3-Cl | 4-Cl | 1 | 1 | HCl | R | Amorphous |
| 170 | 3,4,5-Trimethoxybenzoyl | Phenyl | —SOCH₂— | | S | CH₃ | O | Amide bond | 3-Cl | 4-Cl | 1 | 1 | HCl | R | Amorphous |
| 171 | 3,4,5-Trimethoxybenzoyl | 3-Methoxyphenyl | —SOCH₂— | | S | CH₃ | O | Amide bond | 3-Cl | 4-Cl | 1 | 1 | HCl | R | Amorphous |
| 172 | 3,4,5-Trimethoxybenzoyl | Cyclohexyl | —SOCH₂— | | S | CH₃ | O | Amide bond | 3-Cl | 4-Cl | 1 | 1 | HCl | S | Amorphous |
| 173 | 3,4,5-Trimethoxybenzoyl | 3-Fluorophenyl | —SOCH₂— | | S | CH₃ | O | Amide bond | 3-Cl | 4-Cl | 1 | 1 | HCl | racemic | Amorphous |
| 174 | 3,4,5-Trimethoxybenzoyl | 3-Chlorophenyl | —SOCH₂— | | S | CH₃ | O | Amide bond | 3-Cl | 4-Cl | 1 | 1 | HCl | racemic | Amorphous |
| 175 | 3,4,5-Trimethoxybenzoyl | 2-Chlorophenyl | —SOCH₂— | | S | CH₃ | O | Amide bond | 3-Cl | 4-Cl | 1 | 1 | HCl | racemic | Amorphous |
| 176 | 3,4,5-Trimethoxybenzoyl | 3-Methoxy-5-trifluoromethylphenyl | —SOCH₂— | | S | CH₃ | O | Amide bond | 3-Cl | 4-Cl | 1 | 1 | HCl | racemic | Amorphous |
| 177 | 3,4,5-Trimethoxybenzoyl | 3,5-Difluorophenyl | —SOCH₂— | | S | CH₃ | O | Amide bond | 3-Cl | 4-Cl | 1 | 1 | HCl | racemic | Amorphous |
| 178 | 3,4,5-Trimethoxybenzoyl | 3-Methoxyphenyl | —SOCH₂— | | S | CH₃ | O | Amide bond | 3-Cl | 4-Cl | 1 | 1 | HCl | racemic | Amorphous |
| 179 | 3,4,5-Trimethoxybenzoyl | 3-Trifluoromethylphenyl | —SOCH₂— | | S | CH₃ | O | Amide bond | 3-Cl | 4-Cl | 1 | 1 | HCl | S | Amorphous |
| 180 | 3,4,5-Trimethoxybenzoyl | 3,5-Difluorophenyl | —SOCH₂— | | S | CH₃ | O | Amide bond | 3-Cl | 4-Cl | 1 | 1 | HCl | S | Amorphous |
| 181 | 3,4,5-Trimethoxybenzoyl | 3-Fluorophenyl | —SOCH₂— | | S | CH₃ | O | Amide bond | 3-Cl | 4-Cl | 1 | 1 | HCl | S | Amorphous |
| 182 | 3,4,5-Trimethoxybenzoyl | 2-Chloro-3,5-dimethyl | —SOCH₂— | | S | CH₃ | O | Amide bond | 3-Cl | 4-Cl | 1 | 1 | HCl | S | Amorphous |
| 183 | 3,4,5-Trimethoxybenzoyl | Diphenylmethyl | —SOCH₂— | | S | CH₃ | NCH₃ | Amide bond | 3-Cl | 4-Cl | 1 | 1 | HCl | racemic | Amorphous |
| 184 | 3,4,5-Trimethoxybenzoyl | 1-Naphthyl | —SOCH₂— | | S | CH₃ | NCH₃ | Amide bond | 3-Cl | 4-Cl | 1 | 1 | HCl | S | Amorphous |
| 185 | 3,4,5-Trimethoxybenzoyl | 8-Tetrahydronaphthyl | —SOCH₂— | | S | CH₃ | NCH₃ | Amide bond | 3-Cl | 4-Cl | 1 | 1 | HCl | racemic | Amorphous |
| | 3,4,5-Trimethoxybenzoyl | 1-Naphthyl | —SOCH₂— | | S | CH₃ | NCH₃ | Amide bond | 3-Cl | 4-Cl | 1 | 1 | HCl | S | Amorphous |

TABLE 1-continued

| Compound No. | R¹ | R² | R³ | R⁴ Spiro | R⁵ | X¹ | X² | X³ | X⁴ | n1 | n2 | Salt | Quaternary carbon | Form |
|---|---|---|---|---|---|---|---|---|---|---|---|---|---|---|
| 186 | 3,4,5-Trimethoxybenzoyl | Dicyclohexylmethyl | —SOCH₂— | S | CH₃ | NCH₃ | Amide bond | 3-Cl | 4-Cl | 1 | 1 | HCl | S | Amorphous |
| 187 | 3,4,5-Trimethoxybenzoyl | Cyclohexyl | —SOCH₂— | S | CH₃ | NCH₃ | Amide bond | 3-Cl | 4-Cl | 1 | 1 | HCl | racemic | Amorphous |
| 188 | 3,4,5-Trimethoxybenzoyl | Phenyl | —SOCH₂— | S | CH₃ | NCH₃ | Amide bond | 3-Cl | 4-Cl | 1 | 1 | HCl | racemic | Amorphous |
| 189 | 3,4,5-Trimethoxybenzoyl | n-Hexyl | —SOCH₂— | S | CH₃ | NCH₃ | Amide bond | 3-Cl | 4-Cl | 1 | 1 | HCl | racemic | Amorphous |
| 190 | 3,4,5-Trimethoxybenzoyl | Cyclopentyl | —SOCH₂— | S | CH₃ | NCH₃ | Amide bond | 3-Cl | 4-Cl | 1 | 1 | HCl | racemic | Amorphous |
| 191 | 3,4,5-Trimethoxybenzoyl | Benzyl | —SOCH₂— | S | CH₃ | NCH₃ | Amide bond | 3-Cl | 4-Cl | 1 | 1 | HCl | racemic | Amorphous |
| 192 | 3,4,5-Trimethoxybenzoyl | 3-Tolyl | —SOCH₂— | S | CH₃ | NCH₃ | Amide bond | 3-Cl | 4-Cl | 1 | 1 | HCl | racemic | Amorphous |
| 193 | 3,4,5-Trimethoxybenzoyl | 2-Chlorophenyl | —SOCH₂— | S | CH₃ | NCH₃ | Amide bond | 3-Cl | 4-Cl | 1 | 1 | HCl | racemic | Amorphous |
| 194 | 3,4,5-Trimethoxybenzoyl | 3-Methoxyphenyl | —SOCH₂— | S | CH₃ | NCH₃ | Amide bond | 3-Cl | 4-Cl | 1 | 1 | HCl | racemic | Amorphous |
| 195 | 3,4,5-Trimethoxybenzoyl | 2-Chlorophenyl | —SOCH₂— | S | CH₃ | NCH₃ | Amide bond | 3-Cl | 4-Cl | 1 | 1 | HCl | racemic | Amorphous |
| 196 | 3,4,5-Trimethoxybenzoyl | tert-Butyl | —SOCH₂— | S | CH₃ | NCH₃ | Amide bond | 3-Cl | 4-Cl | 1 | 1 | HCl | racemic | Amorphous |
| 197 | 3,4,5-Trimethoxybenzoyl | 2-Fluorophenyl | —SOCH₂— | S | CH₃ | NCH₃ | Amide bond | 3-Cl | 4-Cl | 1 | 1 | HCl | racemic | Amorphous |
| 198 | 3,4,5-Trimethoxybenzoyl | 3-Fluorophenyl | —SOCH₂— | S | CH₃ | NCH₃ | Amide bond | 3-Cl | 4-Cl | 1 | 1 | HCl | racemic | Amorphous |
| 199 | 3,4,5-Trimethoxybenzoyl | 4-Fluorophenyl | —SOCH₂— | S | CH₃ | NCH₃ | Amide bond | 3-Cl | 4-Cl | 1 | 1 | HCl | racemic | Amorphous |
| 200 | 3,4,5-Trimethoxybenzoyl | 3,4-Difluorophenyl | —SOCH₂— | S | CH₃ | NCH₃ | Amide bond | 3-Cl | 4-Cl | 1 | 1 | HCl | racemic | Amorphous |
| 201 | 3,4,5-Trimethoxybenzoyl | 3-Trifluoromethylphenyl | —SOCH₂— | S | CH₃ | NCH₃ | Amide bond | 3-Cl | 4-Cl | 1 | 1 | HCl | racemic | Amorphous |
| 202 | 3,4,5-Trimethoxybenzoyl | 2-Methoxyphenyl | —SOCH₂— | S | CH₃ | NCH₃ | Amide bond | 3-Cl | 4-Cl | 1 | 1 | HCl | racemic | Amorphous |
| 203 | 3,4,5-Trimethoxybenzoyl | 4-Tolyl | —SOCH₂— | S | CH₃ | NCH₃ | Amide bond | 3-Cl | 4-Cl | 1 | 1 | HCl | racemic | Amorphous |
| 204 | 3,4,5-Trimethoxybenzoyl | 2-Phenylphenyl | —SOCH₂— | S | CH₃ | NCH₃ | Amide bond | 3-Cl | 4-Cl | 1 | 1 | HCl | racemic | Amorphous |
| 205 | 3,4,5-Trimethoxybenzoyl | 2-Trifluoromethylphenyl | —SOCH₂— | S | CH₃ | NCH₃ | Amide bond | 3-Cl | 4-Cl | 1 | 1 | HCl | racemic | Amorphous |
| 206 | 3,4,5-Trimethoxybenzoyl | 3-Trifluoromethoxyphenyl | —SOCH₂— | S | CH₃ | NCH₃ | Amide bond | 3-Cl | 4-Cl | 1 | 1 | HCl | racemic | Amorphous |
| 207 | 3,4,5-Trimethoxybenzoyl | 2,3-Difluorophenyl | —SOCH₂— | S | CH₃ | NCH₃ | Amide bond | 3-Cl | 4-Cl | 1 | 1 | HCl | racemic | Amorphous |
| 208 | 3,4,5-Trimethoxybenzoyl | 2,4-Difluorophenyl | —SOCH₂— | S | CH₃ | NCH₃ | Amide bond | 3-Cl | 4-Cl | 1 | 1 | HCl | racemic | Amorphous |
| 209 | 3,4,5-Trimethoxybenzoyl | 2,5-Difluorophenyl | —SOCH₂— | S | CH₃ | NCH₃ | Amide bond | 3-Cl | 4-Cl | 1 | 1 | HCl | racemic | Amorphous |
| 210 | 3,4,5-Trimethoxybenzoyl | 2,6-Difluorophenyl | —SOCH₂— | S | CH₃ | NCH₃ | Amide bond | 3-Cl | 4-Cl | 1 | 1 | HCl | racemic | Amorphous |
| 211 | 3,4,5-Trimethoxybenzoyl | 2-Trifluoromethylphenyl | —SOCH₂— | S | CH₃ | NCH₃ | Amide bond | 3-Cl | 4-Cl | 1 | 1 | HCl | racemic | Amorphous |
| 212 | 3,4,5-Trimethoxybenzoyl | 4-Trifluoromethylphenyl | —SOCH₂— | S | CH₃ | NCH₃ | Amide bond | 3-Cl | 4-Cl | 1 | 1 | HCl | racemic | Amorphous |
| 213 | 3,4,5-Trimethoxybenzoyl | 2-Methoxy-5-trifluorophenyl | —SOCH₂— | S | CH₃ | NCH₃ | Amide bond | 3-Cl | 4-Cl | 1 | 1 | HCl | racemic | Amorphous |
| 214 | 3,4,5-Trimethoxybenzoyl | 4-Trifluoromethylphenyl | —SOCH₂— | S | CH₃ | NCH₃ | Amide bond | 3-Cl | 4-Cl | 1 | 1 | HCl | racemic | Amorphous |
| 215 | 3,4,5-Trimethoxybenzoyl | Methoxy-5-trifluoromethylphenyl | —SOCH₂— | S | CH₃ | NCH₃ | Amide bond | 3-Cl | 4-Cl | 1 | 1 | HCl | racemic | Amorphous |
| 216 | 3,4,5-Trimethoxybenzoyl | 3,5-Difluorophenyl | —SOCH₂— | S | CH₃ | NCH₃ | Amide bond | 3-Cl | 4-Cl | 1 | 1 | HCl | racemic | Amorphous |
| 217 | 3,4,5-Trimethoxybenzoyl | 2-Tolyl | —SOCH₂— | S | CH₃ | NCH₃ | Amide bond | 3-Cl | 4-Cl | 1 | 1 | HCl | racemic | Amorphous |
| 218 | 3,4,5-Trimethoxybenzoyl | 3-Methoxyphenyl | —SOCH₂— | S | CH₃ | NCH₃ | Amide bond | 3-Cl | 4-Cl | 1 | 1 | HCl | S | Amorphous |
| 219 | 3,4,5-Trimethoxybenzoyl | Cyclohexyl | —SOCH₂— | S | CH₃ | NCH₃ | Amide bond | 3-Cl | 4-Cl | 1 | 1 | HCl | S | Amorphous |
| 220 | 3,4,5-Trimethoxybenzoyl | Cyclohexyl | —SOCH₂— | S | CH₃ | NCH₃ | Amide bond | 3-Cl | 4-Cl | 1 | 1 | HCl | R | Amorphous |
| 221 | 3,4,5-Trimethoxybenzoyl | 3-Methoxyphenyl | —SOCH₂— | S | CH₃ | NCH₃ | Amide bond | 3-Cl | 4-Cl | 1 | 1 | HCl | R | Amorphous |
| 222 | 3,4,5-Trimethoxybenzoyl | 2-Chlorophenyl | —SOCH₂— | S | CH₃ | NCH₃ | Amide bond | 3-Cl | 4-Cl | 1 | 1 | HCl | R | Amorphous |
| 223 | 3,4,5-Trimethoxybenzoyl | 3-Fluorophenyl | —SOCH₂— | S | CH₃ | NCH₃ | Amide bond | 3-Cl | 4-Cl | 1 | 1 | HCl | R | Amorphous |
| 224 | 3,4,5-Trimethoxybenzoyl | 3,5-Difluorophenyl | —SOCH₂— | S | CH₃ | NCH₃ | Amide bond | 3-Cl | 4-Cl | 1 | 1 | HCl | S | Amorphous |
| 225 | 3,4,5-Trimethoxybenzoyl | 3-Methoxy-5-trifluoromethylphenyl | —SOCH₂— | S | CH₃ | NCH₃ | Amide bond | 3-Cl | 4-Cl | 1 | 1 | HCl | S | Amorphous |
| 226 | 3,4,5-Trimethoxybenzoyl | 3-Fluorophenyl | —SOCH₂— | S | CH₃ | NCH₃ | Amide bond | 3-Cl | 4-Cl | 1 | 1 | HCl | S | Amorphous |
| 227 | 3,4,5-Trimethoxybenzoyl | 3,5-Difluorophenyl | —SOCH₂— | S | CH₃ | NCH₃ | Amide bond | 3-Cl | 4-Cl | 1 | 1 | HCl | S | Amorphous |
| 228 | 3,4,5-Trimethoxybenzoyl | 3-Trifluoromethylphenyl | —SOCH₂— | S | CH₃ | NCH₃ | Amide bond | 3-Cl | 4-Cl | 1 | 1 | HCl | S | Amorphous |
| 229 | 3,4,5-Trimethoxybenzoyl | 2-Tolyl | —SOCH₂— | S | CH₃ | NCH₃ | Amide bond | 3-Cl | 4-Cl | 1 | 1 | HCl | S | Amorphous |
| 230 | 3,4,5-Trimethoxybenzoyl | 2-Chlorophenyl | —SOCH₂— | S | CH₃ | NCH₃ | Amide bond | 3-Cl | 4-Cl | 1 | 1 | HCl | S | Amorphous |
| 231 | 3,4,5-Trimethoxybenzoyl | 3-Chlorophenyl | —SOCH₂— | S | CH₃ | NCH₃ | Amide bond | 3-Cl | 4-Cl | 1 | 1 | HCl | S | Amorphous |
| 232 | 3,4,5-Trimethoxybenzoyl | 3,5-Difluorobenzyl | —SOCH₂— | S | CH₃ | NCH₃ | Amide bond | 3-Cl | 4-Cl | 1 | 1 | HCl | racemic | Amorphous |
| 233 | 3,4,5-Trimethoxybenzoyl | 3,5-Dimethoxyphenyl | —SOCH₂— | S | CH₃ | NCH₃ | Amide bond | 3-Cl | 4-Cl | 1 | 1 | HCl | racemic | Amorphous |

TABLE 1-continued

| Compound No. | R¹ | R² | R³ | R⁴ | Spiro | R⁵ | X¹ | X² | X³ | X⁴ | n1 | n2 | Salt | Quaternary carbon | Form |
|---|---|---|---|---|---|---|---|---|---|---|---|---|---|---|---|
| 234 | 3,4,5-Trimethoxybenzoyl | 3,5-Difluorophenyl | —SOCH₂— | | S | CH₃ | NCH₃ | Amide bond | 3-Cl | 4-Cl | 1 | 1 | HCl | racemic | Amorphous |
| 235 | 3,4,5-Trimethoxybenzoyl | 2,3-Difluorophenyl | —SOCH₂— | | S | CH₃ | NCH₃ | Amide bond | 3-Cl | 4-Cl | 1 | 1 | HCl | S | Amorphous |
| 236 | 3,4,5-Trimethoxybenzoyl | 2,3-Dichlorophenyl | —SOCH₂— | | S | CH₃ | NCH₃ | Amide bond | 3-Cl | 4-Cl | 1 | 1 | HCl | S | Amorphous |
| 237 | 3,4,5-Trimethoxybenzoyl | 2,5-Dichlorophenyl | —SOCH₂— | | S | CH₃ | NCH₃ | Amide bond | 3-Cl | 4-Cl | 1 | 1 | HCl | S | Amorphous |
| 238 | 3,4,5-Trimethoxybenzoyl | 2,5-Dichlorophenyl | —SOCH₂— | | S | CH₃ | NCH₃ | Amide bond | 3-Cl | 4-Cl | 1 | 1 | HCl | S | Amorphous |
| 239 | 3,4,5-Trimethoxybenzoyl | 2,6-Dichloro-3-methylphenyl | —SOCH₂— | | S | CH₃ | NCH₃ | Amide bond | 3-Cl | 4-Cl | 1 | 1 | HCl | S | Amorphous |
| 240 | 3,4,5-Trimethoxybenzoyl | 2-Chloro-5-methylphenyl | —SOCH₂— | | S | CH₃ | NCH₃ | Amide bond | 3-Cl | 4-Cl | 1 | 1 | HCl | S | Amorphous |
| 241 | 3,4,5-Trimethoxybenzoyl | 2,3,5-Trichlorophenyl | —SOCH₂— | | S | CH₃ | NCH₃ | Amide bond | 3-Cl | 4-Cl | 1 | 1 | HCl | S | Amorphous |
| 242 | 3,4,5-Trimethoxybenzoyl | 2-Chloro-5-methoxyphenyl | —SOCH₂— | | S | CH₃ | NCH₃ | Amide bond | 3-Cl | 4-Cl | 1 | 1 | HCl | S | Amorphous |
| 243 | 3,4,5-Trimethoxybenzoyl | 2-Chloro-3-methoxyphenyl | —SOCH₂— | | S | CH₃ | NCH₃ | Amide bond | 3-Cl | 4-Cl | 1 | 1 | HCl | S | Amorphous |
| 244 | 3,4,5-Trimethoxybenzoyl | 2-Chloro-3,5-dimethyl | —SOCH₂— | | S | CH₃ | NCH₃ | Amide bond | 3-Cl | 4-Cl | 1 | 1 | HCl | S | Amorphous |
| 245 | 3,4,5-Trimethoxybenzoyl | 2-Chloro-3-fluoro-5-methoxyphenyl | —SOCH₂— | | S | CH₃ | NCH₃ | Amide bond | 3-Cl | 4-Cl | 1 | 1 | HCl | S | Amorphous |
| 246 | 3,4,5-Trimethoxybenzoyl | 2-Chloro-3-fluoro-5-methoxyphenyl | —SOCH₂— | | S | CH₃ | NCH₃ | Amide bond | 3-Cl | 4-Cl | 1 | 1 | HCl | S | Amorphous |
| 247 | 3,4,5-Trimethoxybenzoyl | 3-(Dimethylamino)phenyl | —SOCH₂— | | S | CH₃ | NCH₃ | Amide bond | 3-Cl | 4-Cl | 1 | 1 | HCl | S | Amorphous |
| 248 | 3,4,5-Trimethoxybenzoyl | 2-Chlorophenyl | —SO₂CH₂— | | S | CH₃ | NCH₃ | Amide bond | 3-Cl | 4-Cl | 1 | 1 | HCl | S | Amorphous |
| 249 | 3,4,5-Trimethoxybenzoyl | 2-Chlorophenyl | —SO₂CH₂— | | | CH₃ | NCH₃ | Amide bond | 3-Cl | 4-Cl | 1 | 1 | HCl | R | Amorphous |
| 250 | 3,4,5-Trimethoxybenzoyl | 2-Chlorophenyl | —SCH₂— | | R | CH₃ | NCH₃ | Amide bond | 3-Cl | 4-Cl | 1 | 1 | HCl | R | Amorphous |
| 251 | 3,4,5-Trimethoxybenzoyl | 2-Chlorophenyl | —NHCOCH₂— | | | CH₃ | NCH₃ | Amide bond | 3-Cl | 4-Cl | 1 | 1 | HCl | R | Amorphous |
| 252 | 3,4,5-Trimethoxybenzoyl | 2-Chlorophenyl | —SOCH₂— | | R | CH₃ | NCH₃ | Amide bond | 3-Cl | 4-Cl | 1 | 1 | HCl | R | Amorphous |
| 253 | 3,4,5-Trimethoxybenzoyl | 2-Chlorophenyl | —NHCOCH₂— | | | CH₃ | NCH₃ | Amide bond | 3-Cl | 4-Cl | 1 | 1 | HCl | S | Amorphous |
| 254 | 3,4,5-Trimethoxybenzoyl | 2-Chlorophenyl | —SCH₂— | | | CH₃ | NCH₃ | Amide bond | 3-Cl | 4-Cl | 1 | 1 | HCl | S | Amorphous |
| 255 | 3,4,5-Trimethoxybenzoyl | 2-Chlorophenyl | —NHCOCH₂— | | | CH₃ | NCH₃ | Amide bond | 3-Cl | 4-Cl | 1 | 1 | HCl | S | Amorphous |
| 256 | Trifluoroacetyl | Benzyl | CONH₂ | | | CH₃ | NCH₃ | O | 3-Cl | 4-Cl | 1 | 1 | Free | racemic | Amorphous |
| 257 | Methyl | Benzyl | —SOCH₂— | H | | CH₃ | O | O | 3-Cl | 4-Cl | 1 | 1 | HCl | S | Amorphous |
| 258 | Methyl | Phenyl | —SOCH₂— | | S | CH₃ | O | O | 3-Cl | 4-Cl | 1 | 1 | HCl | racemic | Amorphous |
| 259 | Benzyl | Benzyl | —SOCH₂— | | S | CH₃ | O | O | 3-Cl | 4-Cl | 1 | 1 | HCl | racemic | Amorphous |
| 260 | Benzoyl | tert-Butyl | CONH₂ | H | | CH₃ | NCH₃ | O | 3-Cl | 4-Cl | 1 | 1 | HCl | racemic | Amorphous |
| 261 | Acetyl | Benzyl | CONH₂ | H | | CH₃ | NH | O | 3-Cl | 4-Cl | 1 | 1 | free | racemic | Amorphous |
| 262 | 4-Cyanobenzyl | tert-Butyl | CONH₂ | H | | CH₃ | O | O | 3-Cl | 4-Cl | 1 | 1 | Free | racemic | Amorphous |
| 263 | 4-Cyanobenzyl | Benzyl | CONH₂ | H | | CH₃ | O | O | 3-Cl | 4-Cl | 1 | 1 | Free | racemic | Amorphous |
| 264 | 3,5-Bis(trifluoromethyl)benzyl | Phenyl | CONH₂ | H | | CH₃ | O | O | 3-Cl | 4-Cl | 1 | 1 | Free | racemic | Amorphous |
| 265 | 3,4,5-Trimethoxybenzyl | 9H-Fluoren-9-yl-methyl | CONH₂ | H | | CH₃ | O | O | 3-Cl | 4-Cl | 1 | 1 | Free | S | Amorphous |
| 266 | 3,4,5-Trimethoxybenzyl | 2-Indanyl | —SOCH₂— | | S | CH₃ | O | O | 3-Cl | 4-Cl | 1 | 1 | HCl | R | Amorphous |
| 267 | 3,4,5-Trimethoxybenzyl | tert-Butyl | CONH₂ | H | | CH₃ | O | O | 3-Cl | 4-Cl | 1 | 1 | Free | racemic | Amorphous |
| 268 | 3,4,5-Trimethoxybenzyl | Ethyl | CONH₂ | H | | CH₃ | O | O | 3-Cl | 4-Cl | 1 | 1 | Free | racemic | Amorphous |
| 269 | 3,4,5-Trimethoxybenzyl | tert-Butyl | CONH₂ | H | | CH₃ | O | O | 3-Cl | 4-Cl | 1 | 1 | Free | racemic | Amorphous |
| 270 | 3,4,5-Trimethoxybenzyl | n-Pentyl | CONH₂ | H | | CH₃ | O | O | 3-Cl | 4-Cl | 1 | 1 | Free | racemic | Amorphous |
| 271 | 3,4,5-Trimethoxybenzyl | Benzyl | CONH₂ | H | | CH₃ | O | O | 3-Cl | 4-Cl | 1 | 1 | HCl | racemic | Amorphous |
| 272 | 3,4,5-Trimethoxybenzyl | Methyl | CONH₂ | H | | CH₃ | O | O | 3-Cl | 4-Cl | 1 | 1 | Free | racemic | Amorphous |
| 273 | 3,4,5-Trimethoxybenzyl | n-Propyl | CONH₂ | H | | CH₃ | O | O | 3-Cl | 4-Cl | 1 | 1 | Free | racemic | Amorphous |
| 274 | 3,4,5-Trimethoxybenzyl | Allyl | CONH₂ | H | | CH₃ | O | O | 3-Cl | 4-Cl | 1 | 1 | Free | racemic | Amorphous |
| 275 | 3,4,5-Trimethoxybenzyl | Cyclohexylmethyl | CONH₂ | H | | CH₃ | O | O | 3-Cl | 4-Cl | 1 | 1 | Free | racemic | Amorphous |
| 276 | 3,4,5-Trimethoxybenzyl | iso-Propyl | CONH₂ | H | | CH₃ | O | O | 3-Cl | 4-Cl | 1 | 1 | Free | racemic | Amorphous |
| 277 | 3,4,5-Trimethoxybenzyl | Cyclohexylmethyl | CONH₂ | H | | CH₃ | O | O | 3-Cl | 4-Cl | 1 | 1 | Free | racemic | Amorphous |
| 278 | 3,4,5-Trimethoxybenzyl | Cyclohexyl | CONH₂ | H | | H | O | O | 3-Cl | 4-Cl | 1 | 1 | Free | racemic | Amorphous |
| 279 | 3,4,5-Trimethoxybenzyl | Cyclopentyl | CONH₂ | H | | CH₃ | O | O | 3-Cl | 4-Cl | 1 | 1 | Free | racemic | Amorphous |
| 280 | 3,4,5-Trimethoxybenzyl | Benzyl | —SOCH₂— | | S | CH₃ | O | O | 3-Cl | 4-Cl | 1 | 1 | HCl | racemic | Amorphous |
| 281 | 3,4,5-Trimethoxybenzyl | iso-Butyl | CONH₂ | H | | CH₃ | O | O | 3-Cl | 4-Cl | 1 | 1 | HCl | racemic | Amorphous |

TABLE 1-continued

| Compound No. | R¹ | R² | R³ | R⁴ | Spiro | R⁵ | X¹ | X² | X³ | X⁴ | n1 | n2 | Salt | Quaternary carbon | Form |
|---|---|---|---|---|---|---|---|---|---|---|---|---|---|---|---|
| 282 | 3,4,5-Trimethoxybenzoyl | Benzyl | —NHCOCH₂— | | S | CH₃ | O | O | 3-Cl | 4-Cl | 1 | 1 | HCl | racemic | Amorphous |
| 283 | 3,4,5-Trimethoxybenzoyl | 4-Nitrophenyl | —SOCH₂— | | S | CH₃ | O | O | 3-Cl | 4-Cl | 1 | 1 | HCl | racemic | Amorphous |
| 284 | 3,4,5-Trimethoxybenzoyl | 3-Nitrobenzyl | —SOCH₂— | | S | CH₃ | O | O | 3-Cl | 4-Cl | 1 | 1 | HCl | racemic | Amorphous |
| 285 | 3,4,5-Trimethoxybenzoyl | 2-Methylbenzyl | —SOCH₂— | | S | CH₃ | O | O | 3-Cl | 4-Cl | 1 | 1 | HCl | racemic | Amorphous |
| 286 | 3,4,5-Trimethoxybenzoyl | 4-Nitrobenzyl | —SOCH₂— | | S | CH₃ | O | O | 3-Cl | 4-Cl | 1 | 1 | HCl | racemic | Amorphous |
| 287 | 3,4,5-Trimethoxybenzoyl | 4-Methoxybenzyl | —SOCH₂— | | S | CH₃ | O | O | 3-Cl | 4-Cl | 1 | 1 | HCl | racemic | Amorphous |
| 288 | 3,4,5-Trimethoxybenzoyl | 3-Methylbenzyl | —SOCH₂— | | S | CH₃ | O | O | 3-Cl | 4-Cl | 1 | 1 | HCl | racemic | Amorphous |
| 289 | 3,4,5-Trimethoxybenzoyl | 4-Chlorobenzyl | —SOCH₂— | | S | CH₃ | O | O | 3-Cl | 4-Cl | 1 | 1 | HCl | racemic | Amorphous |
| 290 | 3,4,5-Trimethoxybenzoyl | 2-Methylbenzyl | —SOCH₂— | | S | CH₃ | O | O | 3-Cl | 4-Cl | 1 | 1 | HCl | racemic | Amorphous |
| 291 | 3,4,5-Trimethoxybenzoyl | 2-Chlorophenyl | —SOCH₂— | | S | CH₃ | O | O | 3-Cl | 4-Cl | 1 | 1 | HCl | racemic | Amorphous |
| 292 | 3,4,5-Trimethoxybenzoyl | 2-Chlorobenzyl | —SOCH₂— | | S | CH₃ | O | O | 3-Cl | 4-Cl | 1 | 1 | HCl | racemic | Amorphous |
| 293 | 3,4,5-Trimethoxybenzoyl | 4-Bromobenzyl | —SOCH₂— | | S | CH₃ | O | O | 3-Cl | 4-Cl | 1 | 1 | HCl | racemic | Amorphous |
| 294 | 3,4,5-Trimethoxybenzoyl | Benzyl | —SOCH₂— | | S | CH₃ | O | O | 3-Cl | 4-Cl | 1 | 1 | HCl | S | Amorphous |
| 295 | 3,4,5-Trimethoxybenzoyl | Benzyl | —SOCH₂— | | S | CH₃ | O | O | 3-Cl | 4-Cl | 1 | 1 | HCl | R | Amorphous |
| 296 | 3,4,5-Trimethoxybenzoyl | 2-Chlorobenzyl | —SOCH₂— | | S | CH₃ | O | O | 3-Cl | 4-Cl | 1 | 1 | HCl | R | Amorphous |
| 297 | 3,4,5-Trimethoxybenzoyl | 2-Methylbenzyl | —SOCH₂— | | S | CH₃ | O | O | 3-Cl | 4-Cl | 1 | 1 | HCl | R | Amorphous |
| 298 | 3,4,5-Trimethoxybenzoyl | tert-Butyl | —SOCH₂— | | S | CH₃ | O | O | 3-Cl | 4-Cl | 1 | 1 | HCl | R | Amorphous |
| 299 | 3,4,5-Trimethoxybenzoyl | 3-Methylbenzyl | —SOCH₂— | | S | CH₃ | O | O | 3-Cl | 4-Cl | 1 | 1 | HCl | R | Amorphous |
| 300 | 3,4,5-Trimethoxybenzoyl | 4-Methoxybenzyl | —SOCH₂— | | S | CH₃ | O | O | 3-Cl | 4-Cl | 1 | 1 | HCl | S | Amorphous |
| 301 | 3,4,5-Trimethoxybenzoyl | 3-Chlorobenzyl | —SOCH₂— | | S | CH₃ | O | O | 3-Cl | 4-Cl | 1 | 1 | HCl | S | Amorphous |
| 302 | 3,4,5-Trimethoxybenzoyl | Phenyl | CONH₂ | H | | CH₃ | NCH₃ | O | 3-Cl | 4-Cl | 1 | 1 | HCl | racemic | Amorphous |
| 303 | 3,4,5-Trimethoxybenzoyl | tert-Butyl | CONH₂ | H | | CH₃ | NCH₃ | O | 3-Cl | 4-Cl | 1 | 1 | HCl | racemic | Amorphous |
| 304 | 3,4,5-Trimethoxybenzoyl | Benzyl | CONH₂ | H | | CH₃ | NCH₃ | O | 3-Cl | 4-Cl | 1 | 1 | HCl | racemic | Amorphous |
| 305 | 3,4,5-Trimethoxybenzoyl | tert-Butyl | —SOCH₂— | | S | CH₃ | NCH₃ | O | 3-Cl | 4-Cl | 1 | 1 | HCl | racemic | Amorphous |
| 306 | 3,4,5-Trimethoxybenzoyl | Benzyl | —SOCH₂— | | S | CH₃ | NCH₃ | O | 3-Cl | 4-Cl | 1 | 1 | Free | racemic | Amorphous |
| 307 | 3,4,5-Trimethoxybenzoyl | tert-Butyl | —SOCH₂— | | S | CH₃ | O | O | 3-Cl | 4-Cl | 1 | 1 | Free | racemic | Amorphous |
| 308 | 3,4,5-Trimethoxybenzoyl | Benzyl | —SOCH₂— | | S | CH₃ | NCH₃ | O | 3-Cl | 4-Cl | 1 | 1 | HCl | racemic | Amorphous |
| 309 | 3,4,5-Trimethoxybenzoyl | tert-Butyl | —SOCH₂— | | S | CH₃ | NH | O | 3-Cl | 4-Cl | 1 | 1 | Free | racemic | Amorphous |
| 310 | 3,4,5-Trimethoxybenzoyl | Benzyl | —SOCH₂— | | S | CH₃ | NCH₃ | O | 3-Cl | 4-Cl | 1 | 1 | Free | R | Amorphous |
| 311 | 3,4,5-Trimethoxybenzoyl | Cyclopentyl | —SOCH₂— | | S | CH₃ | O | O | 3-Cl | 4-Cl | 1 | 1 | HCl | R | Amorphous |
| 312 | 3,4,5-Trimethoxybenzoyl | 3-Chlorobenzyl | —SOCH₂— | | S | CH₃ | NCH₃ | O | 3-Cl | 4-Cl | 1 | 1 | HCl | S | Amorphous |
| 313 | 3,4,5-Trimethoxybenzoyl | Phenyl | CONH₂ | H | | CH₃ | O | O | 3-Cl | 4-Cl | 1 | 1 | HCl | S | Amorphous |
| 314 | 3,4,5-Trimethoxybenzoyl | Phenyl | —SOCH₂— | | S | CH₃ | NCH₃ | O | 3-Cl | 4-Cl | 1 | 1 | HCl | S | Amorphous |
| 315 | 3,4,5-Trimethoxybenzoyl | Phenyl | CONH₂ | H | | CH₃ | NCH₃ | O | 3-Cl | 4-Cl | 1 | 1 | HCl | R | Amorphous |
| 316 | Trifluoroacetyl | Diphenylmethyl | —SOCH₂— | | S | CH₃ | NCH₃ | NH | 3-Cl | 4-Cl | 1 | 1 | HCl | A | Amorphous |
| 317 | Trifluoroacetyl | Diphenylmethyl | —SO₂CH₂— | | | CH₃ | NCH₃ | NH | 3-Cl | 4-Cl | 1 | 1 | HCl | S | Amorphous |
| 318 | Trifluoroacetyl | Diphenylmethyl | —C(OH)CH₂— | | | CH₃ | NCH₃ | NH | 3-Cl | 4-Cl | 1 | 1 | HCl | S | Amorphous |
| 319 | Trifluoroacetyl | Diphenylmethyl | CONH₂ | H | | CH₃ | NCH₃ | NH | 3-Cl | 4-Cl | 1 | 1 | HCl | S | Amorphous |
| 320 | Trifluoroacetyl | Diphenylmethyl | NHAc | | | CH₃ | NCH₃ | NH | 3-Cl | 4-Cl | 1 | 1 | HCl | S | Amorphous |
| 321 | Trifluoroacetyl | Diphenylmethyl | —OCH₃ | | | CH₃ | NCH₃ | NH | 3-Cl | 4-Cl | 1 | 1 | HCl | S | Amorphous |
| 322 | Trifluoroacetyl | 9H-Fluoren-9-yl | —NHCOCH₂— | | | CH₃ | NCH₃ | NH | 3-Cl | 4-Cl | 1 | 1 | HCl | S | Amorphous |
| 323 | Trifluoroacetyl | 1-(1-Phenyl)cyclopentyl | —NHCOCH₂— | | | CH₃ | NCH₃ | NH | 3-Cl | 4-Cl | 1 | 1 | HCl | S | Amorphous |
| 324 | Trifluoroacetyl | Cyclopentyl(phenyl)methyl | —NHCOCH₂— | | | CH₃ | NCH₃ | NH | 3-Cl | 4-Cl | 1 | 1 | HCl | S | Amorphous |
| 325 | Trifluoroacetyl | 9H-Xanthen-9-yl | —NHCOCH₂— | | | CH₃ | NCH₃ | NH | 3-Cl | 4-Cl | 1 | 1 | HCl | S | Amorphous |
| 326 | Trifluoroacetyl | Dicyclohexylmethyl | —NHCOCH₂— | | | CH₃ | NCH₃ | NH | 3-Cl | 4-Cl | 1 | 1 | HCl | S | Amorphous |
| 327 | Trifluoroacetyl | Bis(4-chlorophenyl)methyl | —NHCOCH₂— | | | CH₃ | NCH₃ | NH | 3-Cl | 4-Cl | 1 | 1 | HCl | S | Amorphous |
| 328 | Trifluoroacetyl | Bis(4-methoxyphenyl)methyl | —NHCOCH₂— | | | CH₃ | NCH₃ | NH | 3-Cl | 4-Cl | 1 | 1 | HCl | S | Amorphous |
| 329 | Trifluoroacetyl | Diphenylmethyl | —NHCOCH₂— | | | CH₃ | NCH₃ | NH | 3-Cl | 4-Cl | 1 | 1 | HCl | R | Amorphous |

TABLE 1-continued

| Compound No. | R¹ | R² | R³ | R⁴ | Spiro | R⁵ | X¹ | X² | X³ | X⁴ | n1 | n2 | Salt | Quaternary carbon | Form |
|---|---|---|---|---|---|---|---|---|---|---|---|---|---|---|---|
| 330 | Trifluoroacetyl | Benzyl | —NHCOCH₂— | | | CH₃ | NCH₃ | NH | 3-Cl | 4-Cl | 1 | 1 | HCl | S | Amorphous |
| 331 | Trifluoroacetyl | 2-Chlorobenzyl | —NHCOCH₂— | | | CH₃ | NCH₃ | NH | 3-Cl | 4-Cl | 1 | 1 | HCl | S | Amorphous |
| 332 | Trifluoroacetyl | 2-Methylbenzyl | —NHCOCH₂— | | | CH₃ | NCH₃ | NH | 3-Cl | 4-Cl | 1 | 1 | HCl | S | Amorphous |
| 333 | Trifluoroacetyl | 2-Fluorobenzyl | —NHCOCH₂— | | | CH₃ | NCH₃ | NH | 3-Cl | 4-Cl | 1 | 1 | HCl | S | Amorphous |
| 334 | Trifluoroacetyl | 4-Chlorobenzyl | —NHCOCH₂— | | | CH₃ | NCH₃ | NH | 3-Cl | 4-Cl | 1 | 1 | HCl | S | Amorphous |
| 335 | Trifluoroacetyl | 2-Trifluoromethylbenzyl | —NHCOCH₂— | | | CH₃ | NCH₃ | NH | 3-Cl | 4-Cl | 1 | 1 | HCl | S | Amorphous |
| 336 | Trifluoroacetyl | 3-Chlorophenyl | —NHCOCH₂— | | | CH₃ | NCH₃ | NH | 3-Cl | 4-Cl | 1 | 1 | HCl | S | Amorphous |
| 337 | Trifluoroacetyl | Phenoxy | —NHCOCH₂— | | | CH₃ | NCH₃ | NH | 3-Cl | 4-Cl | 1 | 1 | HCl | S | Amorphous |
| 338 | Trifluoroacetyl | 2-Phenethyl | —NHCOCH₂— | | | CH₃ | NCH₃ | NH | 3-Cl | 4-Cl | 1 | 1 | HCl | S | Amorphous |
| 339 | Propionyl | Diphenylmethyl | —SOCH₂— | | S | CH₃ | NCH₃ | NH | 3-Cl | 4-Cl | 1 | 1 | HCl | S | Amorphous |
| 340 | Propionyl | 1-(1-Phenyl)cyclopentyl | —NHCOCH₂— | | | CH₃ | NCH₃ | NH | 3-Cl | 4-Cl | 1 | 1 | HCl | S | Amorphous |
| 341 | Propionyl | Diphenylmethyl | —NHCOCH₂— | | | CH₃ | NCH₃ | NH | 3-Cl | 4-Cl | 1 | 1 | HCl | S | Amorphous |
| 342 | Pivaloyl | Diphenylmethyl | —NHCOCH₂— | | | CH₃ | NCH₃ | NH | 3-Cl | 4-Cl | 1 | 1 | HCl | S | Amorphous |
| 343 | Methyl | Diphenylmethyl | —SOCH₂— | | S | CH₃ | O | NH | 3-Cl | 4-Cl | 1 | 1 | HCl | S | Amorphous |
| 344 | Methyl | Diphenylmethyl | —SOCH₂— | | S | CH₃ | O | NH | 3-Cl | 4-Cl | 1 | 1 | HCl | S | Amorphous |
| 345 | Methyl | Diphenylmethyl | CONH₂ | H | | CH₃ | NH | NH | 3-Cl | 4-Cl | 1 | 1 | HCl | S | Amorphous |
| 346 | Methyl | (S)-1-Indanyl | —SOCH₂— | | S | CH₃ | NCH₃ | NH | 3-Cl | 4-Cl | 1 | 1 | HCl | S | Amorphous |
| 347 | Methansulphonyl | Diphenylmethyl | —NHCOCH₂— | | | CH₃ | NCH₃ | NH | 3-Cl | 4-Cl | 1 | 1 | HCl | S | Amorphous |
| 348 | iso-Butyryl | Diphenylmethyl | —SO₂CH₂— | | S | CH₃ | NCH₃ | NH | 3-Cl | 4-Cl | 1 | 1 | HCl | S | Amorphous |
| 349 | iso-Butyryl | 1-(1-Phenyl)cyclopentyl | —NHCOCH₂— | | | CH₃ | NCH₃ | NH | 3-Cl | 4-Cl | 1 | 1 | HCl | S | Amorphous |
| 350 | H | Diphenylmethyl | —SOCH₂— | | S | CH₃ | NCH₃ | NH | 3-Cl | 4-Cl | 1 | 2HCl | | S | Amorphous |
| 351 | H | Diphenylmethyl | —SOCH₂— | | S | CH₃ | NCH₃ | NH | 3-Cl | 4-Cl | 1 | 2HCl | | R | Amorphous |
| 352 | H | Diphenylmethyl | —SOCH₂— | | S | CH₃ | O | NH | 3-Cl | 4-Cl | 1 | 2HCl | | S | Amorphous |
| 353 | H | Cyclopenyl(phenyl)methyl | —SOCH₂— | | S | CH₃ | NCH₃ | NH | 3-Cl | 4-Cl | 1 | 2HCl | | S | Amorphous |
| 354 | H | 1-(1-Phenyl)cyclopentyl | —SOCH₂— | | S | CH₃ | NCH₃ | NH | 3-Cl | 4-Cl | 1 | 2HCl | | S | Amorphous |
| 355 | H | Cyclopentyl | —SOCH₂— | | S | CH₃ | NCH₃ | NH | 3-Cl | 4-Cl | 1 | 2HCl | | S | Amorphous |
| 356 | H | n-Propyl | —SOCH₂— | | S | CH₃ | NCH₃ | NH | 3-Cl | 4-Cl | 1 | 2HCl | | S | Amorphous |
| 357 | H | 2-Chlorobenzyl | —SOCH₂— | | S | CH₃ | NCH₃ | NH | 3-Cl | 4-Cl | 1 | 2HCl | | S | Amorphous |
| 358 | H | 1-Phenethyl(SorR) | —SOCH₂— | | S | CH₃ | NCH₃ | NH | 3-Cl | 4-Cl | 1 | 2HCl | | S | Amorphous |
| 359 | H | 1-Phenethyl(SorR) | —SOCH₂— | | S | CH₃ | NCH₃ | NH | 3-Cl | 4-Cl | 1 | 2HCl | | R | Amorphous |
| 360 | Ethoxycarbonylmethyl | Diphenylmethyl | —NHCOCH₂— | | | CH₃ | NCH₃ | NH | 3-Cl | 4-Cl | 1 | 1 | HCl | S | Amorphous |
| 361 | Diphenylmethylcarbamoyl | Diphenylmethyl | —NHCOCH₂— | | | CH₃ | NCH₃ | NH | 3-Cl | 4-Cl | 1 | 1 | HCl | S | Amorphous |
| 362 | Difluoroacetyl | 1-Phenylcyclopentyl | —NHCOCH₂— | | | CH₃ | NCH₃ | NH | 3-Cl | 4-Cl | 1 | 1 | HCl | S | Amorphous |
| 363 | Chloroacetyl | Diphenylmethyl | —SOCH₂— | | S | CH₃ | NCH₃ | NH | 3-Cl | 4-Cl | 1 | 1 | HCl | S | Amorphous |
| 364 | Carbamoyl | Diphenylmethyl | —SOCH₂— | | S | CH₃ | NCH₃ | NH | 3-Cl | 4-Cl | 1 | 1 | HCl | R | Amorphous |
| 365 | Carbamoyl | Diphenylmethyl | —NHCOCH₂— | | | CH₃ | NH | NH | 3-Cl | 4-Cl | 1 | 1 | HCl | S | Amorphous |
| 366 | Benzyl | Phenyl | CONH₂ | H | | CH₃ | O | NH | 3-Cl | 4-Cl | 1 | 1 | Free | racemic | Amorphous |
| 367 | Acetyl | Diphenylmethyl | —SOCH₂— | | S | CH₃ | NCH₃ | NH | 3-Cl | 4-Cl | 1 | 1 | HCl | S | Amorphous |
| 368 | Acetyl | Diphenylmethyl | —SOCH₂— | | S | CH₃ | NCH₃ | NH | 3-Cl | 4-Cl | 1 | 1 | HCl | S | Amorphous |
| 369 | Acetyl | Diphenylmethyl | —SO₂CH₂— | | S | CH₃ | NCH₃ | NH | 3-Cl | 4-Cl | 1 | 1 | HCl | S | Amorphous |
| 370 | Acetyl | Diphenylmethyl | —NHCOCH₂— | | | CH₃ | NCH₃ | NH | 3-Cl | 4-Cl | 1 | 1 | HCl | S | Amorphous |
| 371 | Acetyl | Diphenylamino | —NHCOCH₂— | | | CH₃ | NH | NH | 3-Cl | 4-Cl | 1 | 1 | HCl | S | Amorphous |
| 372 | Acetyl | 2-Chlorobenzyl | —NHCOCH₂— | | | CH₃ | NCH₃ | NH | 3-Cl | 4-Cl | 1 | 1 | HCl | S | Amorphous |
| 373 | Acetyl | Phenyl | —NHCOCH₂— | | | CH₃ | NCH₃ | NH | 3-Cl | 4-Cl | 1 | 1 | HCl | R | Amorphous |
| 374 | Acetyl | n-Propyl | —SOCH₂— | | S | CH₃ | NCH₃ | NH | 3-Cl | 4-Cl | 1 | 1 | HCl | S | Amorphous |
| 375 | Acetyl | Benzyl | —SOCH₂— | | S | CH₃ | NCH₃ | NH | 3-Cl | 4-Cl | 1 | 1 | HCl | S | Amorphous |
| 376 | Acetyl | Cyclopentyl | —SOCH₂— | | S | CH₃ | NCH₃ | NH | 3-Cl | 4-Cl | 1 | 1 | HCl | S | Amorphous |
| 377 | 4-Hydroxy-3,5- | (S)-1-Indanyl | —SOCH₂— | | S | CH₃ | NCH₃ | NH | 3-Cl | 4-Cl | 1 | 1 | HCl | S | Amorphous |

TABLE 1-continued

| Compound No. | R¹ | R² | R³ | R⁴ | Spiro | R⁵ | X¹ | X² | X³ | X⁴ | n1 | n2 | Salt | Quaternary carbon | Form |
|---|---|---|---|---|---|---|---|---|---|---|---|---|---|---|---|
| 378 | Dimethoxybenzoyl 4-Cyanobenzyl | Phenyl | CONH₂ | H | | CH₃ | O | NH | 3-Cl | 4-Cl | 1 | 1 | Free | racemic | Amorphous |
| 379 | 4,4,4-Trifluorobutyryl | Diphenylmethyl | —SOCH₂— | | S | CH₃ | NCH₃ | NH | 3-Cl | 4-Cl | 1 | 1 | HCl | S | Amorphous |
| 380 | 4,4,4-Trifluorobutyryl | Diphenylmethyl | —NHCOCH₂— | | | CH₃ | NCH₃ | NH | 3-Cl | 4-Cl | 1 | 1 | HCl | S | Amorphous |
| 381 | 3,5-Dimethoxybenzyl | Benzyl | CONH₂ | H | | CH₃ | O | NH | 3-Cl | 4-Cl | 1 | 1 | HCl | S | Amorphous |
| 382 | 3,5-Dimethoxybenzyl | Benzyl | —SOCH₂— | | S | CH₃ | O | NH | 3-Cl | 4-Cl | 1 | 1 | HCl | S | Amorphous |
| 383 | 3,5-Dimethoxybenzoyl | (S)-1-Indanyl | —SOCH₂— | | S | CH₃ | NCH₃ | NH | 3-Cl | 4-Cl | 1 | 1 | HCl | S | Amorphous |
| 384 | 3,5-Bis(trifluoromethyl)benzyl | Benzyl | CONH₂ | H | | CH₃ | O | NH | 3-Cl | 4-Cl | 1 | 1 | HCl | S | Amorphous |
| 385 | 3,5-Bis(trifluoromethyl)benzyl | Benzyl | —SOCH₂— | | | CH₃ | O | NH | 3-Cl | 4-Cl | 1 | 1 | HCl | S | Amorphous |
| 386 | 3,5-Bis(trifluoromethyl)benzoyl | (S)-1-Indanyl | —SOCH₂— | | | CH₃ | NCH₃ | NH | 3-Cl | 4-Cl | 1 | 1 | HCl | S | Amorphous |
| 387 | 3,4-Dimethoxybenzoyl | 1-Naphthyl | CONH₂ | H | | CH₃ | O | NH | 3-Cl | 4-Cl | 1 | 1 | Free | racemic | Amorphous |
| 388 | 3,4,5-Trimethoxybenzyl | Diphenylmethyl | —SOCH₂— | | S | CH₃ | O | NH | 3-Cl | 4-Cl | 1 | 1 | HCl | S | Amorphous |
| 389 | 3,4,5-Trimethoxybenzyl | Phenyl | CONH₂ | H | | CH₃ | O | NH | 3-Cl | 4-Cl | 1 | 1 | Free | racemic | Amorphous |
| 390 | 3,4,5-Trimethoxybenzyl | n-Propyl | CONH₂ | H | | CH₃ | O | NH | 3-Cl | 4-Cl | 1 | 1 | Free | racemic | Amorphous |
| 391 | 3,4,5-Trimethoxybenzyl | iso-Propyl | CONH₂ | H | | CH₃ | O | NH | 3-Cl | 4-Cl | 1 | 1 | Free | racemic | Amorphous |
| 392 | 3,4,5-Trimethoxybenzyl | Cyclohexyl | CONH₂ | H | | CH₃ | O | NH | 3-Cl | 4-Cl | 1 | 1 | Free | racemic | Amorphous |
| 393 | 3,4,5-Trimethoxybenzyl | Benzyl | CONH₂ | H | | CH₃ | O | NH | 3-Cl | 4-Cl | 1 | 1 | Free | racemic | Amorphous |
| 394 | 3,4,5-Trimethoxybenzyl | Cyclopentyl | CONH₂ | H | | CH₃ | O | NH | 3-Cl | 4-Cl | 1 | 1 | HCl | racemic | Amorphous |
| 395 | 3,4,5-Trimethoxybenzyl | 3,4-Trimethoxyphenyl | CONH₂ | H | | CH₃ | O | NH | 3-Cl | 4-Cl | 1 | 1 | Free | racemic | Amorphous |
| 396 | 3,4,5-Trimethoxybenzyl | 4-Trifluoromethylphenyl | CONH₂ | | | CH₃ | O | NH | 3-Cl | 4-Cl | 1 | 1 | Free | racemic | Amorphous |
| 397 | 3,4,5-Trimethoxybenzyl | Benzyl | —SOCH₂— | | S | CH₃ | O | NH | 3-Cl | 4-Cl | 1 | 1 | HCl | racemic | Amorphous |
| 398 | 3,4,5-Trimethoxybenzyl | Cyclopentyl | —SOCH₂— | | S | CH₃ | O | NH | 3-Cl | 4-Cl | 1 | 1 | HCl | racemic | Amorphous |
| 399 | 3,4,5-Trimethoxybenzyl | 2-Chlorobenzyl | —SOCH₂— | | S | CH₃ | O | NH | 3-Cl | 4-Cl | 1 | 1 | HCl | racemic | Amorphous |
| 400 | 3,4,5-Trimethoxybenzyl | Cyclopentyl | —SOCH₂— | | S | CH₃ | O | NH | 3-Cl | 4-Cl | 1 | 1 | HCl | R | Amorphous |
| 401 | 3,4,5-Trimethoxybenzyl | Benzyl | CONH₂ | H | | CH₃ | O | NH | 3-Cl | 4-Cl | 1 | 1 | HCl | R | Amorphous |
| 402 | 3,4,5-Trimethoxybenzoyl | Cyclopentyl | —SOCH₂— | | S | CH₃ | NCH₃ | NH | 3-Cl | 4-Cl | 1 | 1 | HCl | S | Amorphous |
| 403 | 3,4,5-Trimethoxybenzoyl | n-Propyl | —SOCH₂— | | S | CH₃ | NCH₃ | NH | 3-Cl | 4-Cl | 1 | 1 | HCl | S | Amorphous |
| 404 | 3,4,5-Trimethoxybenzoyl | Phenyl | —SOCH₂— | | S | CH₃ | NCH₃ | NH | 3-Cl | 4-Cl | 1 | 1 | HCl | S | Amorphous |
| 405 | 3,4,5-Trimethoxybenzoyl | 2-Phenethyl | —SOCH₂— | | S | CH₃ | NCH₃ | NH | 3-Cl | 4-Cl | 1 | 1 | HCl | S | Amorphous |
| 406 | 3,4,5-Trimethoxybenzoyl | Diphenylmethyl | —SOCH₂— | | S | CH₃ | NCH₃ | NH | 3-Cl | 4-Cl | 1 | 1 | HCl | racemic | Amorphous |
| 407 | 3,4,5-Trimethoxybenzoyl | 9H-Fluoren-9-yl | —SOCH₂— | | S | CH₃ | NCH₃ | NH | 3-Cl | 4-Cl | 1 | 1 | HCl | racemic | Amorphous |
| 408 | 3,4,5-Trimethoxybenzoyl | Diphenylmethyl | —SOCH₂— | | S | CH₃ | NCH₃ | NH | 3-Cl | 4-Cl | 1 | 1 | HCl | S | Amorphous |
| 409 | 3,4,5-Trimethoxybenzoyl | Diphenylmethyl | —SOCH₂— | | S | CH₃ | NCH₃ | NH | 3-Cl | 4-Cl | 1 | 1 | HCl | R | Amorphous |
| 410 | 3,4,5-Trimethoxybenzoyl | 1-Naphthylmethyl | —SOCH₂— | | S | CH₃ | NCH₃ | NH | 3-Cl | 4-Cl | 1 | 1 | HCl | S | Amorphous |
| 411 | 3,4,5-Trimethoxybenzoyl | 9H-Fluoren-9-yl | —SOCH₂— | | S | CH₃ | NCH₃ | NH | 3-Cl | 4-Cl | 1 | 1 | HCl | S | Amorphous |
| 412 | 3,4,5-Trimethoxybenzoyl | 1,2,3,4-Tetrahydronaphthalen-1-yl | —SOCH₂— | | S | CH₃ | NCH₃ | NH | 3-Cl | 4-Cl | 1 | 1 | HCl | S | Amorphous |
| 413 | 3,4,5-Trimethoxybenzoyl | 2-Tetrahydronaphthyl | —SOCH₂— | | S | CH₃ | NCH₃ | NH | 3-Cl | 4-Cl | 1 | 1 | HCl | S | Amorphous |
| 414 | 3,4,5-Trimethoxybenzoyl | (R)-1-Indanyl | —SOCH₂— | | S | CH₃ | NCH₃ | NH | 3-Cl | 4-Cl | 1 | 1 | HCl | S | Amorphous |
| 415 | 3,4,5-Trimethoxybenzoyl | (S)-1-Indanyl | —SOCH₂— | | S | CH₃ | NCH₃ | NH | 3-Cl | 4-Cl | 1 | 1 | HCl | S | Amorphous |
| 416 | 3,4,5-Trimethoxybenzoyl | Cyclopentyl(phenyl)methyl | —SOCH₂— | | S | CH₃ | NCH₃ | NH | 3-Cl | 4-Cl | 1 | 1 | HCl | S | Amorphous |
| 417 | 3,4,5-Trimethoxybenzoyl | 1-(1-Phenyl)cyclopentyl | —SOCH₂— | | S | CH₃ | NCH₃ | NH | 3-Cl | 4-Cl | 1 | 1 | HCl | S | Amorphous |
| 418 | 3,4,5-Trimethoxybenzoyl | Bis(4-chlorophenyl)methyl | —SOCH₂— | | S | CH₃ | NCH₃ | NH | 3-Cl | 4-Cl | 1 | 1 | HCl | S | Amorphous |
| 419 | 3,4,5-Trimethoxybenzoyl | 9H-Xanthen-9-yl | —SOCH₂— | | S | CH₃ | NCH₃ | NH | 3-Cl | 4-Cl | 1 | 1 | HCl | S | Amorphous |
| 420 | 3,4,5-Trimethoxybenzoyl | 1,1-Diphenylethyl | —SOCH₂— | | S | CH₃ | NCH₃ | NH | 3-Cl | 4-Cl | 1 | 1 | HCl | S | Amorphous |
| 421 | 3,4,5-Trimethoxybenzoyl | 4-Chlorophenyl(phenyl)methyl | —SOCH₂— | | S | CH₃ | NCH₃ | NH | 3-Cl | 4-Cl | 1 | 1 | HCl | S | Amorphous |
| 422 | 3,4,5-Trimethoxybenzoyl | Cyclohexyl(phenyl)methyl | —SOCH₂— | | S | CH₃ | NCH₃ | NH | 3-Cl | 4-Cl | 1 | 1 | HCl | S | Amorphous |
| 423 | 3,4,5-Trimethoxybenzoyl | Diphenylmethyl | —SOCH₂— | | R | CH₃ | NCH₃ | NH | 3-Cl | 4-Cl | 1 | 1 | HCl | R | Amorphous |

TABLE 1-continued

| Compound No. | R$^1$ | R$^2$ | R$^3$ | R$^4$ | Spiro | R$^5$ | X$^1$ | X$^2$ | X$^3$ | X$^4$ | n1 | n2 | Salt | Quaternary carbon | Form |
|---|---|---|---|---|---|---|---|---|---|---|---|---|---|---|---|
| 424 | 3,4,5-Trimethoxybenzoyl | Diphenylmethyl | —NHCOCH$_2$— | | | CH$_3$ | NCH$_3$ | NH | 3-Cl | 4-Cl | 1 | 1 | HCl | R | Amorphous |
| 425 | 3,4,5-Trimethoxybenzoyl | Diphenylmethyl | —SOCH$_2$— | | R | CH$_3$ | NCH$_3$ | NH | 3-Cl | 4-Cl | 1 | 1 | HCl | S | Amorphous |
| 426 | 3,4,5-Trimethoxybenzoyl | Diphenylmethyl | —NHCOCH$_2$— | | | CH$_3$ | NCH$_3$ | NH | 3-Cl | 4-Cl | 1 | 1 | HCl | S | Amorphous |
| 427 | 3,4,5-Trimethoxybenzoyl | Diphenylmethyl | —SCH2— | | | CH$_3$ | NCH$_3$ | NH | 3-Cl | 4-Cl | 1 | 1 | HCl | S | Amorphous |
| 428 | 3,4,5-Trimethoxybenzoyl | 1-Naphthylmethyl | —SOCH$_2$— | | S | CH$_3$ | NCH$_3$ | NH | 3-Cl | 4-Cl | 1 | 1 | HCl | racemic | Amorphous |
| 429 | 3,4,5-Trimethoxybenzoyl | 2-Indanyl | —SOCH$_2$— | | S | CH$_3$ | NCH$_3$ | NH | 3-Cl | 4-Cl | 1 | 1 | HCl | R | Amorphous |
| 430 | 3,4,5-Trimethoxybenzoyl | (R)-1-Indanyl | —SOCH$_2$— | | S | CH$_3$ | NCH$_3$ | NH | 3-Cl | 4-Cl | 1 | 1 | HCl | R | Amorphous |
| 431 | 3,4,5-Trimethoxybenzoyl | (S)-1-Indanyl | —SOCH$_2$— | | S | CH$_3$ | NCH$_3$ | NH | 3-Cl | 4-Cl | 1 | 1 | HCl | R | Amorphous |
| 432 | 3,4,5-Trimethoxybenzoyl | Bis(4-methoxyphenyl)methyl | —SOCH$_2$— | | | CH$_3$ | NCH$_3$ | NH | 3-Cl | 4-Cl | 1 | 1 | HCl | R | Amorphous |
| 433 | 3,4,5-Trimethoxybenzoyl | 1-(1-Phenyl)cyclopentyl | —SOCH$_2$— | | | CH$_3$ | NCH$_3$ | NH | 3-Cl | 4-Cl | 1 | 1 | HCl | S | Amorphous |
| 434 | 3,4,5-Trimethoxybenzoyl | (4-Dimethylaminophenyl)(phenyl)methyl | —SOCH$_2$— | | S | CH$_3$ | NCH$_3$ | NH | 3-Cl | 4-Cl | 1 | 1 | HCl | S | Amorphous |
| 435 | 3,4,5-Trimethoxybenzoyl | Diphenylmethyl | —SO$_2$CH$_2$— | | | CH$_3$ | NCH$_3$ | NH | 3-Cl | 4-Cl | 1 | 1 | HCl | S | Amorphous |
| 436 | 3,4,5-Trimethoxybenzoyl | (S)-1-Indanyl | —SO$_2$CH$_2$— | | | CH$_3$ | NCH$_3$ | NH | 3-Cl | 4-Cl | 1 | 1 | HCl | S | Amorphous |
| 437 | 3,4,5-Trimethoxybenzoyl | (S)-1-Indanyl | —SO$_2$CH$_2$— | | | CH$_3$ | NCH$_3$ | NH | 3-Cl | 4-Cl | 1 | 1 | HCl | R | Amorphous |
| 438 | 3,4,5-Trimethoxybenzoyl | (S)-1-Indanyl | —NHCOCH$_2$— | | R | CH$_3$ | NCH$_3$ | NH | 3-Cl | 4-Cl | 1 | 1 | HCl | R | Amorphous |
| 439 | 3,4,5-Trimethoxybenzoyl | Diphenylmethyl | —SOCH$_2$— | | | CH$_3$ | NCH$_3$ | NH | 3-Cl | 4-Cl | 1 | 1 | HCl | S | Amorphous |
| 440 | 3,4,5-Trimethoxybenzoyl | (S)-1-Indanyl | —SOCH$_2$— | | | CH$_3$ | O | NH | 3-Cl | 4-Cl | 1 | 1 | HCl | S | Amorphous |
| 441 | 3,4,5-Trimethoxybenzoyl | (S)-1-Indanyl | —NHCOCH2— | | | CH$_3$ | NCH$_3$ | NH | 3-Cl | 4-Cl | 1 | 1 | HCl | S | Amorphous |
| 442 | 3,4,5-Trimethoxybenzoyl | Benzyl | CONH$_2$ | H | | CH$_3$ | NCH$_3$ | NH | 3-Cl | 4-Cl | 1 | 1 | Free | racemic | Amorphous |
| 443 | 3,4,5-Trimethoxybenzoyl | Phenyl | CONH$_2$ | H | | CH$_3$ | NCH$_3$ | NH | 3-Cl | 4-Cl | 1 | 1 | Free | racemic | Amorphous |
| 444 | 3,4,5-Trimethoxybenzoyl | Cyclohexyl | CONH$_2$ | H | | CH$_3$ | NCH$_3$ | NH | 3-Cl | 4-Cl | 1 | 1 | Free | racemic | Amorphous |
| 445 | 3,4,5-Trimethoxybenzoyl | Cyclopentyl | CONH$_2$ | H | | CH$_3$ | NCH$_3$ | NH | 3-Cl | 4-Cl | 1 | 1 | Free | racemic | Amorphous |
| 446 | 3,4,5-Trimethoxybenzoyl | 3,4,5-Trimethoxyphenyl | CONH$_2$ | H | | CH$_3$ | NCH$_3$ | NH | 3-Cl | 4-Cl | 1 | 1 | Free | racemic | Amorphous |
| 447 | 3,4,5-Trimethoxybenzoyl | 3,4-Dichlorophenyl | CONH$_2$ | H | | CH$_3$ | NCH$_3$ | NH | 3-Cl | 4-Cl | 1 | 1 | Free | racemic | Amorphous |
| 448 | 3,4,5-Trimethoxybenzoyl | 3,4-Dichlorophenyl | CONH$_2$ | | | CH$_3$ | NCH$_3$ | NH | 3-Cl | 4-Cl | 1 | 1 | Free | racemic | Amorphous |
| 449 | 3,4,5-Trimethoxybenzoyl | Cyclopentyl | CONH$_2$ | | | CH$_3$ | NCH$_3$ | NH | 3-Cl | 4-Cl | 1 | 1 | Free | racemic | Amorphous |
| 450 | 3,4,5-Trimethoxybenzoyl | Benzyl | —SOCH$_2$— | | S | CH$_3$ | NCH$_3$ | NH | 3-Cl | 4-Cl | 1 | 1 | HCl | racemic | Amorphous |
| 451 | 3,4,5-Trimethoxybenzoyl | n-Propyl | —SOCH$_2$— | | S | CH$_3$ | NCH$_3$ | NH | 3-Cl | 4-Cl | 1 | 1 | HCl | racemic | Amorphous |
| 452 | 3,4,5-Trimethoxybenzoyl | iso-Propyl | —SOCH$_2$— | | S | CH$_3$ | NCH$_3$ | NH | 3-Cl | 4-Cl | 1 | 1 | HCl | racemic | Amorphous |
| 453 | 3,4,5-Trimethoxybenzoyl | tert-Butyl | —SOCH$_2$— | | S | CH$_3$ | NCH$_3$ | NH | 3-Cl | 4-Cl | 1 | 1 | HCl | racemic | Amorphous |
| 454 | 3,4,5-Trimethoxybenzoyl | n-Octyl | —SOCH$_2$— | | S | CH$_3$ | NCH$_3$ | NH | 3-Cl | 4-Cl | 1 | 1 | HCl | racemic | Amorphous |
| 455 | 3,4,5-Trimethoxybenzoyl | Cyclohexyl | —SOCH$_2$— | | S | CH$_3$ | NCH$_3$ | NH | 3-Cl | 4-Cl | 1 | 1 | HCl | racemic | Amorphous |
| 456 | 3,4,5-Trimethoxybenzoyl | Phenyl | —SOCH$_2$— | | S | CH$_3$ | NCH$_3$ | NH | 3-Cl | 4-Cl | 1 | 1 | HCl | racemic | Amorphous |
| 457 | 3,4,5-Trimethoxybenzoyl | 4-Trifluoromethoxyphenyl | —SOCH$_2$— | | S | CH$_3$ | NCH$_3$ | NH | 3-Cl | 4-Cl | 1 | 1 | HCl | racemic | Amorphous |
| 458 | 3,4,5-Trimethoxybenzoyl | Benzoyl | —SOCH$_2$— | | S | CH$_3$ | NCH$_3$ | NH | 3-Cl | 4-Cl | 1 | 1 | HCl | racemic | Amorphous |
| 459 | 3,4,5-TrimethoxybenzoylL | Benzyl | —SOCH$_2$— | | S | CH$_3$ | NCH$_3$ | NH | 3-Cl | 4-Cl | 1 | 1 | HCl | racemic | Amorphous |
| 460 | 3,4,5-Trimethoxybenzoyl | 4-Bromobenzyl | —SOCH$_2$— | | S | CH$_3$ | NCH$_3$ | NH | 3-Cl | 4-Cl | 1 | 1 | HCl | racemic | Amorphous |
| 461 | 3,4,5-Trimethoxybenzoyl | 4-Fluorobenzyl | —SOCH$_2$— | | S | CH$_3$ | NCH$_3$ | NH | 3-Cl | 4-Cl | 1 | 1 | HCl | racemic | Amorphous |
| 462 | 3,4,5-Trimethoxybenzoyl | 4-Methylbenzyl | —SOCH$_2$— | | S | CH$_3$ | NCH$_3$ | NH | 3-Cl | 4-Cl | 1 | 1 | HCl | racemic | Amorphous |
| 463 | 3,4,5-Trimethoxybenzoyl | 4-Methoxybenzyl | —SOCH$_2$— | | S | CH$_3$ | NCH$_3$ | NH | 3-Cl | 4-Cl | 1 | 1 | HCl | racemic | Amorphous |
| 464 | 3,4,5-Trimethoxybenzoyl | 2-Fluorobenzyl | —SOCH$_2$— | | S | CH$_3$ | NCH$_3$ | NH | 3-Cl | 4-Cl | 1 | 1 | HCl | racemic | Amorphous |
| 465 | 3,4,5-Trimethoxybenzoyl | 2-Methylbenzyl | —SOCH$_2$— | | S | CH$_3$ | NCH$_3$ | NH | 3-Cl | 4-Cl | 1 | 1 | HCl | racemic | Amorphous |
| 466 | 3,4,5-Trimethoxybenzoyl | 3-Methylbenzyl | —SOCH$_2$— | | S | CH$_3$ | NCH$_3$ | NH | 3-Cl | 4-Cl | 1 | 1 | HCl | racemic | Amorphous |
| 467 | 3,4,5-Trimethoxybenzoyl | 2,4-Difluorobenzyl | —SOCH$_2$— | | S | CH$_3$ | NCH$_3$ | NH | 3-Cl | 4-Cl | 1 | 1 | HCl | racemic | Amorphous |
| 468 | 3,4,5-Trimethoxybenzoyl | 3,4-Dichlorobenzyl | —SOCH$_2$— | | S | CH$_3$ | NCH$_3$ | NH | 3-Cl | 4-Cl | 1 | 1 | HCl | racemic | Amorphous |
| 469 | 3,4,5-Trimethoxybenzoyl | 2-Phenylethyl | —SOCH$_2$— | | S | CH$_3$ | NCH$_3$ | NH | 3-Cl | 4-Cl | 1 | 1 | HCl | racemic | Amorphous |
| 470 | 3,4,5-Trimethoxybenzoyl | Allyl | —SOCH$_2$— | | S | CH$_3$ | NCH$_3$ | NH | 3-Cl | 4-Cl | 1 | 1 | HCl | racemic | Amorphous |
| 471 | 3,4,5-Trimethoxybenzoyl | Chloromethylcarbonyl | —SOCH$_2$— | | S | CH$_3$ | NCH$_3$ | NH | 3-Cl | 4-Cl | 1 | 1 | HCl | racemic | Amorphous |

TABLE 1-continued

| Compound No. | R¹ | R² | R³ | R⁴ | Spiro | R⁵ | X¹ | X² | X³ | X⁴ | n1 | n2 | Salt | Quaternary carbon | Form |
|---|---|---|---|---|---|---|---|---|---|---|---|---|---|---|---|
| 472 | 3,4,5-Trimethoxybenzoyl | 4-Chlorophenyl | —SOCH₂— | | S | CH₃ | NCH₃ | NH | 3-Cl | 4-Cl | 1 | 1 | HCl | racemic | Amorphous |
| 473 | 3,4,5-Trimethoxybenzoyl | 2-Chlorobenzyl | —SOCH₂— | | S | CH₃ | NCH₃ | NH | 3-Cl | 4-Cl | 1 | 1 | HCl | racemic | Amorphous |
| 474 | 3,4,5-Trimethoxybenzoyl | 3-Fluorobenzyl | —SOCH₂— | | S | CH₃ | NCH₃ | NH | 3-Cl | 4-Cl | 1 | 1 | HCl | racemic | Amorphous |
| 475 | 3,4,5-Trimethoxybenzoyl | 2,4-Difluorobenzyl | —SOCH₂— | | S | CH₃ | NCH₃ | NH | 3-Cl | 4-Cl | 1 | 1 | HCl | racemic | Amorphous |
| 476 | 3,4,5-Trimethoxybenzoyl | 2,5-Difluorobenzyl | —SOCH₂— | | S | CH₃ | NCH₃ | NH | 3-Cl | 4-Cl | 1 | 1 | HCl | racemic | Amorphous |
| 477 | 3,4,5-Trimethoxybenzoyl | 2,6-Difluorobenzyl | —SOCH₂— | | S | CH₃ | NCH₃ | NH | 3-Cl | 4-Cl | 1 | 1 | HCl | racemic | Amorphous |
| 478 | 3,4,5-Trimethoxybenzoyl | 3,4-Difluorobenzyl | —SOCH₂— | | S | CH₃ | NCH₃ | NH | 3-Cl | 4-Cl | 1 | 1 | HCl | racemic | Amorphous |
| 479 | 3,4,5-Trimethoxybenzoyl | 3,5-Difluorobenzyl | —SOCH₂— | | S | CH₃ | NCH₃ | NH | 3-Cl | 4-Cl | 1 | 1 | HCl | racemic | Amorphous |
| 480 | 3,4,5-Trimethoxybenzoyl | Cyclohexylmethyl | —SOCH₂— | | S | CH₃ | NCH₃ | NH | 3-Cl | 4-Cl | 1 | 1 | HCl | racemic | Amorphous |
| 481 | 3,4,5-Trimethoxybenzoyl | 3-Pyridylmethyl | —SOCH₂— | | S | CH₃ | NCH₃ | NH | 3-Cl | 4-Cl | 1 | 1 | HCl | racemic | Amorphous |
| 482 | 3,4,5-Trimethoxybenzoyl | 4-Trifluoromethoxybenzyl | —SOCH₂— | | S | CH₃ | NCH₃ | NH | 3-Cl | 4-Cl | 1 | 1 | HCl | racemic | Amorphous |
| 483 | 3,4,5-Trimethoxybenzoyl | 2-Trifluoromethylbenzyl | —NHCOCH₂— | | | CH₃ | NCH₃ | NH | 3-Cl | 4-Cl | 1 | 1 | HCl | racemic | Amorphous |
| 484 | 3,4,5-Trimethoxybenzoyl | 3-Trifluorobenzyl | —SOCH₂— | | S | CH₃ | NCH₃ | NH | 3-Cl | 4-Cl | 1 | 1 | HCl | racemic | Amorphous |
| 485 | 3,4,5-Trimethoxybenzoyl | 4-Trifluoromethylbenzyl | —SOCH₂— | | S | CH₃ | NCH₃ | NH | 3-Cl | 4-Cl | 1 | 1 | HCl | racemic | Amorphous |
| 486 | 3,4,5-Trimethoxybenzoyl | 2,3-Dimethoxybenzyl | —SOCH₂— | | S | CH₃ | NCH₃ | NH | 3-Cl | 4-Cl | 1 | 1 | HCl | racemic | Amorphous |
| 487 | 3,4,5-Trimethoxybenzoyl | 2,4-Dimethoxybenzyl | —SOCH₂— | | S | CH₃ | NCH₃ | NH | 3-Cl | 4-Cl | 1 | 1 | HCl | racemic | Amorphous |
| 488 | 3,4,5-Trimethoxybenzoyl | 3,4-Dimethoxybenzyl | —SOCH₂— | | S | CH₃ | NCH₃ | NH | 3-Cl | 4-Cl | 1 | 1 | HCl | racemic | Amorphous |
| 489 | 3,4,5-Trimethoxybenzoyl | 3,5-Dimethoxybenzyl | —SOCH₂— | | S | CH₃ | NCH₃ | NH | 3-Cl | 4-Cl | 1 | 1 | HCl | racemic | Amorphous |
| 490 | 3,4,5-Trimethoxybenzoyl | 2-Chlorobenzyl | —SOCH₂— | | S | CH₃ | NCH₃ | NH | H | 4-F | 1 | 1 | HCl | racemic | Amorphous |
| 491 | 3,4,5-Trimethoxybenzoyl | 2-Chlorobenzyl | —SOCH₂— | | S | CH₃ | NCH₃ | NH | 3-Cl | 4-Cl | 1 | 1 | HCl | S | Amorphous |
| 492 | 3,4,5-Trimethoxybenzoyl | Benzyl | —SOCH₂— | | S | CH₃ | NCH₃ | NH | 3-Cl | 4-Cl | 1 | 1 | HCl | S | Amorphous |
| 493 | 3,4,5-Trimethoxybenzoyl | 2-Methylbenzyl | —SOCH₂— | | S | CH₃ | NCH₃ | NH | 3-Cl | 4-Cl | 1 | 1 | HCl | S | Amorphous |
| 494 | 3,4,5-Trimethoxybenzoyl | 3-Fluorobenzyl | —SOCH₂— | | S | CH₃ | NCH₃ | NH | 3-Cl | 4-Cl | 1 | 1 | HCl | S | Amorphous |
| 495 | 3,4,5-Trimethoxybenzoyl | 3,5-Difluorobenzyl | —SOCH₂— | | S | CH₃ | NCH₃ | NH | 3-Cl | 4-Cl | 1 | 1 | HCl | S | Amorphous |
| 496 | 3,4,5-Trimethoxybenzoyl | 2-Trifluoromethylbenzyl | —SOCH₂— | | S | CH₃ | NCH₃ | NH | 3-Cl | 4-Cl | 1 | 1 | HCl | S | Amorphous |
| 497 | 3,4,5-Trimethoxybenzoyl | 3-Trifluoromethylbenzyl | —SOCH₂— | | S | CH₃ | NCH₃ | NH | 3-Cl | 4-Cl | 1 | 1 | HCl | R | Amorphous |
| 498 | 3,4,5-Trimethoxybenzoyl | Cyclohexylmethyl | —SOCH₂— | | S | CH₃ | NCH₃ | NH | 3-Cl | 4-Cl | 1 | 1 | HCl | R | Amorphous |
| 499 | 3,4,5-Trimethoxybenzoyl | 2-Chlorobenzyl | —SOCH₂— | | S | CH₃ | NCH₃ | NH | 3-Cl | 4-Cl | 1 | 1 | HCl | R | Amorphous |
| 500 | 3,4,5-Trimethoxybenzoyl | 2-Methylbenzyl | —SOCH₂— | | S | CH₃ | NCH₃ | NH | H | 4-Cl | 1 | 1 | HCl | racemic | Amorphous |
| 501 | 3,4,5-Trimethoxybenzoyl | 2-Chlorobenzyl | —SOCH₂— | | S | CH₃ | NCH₃ | NH | 3-Cl | 4-Cl | 1 | 1 | HCl | S | Amorphous |
| 502 | 3,4,5-Trimethoxybenzoyl | Bis(trifluoromethyl)phenyl | —SOCH₂— | | S | CH₃ | NCH₃ | NH | 3-Cl | 4-Cl | 1 | 1 | HCl | S | Amorphous |
| 503 | 3,4,5-Trimethoxybenzoyl | Adamantyl | —SOCH₂— | | S | CH₃ | NCH₃ | NH | 3-Cl | 4-Cl | 1 | 1 | HCl | S | Amorphous |
| 504 | 3,4,5-Trimethoxybenzoyl | 1-Phenethyl | —SOCH₂— | | S | CH₃ | NCH₃ | NH | 3-Cl | 4-Cl | 1 | 1 | HCl | S | Amorphous |
| 505 | 3,4,5-Trimethoxybenzoyl | Adamantylmethyl | —SOCH₂— | | S | CH₃ | NCH₃ | NH | 3-Cl | 4-Cl | 1 | 1 | HCl | S | Amorphous |
| 506 | 3,4,5-Trimethoxybenzoyl | n-Propyl | —SOCH₂— | | S | CH₃ | NCH₃ | NH | 3-Cl | 4-Cl | 1 | 1 | HCl | R | Amorphous |
| 507 | 3,4,5-Trimethoxybenzoyl | Ethyl | —SOCH₂— | | S | CH₃ | NCH₃ | NH | 3-Cl | 4-Cl | 1 | 1 | HCl | S | Amorphous |
| 508 | 3,4,5-Trimethoxybenzoyl | 2-Fluorobenzyl | —SOCH₂— | | S | CH₃ | NCH₃ | NH | 3-Cl | 4-Cl | 1 | 1 | HCl | S | Amorphous |
| 509 | 3,4,5-Trimethoxybenzoyl | 2-Fluorophenyl | —SOCH₂— | | S | CH₃ | NCH₃ | NH | 3-Cl | 4-Cl | 1 | 1 | HCl | R | Amorphous |
| 510 | 3,4,5-Trimethoxybenzoyl | 2-Trifluoromethylbenzyl | —SOCH₂— | | S | CH₃ | NCH₃ | NH | 3-Cl | 4-Cl | 1 | 1 | HCl | R | Amorphous |
| 511 | 3,4,5-Trimethoxybenzoyl | Cyclohexylmethyl | —SOCH₂— | | S | CH₃ | NCH₃ | NH | 3-Cl | 4-Cl | 1 | 1 | HCl | R | Amorphous |
| 512 | 3,4,5-Trimethoxybenzoyl | Benzyl | CONH₂ | H | | CH₃ | NCH₃ | NH | 3-Cl | 4-Cl | 1 | 1 | HCl | R | Amorphous |
| 513 | 3,3,3-Trifluoropropionyl | Diphenylmethyl | —SOCH₂— | | S | CH₃ | NCH₃ | NH | 3-Cl | 4-Cl | 1 | 1 | HCl | S | Amorphous |
| 514 | 3,3,3-Trifluoropropionyl | Diphenylmethyl | —NHCOCH₂— | | | CH₃ | NCH₃ | NH | 3-Cl | 4-Cl | 1 | 1 | HCl | S | Amorphous |
| 515 | 3,3,3-Trifluoropropionyl | Diphenylmethyl | NHAc | H | | CH₃ | NCH₃ | NH | 3-Cl | 4-Cl | 1 | 1 | HCl | S | Amorphous |
| 516 | 3,3,3-Trifluoropropionyl | Diphenylmethyl | —C(OH)CH₂— | | | CH₃ | NCH₃ | NH | 3-Cl | 4-Cl | 1 | 1 | HCl | | Amorphous |
| 517 | 3,3,3-Trifluoropropionyl | Diphenylmethyl | —SO₂CH₂— | | | CH₃ | NCH₃ | NH | 3-Cl | 4-Cl | 1 | 1 | HCl | S | Amorphous |
| 518 | 3,3,3-Trifluoropropionyl | 9H-Fluoren-9-yl | —SOCH₂— | | S | CH₃ | NCH₃ | NH | 3-Cl | 4-Cl | 1 | 1 | HCl | S | Amorphous |
| 519 | 3,3,3-Trifluoropropionyl | 1-(1-Phenyl)cyclopentyl | —SOCH₂— | | S | CH₃ | NCH₃ | NH | 3-Cl | 4-Cl | 1 | 1 | HCl | S | Amorphous |

TABLE 1-continued

| Compound No. | R¹ | R² | R³ | R⁴ | Spiro | R⁵ | X¹ | X² | X³ | X⁴ | n1 | n2 | Salt | Quaternary carbon | Form |
|---|---|---|---|---|---|---|---|---|---|---|---|---|---|---|---|
| 520 | 3,3,3-Trifluoropropionyl | 2-Chlorobenzyl | —SOCH$_2$— |  | S | CH$_3$ | NCH$_3$ | NH | 3-Cl | 4-Cl | 1 | 1 | HCl | S | Amorphous |
| 521 | 2-Difluoroacetyl | Diphenylmethyl | —NHCOCH$_2$— |  |  | CH$_3$ | NCH$_3$ | NH | 3-Cl | 4-Cl | 1 | 1 | HCl | S | Amorphous |
| 522 | 2-Difluoroacetyl | Diphenylmethyl | —SOCH$_2$— |  | S | CH$_3$ | NCH$_3$ | NH | 3-Cl | 4-Cl | 1 | 1 | HCl | S | Amorphous |
| 523 | 2-Chloro-2,2-difluoroacetyl | Diphenylmethyl | —NHCOCH$_2$— |  |  | CH$_3$ | NCH$_3$ | NH | 3-Cl | 4-Cl | 1 | 1 | HCl | S | Amorphous |
| 524 | 2-Chloro-2,2-difluoroacetyl | 9H-Fluoren-9-yl | —SOCH$_2$— |  | S | CH$_3$ | NCH$_3$ | NH | 3-Cl | 4-Cl | 1 | 1 | HCl | S | Amorphous |
| 525 | 2-Chloro-2,2-difluoroacetyl | Cyclopentyl(phenyl)methyl | —SOCH$_2$— |  | S | CH$_3$ | NCH$_3$ | NH | 3-Cl | 4-Cl | 1 | 1 | HCl | S | Amorphous |
| 526 | 2-Chloro-2,2-difluoroacetyl | 9H-Xanthen-9-yl | —SOCH$_2$— |  | S | CH$_3$ | NCH$_3$ | NH | 3-Cl | 4-Cl | 1 | 1 | HCl | S | Amorphous |
| 527 | 2-Chloro-2,2-difluoroacetyl | Benzyl | —SOCH$_2$— |  | S | CH$_3$ | NCH$_3$ | NH | 3-Cl | 4-Cl | 1 | 1 | HCl | S | Amorphous |
| 528 | 2-Chloro-2,2-difluoroacetyl | 2-Chlorobenzyl | —SOCH$_2$— |  | S | CH$_3$ | NCH$_3$ | NH | 3-Cl | 4-Cl | 1 | 1 | HCl | S | Amorphous |
| 529 | 2-Chloro-2,2-difluoroacetyl | 1-(1-Phenyl)cyclopentyl | —SOCH$_2$— |  | S | CH$_3$ | NCH$_3$ | NH | 3-Cl | 4-Cl | 1 | 1 | HCl | S | Amorphous |
| 530 | 2-Aminoacetyl | Diphenylmethyl | —SOCH$_2$— |  | S | CH$_3$ | NCH$_3$ | NH | 3-Cl | 4-Cl | 1 | 1 | 2HCl | S | Amorphous |
| 531 | (2-Chlorophenylcarbamoyl)formyl | Diphenylmethyl | —SOCH$_2$— |  | S | CH$_3$ | NCH$_3$ | NH | 3-Cl | 4-Cl | 1 | 1 | 2HCl | S | Amorphous |
| 532 | 3,5-Bis(trifluromethyl)benzyl | Phenyl | CONH$_2$ | H |  | CH$_3$ | O | CO | 3-Cl | 4-Cl | 1 | 1 | Free | racemic | Amorphous |
| 533 | 3,4,5-Trimethoxybenzyl | Methyl | CONH$_2$ | H |  | CH$_3$ | O | CO | 3-Cl | 4-Cl | 1 | 1 | Free | racemic | Amorphous |
| 534 | 3,4,5-Trimethoxybenzyl | N,N-Diphenylamino | —SOCH$_2$— |  | S | CH$_3$ | NCH$_3$ | CO | 3-Cl | 4-Cl | 1 | 1 | HCl | racemic | Amorphous |
| 535 | 3,4,5-Trimethoxybenzyl | Phenyl | CONH$_2$ |  |  | CH$_3$ | NCH$_3$ | CO | 3-Cl | 4-Cl | 1 | 1 | HCl | racemic | Amorphous |
| 536 | 3,4,5-Trimethoxybenzyl | N-Methyl-N-phenylamino | —SOCH$_2$— |  | S | CH$_3$ | NCH$_3$ | CO | 3-Cl | 4-Cl | 1 | 1 | HCl | racemic | Amorphous |
| 537 | 3,4,5-Trimethoxybenzyl | 1-Piperidyl | —SOCH$_2$— |  | S | CH$_3$ | NCH$_3$ | CO | 3-Cl | 4-Cl | 1 | 1 | HCl | racemic | Amorphous |
| 538 | 3,4,5-Trimethoxybenzyl | 4-Morpholinyl | —SOCH$_2$— |  | S | CH$_3$ | NCH$_3$ | CO | 3-Cl | 4-Cl | 1 | 1 | HCl | racemic | Amorphous |
| 539 | 3,4,5-Trimethoxybenzyl | N-Methyl-N-phenylamino | —SOCH$_2$— |  | S | CH$_3$ | NCH$_3$ | CO | 3-Cl | 4-Cl | 1 | 1 | HCl | S | Amorphous |
| 540 | 3,4,5-Trimethoxybenzyl | N-Cyolohexyl-N-methylamino | —SOCH$_2$— |  | S | CH$_3$ | NCH$_3$ | CO | 3-Cl | 4-Cl | 1 | 1 | HCl | racemic | Amorphous |
| 541 | 3,4,5-Trimethoxybenzyl | N-Methyl-N-phenylamino | —SOCH$_2$— |  | S | CH$_3$ | NCH$_3$ | CO | 3-Cl | 4-Cl | 1 | 1 | HCl | R | Amorphous |
| 542 | 3,4,5-Trimethoxybenzyl | N-Methyl-N-(2-tolyl)amino | —SOCH$_2$— |  | S | CH$_3$ | NCH$_3$ | CO | 3-Cl | 4-Cl | 1 | 1 | HCl | racemic | Amorphous |
| 543 | 3,4,5-Trimethoxybenzyl | N-Methyl-N-(2-tolyl)amino | —SOCH$_2$— |  | S | CH$_3$ | NCH$_3$ | CO | 3-Cl | 4-Cl | 1 | 1 | HCl | S | Amorphous |
| 544 | 3,4,5-Trimethoxybenzyl | 2-Tetrahydroquinoliyl | —SOCH$_2$— |  | S | CH$_3$ | NCH$_3$ | CO | 3-Cl | 4-Cl | 1 | 1 | HCl | racemic | Amorphous |
| 545 | 3,4,5-Trimethoxybenzyl | N-Methyl-N-2-chlorophenylamino | —SOCH$_2$— |  | S | CH$_3$ | NCH$_3$ | CO | 3-Cl | 4-Cl | 1 | 1 | HCl | racemic | Amorphous |
| 546 | 3,3,5-Trifluoropropionyl | Diphenylamino | —SOCH$_2$— |  | S | CH$_3$ | NCH$_3$ | CO | 3-Cl | 4-Cl | 1 | 1 | HCl | S | Amorphous |
| 547 | 3,3,5-Trifluoropropionyl | 1-Indoliyl | —SOCH$_2$— |  | S | CH$_3$ | NCH$_3$ | CO | 3-Cl | 4-Cl | 1 | 1 | HCl | S | Amorphous |
| 548 | 3,3,5-Trifluoropropionyl | 2-Tetrahydroquinoliyl | —SOCH$_2$— |  | S | CH$_3$ | NCH$_3$ | CO | 3-Cl | 4-Cl | 1 | 1 | HCl | S | Amorphous |
| 549 | Methyl | 3,4,5-Trimethoxyphenyl | CONH$_2$ | H |  | CH$_3$ | O | Single bond | 3-Cl | 4-Cl | 2 | 1 | Free | racemic | Amorphous |
| 550 | 4-Cyanobenzyl | 3,4,5-Trimethoxyphenyl | CONH$_2$ | H |  | CH$_3$ | O | Single bond | 3-Cl | 4-Cl | 2 | 1 | Free | racemic | Amorphous |
| 551 | 3,4,5-Trimethoxybenzyl | Methyl | —SOCH$_2$— |  | S | CH$_3$ | O | Single bond | 3-Cl | 4-Cl | 2 | 0 | Free | S | Amorphous |
| 552 | 3,4,5-Trimethoxybenzyl | Methyl | —SOCH$_2$— |  | S | CH$_3$ | O | Single bond | 3-Cl | 4-Cl | 2 | 0 | Free | S | Amorphous |
| 553 | 3,4,5-Trimethoxybenzyl | Methyl | —SOCH$_2$— |  | S | CH$_3$ | O | Single bond | 3-Cl | 4-Cl | 2 | 0 | Free | R or S | Amorphous |
| 554 | 3,4,5-Trimethoxybenzyl | Methyl | —SOCH$_2$— |  | S | CH$_3$ | O | Single bond | 3-Cl | 4-Cl | 2 | 0 | Free | R or S | Amorphous |
| 555 | 3,4,5-Trimethoxybenzyl | H | CONH$_2$ | H |  | CH$_3$ | O | Single bond | 3-Cl | 4-Cl | 2 | 1 | Free | racemic | Amorphous |
| 556 | 3,4,5-Trimethoxybenzyl | n-Propyl | CONH$_2$ | H |  | CH$_3$ | O | Single bond | 3-Cl | 4-Cl | 2 | 1 | Free | racemic | Amorphous |
| 557 | 3,4,5-Trimethoxybenzyl | Benzyl | CONH$_2$ | H |  | CH$_3$ | O | Single bond | 3-Cl | 4-Cl | 2 | 1 | Free | racemic | Amorphous |
| 558 | 3,4,5-Trimethoxybenzyl | 2,2-Dimethylpropyl | CONH$_2$ | H |  | CH$_3$ | O | Single bond | 3-Cl | 4-Cl | 2 | 1 | Free | racemic | Amorphous |
| 559 | 3,4,5-Trimethoxybenzyl | Methyl | CONH$_2$ | H |  | CH$_3$ | O | Single bond | 3-Cl | 4-Cl | 2 | 1 | Free | racemic | Amorphous |
| 560 | 3,4,5-Trimethoxybenzyl | 3,4,5-Trimethoxyphenyl | CONH$_2$ | H |  | CH$_3$ | O | Single bond | 3-Cl | 4-Cl | 2 | 1 | Free | racemic | Amorphous |
| 561 | 3,4,5-Trimethoxybenzyl | 3,4,5-Trimethoxybenzyl | CONH$_2$ | H |  | CH$_3$ | O | Single bond | 3-Cl | 4-Cl | 2 | 1 | Free | racemic | Amorphous |
| 562 | 3,4,5-Trimethoxybenzyl | Methyl | CONH$_2$ |  |  | CH$_3$ | NCH$_3$ | Single bond | 3-Cl | 4-Cl | 2 | 0 | Free | racemic | Amorphous |
| 563 | 3,4,5-Trimethoxybenzyl | H | CONH$_2$ |  |  | CH$_3$ | NCH$_3$ | Single bond | 3-Cl | 4-Cl | 2 | 0 | Free | racemic | Amorphous |
| 564 | 3,4,5-Trimethoxybenzyl | 2,2-Dimethylpropyl | CONH$_2$ |  |  | CH$_3$ | NCH$_3$ | Single bond | 3-Cl | 4-Cl | 2 | 1 | Free | racemic | Amorphous |
| 565 | 3,4,5-Trimethoxybenzyl | Benzyl | CONH$_2$ |  |  | CH$_3$ | NCH$_3$ | Single bond | 3-Cl | 4-Cl | 2 | 0 | Free | racemic | Amorphous |
| 566 | 3,4,5-Trimethoxybenzyl | Ethyl | CONH$_2$ |  |  | CH$_3$ | O | Ester bond | 3-Cl | 4-Cl | 2 | 1 | Free | racemic | Amorphous |

TABLE 1-continued

| Compound No. | R¹ | R² | R³ | R⁴ | Spiro | R⁵ | X¹ | X² | X³ | X⁴ | n1 | n2 | Salt | Quaternary carbon | Form |
|---|---|---|---|---|---|---|---|---|---|---|---|---|---|---|---|
| 567 | 3,4,5-Trimethoxybenzyl | Cyclopentyl | —SOCH$_2$— | | S | CH$_3$ | O | Ester bond | 3-Cl | 4-Cl | 2 | 1 | HCl | racemic | Amorphous |
| 568 | Methyl | Phenyl | CONH$_2$ | H | | CH$_3$ | O | NH | 3-Cl | 4-Cl | 2 | 1 | Free | racemic | Amorphous |
| 569 | iso-Butyryl | Diphenylmethyl | —NHCOCH$_2$— | | | CH$_3$ | NCH$_3$ | NH | 3-Cl | 4-Cl | 2 | 1 | HCl | S | Amorphous |
| 570 | Benzyl | Phenyl | CONH$_2$ | H | | CH$_3$ | O | NH | 3-Cl | 4-Cl | 2 | 1 | Free | racemic | Amorphous |
| 571 | 3,4,5-Trimethoxybenzyl | Benzyl | CONH$_2$ | H | | CH$_3$ | NCH$_3$ | NH | 3-Cl | 4-Cl | 2 | 1 | Free | racemic | Amorphous |
| 572 | 3,4,5-Trimethoxybenzyl | Phenyl | CONH$_2$ | H | | CH$_3$ | NCH$_3$ | NH | 3-Cl | 4-Cl | 2 | 1 | Free | racemic | Amorphous |
| 573 | 3,4,5-Trimethoxybenzyl | Cyclohexyl | CONH$_2$ | H | | CH$_3$ | NCH$_3$ | NH | 3-Cl | 4-Cl | 2 | 1 | HCl | racemic | Amorphous |
| 574 | 3,4,5-Trimethoxybenzyl | Benzyl | CONH$_2$ | H | | CH$_3$ | NCH$_3$ | NH | 3-Cl | 4-Cl | 2 | 1 | HCl | S | Amorphous |
| 575 | 3,4,5-Trimethoxybenzyl | Benzyl | CONH$_2$ | H | | CH$_3$ | NCH$_3$ | NH | 3-Cl | 4-Cl | 2 | 1 | HCl | R | Amorphous |
| 576 | 3,4,5-Trimethoxybenzyl | Benzyl | —SOCH$_2$— | | S | CH$_3$ | NCH$_3$ | NH | 3-Cl | 4-Cl | 2 | 1 | HCl | S | Amorphous |
| 577 | 3,4,5-Trimethoxybenzyl | Phenyl | —SOCH$_2$— | | S | CH$_3$ | NCH$_3$ | NH | 3-Cl | 4-Cl | 2 | 1 | HCl | S | Amorphous |
| 579 | 3,5-Bis(trifluoromethyl)benzoyl | Phenyl | CONH$_2$ | H | | CH$_3$ | NCH$_3$ | NH | 3-Cl | 4-Cl | 2 | 1 | HCl | S | Amorphous |
| 580 | 3,4,5-Trimethoxybenzyl | tert-Butyl | CONH$_2$ | H | | CH$_3$ | O | O | 3-Cl | 4-Cl | 2 | 1 | Free | racemic | Amorphous |
| 581 | 3,4,5-Trimethoxybenzyl | Benzyl | CONH$_2$ | H | | CH$_3$ | O | O | 3-Cl | 4-Cl | 2 | 1 | HCl | S | Amorphous |
| 582 | 3,4,5-Trimethoxybenzyl | Phenyl | CONH$_2$ | H | | CH$_3$ | O | O | 3-Cl | 4-Cl | 2 | 1 | HCl | racemic | Amorphous |
| 583 | 3,4,5-Trimethoxybenzyl | Phenyl | CONH$_2$ | H | | CH$_3$ | O | O | 3-Cl | 4-Cl | 2 | 1 | HCl | S | Amorphous |
| 584 | 3,4,5-Trimethoxybenzyl | Phenyl | —SOCH$_2$— | | S | CH$_3$ | O | O | 3-Cl | 4-Cl | 2 | 1 | Free | S | Amorphous |
| 585 | 3,4,5-Trimethoxybenzyl | Phenyl | CONH$_2$ | H | | CH$_3$ | NCH$_3$ | O | 3-Cl | 4-Cl | 2 | 1 | HCl | S | Amorphous |
| 586 | 3,4,5-Trimethoxybenzyl | tert-Butyl | CONH$_2$ | H | | CH$_3$ | NCH$_3$ | O | 3-Cl | 4-Cl | 2 | 1 | HCl | S | Amorphous |
| 587 | 3,4,5-Trimethoxybenzyl | Phenyl | —SOCH$_2$— | | S | CH$_3$ | NCH$_3$ | O | 3-Cl | 4-Cl | 2 | 1 | Free | racemic | Amorphous |
| 588 | 3,4,5-Trimethoxybenzyl | Phenyl | —SOCH$_2$— | | S | CH$_3$ | NCH$_3$ | O | 3-Cl | 4-Cl | 2 | 1 | HCl | S | Amorphous |
| 590 | 3,3,3-Trifluoropropionyl | Benzyl | —SOCH$_2$— | | S | CH$_3$ | NCH$_3$ | O | 3-Cl | 4-Cl | 2 | 1 | HCl | R | Amorphous |
| 592 | 3,3,3-Trifluoropropionyl | 2-Phenethyl | —SOCH$_2$— | | S | CH$_3$ | O | NH | 3-Cl | 4-Cl | 2 | 1 | HCl | S | Amorphous |
| 593 | 4-Cyanobenzyl | Phenyl | CONH$_2$ | H | | CH$_3$ | O | NH | 3-Cl | 4-Cl | 2 | 1 | Free | racemic | Amorphous |
| 594 | 3,5-Bis(trifluoromethyl)benzyl | Benzyl | —SOCH$_2$— | | S | CH$_3$ | O | NH | 3-Cl | 4-Cl | 2 | 1 | HCl | S | Amorphous |
| 595 | 3,5-Bis(trifluoromethyl)benzyl | Benzyl | —SOCH$_2$— | | S | CH$_3$ | O | NH | 3-Cl | 4-Cl | 2 | 1 | HCl | S | Amorphous |
| 596 | 3,4,5-Trimethoxybenzyl | Methyl | CONH$_2$ | H | | CH$_3$ | O | NH | 3-Cl | 4-Cl | 2 | 1 | Free | racemic | Amorphous |
| 597 | 3,4,5-Trimethoxybenzyl | iso-Propyl | CONH$_2$ | H | | CH$_3$ | O | NH | 3-Cl | 4-Cl | 2 | 1 | Free | racemic | Amorphous |
| 598 | 3,4,5-Trimethoxybenzyl | 1-Naphthyl | CONH$_2$ | H | | CH$_3$ | O | NH | 3-Cl | 4-Cl | 2 | 1 | Free | racemic | Amorphous |
| 600 | 3,4,5-Trimethoxybenzyl | n-Propyl | CONH$_2$ | H | | CH$_3$ | O | NH | 3-Cl | 4-Cl | 2 | 1 | HCl | racemic | Amorphous |
| 601 | 3,4,5-Trimethoxybenzyl | n-Octyl | CONH$_2$ | H | | CH$_3$ | O | NH | 3-Cl | 4-Cl | 2 | 1 | HCl | racemic | Amorphous |
| 602 | 3,4,5-Trimethoxybenzyl | Cyclopentyl | CONH$_2$ | H | | CH$_3$ | O | NH | 3-Cl | 4-Cl | 2 | 1 | HCl | racemic | Amorphous |
| 603 | 3,4,5-Trimethoxybenzyl | Phenyl | —SOCH$_2$— | | S | CH$_3$ | O | NH | 3-Cl | 4-Cl | 2 | 1 | HCl | S | Amorphous |
| 604 | 3,4,5-Trimethoxybenzyl | Benzyl | CONH$_2$ | H | | CH$_3$ | O | NH | 3-Cl | 4-Cl | 2 | 1 | HCl | S | Amorphous |
| 605 | 3,4,5-Trimethoxybenzyl | Benzyl | CONH$_2$ | H | | CH$_3$ | O | NH | 3-Cl | 4-Cl | 2 | 1 | HCl | S | Amorphous |
| 606 | 3,4,5-Trimethoxybenzyl | Benzyl | CONH$_2$ | H | | CH$_3$ | O | NH | 3-Cl | 4-Cl | 2 | 1 | HCl | S | Amorphous |
| 607 | 3,4,5-Trimethoxybenzyl | Benzyl | —SOCH$_2$— | | S | CH$_3$ | O | NH | 3-Cl | 4-Cl | 2 | 1 | HCl | S | Amorphous |
| 608 | 3,4,5-Trimethoxybenzyl | Cyclopentyl | —SOCH$_2$— | | S | CH$_3$ | O | NH | 3-Cl | 4-Cl | 2 | 1 | HCl | S | Amorphous |
| 609 | 3,4,5-Trimethoxybenzyl | n-Propyl | —SOCH$_2$— | | S | CH$_3$ | O | NH | 3-Cl | 4-Cl | 2 | 1 | HCl | S | Amorphous |
| 610 | 3,4,5-Trimethoxybenzyl | Phenyl | —SOCH$_2$— | | S | CH$_3$ | O | NH | 3-Cl | 4-Cl | 2 | 1 | HCl | S | Amorphous |
| 611 | 3,4,5-Trimethoxybenzyl | 2-Phenethyl | —SOCH$_2$— | | S | CH$_3$ | O | NH | 3-Cl | 4-Cl | 2 | 1 | HCl | S | Amorphous |
| 612 | 3,4,5-Trimethoxybenzyl | Benzyl | NHAc | H | | CH$_3$ | O | NH | 3-Cl | 4-Cl | 2 | 1 | HCl | S | Amorphous |
| 613 | 3,4,5-Trimethoxybenzyl | Benzyl | CH$_2$OCH$_2$Ph | H | | CH$_3$ | O | NH | 3-Cl | 4-Cl | 2 | 1 | HCl | S | Amorphous |
| 619 | 3,4,5-Trimethoxybenzyl | Cyclohexyl | —SOCH$_2$— | | S | CH$_3$ | O | NH | 3-Cl | 4-Cl | 2 | 1 | HCl | S | Amorphous |
| 620 | 3,4,5-Trimethoxybenzyl | iso-Propyl | —SOCH$_2$— | | S | CH$_3$ | O | NH | 3-Cl | 4-Cl | 2 | 1 | HCl | S | Amorphous |
| 621 | 3,4,5-Trimethoxybenzyl | tert-Butyl | —SOCH$_2$— | | S | CH$_3$ | O | NH | 3-Cl | 4-Cl | 2 | 1 | HCl | S | Amorphous |
| 622 | 3,4,5-Trimethoxybenzyl | 4-Trifluoromethoxyphenyl | —SOCH$_2$— | | S | CH$_3$ | O | NH | 3-Cl | 4-Cl | 2 | 1 | HCl | S | Amorphous |
| 623 | 3,4,5-Trimethoxybenzyl | 3,5-Bis(trifluoromethyl)phenyl | —SOCH$_2$— | | S | CH$_3$ | O | NH | 3-Cl | 4-Cl | 2 | 1 | HCl | S | Amorphous |

TABLE 1-continued

| Compound No. | R¹ | R² | R³ | R⁴ Spiro | R⁵ | X¹ | X² | X³ | X⁴ | n1 | n2 | Salt | Quaternary carbon | Form |
|---|---|---|---|---|---|---|---|---|---|---|---|---|---|---|
| 624 | 3,4,5-Trimethoxybenzyl | Benzyl | —NHCOCH₂— | | CH₃ | O | NH | 3-Cl | 4-Cl | 2 | 1 | HCl | S | Amorphous |
| 625 | 3,4,5-Trimethoxybenzyl | Benzyl | —OCH₂— | | CH₃ | O | NH | 3-Cl | 4-Cl | 2 | 1 | HCl | S | Amorphous |
| 626 | 3,4,5-Trimethoxybenzyl | Benzyl | —OCO— | | CH₃ | O | NH | 3-Cl | 4-Cl | 2 | 1 | HCl | S | Amorphous |
| 627 | 3,3,3-Trifluoropropionyl | 4-Methylbenzyl | —SOCH₂— | S | CH₃ | NCH₃ | O | 3-Cl | 4-Cl | 2 | 1 | HCl | S | Amorphous |
| 628 | 3,3,3-Trifluoropropionyl | 4-Chlorobenzyl | —SOCH₂— | S | CH₃ | NCH₃ | O | 3-Cl | 4-Cl | 2 | 1 | HCl | S | Amorphous |
| 629 | 3,3,3-Trifluoropropionyl | Cyclopentylmethyl | —SOCH₂— | S | CH₃ | NCH₃ | O | 3-Cl | 4-Cl | 2 | 1 | HCl | S | Amorphous |
| 630 | 3,3,3-Trifluoropropionyl | n-Propyl | —SOCH₂— | S | CH₃ | NCH₃ | O | 3-Cl | 4-Cl | 2 | 1 | HCl | S | Amorphous |
| 631 | 3,3,3-Trifluoropropionyl | n-Hexyl | —SOCH₂— | S | CH₃ | NCH₃ | O | 3-Cl | 4-Cl | 2 | 1 | HCl | S | Amorphous |
| 632 | 3,3,3-Trifluoropropionyl | iso-Butyl | —SOCH₂— | S | CH₃ | NCH₃ | O | 3-Cl | 4-Cl | 2 | 1 | HCl | S | Amorphous |
| 635 | 3,3,3-Trifluoropropionyl | tert-Butyl | —SOCH₂— | S | CH₃ | NCH₃ | O | 3-Cl | 4-Cl | 2 | 1 | HCl | S | Amorphous |
| 641 | 3,3,3-Trifluoropropionyl | 4-Trifluoromethylphenyl | —SOCH₂— | S | CH₃ | NCH₃ | O | 3-Cl | 4-Cl | 2 | 1 | HCl | S | Amorphous |
| 643 | 3,3,3-Trifluoropropionyl | Phenoxymethyl | —SOCH₂— | S | CH₃ | NCH₃ | O | 3-Cl | 4-Cl | 2 | 1 | HCl | S | Amorphous |
| 644 | Trifluoroacetyl | Benzyl | —SOCH₂— | S | CH₃ | NCH₃ | Single bond | 3-Cl | 4-Cl | 2 | 1 | HCl | S | Amorphous |
| 645 | 3,3,3-Trifluoropropionyl | Benzyl | —SOCH₂— | S | CH₃ | NCH₃ | Single bond | 3-Cl | 4-Cl | 2 | 1 | HCl | S | Amorphous |
| 646 | 3,3,3-Trifluoropropionyl | 2-Phenethyl | —SOCH₂— | S | CH₃ | NCH₃ | Single bond | 3-Cl | 4-Cl | 2 | 1 | HCl | S | Amorphous |
| 647 | 3,3,3-Trifluoropropionyl | 2,2-Diphenylethyl | —SOCH₂— | S | CH₃ | NCH₃ | Single bond | 3-Cl | 4-Cl | 2 | 1 | HCl | S | Amorphous |
| 648 | 3,3,3-Trifluoropropionyl | Phenyl | —SOCH₂— | S | CH₃ | NCH₃ | Single bond | 3-Cl | 4-Cl | 2 | 1 | HCl | S | Amorphous |
| 649 | 3,3,3-Trifluoropropionyl | Diphenylmethyl | —SOCH₂— | S | CH₃ | NCH₃ | NH | 3-Cl | 4-Cl | 2 | 1 | HCl | S | Amorphous |
| 650 | 3,3,3-Trifluoropropionyl | Diphenylmethyl | —SOCH₂— | S | CH₃ | NCH₃ | NH | 3-Cl | 4-Cl | 2 | 1 | HCl | S | Amorphous |
| 651 | 3,3,3-Trifluoropropionyl | Benzyl | —NHCOCH₂— | | CH₃ | NCH₃ | NH | 3-Cl | 4-Cl | 2 | 1 | HCl | S | Amorphous |
| 656 | Trifluoroacetyl | Benzyl | —SOCH₂— | S | CH₃ | NCH₃ | Single bond | 3-Cl | 4-Cl | 1 | 1 | HCl | S | Amorphous |
| 657 | Trifluoroacetyl | 2-Phenethyl | —NHCOCH₂— | | CH₃ | NCH₃ | Single bond | 3-Cl | 4-Cl | 1 | 1 | HCl | S | Amorphous |
| 658 | Trifluoroacetyl | Phenyl | —SO₂CH₂— | S | CH₃ | NCH₃ | Single bond | 3-Cl | 4-Cl | 1 | 1 | HCl | S | Amorphous |
| 659 | Trifluoroacetyl | 2-Trifluoromethylphenyl | —NHCOCH₂— | | CH₃ | NCH₃ | Single bond | 3-Cl | 4-Cl | 1 | 1 | HCl | S | Amorphous |
| 660 | Trifluoroacetyl | 3-Fluorophenyl | —NHCOCH₂— | | CH₃ | NCH₃ | Single bond | 3-Cl | 4-Cl | 1 | 1 | HCl | S | Amorphous |
| 661 | Trifluoroacetyl | 2-Fluorophenyl | —NHCOCH₂— | | CH₃ | NCH₃ | Single bond | 3-Cl | 4-Cl | 1 | 1 | HCl | S | Amorphous |
| 662 | Trifluoroacetyl | 3-Fluorophenyl | —SOCH₂— | S | CH₃ | NCH₃ | Single bond | 3-Cl | 4-Cl | 1 | 1 | HCl | S | Amorphous |
| 663 | Trifluoroacetyl | 4-Fluorophenyl | —NHCOCH₂— | | CH₃ | NCH₃ | Single bond | 3-Cl | 4-Cl | 1 | 1 | HCl | S | Amorphous |
| 664 | Trifluoroacetyl | Phenyl | —NHCOCH₂— | | CH₃ | NCH₃ | Single bond | 3-Cl | 4-Cl | 1 | 1 | HCl | S | Amorphous |
| 665 | Trifluoroacetyl | 2,4-Difluorophenyl | —NHCOCH₂— | | CH₃ | NCH₃ | Single bond | 3-Cl | 4-Cl | 1 | 1 | HCl | S | Amorphous |
| 666 | Trifluoroacetyl | 3,4-Difluorophenyl | —NHCOCH₂— | | CH₃ | NCH₃ | Single bond | 3-Cl | 4-Cl | 1 | 1 | HCl | S | Amorphous |
| 667 | Trifluoroacetyl | 2,6-Difluorophenyl | —NHCOCH₂— | | CH₃ | NCH₃ | Single bond | 3-Cl | 4-Cl | 1 | 1 | HCl | S | Amorphous |
| 668 | Propionyl | Phenyl | —NHCOCH₂— | | CH₃ | NCH₃ | Single bond | 3-Cl | 4-Cl | 1 | 1 | HCl | S | Amorphous |
| 669 | Pivaloyl | Benzyl | —SOCH₂— | S | CH₃ | NCH₃ | Single bond | 3-Cl | 4-Cl | 1 | 1 | HCl | S | Amorphous |
| 670 | Pivaloyl | Phenyl | —SOCH₂— | S | CH₃ | NCH₃ | Single bond | 3-Cl | 4-Cl | 1 | 1 | HCl | S | Amorphous |
| 671 | Pivaloyl | Phenyl | —NHCOCH₂— | | CH₃ | NCH₃ | Single bond | 3-Cl | 4-Cl | 1 | 1 | HCl | S | Amorphous |
| 672 | Pivaloyl | Benzyl | —NHCOCH₂— | | CH₃ | NCH₃ | Single bond | 3-Cl | 4-Cl | 1 | 1 | HCl | S | Amorphous |
| 673 | iso-Butyryl | Benzyl | —SOCH₂— | S | CH₃ | NCH₃ | Single bond | 3-Cl | 4-Cl | 1 | 1 | HCl | S | Amorphous |
| 674 | iso-Butyryl | Phenyl | —NHCOCH₂— | | CH₃ | NCH₃ | Single bond | 3-Cl | 4-Cl | 1 | 1 | HCl | S | Amorphous |
| 675 | iso-Butyryl | Benzyl | —NHCOCH₂— | | CH₃ | NCH₃ | Single bond | 3-Cl | 4-Cl | 1 | 1 | HCl | S | Amorphous |
| 676 | Acetyl | Phenyl | —NHCOCH₂— | | CH₃ | NCH₃ | Single bond | 3-Cl | 4-Cl | 1 | 1 | HCl | S | Amorphous |
| 677 | Acetyl | n-Propyl | —SOCH₂— | S | CH₃ | NCH₃ | Single bond | 3-Cl | 4-Cl | 1 | 1 | HCl | S | Amorphous |
| 678 | Acetyl | Benzyl | —SOCH₂— | S | CH₃ | NCH₃ | Single bond | 3-Cl | 4-Cl | 1 | 1 | HCl | S | Amorphous |
| 679 | Acetyl | Cyclopentyl | —NHCOCH₂— | | CH₃ | NCH₃ | Single bond | 3-Cl | 4-Cl | 1 | 1 | HCl | S | Amorphous |
| 680 | Acetyl | 2,2,2-Trifluoroethyl | —SOCH₂— | S | CH₃ | NCH₃ | Single bond | 3-Cl | 4-Cl | 1 | 1 | HCl | S | Amorphous |
| 681 | 3,3,3-Trifluoropropionyl | 2-Phenethyl | —SOCH₂— | S | CH₃ | NCH₃ | Single bond | 3-Cl | 4-Cl | 1 | 1 | HCl | S | Amorphous |
| 682 | 3,3,3-Trifluoropropionyl | Benzyl | —NHCOCH₂— | | CH₃ | NCH₃ | Single bond | 3-Cl | 4-Cl | 1 | 1 | HCl | S | Amorphous |
| 683 | 3,3,3-Trifluoropropionyl | Cyclohexyl | —SOCH₂— | S | CH₃ | NCH₃ | Single bond | 3-Cl | 4-Cl | 1 | 1 | HCl | S | Amorphous |

TABLE 1-continued

| Compound No. | R¹ | R² | R³ | R⁴ | Spiro | R⁵ | X¹ | X² | X³ | X⁴ | n1 | n2 | Salt | Quaternary carbon | Form |
|---|---|---|---|---|---|---|---|---|---|---|---|---|---|---|---|
| 684 | 3,3,3-Trifluoropropionyl | 2-Methylpropyl | —SO₂CH₃ | | | CH₃ | NCH₃ | Single bond | 3-Cl | 4-Cl | 1 | 1 | HCl | S | Amorphous |
| 685 | 3,3,3-Trifluoropropionyl | Phenyl | —SOCH₂— | | S | CH₃ | NCH₃ | Single bond | 3-Cl | 4-Cl | 1 | 1 | HCl | S | Amorphous |
| 686 | 3,3,3-Trifluoropropionyl | 2,2-Dimethylpropyl | —SOCH₂— | | S | CH₃ | NCH₃ | Single bond | 3-Cl | 4-Cl | 1 | 1 | HCl | S | Amorphous |
| 687 | 3,3,3-Trifluoropropionyl | 4-Tolyl | —SOCH₂— | | S | CH₃ | NCH₃ | Single bond | 3-Cl | 4-Cl | 1 | 1 | HCl | S | Amorphous |
| 688 | 3,3,3-Trifluoropropionyl | 4-Fluorophenyl | —SOCH₂— | | S | CH₃ | NCH₃ | Single bond | 3-Cl | 4-Cl | 1 | 1 | HCl | S | Amorphous |
| 689 | 3,3,3-Trifluoropropionyl | Cyclohexylmethyl | —SOCH₂— | | S | CH₃ | NCH₃ | Single bond | 3-Cl | 4-Cl | 1 | 1 | HCl | S | Amorphous |
| 690 | 3,3,3-Trifluoropropionyl | 3-Fluorophenyl | —SOCH₂— | | S | CH₃ | NCH₃ | Single bond | 3-Cl | 4-Cl | 1 | 1 | HCl | S | Amorphous |
| 691 | 3,3,3-Trifluoropropionyl | 4-Chlorophenyl | —SOCH₂— | | S | CH₃ | NCH₃ | Single bond | 3-Cl | 4-Cl | 1 | 1 | HCl | S | Amorphous |
| 692 | 3,3,3-Trifluoropropionyl | 4-Methoxyphenyl | —SOCH₂— | | S | CH₃ | NCH₃ | Single bond | 3-Cl | 4-Cl | 1 | 1 | HCl | S | Amorphous |
| 693 | 3,3,3-Trifluoropropionyl | Phenyl | —OCH₂— | | | CH₃ | NCH₃ | Single bond | 3-Cl | 4-Cl | 1 | 1 | HCl | S | Amorphous |
| 694 | 3,3,3-Trifluoropropionyl | Phenyl | —OCO— | | | CH₃ | NCH₃ | Single bond | 3-Cl | 4-Cl | 1 | 1 | HCl | S | Amorphous |
| 695 | 3,3,3-Trifluoropropionyl | Phenyl | NHAc | H | | CH₃ | NCH₃ | Single bond | 3-Cl | 4-Cl | 1 | 1 | HCl | S | Amorphous |
| 696 | 3,3,3-Trifluoropropionyl | Phenyl | CH₂OCH₂Ph | H | | CH₃ | NCH₃ | Single bond | 3-Cl | 4-Cl | 1 | 1 | HCl | S | Amorphous |
| 697 | 3,3,3-Trifluoropropionyl | Phenyl | CONH₂ | H | | CH₃ | NCH₃ | Single bond | 3-Cl | 4-Cl | 1 | 1 | HCl | S | Amorphous |
| 698 | 3,3,3-Trifluoropropionyl | 2-Fluorophenyl | —NHCOCH₂— | | | CH₃ | NCH₃ | Single bond | 3-Cl | 4-Cl | 1 | 1 | HCl | S | Amorphous |
| 699 | 3,3,3-Trifluoropropionyl | 3-Fluorophenyl | —NHCOCH₂— | | | CH₃ | NCH₃ | Single bond | 3-Cl | 4-Cl | 1 | 1 | HCl | S | Amorphous |
| 700 | 3,3,3-Trifluoropropionyl | 4-Fluorophenyl | —NHCOCH₂— | | | CH₃ | NCH₃ | Single bond | 3-Cl | 4-Cl | 1 | 1 | HCl | S | Amorphous |
| 701 | 3,3,3-Trifluoropropionyl | 4-Trifluoromethylphenyl | —NHCOCH₂— | | | CH₃ | NCH₃ | Single bond | 3-Cl | 4-Cl | 1 | 1 | HCl | S | Amorphous |
| 702 | 3,3,3-Trifluoropropionyl | 2-Trifluoromethylphenyl | —NHCOCH₂— | | | CH₃ | NCH₃ | Single bond | 3-Cl | 4-Cl | 1 | 1 | HCl | S | Amorphous |
| 703 | 3,3,3-Trifluoropropionyl | 3-Trifluoromethylphenyl | —NHCOCH₂— | | | CH₃ | NCH₃ | Single bond | 3-Cl | 4-Cl | 1 | 1 | HCl | S | Amorphous |
| 704 | 3,3,3-Trifluoropropionyl | 2,4-Difluorophenyl | —NHCOCH₂— | | | CH₃ | NCH₃ | Single bond | 3-Cl | 4-Cl | 1 | 1 | HCl | S | Amorphous |
| 705 | 3,3,3-Trifluoropropionyl | 2,6-Difluorophenyl | —NHCOCH₂— | | | CH₃ | NCH₃ | Single bond | 3-Cl | 4-Cl | 1 | 1 | HCl | S | Amorphous |
| 706 | 3,3,3-Trifluoropropionyl | 3,4-Difluorophenyl | —NHCOCH₂— | | | CH₃ | NCH₃ | Single bond | 3-Cl | 4-Cl | 1 | 1 | HCl | S | Amorphous |
| 707 | 2-Chloro-2,2-difluoroacetyl | 2-Phenethyl | —SOCH₂— | | S | CH₃ | NCH₃ | Single bond | 3-Cl | 4-Cl | 1 | 1 | HCl | S | Amorphous |
| 708 | Trifluoroacetyl | 3,5-Difluorophenyl | —NHCOCH₂— | | | CH₃ | NCH₃ | Amide bond | 3-Cl | 4-Cl | 1 | 1 | HCl | S | Amorphous |
| 709 | Trifluoroacetyl | 2-Chlorophenyl | —NHCOCH₂— | | | CH₃ | NCH₃ | Amide bond | 3-Cl | 4-Cl | 1 | 1 | HCl | S | Amorphous |
| 710 | Trifluoroacetyl | 3-Methoxy-5-trifluoromethylphenyl | —NHCOCH₂— | | | CH₃ | NCH₃ | Amide bond | 3-Cl | 4-Cl | 1 | 1 | HCl | S | Amorphous |
| 711 | Trifluoroacetyl | Phenyl | —SOCH₂— | | S | CH₃ | NCH₃ | Amide bond | 3-Cl | 4-Cl | 1 | 1 | HCl | S | Amorphous |
| 712 | Pivaloyl | Phenyl | —SOCH₂— | | S | CH₃ | NCH₃ | Amide bond | 3-Cl | 4-Cl | 1 | 1 | HCl | S | Amorphous |
| 713 | Pivaloyl | Phenyl | —NHCOCH₂— | | | CH₃ | NCH₃ | Amide bond | 3-Cl | 4-Cl | 1 | 1 | HCl | S | Amorphous |
| 714 | iso-Butyryl | Phenyl | —SOCH₂— | | S | CH₃ | NCH₃ | Amide bond | 3-Cl | 4-Cl | 1 | 1 | HCl | S | Amorphous |
| 715 | iso-Butyryl | Phenyl | —NHCOCH₂— | | | CH₃ | NCH₃ | Amide bond | 3-Cl | 4-Cl | 1 | 1 | HCl | S | Amorphous |
| 716 | Acetyl | Benzyl | —SOCH₂— | | S | CH₃ | NCH₃ | Amide bond | 3-Cl | 4-Cl | 1 | 1 | HCl | S | Amorphous |
| 717 | Acetyl | Cyclopentyl | —SOCH₂— | | S | CH₃ | NCH₃ | Amide bond | 3-Cl | 4-Cl | 1 | 1 | HCl | S | Amorphous |
| 718 | Acetyl | n-Propyl | —SOCH₂— | | S | CH₃ | NCH₃ | Amide bond | 3-Cl | 4-Cl | 1 | 1 | HCl | S | Amorphous |
| 719 | Acetyl | Phenyl | —SO₂CH₃ | | | CH₃ | NCH₃ | Amide bond | 3-Cl | 4-Cl | 1 | 1 | HCl | S | Amorphous |
| 720 | 3,3,3-Trifluoropropionyl | n-Propyl | —NHCOCH₂— | | | CH₃ | NCH₃ | NH | 3-Cl | 4-Cl | 1 | 1 | HCl | S | Amorphous |
| 721 | 3,3,3-Trifluoropropionyl | Cyclopentyl | —SOCH₂— | | S | CH₃ | NCH₃ | NH | 3-Cl | 4-Cl | 1 | 1 | HCl | S | Amorphous |
| 722 | 3,3,3-Trifluoropropionyl | Benzyl | —SOCH₂— | | S | CH₃ | NCH₃ | NH | 3-Cl | 4-Cl | 1 | 1 | HCl | S | Amorphous |
| 723 | 3,3,3-Trifluoropropionyl | Phenyl | —NHCOCH₂— | | | CH₃ | NCH₃ | Amide bond | 3-Cl | 4-Cl | 1 | 1 | Free | racemic | Amorphous |
| 724 | 3,3,3-Trifluoropropionyl | Phenyl | —SO₂CH₃ | | | CH₃ | O | NH | 3-Cl | 4-Cl | 1 | 1 | 2HCl | S | Amorphous |
| 725 | 3,3,3-Trifluoropropionyl | Phenyl | —NHCOCH₂— | | | CH₃ | NCH₃ | Amide bond | 3-Cl | 4-Cl | 1 | 1 | 2HCl | S | Amorphous |
| 726 | Methyl | Phenyl | CONH₂ | H | | CH₃ | NCH₃ | NH | 3-Cl | 4-Cl | 1 | 1 | HCl | S | Amorphous |
| 727 | Methyl | iso-Propyl | —SOCH₂— | | S | CH₃ | NCH₃ | NH | 3-Cl | 4-Cl | 1 | 1 | HCl | S | Amorphous |
| 728 | Methyl | Benzyl | —SOCH₂— | | S | CH₃ | O | CO | 3-Cl | 4-Cl | 1 | 1 | HCl | S | Amorphous |
| 729 | Methyl | Benzyl | —SOCH₂— | | S | CH₃ | NCH₃ | CO | 3-Cl | 4-Cl | 1 | 1 | HCl | S | Amorphous |
| 730 | Trifluoroacetyl | N-Methyl-N-phenylamino | —NHCOCH₂— | | | CH₃ | NCH₃ | CO | 3-Cl | 4-Cl | 1 | 1 | HCl | S | Amorphous |
| 731 | Trifluoroacetyl | N-Methyl-N-phenylamino | —SOCH₂— | | S | CH₃ | NCH₃ | CO | 3-Cl | 4-Cl | 1 | 1 | HCl | S | Amorphous |

TABLE 1-continued

| Compound No. | $R^1$ | $R^2$ | $R^3$ | $R^4$ | Spiro | $R^5$ | $X^1$ | $X^2$ | $X^3$ | $X^4$ | n1 | n2 | Salt | Quaternary carbon | Form |
|---|---|---|---|---|---|---|---|---|---|---|---|---|---|---|---|
| 732 | Propionyl | N-Methyl-N-phenylamino | —NHCOCH$_2$— | | | CH$_3$ | NCH$_3$ | CO | 3-Cl | 4-Cl | 1 | 1 | HCl | S | Amorphous |
| 733 | Pivaloyl | N-Methyl-N-phenylamino | —SOCH$_2$— | | s | CH$_3$ | NCH$_3$ | CO | 3-Cl | 4-Cl | 1 | 1 | HCl | S | Amorphous |
| 734 | Pivaloyl | N-Methyl-N-phenylamino | —NHCOCH$_2$— | | | CH$_3$ | NCH$_3$ | CO | 3-Cl | 4-Cl | 1 | 1 | HCl | S | Amorphous |
| 735 | iso-Butyryl | N-Methyl-N-phenylamino | —NHCOCH$_2$— | | | CH$_3$ | NCH$_3$ | CO | 3-Cl | 4-Cl | 1 | 1 | HCl | S | Amorphous |
| 736 | Acetyl | N-Methyl-N-phenylamino | —SOCH$_2$— | | s | CH$_3$ | NCH$_3$ | CO | 3-Cl | 4-Cl | 1 | 1 | HCl | S | Amorphous |
| 737 | Acetyl | N-Methyl-N-phenylamino | —NHCOCH$_2$— | | | CH$_3$ | NCH$_3$ | CO | 3-Cl | 4-Cl | 1 | 1 | HCl | S | Amorphous |
| 738 | 3,3,3-Trifluoropropionyl | N-Methyl-N-phenylamino | —SO$_2$CH$_2$— | | | CH$_3$ | NCH$_3$ | CO | 3-Cl | 4-Cl | 1 | 1 | HCl | S | Amorphous |
| 739 | 3,3,3-Trifluoropropionyl | N-Cyclohexyl-N-phenylamino | —SOCH$_2$— | | s | CH$_3$ | NCH$_3$ | CO | 3-Cl | 4-Cl | 1 | 1 | HCl | S | Amorphous |
| 740 | 3,3,3-Trifluoropropionyl | N-Cyclohexyl-N-methylamino | —SOCH$_2$— | | s | CH$_3$ | NCH$_3$ | CO | 3-Cl | 4-Cl | 1 | 1 | HCl | S | Amorphous |
| 741 | 3,3,3-Trifluoropropionyl | N-Methyl-N-phenylamino | —OCH$_2$— | | | CH$_3$ | NCH$_3$ | CO | 3-Cl | 4-Cl | 1 | 1 | HCl | S | Amorphous |
| 742 | 3,3,3-Trifluoropropionyl | N-Methyl-N-phenylamino | NHAc | H | | CH$_3$ | NCH$_3$ | CO | 3-Cl | 4-Cl | 1 | 1 | HCl | S | Amorphous |
| 743 | 3,3,3-Trifluoropropionyl | 2,3-Dichlorophenyl | —SOCH$_2$— | CH$_3$ | | CH$_3$ | NCH$_3$ | O | 3-Cl | 4-Cl | 2 | 1 | HCl | S | Amorphous |
| 745 | 3,3,3-Trifluoropropionyl | 3,4-Dichlorophenyl | —SOCH$_2$— | CH$_3$ | | CH$_3$ | NCH$_3$ | O | 3-Cl | 4-Cl | 2 | 1 | HCl | S | Amorphous |
| 746 | 3,3,3-Trifluoropropionyl | 2,3-Difluorophenyl | —SOCH$_2$— | CH$_3$ | | CH$_3$ | NCH$_3$ | O | 3-Cl | 4-Cl | 2 | 1 | HCl | S | Amorphous |
| 747 | 3,3,3-Trifluoropropionyl | 2,4-Difluorophenyl | —SOCH$_2$— | CH$_3$ | | CH$_3$ | NCH$_3$ | O | 3-Cl | 4-Cl | 2 | 1 | HCl | S | Amorphous |
| 748 | 3,3,3-Trifluoropropionyl | 2,5-Difluorophenyl | —SOCH$_2$— | CH$_3$ | | CH$_3$ | NCH$_3$ | O | 3-Cl | 4-Cl | 2 | 1 | HCl | S | Amorphous |
| 749 | 3,3,3-Trifluoropropionyl | 3,5-Difluorophenyl | —SOCH$_2$— | CH$_3$ | | CH$_3$ | NCH$_3$ | O | 3-Cl | 4-Cl | 2 | 1 | HCl | S | Amorphous |
| 750 | 3,3,3-Trifluoropropionyl | 2,3-Dimethoxyphenyl | —SOCH$_2$— | CH$_3$ | | CH$_3$ | NCH$_3$ | O | 3-Cl | 4-Cl | 2 | 1 | HCl | S | Amorphous |
| 751 | 3,3,3-Trifluoropropionyl | 3,4-Dimethoxyphenyl | —SOCH$_2$— | CH$_3$ | | CH$_3$ | NCH$_3$ | O | 3-Cl | 4-Cl | 2 | 1 | HCl | S | Amorphous |
| 752 | 3,3,3-Trifluoropropionyl | 3,5-Dimethoxyphenyl | —SOCH$_2$— | CH$_3$ | | CH$_3$ | NCH$_3$ | O | 3-Cl | 4-Cl | 2 | 1 | HCl | S | Amorphous |
| 753 | 3,3,3-Trifluoropropionyl | 3,5-Difluorophenyl | —SOCH$_2$— | CH$_3$ | | CH$_3$ | NCH$_3$ | O | 3-Cl | 4-Cl | 2 | 1 | HCl | S | Amorphous |

Test Example 1

1. NK-1 Receptor-binding Test

1) Preparation of Human NK-1 Receptor Expression Cells

FuGene 6 transfection reagent (Boegringer Mannheim) (3 µL) was diluted in an F-12 culture broth (97 µL), and pCR3.1 plasmid to which human NK-1 receptor cDNA had been introduced (Invitrogen) (10 µL) was added thereto. The mixture was mixed and incubated for 15 minutes (transfection reagent). CHO-K1 cells (ATCC: CCL-61) were cultured for 24 hours, and the whole reagent prepared above was added to the cultured CHO-K1 cells ($2 \times 10^{-5}$ cells). Subsequently, culture was performed in the presence of G418 (Stratagene), and the resistant cells were employed as cells into which human NK-1 receptor gene was introduced (hNK1-CHO).

2) Subcultivation of hNK1-CHO Cells

The hNK1-CHO cells were treated with trypsin-EDTA and subcultivated in an F-12 culture broth (containing 10% fetal bovine serum, 10 mM HEPES, 100 U/mL, penicillin, 100 µg/mL streptmycin, 400 µg/mL G418) in a 75-$cm^2$ flask (FALCON). Cells to be employed in the receptor-binding experiment were added to a 24-well plate (IWAKI) at $1 \times 10^5$ cells/well, and subcultured for 48 hours at 37° C. under 95% $O_2$ and 5% $CO_2$.

3) Receptor-binding Experiment

When the hNK1-CHO cells became subconfluent on the 24-well plate, an F-12 culture broth (containing 10 mM HEPES and 0.1% fetal bovine serum) (450 µL), [$^3$H]-Substance P (Amersham, final concentration 0.5 nM), and a test compound were added to the cells, and the mixture was incubated for 40 minutes at 37° C. For the measurement of non-specific binding, L703606 (Sigma) was added instead of the test compound. After completion of incubation, the mixture was washed with ice-cooled phosphate buffered saline containing 0.1% fetal bovine serum, and the cells were lysed with 1N NaOH (0.5 mL). The lysate was transferred to a plastic vial containing UltimaGold MV (5 mL), and the radioactivity was determined by means of a liquid liquid scintillation counter (Packard, 2000CA).

2. NK-2 Receptor-binding Experiment

Cloned Neurokinin Receptor Subtype 2 Human (CHO cells, Biosignal Packard), [$^3$H]-SR48968 (Amersham, final concentration 0.85 nM), and a test compound were mixed with 20 mM HEPES buffer, and the mixture was incubated for 50 minutes at 27° C. After completion of incubation, membrane components were collected by means of an automatic filtration apparatus (Brandel) onto a GF/C glass fiber filter (Whatman).

Before use, in order to prevent non-specific binding, the glass fiber filter had been pre-treated with 0.1% polyethylene imine solution for about 4 hours.

The filter employed to collect the membrane components was transferred to a plastic vial containing UltimaGold MV (5 mL), and measured by means of a liquid scintillation counter (Packard, 2000CA) in terms of the radioactivity.

3. Data Analysis

Percent radioactive ligand-receptor binding inhibition of each test compound was calculated by use of the following equation, and $IC_{50}$ (nM) was determined through pseudo-Hill analysis.

Percent inhibition (%)=$[1-(C-A)/(B-A)] \times 100$

A: Radioactivity attributed to non-specific binding
B: Radioactivity without test compound
C: Radioactivity with test compound Tables 2 to 4 shows the results obtained from the compounds of the present invention which exhibit particularly excellent antagonism effect to NK-1 receptor, to NK-2 receptor, and to NK-1 and NK-2 receptors, respectively.

TABLE 2

| Compound No. | NK-1(nM) |
|---|---|
| 15 | 0.9 |
| 16 | 3.5 |
| 17 | 1.5 |
| 578 | 9.5 |
| 589 | 0.53 |
| 591 | 6.9 |
| 599 | 0.73 |
| 615 | 0.58 |
| 617 | 0.54 |
| 616 | 2.0 |
| 618 | 1.2 |
| 621 | 0.94 |
| 633 | 8.3 |
| 634 | 2.0 |
| 636 | 0.9 |
| 637 | 1.7 |
| 638 | 6.0 |
| 639 | 4.0 |
| 640 | 6.0 |
| 642 | 3.7 |
| 652 | 2.7 |
| 653 | 1.6 |
| 654 | 3.0 |
| 655 | 1.3 |

TABLE 3

| Compound No. | NK-2(nM) |
|---|---|
| 3 | 1.7 |
| 9 | 7.2 |
| 10 | 4.1 |
| 11 | 8.1 |
| 13 | 2.6 |
| 14 | 0.34 |
| 21 | 8.7 |
| 22 | 0.95 |
| 23 | 1.7 |
| 24 | 2.9 |
| 25 | 0.58 |
| 26 | 0.85 |
| 27 | 6.7 |
| 28 | 2.6 |
| 29 | 4.0 |
| 30 | 1.2 |
| 31 | 0.75 |
| 32 | 1.0 |
| 33 | 0.65 |
| 34 | 0.96 |
| 35 | 4.6 |
| 36 | 0.85 |
| 37 | 1.8 |
| 38 | 1.9 |
| 39 | 1.0 |
| 40 | 0.73 |
| 41 | 0.84 |

TABLE 4

| Compound No. | NK-1(nM) | NK-2(nM) |
|---|---|---|
| 1 | 1.2 | 1.6 |
| 2 | 4.3 | 2.1 |
| 4 | 3.4 | 1.5 |
| 5 | 6.3 | 1.9 |
| 12 | 11.0 | 6.1 |
| 42 | 2.1 | 4.0 |

TABLE 4-continued

| Compound No. | NK-1(nM) | NK-2(nM) |
|---|---|---|
| 43 | 7.7 | 2.1 |
| 44 | 11.0 | 2.4 |
| 45 | 4.9 | 2.8 |
| 46 | 10.1 | 1.8 |

The invention claimed is:

1. A benzylamine or its salt represented by formula (1):

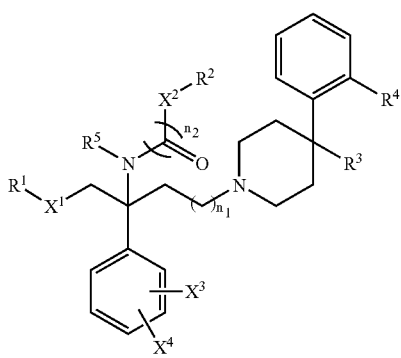

(1)

wherein $X^1$ represents —N(CH$_3$)—, —NH—, or —O—; $X^2$ represents a single bond, —NH—, an amido bond, an ester bond, —O—, —S—, or —CO—;
each of $X^3$ and $X^4$ represents a hydrogen atom or a halogen atom;
$R^1$ represents a hydrogen atom; a lower alkyl group; a phenyl group which may be substituted by 1 to 3 halogen atoms or cyano groups; a benzyl group which may be substituted by 1 to 3 lower alkyl groups, cyano groups, halogeno(lower alkyl) groups, or lower alkoxy groups; a benzoyl group which may be substituted by 1 to 3 lower alkyl groups, hydroxyl groups, halogeno(lower alkyl) groups, or lower alkoxy groups; a lower alkanoyl group which may be substituted by 1 to 5 halogen atoms, amino groups, or carbamoyl groups; a hydroxyl group; a carbamoyl group; a lower alkylsulfonyl group; a lower alkoxycarbonyl-lower alkyl group; a thienylcarbonyl group; a pyridylcarbonyl group; a lower alkylcarbonyl group; or a phenoxycarbonyl group;
$R^2$ represents a hydrogen atom, a lower alkyl group, a lower alkenyl group, a lower alkylsulfonyl group, a C3-C7 cycloalkyl group, a C6-C14 cycloalkyl-alkyl group, a C6-C14 aryl group, a C6-C14 aryloxy group, a C6-C14 aryloxy-lower alkyl group, C6-C14 arylthio-lower alkyl group, a C7-C16 aralkyl group, a lower alkoxycarbonyl-lower alkyl group, a lower alkoxy-lower alkyl group, an amino-lower alkyl group, a C7-C16 aralkyl group substituted by a C3-C7 cycloalkyl group, a halogeno(lower alkyl)carbonyl group, an indanyl group, a 1,2,3,4-tetrahydronaphthalenyl group, a xanthenyl group, a piperidinyl group, a pyrrolidinyl group, a morpholino group, a tetrahydroisoquinolyl group, an indolyl group, a chromenyl group, an isobenzofuranyl group, a tetrahydropyranyl group, a benzothienyl group, an adamantyl group, an adamantyl(lower alkyl) group, a fluorenyl group, a fluorenyl(lower alkyl) group, a pyridyl(lower alkyl) group, or an amino group which may be substituted by a phenyl group or a lower alkyl group wherein a ring hydrogen of these group may be substituted by 1 to 5 atoms or groups selected from among a halogen atom, a lower alkyl group, a lower alkoxy group, a nitro group, an oxo group, a halogeno(lower alkyl) group, a C6-C14 aryl group, and a lower alkylamino group;
when $R^3$ represents a (lower alkanoyl)amino group, an amino(lower alkanoyl) group, an amino(lower alkanoyl)amino group, a di(lower alkyl)carbamoylamino group, or a C7-C16 aralkyloxy(lower alkyl) group, $R^4$ represents a hydrogen atom; or $R^3$ and $R^4$ may together form —SOCH$_2$—, —SO$_2$CH$_2$—, —NHCOCH$_2$—, —CH(OH)CH$_2$—, —OCH$_2$—, or —C(=NOH)CH$_2$—; $R^5$ represents a hydrogen atom or a lower alkyl group; $n_1$ is 1 or 2; and $n_2$ is 0 or 1.

2. The benzylamine or its salt of claim 1, wherein $R^3$ and $R^4$ together form —SOCH$_2$—, —SO$_2$CH$_2$—, —NHCOCH$_2$—, —CH(OH)CH$_2$—, —OCH$_2$—, or —(=NOH)CH$_2$—.

3. The benzylamine or its salt of claim 1, wherein $X^1$ is —N(CH$_3$)— or —O—.

4. The benzylamine or its salt of claim 1, wherein $X^2$ is a single bond, —NH—, an amido bond, an ester bond, —O—, or —CO—.

5. The benzylamine or its salt of claim 1, wherein $R^2$ is a C7-C16 aralkyl group, a lower alkyl group, a C6-C14 aryl group, a C3-C7 cycloalkyl group, or an amino group which is optionally substituted by a phenyl group or a lower alkyl group.

6. A composition comprising the benzylamine or its salt of claim 2 and a pharmaceutically acceptable carrier.

7. A composition comprising the benzylamine or its salt of claim 1 and a pharmaceutically acceptable carrier.

8. A method for producing a benzylamine or its salt of formula (1-a) or formula (1-b), comprising
protecting the amino group of a compound of formula (12) to give a compound of formula (13),
oxidizing and N-methylating the compound of formula (13) to give a compound of formula (14),
acylating the compound of formula (14) to produce an intermediate of formula (15),
oxidizing the alkene of the intermediate of formula (15) to produce an aldehyde,
wherein the terminal carbon of the alkene is lost in the oxidation, and,
reductively aminating the aldehyde with either the amine of formula (16) or the amine of formula (18) to produce, respectively, either the intermediate of formula (17) or the intermediate of formula (19), and
deprotecting either the intermediate of formula (17) or the intermediate of formula (19), followed by reacting the deprotected compound with an active carbonyl species to produce the compound of either formula (1-a) or formula (1-b),
wherein $X^2$ represents a single bond, —NH—, an amido bond, an ester bond, —O—, —S—, or —CO—;
wherein each of $X^3$ and $X^4$ represents a hydrogen atom or a halogen atom;
wherein $R^1$ represents a hydrogen atom; a lower alkyl group; a phenyl group which may be substituted by 1 to 3 halogen atoms or cyano groups; a benzyl group which may be substituted by 1 to 3 lower alkyl groups, cyano groups, halogeno(lower alkyl) groups, or lower alkoxy groups; a benzoyl group which may be substituted by 1 to 3 lower alkyl groups, hydroxyl groups, halogeno(lower alkyl) groups, or lower alkoxy groups; a lower alkanoyl group which may be substituted by 1 to 5 halogen atoms, amino groups, or carbamoyl groups; a hydroxyl group; a carbamoyl group; a lower alkylsulfonyl group; a lower alkoxycarbonyl-lower alkyl group; a thienylcarbonyl group; a pyridylcarbonyl group; a lower alkylcarbonyl group; or a phenoxycarbonyl group;

wherein $R^2$ represents a hydrogen atom, a lower alkyl group, a lower alkenyl group, a lower alkylsulfonyl group, a C3-C7 cycloalkyl group, a C6-C14 cycloalkylalkyl group, a C6-C14 aryl group, a C6-C14 aryloxy a phenyl group or a lower alkyl group wherein a ring hydrogen of these group may be substituted by 1 to 5 atoms or groups selected from among a halogen atom, a lower alkyl group, a lower alkoxy group, a nitro group, an oxo group, a halogeno(lower alkyl) group, a C6-C14 aryl group, and a lower alkylamino group; and wherein $R_6$ is a protecting group;

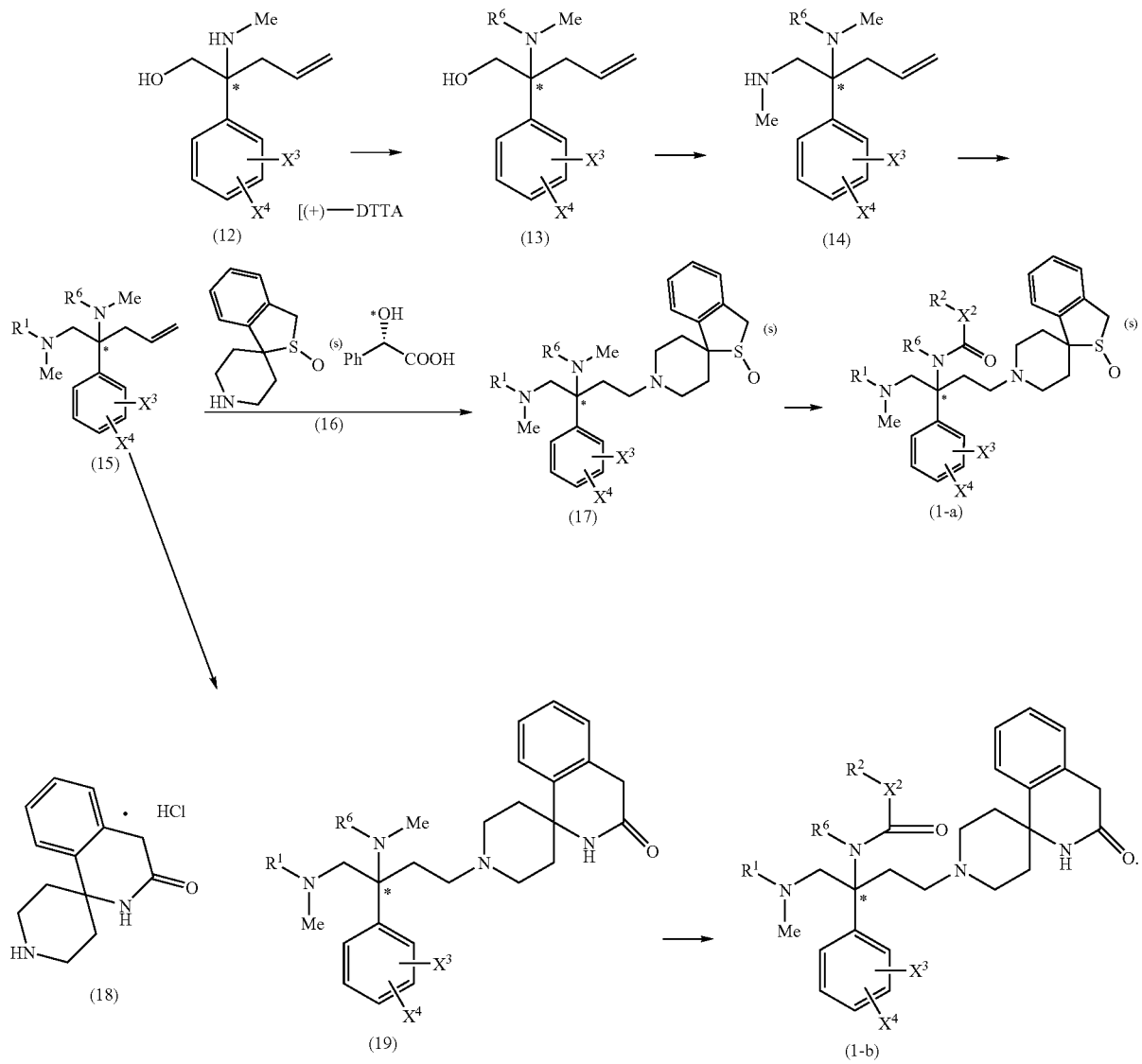

group, a C6-C14 aryloxy-lower alkyl group, C6-C14 arylthio-lower alkyl group, a C7-C16 aralkyl group, a lower alkoxycarbonyl-lower alkyl group, a lower alkoxy-lower alkyl group, an amino-lower alkyl group, a C7-C16 aralkyl group substituted by a C3-C7 cycloalkyl group, a halogeno(lower alkyl)carbonyl group, an indanyl group, a 1,2,3,4-tetrahydronaphthalenyl group, a xanthenyl group, a piperidinyl group, a pyrrolidinyl group, a morpholino group, a tetrahydroisociuinolyl group, an indolyl group, a chromenyl group, an isobenzofuranyl group, a tetrahydropyranyl group, a benzothienyl group, an adamantyl group, an adamantyl(lower alkyl) group, a fluorenyl group, a fluorenyl(lower alkyl) group, a pyridyl(lower alkyl) group, or an amino group which may be substituted by 9. A method for treating at least one disease in a patient in need thereof, wherein the at least one disease is selected from the group consisting of irritable bowel syndrome, pain, anxiety, and vomiting, which comprises administering the benzylamine or its salt of claim 1 to patient in need thereof in an amount sufficient to treat the at least one disease.

10. The method of claim 8, wherein the compound of formula (1-a) is produced.

11. The method of claim 8, wherein the compound of formula (1-b) is produced.

* * * * *

UNITED STATES PATENT AND TRADEMARK OFFICE
CERTIFICATE OF CORRECTION

PATENT NO.        : 7,276,511 B2
APPLICATION NO. : 10/566252
DATED             : October 2, 2007
INVENTOR(S)       : Masaaki Nagasawa et al.

It is certified that error appears in the above-identified patent and that said Letters Patent is hereby corrected as shown below:

Column 12, figure (1-a), "$R^6$" should read --$CH^3$--.
Column 253, lines 6-7 from the bottom, "tetrahydroisociuinoly" should read --tetrahydroisoquinolyl--.
Columns 253 and 254, figures (16), (17) and (1-a), "S-O" should read --S→O--.
Column 254, figures (1-a) and (1-b), "$R^6$" should read --$CH^3$--.
Column 254, line 6 from the bottom, please insert --the-- between "to" and "patient"

Signed and Sealed this

Eighteenth Day of March, 2008

JON W. DUDAS
*Director of the United States Patent and Trademark Office*